(12) United States Patent
Kubo et al.

(10) Patent No.: US 11,946,086 B2
(45) Date of Patent: Apr. 2, 2024

(54) GENE INVOLVED IN SYNTHESIS OF CYCLIC PEPTIDE COMPOUND, METHOD FOR PRODUCING CYCLIC PEPTIDE COMPOUND USING THE SAME, AND TRANSFORMANT COMPRISING THE SAME

(71) Applicants: NATIONAL INSTITUTE OF ADVANCED INDUSTRIAL SCIENCE AND TECHNOLOGY, Tokyo (JP); TOHOKU UNIVERSITY, Sendai (JP); KUMIAI CHEMICAL INDUSTRY CO., LTD., Tokyo (JP)

(72) Inventors: Takashi Kubo, Sapporo (JP); Masayuki Machida, Sapporo (JP); Maiko Umemura, Sapporo (JP); Keietsu Abe, Sendai (JP); Akira Yoshimi, Sendai (JP); Tomonori Fujioka, Tokyo (JP); Shigenari Yamaguchi, Tokyo (JP); Kiyoshi Kawai, Tokyo (JP)

(73) Assignees: TOHOKU UNIVERSITY, Sendai (JP); KUMIAI CHEMICAL INDUSTRY CO., LTD., Tokyo (JP)

( * ) Notice: Subject to any disclaimer, the term of this patent is extended or adjusted under 35 U.S.C. 154(b) by 143 days.

(21) Appl. No.: 17/549,492

(22) Filed: Dec. 13, 2021

(65) Prior Publication Data
US 2022/0259634 A1 Aug. 18, 2022

Related U.S. Application Data

(62) Division of application No. 16/476,000, filed as application No. PCT/JP2017/046858 on Dec. 27, 2017, now Pat. No. 11,230,726.

(30) Foreign Application Priority Data

Jan. 5, 2017 (JP) .................................. 2017-000770

(51) Int. Cl.
| | |
|---|---|
| *C12N 9/10* | (2006.01) |
| *C07K 7/64* | (2006.01) |
| *C12N 15/80* | (2006.01) |
| *C12P 21/02* | (2006.01) |
| *A61K 38/10* | (2006.01) |

(52) U.S. Cl.
CPC .............. *C12P 21/02* (2013.01); *C07K 7/64* (2013.01); *C12N 15/80* (2013.01); *A61K 38/10* (2013.01)

(58) Field of Classification Search
CPC . A61K 38/10; C07K 7/64; C12N 1/16; C12N 1/20; C12P 21/02
USPC ............................................ 435/252.3, 69.7
See application file for complete search history.

(56) References Cited

FOREIGN PATENT DOCUMENTS

| JP | 8-504165 A | 5/1996 |
|---|---|---|
| JP | 9-157168 A | 6/1997 |
| WO | WO 92/05191 A1 | 4/1992 |
| WO | WO 93/12659 A1 | 7/1993 |

OTHER PUBLICATIONS

Brakhage et al., "Fungal secondary metabolites—Strategies to activate silent gene clusters", Fungal Genetics and Biology, vol. 48, 2011, pp. 15-22 (8 pages).
Devos et al., Proteins: Structure, Function and Genetics, 2000, vol. 41: 98-107.
Georgianna et al., "Beyond aflatoxin: four distinct expression patterns and functional roles associated with Aspergillus flavus secondary metabolism gene clusters", Molecular Plant Pathology, vol. 11, No. 2, 2010, pp. 213-226 (14 pages).
Kisselev L., Structure, 2002, vol. 10: 8-9.
Machida et al., "Genome sequencing and analysis of Aspergillus oryzae", Nature, vol. 438, No. 22, Dec. 29, 2005, pp. 1157-1161 (5 pages).
Whisstock et al., Quarterly Reviews of Biophysics 2003, vol. 36 (3): 307-340.
Witkowski et al., Biochemistry 38:11643-11650, 1999.
Yamaguchi et al., "The identification of biosynthetic gene cluster for the antimicrobial cyclic peptide produced by Curvularia clavata", Annual Meeting of the Japan Society for Bioscience, Biotechnology, and Agrochemistry, 2017, 3 pages (with translation).
Yoshimi et al., "Heterologous production of the antifungal cyclic peptide, KK-1, in Aspergillus oryzae", Annual Meeting of the Japan Society of Bioscience, Biotechnology, and Agrochemistry, 2017, 4 pages (with translation).
Chinese Office Action and Search Report for Chinese Application No. 201780088071.3, dated Feb. 27, 2023.
Liang et al., "Fungi Ó in the Rhizosphere of Farmland Crops in Liaoning Province," Journal of Shenyang Agricultural University, vol. 33, No. 4, 2002, pp. 266-269, with an English translation.
Philippines Office Action for Philippines Application No. 12019501577, dated Jul. 5, 2023.
Vassaux et al., "Nonribosomal peptides in fungal cell factories: from genome mining to optimized heterologous production," Biotechnology Advances, vol. 37, 2019 (Available online Sep. 10, 2019), p. 107449 (23 pages total).
Taiwanese Office Action and Search Report for corresponding Taiwanese Application No. 106146199, dated May 22, 2023.

*Primary Examiner* — Robert B Mondesi
*Assistant Examiner* — Mohammad Y Meah
(74) *Attorney, Agent, or Firm* — Birch, Stewart, Kolasch & Birch, LLP

(57) ABSTRACT

This invention is intended to identify a gene cluster involved in biosynthesis of a cyclic peptide compound produced by a filamentous fungus of the *Curvularia* species and to establish a system for synthesizing such cyclic peptide compound. The gene is composed of a first module to a tenth module and encodes a protein having activity of synthesizing a nonribosomal peptide constituting a basic peptide backbone of a cyclic peptide compound produced by a filamentous fungus of the *Curvularia* species.

5 Claims, 27 Drawing Sheets

Figure 1:
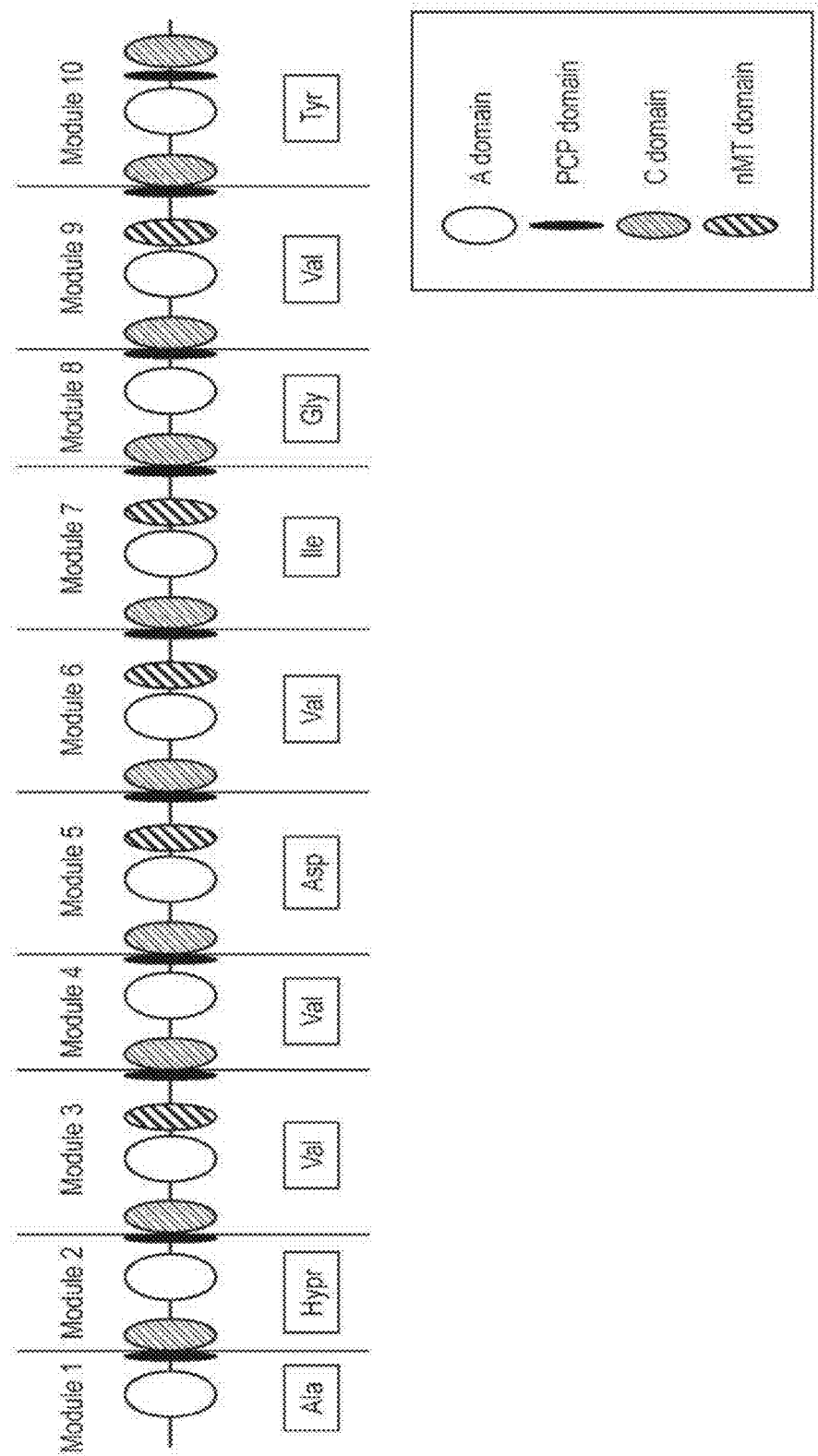

Specification includes a Sequence Listing.

Fig. 4

| Gene ID | Annotation |
|---|---|
| TRAF010001350000015 | similar to ubiquinol-cytochrome-c reductase [Alternaria alternata] |
| TRAF010001350000014 | kinesin light chain 3 [Pyrenophora tritici-repentis Pt-1C-BFP] |
| TRAF010001350000013 | kinesin light chain 3 [Pyrenophora tritici-repentis Pt-1C-BFP] |
| TRAF010001350000012 | transposase [Aspergillus niger CBS 513.88] |
| TRAF010001350000011 | hypothetical protein BcDW1_6707 [Botryotinia fuckeliana BcDW1] |
| TRAF010001350000010 | similar to kinesin light chain [Botryotinia fuckeliana T4] |
| TRAF010001350000009 | hypothetical protein COCC4DRAFT_76928 [Bipolaris maydis ATCC 48331] |
| TRAF010001350000008 | related to HETEROKARYON incompatibility protein [Fusarium fujikuroi IMI 58289] |
| TRAF010001350000007 | Ankyrin repeat protein [Aspergillus fumigatus A1163] |
| TRAF010001350000006 | hypothetical protein COCSADRAFT_42061 [Bipolaris sorokiniana ND90Pr] |
| TRAF010001350000005 | kinesin, putative [Talaromyces marneffei ATCC 18224] |
| TRAF010001350000004 | |
| TRAF010001350000003 | O-methyltransferase, putative [Talaromyces marneffei ATCC 18224] |
| TRAF010001350000002_J3G | Nonribosomal peptide synthetase (NRPS) |
| TRAF010000680000002 | amidase [Mycosphaerella populorum SO2202] |
| TRAF010000680000003 | hypothetical protein MYCGRDRAFT_97764 [Zymoseptoria tritici IPO323] |
| TRAF010000680000004 | hypothetical protein ARB_03427 [Arthroderma benhamiae CBS 112371] |
| TRAF010000680000005 | putative transcriptional regulator protein [Neofusicoccum parvum UCRNP2] |
| TRAF010000680000006 | leptomycin B resistance protein pmd1 [Pyrenophora tritici-repentis Pt-1C-BFP] |
| TRAF010000680000007 | putative d-lactate dehydrogenase protein [Togninia minima UCRPA7] |
| TRAF010000680000008 | pyrroline-5-carboxylate reductase-like protein [Glarea lozoyensis ATCC 20868] |
| TRAF010000680000009 | alphabeta-Hydrolase [Glarea lozoyensis ATCC 20868] |
| TRAF010000680000010 | hypothetical protein COCSADRAFT_343231, partial [Bipolaris sorokiniana ND90Pr] |
| TRAF010000680000011 | GDP-mannose transporter [Trichophyton equinum CBS 127.97] |
| TRAF010000680000012 | hypothetical protein PTT_11656 [Pyrenophora teres f. teres 0-1] |
| TRAF010000680000013 | hypothetical protein SETTUDRAFT_24621 [Setosphaeria turcica Et28A] |
| TRAF010000680000014 | histone H3, putative [Perkinsus marinus ATCC 50983] |
| TRAF010000680000015 | SNF2-related protein [Macrophomina phaseolina MS6] |

Putative biosynthetic cluster (about 75 kb): TRAF010001350000002_J3G through TRAF010000680000009

A

B

| Gene | Restriction enzyme |
|---|---|
| TRAF01000135000002 | HindIII |
| TRAF01000135000001 | EcoRI |
| TRAF01000068000002 | EcoRI |
| TRAF01000068000003 | EcoRI |
| TRAF01000068000004 | EcoRI |
| TRAF01000068000006 | KpnI |
| TRAF01000068000007 | HindIII |
| TRAF01000068000008 | HindIII |
| TRAF01000068000009 | EcoRI |

Fig. 24
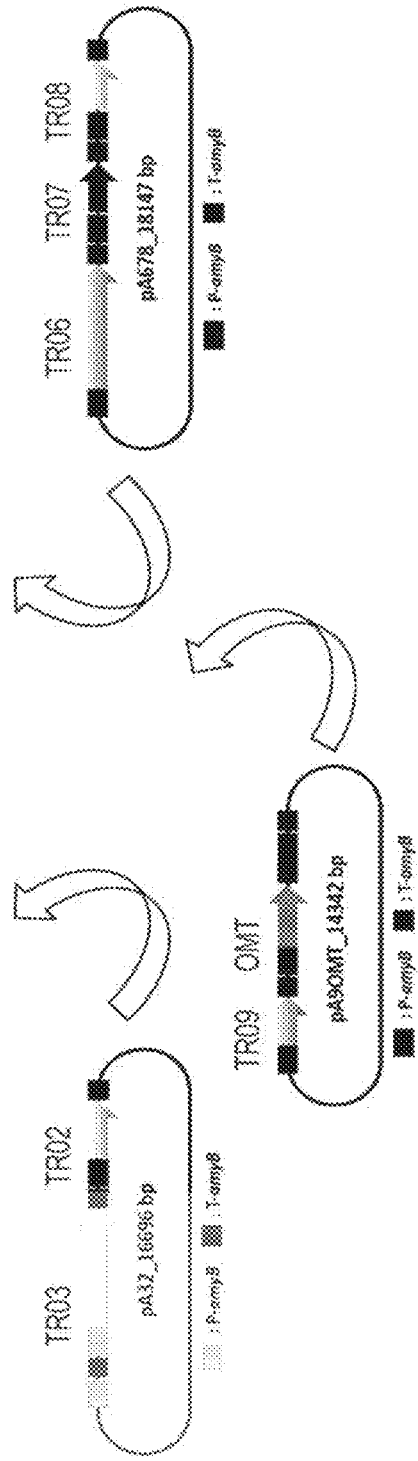

GENE INVOLVED IN SYNTHESIS OF CYCLIC PEPTIDE COMPOUND, METHOD FOR PRODUCING CYCLIC PEPTIDE COMPOUND USING THE SAME, AND TRANSFORMANT COMPRISING THE SAME

CROSS-REFERENCE TO RELATED APPLICATIONS

This application is a Divisional of co-pending U.S. application Ser. No. 16/476,000, filed on Jul. 3, 2019, which is the National Phase under 35 U.S.C. § 371 of International Application No. PCT/JP2017/046858, filed on Dec. 27, 2017, which claims priority under 35 U. S. C. § 119(a) to Application No. 2017-000770, filed in Japan on Jan. 5, 2017, all of which are hereby expressly incorporated by reference into the present application.

TECHNICAL FIELD

The present invention relates to a novel gene involved in the synthesis of a cyclic peptide compound having bactericidal activity against fungi produced by a filamentous fungus of the *Curvularia* species, a method for producing a cyclic peptide compound using the gene involved in the synthesis of a cyclic peptide compound, and a transformant comprising the gene involved in the synthesis of a cyclic peptide compound.

BACKGROUND ART

A particular cyclic peptide compound that is known as "CAS143380-71-6" produced by a filamentous fungus of the *Curvularia* species (hereafter, referred to as "KK-1") is known to exert potent bactericidal activity against plant pathogenic bacteria, and, in particular, against fungi (JP H8-504165 A (1996)). While KK-1 shows potent bactericidal activity, commercial use thereof as an agricultural chemical has not yet been realized for the following reasons. For example, KK-1 has a complicated chemical structure, so that chemical synthesis thereof is difficult. Even if KK-1 could be chemically synthesized, in addition, a complicated chemical structure of KK-1 would disadvantageously increase the cost. While production of KK-1 is intended via culture of filamentous fungi of the *Curvularia* species, the amount of production may not be sufficient.

To date, pharmaceutical products and agricultural chemicals have been developed from secondary metabolites produced by microorganisms, including mycetes, actinomycetes, and bacteria. As a result of genome analysis of several types of mycetes, specifically, *Aspergillus*, which is the same filamentous fungus as the *Curvularia* species, the presence of a biosynthetic gene cluster involved in the biosynthesis of a variety of secondary metabolites, including polyketide compounds, nonribosomal peptides, terpenes, and alkaloyds, has been elucidated (Machida, M., et al., Nature, 2005, 438 (7071), pp. 1157-1161). According to the results of genome analysis and molecular biological research on filamentous fungi of recent years, the transcription level of secondary metabolite-biosynthesizing genes of filamentous fungi was found to be low by a general filamentous fungi culture technique (Georgianna, D. R. et al., Mol. Plant. Pathol., 11, 213, 2010).

In order to exert a potential ability to produce secondary metabolites, accordingly, so-called synthetic biology techniques aimed at synthesis of sufficient quantities of secondary metabolites through activation of a biosynthetic gene cluster (Brakhage, Fungal Genetics and Biology, 2011, 48 (1), pp. 15-22) and expression in adequate heterologs, such as budding yeast, have been attempted.

SUMMARY OF THE INVENTION

Objects to Be Attained by the Invention

As with the case of secondary metabolites described above, KK-1 produced by a filamentous fungus of the *Curvularia* species may also be produced via synthetic biology techniques. However, the genome of a filamentous fungus of the *Curvularia* species has not been substantially elucidated, and the gene cluster involved in the production of KK-1 has not been identified.

Under the above circumstances, it is an object of the present invention to identify a gene cluster involved in the biosynthesis of KK-1 produced by a filamentous fungus of the *Curvularia* species to provide a system for synthesizing KK-1.

Means for Attaining the Objects

The present inventors have conducted concentrated studies in order to attain the above objects. As a result, they succeeded in identifying a plurality of nonribosomal peptide synthetase (NRPS) genes from the genome of *Curvularia clavata* and identifying a NRPS gene involved in the synthesis of KK-1 and a gene cluster including such NRPS gene from among the identified NRPS genes. This has led to the completion of the present invention.

The present invention encompasses the following.

(1) A gene involved in the synthesis of a cyclic peptide compound, wherein the gene encodes a protein having activity of synthesizing a nonribosomal peptide of a cyclic peptide compound produced by a filamentous fungus of the *Curvularia* species, and comprising successively from the N terminus the modules described below:

a first module comprising successively from the N terminus a first adenylation domain comprising the amino acid sequence as shown in SEQ ID NO: 1 or an amino acid sequence having 70% or higher identity to the amino acid sequence as shown in SEQ ID NO: 1 and a first peptidyl carrier protein domain comprising the amino acid sequence as shown in SEQ ID NO: 2 or an amino acid sequence having 70% or higher identity to the amino acid sequence as shown in SEQ ID NO: 2;

a second module comprising successively from the N terminus a first condensation domain comprising the amino acid sequence as shown in SEQ ID NO: 3 or an amino acid sequence having 70% or higher identity to the amino acid sequence as shown in SEQ ID NO: 3, a second adenylation domain comprising the amino acid sequence as shown in SEQ ID NO: 4 or an amino acid sequence having 70% or higher identity to the amino acid sequence as shown in SEQ ID NO: 4, and a second peptidyl carrier protein domain comprising the amino acid sequence as shown in SEQ ID NO: 5 or an amino acid sequence having 70% or higher identity to the amino acid sequence as shown in SEQ ID NO: 5;

a third module comprising successively from the N terminus a second condensation domain comprising the amino acid sequence as shown in SEQ ID NO: 6 or an amino acid sequence having 70% or higher identity to the amino acid sequence as shown in SEQ ID NO: 6, a third adenylation domain comprising the amino acid sequence as shown in SEQ ID NO: 7 or an amino acid sequence having 70% or higher identity to the amino acid sequence as shown in SEQ ID NO: 7, a first N-methyl transferase domain comprising the amino acid sequence as shown in SEQ ID NO: 8 or an amino acid sequence having 70% or higher identity to the amino acid sequence as shown in SEQ ID NO: 8, and a third peptidyl carrier protein domain comprising the amino acid sequence as shown in SEQ ID NO: 9 or an amino acid sequence having 70% or higher identity to the amino acid sequence as shown in SEQ ID NO: 9;

a fourth module comprising successively from the N terminus a third condensation domain comprising the amino acid sequence as shown in SEQ ID NO: 10 or an amino acid sequence having 70% or higher identity to the amino acid sequence as shown in SEQ ID NO: 10, a fourth adenylation domain comprising the amino acid sequence as shown in SEQ ID NO: 11 or an amino acid sequence having 70% or higher identity to the amino acid sequence as shown in SEQ ID NO: 11, and a fourth peptidyl carrier protein domain comprising the amino acid sequence as shown in SEQ ID NO: 12 or an amino acid sequence having 70% or higher identity to the amino acid sequence as shown in SEQ ID NO: 12;

a fifth module comprising successively from the N terminus a fourth condensation domain comprising the amino acid sequence as shown in SEQ ID NO: 13 or an amino acid sequence having 70% or higher identity to the amino acid sequence as shown in SEQ ID NO: 13, a fifth adenylation domain comprising the amino acid sequence as shown in SEQ ID NO: 14 or an amino acid sequence having 70% or higher identity to the amino acid sequence as shown in SEQ ID NO: 14, a second N-methyl transferase domain comprising the amino acid sequence as shown in SEQ ID NO: 15 or an amino acid sequence having 70% or higher identity to the amino acid sequence as shown in SEQ ID NO: 15, and a fifth peptidyl carrier protein domain comprising the amino acid sequence as shown in SEQ ID NO: 16 or an amino acid sequence having 70% or higher identity to the amino acid sequence as shown in SEQ ID NO: 16;

a sixth module comprising successively from the N terminus a fifth condensation domain comprising the amino acid sequence as shown in SEQ ID NO: 17 or an amino acid sequence having 70% or higher identity to the amino acid sequence as shown in SEQ ID NO: 17, a sixth adenylation domain comprising the amino acid sequence as shown in SEQ ID NO: 18 or an amino acid sequence having 70% or higher identity to the amino acid sequence as shown in SEQ ID NO: 18, a third N-methyl transferase domain comprising the amino acid sequence as shown in SEQ ID NO: 19 or an amino acid sequence having 70% or higher identity to the amino acid sequence as shown in SEQ ID NO: 19, and a sixth peptidyl carrier protein domain comprising the amino acid sequence as shown in SEQ ID NO: 20 or an amino acid sequence having 70% or higher identity to the amino acid sequence as shown in SEQ ID NO: 20;

a seventh module comprising successively from the N terminus a sixth condensation domain comprising the amino acid sequence as shown in SEQ ID NO: 21 or an amino acid sequence having 70% or higher identity to the amino acid sequence as shown in SEQ ID NO: 21, a seventh adenylation domain comprising the amino acid sequence as shown in SEQ ID NO: 22 or an amino acid sequence having 70% or higher identity to the amino acid sequence as shown in SEQ ID NO: 22, a fourth N-methyl transferase domain comprising the amino acid sequence as shown in SEQ ID NO: 23 or an amino acid sequence having 70% or higher identity to the amino acid sequence as shown in SEQ ID NO: 23, and a seventh peptidyl carrier protein domain comprising the amino acid sequence as shown in SEQ ID NO: 24 or an amino acid sequence having 70% or higher identity to the amino acid sequence as shown in SEQ ID NO: 24;

an eighth module comprising successively from the N terminus a seventh condensation domain comprising the amino acid sequence as shown in SEQ ID NO: 25 or an amino acid sequence having 70% or higher identity to the amino acid sequence as shown in SEQ ID NO: 25, an eighth adenylation domain comprising the amino acid sequence as shown in SEQ ID NO: 26 or an amino acid sequence having 70% or higher identity to the amino acid sequence as shown in SEQ ID NO: 26, and an eighth peptidyl carrier protein domain comprising the amino acid sequence as shown in SEQ ID NO: 27 or an amino acid sequence having 70% or higher identity to the amino acid sequence as shown in SEQ ID NO: 27;

a ninth module comprising successively from the N terminus an eighth condensation domain comprising the amino acid sequence as shown in SEQ ID NO: 28 or an amino acid sequence having 70% or higher identity to the amino acid sequence as shown in SEQ ID NO: 28, a ninth adenylation domain comprising the amino acid sequence as shown in SEQ ID NO: 29 or an amino acid sequence having 70% or higher identity to the amino acid sequence as shown in SEQ ID NO: 29, a fifth N-methyl transferase domain comprising the amino acid sequence as shown in SEQ ID NO: 30 or an amino acid sequence having 70% or higher identity to the amino acid sequence as shown in SEQ ID NO: 30, and a ninth peptidyl carrier protein domain comprising the amino acid sequence as shown in SEQ ID NO: 31 or an amino acid sequence having 70% or higher identity to the amino acid sequence as shown in SEQ ID NO: 31; and a tenth module comprising successively from the N terminus a ninth condensation domain comprising the amino acid sequence as shown in SEQ ID NO: 32 or an amino acid sequence having 70% or higher identity to the amino acid sequence as shown in SEQ ID NO: 32, a tenth adenylation domain comprising the amino acid sequence as shown in SEQ ID NO: 33 or an amino acid sequence having 70% or higher identity to the amino acid sequence as shown in SEQ ID NO: 33, a tenth peptidyl carrier protein domain comprising the amino acid sequence as shown in SEQ ID NO: 34 or an amino acid sequence having 70% or higher identity to the amino acid sequence as shown in SEQ ID NO: 34, and a tenth condensation domain comprising the amino acid sequence as shown in SEQ ID NO: 35 or an amino acid sequence having 70% or higher identity to the amino acid sequence as shown in SEQ ID NO: 35.

(2) The gene involved in the synthesis of a cyclic peptide compound according to (1), wherein the protein is any of the proteins (a) to (c) below:

(a) a protein comprising the amino acid sequence as shown in SEQ ID NO: 37;

(b) a protein comprising an amino acid sequence having 70% or higher identity to the amino acid sequence as shown in SEQ ID NO: 37 and having activity of synthesizing a nonribosomal peptide of a cyclic peptide compound produced by a filamentous fungus of the *Curvularia* species; and (c) a protein encoded by a polynucleotide hybridizing under stringent conditions to a complementary strand of the nucleotide sequence as shown in SEQ ID NO: 36 and having activity of synthesizing a nonribosomal peptide of a cyclic peptide compound produced by a filamentous fungus of the *Curvularia* species.

(3) The gene involved in the synthesis of a cyclic peptide compound according to (1), which is derived from a filamentous fungus of the *Curvularia* species.

(4) The gene involved in the synthesis of a cyclic peptide compound according to (3), wherein the filamentous fungus is *Curvularia clavata*.

(5) A gene involved in the synthesis of a cyclic peptide compound encoding any of proteins (a) to (c) below:

(a) a protein comprising the amino acid sequence as shown in SEQ ID NO: 39;

(b) a protein comprising an amino acid sequence having 70% or higher identity to the amino acid sequence as shown in SEQ ID NO: 39 and having transcription factor activity; and (c) a protein encoded by a polynucleotide hybridizing under stringent conditions to a complementary strand of the nucleotide sequence as shown in SEQ ID NO: 38 and having transcription factor activity.

(6) The gene involved in the synthesis of a cyclic peptide compound according to (5), which is derived from a filamentous fungus of the *Curvularia* species.

(7) The gene involved in the synthesis of a cyclic peptide compound according to (6), wherein the filamentous fungus is *Curvularia clavata*.

(8) A method for producing a cyclic peptide compound, wherein the compound is produced by a filamentous fungus of the *Curvularia* species, comprising:

a step of culturing a transformant into which the gene involved in the synthesis of a cyclic peptide compound according to any of (1) to (4) and a group of genes involved in the production of a cyclic peptide compound in a filamentous fungus of the *Curvularia* species; and a step of collecting the cyclic peptide compound from the cultured transformant and/or culture solution.

(9) The method for producing a cyclic peptide compound according to (8), wherein the group of genes includes genes [1] to [7] below:

[1] a gene encoding a protein comprising the amino acid sequence as shown in SEQ ID NO: 41 or an amino acid sequence having 70% or higher identity to the amino acid sequence as shown in SEQ ID NO: 41;

[2] a gene encoding a protein comprising the amino acid sequence as shown in SEQ ID NO: 43 or an amino acid sequence having 70% or higher identity to the amino acid sequence as shown in SEQ ID NO: 43;

[3] a gene encoding a protein comprising the amino acid sequence as shown in SEQ ID NO: 45 or an amino acid sequence having 70% or higher identity to the amino acid sequence as shown in SEQ ID NO: 45;

[4] a gene encoding a protein comprising the amino acid sequence as shown in SEQ ID NO: 47 or an amino acid sequence having 70% or higher identity to the amino acid sequence as shown in SEQ ID NO: 47;

[5] a gene encoding a protein comprising the amino acid sequence as shown in SEQ ID NO: 49 or an amino acid sequence having 70% or higher identity to the amino acid sequence as shown in SEQ ID NO: 49;

[6] a gene encoding a protein comprising the amino acid sequence as shown in SEQ ID NO: 51 or an amino acid sequence having 70% or higher identity to the amino acid sequence as shown in SEQ ID NO: 51; and

[7] a gene encoding a protein comprising the amino acid sequence as shown in SEQ ID NO: 53 or an amino acid sequence having 70% or higher identity to the amino acid sequence as shown in SEQ ID NO: 53.

(10) The method for producing a cyclic peptide compound according to (8), wherein the transformant is obtained by using *Aspergillus oryzae* as a host.

(11) A transformant into which the gene involved in the synthesis of a cyclic peptide compound according to any of (1) to (4) and a group of genes involved in the production of a cyclic peptide compound in a filamentous fungus of the *Curvularia* species have been introduced.

(12) The transformant according to (11), wherein the group of genes includes genes [1] to [7] below:

[1] a gene encoding a protein comprising the amino acid sequence as shown in SEQ ID NO: 41 or an amino acid sequence having 70% or higher identity to the amino acid sequence as shown in SEQ ID NO: 41;

[2] a gene encoding a protein comprising the amino acid sequence as shown in SEQ ID NO: 43 or an amino acid sequence having 70% or higher identity to the amino acid sequence as shown in SEQ ID NO: 43;

[3] a gene encoding a protein comprising the amino acid sequence as shown in SEQ ID NO: 45 or an amino acid sequence having 70% or higher identity to the amino acid sequence as shown in SEQ ID NO: 45;

[4] a gene encoding a protein comprising the amino acid sequence as shown in SEQ ID NO: 47 or an amino acid sequence having 70% or higher identity to the amino acid sequence as shown in SEQ ID NO: 47;

[5] a gene encoding a protein comprising the amino acid sequence as shown in SEQ ID NO: 49 or an amino acid sequence having 70% or higher identity to the amino acid sequence as shown in SEQ ID NO: 49;

[6] a gene encoding a protein comprising the amino acid sequence as shown in SEQ ID NO: 51 or an amino acid sequence having 70% or higher identity to the amino acid sequence as shown in SEQ ID NO: 51; and

[7] a gene encoding a protein comprising the amino acid sequence as shown in SEQ ID NO: 53 or an amino acid sequence having 70% or higher identity to the amino acid sequence as shown in SEQ ID NO: 53.

(13) The transformant according to (11), which is obtained by using *Aspergillus oryzae* as a host.

(14) A filamentous fungus of the *Curvularia* species comprising the gene involved in the synthesis of a cyclic peptide compound according to any of (1) to (4) above.

(15) The filamentous fungus of the *Curvularia* species according to (14), which is *Curvularia clavata*.

(16) The filamentous fungus of the *Curvularia* species according to (14), which is under Accession Number NITE BP-02399.

Effects of the Invention

The present invention can provide a gene encoding a nonribosomal peptide synthetase involved in the synthesis of a cyclic peptide compound produced by a filamentous fungus of the *Curvularia* species and a group of genes involved in the synthesis of other cyclic peptide compounds. With the use of the gene involved in the synthesis of a cyclic peptide compound according to the present invention, a system for synthesizing a cyclic peptide compound produced by a filamentous fungus of the *Curvularia* species can be constructed, and such cyclic peptide compound can be produced with high efficiency.

BRIEF DESCRIPTION OF THE DRAWINGS

FIG. 1 schematically shows module structures and domain structures of the gene involved in the synthesis of a cyclic peptide compound according to the present invention.

FIG. 2 shows the structure of the cyclic peptide compound produced by the *C. clavata* BAUA-2787 strain.

FIG. 3-1 shows the results of antiSMASH analysis of the NRPS domain structure deduced in the examples using the InterProScan and anti SMASH programs.

FIG. 3-2 shows the results of antiSMASH analysis of the NRPS domain structure deduced in the examples using the InterProScan and anti SMASH programs.

FIG. 4 shows the results of blastp search of the genes located upstream and downstream of the NRPS gene (TRAF01000135000001_J3G).

FIG. 5 shows a region deduced as the KK-1 biosynthetic gene cluster.

FIG. 6 shows a characteristic diagram demonstrating the results of MIDDAS-M cluster detection based on gene expression under KK-1-producing and non-producing conditions.

FIG. 7 schematically shows a construct achieving high-level expression of a transcription factor gene (the TF068-005 gene).

FIG. 8 shows a characteristic diagram demonstrating the results of inspection of the transcription level of genes constituting the KK-1 biosynthetic gene cluster when wild-type strains and strains achieving high-level expression of transcription factor genes are cultured under "Culture 1" conditions.

FIG. 9 shows characteristic diagrams demonstrating the results of inspection of the transcription level of genes constituting the KK-1 biosynthetic gene cluster when wild-type strains and strains achieving high-level expression of transcription factor genes are cultured under "Culture 2" conditions.

FIG. 10 shows characteristic diagrams demonstrating the results of inspection of the levels of KK-1 production of wild-type strains and strains achieving high-level expression of transcription factor genes outside and inside the cells at 3 days and 7 days after the initiation of culture.

FIG. 11 shows characteristic diagrams demonstrating the results of inspection of the KK-1 production level when wild-type strains and strains achieving high-level expression of transcription factor genes are cultured under "Culture 3" conditions and a state of the solid culture thereof.

FIG. 12 schematically shows constitution of a plasmid for CcpyrG gene deletion.

FIG. 13 schematically shows a construct for deleting a transcription factor gene (the TF068-005 gene).

FIG. 14 shows an electrophoretic pattern of the upstream region of the TF068-005 gene amplified via PCR, the downstream region thereof, and the selection marker gene pyrG.

FIG. 15 schematically shows a method for transforming the CcpyrG gene-deleted strain with the aid of the TF068-005 gene-deleted construct.

FIG. 16 shows characteristic diagrams showing the results of antibacterial activity tests performed on the transcription factor gene (the TF068-005 gene)-deleted strains and wild-type strains.

FIG. 17 shows characteristic diagrams showing the results of comprehensive gene expression analysis (RNA-seq) performed on the transcription factor gene (the TF068-005 gene)-deleted strain.

FIG. 18 shows a characteristic diagram showing the results of analysis of the KK-1 production level performed on the transcription factor gene (the TF068-005 gene)-deleted strain.

FIG. 19 schematically shows a gene-deleted construct prepared for each gene included in the KK-1 biosynthetic gene cluster.

FIG. 20 schematically shows a method for transforming the CcpyrG gene-deleted strain with a gene-deleted construct prepared for each gene included in the KK-1 biosynthetic gene cluster.

FIG. 21 shows a characteristic diagram showing the results of inspection of KK-1 productivity of gene-deleted strains and transcription factor gene-deleted strains.

FIG. 22 schematically shows a scheme for constructing a vector used when introducing the KK-1 biosynthetic gene cluster.

FIG. 23 schematically shows a scheme for introducing the front half portion and the rear half portion of the NRPS gene using the Cre-loxP system in two steps.

FIG. 24 schematically shows a scheme for simultaneously introducing three types of vectors carrying 7 genes after the front half portion and the rear half portion of the NRPS gene are introduced in two steps.

FIG. 25 shows a characteristic diagram demonstrating the results of analysis via quantitative real-time PCR of the expression levels of the introduced genes in *Aspergillus oryzae* into which the KK-1 biosynthetic gene cluster had been introduced.

FIG. 26 shows characteristic diagrams demonstrating the results of LC/MS analysis of KK-1 in *Aspergillus oryzae* into which the KK-1 biosynthetic gene cluster had been introduced and the results of antibacterial activity test against the *Aspergillus oryzae*.

EMBODIMENTS FOR CARRYING OUT THE INVENTION

Hereafter, the present invention is described in detail.

According to the present invention, the term "the gene involved in the synthesis of a cyclic peptide compound" refers to each gene included in the group of genes (i.e., a gene cluster) involved in the synthesis of a cyclic peptide compound produced by a filamentous fungus of the *Curvularia* species. Such cyclic peptide compound is represented by the chemical formula shown below, as disclosed in JP H8-504165 A (1996) (or WO 93/12659):

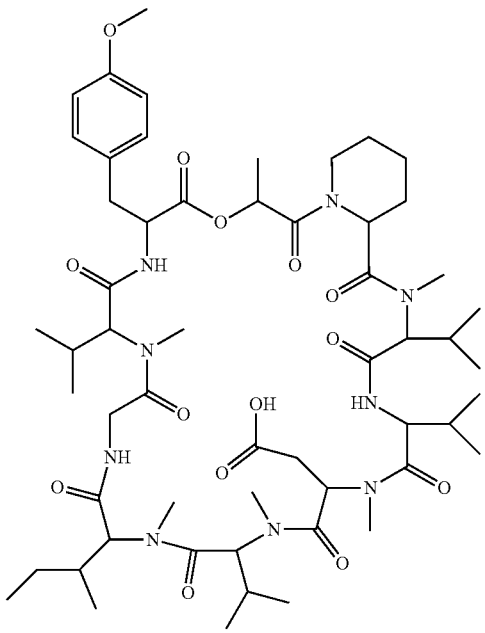 [SMILES: CCC(C)C1C(=O)NCC(=O)N(C)C(C(C)C)C(=O)NC(Cc2ccc(OC)cc2)C(=O)OC(C)C(=O)N2CCCCC2C(=O)N(C)C(C(C)C)C(=O)NC(C(C)C)C(=O)N(C)C(CC(=O)O)C(=O)N(C)C(C(C)C)C(=O)N1C]

wherein each amino acid residue and lactate residue can independently be in an L-form or D-form.

The name of the cyclic peptide compound (hereafter, it is occasionally referred to as "KK-1") is Tyrosine, N-[N-[N-[N-[N-[N-[N-[N-[[1-(2-hydroxy-1-oxopropyl)-2-piperidinyl]carbonyl]-N-methylvalyl]valyl]-N-methyl-a-aspartyl]-N-methylvalyl]-N-methylisoleucyl]glycyl]-N-methylvalyl]-O-methyl-, d2-lactone (9CI).

A representative example of a filamentous fungus of the Curvularia species producing such cyclic peptide compound is Curvularia clavata and other examples include C. affinis, C. brachyspora, C. caricae-papayae, C. eragrostidis (Cochliobolus eragrostidis), C. fallax, C. geniculata (Cochliobolus geniculatus), C. harveyi, C. lunata (Cochliobolus lunatus), C. ovoidea, C. pallescens, C. penniseti, C. prasadii, C. protuberata, C. senegalensis, C. trifolii, and C. tuberculata (Cochliobolus tuberculatus). An example of Curvularia clavata is the Curvularia clavata BAUA-2787 strain provided by Akita Konno Co., Ltd. The Curvularia clavata BAUA-2787 strain was deposited at Patent Microorganisms Depositary (NPMD), National Institute of Technology and Evaluation (NITE), #122, 2-5-8 Kazusakamatari, Kisarazushi, Chiba 292-0818 Japan as of Dec. 28, 2016 under the accession number NITE BP-02399.

As described in the examples below, a group of genes involved in the synthesis of the cyclic peptide compound can be defined as a group of genes including 10 types of genes, and preferably 9 types of genes.

These 10 types of genes are the O-methyltransferase gene, the nonribosomal peptide synthetase gene (the NRPS gene), the amidase gene, genes whose functions remain unknown (2 types), the transcription factor gene, the pmd1 gene encoding the leptomycin B-tolerant protein, the pyroline-5-carboxylate reductase-like gene, and the α/β hydrolase gene. Among such 10 types of genes, in particular, the O-methyltransferase gene, the nonribosomal peptide synthetase gene (the NRPS gene), the amidase gene, a gene whose functions remain unknown (1 type), the transcription factor gene, the pmd1 gene encoding the leptomycin B-tolerant protein, the pyroline-5-carboxylate reductase-like gene, and the α/β hydrolase gene can be defined as a group of genes that are strongly involved in the synthesis of a cyclic peptide compound.

NRPS Genes

Among the group of genes described above, the NRPS gene encodes NRPS having functions of forming a basic backbone of the cyclic peptide compound. Specifically, such NRPS forms a peptide backbone composed of 10 amino acids; that is, alanine (Ala)-pipecolic acid (Pip)-valine (Val)-valine-aspartic acid (Asp)-valine-isoleucine (Ile)-glycine (Gly)-valine-tyrosine (Tyr). More specifically, such NRPS has activity of forming peptide bonds between a carboxyl group of alanine and an amino group of pipecolic acid; between a carboxyl group of the pipecolic acid and an amino group of valine; between a carboxyl group of the valine and an amino group of valine; between a carboxyl group of the valine and an amino group of aspartic acid; between a carboxyl group of the aspartic acid and an amino group of valine; between a carboxyl group of the valine and an amino group of isoleucine; between a carboxyl group of the isoleucine and an amino group of glycine; between a carboxyl group of the glycine and an amino group of valine; between a carboxyl group of the valine and an amino group of tyrosine; and between a carboxyl group of the tyrosine and an amino group of the above alanine. Also, the NRPS has activity of methylating peptide bonds between pipecolic acid and valine; between valine and aspartic acid; between aspartic acid and valine; between valine and isoleucine; and between glycine and valine The NRPS comprises 10 modules corresponding to 10 amino acids constituting the basic peptide backbone describe above (i.e., alanine-pipecolic acid-valine-valine-aspartic acid-valine-isoleucine-glycine-valine-tyrosine). Each module comprises an adenylation domain (an A domain) that incorporates a target amino acid and binds adenosine monophosphate (AMP) to the amino acid, so as to synthesize aminoacyl AMP. Also, each module comprises a peptidyl carrier protein (PCP) domain having phosphopantetheine that binds the aminoacyl AMP with the aid of thioester formed between the serine site of phosphopantetheine and the aminoacyl AMP. In addition, each module comprises a condensation domain (a C domain) that forms a peptide bond between aminoacyl AMPs bound to the adjacent PCP domain. Further, some modules comprise an N-methyltransferase (nMT) domain that methylates a formed peptide bond.

As shown in FIG. 1, NRPS having the activity described above is composed of the first to the tenth modules. The positions of the modules in NRPS correspond to the positions of amino acids constituting the synthesized peptide backbone. Also, the positions of modules comprising the nMT domains correspond to the positions of N-methylated peptide bonds.

The first module comprises successively from the N terminus a first A domain comprising the amino acid sequence as shown in SEQ ID NO: 1 and a first PCP domain comprising the amino acid sequence as shown in SEQ ID NO: 2. In the first module, amino acid sequences constituting the first A domain and the first PCP domain are not limited to the amino acid sequences as shown in SEQ ID NOs: 1 and 2, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 1 and 2 may be sufficient if such sequences function as the A domain and the PCP domain, respectively.

The second module comprises successively from the N terminus a first C domain comprising the amino acid sequence as shown in SEQ ID NO: 3, a second A domain comprising the amino acid sequence as shown in SEQ ID NO: 4, and a second PCP domain comprising the amino acid sequence as shown in SEQ ID NO: 5. In the second module, amino acid sequences constituting the first C domain, the second A domain, and the second PCP domain are not limited to the amino acid sequences as shown in SEQ ID NOs: 3, 4, and 5, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 3, 4, and 5 may be sufficient if such sequences function as the C domain, the A domain, and the PCP domain, respectively.

The third module comprises successively from the N terminus a second C domain comprising the amino acid sequence as shown in SEQ ID NO: 6, a third A domain comprising the amino acid sequence as shown in SEQ ID NO: 7, a first nMT domain comprising the amino acid sequence as shown in SEQ ID NO: 8, and a third PCP domain comprising the amino acid sequence as shown in SEQ ID NO: 9. In the third module, amino acid sequences constituting the second C domain, the third A domain, the first nMT domain, and the third PCP domain are not limited to the amino acid sequences as shown in SEQ ID NOs: 6, 7, 8, and 9, respectively. Amino acid sequences having identity of 70% or higher, preferably 80% or higher, more preferably 90% or higher, further preferably 95% or higher, and most preferably 97% or higher to the amino acid sequences as shown in SEQ ID NO: 6, 7, 8, and 9 may be sufficient if such sequences function as the C domain, the A domain, the nMT domain, and the PCP domain, respectively.

The fourth module comprises successively from the N terminus a third C domain comprising the amino acid sequence as shown in SEQ ID NO: 10, a fourth A domain comprising the amino acid sequence as shown in SEQ ID NO: 11, and a fourth PCP domain comprising the amino acid sequence as shown in SEQ ID NO: 12. In the fourth module, amino acid sequences constituting the third C domain, the fourth A domain, and the fourth PCP domain are not limited to the amino acid sequences as shown in SEQ ID NO: 10, 11, and 12, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 10, 11, and 12 may be sufficient if such sequences function as the C domain, the A domain, and the PCP domain, respectively.

The fifth module comprises successively from the N terminus a fourth C domain comprising the amino acid sequence as shown in SEQ ID NO: 13, a fifth A domain comprising the amino acid sequence as shown in SEQ ID NO: 14, a second nMT domain comprising the amino acid sequence as shown in SEQ ID NO: 15, and a fifth PCP domain comprising the amino acid sequence as shown in SEQ ID NO: 16. In the fifth module, amino acid sequences constituting the fourth C domain, the fifth A domain, the second nMT domain, and the fifth PCP domain are not limited to the amino acid sequences as shown in SEQ ID NOs: 13, 14, 15, and 16, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 13, 14, 15, and 16 may be sufficient if such sequences function as the C domain, the A domain, the nMT domain, and the PCP domain, respectively.

The sixth module comprises successively from the N terminus a fifth C domain comprising the amino acid sequence as shown in SEQ ID NO: 17, a sixth A domain comprising the amino acid sequence as shown in SEQ ID NO: 18, a third nMT domain comprising the amino acid sequence as shown in SEQ ID NO: 19, and a sixth PCP domain comprising the amino acid sequence as shown in SEQ ID NO: 20. In the sixth module, amino acid sequences constituting the fifth C domain, the sixth A domain, the third nMT domain, and the sixth PCP domain are not limited to the amino acid sequences as shown in SEQ ID NOs: 17, 18, 19, and 20, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 17, 18, 19, and 20 may be sufficient if such sequences function as the C domain, the A domain, the nMT domain, and the PCP domain, respectively.

The seventh module comprises successively from the N terminus a sixth C domain comprising the amino acid sequence as shown in SEQ ID NO: 21, a seventh A domain comprising the amino acid sequence as shown in SEQ ID NO: 22, a fourth nMT domain comprising the amino acid sequence as shown in SEQ ID NO: 23, and a seventh PCP domain comprising the amino acid sequence as shown in SEQ ID NO: 24. In the seventh module, amino acid sequences constituting the sixth C domain, the seventh A domain, the fourth nMT domain, and the seventh PCP domain are not limited to the amino acid sequences as shown in SEQ ID NOs: 21, 22, 23, and 24, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 21, 22, 23, and 24 may be sufficient if such sequences function as the C domain, the A domain, the nMT domain, and the PCP domain, respectively.

The eighth module comprises successively from the N terminus a seventh C domain comprising the amino acid sequence as shown in SEQ ID NO: 25, an eighth A domain comprising the amino acid sequence as shown in SEQ ID NO: 26, and an eighth PCP domain comprising the amino acid sequence as shown in SEQ ID NO: 27. In the eighth module, amino acid sequences constituting the seventh C domain, the eighth A domain, and the eighth PCP domain are not limited to the amino acid sequences as shown in SEQ ID NOs: 25, 26, and 27, respectively. Amino acid sequences having identity of 70% or higher, preferably 80% or higher, more preferably 90% or higher, further preferably 95% or higher, and most preferably 97% or higher to the amino acid sequences as shown in SEQ ID NO: 25, 26, and 27 may be sufficient if such sequences function as the C domain, the A domain, and the PCP domain, respectively.

The ninth module comprises successively from the N terminus an eighth C domain comprising the amino acid sequence as shown in SEQ ID NO: 28, a ninth A domain comprising the amino acid sequence as shown in SEQ ID NO: 29, a fifth nMT domain comprising the amino acid sequence as shown in SEQ ID NO: 30, and a ninth PCP domain comprising the amino acid sequence as shown in SEQ ID NO: 31. In the ninth module, amino acid sequences constituting the eighth C domain, the ninth A domain, the fifth nMT domain, and the ninth PCP domain are not limited to the amino acid sequences as shown in SEQ ID NOs: 28, 29, 30, and 31, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 28, 29, 30, and 31 may be sufficient if such sequences function as the C domain, the A domain, the nMT domain, and the PCP domain, respectively.

The tenth module comprises successively from the N terminus a ninth C domain comprising the amino acid sequence as shown in SEQ ID NO: 32, a tenth A domain comprising the amino acid sequence as shown in SEQ ID NO: 33, a tenth PCP domain comprising the amino acid sequence as shown in SEQ ID NO: 34, and a tenth C domain comprising the amino acid sequence as shown in SEQ ID NO: 35. In the tenth module, amino acid sequences constituting the ninth C domain, the tenth A domain, the tenth PCP domain, and the tenth C domain are not limited to the amino acid sequences as shown in SEQ ID NOs: 32, 33, 34, and 35, respectively. Amino acid sequences having identity of 70% or higher, preferably 80% or higher, more preferably 90% or higher, further preferably 95% or higher, and most preferably 97% or higher to the amino acid sequences as shown in SEQ ID NOs: 32, 33, 34, and 35 may be sufficient if such sequences function as the C domain, the A domain, the PCP domain, and the C domain, respectively.

When the first A domain does not comprise the amino acid sequence as shown in SEQ ID NO: 1, whether or not it can function as the A domain corresponding to alanine can be evaluated in the manner described below. At the outset, a mutant NRPS gene is designed to encode a first mutant A domain that is designed to comprise a sequence different from the amino acid sequence as shown in SEQ ID NO: 1. The resulting mutant NRPS gene is allowed to express in an adequate host, and whether or not a compound comprising a basic peptide backbone of the cyclic peptide compound is synthesized in the host and in metabolites in the culture supernatant is inspected. When a compound comprising a basic peptide backbone of the cyclic peptide compound is synthesized in the metabolite, the designed first mutant A domain can be evaluated as functioning as the A domain corresponding to alanine. When the second to the tenth A domains comprise amino acid sequences different from the amino acid sequences as shown in SEQ ID NOs: 4, 7, 11, 14, 18, 22, 26, 29, and 33, respectively, whether or not such domains can function as the A domains can be evaluated in the same manner.

When the first PCP domain does not comprise the amino acid sequence as shown in SEQ ID NO: 2, whether or not it can function as the PCP domain can be evaluated in the manner described below. At the outset, a mutant NRPS gene is designed to encode a first mutant PCP domain that is designed to comprise a sequence different from the amino acid sequence as shown in SEQ ID NO: 2. The resulting mutant NRPS gene is allowed to express in an adequate host, and whether or not a compound comprising a basic peptide backbone of the cyclic peptide compound is synthesized in the host or in metabolites in the culture supernatant is inspected. When a compound comprising a basic peptide backbone of the cyclic peptide compound is synthesized in the metabolite, the designed first mutant PCP domain can be evaluated as functioning as the PCP domain. When the second to the tenth PCP domains comprise amino acid sequences different from the amino acid sequences as shown in SEQ ID NOs: 5, 9, 12, 16, 20, 24, 27, 31, and 34, respectively, whether or not such domains can each function as the PCP domain can be evaluated in the same manner.

When the first C domain does not comprise the amino acid sequence as shown in SEQ ID NO: 3, whether or not it can function as the C domain can be evaluated in the manner described below. At the outset, a mutant NRPS gene is designed to encode a first mutant C domain that is designed to comprise a sequence different from the amino acid sequence as shown in SEQ ID NO: 3. The resulting mutant NRPS gene is allowed to express in an adequate host, and whether or not a compound comprising a basic peptide backbone of the cyclic peptide compound is synthesized in the host or in metabolites in the culture supernatant is inspected. When a compound comprising a basic peptide backbone of the cyclic peptide compound is synthesized in the metabolite, the designed first mutant C domain can be evaluated as functioning as the C domain. When the second to the tenth C domains comprise amino acid sequences different from the amino acid sequences as shown in SEQ ID NOs: 6, 10, 13, 17, 21, 25, 28, 32, and 35, respectively, whether or not such domains can function as the C domains can be evaluated in the same manner.

When the first nMT domain does not comprise the amino acid sequence as shown in SEQ ID NO: 8, whether or not it can function as the nMT domain can be evaluated in the manner described below. At the outset, a mutant NRPS gene is designed to encode the first mutant nMT domain that is designed to comprise a sequence different from the amino acid sequence as shown in SEQ ID NO: 8. The resulting mutant NRPS gene is allowed to express in an adequate host, and whether or not a compound comprising a basic peptide backbone of the cyclic peptide compound is synthesized in the host or in metabolites in the culture supernatant is inspected. When a compound comprising a basic peptide backbone of the cyclic peptide compound is synthesized in the metabolite, the designed first mutant nMT domain can be evaluated as functioning as the nMT domain. When the second to the fifth nMT domains comprise amino acid sequences different from the amino acid sequences as shown in SEQ ID NOs: 15, 19, 23, and 30, respectively, whether or not such domains can function as the nMT domains can be evaluated in the same manner.

As described above, NRPS that synthesizes the basic peptide backbone of the cyclic peptide compound can be defined with the first module to the tenth module. For example, SEQ ID NO: 37 shows the amino acid sequence of NRPS derived from *Curvularia clavata* and having activity of synthesizing a basic peptide backbone of the cyclic peptide compound, and SEQ ID NO: 36 shows the nucleotide sequence of a coding region corresponding to the amino acid sequence as shown in SEQ ID NO: 37.

Accordingly, the NRPS gene of the present invention comprises the first module to the tenth module defined by the amino acid sequences as shown in SEQ ID NOs: 1 to 35, and it may encode a protein comprising an amino acid sequence having identity of 70% or higher, preferably 80% or higher, more preferably 90% or higher, further preferably 95% or higher, and most preferably 97% or higher to the amino acid sequence as shown in SEQ ID NO: 37 and having activity of synthesizing a basic peptide backbone of the cyclic peptide compound. The value of identity between amino acid sequences can be calculated based on default setting using the BLASTN or BLASTX program equipped with the BLAST algorithm. Specifically, the value of identity is determined by calculating the number of amino acid residues that completely match the others when a pairwise alignment analysis is conducted for a pair of amino acid sequences and then determining the proportion of the number of such residues in all the amino acid residues compared.

The NRPS gene of the present invention may comprise the first module to the tenth module defined by the amino acid sequences as shown in SEQ ID NOs: 1 to 35, and it may encode a protein comprising an amino acid sequence derived from the amino acid sequence as shown in SEQ ID NO: 37 by substitution, deletion, addition, or insertion of 1 or several amino acids and having activity of synthesizing a basic peptide backbone in the cyclic peptide compound. The term "several" used herein refers to, for example, 2 to 1300, preferably 2 to 1000, more preferably 2 to 700, still more preferably 2 to 500, further preferably 2 to 250, more further preferably 2 to 100, and still further preferably 2 to 50, respectively.

In addition, the NRPS gene of the present invention may comprise the first module to the tenth module defined by the amino acid sequences as shown in SEQ ID NOs: 1 to 35, it may hybridize under stringent conditions to all or a part of a complementary strand of DNA comprising the nucleotide sequence as shown in SEQ ID NO: 36, and it may encode a protein having activity of synthesizing a basic peptide backbone of the cyclic peptide compound. Under "stringent conditions," a so-called specific hybrid is formed, but a non-specific hybrid is not formed. For example, such conditions can be adequately determined with reference to the Molecular Cloning: A Laboratory Manual (Third Edition). Specifically, stringency can be set based on the temperature and the concentration of salts contained in a solution for southern hybridization, and the temperature and the concentration of salts contained in a solution for a washing step of southern hybridization. Under stringent conditions, more precisely, sodium concentration is, for example, the sodium concentration of 25 to 500 mM, and preferably 25 to 300 mM, and the temperature is 42° C. to 68° C., and preferably 42° C. to 65° C. Further specifically, sodium concentration is 5×SSC (83 mM NaCl, 83 mM sodium citrate), and the temperature is 42° C.

The NRPS gene of the present invention is not limited to the gene encoding a protein comprising the first module to the tenth module defined by the amino acid sequences as shown in SEQ ID NOs: 1 to 35. As described above, SEQ ID NO: 37 shows the amino acid sequence of NRPS derived from *Curvularia clavata* and having activity of synthesizing a basic peptide backbone of the cyclic peptide compound, and SEQ ID NO: 36 shows the nucleotide sequence of a coding region corresponding to the amino acid sequence as shown in SEQ ID NO: 37. The NRPS gene of the present invention can also be defined by SEQ ID NOs: 36 and 37.

Specifically, the NRPS gene of the present invention can be a gene encoding the protein comprising the amino acid sequence as shown in SEQ ID NO: 37.

The NRPS gene of the present invention may be a gene that encodes a protein comprising an amino acid sequence having identity of 70% or higher, preferably 80% or higher, more preferably 90% or higher, further preferably 95% or higher, and most preferably 97% or higher to the amino acid sequence as shown in SEQ ID NO: 37 and having activity of synthesizing a basic peptide backbone of the cyclic peptide compound. The value of identity between amino acid sequences can be calculated based on default setting using the BLASTN or BLASTX program equipped with the BLAST algorithm as described above. Specifically, the value of identity is determined by calculating the number of amino acid residues that completely match the others when a pairwise alignment analysis is conducted for a pair of amino acid sequences and then determining the proportion of the number of such residues in all the amino acid residues compared.

With the use of known databases storing nucleotide sequence information, genes that satisfy the conditions such as a high coverage, a low E-value, and a high value of identity with the nucleotide sequence as shown in SEQ ID NO: 36 can be identified with regard to the NRPS gene of the present invention. The genes to be identified are expected to show a coverage of 90% or higher, preferably 95% or higher, and more preferably 99% or higher. Also, the genes to be identified are expected to show an E-value of 1.0e-5 or lower, preferably 1.0e-15 or lower, and more preferably 0.0. Further, the genes to be identified are expected to show a value of identity of 70% or higher, preferably 75% or higher, and more preferably 80% or higher. The gene identified to satisfy such conditions is highly likely to be homologous to the NRPS gene comprising the nucleotide sequence as shown in SEQ ID NO: 36, and such gene can be identified as a gene encoding a protein having activity of synthesizing a basic peptide backbone of the cyclic peptide compound as with the NRPS gene comprising the nucleotide sequence as shown in SEQ ID NO: 36.

Whether or not the identified gene encodes a protein having activity of synthesizing a basic peptide backbone of the cyclic peptide compound may be determined by obtaining microorganisms comprising such gene and examining the ability thereof to synthesize the cyclic peptide compound. The ability of the obtained microorganisms to synthesize the cyclic peptide compound can be examined by culturing the microorganisms and inspecting whether or not the cultured cells or the culture supernatant contains the cyclic peptide compound.

If the nucleotide sequence of the NRPS gene of the present invention is identified, the NRPS gene of interest can be prepared via chemical synthesis, PCR using the genomic DNA as a template, or hybridization involving the use of a DNA fragment comprising such nucleotide sequence as a probe. A gene comprising a nucleotide sequence different from SEQ ID NO: 36 or a gene encoding an amino acid sequence different from SEQ ID NO: 37 can be synthesized by subjecting a polynucleotide comprising the nucleotide sequence as shown in SEQ ID NO: 36 to site-directed mutagenesis. A mutation can be introduced into a polynucleotide comprising the nucleotide sequence as shown in SEQ ID NO: 36 by known techniques, such as the Kunkel's method or the Gapped duplex method, or techniques in accordance therewith. For example, mutagenesis can be carried out using a mutagenesis kit using site-directed mutagenesis (e.g., Mutant-K (Takara Bio Inc.) and Mutant-G (Takara Bio Inc.)) or a LA PCR in vitro Mutagenesis series kit (Takara Bio Inc.).

In particular, the NRPS gene of the present invention can be isolated from microorganisms known to produce the cyclic peptide compound. An example is the NRPS gene (i.e., the NRPS gene encoding the amino acid sequence as shown in SEQ ID NO: 37) isolated from *Curvularia clavata*.

The NRPS gene of the present invention is highly likely to be isolated from a filamentous fungus of the *Curvularia* species other than *Curvularia clavata* with the use of the nucleotide sequence as shown in SEQ ID NO: 36. Specifically, hybridization may be carried out with the use of a polynucleotide comprising continuous nucleotides that constitutes a part of the nucleotide sequence as shown in SEQ ID NO: 36 as a probe, so that the NRPS gene of the present invention can be isolated from the genome of a filamentous fungus of the *Curvularia* species other than *Curvularia clavata* or from cDNA derived from a transcription product. A filamentous fungus of the *Curvularia* species other than *Curvularia clavata* may or may not produce the cyclic peptide compound because a filamentous fungus of the *Curvularia* species that does not produce the cyclic peptide compound may comprise the NRPS gene of the present invention.

Examples of filamentous fungi of the *Curvularia* species other than *Curvularia clavata* include *C. affinis, C. brachyspora, C. caricae-papayae, C. eragrostidis* (*Cochliobolus eragrostidis* (Teleomorph)), *C. fallax, C. geniculata* (*Cochliobolus geniculatus* (Teleomorph)), *C. harveyi, C. lunata* (*Cochliobolus lunatus* (Teleomorph)), *C. ovoidea, C. pallescens, C. penniseti, C. prasadii, C. protuberata, C. senegalensis, C. trifolii,* and *C. tuberculata* (*Cochliobolus tuberculatus* (Teleomorph)).

Filamentous Fungi of the *Curvularia* Species

The filamentous fungus of the *Curvularia* species of the present invention comprises the NRPS gene described above. The NRPS gene of the present invention is highly likely to be isolated from a filamentous fungus of the *Curvularia* species other than *Curvularia clavata*, as described above. That is, the filamentous fungi of the *Curvularia* species of the present invention are not limited to *Curvularia clavata*, and examples thereof include *C. affinis, C. brachyspora, C. caricae-papayae, C. eragrostidis* (*Cochliobolus eragrostidis*), *C. fallax, C. geniculata* (*Cochliobolus geniculatus*), *C. harveyi, C. lunata* (*Cochliobolus lunatus*), *C. ovoidea, C. pallescens, C. penniseti, C. prasadii, C. protuberata, C. senegalensis, C. trifolii,* and *C. tuberculata* (*Cochliobolus tuberculatus*) producing cyclic peptide compounds.

The filamentous fungus of the *Curvularia* species of the present invention is particularly preferably *Curvularia clavata*. A specific example of the filamentous fungus of the *Curvularia* species of the present invention is the *Curvularia clavata* BAUA-2787 strain provided by Akita Konno Co., Ltd. The *Curvularia clavata* BAUA-2787 strain was deposited at Patent Microorganisms Depositary (NPMD), National Institute of Technology and Evaluation (NITE), #122, 2-5-8 Kazusakamatari, Kisarazu-shi, Chiba 292-0818 Japan as of Dec. 28, 2016 under the accession number NITE BP-02399.

Transcription Factor Gene

Transcription factor genes included in the group of genes involved in the synthesis of the cyclic peptide compound encode proteins capable of positively regulating the expression of the genes included in such group of genes at the level of transcription. An example of the transcription factor gene of the present invention is derived from *Curvularia clavata*. SEQ ID NO: 39 shows the amino acid sequence of a protein having transcription enhancing activity on a gene included in the group of genes involved in the synthesis of the cyclic peptide compound, and SEQ ID NO: 38 shows the nucleotide sequence of a coding region corresponding to such amino acid sequence. The transcription factor gene of the present invention can be defined with SEQ ID NOs: 38 and 39.

Specifically, the transcription factor gene of the present invention can be a gene encoding the protein comprising the amino acid sequence as shown in SEQ ID NO: 39.

The transcription factor gene of the present invention may be a gene encoding a protein comprising an amino acid sequence having identity of 70% or higher, preferably 80% or higher, more preferably 90% or higher, further preferably 95% or higher, and most preferably 97% or higher to the amino acid sequence as shown in SEQ ID NO: 39 and having the transcription enhancing activity described above. The value of identity between amino acid sequences can be calculated based on default setting using the BLASTN or BLASTX program equipped with the BLAST algorithm, as described above. Specifically, the value of identity is determined by calculating the number of amino acid residues that completely match the others when a pairwise alignment analysis is conducted for a pair of amino acid sequences and then determining the proportion of the number of such residues in all the amino acid residues compared.

The transcription factor gene of the present invention may encode a protein comprising an amino acid sequence derived from the amino acid sequence as shown in SEQ ID NO: 39 by substitution, deletion, addition, or insertion of 1 or several amino acids and having the transcription enhancing activity. The term "several" used herein refers to, for example, 2 to 40, preferably 2 to 30, more preferably 2 to 20, further preferably 2 to 10, and still further preferably 2 to 5, as described above.

The transcription factor gene of the present invention may hybridize under stringent conditions to all or a part of a complementary strand of DNA comprising the nucleotide sequence as shown in SEQ ID NO: 38 and encode a protein having the transcription enhancing activity. Under "stringent conditions," a so-called specific hybrid is formed, but a non-specific hybrid is not formed. For example, such conditions can be adequately determined with reference to the Molecular Cloning: A Laboratory Manual (Third Edition). Specifically, stringency can be set based on the temperature and the concentration of salts contained in a solution for southern hybridization, and the temperature and the concentration of salts contained in a solution for a washing step of southern hybridization. Under stringent conditions, more precisely, sodium concentration is, for example, 25 to 500 mM, and preferably 25 to 300 mM, and the temperature is 42° C. to 68° C., and preferably 42° C. to 65° C. Further specifically, sodium concentration is 5×SSC (83 mM NaCl, 83 mM sodium citrate), and the temperature is 42° C.

As described above, whether or not a gene comprising a nucleotide sequence different from SEQ ID NO: 38 or a gene encoding an amino acid sequence different from SEQ ID NO: 39 encodes a protein having the transcription enhancing activity can be determined by introducing the gene of interest into a host that produces the cyclic peptide compound (e.g., *Curvularia clavata*) in an expressible manner and examining the expression levels of the group of genes involved in the synthesis of the cyclic peptide compound in such host at the level of transcription.

If the nucleotide sequence of the transcription factor gene of the present invention is identified, the transcription factor gene of interest can be prepared via chemical synthesis, PCR using the genomic DNA as a template, or hybridization involving the use of a DNA fragment comprising such nucleotide sequence as a probe. A gene comprising a nucleotide sequence different from SEQ ID NO: 38 or a gene encoding an amino acid sequence different from SEQ ID NO: 39 can be synthesized by subjecting a polynucleotide comprising the nucleotide sequence as shown in SEQ ID NO: 38 to site-directed mutagenesis. A mutation can be introduced into a polynucleotide comprising the nucleotide sequence as shown in SEQ ID NO: 38 by known techniques, such as the Kunkel's method or the Gapped duplex method, or techniques in accordance therewith. For example, mutagenesis can be carried out using a mutagenesis kit using site-directed mutagenesis (e.g., Mutant-K (Takara Bio Inc.) and Mutant-G (Takara Bio Inc.)) or a LA PCR in vitro Mutagenesis series kit (Takara Bio Inc.).

In particular, the transcription factor gene of the present invention can be isolated from microorganisms known to produce the cyclic peptide compound. An example is the transcription factor gene (i.e., the transcription factor gene encoding the amino acid sequence as shown in SEQ ID NO: 39) isolated from *Curvularia clavata*.

The transcription factor gene of the present invention is highly likely to be isolated from a filamentous fungus of the *Curvularia* species other than *Curvularia clavata* with the use of the nucleotide sequence as shown in SEQ ID NO: 38. Specifically, hybridization may be carried out with the use of a polynucleotide comprising continuous nucleotides that constitutes a part of the nucleotide sequence as shown in SEQ ID NO: 38 as a probe, so that the transcription factor gene of the present invention can be isolated from the genome of a filamentous fungus of the *Curvularia* species other than *Curvularia clavata* or from cDNA derived from a transcription product. A filamentous fungus of the *Curvularia* species other than *Curvularia clavata* may or may not produce the cyclic peptide compound because a filamentous fungus of the *Curvularia* species that does not produce the NRPS gene of the present invention may comprise the NRPS gene of the present invention.

Examples of filamentous fungi of the *Curvularia* species other than *Curvularia clavata* include *C. affinis*, *C. brachyspora*, *C. caricae-papayae*, *C. eragrostidis* (*Cochliobolus eragrostidis* (Teleomorph)), *C. fallax*, *C. geniculata* (*Cochliobolus geniculatus* (Teleomorph)), *C. harveyi*, *C. lunata* (*Cochliobolus lunatus* (Teleomorph)), *C. ovoidea*, *C. pallescens*, *C. penniseti*, *C. prasadii*, *C. protuberata*, *C. senegalensis*, *C. trifolii*, and *C. tuberculata* (*Cochliobolus tuberculatus* (Teleomorph)).

Transformant

Among the genes involved in the synthesis of a cyclic peptide compound of the present invention, the NRPS gene is introduced into a host in an expressible manner, so that a transformant capable of synthesizing a compound comprising a basic peptide backbone of the cyclic peptide compound can be prepared. Also, genes capable of synthesizing a cyclic peptide compound other than the NRPS gene are introduced into a host in combination with the NRPS gene in an expressible manner, so that a transformant capable of synthesizing the cyclic peptide compound can be prepared.

When preparing a transformant capable of synthesizing the cyclic peptide compound, the transcription factor gene described above may or may not be introduced as a gene involved in the synthesis of a cyclic peptide compound other than the NRPS gene. For example, the NRPS gene and other genes may be introduced into a host in a position located downstream of a constitutive expression promoter capable of functioning in a host. Thus, such NRPS gene and other genes can be induced to be constitutively expressed. In such a case, genes involved in the synthesis of a cyclic peptide compound can be expressed without the introduction of the transcription factor gene, and the cyclic peptide compound can be prepared.

Any organisms and, in particular, any microorganisms, can serve as hosts without particular limitation. Examples of microorganisms that can be used as hosts include, but are not particularly limited to: bacteria of *Escherichia* such as *Escherichia coli*, *Coryncbacterium* such as *Corynebacterium glutamicum*, *Bacillus* such as *Bacillus subtilis*, *Pseudomonas* such as *Pseudomonas putida*, and *Rhizobium* such as *Rhizobium meliloti*; and mycetes including yeast and filamentous fungi, such as *Saccharomyces cerevisiae*, *Schizosaccharomyces pombe*, and *Pichia pastoris*.

When bacteria such as *E. coli* are hosts, the expression vector is preferably capable of autonomous replication in the bacteria, and it is preferably composed of a promoter, a ribosome-binding sequence, the gene described above, and a transcription terminator sequence. The expression vector may comprise a gene regulating promoter activity.

Any promoter may be used, provided that it can express a gene of interest in an *E. coli* or other host. For example, *E. coli*-derived promoters, such as trp promoter, lac promoter, PL promoter, and PR promoter, and phage-derived promoters, such as T7 promoter, may be used. An artificially designed or modified promoter, such as tac promoter, may also be used.

A method for introducing an expression vector is not particularly limited, provided that DNA is introduced into bacteria by such method. Examples include a method involving the use of calcium ions (Cohen, S. N., et al., Proc. Natl. Acad. Sci., U.S.A., 69: 2110-2114, 1972) and electroporation.

Examples of yeasts that can be used as hosts include, but are not particularly limited to, yeasts of *Candida* such as *Candida shehatae*, yeasts of *Pichia* such as *Pichia stipites*, yeasts of *Pachysolen* such as *Pachysolen tannophilus*, yeasts of *Saccharomyces* such as *Saccharomyces cerevisiae*, and yeasts of *Schizosaccharomyces* such as *Schizosaccharomyces pombe*, with *Saccharomyces cerevisiae* being preferable.

The expression levels of the NRPS gene and other genes are intensified with the use of an adequate promoter having high transcription activity. Examples of promoters that can be used include, but are not particularly limited to, the glyceraldehyde-3-phosphate dehydrogenase (TDH3) gene promoter, the 3-phosphoglycerate kinase (PGK1) gene promoter, and the hyperosmolarity-responsive 7 (HOR7) gene promoter. In particular, the pyruvate decarboxylase (PDC1) gene promoter is preferable because of a high capacity for achieving high-level expression of the target downstream genes. Alternatively, gal1 promoter, gal10 promoter, heat shock protein promoter, MFα1 promoter, PHOS promoter, GAP promoter, ADH promoter, AOX1 promoter, or the like may be used to allow forced expression of downstream genes.

Examples of filamentous fungi that can be used as hosts include, but are not particularly limited to: filamentous fungi of *Aspergillus*, such as *Aspergillus nidulans*, *Aspergillus niger*, *Aspergillus oryzae*, *Aspergillus sojae*, and *Aspergillus glaucus*; filamentous fungi of *Trichoderma*, such as *Trichoderma reesei* and *Trichoderma viride*; filamentous fungi of *Rhizomucor*, such as *Rhizomucor pusillus* and *Rhizomucor miehei*; filamentous fungi of *Penicillium*, such as *Penicillium notatum* and *Penicillium chrysogenum*; filamentous fungi of *Rhizopus*, such as *Rhizopus oryzae*; *Acremonium cellulolyticus*; *Humicola grisea*; and *Thermoaseus aurantiacus*. Specifically, hosts are preferably filamentous fungi of *Aspergillus* and particularly preferably *Aspergillus oryzae*.

The NRPS gene and other genes can be expressed in filamentous fungi with the use of, for example, α-amylase (amyB) gene promoter, α-glucosidase (agdA) gene promoter, glucoamylase (glaA) gene promoter, tryptophan biosynthesizing (trpC) gene promoter, alcohol dehydrogenase (alcA) gene promoter, translation elongation factor (tef1) promoter, triose-phosphate isomerase (tpiA) gene promoter, glyceraldehyde-3-phosphate dehydrogenase (gpdA) gene promoter, enolase (enoA) promoter, pyruvate carboxylase (pdcA) promoter, or cellobiohydrolase (cbh1) gene promoter.

Any conventional techniques known to transform yeasts and filamentous fungi can be employed as methods for introducing the genes described above. Specific examples thereof include transformation, transfection, conjugation, the protoplast method, the spheroplast method, electroporation, lipofection, and the lithium acetate method.

Production of Cyclic Peptide Compound

With the use of the transformant described above, the target cyclic peptide compound can be produced.

Among the genes involved in the synthesis of a cyclic peptide compound of the present invention, specifically, a transformant into which the NRPS gene has been introduced in an expressible manner is used. Thus, a compound comprising a basic peptide backbone of the cyclic peptide compound can be produced. For example, the cyclic peptide compound can be produced from a compound obtained via chemical synthesis. With the use of a transformant into which the NRPS gene and other genes have been introduced in an expressible manner, in addition, the cyclic peptide compound can be produced.

The cyclic peptide compound synthesized in a transformant or a compound comprising a basic peptide backbone thereof can be extracted from the culture supernatant by separating cells with the use of a centrifuge, Miracloth, or the like and adding an organic solvent such as ethyl acetate. The compound can be extracted from cells by releasing the compound extracellularly via physical disruption (e.g., homogenization, glass bead crushing, or freezing-thawing) or chemical disruption (e.g., treatment with a solvent, acid, base, osmotic pressure, or enzyme) and adding an organic solvent such as ethyl acetate. The extracted cyclic peptide compound or a compound comprising the basic peptide backbone thereof can be purified via a known purification technique (e.g., column chromatography or salt sedimentation). Such techniques can be employed in adequate combination, according to need.

The cyclic peptide compound produced as described above can be used as an antibacterial agent having bactericidal activity against, for example, plant pathogenic bacteria and, in particular, against fungi. When the cyclic peptide compound is used as an antibacterial agent, more specifically, such compound may be used in that state. In general, a solid carrier, liquid carrier, surfactant, or other adjuvant may be mixed with such compound to prepare an agent of any dosage form, such as an emulsion, EW agent, liquid preparation, suspension, wettable powder, granule wettable powder, powder, DL powder, microgranule powder, microgranule powder F, granule, tablet, oil, aero sol, flowable agent, dry flowable agent, or microcapsule.

Examples of solid carriers include animal- or plant-derived powders, such as starch, active carbon, soybean flour, wheat flour, wood flour, fish meal, and powdered milk, and inorganic powders, such as talc, kaolin, bentonite, calcium carbonate, zeolite, diatomaceous earth, white carbon, clay, alumina, ammonium sulfate, and urea.

Examples of liquid carriers include: water; an alcohol, such as isopropyl alcohol and ethylene glycol; a ketone, such as cyclohexane and methyl ethyl ketone; an ether, such as dioxane and tetrahydrofuran; an aliphatic hydrocarbon, such as kerosine and light oil; an aromatic hydrocarbon, such as xylene, trimethylbenzene, tetramethylbenzene, methylnaphthalin, and solvent naphtha; a halogenated hydrocarbon, such as chlorobenzene; an acid amide, such as dimethylacetamide; an ester, such as glycerin fatty acid ester; a nitrile, such as acetonitrile; and a sulfur-containing compound, such as dimethyl sulfoxide.

Examples of surfactants include metal salt of alkyl benzene sulfonic acid, metal salt of dinaphthylmethane disulfonic acid, alcohole-sulfate ester salt, alkyl aryl sulfonic acid salt, lignin sulfonic acid salt, polyoxyethylene glycol ether, polyoxyethylene alkyl aryl ether, and polyoxyethylene sorbitan monoalkylate.

Examples of other adjuvants that can be used include fixing agents or thickeners, such as carboxy methyl cellulose, gum Arabic, sodium alginate, guar gum, gum tragacanth, and polyvinyl alcohol, defoaming agents, such as metal soap, agents for improving physical properties, such as fatty acid, alkyl phosphate, silicone, and paraffin, and coloring agents.

Various types of formulations of antibacterial agents or diluents thereof can generally be applied in accordance with a common technique. Specifically, application thereof can be carried out by means of, for example, dispersion (e.g., spraying, misting, atomizing, dusting, granule application, water surface application, and in-box application), soil application (e.g., inclusion and affusion), surface application (e.g., coating, powder-coating, and covering), soaking, bait poisoning, and smoke application. Also, so-called ultra-high concentration and small-dose spraying can be employed. In such a case, active ingredient content can be 100%.

In an antibacterial agent comprising, as an active ingredient, the cyclic peptide compound, in addition, the cyclic peptide compound is sufficiently effective as an active ingredient by itself. According to need, the antibacterial agent can be mixed with or used in combination with, for example, another fertilizer or an agricultural chemical, such as an insecticide, miticide, nematicide, another antibacterial agent, anti-viral agent, attractant, herbicide, or plant growth regulator. In such a case, the effects thereof can occasionally be particularly high. Examples of plant pathogenic bacteria on which KK-1 itself exerts control effects include, but are not particularly limited to; gray molds (*Botrytis cinerea*), powdery mildew (*Blumeria graminis*), blast disease (*Magnaporthe oryzae*), and *Rhizoctonia solani* (*Thanatephorus cucumeris* (Frank) Donk).

EXAMPLES

Hereafter, the present invention is described in greater detail with reference to the examples, although the technical scope of the present invention is not limited to the following examples.

Example 1

Genomic Analysis of *Curvularia clavata*

Conidiospores of the *C. clavata* BAUA-2787 strain provided by Akita Konno Co., Ltd. were inoculated into 200 ml of CM liquid medium (a 500-ml triangular flask), and culture was conducted at 26° C. and 130 rpm for 48 hours. The cultured cells were harvested with the use of Miracloth, a spatula was pressed against the cells for dehydration, the dehydrated cells were introduced into a mortar, which had been cooled to −20° C. in advance, and liquid nitrogen was injected thereinto for freezing. The frozen cells were quickly fractured with the use of a pestle to result in a powder state, and genomic DNA was then extracted using the DNeasy Plant Maxi Kit.

Genomic analysis was performed using two types of next-generation sequencers (5500xl SOLiD (life technologies) and MiSeq (illumina)). A library was prepared from genomic DNA of the *C. clavata* strain using the 5500 SOLiD Mate-Paired Library Kit (for 5500xl SOLiD) and the Nextera DNA Sample Prep Kit (MiSeq), and genomic analysis was then conducted using the next-generation sequencers.

Search of the NRPS Gene of *C. clavata*

Figure 2:
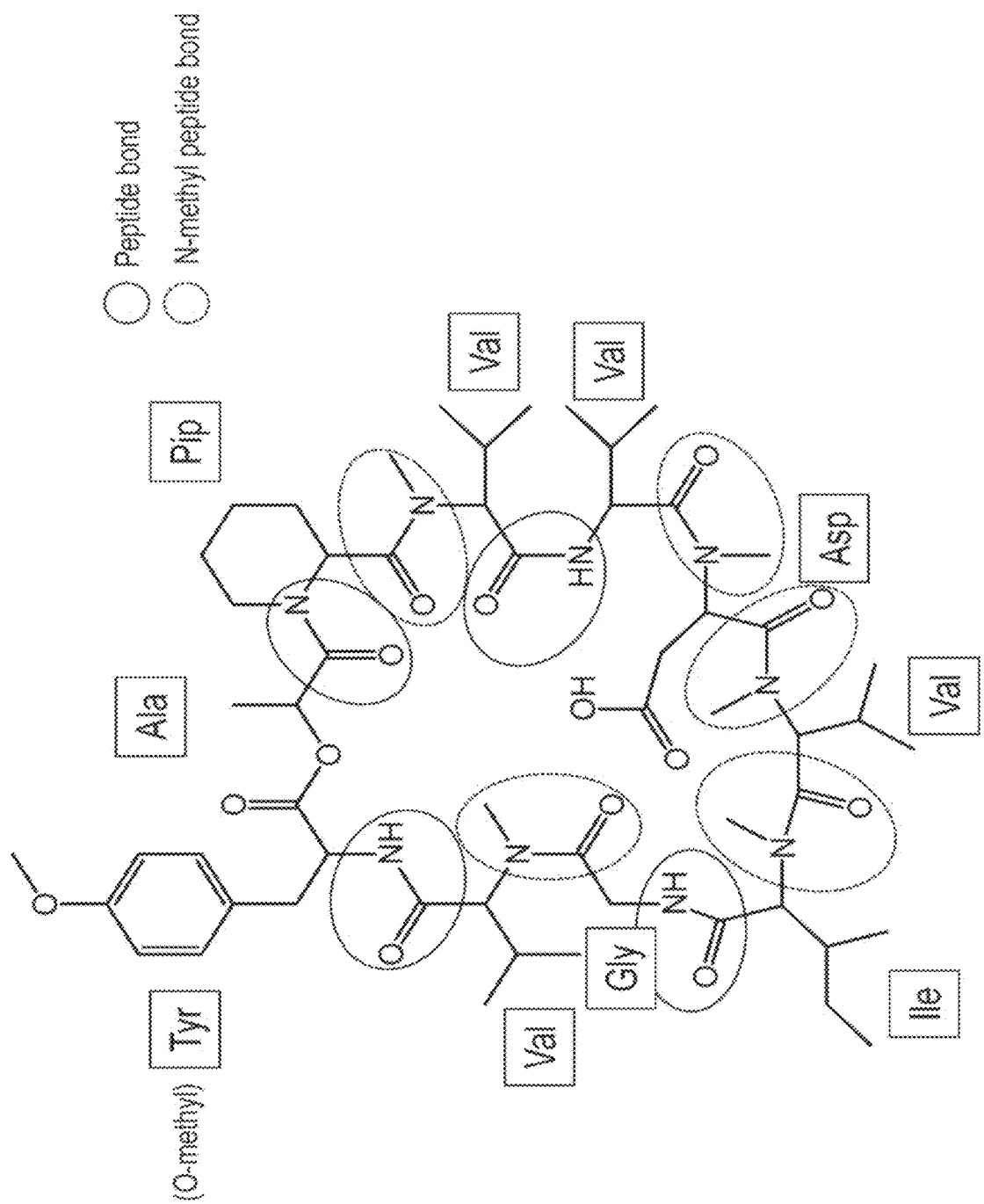

As shown in FIG. 2, a cyclic peptide produced by the *C. clavata* BAUA-2787 strain (hereafter, it is referred to as "KK-1") comprises 10 amino acids in which 5 out of 9 peptide bonds are N-methylated and the tyrosine (Tyr) residues in the molecules are O-methylated. In this example, the nonribosomal peptide synthetase (NRPS) gene synthesizing the basic backbone of the KK-1 was searched.

At the outset, the NRPS gene biosynthesizing the peptide basic backbone was deduced on the basis of the genome sequence information of the *C. clavata* BAUA-2787 strain, so as to deduce the KK-1 biosynthetic gene cluster.

NRPS is an enzyme that synthesizes a peptide by linking amino acids without the aid of ribosomes, and it has module structures consistent with the number and the order of the amino acid residues constituting the resulting peptide. Accordingly, NRPS comprising the module structures and the domain structures consistent with the structural features of the compound can be deduced to be NRPS biosynthesizing the peptide backbone of the compound.

Since the sequence of the gene of the *C. clavata* BAUA-2787 strain and that of a protein encoded thereby were deduced based on the genomic analysis of the *C. clavata* BAUA-2787 strain, all the genes that were deduced to encode NRPS in the *C. clavata* genome were searched. On the basis of the structural features of the putative protein, genes biosynthesizing the peptide basic backbone of KK-1 were then deduced.

At the outset, all the NRPS genes of *C. clavata* were retrieved by homology search with NRPS of *Cochliobolus heterostrophus* as related filamentous fungi. In *C. heterostrophus*, 12 NRPS genes (i.e., NPS1 to NPS12) have been found. As a result of inspection of the domain structures of these 12 NRPS genes, NPS7 was found to be a hybrid NRPS with PKS (polyketide synthase), and NPS10 and NPS12 were found to be NRPS-like proteins without C domains. Thus, the amino acid sequences of NPS1 to NPS6, NPS8, NPS9, and NPS11 excluding the 3 NRPS genes indicated above were subjected to blastp search as query sequences on the amino acid sequence database of the putative proteins of *C. clavata*. On the basis of the report such that a filamentous fungus comprise about 10 NRPS genes (e.g., *C. heterostrophus* comprises 12 NRPS genes and *Aspergillus fumigatus* comprises 14 NRPS genes), the top 20 genes matched with the query genes were extracted, and the 24 genes indicated below were identified; that is, TRAF01000140000154, TRAF01000135000001, TRAF01000070000001, TRAF01000068000001, TRAF01000108000067, TRAF01000130000847, TRAF01000117000049, TRAF01000117000050, TRAF01000099000028, TRAF01000088000002, TRAF01000082000001, TRAF01000081000001, TRAF01000117000368, TRAF01000142000376, TRAF01000109000032, TRAF01000142000383, TRAF01000136000233, TRAF01000100000101, TRAF01000061000021, TRAF01000108000142, TRAF01000139000099, TRAF01000140000122, TRAF01000117000201, and TRAF01000136000219.

The gene sequence of *C. clavata* (CDS) has been predicted using a dedicated program on the basis of the genomic DNA sequence analyzed using a next-generation sequencer. However, such CDS prediction is often erroneous. Because of the presence of the intron, in particular, the 5'- and 3'-sequences of CDS are deleted, and a sequence that is shorter than the actual CDS is often predicted. In order to more accurately predict CDS, accordingly, it is necessary to thoroughly examine the sequences one by one with the use of, for example, information concerning sequences in the vicinity of the genomic region where the gene of interest is located. Thus, the genomic DNA sequence from a position 3,000-bp upstream of the putative initiation codon to a position 3,000-bp downstream of the putative termination codon of the 24 identified genes were subjected to blastx search as query sequences on the GenBank database. As a result, a region exhibiting a homology to a known protein sequence was identified, and the initiation codon and the termination codon of the gene of interest were deduced. On the basis of homology to the known protein sequence, the position of the intron was also indicated. Accordingly, the site of the intron was predicted in accordance with the GU-AG rule, and CDS was deduced more accurately.

While TRAF01000117000049 and TRAF01000117000050 were deduced to be different genes, these genes were found to be a single gene (such single gene is designated as "TRAF01000117000049-50") as a result of the search. Since the genomic DNA sequence in the vicinity of the gene subjected to the search could not be sufficiently identified, some genes were determined to lack the 5'-side (the initiation codon could not be detected) or the 3'-side (the termination codon could not be detected). Such genes are indicated below.

TRAF01000135000001 (5'-deleted)
TRAF01000070000001 (5'-deleted and 3'-deleted)
TRAF01000068000001 (3'-deleted)
TRAF01000088000002 (3'-deleted)
TRAF01000082000001 (5'-deleted)
TRAF01000081000001 (3'-deleted)
TRAF01000117000368 (5'-deleted)

These sequences were analyzed in greater detail. As a result, the completely identical 2,285-bp sequences were detected at the 3'-terminus of TRAF01000068000001, the 5'-terminus and the 3'-terminus of TRAF01000070000001, and the 5'-terminus of TRAF01000135000001. That is, these 3 genes were deduced to be a single gene composed of TRAF01000068000001, TRAF01000070000001, and TRAF01000135000001 sequentially linked to each other (such single gene is designated as "TRAF01000135000001_J3G").

Also, the completely identical 2,959-bp sequences were detected at the 3'-termini of TRAF01000088000002 and TRAF01000081000001 and at the 5'-termini of TRAF01000082000001 and TRAF01000117000368. That is, these 4 genes were deduced to be 2 genes. While these genes may be linked to each other in any of the 4 combinations shown below, the correct combination could not be determined on the basis of sequence information:

1) TRAF01000088000002 and TRAF01000082000001;
2) TRAF01000088000002 and TRAF01000117000368;
3) TRAF01000081000001 and TRAF01000082000001; and
4) TRAF01000081000001 and TRAF01000117000368.

Figures 1, 3:
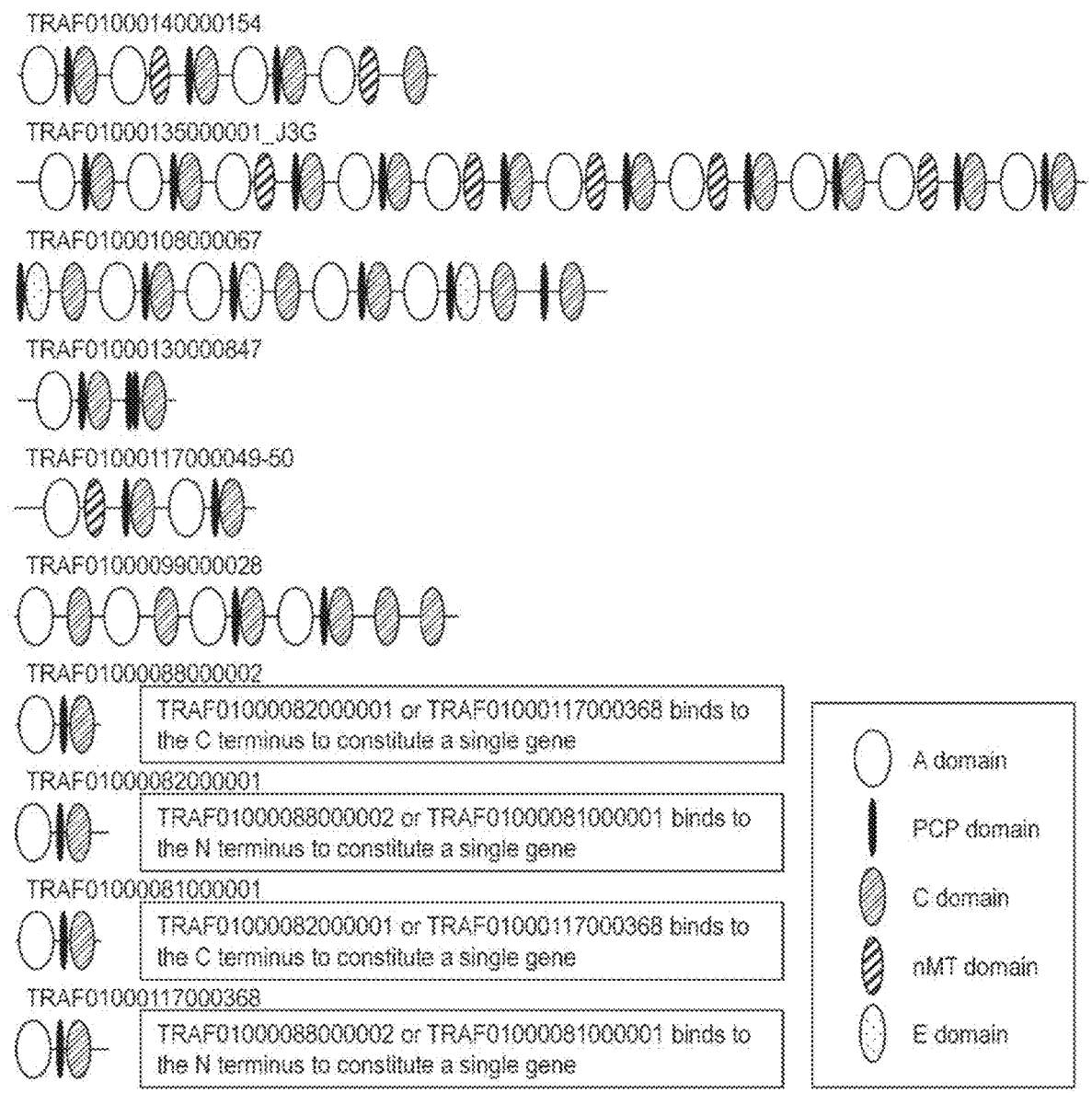
Figures 2, 3:
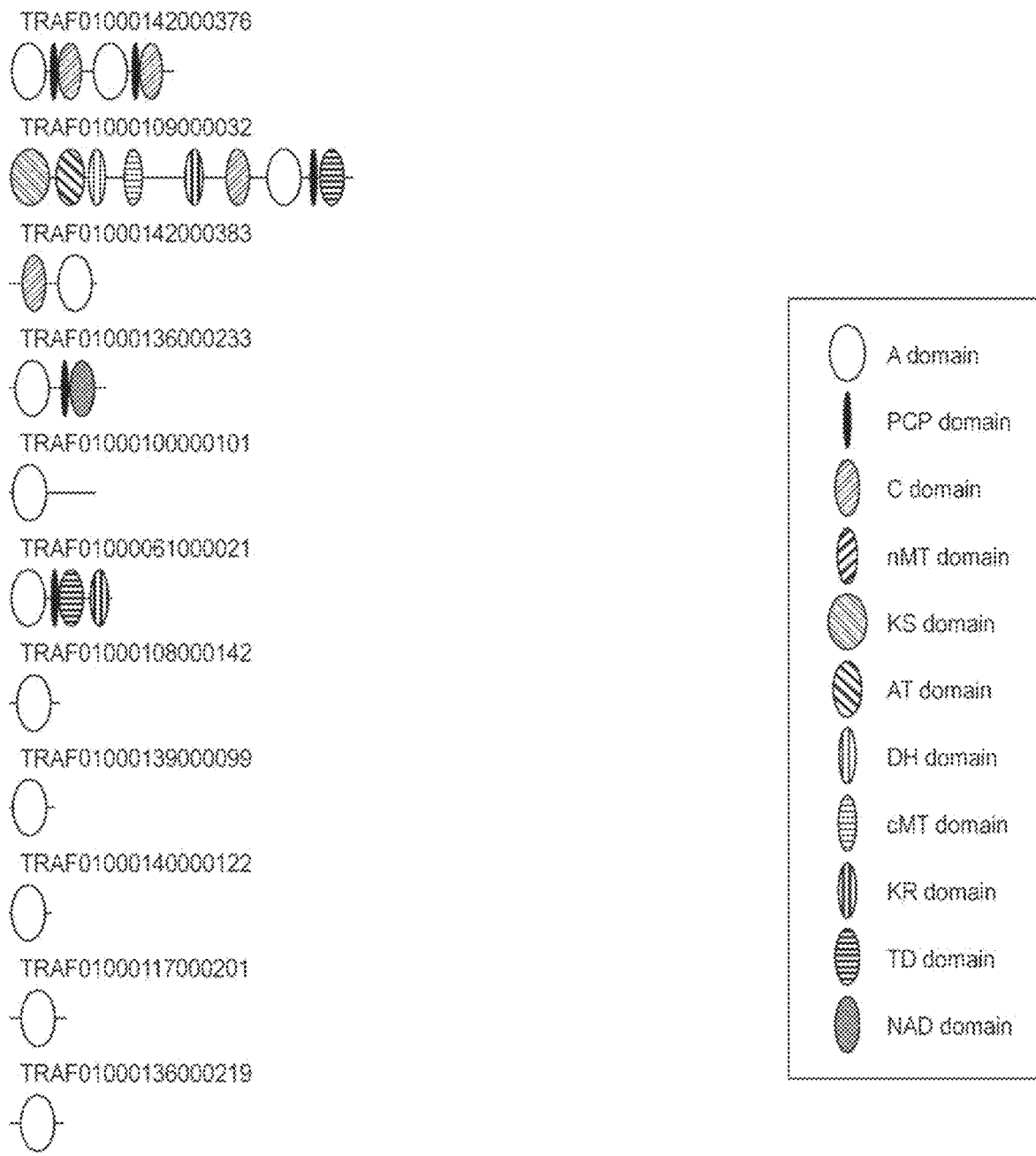

Subsequently, the domain structures of proteins encoded by the genes subjected to CDS prediction were predicted using the InterProScan and antiSMASH programs. The results of antiSMASH analysis are shown in FIGS. 3-1 and 3-2. The genes comprising the A domain, the PCP domain, and the C domain necessary for NRPS functions are the following 14 genes: TRAF01000135000001_J3G, TRAF01000108000067, TRAF01000130000847, TRAF01000117000049, TRAF01000117000050, TRAF01000099000028, TRAF01000088000002, TRAF01000082000001, TRAF01000081000001, TRAF01000117000368, TRAF01000142000376, TRAF01000109000032, and TRAF01000142000383. As described above, 4 of these genes (i.e., TRAF01000088000002, TRAF01000082000001, TRAF01000081000001, and TRAF01000117000368) each result from segmentation of 2 genes. This indicates that the C. clavata BAUA-2787 strain comprises 12 NRPS genes. In TRAF01000142000383, only the A domain and the C domain were detected via anti SMASH analysis. As a result of InterProScan analysis, however, a PCP domain-like sequence was detected at the N-terminal side. Accordingly, TRAF01000142000383 was deduced to be NRPS. Since TRAF01000109000032 comprises a typical polyketide synthase (PKS) domain at the N-terminal side, it was considered to be a PKS-NRPS hybrid.

Deduction of NRPS Involved in Biosynthesis of KK-1

The C. clavata BAUA-2787 strain was considered to comprise 12 NRPS genes. Thus, genes biosynthesizing the basic peptide backbone of KK-1 were searched from among such 12 genes. As shown in FIG. 2, KK-1 comprises a cyclic peptide of 10 amino acids as a basic backbone. A peptide bond is not formed between Tyr and Ala, but an ester bond is formed due to some sort of modification. A peptide biosynthesized by NRPS comprises amino acids, the number of which is consistent with that of biosynthetic NRPS modules. Thus, NRPS biosynthesizing the KK-1 basic peptide backbone comprising 10 amino acids is considered to comprise 10 modules (i.e., 10 A domains). As a result of inspection of the number of the A domains in 12 putative NRPS genes of C. clavata, only TRAF01000135000001_J3G was found to comprise 10 A domains. This indicates that the gene is NRPS involved in the biosynthesis of KK-1 (FIG. 3-1).

In the domain structure of TRAF01000135000001_J3G, as shown in FIG. 1, there are 5 N-methyl transferase domains (nMT domains) that N-methylate peptide bonds and such domains are located in the third module, the fifth module, the sixth module, the seventh module, and the ninth module. The position of each module in NRPS is consistent with the position of the amino acids constituting the biosynthesized peptide. Also, the position of the module comprising the nMT domain is consistent with the position of the N-methylated peptide bond. If the first module of TRAF01000135000001_J3G is hypothesized to correspond to the Ala residue of KK-1, the position of the module comprising the nMT domain is completely consistent with the position of the N-methylated peptide bond. This strongly suggests that TRAF01000135000001_J3G is NRPS that biosynthesizes the basic peptide backbone of KK-1.

It was further deduced that a peptide (Ala-Pip-(N-methyl) Val-Val-(N-methyl)Asp-(N-methyl)Val-(N-methyl)Ile-Gly-(N-methyl)Val-Tyr) was first synthesized by TRAF01000135000001_J3G, and cyclization and modification were then performed. In the case of well-known bacteria-derived NRPS, the TE domain is known to involve in the cyclization. In the case of filamentous fungi, in contrast, many NRPSs lack the TE domains but comprise the C domains. In recent years, the C domains have been found to involve in the peptide cyclization in filamentous fungi.

Also, TRAF01000135000001_J3G comprises the C domain at the C terminus of the tenth module, and the C domain may be involved in the cyclization. It is also deduced that the basic peptide backbone is biosynthesized by TRAF01000135000001_J3G, the resultant is modified with various enzymes, and KK-1 is then biosynthesized. The modifying enzyme genes are considered to form a gene cluster in the genome of the C. clavata BAUA-2787 strain together with TRAF01000135000001_J3G.

Domains in the first module to the tenth module constituting the deduced NRPSs, SEQ ID NOs of amino acid sequences thereof, and other information are summarized in Table 1 below.

TABLE 1

| Module | Domain | Amino acid sequence | SEQ ID NO: |
|---|---|---|---|
| First module | A | 286 to 678 | 1 |
|  | PCP | 795 to 863 | 2 |
| Second module | C | 877 to 1174 | 3 |
|  | A | 1361 to 1758 | 4 |
|  | PCP | 1870 to 1938 | 5 |
| Third module | C | 1952 to 2248 | 6 |
|  | A | 2435 to 2836 | 7 |
|  | nMT | 2903 to 3126 | 8 |
|  | PCP | 3358 to 3426 | 9 |
| Fourth module | C | 3440 to 3734 | 10 |
|  | A | 3921 to 4324 | 11 |
|  | PCP | 4417 to 4485 | 12 |
| Fifth module | C | 4499 to 4796 | 13 |
|  | A | 4983 to 5385 | 14 |
|  | nMT | 5454 to 5677 | 15 |
|  | PCP | 5902 to 5970 | 16 |
| Sixth module | C | 5984 to 6281 | 17 |
|  | A | 6468 to 6869 | 18 |
|  | nMT | 6936 to 7157 | 19 |
|  | PCP | 7391 to 7459 | 20 |
| Seventh module | C | 7473 to 7767 | 21 |
|  | A | 7954 to 8359 | 22 |
|  | nMT | 8427 to 8647 | 23 |
|  | PCP | 8876 to 8944 | 24 |
| Eighth module | C | 8958 to 9255 | 25 |
|  | A | 9442 to 9846 | 26 |
|  | PCP | 9948 to 10016 | 27 |
| Ninth module | C | 10003 to 10328 | 28 |
|  | A | 10514 to 10916 | 29 |
|  | nMT | 10983 to 11207 | 30 |
|  | PCP | 11433 to 11501 | 31 |
| Tenth module | C | 11515 to 11810 | 32 |
|  | A | 11997 to 12401 | 33 |
|  | PCP | 12500 to 12566 | 34 |
|  | C | 12616 to 12892 | 35 |

In Table 1, the numerical ranges in the "Amino acid sequence" column indicate the positions of the amino acid residues in the full-length amino acid sequence of the deduced NRPS (SEQ ID NO: 37).

Deduction of KK-1 Biosynthetic Gene Cluster

As described above, TRAF01000135000001_J3G was deduced to be the NRPS gene constituting the KK-1 basic peptide backbone. It was thus considered that a group of genes constituting the KK-1 biosynthetic gene cluster was present in a region including this NRPS (TRAF01000135000001_J3G). Among the genes located in the vicinity of such NRPS, accordingly, deduction of a group of genes constituting the biosynthetic gene cluster was attempted based on the amino acid sequences of proteins encoded by such genes and functions deduced based on the amino acid sequences. Since TRAF01000135000001_J3G is composed of three sequences that were separate sequences at the time of genome sequencing and gene prediction, the sequence constituted by linking these separate sequences was used for prediction of the gene cluster described below.

Figure 5:
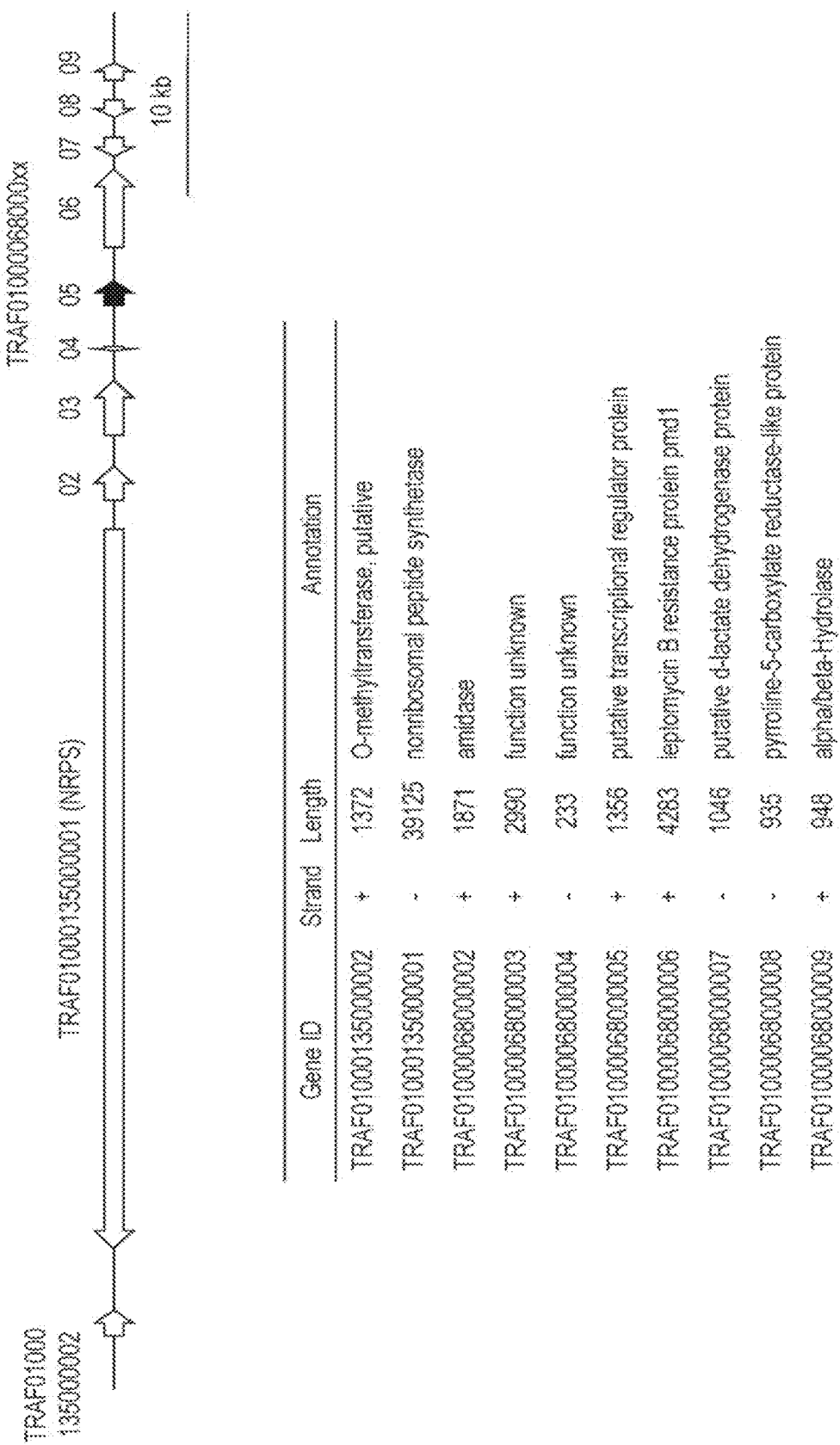

At the outset, 14 genes were extracted from the upstream region and the downstream region of the NRPS gene (TRAF01000135000001_J3G), respectively, and these genes were then annotated on the basis of the results of blastp search on the GenBank database. The results are shown in FIG. 4. On the basis of the annotation, a region including genes that may be involved in the secondary metabolism (i.e., a region from TRAF01000135000002 to TRAF01000068000009) was deduced to constitute the KK-1 biosynthetic gene cluster. FIG. 5 schematically shows the structure of the putative biosynthetic gene cluster. The cluster size was approximately 75 kb and the majority thereof was occupied by the NRPS genes. Concerning the functions of genes constituting the cluster, TRAF01000135000002 was annotated with "O-methyltransferase," and TRAF01000135000002 was thus considered to be involved in O-methylation of the tyrosine (Tyr) residue in the KK-1 molecule. TRAF01000068000006 that is annotated with "pmd1" encoding the leptomycin B-tolerant protein is an ABC transporter in view of protein functions, and it may be involved in efflux of KK-1 to the outside of the cells. Also, the transcription factor gene (TRAF01000068000005) was present in the cluster. In general, expression of genes constituting the biosynthetic gene cluster is often regulated in common by the transcription factor existing in the cluster. In the gene cluster, TRAF01000068000005 was deduced to regulate the transcription of all the genes constituting the cluster. By regulating the expression of this transcription factor, accordingly, the expression of the gene cluster may be regulated, and such gene may be critical if high-level KK-1 production is intended.

Deduction of KK-1 Biosynthetic Gene Cluster Based on Gene Expression Information When deducing the KK-1 biosynthetic gene cluster, cluster detection was also carried out in accordance with a bioinformatics technique using the MIDDAS-M algorithm (Umemura, M. et. al., Plos one, 8 (5), e63673, 2013).

According to MIDDAS-M, a gene cluster is detected based on the gene expression information. When detecting the biosynthetic gene cluster of the secondary metabolite, extensive gene expression information in the production host under the condition in which a substance of interest is produced is compared with that under the condition in which a substance of interest is not produced, and a group of genes expressing under the former condition is detected as a cluster. By arranging the genes in the order of the genome positions along the horizontal axis and plotting the scores (the expression levels) along the vertical axis, a region in which genes exhibiting fluctuation in expression levels aggregate is detected as a peak.

Figure 6:
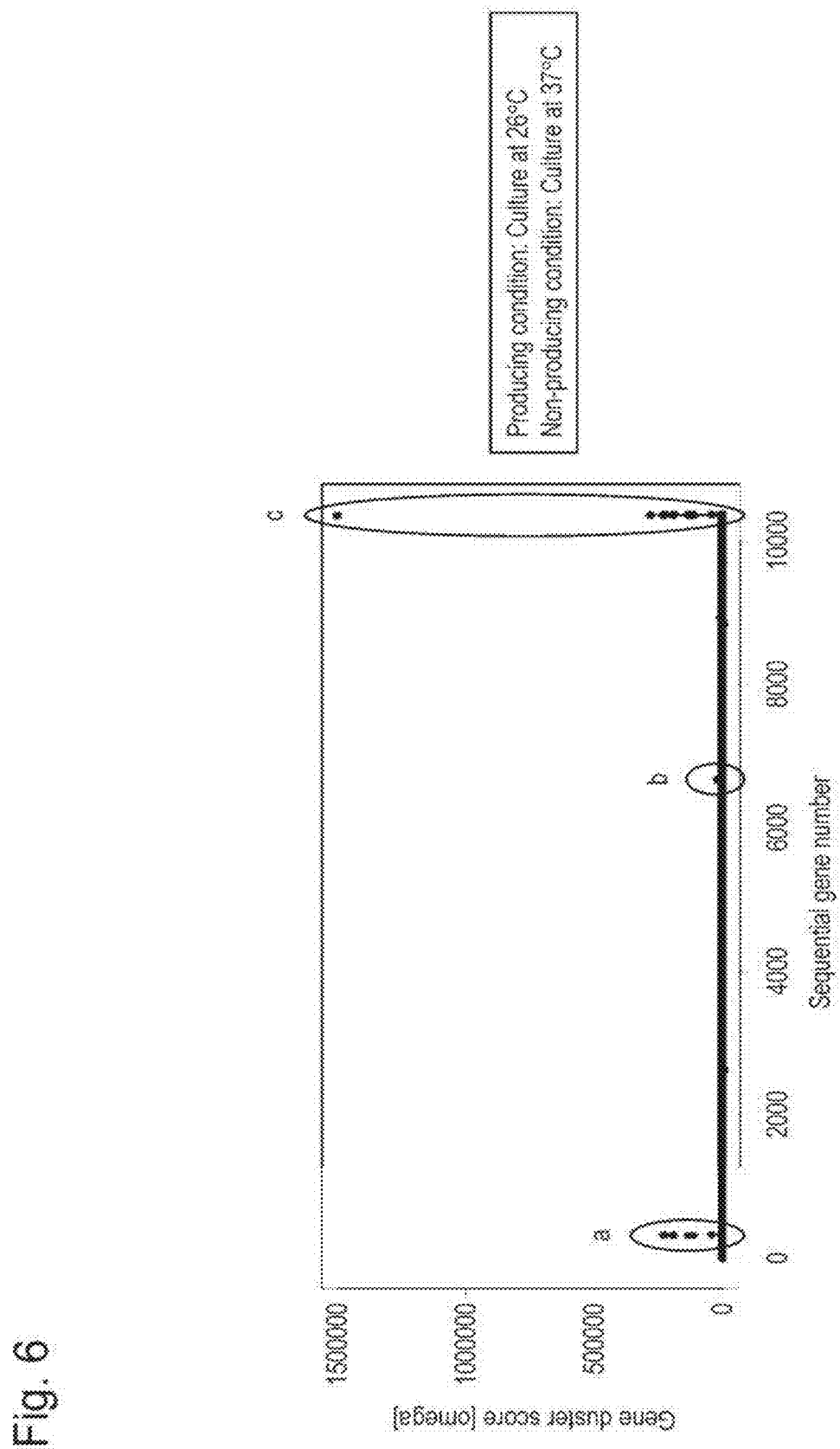

When the C. clavata BAUA-2786 strain is subjected to CM liquid culture, KK-1 production is not observed if the culture temperature is raised to 37° C. Accordingly, general culture temperature of 26° C. was designated as "Producing conditions," and that of 37° C. was designated as "Non-producing conditions." Under such conditions, C. clavata gene expression was extensively analyzed via RNA-seq using the next-generation DNA sequencer, and cluster detection was carried out via MIDDAS-M. As a result, as shown in FIG. 6, the group of genes identical to the gene cluster deduced based on the sequence information was detected (a and b in FIG. 6). Two peaks were detected because such gene cluster was fragmented when the initial genome sequence data was attained, as described above. The putative cluster sequence manually linked was bound to the end of the genome sequence (the right end on the horizontal axis) was simultaneously subjected to the MIDDAS-M-based analysis. As a result, genes in the region of interest were detected at a significant level (c in FIG. 6).

The results strongly suggest that the gene cluster including 10 genes deduced on the basis of gene sequence information may be involved in biosynthesis of KK-1. Concerning the 10 genes included in the putative gene cluster, the nucleotide sequences and the amino acid sequences of the coding regions are summarized in the table below.

TABLE 2

| Gene ID | Nucleotide sequence | Amino acid sequence |
| --- | --- | --- |
| TRAF01000135000002 | SEQ ID NO: 40 | SEQ ID NO: 41 |
| TRAF01000135000001_J3G | SEQ ID NO: 36 | SEQ ID NO: 37 |
| TRAF01000068000002 | SEQ ID NO: 42 | SEQ ID NO: 43 |
| TRAF01000068000003 | SEQ ID NO: 44 | SEQ ID NO: 45 |
| TRAF01000068000004 | SEQ ID NO: 46 | SEQ ID NO: 47 |
| TRAF01000068000005 | SEQ ID NO: 38 | SEQ ID NO: 39 |
| TRAF01000068000006 | SEQ ID NO: 48 | SEQ ID NO: 49 |
| TRAF01000068000007 | SEQ ID NO: 50 | SEQ ID NO: 51 |
| TRAF01000068000008 | SEQ ID NO: 52 | SEQ ID NO: 53 |
| TRAF01000068000009 | SEQ ID NO: 54 | SEQ ID NO: 55 |

Example 2

In this example, functions of the transcription factor genes among the group of genes included in the KK-1 biosynthetic gene cluster deduced in Example 1 were analyzed. In this example, the gene encoding the transcription factor denoted as "TRAF01000068000005" in Example 1 is denoted as "TF068-005."

Analysis Using Transcription Factor High-Expression Strain

Figure 7:
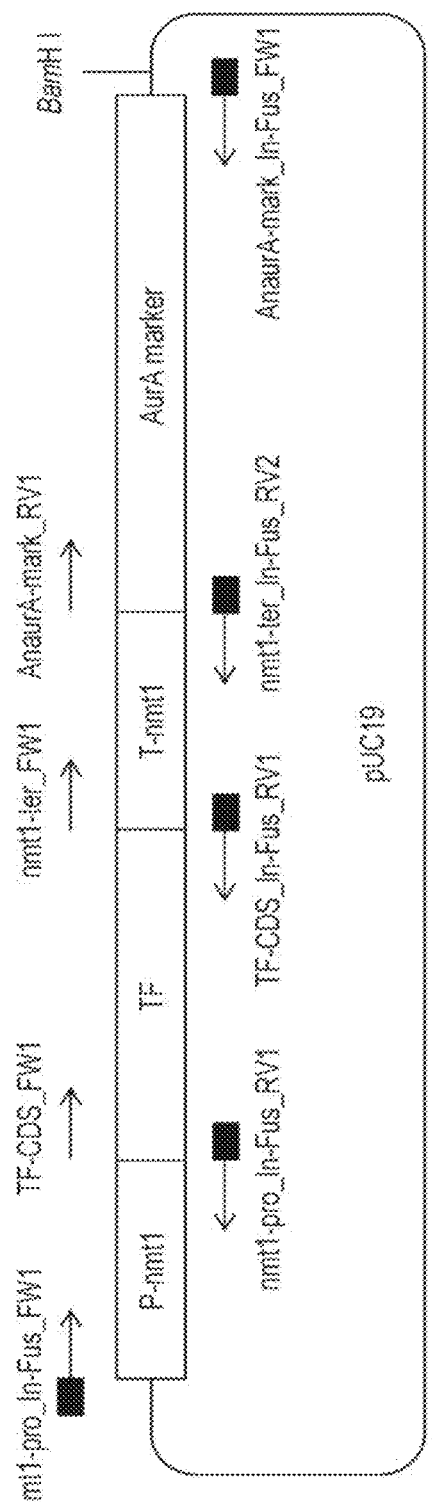

1) Construction of TF068-005 High Expression Construct (FIG. 7)

FIG. 7 schematically shows a construct achieving high-level expression of the TF068-005 gene. In this construct, a region from the initiation codon to a position 1,000-bp upstream therefrom of the Ccnmt1 (TRAF01000124000183) gene of the C. clavata BAUA-2787 strain was designated as the promoter, a 355-bp downstream region of the Ccnmt1 gene was designated as the terminator, and the Aureobasidin A (AurA)-tolerant gene was used as the selection marker. The promoter and the terminator of the Ccnmt1 gene were amplified via PCR using C. clavata genomic DNA as a template, the Aureobasidin A (AurA)-tolerant gene was amplified via PCR using the pAUR316 plasmid (TaKaRa) as a template, and the TF068-005 gene was amplified via PCR using C. clavata cDNA as a template.

Subsequently, the in-fusion reaction was carried out with linear pUC19 of the In-Fusion HD Cloning Kit (Clontech) to prepare a target plasmid (pUC-Pnmt1-TF-Tnmt1-aurA). The primers and the reaction conditions employed are shown below.

nmt1-pro_In-Fus_FW1:
(SEQ ID NO: 56)
5'-cggtacccggggatcTAGTCTGTTGATTACTCG-3' nmt1-pro_In-Fus_RV1:
(SEQ ID NO: 57)
5'-ctcgacaaaggtcatTTTGACTTTGAATACCGGTG-3' nmt1-ter_FW1:
(SEQ ID NO: 58)
5'-GCAGTTGCCGTTGGACCAGAGG-3' nmt1-ter_In-Fus_RV2:
(SEQ ID NO: 59)
5'-atagtcataacaagcCGCGACACTGTAATATTAAAGC-3'

TF-CDS_FW1:
(SEQ ID NO: 60)
5'-ATGACCTTTGTCGAGACTGTAGCC-3'

TF-CDS_In-Fus_RV1:
(SEQ ID NO: 61)
5'-TCCAACGGCAACTGCCTATGATATACTCATGTTCTCGTC-3'

PCR was carried out with the use of Phusion Hot Start II High-Fidelity DNA Polymerase (Thermo Fisher Scientific). The temperature conditions were: initial denaturation at 98° C. for 30 seconds; a cycle of denaturation at 98° C. for 10 seconds, annealing at 60° C. for 30 seconds, and extension at 72° C. for 30 seconds repeated 30 times; and final extension at 72° C. for 7 minutes.

AnaurA-mark_In-Fus_FW1:
(SEQ ID NO: 62)
5'-cgactctagaggatcCTGATGGTCAGATGGATCTG-3'

AnaurA-mark_RV1:
(SEQ ID NO: 63)
5'-GCTTGTTATGACTATGTATACATATGCG-3'

PCR was carried out with the use of Phusion Hot Start II High-Fidelity DNA Polymerase (Thermo Fisher Scientific). The temperature conditions were: initial denaturation at 98° C. for 30 seconds; a cycle of denaturation at 98° C. for 10 seconds, annealing at 60° C. for 30 seconds, and extension at 72° C. for 2 minutes repeated 30 times; and final extension at 72° C. for 7 minutes.

2) Transformation of C. clavata BAUA-2787 Strain

A spore suspension of the C. clavata BAUA-2787 strain was inoculated into 100 ml of CM medium (a 300-ml triangular flask), shake culture was carried out at 30° C. for 40 hours, mycelial threads were collected via filtration using a glass strainer (11G1), the collected mycelial threads were washed with sterilized water, and a spatula or the like was pressed against the washed mycelial threads for thorough dehydration. The cells were added to 10 ml of a solution for protoplast formation (an YL composition) to prepare a suspension, and the suspension was moderately shaken at 30° C. for 3 hours to form protoplasts. The resultant was filtered through Miracloth, the filtrate was centrifuged at 1,500×g for 5 minutes, and protoplasts were collected, followed by washing two times with 0.8 M NaCl. The protoplasts were suspended in Solution 1 (0.8 M NaCl, 10 mM $CaCl_2$, 10 mM Tris-HCl (pH 8.0)) at $2×10^8$/ml, 0.2 vol. of Solution 2 (40% (w/v) PEG4000, 50 mM $CaCl_2$, 50 mM Tris-HCl (pH8.0)) was moderately mixed therewith to prepare a protoplast suspension, pUC-Pnmt1-TF-Tnmt1-aurA (7.8 μm/20 μl) was added to 0.2 ml of the protoplast suspension, and the mixture was then allowed to stand in ice for 10 minutes. Solution 2 (1 ml) was moderately mixed therewith to prepare a suspension, and the suspension was then allowed to stand at room temperature for 15 minutes. Solution 1 (10 ml) was moderately mixed therewith to prepare a suspension, the protoplasts were collected via centrifugation, the supernatant was removed as much as possible, and the protoplasts were then suspended in 1 ml of Solution 1. The protoplast suspension (0.2 ml each) was applied to each of the 5 CM+1.2 M sucrose+10 μg/ml AbA selection plates, 6 to 7 ml (per 90-mm (φ) petri dish) of CM+1.2 M sucrose+10 μg/ml AbA soft agar (1%) selection medium was quickly overlaid thereto to homogeneously disperse the protoplasts, and culture was then conducted at 26° C. for 6 days.

C. clavata transformation involving the use of the pUC-Pnmt1-TF-Tnmt1-aurA plasmid was carried out in two ways (i.e., transformation with the use of the cyclic plasmid and transformation with the use of the linear plasmid cleaved with the BamHI restriction enzyme at one site).

3) Culture Conditions for TF068-005 High-Expression Strain

The TF068-005 high-expression strain was cultured in three different conditions as described below, and RNA preparation and KK-1 production were inspected.

Culture 1

Conidiospores of wild-type strains and TF068-005 high-expression strains were inoculated into 100 ml of CM medium (a 500-ml triangular flask), and shake culture was carried out at 26° C. and 160 rpm for 72 hours.

Culture 2

Conidiospores of wild-type strains and TF068-005 high-expression strains were inoculated into 30 ml of K1 medium (a 100-ml baffled triangular flask), preculture was carried out at 26° C. and 200 rpm for 72 hours, 500 μl of the culture solution was transferred to a CM medium in which glucose content was 5% (a 500-ml baffled triangular flask), and the main culture was then carried out at 26° C. and 130 rpm.

Culture 3

To a 50-ml Falcon tube, 2.5 g of brown rice and 2 ml of water were introduced, and the Falcon tube was introduced into an autoclave. Conidiospores of wild-type strains and TF068-005 high-expression strains were inoculated thereinto, and stationary culture was then carried out at 26° C. for 8 days.

4) RNA-Seq Analysis of TF068-005 High-Expression Strains

The cells subjected to liquid culture was frozen with liquid nitrogen, the product was grounded with the use of a pestle in a mortar, and total RNA was then prepared using ISOGEN (Nippon Gene). An RNA-Seq library was prepared from the total RNA using the Truseq RNA Sample Prep Kit v2, and the library was then applied to the next-generation sequencer (MiSeq) (Paired-End, Read Length 75). The obtained sequence data were mapped against the C. clavata genomic sequence using the TopHat program.

5) KK-1 Extraction and Quantification

In liquid culture, 15 ml of ethyl acetate was directly added to a 30-ml culture system, shake culture was carried out at 130 rpm for 1 hour, and centrifugation was then carried out at 4,700×g for 15 minutes. The supernatant was collected, subjected to centrifugal condensation, and then designated as an extracellular fraction. Subsequently, 15 ml of acetone was added to an aqueous layer after ethyl acetate was collected, and the mixture was vortex-stirred, followed by centrifugation at 4,700×g for 15 minutes. The supernatant was collected via decantation and acetone was removed via centrifugal condensation. Ethyl acetate (15 ml) was added thereto, followed by centrifugation at 4,700×g for 15 minutes. The ethyl acetate layer was collected in a 50-ml tube, and the product of centrifugal condensation was designated as an intracellular fraction.

In solid culture, 25 ml of 80% acetone was added to the culture system, followed by vortex-stirring. Acetone was removed via centrifugal condensation, and 10 ml of ethyl acetate was added, followed by vortex-stirring. The ethyl acetate layer was collected via centrifugation, and the product of spin-column purification was then designated as a sample.

KK-1 quantification was carried out via UPLC under the following conditions.
 Apparatus: ACQUITY UPLC I-Class System (Waters)
 Column: Acquity UPLC BEH C18, 2.1×100 mm
 Solvent: Gradient 50%-98% Acetonitrile+0.1% Formic Acid 3 min)
 Flow rate: 0.6 ml/min
 Detection wavelength: 273 nm Results and Discussion In this example, the promoter and the terminator of the nmt-1 gene homolog (TRAF01000124000183; Ccnmt1) detected as the high-level expression gene in *C. clavata* were used to prepare a construct that allows high-level expression of the transcription factor (pUC-Pnmt1-TF-Tnmt1-aurA) (FIG. 7). *C. clavata* transformation involving the use of the plasmid was carried out in two ways (i.e., transformation with the use of the cyclic plasmid and transformation with the use of the linear plasmid cleaved at one site). The resulting strain into which the plasmid had been introduced linearly (i.e., ox_TF_1) and the strain into which the plasmid had been introduced cyclically (i.e., (ox_TF_2) were subjected to RNA-seq analysis and evaluation in terms of KK-1 productivity.

Figure 8:
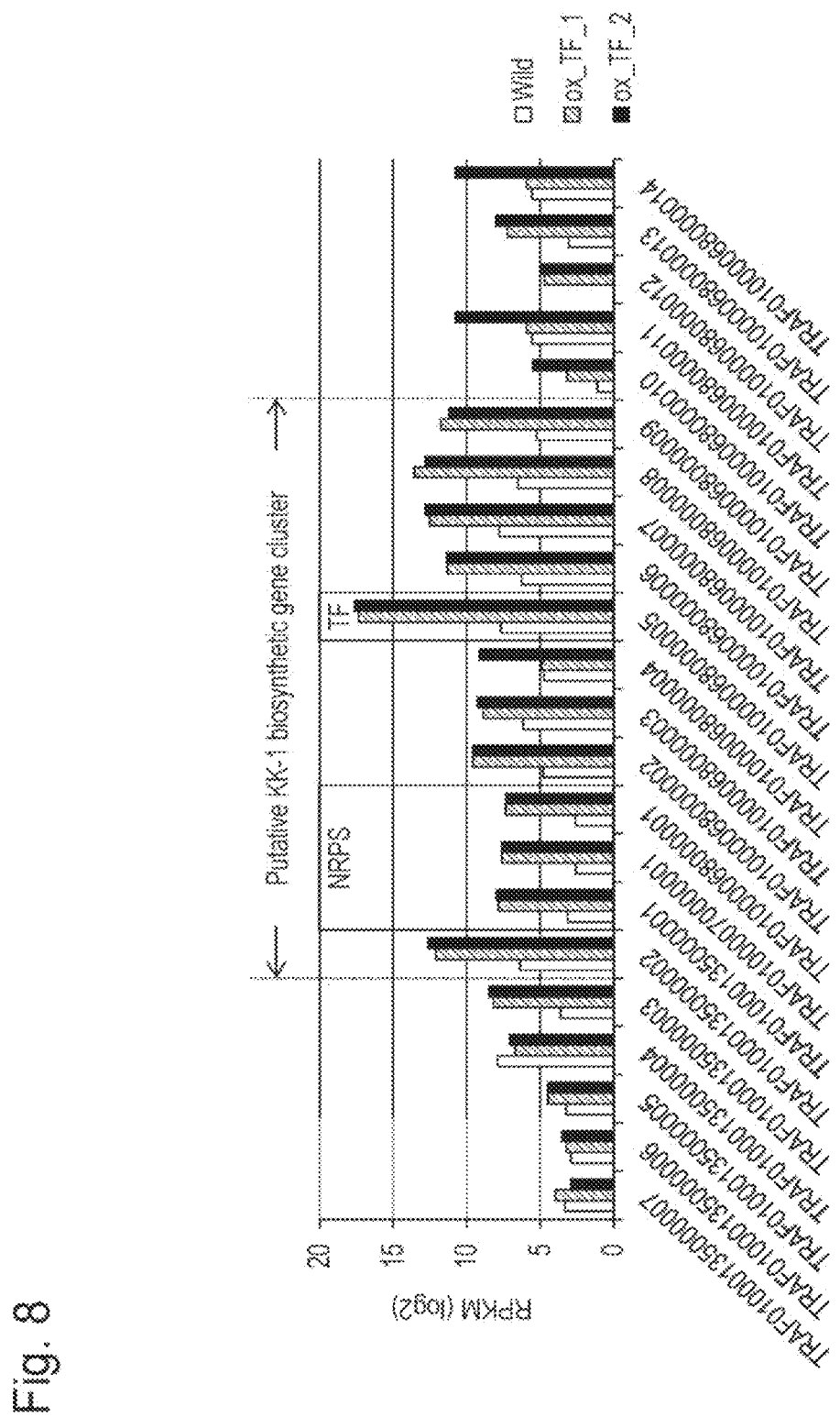

At the outset, conidiospores of wild-type strains and TF068-005 high-expression strains (ox_TF_1 and ox_TF_2) were subjected to shake culture in CM liquid medium at 26° C. and 160 rpm for 72 hours and then subjected to RNA-seq analysis ("Culture 1"). FIG. 8 shows the results of inspection of the transcription level of the genes constituting the KK-1 biosynthetic gene cluster. As shown in FIG. 8, the gene expression level in the TF068-005 high-expression strains was approximately 8 times greater than that in wild-type strains. There were no difference in transcription levels between the ox_TF_1 strain and the ox_TF_2 strain.

Figure 9:
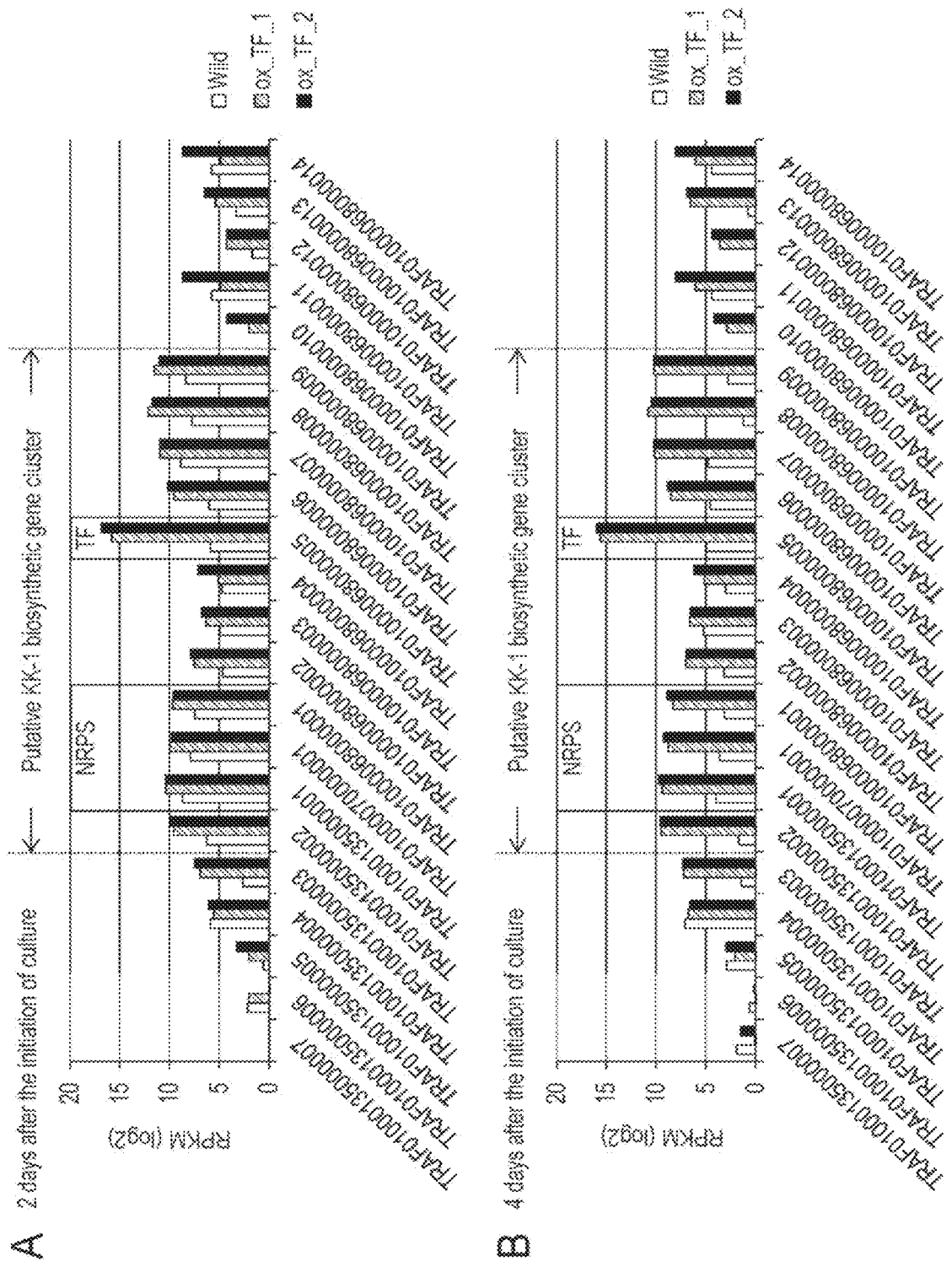

Accordingly, KK-1 productivity in the TF068-005 high-expression strains was to be inspected, and RNA-seq analysis was carried out simultaneously. In this case, preculture was carried out in K1 medium containing soybean flour and the main culture was then carried out in CM medium, so as to stabilize the shape of the cells at the time of liquid culture ("Culture 2"). FIG. 9 shows the results of RNA-seq analysis of the gene transcription levels 2 days and 4 days after the initiation of the main culture. As shown in FIG. 9, the transcription level of the genes constituting the KK-1 biosynthetic gene cluster in the TF068-005 high-expression strains was significantly higher than that in wild-type strain. Also, a difference in the expression levels compared with wild-type strains 4 days after the initiation of the main culture was greater than that 2 days after the initiation of the main culture.

Figure 10:
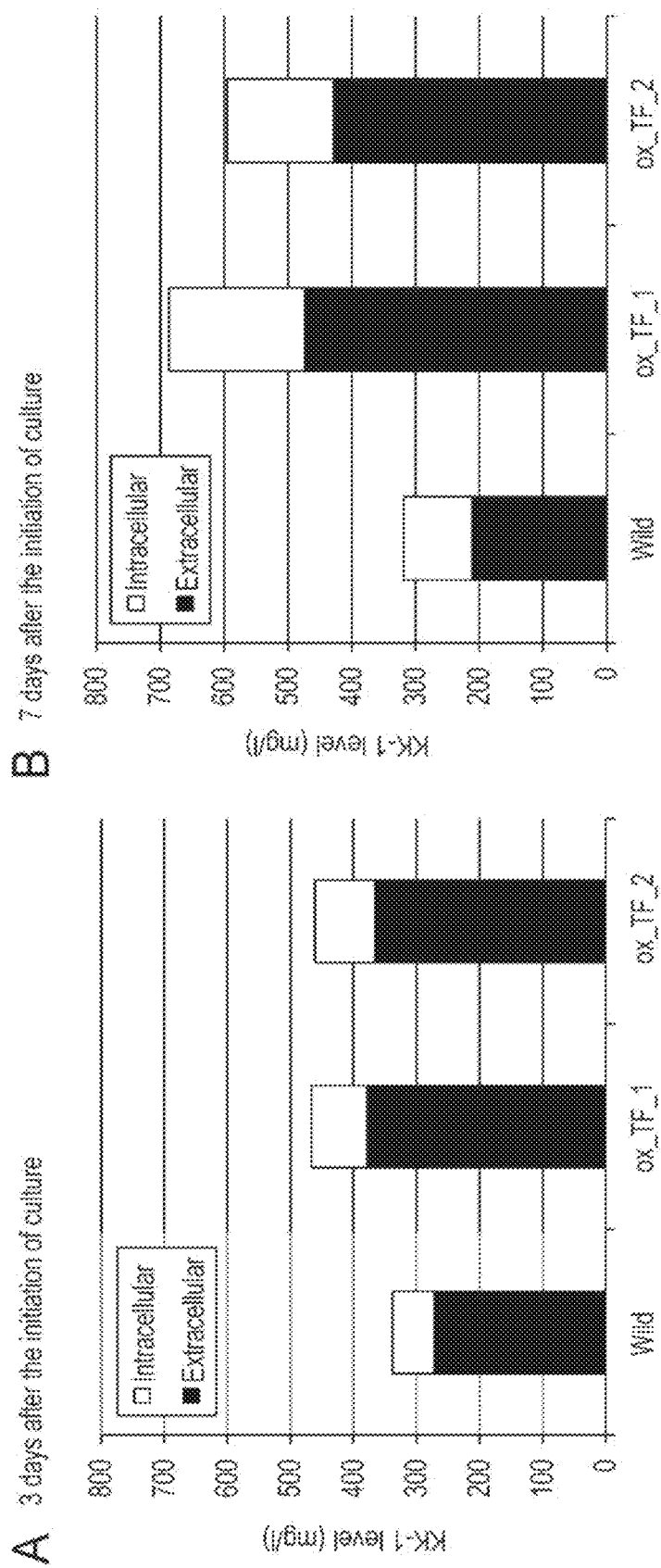

Subsequently, the KK-1 production level was inspected extracellularly and intracellularly 3 days and 7 days after the initiation of the main culture. FIG. 10 shows the results thereof. As shown in FIG. 10, the total amount of KK-1 in the culture system (a total of the extracellular production level and the intracellular production level) became greater in the TF068-005 high-expression strains both on 3 days and 7 days after the initiation of culture, and it was approximately two times greater than that of wild-type strains 7 days after the initiation of culture. On the basis of the results shown in FIG. 10, approximately 20% to 30% of the total amount of KK-1 may be accumulated in the cells.

Figure 11:
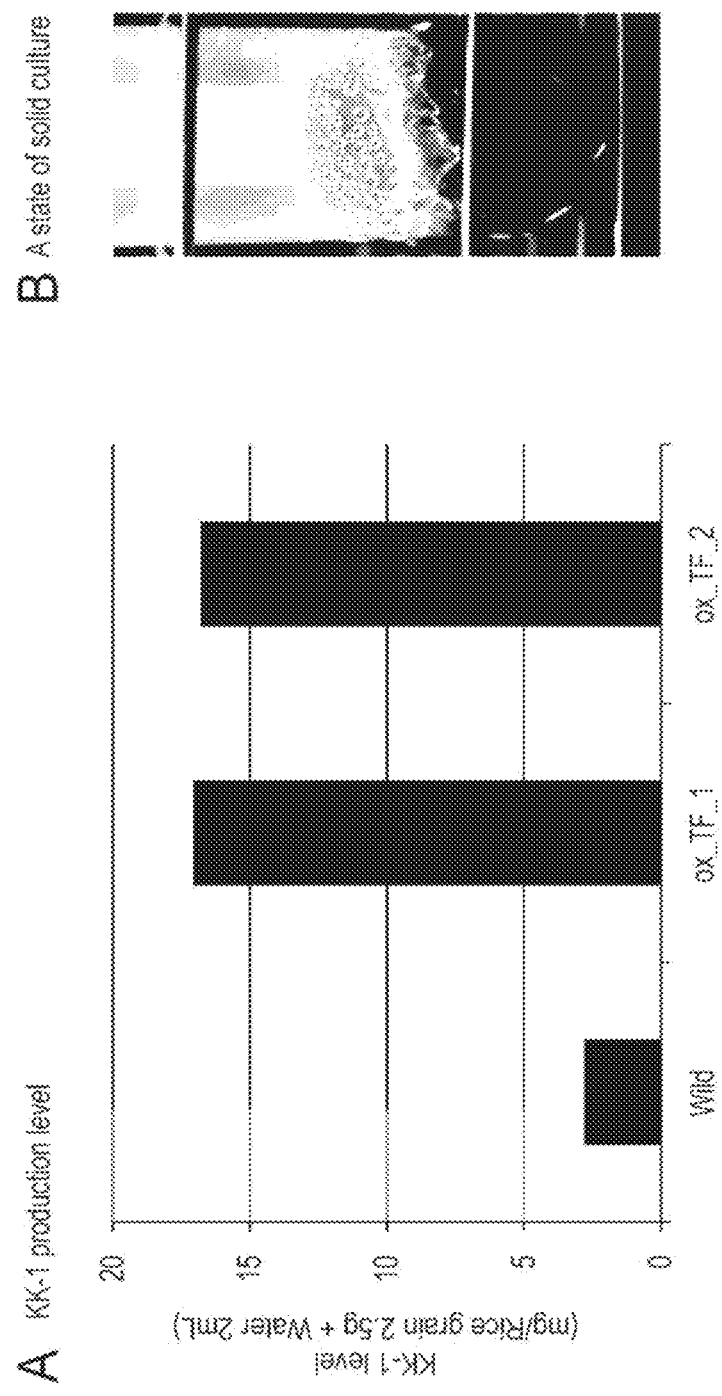

Further, FIG. 11 shows the results of inspection of KK-1 productivity under solid culture conditions involving the use of brown rice ("Culture 3"). FIG. 11 also shows a photograph demonstrating solid-culture of the TF068-005 high-expression strains. As shown in FIG. 11, KK-1 productivity in the TF068-005 high-expression strains was approximately 6 times greater than that in wild-type strains as a result of solid culture.

The results demonstrate that high-level expression of the TF068-005 gene results in elevated expression levels of the genes included in the putative gene cluster. Accordingly, the TF068-005 gene was identified as a transcription factor capable of positively regulating the expression level of particular genes at the level of transcription. In addition, KK-1 productivity was improved as a result of high-level expression of the TF068-005 gene encoding the transcription factor. Accordingly, a group of genes whose expression levels had been elevated by regulating the transcription factor was found to constitute a gene cluster involved in KK-1 production.

Analysis Using Transcription Factor-Deleted Strain

Figure 12:
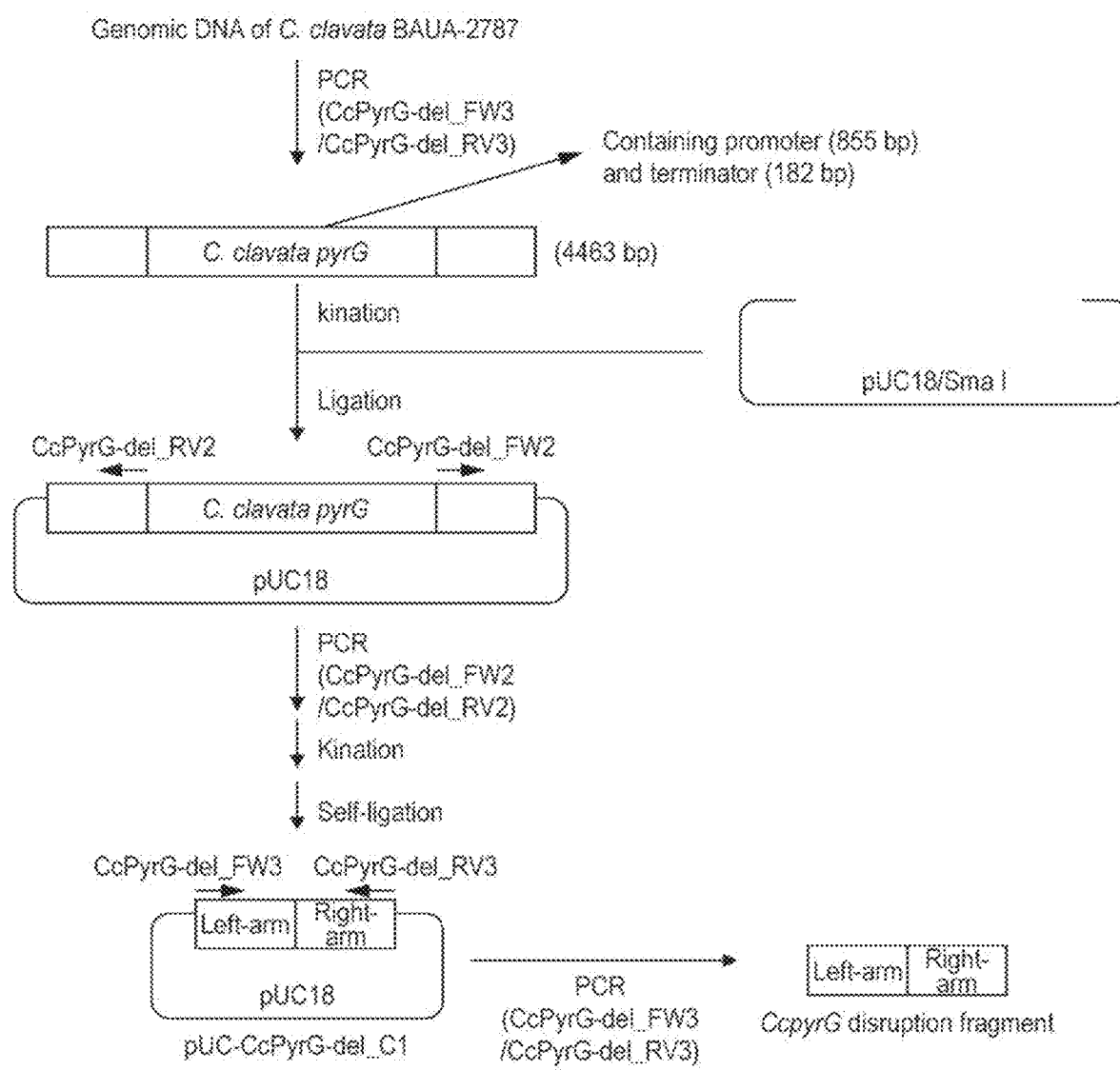

1) Construction of Plasmid for CcpyrG Gene Deletion (FIG. 12)

FIG. 12 demonstrates a scheme for constructing a plasmid used for deleting the pyrG gene in the *C. clavata* BAUA-2787 strain (the CcpyrG gene). Since pyrG gene-deleted strain cannot convert 5-fluoroorotic acid (5-FOA) into 5-fluorouridine phosphoric acid (a thymine biosynthetase inhibitor), it can grow in a medium containing 5-FOA.

As shown in FIG. 12, at the outset, PCR was carried out with the use of genomic DNA of the *C. clavata* BAUA-2787 strain as a template and the set of primers shown below, so as to amplify a region from 2,005-bp upstream of the initiation codon to 1,261-bp downstream of the termination codon of the CcpyrG gene.

```
CcPyrG-del_FW3:
                                (SEQ ID NO: 64)
5'-GACAGACTCTTCGTCGACGTC-3'

CcPyrG-del_RV3:
                                (SEQ ID NO: 65)
5'-GTTGTGGTTGGTGTTCCTGAGG-3'
```

PCR was carried out with the use of Phusion Hot Start II High-Fidelity DNA Polymerase (Thermo Fisher Scientific). The temperature conditions were: initial denaturation at 98° C. for 3 minutes; a cycle of denaturation at 98° C. for 10 seconds, annealing at 60° C. for 30 seconds, and extension at 72° C. for 2.5 minutes repeated 30 times; and final extension at 72° C. for 7 minutes.

Subsequently, the terminus of a DNA fragment (4,463-bp) containing the amplified CcpyrG gene was phosphorylated with T4 polynucleotide kinase (TOYOBO). After pUC18 was digested with SmaI, it was dephosphorylated with *E. coli* alkaline phosphatase (TOYOBO), and the resultant was ligated to the DNA fragment containing the phosphorylated CcpyrG gene. Subsequently, a pUC18 region including the upstream and downstream regions of the CcpyrG gene was amplified via PCR using the set of primers shown below, so as to delete a region including the CcpyrG gene.

```
cPyrG-del_FW2:
                                    (SEQ ID NO: 66)
5'-CACTCGATCTACCAAATCGACG-3' cPyrG-del_RV2:
                                    (SEQ ID NO: 67)
5'-CCTATCCGGATATGCAGTCAC-3'
```

PCR was carried out with the use of Phusion Hot Start II High-Fidelity DNA Polymerase. The temperature conditions were: initial denaturation at 98° C. for 3 minutes; a cycle of denaturation at 98° C. for 10 seconds, annealing at 60° C. for 30 seconds, and extension at 72° C. for 3 minutes repeated 30 times; and final extension at 72° C. for 7 minutes.

Subsequently, the resulting PCR fragment was phosphorylated with T4 polynucleotide kinase and self-ligated, to construct a target CcpyrG gene-deleted construct (pUC-CcPyrG-del_C1).

2) Transformation Via CcpyrG Gene Deletion of *C. clavata* BAUA-2787 Strain

An amplified fragment obtained via PCR with the use of pUC-CcPyrG-del_C1 as a template and the set of primers (CcPyrG-del_FW3 and CcPyrG-del_RV3) was used for CcpyrG gene deletion. PCR was carried out with the use of Phusion Hot Start II High-Fidelity DNA Polymerase. The temperature conditions were: initial denaturation at 98° C. for 30 seconds; a cycle of denaturation at 98° C. for 10 seconds, annealing at 63° C. for 30 seconds, and extension at 72° C. for 30 seconds repeated 35 times; and final extension at 72° C. for 5 minutes.

The *C. clavata* BAUA-2787 strain was transformed basically in accordance with the procedure described in the section [Analysis using transcription factor high-expression strain] above, except that CM+1 mg/ml 5-FOA+0.2% uridine+0.02% uracil was used as the selection medium.

Figure 13:
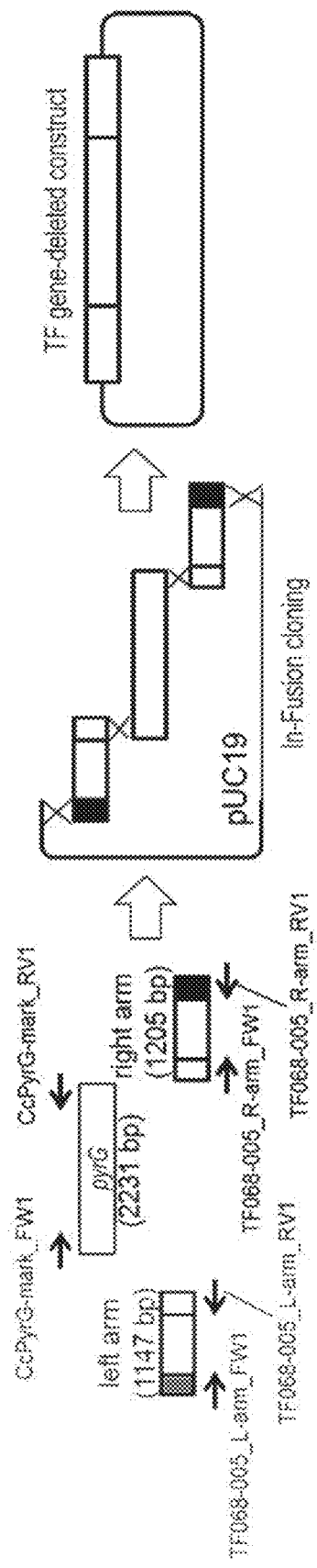

3) Construction of TF068-005 Gene-Deleted Construct (FIG. 13)

FIG. 13 shows a scheme for constructing the TF068-005 gene-deleted construct that was found to encode a transcription factor as described above.

Figure 14:
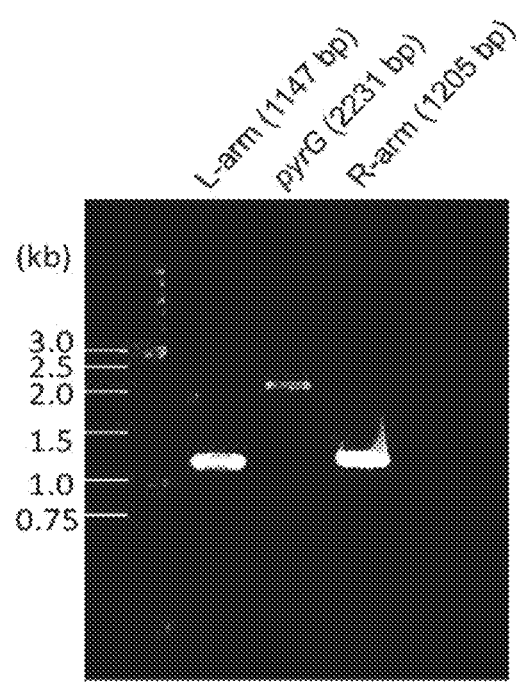

As shown in FIG. 13, the left arm (1,147 bp) was first amplified using the genome of the *C. clavata* BAUA-2787 strain as a template and primers complementary to the upstream region of the TF068-005 gene (i.e., TF068-005_L-arm_FW1 and TF068-005_L-arm_RV1). Also, the right arm (1,205 bp) was amplified using the primers complementary to the downstream region of the TF068-005 gene (i.e., TF068-005_R-arm_FW1 and TF068-005_R-arm_RV1). In addition, the selection marker gene (pyrG, 2,231 bp) was amplified with the use of the primers (i.e., CcPyrG-mark_FW1 and the cPyrG-mark_RV1). FIG. 14 shows an electrophoretic photograph of the amplified fragments.

In accordance with the protocol of the In-Fusion HD cloning Kit (Clontech), subsequently, the left arm, the pyrG marker, and the right arm amplified via PCR as described above were successively introduced into the linear pUC19 plasmid vector included in the kit. The resultant was introduced into the *E. coli* JM109 strain, and the plasmid was prepared from 3 clones of the transformant, followed by sequencing.

The sequences of the primers used for amplification of DNA fragments are shown below.

```
TF068-005_L-arm_FW1:
                                    (SEQ ID NO: 68)
5'-CGGTACCCGGGGATCCTCTGAAGCGGTCAAGGATAACG-3'

TF068-005_L-arm_RV1:
                                    (SEQ ID NO: 69)
5'-ATGAAGCAGAGCGGCGAGCCTAAGATATGCCAGGAGG-3'

TF068-005_R-arm_FW1:
                                    (SEQ ID NO: 70)
5'-CTAGCAACCGTCATGCCATAGACGTGGCACTCGAACG-3'

TF068-005_R-arm_RV1:
                                    (SEQ ID NO: 71)
5'-CGACTCTAGAGGATCCGTCTTAAGGATGGTTCAGCTGC-3'

CcPyrG-mark_FW1:
                                    (SEQ ID NO: 72)
5'-CATGACGGTTGCTAGGGTCG-3'

CcPyrG-mark_RV1:
                                    (SEQ ID NO: 73)
5'-GCCGCTCTGCTTCATTGCTG-3'
```
(The underlined portions are 15-bp overlap sequences for the in-fusion reaction.)

Figure 15:
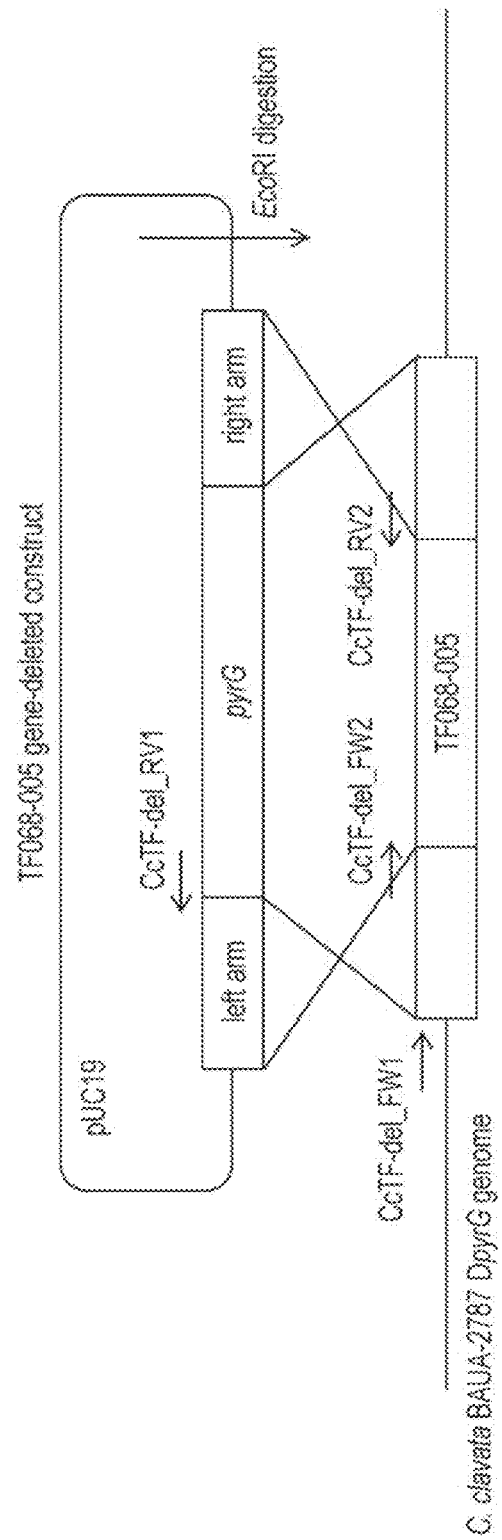

4) Transformation with TF068-005 Gene-Deleted Construct (FIG. 15)

FIG. 15 schematically shows the method for transforming the CcpyrG gene-deleted strain of the *C. clavata* BAUA-2787 strain prepared in 2) above with the TF068-005 gene-deleted construct. At the outset, the TF068-005 gene-deleted construct was linearized via digestion with the EcoRI restriction enzyme (TaKaRa) and purified with Ethachinimate (Nippon Gene, Co. Ltd.). Subsequently, the linearized construct was introduced into the *C. clavata* BAUA-2787 pyrG gene-deleted strain for transformation. Transformation was carried out basically in accordance with the protocol described in the section [Analysis using transcription factor high-expression strain]. However, the *C. clavata* BAUA-2787 pyrG gene-deleted strain was cultured in the CM+5 mM uridine+5 mM uracil medium, and the transformant was selected using MM agar medium (1% glucose, 0.6% NaNO$_3$, 0.052% KCl, 0.052% MgSO$_4$.7H$_2$O, 0.152% KH$_2$PO$_4$, and Hutner's trace elements (pH 6.5)).

5) Antibacterial Activity Test on TF068-005 Gene-Deleted Strain

The conidiospore suspension of the TF068-005 gene-deleted strain prepared in the manner described above was inoculated into 100 ml of CM medium, and culture was conducted at 26° C. and 130 rpm for 72 hours. The culture solution was filtered through Miracloth to remove the cells, sterilized through a 0.22-μm filter, and allowed to impregnate a paper disc. The paper disc and mycelial threads of gray mold (*Botrytis cinerea*) cut with agar medium were placed on a PDA medium at the interval of approximately 2.5 cm, and dual culture was then carried out at 26° C. for 3 days. A culture solution of a wild-type strain (i.e., the *C. clavata* BAUA-2787 strain) was used as a positive control, and CM medium in which cells were not cultured was used as a negative control.

6) Preparation of Total RNA of Transcription Factor Gene (TF068-005)-Deleted Strain The conidiospore suspension of the TF068-005 gene-deleted strain and that of wild-type strains were inoculated into 30 ml of CM medium, and shake culture was conducted at 26° C. and 130 rpm for 72 hours. Subsequently, the culture solution was filtered through Miracloth to collect the cells. A fraction (0.8 g) of the cells was frozen in liquid nitrogen and then grounded in a mortar using a pestle. The cells were suspended in 10 ml of ISOGEN (Nippon Gene Co., Ltd.), the resulting suspension was allowed to stand for 10 minutes, 2 ml of chloroform was added thereto, and the mixture was vortex-stirred, followed by centrifugation at 4,700×g for 10 minutes. The aqueous layer was collected, 5 ml of isopropanol was added, and the mixture was vortex-stirred, followed by centrifugation at 4,700×g for 10 minutes. The supernatant was discarded, the remnant was washed with the addition of 5 ml of 75% ethanol, centrifugation was carried out at 4,700×g for 10 minutes, the supernatant was discarded again, and RNA pellets were dissolved in 200 μl of nuclease-free water. The resulting RNA solution was purified again with the use of the RNeasy Plant Mini Kit (QIAGEN).

7) RNA-Deq Analysis of Transcription Factor Gene (TF068-005)-Deleted Strain

A library for RNA-Seq was prepared from total RNA prepared in the manner described above using the Truseq RNA Sample Prep Kit v2 (Illumina) and then applied to the next-generation sequencer (MiSeq) (paired-end; read length 75). The sequence data were mapped against the genome sequence of C. clavata using the TopHat program.

8) KK-1 Extraction and Quantification in Transcription Factor Gene-Deleted Strain and Wild-Type Strain The conidiospore suspension of the TF068-005 gene-deleted strain and that of wild-type strains were inoculated into 30 ml of CM medium, and shake culture was conducted at 26° C. and 130 rpm for 10 days. Ethyl acetate (15 ml) was added to the culture solution, and shake culture was carried out for 1 hour, followed by centrifugation at 4,700×g for 15 minutes. The ethyl acetate layer was collected, dehydrated to dryness, and then designated as the extracellular fraction. Subsequently, 10 ml of acetone was added to the aqueous layer after the ethyl acetate layer was collected, the mixture was vortex-stirred, and acetone was removed via centrifugal condensation. Ethyl acetate (15 ml) was added thereto, and the mixture was vortex-stirred, followed by centrifugation at 4,700×g for 10 minutes. The ethyl acetate layer was collected, subjected to centrifugal condensation, and then designated as the intracellular fraction. The resulting extract was dissolved in ethyl acetate again and then subjected to LC/MS analysis.

LC

Apparatus: ACQUITY UPLC I-Class system (Waters)
Column: Acquity UPLC BEH C18 2.1×100 mm
Mobile phase: DW+0.1% formic acid/acetonitrile+0.1% formic acid=50/50 (0.5 min)→2/98 (3.4 min)
Gradient: 50%-98% acetonitrile+0.1% formic acid (0.5-3.4 min)
Flow rate: 0.6 ml/min
Detection wavelength: 273 nm

MS

Apparatus: Xevo G2 QTof (Waters)
Ionization condition: Negative

Results and Discussion

Figure 16:
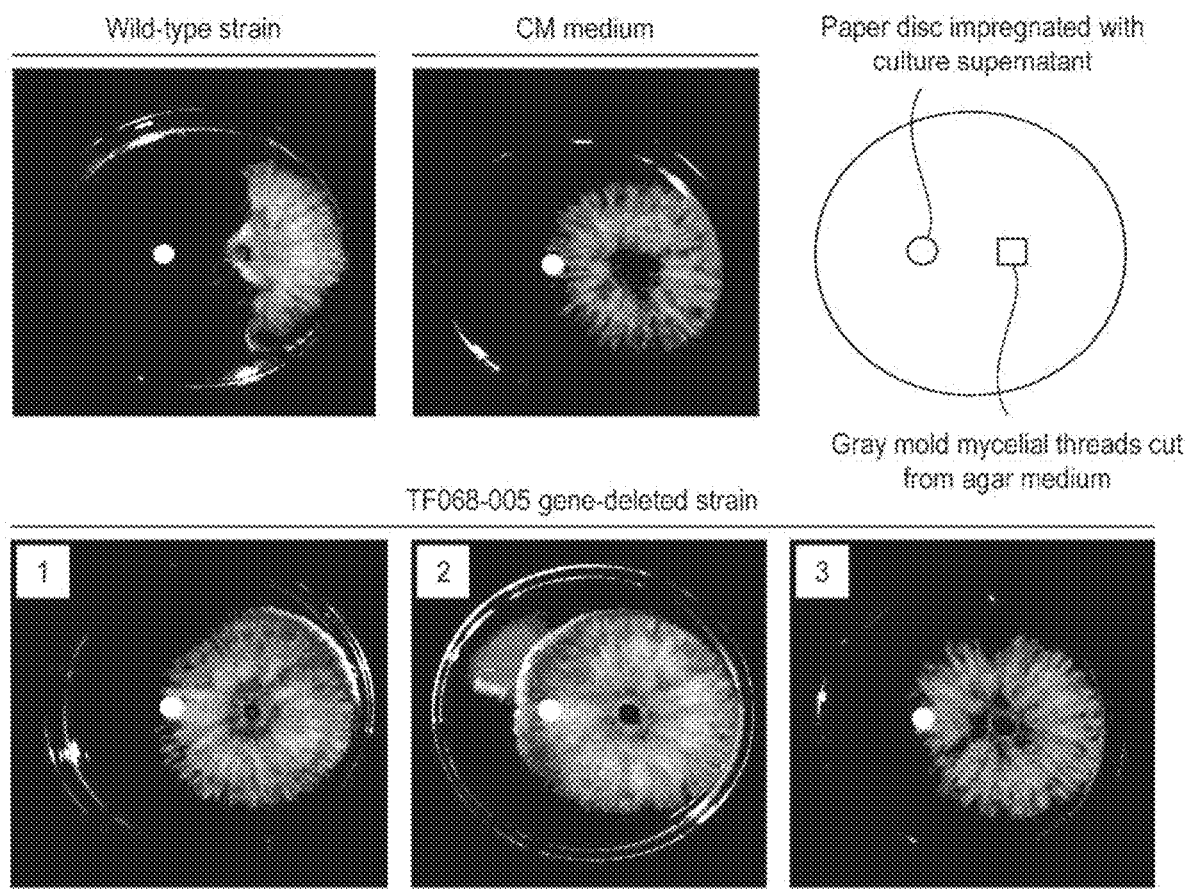

In this example, 5 strains in which TF068-005 gene deletion and nuclear purification had been observed were obtained, and antibacterial activity of the culture supernatant of these strains was inspected. FIG. 16 shows the results of the antibacterial activity test described above. FIG. 16 shows the results of the antibacterial activity test concerning 3 stains among the 5 TF068-005 gene-deleted strains obtained. As shown in FIG. 16, mycelial threads extension of gray mold toward the paper disc side was inhibited in a positive control sample (a culture solution of wild-type strains); however, inhibitory activity was not detected in the culture solution of the TF068-005 gene-deleted strain and the results similar to those concerning the negative control (a culture solution by itself) were obtained. It was thus considered that KK-1 productivity would be significantly lowered in the TF068-005 gene-deleted strain and that the TF068-005 gene would be deeply involved in the biosynthesis of KK-1.

Figure 17:
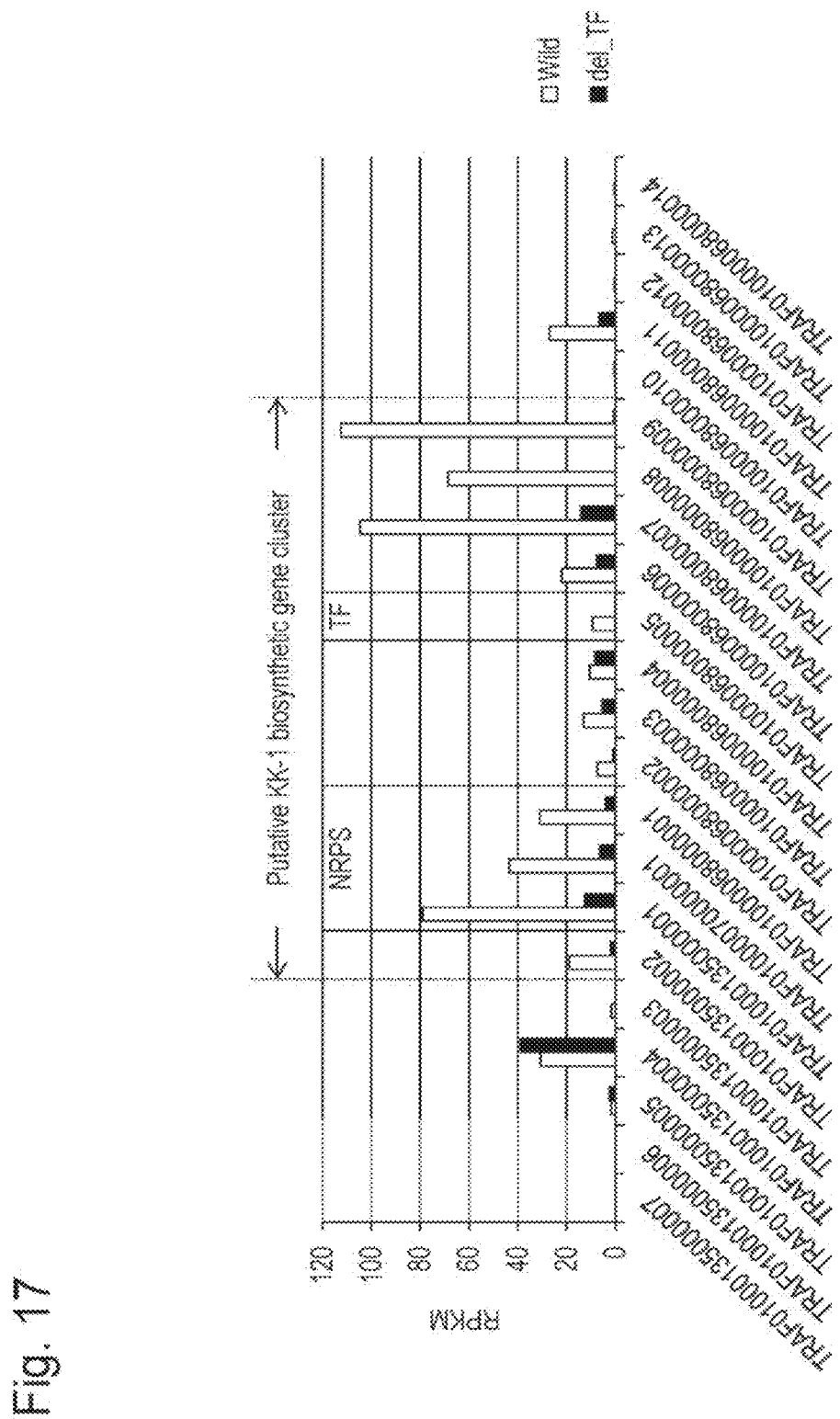

The TF068-005 gene-deleted strain was subjected to extensive gene expression analysis (RNA-seq) and analysis of KK-1 production level. In extensive gene expression analysis (RNA-seq), two TF068-005 gene-deleted strains were analyzed in comparison with wild-type strains. FIG. 17 shows the results of analysis. In FIG. 17, "del_TF" indicates the results concerning the TF068-005 gene-deleted strain. In the chart shown in FIG. 17, also, "RPKM" on the vertical axis indicates "reads per kilobase of exon per million mapped sequence reads," which are values obtained by normalizing the number of mapped sequences (lead sequences) with the total number of leads and the sequence length of the transcription product.

As shown in FIG. 17, the expression levels of the genes included in the putative biosynthetic cluster in the TF068-005 gene-deleted strain are significantly lower than those in wild-type strains. In contrast, the expression levels of the group of genes in the vicinity of the cluster (i.e., the outside of the cluster) was found to be equivalent to that in wild-type strains, except for the TRAF01000068000011 gene. On the basis of the annotated information, the TRAF01000068000011 gene is deduced to be a nucleotide-sugar transporter involved in transportation of a sugar nucleotide synthesized in a cytosol or nucleus to an endoplasmic reticulum or Golgi apparatus. Because of the absence of a sugar nucleotide in the KK-1 structure, the gene of interest was considered less likely to be involved in biosynthesis.

Figure 18:
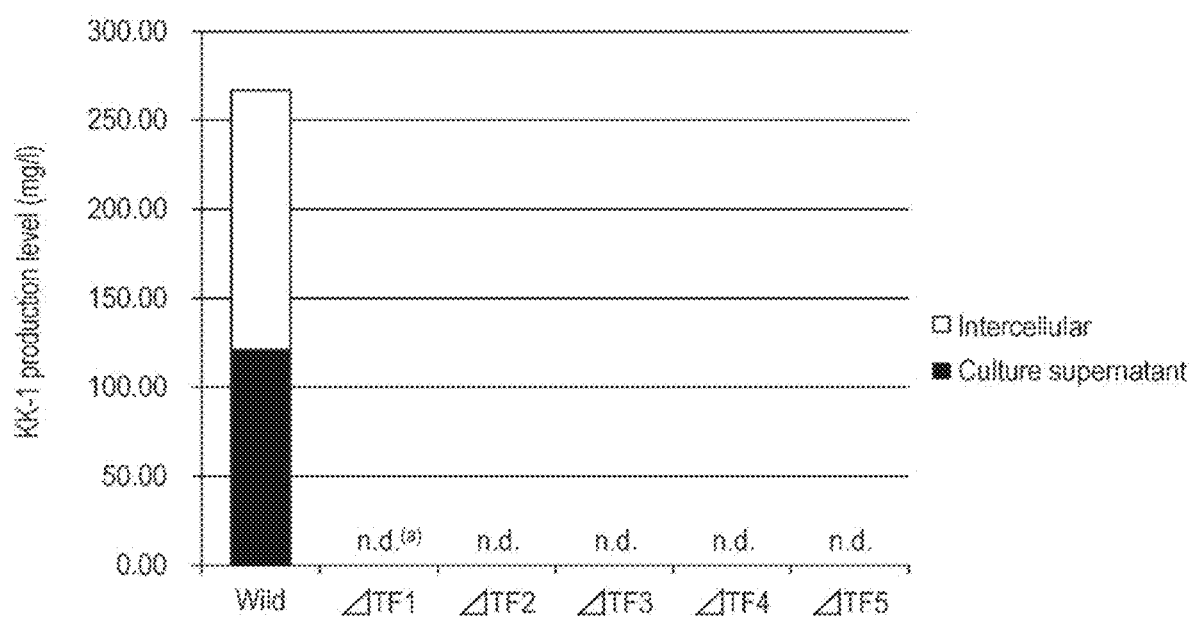

FIG. 18 shows the results of KK-1 production levels in the 5 TF068-005 gene-deleted strains analyzed via LC/MS. As shown in FIG. 18, KK-1 was not detected in the culture supernatant or in the cells in any of the 5 TF068-005 gene-deleted strains.

On the basis of the results concerning the TF068-005 gene-deleted strains and a significant increase in gene expression levels and KK-1 production levels in TF068-005 high-expression strains, it was found that the putative gene cluster would play a key role in KK-1 biosynthesis and the TF068-005 gene regulates transcription of the genes constituting the KK-1 biosynthetic gene cluster.

Example 3

In this example, gene-deleted strains of the genes included in the KK-1 biosynthetic gene cluster deduced in Example 1 were prepared and functions of the genes were analyzed.

Figure 19:
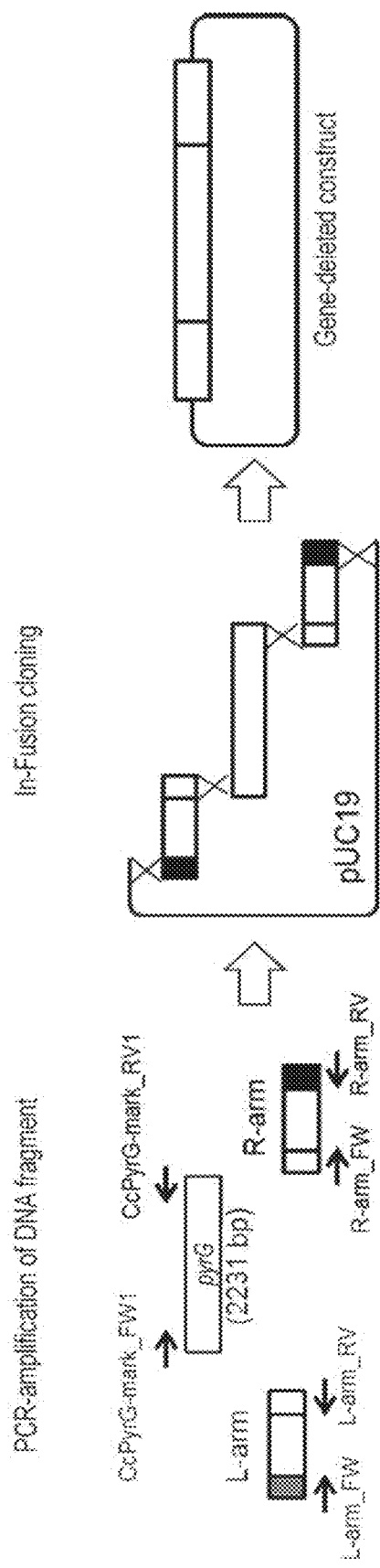

1) Construction of Cluster Gene-Deleted Construct (FIG. 19)

Except for the TRAF01000068000005 (i.e., the transcription factor gene) examined in Example 2, an upstream region of about 1,000 bp and a downstream region of about 1,000 bp of each gene included in the KK-1 biosynthetic gene cluster were designated as L-arm and R-arm, respectively, and both gene-fragments were obtained via PCR using genomic DNA of the *C. clavata* BAUA-2787 strain as a template. Also, the pyrG gene serving as a transformant selection marker was amplified via PCR. Subsequently, L-arm, the pyrG gene, and R-arm amplified via PCR were successively ligated to each other, and the resulting fragment was inserted into pUC19 using the In-Fusion Cloning Kit (Clontech), so as to prepare a gene-deleted construct (FIG. 19).

The sequences of the primers used for PCR amplification of DNA fragments constituting each construct and PCR conditions are described below. The 15-bp overlap sequences to be subjected to the in-fusion reaction are underlined.

For amplification of pyrG selection marker (the primers used in Example 2)

```
CcPyrG-mark_FW1:
                                      (SEQ ID NO: 72)
5'-CATGACGGTTGCTAGGGTCG-3'

CcPyrG-mark_RV1:
                                      (SEQ ID NO: 73)
5'-GCCGCTCTGCTTCATTGCTG-3'
```

For amplification of L-arm (982 bp) of TRAF01000135000002-deleted construct

```
TRAF135-002_del_L-arm_FW:
                                      (SEQ ID NO: 74)
5'-CGGTACCCGGGGATCGACCCATTGCAGCTTGTG-3'

TRAF135-002_del_L-arm_RV:
                                      (SEQ ID NO: 75)
5'-ATGAAGCAGAGCGGCGTGCAGTATGGTGTCTAAAACG-3'
```

For amplification of R-arm (950 bp) of TRAF01000135000002-deleted construct

```
TRAF135-002_del_R-arm_FW:
                                      (SEQ ID NO: 76)
5'-CTAGCAACCGTCATGGATGAATGAGCACCCTGTTAG-3'

TRAF135-002_del_R-arm_RV:
                                      (SEQ ID NO: 77)
5'-CGACTCTAGAGGATCGTACATTACAAAAACCTGTTGCAG-3'
```

For amplification of L-arm (1,000 bp) of TRAF01000135000001-deleted construct

```
TRAF135-001_del_L-arm_FW:
                                      (SEQ ID NO: 78)
5'-CGGTACCCGGGGATCGTCCCACGTGCAGCTTCAAC-3'

TRAF135-001_del_L-arm_RV:
                                      (SEQ ID NO: 79)
5'-ATGAAGCAGAGCGGCCGTGGAGTATCCCAGGATGG-3'
```

For amplification of R-arm (982 bp) of TRAF01000135000001-deleted construct

```
TRAF135-001_del_R-arm_FW:
                                      (SEQ ID NO: 80)
5'-CTAGCAACCGTCATGCCAGCCAAAGGGTATCATGG-3'

TRAF135-001_del_R-arm_RV:
                                      (SEQ ID NO: 81)
5'-CGACTCTAGAGGATCTGAGGGCAGCGTAGCCTG-3'
```

For amplification of L-arm (992 bp) of TRAF01000068000002-deleted construct

```
TRAF068-002_del_L-arm_FW:
                                      (SEQ ID NO: 82)
5'-CGGTACCCGGGGATCGTGGATAAATTCGTACCCTTTG-3'

TRAF068-002_del_L-arm_RV:
                                      (SEQ ID NO: 83)
5'-ATGAAGCAGAGCGGCCTGATCTTTGTTGTGGTCGTG-3'
```

For amplification of R-arm (1,014 bp) of TRAF01000068000002-deleted construct

```
TRAF068-002_del_R-arm_FW:
                                      (SEQ ID NO: 84)
5'-CTAGCAACCGTCATGCAGTTTGGCACTTGAGCATC-3'

TRAF068-002_del_R-arm_RV:
                                      (SEQ ID NO: 85)
5'-CGACTCTAGAGGATCCACGGAAAGGAACTCCTACAG-3'
```

For amplification of L-arm (912 bp) of TRAF01000068000003-deleted construct

```
TRAF068-003_del_L-arm_FW:
                                      (SEQ ID NO: 86)
5'-CGGTACCCGGGGATCCTCTGGGAAAAGCGGTTAG-3'

TRAF068-003_del_L-arm_RV:
                                      (SEQ ID NO: 87)
5'-ATGAAGCAGAGCGGCGAAGAACCGAGAGCGAGAG-3'
```

For amplification of R-arm (995 bp) of TRAF01000068000003-deleted construct

```
TRAF068-003_del_R-arm_FW:
                                      (SEQ ID NO: 88)
5'-CTAGCAACCGTCATGCTTGCATCTACCTAGATATTTCACG-3'

TRAF068-003_del_R-arm_RV:
                                      (SEQ ID NO: 89)
5'-CGACTCTAGAGGATCCAGAGAATCAGCAGAGACACC-3'
```

For amplification of L-arm (991 bp) of TRAF01000068000004-deleted construct

```
TRAF068-004_del_L-arm_FW:
                                      (SEQ ID NO: 90)
5'-CGGTACCCGGGGATCCCCTGGTAGTTCAGTGGAAGTAAG-3'

TRAF068-004_del_L-arm_RV:
                                      (SEQ ID NO: 91)
5'-ATGAAGCAGAGCGGCTGATAGAGGTACGGGGGTG-3'
```

For amplification of R-arm (1,003 bp) of TRAF01000068000004-deleted construct

```
TRAF068-004_del_R-arm_FW:
                                      (SEQ ID NO: 92)
5'-CTAGCAACCGTCATGTGCTTGGCTGCTTCAAATC-3'

TRAF068-004_del_R-arm_RV:
                                      (SEQ ID NO: 93)
5'-CGACTCTAGAGGATCCTAATACTTGTCGTCCCACTGATG-3'
```

For amplification of L-arm (993 bp) of TRAF01000068000006-deleted construct

```
TRAF068-006_del_L-arm_FW:
                                          (SEQ ID NO: 94)
5'-CGGTACCCGGGGATCGCAGTACATCGTCAGGGTC-3'

TRAF068-006_del_L-arm_RV:
                                          (SEQ ID NO: 95)
5'-ATGAAGCAGAGCGGCGATGAATAAGGCGAAGGAAAG-3'
```

For amplification of R-arm (579 bp) of TRAF01000068000006-deleted construct

```
TRAF068-006_del_R-arm_FW:
                                          (SEQ ID NO: 96)
5'-CTAGCAACCGTCATGCCCTCTTTTTTCTTGCTGTCTC-3'

TRAF068-006_del_R-arm_RV:
                                          (SEQ ID NO: 97)
5'-CGACTCTAGAGGATCGAAGGAAGGACGGATACTGG-3'
```

For amplification of L-arm (769 bp) of TRAF01000068000007-deleted construct

```
TRAF068-007_del_L-arm_FW:
                                          (SEQ ID NO: 98)
5'-CGGTACCCGGGGATCGATGAGCGTAGAATTCGTAAAAAG-3'

TRAF068-007_del_L-arm_RV:
                                          (SEQ ID NO: 99)
5'-ATGAAGCAGAGCGGCGCGAACGGGCGTTTTTC-3'
```

For amplification of R-arm (579 bp) of TRAF01000068000007-deleted construct

```
TRAF068-007_del_R-arm_FW:
                                          (SEQ ID NO: 100)
5'-CTAGCAACCGTCATGGAAGGAAGGACGGATACTGG-3'

TRAF068-007_del_R-arm_RV:
                                          (SEQ ID NO: 101)
5'-CGACTCTAGAGGATCCCCTCTTTTTTCTTGCTGTCTC-3'
```

For amplification of L-arm (716 bp) of TRAF01000068000008-deleted construct

```
TRAF068-008_del_L-arm_FW:
                                          (SEQ ID NO: 102)
5'-CGGTACCCGGGGATCCTCCTTATTTTGCAACTTCTGATAC-3'

TRAF068-008_del_L-arm_RV:
                                          (SEQ ID NO: 103)
5'-ATGAAGCAGAGCGGCCGTGTTGATTTTGGTAATTTTG-3'
```

For amplification of R-arm (769 bp) of TRAF01000068000008-deleted construct

```
TRAF068-008_del_R-arm_FW:
                                          (SEQ ID NO: 104)
5'-CTAGCAACCGTCATGGATGAGCGTAGAATTCGTAAAAAG-3'

TRAF068-008_del_R-arm_RV:
                                          (SEQ ID NO: 105)
5'-CGACTCTAGAGGATCGCGAACGGGCGTTTTTC-3'
```

For amplification of L-arm (716 bp) of TRAF01000068000009-deleted construct

```
TRAF068-009_del_L-arm_FW:
                                          (SEQ ID NO: 106)
5'-CGGTACCCGGGGATCCGTGTTGATTTTGGTAATTTTG-3'

TRAF068-009_del_L-arm_RV:
                                          (SEQ ID NO: 107)
5'-ATGAAGCAGAGCGGCCTCCTTATTTTGCAACTTCTGATAC-3'
```

For amplification of R-arm (989 bp) of TRAF01000068000009-deleted construct

```
TRAF068-009_del_R-arm_FW:
                                          (SEQ ID NO: 108)
5'-CTAGCAACCGTCATGCTAGCAGCCATAAGAGACGTAACC-3'

TRAF068-009_del_R-arm_RV:
                                          (SEQ ID NO: 109)
5'-CGACTCTAGAGGATCGTTTTCATTGCATGCTCCG-3'
```

PCR conditions

PCR was carried out with the use of the Phusion High-Fidelity DNA Polymerase (Thermo Fisher Scientific). The temperature conditions were: initial denaturation at 98° C. for 30 seconds; a cycle of denaturation at 98° C. for 10 seconds, annealing at 60° C. for 30 seconds, and extension at 72° C. for 45 seconds repeated 30 times; and final extension at 72° C. for 5 minutes.

2) Transformation of C. clavata pyrG-Deleted Strain

Figure 20:
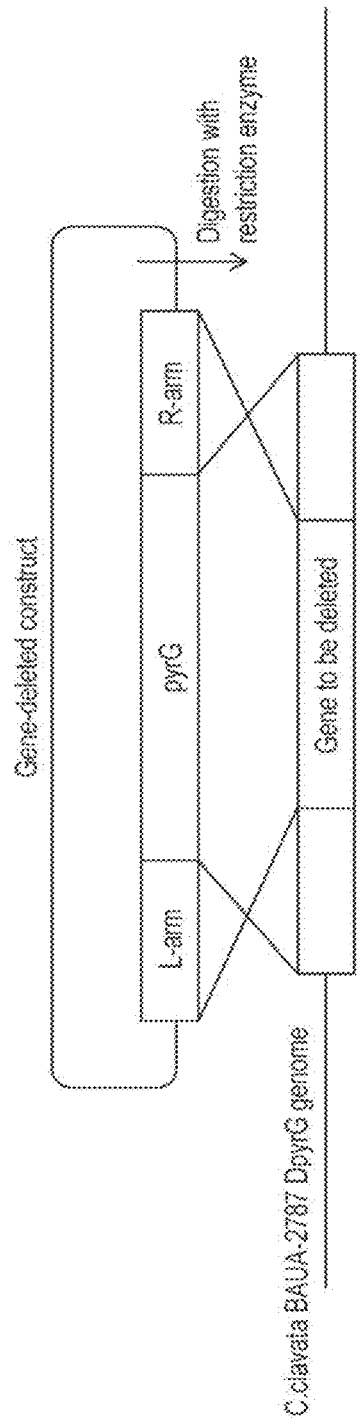

FIG. 20A schematically shows a method for transforming the CcpyrG gene-deleted strain of the C. clavata BAUA-2787 strain prepared in Example 2 2) with a relevant gene-deleted construct. The resulting gene-deleted construct was linearized with a given restriction enzyme (shown in FIG. 20B). Subsequently, the linearized construct was introduced into the C. clavata BAUA-2787 pyrG gene-deleted strain in accordance with the protocol described in the section [Analysis using transcription factor high-expression strain] in Example 2. When culturing the host C. clavata BAUA-2787 pyrG gene-deleted strain, liquid CM medium supplemented with 5 mM uridine and uracil was used, and transformant selection was carried out in MM agar medium.

3) Culture of Cluster Gene-Deleted Strain

The conidiospore suspension of the gene-deleted strains obtained in 2) above was inoculated into 30 ml of KM medium (a 100-ml baffled triangular flask), shake culture was conducted at 26° C. and 130 rpm for 3 days, and the product was designated as a "preculture solution." Subsequently, 300 μl of the preculture solution was inoculated into 30 ml of the CM medium (a 100-ml baffled triangular flask), and shake culture was then conducted at 26° C. and 130 rpm for 7 days.

4) Extraction and Analysis of Metabolite in the Culture System

Ethyl acetate (15 ml) was added to the culture solution obtained in 3) above, shake culture was carried out at 130 rpm for 1 hour, and centrifugation was then carried out at 4,200×g for 15 minutes. The ethyl acetate layer was collected, subjected to centrifugal condensation, and then designated as an extracellular fraction. Subsequently, 10 ml of acetone was added to an aqueous layer after the ethyl acetate layer was collected, the mixture was vortex-stirred, and acetone was removed via centrifugal condensation. Ethyl acetate (15 ml) was added thereto, and the mixture was vortex-stirred, followed by centrifugation at 4,200×g for 10 minutes. The ethyl acetate layer was collected, subjected to centrifugal condensation, and then designated as an intracellular fraction. After the extracellular fraction was dissolved in 500 µl of ethyl acetate in combination with the intracellular fraction, 1 µl of the extract was subjected to LC/MS analysis.

Conditions for LC/MS analysis

LC

Apparatus: ACQUITY UPLC I-Class System (Waters)
Column: Acquity UPLC BEH C18, 2.1×100 mm
Mobile phase: DW/MeCN=50/50 (0.5 min)→2/98 (3.4 min) (each solvent contains 0.1% formic acid)
Flow rate: 0.6 ml/min
Detection wavelength: 273 nm

MS

Apparatus: Xevo G2 QTof (Waters)
Ionization condition: Negative

Results and Discussion

Figure 21:
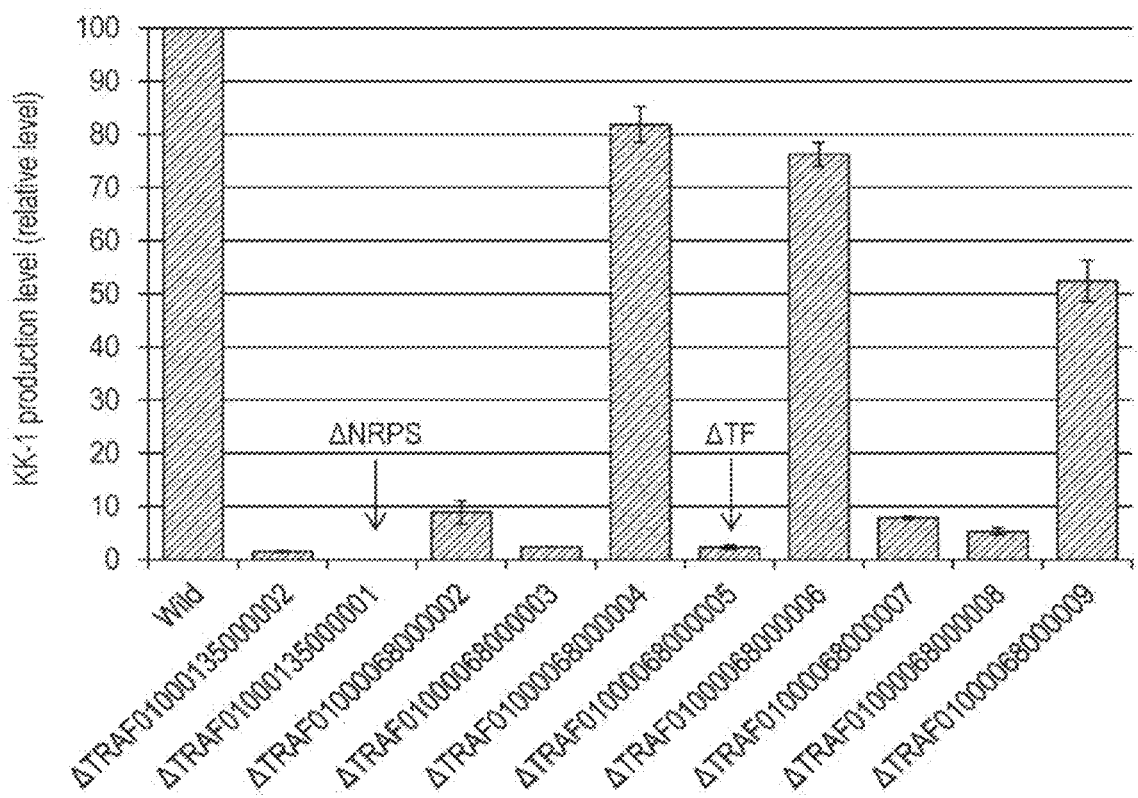

The gene-deleted strains prepared in this example and the transcription factor gene-deleted strains prepared in Example 2 were inspected in terms of KK-1 productivity. The results are shown in FIG. 21. In FIG. 21, the KK-1 production level of each strain (i.e., the amount relative to a wild-type strain) is indicated in terms of "mean±standard error (n=2)." As shown in FIG. 21, KK-1 production was completely quenched in a strain in which the NRPS (TRAF01000135000001) gene biosynthesizing a cyclic peptide in a basic backbone had been deleted. This indicates that such gene is essential for biosynthesis of KK-1.

As shown in FIG. 21, also, the KK-1 production levels of strains lacking 5 types of genes (i.e., TRAF01000135000002, TRAF01000068000002, TRAF01000068000003, TRAF01000068000007, and TRAF01000068000008) among the group of genes included in the gene cluster were significantly lower than those in wild-type strains. Accordingly, these genes were considered to be deeply involved in KK-1 production at the time of, for example, modification of the cyclic peptide backbone biosynthesized by NRPS.

In the strains lacking 3 types of genes (i.e., TRAF01000068000004, TRAF01000068000006, and TRAF01000068000009), as shown in FIG. 21, the KK-1 production levels were lower than those in wild-type strains, although a range of fluctuation was smaller than the 5 types of genes described above. This indicates that these 3 types of genes are also involved in KK-1 production. In fact, a protein encoded by TRAF01000068000006 is deduced to be an ABC transporter, and it is considered to be involved in efflux of KK-1 produced in the cells toward the outside of the cells. Regarding TRAF01000068000009 annotated as "α/β hydrolase," a gene encoding thioesterase that hydrolyzes an erroneously incorporated substrate is included in the lankamycin biosynthetic cluster, which is a polyketide antibiotics produced by *Actinomycetes*, i.e., *Streptomyces rochei* 7434AN4. Accordingly, such gene was considered to function in the same manner. Since TRAF01000068000004 is as small as 8.1 kDa and there is no protein similar thereto, it may not have particular functions.

Example 4

In this example, the KK-1 biosynthetic gene cluster subjected to function analysis in Examples 1 to 3 was introduced into *Aspergillus oryzae*, and heterologous production of KK-1 in *Aspergillus oryzae* was examined.

1) *Aspergillus oryzae* strain and medium (*A. oryzae* strain and growth medium)

As parent *Aspergillus oryzae* (*A. oryzae*) strains into which the KK-1 biosynthetic gene cluster was to be introduced, the NS4 ΔadeA strains (sC-, niaD-, ΔligD::sC, ΔadeA::ptrA) were used. General growth and conidiospore formation were implemented in the Czapek-dox (CD) minimal medium satisfying auxotrophy of the strains (0.6% NaNO₃, 0.052% KCl, 0.152% KH₂PO₄, 0.0001% FeSO₄.7H₂O, 0.00088% ZnSO₄.7H₂O, 0.00004% CuSO₄.5H₂O, 0.000015% MnSO₄.4H₂O, 0.00001% Na₂B₄O₇.10H₂O, 0.000005% (NH₄)₆Mo₇O₂₄.4H₂O, 0.059% MgSO₄.7H₂O, and 2% glucose). Specifically, a medium supplemented with 70 mM sodium glutamate instead of NaNO₃ as a nitrogen source (CDE) or a medium prepared by supplementing CDE with 0.01% adenine (CDEA) was used. YPM medium (1% yeast extract, 2% polypeptone, 2% maltose) was used to induce expression of the gene introduced with the aid of the *Aspergillus oryzae* amyB promoter, and YPM medium was also used to evaluate KK-1 productivity.

Figure 22:
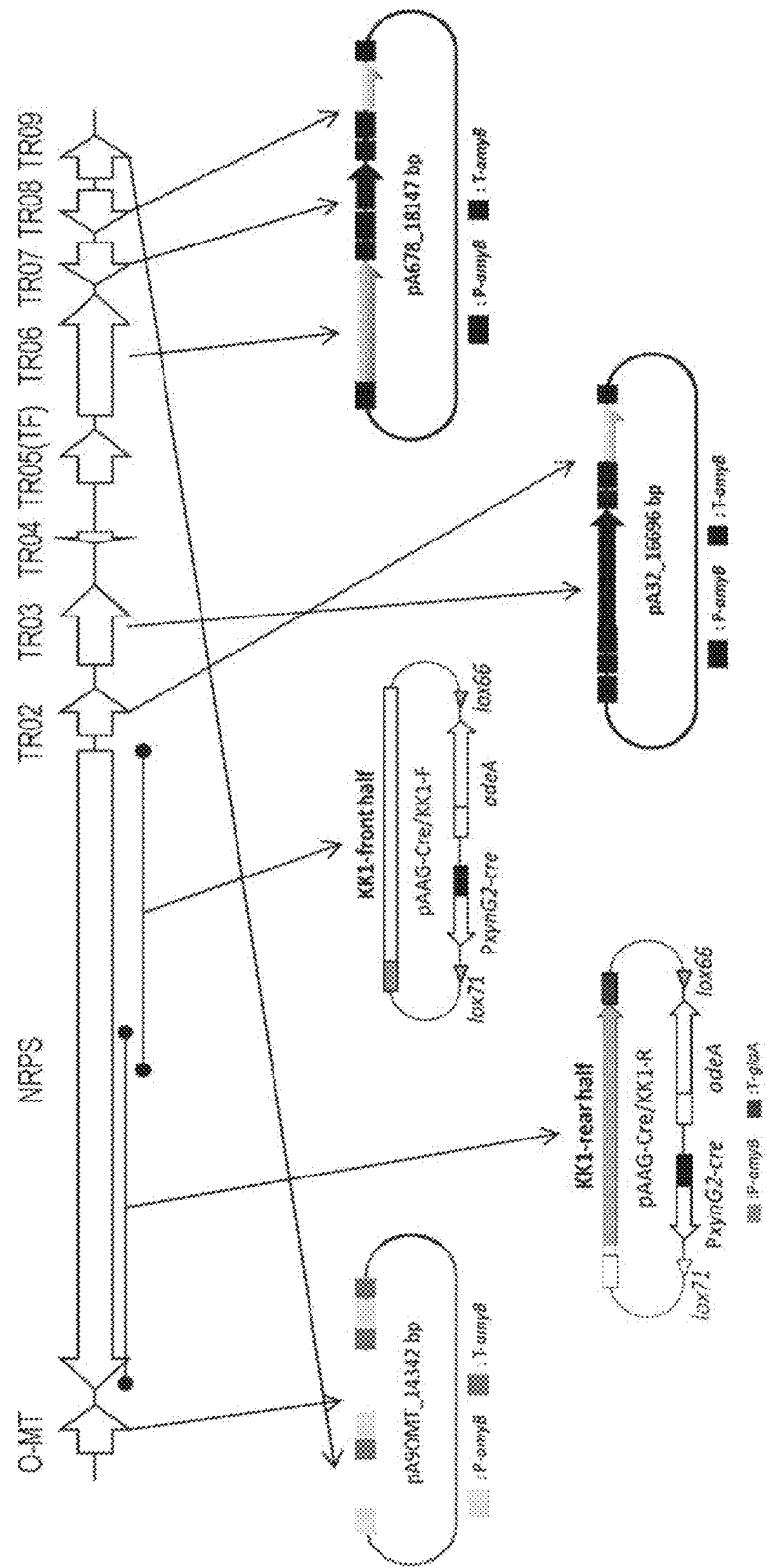

2) Construction of Vector for Separate Introduction of NRPS Gene (FIG. 22)

FIG. 22 schematically shows a scheme for constructing a vector used when introducing the KK-1 biosynthetic gene cluster. Among the genes included in the KK-1 biosynthetic gene cluster, as shown in FIG. 22, the NRPS gene was divided into two fragments and introduced into *Aspergillus oryzae*. Specifically, a 39-kb gene (full-length) was divided into a front half portion (about 20 kb) and a rear half portion (about 20 kb) and separately subcloned into a plasmid vector, and the resultants were then introduced into *Aspergillus oryzae*. Thereafter, a transformant, the both fragments of which had been ligated to each other in *Aspergillus oryzae*, were selected. As a plasmid vector, pAAG-Cre whose marker could be reused via expression of endogenous Cre recombinase was used.

At the outset, PCR was carried out with the use of the primers (NRPS-fh-F and NRPS-fh-R) to amplify the gene of the front half portion. PCR was carried out with the use of genomic DNA of the *C. clavata* BAUA-2787 strain as a template and PrimeSTAR GXL DNA Polymerase (Takara) as an enzyme in accordance with the manufacturer's instructions. The PCR product was ligated to the EcoRV-cleavage site of pZErO-2 (Invitrogen). The front half portion of the NRPS gene was cleaved from the plasmid with NotI and ligated to the corresponding site of pAAG-Cre. A plasmid in which the PamyB promoter for *Aspergillus oryzae* and the NRPS gene had been ligated in the correct orientation was selected and designated as the vector for introduction of the front half of the NRPS gene (pAAG-Cre/KK1-F).

It was difficult to subject the gene of the rear half portion of the NRPS gene to cloning via PCR amplification through a single procedure. Thus, the portion was further divided into three fragments, the fragments were separately amplified, and the amplified fragments were then ligated to each other via in-fusion cloning. First of all, the fragments A, B, and C of the rear half portion were amplified via PCR. The fragment A of the rear half portion was amplified with the use of primers NRPS-rh-IF-Fa and NRPS-rh-IF-Ra, the fragment B was amplified with the use of primers NRPS-rh-IF-Fb and NRPS-rh-IF-Rb, and the fragment C was amplified with the use of primers NRPS-rh-IF-Fc and NRPS-rh-IF-Rc. These fragments were each ligated to the NotI-digested pAAG-Cre via in-fusion cloning, and the plasmid ligated in the correct orientation was designated as the vector for introduction of the rear half of the NRPS gene (pAAG-Cre/NRPSrh).

In-fusion cloning was carried out with the use of the In-Fusion HD Cloning kit (Clontech) in accordance with the manufacturer's instructions. The gene sequences of the vector for introduction of the front half of the NRPS gene and the vector for introduction of the rear half thereof were inspected to confirm that no variation would occur in NRPS.

The sequences of the primers used are shown below.

```
NRPS-fh-F:
                                 (SEQ ID NO: 110)
TCGACAAGCTTGCGGCCGCCACGTGACTAGTATGGCCAGCGACATCAATAC
TCATCCAG

NRPS-fh-R:
                                 (SEQ ID NO: 111)
ACTAGTCACGTGGCGGCCGCGGCGCGCCAAGATCGTCTTGCTGTACG

NRPS-rh-IF-Fa:
                                 (SEQ ID NO: 112)
GATGCGCTAGCGGCCGCGAAGTGGTCCTTGTCGCTGGTGAC

NRPS-rh-IF-Ra:
                                 (SEQ ID NO: 113)
TGCCGTTCGCATTCATAGGCATCTCGTC

NRPS-rh-IF-Fb:
                                 (SEQ ID NO: 114)
TGAATGCGAACGGCAAGGTTGACAG

NRPS-rh-IF-Rb:
                                 (SEQ ID NO: 115)
CTTGGTTGCTGGCTTCGTCGTTGTC

NRPS-rh-IF-Fc:
                                 (SEQ ID NO: 116)
AAGCCAGCAACCAAGTCGAAGATTG

NRPS-rh-IF-Rc:
                                 (SEQ ID NO: 117)
GTCACTAGTGCGGCCGCCTATTTTTGCAAGATCTTGTTCAAAC
```

3) Construction of Vector for Cluster Gene Introduction (FIG. 22)

Among the genes included in the KK-1 biosynthetic gene cluster, as described in Example 2, TRAF01000068000004 is not essential for biosynthesis of KK-1. Since TRAF01000068000005 is a transcription factor that regulates cluster gene expression, when all genes are to be regulated by a promoter for *Aspergillus oryzae*, accordingly, this gene may not be necessary. In order to introduce 7 genes except for the NRPS gene and these 2 genes into *Aspergillus oryzae*, as shown in FIG. 22, a gene introduction vector carrying such genes was constructed.

As a plasmid carrying the genes of interest, pA3AXPC capable of simultaneously carrying 3 genes at most and regulating all genes with the amyB promoter was selected (pA3AXPC can be provided by Professor Katsuya Gomi, Laboratory of Bioindustrial Genomics, Tohoku University). The plasmid carries the Cre-loxP marker recycling system utilizing Cre recombinase and loxP sequences, and it is a vector suitable for gene introduction at multiple stages.

At the outset, PCR was carried out using cDNA of the *C. clavata* BAUA-2787 strain as a template to amplify the genes. The TRAF01000068000002 gene was amplified with the use of the set of primers TR02-SpeI-F and TR02-SpeI-R, and the TRAF01000068000003 gene was amplified with the use of the set of primers TR03-NotI-F and TR03-NotI-R. The amplified fragments were ligated to the EcoRV cleavage site of pZErO-2 (referred to as pZTR02 and pZTR03, respectively). Thereafter, the TRAF01000068000002 gene was cleaved from pZTR02 via digestion with SpeI, and the TRAF01000068000003 gene was cleaved from pZTR03 via digestion with NotI. The cleaved TRAF01000068000002 (SpeI) and TRAF01000068000003 (NotI) genes were successively introduced into the SpeI site and the NotI site of pA3AXPC. A plasmid into which these genes had been inserted in the correct orientation was designated as pATR0203.

Subsequently, the TRAF01000068000006 gene was amplified with the use of the set of primers TR06-NheI-F and TR06-NheI-R, the TRAF01000068000007 gene was amplified with the use of the set of primers TR07-NotI-F and TR07-NotI-R, and the TRAF01000068000009 gene was amplified with the use of the set of primers TR08-SpeI-F and TR08-SpeI-R. The PCR-amplified fragments were ligated to the EcoRV cleavage site of pZErO-2 (the resultants are referred to as pZTR06, pZTR07, and pZTR08, respectively). Thereafter, the TRAF01000068000006 gene was cleaved from pZTR06 via digestion with NheI, the TRAF01000068000007 gene was cleaved from pZTR07 via digestion with NotI, and the TRAF01000068000008 gene was cleaved from pZTR08 via digestion with SpeI. The cleaved TRAF01000068000006 (NheI), TRAF01000068000008 (SpeI), and TRAF01000068000007 (NotI) genes were successively introduced into the NheI site, the SpeI site, and the NotI site of pA3AXPC, respectively. A plasmid into which these genes had been inserted in the correct orientation was designated as pATR678.

In the end, the TRAF01000068000009 gene was amplified with the use of the set of primers TR09-NheI-F and TR09-NheI-R, and the TRAF01000135000002 gene was amplified with the use of the set of primers OMT-NotI-F and OMT-NotI-R. The PCR-amplified fragments were ligated to the EcoRV cleavage site of pZErO-2 (the resultants are referred to as pZTR09 and pZOMT, respectively). Thereafter, the TRAF01000068000009 gene was cleaved from pZTR09 via digestion with NheI, and the TRAF01000135000001 gene was cleaved from pZOMT via digestion with NotI. The cleaved TRAF01000068000009 (NheI) and TRAF01000135000001OMT (NotI) genes were successively introduced into the NheI site and the NotI site of pA3AXPC, respectively. A plasmid into which these genes had been inserted in the correct orientation was designated as pATR09OMT.

The sequences of the primers used are shown below.

```
TR02-SpeI-F:
                                 (SEQ ID NO: 118)
GGACTAGTATGACTGAACCCACATGGAAG

TR02-SpeI-R:
                                 (SEQ ID NO: 119)
GGACTAGTTTAATAATCTACTTCAAGCAC

TR03-NotI-F:
                                 (SEQ ID NO: 120)
ATAAGAATGCGGCCGCATGGCGTTGCAAGAGCG

TR03-NotI-R:
                                 (SEQ ID NO: 121)
ATAAGAATGCGGCCGCTCAAGATGGGAAAGCCGCTG

TR06-NheI-F:
                                 (SEQ ID NO: 122)
CTAGCTAGCATGAGTGCTATCGAGCTGC
```

```
TR06-NheI-R:
                                 (SEQ ID NO: 123)
CTAGCTAGCTCAGCGATTGAGGGCCTGG

TR07-NotI-F:
                                 (SEQ ID NO: 124)
ATAAGAATGCGGCCGCATGAAGCTCACCGTTTTCAG

TR07-NotI-R:
                                 (SEQ ID NO: 125)
ATAAGAATGCGGCCGCTCAGAGCCGCGCCAAC

TR08-SpeI-F:
                                 (SEQ ID NO: 126)
GGACTAGTATGACGAAAAGGGAAAGCAAC

TR08-SpeI-R:
                                 (SEQ ID NO: 127)
GGACTAGTCTACGCGTTTTCTTTCGAC

TR09-NheI-F:
                                 (SEQ ID NO: 128)
CTAGCTAGCATGGAGAGCGAAGACAATCC

TR09-NheI-R:
                                 (SEQ ID NO: 129)
CTAGCTAGCTCAGCAGTATCCCATCGG

OMT-NotI-F:
                                 (SEQ ID NO: 130)
ATTTGCGGCCGCATGGACCCGAGACAGTCACGGATC

OMT-NotI-R:
                                 (SEQ ID NO: 131)
ATTTGCGGCCGCTTATGGTGTGGTGGGTTGCCATTC
```

4) Method of Gene Introduction into *Aspergillus oryzae*

Transformation of *Aspergillus oryzae* using various plasmids prepared in 3) above was carried out by the protoplast-PEG method. Conidiospores ($1\times10^7$ cells) of the parent strain (the NS4 ΔadeA strain) were inoculated into 100 ml of YPD liquid medium (1% yeast extract, 2% polypeptone, and 2% glucose) in a 200-ml triangular flask, shake culture was carried out at 30° C. and 160 rpm for 20 hours, and the resulting mycelial threads were collected through Miracloth (CALIBIOCHEM). The collected mycelial threads were washed with sterilized water, and a dry-heat-sterilized spatula was pressed against the cells for dehydration. The collected mycelial threads were introduced into a 50-ml tube, and 25 ml of a solution for protoplast preparation (the solution composed of 10 mg/ml lysing enzymes (Sigma), 5 mg/ml Cellulase Onozuka (Yakult Pharmaceutical Ind. Co., Ltd.), 2.5 mg/ml Yatalase (TAKARA) in 0.8 M NaCl, and 10 mM phosphate buffer (pH 6.0)), which had been filtered through a 0.20-μm filter, was added to prepare a suspension. Shake culture was conducted at 30° C. and 83 rpm for 3 hours to digest the cell wall. Thus, protoplasts were prepared. After the reaction, undigested cells were filtered through sterilized Miracloth, and the filtrate was centrifuged at 4° C. and 2,500×g for 5 minutes to collect protoplasts. The collected protoplasts were washed with 10 ml of 0.8 M NaCl and recentrifuged at 4° C. and 2,500×g for 5 minutes, and the precipitated protoplasts were then collected. Solution I (Sol. I) (0.8 M NaCl, 10 mM $CaCl_2$, 10 mM Tris-HCl (pH 8.0)) was added to prepare a suspension while adjusting the protoplast density to $2\times10^8$ cells/ml, Solution II (Sol. II) (40% (w/v) PEG4000, 50 mM $CaCl_2$, 50 mM Tris-HCl (pH 8.0)) in an amount one-fifth the amount of the suspension was added, and the resultant was then thoroughly mixed. A protoplast solution (240 μl) was fractionated into a 15-ml tube, 5 μg to 20 μg of the DNA solution was added thereto, the resultant was thoroughly mixed, and the mixture was then allowed to stand in ice for 30 minutes. Subsequently, 1 ml of Sol. II was added thereto, the resultant was thoroughly mixed, and the mixture was allowed to stand at room temperature for 20 minutes. Sol. I (10 ml) was added thereto, the resultant was thoroughly mixed, and the mixture was centrifuged at room temperature and 2,500×g for 5 minutes, the supernatant was removed, and 300 μl of Sol. I was added thereto. The protoplasts were homogeneously suspended, the suspension was dispersed in CDE selection agar medium containing 0.8 M NaCl, and 5 ml of soft agar medium (0.6% (w/v) agar) of the same composition that had been heated to 55° C. was poured thereinto from the circumference thereof to overlay the soft agar medium to quickly and homogeneously suspend the protoplasts. Thereafter, culture was continued at 30° C. until colonies were formed.

5) Marker Recycling in *Aspergillus oryzae*

Marker recycling in *Aspergillus oryzae* was carried out in accordance with the method described below. Specifically, the adeA selection marker and Cre recombinase were located between the mutant loxP sequences (lox66 and lox71), Cre recombinase was allowed to express so as to cause a looping out between the loxP sequences, and the adeA selection marker was then removed. The expression of Cre recombinase can be induced with a xylose-inducible promoter. Specifically, the cells comprising the aforementioned system incorporated therein are inoculated into a medium comprising xylose as a carbon source, and Cre recombinase is expressed. Thus, the cells from which the adeA selection marker has been removed can be obtained. In cells from which the adeA selection marker has been removed, adenine-requiring properties are restored. Thus, a gene recombinant can be selected using the adeA selection marker again.

Figure 23:
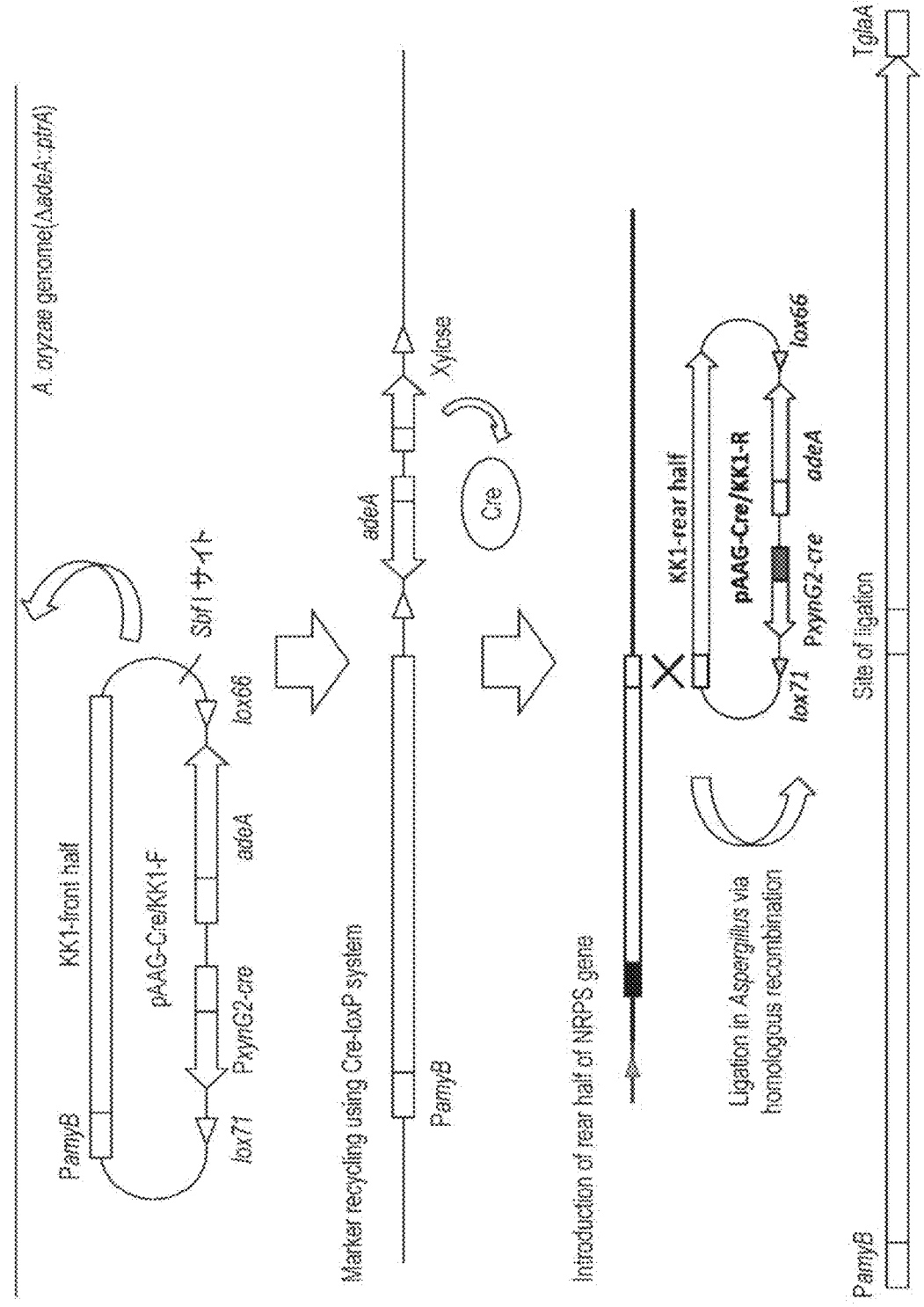

6) Reconstruction of KK-1 NRPS Gene in *Aspergillus oryzae* (FIG. 23)

FIG. 23 schematically shows a scheme for introducing a front half portion and a rear half portion of the NRPS gene with the use of the Cre-loxP system at two stages. As shown in FIG. 23, the pAAG-Cre/NRPSfh vector carrying the front half portion of the NRPS gene was first introduced into *Aspergillus oryzae*. Introduction of the vector into the resulting transformant was inspected via PCR. In order to introduce the rear half portion into the strain, Cre-loxP-mediated marker recycling was performed. In order to express Cre recombinase in the vector (regulated by the xynG2 promoter), cells were allowed to grow in a xylose-containing CDE medium supplemented with adenine (i.e., CDEAX medium). Among the grown cells, reddish colonies indicating deletion of the adeA gene as a marker were selected. The selected colonies were subjected to nuclear purification to confirm that such cells could not grow in an adenine-free medium.

In order to introduce the rear half portion of NRPS into the marker-recycled strain, subsequently, the strain was subjected to transformation by introducing pAAG-Cre/NRPSrh. Among the auxotrophy-restored strains, strains in which the front and rear half portions had been connected were selected via PCR. DNAs were extracted from the final candidate strains, and whether or not the full-length sequence had been connected was examined via PCR. As a result, introduction of the full-length NRPS gene was confirmed.

Subsequently, whether or not the site of connection had been correctly recombined via homologous recombination was inspected by determining the sequence of the site of connection. As a result, no mutations or shifts were observed at the site of connection. These results demonstrate that the NRPS gene was correctly reconstructed in *Aspergillus oryzae*.

In order to introduce other genes in the cluster into the strain, Cre-loxP-mediated marker recycling was carried out. After restoration of adenine-requiring properties was confirmed, strains in which nuclear purification had been observed were designated as parent strains subjected to all instances of gene introduction below.

7) High-Level Expression of Essential Genes in the Cluster in *Aspergillus oryzae*

The pATR0203, pATR678, and pATR09OMT plasmids carrying genes in the cluster prepared in 3) above were successively and repeatedly subjected to marker recycling and introduced into *Aspergillus oryzae*. In the strains into which all plasmids had been introduced, however, deletion of the TRAF01000068000009 gene was observed. Also, partial deletion of the NRPS gene from the strain of this lineage was found. In addition, the presence or absence of gene deletion was inspected in strains of other lineages. As a result, gene deletion was observed repeatedly. These results indicate that a looping out may have occurred between adjacent promoter sequences at the time of marker recycling or transformation. In order to redesign a strategy of introduction and minimize the number of procedures of marker recycling or transformation, as shown in FIG. 24, 3 types of vectors carrying 7 genes were to be simultaneously introduced. As a result, strains in which introduction of all the genes had been confirmed were obtained.

Figure 25:
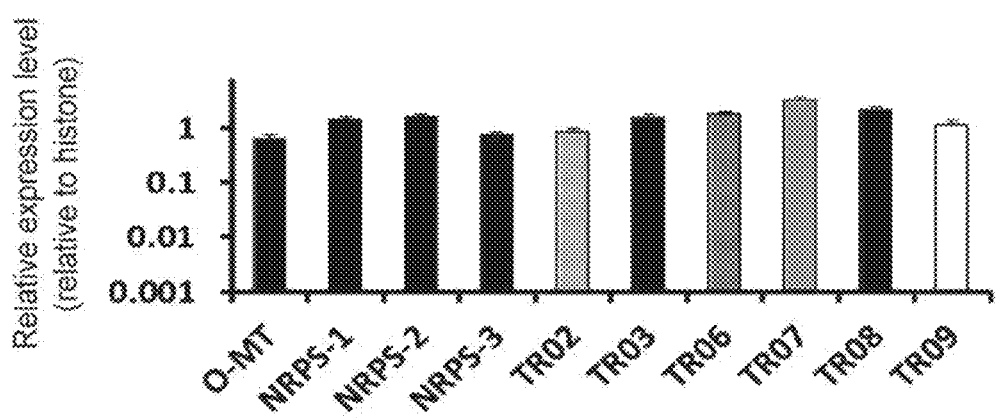

8) Transcription Analysis (FIG. 25)

Subsequently, the transformed *Aspergillus oryzae* into which the KK-1 biosynthetic gene cluster prepared in the manner described above had been introduced was analyzed in respect of expression of the genes introduced. After the cells were shake-cultured in YMP medium (the medium containing 2% maltose as a promoter-derived substrate) for 24 hours, the culture solution was filtered through Miracloth to collect the cells. The cells were immediately frozen with liquid nitrogen and quickly disrupted in liquid nitrogen with the use of a pestle in a mortar. The disrupted cells were transferred to a 1.5-ml Eppendorf tube and RNA was extracted in accordance with the protocol of the RNeasy Plant Mini Kit (QIAGEN). In order to avoid DNA inclusion, DNase treatment was also carried out in an ion column in accordance with the protocol included in the kit. In the end, total RNA was obtained through elution with 50 µl of RNase-free water two times.

Subsequently, cDNA was synthesized from the obtained total RNA. cDNA was synthesized using the high-capacity cDNA Reverse Transcription Kit (Applied Biosystem) by the method in accordance with the protocol included in the kit. Total RNA in an amount equivalent to 4 µg was used for the 40-µl reaction system to synthesize cDNA from mRNA. The reverse transcription reaction was carried out by preincubation at 25° C. for 10 minutes, and reverse transcription at 37° C. for 120 minutes, followed by heating at 85° C. for 5 seconds to terminate the reaction. cDNA obtained was stored at −20° C. before use.

Quantitative real-time PCR (qRT-PCR) was carried out with the use of THUNDERBIRD SYBR qRCR Mix (TOYOBO) in a 20-µl reaction system in accordance with the instructions. The mixed solution contains 400 ng-equivalent cDNA synthesized in reverse transcription. Each sample was subjected to measurement three times. PCR was carried out with the use of the MiniOpticon real-time PCR detection system (BioRad) and analytical software (BioRad CFX Manager 2.1). The relative expression intensity was determined as a ratio of the expression level of each gene relative to the expression level of the internal standard gene (histone H2B) measured under the same conditions.

The sets of primers used are shown below.

For TRAF01000135000001 gene

```
NRPS-RT1-F:
                            (SEQ ID NO: 132)
GACGCCACGAACGCATAGAC

NRPS-RT1-R:
                            (SEQ ID NO: 133)
TTCCCAGAGAGGTAGATCGAC
```

For TRAF01000135000001 gene

```
NRPS-RT2-F:
                            (SEQ ID NO: 134)
GACCGTTACAGCGAGTTCAG

NRPS-RT2-R:
                            (SEQ ID NO: 135)
CTGAATTCCTCGCACAGAAC
```

For TRAF01000135000001 gene

```
NRPS-RT3-F:
                            (SEQ ID NO: 136)
GAAGTTGAGAACGCCATGCT

NRPS-RT3-R:
                            (SEQ ID NO: 137)
GATGCGAGATGGGAGCATGT
```

For TRAF01000068000002 gene

```
TR02-RT-F:
                            (SEQ ID NO: 138)
GCCCTACTAGATCTGACCAC

TR02-RT-R:
                            (SEQ ID NO: 139)
GCTGTTACCTTTTCCTCCTC
```

For TRAF01000068000003 gene

```
TR03-RT-F:
                            (SEQ ID NO: 140)
AGATCTTAGACGAGCTGCTC

TR03-RT-R:
                            (SEQ ID NO: 141)
AAACAGTCGCGAAGCGACTG
```

For TRAF01000068000006 gene

```
TR06-RT-F:
                            (SEQ ID NO: 142)
ACGTCCAGGAAGCTATCGAG

TR06-RT-R:
                            (SEQ ID NO: 143)
ATTGAGGGCCTGGGCTTGAC
```

For TRAF01000068000007 gene

```
TR07-RT-F:
                            (SEQ ID NO: 144)
GTGATGAAGGCGCTGAAGAG
```

-continued

TR07-RT-R:
CTCCGCAATTTCCGTGAGTG (SEQ ID NO: 145)

For TRAF01000068000008 gene

TR08-RT-F:
TGACTCTATGGTGGATGGTG (SEQ ID NO: 146)

TR08-RT-R:
CCTTGTTCAAGTGCCAGTAG (SEQ ID NO: 147)

For TRAF01000068000009 gene

TR09-RT-F:
GATTCCGTCACGAGACACTG (SEQ ID NO: 148)

TR09-RT-R:
AGTATCCCATCGGGCAACAG (SEQ ID NO: 149)

For TRAF01000135000002 gene

OMT-RT-F:
ACGTTCAAGACCTTCCAG (SEQ ID NO: 150)

OMT-RT-R:
GTTCCGGATGATTTGCAG (SEQ ID NO: 151)

FIG. 25 shows the results of quantitative real-time PCR. In FIG. 25, O-MT indicates the TRAF01000135000002 gene, NRPS-1 to NRPS-3 each indicate the TRAF01000135000001 gene (the NRPS gene of Example 1), TRO2 indicates the TRAF01000068000002 gene, TRO3 indicates the TRAF01000068000003 gene, TRO6 indicates the TRAF01000068000006 gene, TRO7 indicates the TRAF01000068000007 gene, TRO8 indicates the TRAF01000068000008 gene, and TRO9 indicates the TRAF01000068000009 gene. As shown in FIG. 25, the expression level of all the introduced genes was equivalent to that of histone, and high-level expression of all the genes necessary for KK-1 biosynthesis was achieved in *Aspergillus oryzae* into which the gene cluster had been introduced.

9) Evaluation of KK-1 Productivity

Transformed *Aspergillus oryzae* into which the KK-1 biosynthetic gene cluster prepared in the manner described above had been introduced was evaluated in terms of KK-1 productivity.

Transformed *Aspergillus oryzae* prepared in this example is designed to be capable of regulating all the introduced genes with the PamyB promoter. When maltose is used as a carbon source, accordingly, all the genes can be induced to express. At the outset, a conidiospore suspension of the transformed *Aspergillus oryzae* prepared in this example was inoculated into 100-ml of YPM (2% maltose) or CM (2% maltose) medium, and shake culture was performed at 26° C. and 140 rpm for 5 days. Subsequently, the cultured cells and the culture solution were extracted with acetone/ethyl acetate, and the extract was solidified to dryness via condensation. The resultant was dissolved in acetonitrile and then subjected to LC/MS analysis. The conditions for LC/MS analysis were in accordance with the conditions for evaluation of KK-1 production in *Curvularia* sp. Also, the antibacterial activity of the extract was evaluated in terms of the growth inhibitory effects on gray mold as the target of evaluation in terms of antibacterial activity. At the outset, the extract was allowed to impregnate the paper disc (thin, φ6 mm), the paper disc and the mycelial threads of gray mold (*Botrytis cinerea*) cut with agar medium were placed on CM agar medium, and dual culture was carried out. Subsequently, antibacterial activity was evaluated on the basis of an extent of gray mold colony extension toward the paper disc.

Figure 26:
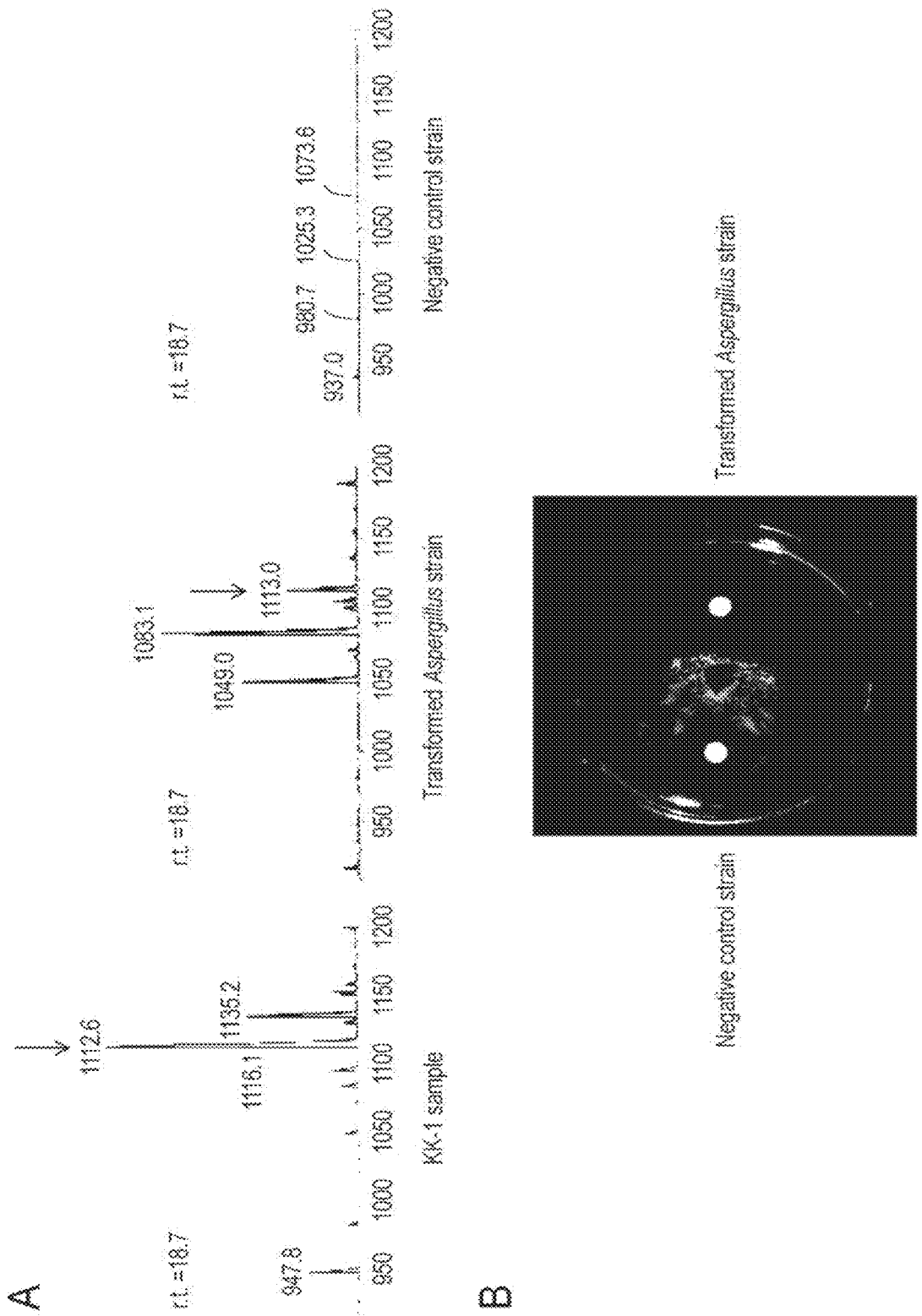

FIG. 26 shows the results. FIG. 26A shows the results of LC/MS analysis and FIG. 26B shows the results of antibacterial activity test. As shown in FIG. 26A, the peak completely consistent with the retention time and the molecular weight of the KK-1 sample was detected in the extract derived from the transformed *Aspergillus oryzae* prepared in this example. As shown in FIG. 26B, in addition, inhibitory activity on extension of gray mold mycelial threads was observed in the extract. The results described above demonstrate that the transformed *Aspergillus oryzae* prepared in this example results from introduction of the KK-1 biosynthetic gene cluster identified in *C. clavata* in a functional manner and that KK-1 heterologs can be produced.

The invention claimed is:

1. A transformant into which the gene involved in the synthesis of a cyclic peptide compound has been introduced, wherein the gene encodes a nonribosomal peptide synthetase (NRPS) having nonribosomal peptide synthase activity comprising, successively from the N terminus, the modules described below:

a first module comprising successively from the N terminus a first adenylation domain comprising the amino acid sequence as shown in SEQ ID NO: 1 or an amino acid sequence having 90% or higher identity to the amino acid sequence as shown in SEQ ID NO: 1 and a first peptidyl carrier protein domain comprising the amino acid sequence as shown in SEQ ID NO: 2 or an amino acid sequence having 90% or higher identity to the amino acid sequence as shown in SEQ ID NO: 2;

a second module comprising successively from the N terminus a first condensation domain comprising the amino acid sequence as shown in SEQ ID NO: 3 or an amino acid sequence having 90% or higher identity to the amino acid sequence as shown in SEQ ID NO: 3, a second adenylation domain comprising the amino acid sequence as shown in SEQ ID NO: 4 or an amino acid sequence having 90% or higher identity to the amino acid sequence as shown in SEQ ID NO: 4, and a second peptidyl carrier protein domain comprising the amino acid sequence as shown in SEQ ID NO: 5 or an amino acid sequence having 90% or higher identity to the amino acid sequence as shown in SEQ ID NO: 5;

a third module comprising successively from the N terminus a second condensation domain comprising the amino acid sequence as shown in SEQ ID NO: 6 or an amino acid sequence having 90% or higher identity to the amino acid sequence as shown in SEQ ID NO: 6, a third adenylation domain comprising the amino acid sequence as shown in SEQ ID NO: 7 or an amino acid sequence having 90% or higher identity to the amino acid sequence as shown in SEQ ID NO: 7, a first N-methyl transferase domain comprising the amino acid sequence as shown in SEQ ID NO: 8 or an amino acid sequence having 90% or higher identity to the amino acid sequence as shown in SEQ ID NO: 8, and a third peptidyl carrier protein domain comprising the amino acid sequence as shown in SEQ ID NO: 9 or an amino acid sequence having 90% or higher identity to the amino acid sequence as shown in SEQ ID NO: 9;

a fourth module comprising successively from the N terminus a third condensation domain comprising the amino acid sequence as shown in SEQ ID NO: 10 or an amino acid sequence having 90% or higher identity to the amino acid sequence as shown in SEQ ID NO: 10, a fourth adenylation domain comprising the amino acid sequence as shown in SEQ ID NO: 11 or an amino acid sequence having 90% or higher identity to the amino acid sequence as shown in SEQ ID NO: 11, and a fourth peptidyl carrier protein domain comprising the amino acid sequence as shown in SEQ ID NO: 12 or an amino acid sequence having 90% or higher identity to the amino acid sequence as shown in SEQ ID NO: 12;

a fifth module comprising successively from the N terminus a fourth condensation domain comprising the amino acid sequence as shown in SEQ ID NO: 13 or an amino acid sequence having 90% or higher identity to the amino acid sequence as shown in SEQ ID NO: 13, a fifth adenylation domain comprising the amino acid sequence as shown in SEQ ID NO: 14 or an amino acid sequence having 90% or higher identity to the amino acid sequence as shown in SEQ ID NO: 14, a second N-methyl transferase domain comprising the amino acid sequence as shown in SEQ ID NO: 15 or an amino acid sequence having 90% or higher identity to the amino acid sequence as shown in SEQ ID NO: 15, and a fifth peptidyl carrier protein domain comprising the amino acid sequence as shown in SEQ ID NO: 16 or an amino acid sequence having 90% or higher identity to the amino acid sequence as shown in SEQ ID NO: 16;

a sixth module comprising successively from the N terminus a fifth condensation domain comprising the amino acid sequence as shown in SEQ ID NO: 17 or an amino acid sequence having 90% or higher identity to the amino acid sequence as shown in SEQ ID NO: 17, a sixth adenylation domain comprising the amino acid sequence as shown in SEQ ID NO: 18 or an amino acid sequence having 90% or higher identity to the amino acid sequence as shown in SEQ ID NO: 18, a third N-methyl transferase domain comprising the amino acid sequence as shown in SEQ ID NO: 19 or an amino acid sequence having 90% or higher identity to the amino acid sequence as shown in SEQ ID NO: 19, and a sixth peptidyl carrier protein domain comprising the amino acid sequence as shown in SEQ ID NO: 20 or an amino acid sequence having 90% or higher identity to the amino acid sequence as shown in SEQ ID NO: 20;

a seventh module comprising successively from the N terminus a sixth condensation domain comprising the amino acid sequence as shown in SEQ ID NO: 21 or an amino acid sequence having 90% or higher identity to the amino acid sequence as shown in SEQ ID NO: 21, a seventh adenylation domain comprising the amino acid sequence as shown in SEQ ID NO: 22 or an amino acid sequence having 90% or higher identity to the amino acid sequence as shown in SEQ ID NO: 22, a fourth N-methyl transferase domain comprising the amino acid sequence as shown in SEQ ID NO: 23 or an amino acid sequence having 90% or higher identity to the amino acid sequence as shown in SEQ ID NO: 23, and a seventh peptidyl carrier protein domain comprising the amino acid sequence as shown in SEQ ID NO: 24 or an amino acid sequence having 90% or higher identity to the amino acid sequence as shown in SEQ ID NO: 24;

an eighth module comprising successively from the N terminus a seventh condensation domain comprising the amino acid sequence as shown in SEQ ID NO: 25 or an amino acid sequence having 90% or higher identity to the amino acid sequence as shown in SEQ ID NO: 25, an eighth adenylation domain comprising the amino acid sequence as shown in SEQ ID NO: 26 or an amino acid sequence having 90% or higher identity to the amino acid sequence as shown in SEQ ID NO: 26, and an eighth peptidyl carrier protein domain comprising the amino acid sequence as shown in SEQ ID NO: 27 or an amino acid sequence having 90% or higher identity to the amino acid sequence as shown in SEQ ID NO: 27;

a ninth module comprising successively from the N terminus an eighth condensation domain comprising the amino acid sequence as shown in SEQ ID NO: 28 or an amino acid sequence having 90% or higher identity to the amino acid sequence as shown in SEQ ID NO: 28, a ninth adenylation domain comprising the amino acid sequence as shown in SEQ ID NO: 29 or an amino acid sequence having 90% or higher identity to the amino acid sequence as shown in SEQ ID NO: 29, a fifth N-methyl transferase domain comprising the amino acid sequence as shown in SEQ ID NO: 30 or an amino acid sequence having 90% or higher identity to the amino acid sequence as shown in SEQ ID NO: 30, and a ninth peptidyl carrier protein domain comprising the amino acid sequence as shown in SEQ ID NO: 31 or an amino acid sequence having 90% or higher identity to the amino acid sequence as shown in SEQ ID NO: 31; and a tenth module comprising successively from the N terminus a ninth condensation domain comprising the amino acid sequence as shown in SEQ ID NO: 32 or an amino acid sequence having 90% or higher identity to the amino acid sequence as shown in SEQ ID NO: 32, a tenth adenylation domain comprising the amino acid sequence as shown in SEQ ID NO: 33 or an amino acid sequence having 90% or higher identity to the amino acid sequence as shown in SEQ ID NO: 33, a tenth peptidyl carrier protein domain comprising the amino acid sequence as shown in SEQ ID NO: 34 or an amino acid sequence having 90% or higher identity to the amino acid sequence as shown in SEQ ID NO: 34, and a tenth condensation domain comprising the amino acid sequence as shown in SEQ ID NO: 35 or an amino acid sequence having 90% or higher identity to the amino acid sequence as shown in SEQ ID NO: 35;

wherein the transformant is not a *Curvularia* sp.

2. The transformant according to claim 1, wherein the transformant is further transformed with the following genes [1], [2], [3], [6] and [7] among genes [1] to [7] below:

[1] a gene encoding a protein comprising the amino acid sequence as shown in SEQ ID NO: 41 or an amino acid sequence having 90% or higher identity to the amino acid sequence as shown in SEQ ID NO: 41;

[2] a gene encoding a protein comprising the amino acid sequence as shown in SEQ ID NO: 43 or an amino acid sequence having 90% or higher identity to the amino acid sequence as shown in SEQ ID NO: 43;

[3] a gene encoding a protein comprising the amino acid sequence as shown in SEQ ID NO: 45 or an amino acid sequence having 90% or higher identity to the amino acid sequence as shown in SEQ ID NO: 45;

[4] a gene encoding a protein comprising the amino acid sequence as shown in SEQ ID NO: 47 or an amino acid sequence having 90% or higher identity to the amino acid sequence as shown in SEQ ID NO: 47;

[5] a gene encoding a protein comprising the amino acid sequence as shown in SEQ ID NO: 49 or an amino acid sequence having 90% or higher identity to the amino acid sequence as shown in SEQ ID NO: 49;

[6] a gene encoding a protein comprising the amino acid sequence as shown in SEQ ID NO: 51 or an amino acid sequence having 90% or higher identity to the amino acid sequence as shown in SEQ ID NO: 51; and

[7] a gene encoding a protein comprising the amino acid sequence as shown in SEQ ID NO: 53 or an amino acid sequence having 90% or higher identity to the amino acid sequence as shown in SEQ ID NO: 53.

3. The transformant according to claim 1, which is *Aspergillus oryzae*.

4. A transformant into which a heterologous gene involved in the synthesis of a cyclic peptide compound has been introduced, wherein said heterologous gene encodes a nonribosomal peptide synthetase (NRPS) having nonribosomal peptide synthase activity comprising, successively from the N terminus, the modules described below:

a first module comprising successively from the N terminus a first adenylation domain comprising the amino acid sequence as shown in SEQ ID NO: 1 or an amino acid sequence having 90% or higher identity to the amino acid sequence as shown in SEQ ID NO: 1 and a first peptidyl carrier protein domain comprising the amino acid sequence as shown in SEQ ID NO: 2 or an amino acid sequence having 90% or higher identity to the amino acid sequence as shown in SEQ ID NO: 2;

a second module comprising successively from the N terminus a first condensation domain comprising the amino acid sequence as shown in SEQ ID NO: 3 or an amino acid sequence having 90% or higher identity to the amino acid sequence as shown in SEQ ID NO: 3, a second adenylation domain comprising the amino acid sequence as shown in SEQ ID NO: 4 or an amino acid sequence having 90% or higher identity to the amino acid sequence as shown in SEQ ID NO: 4, and a second peptidyl carrier protein domain comprising the amino acid sequence as shown in SEQ ID NO: 5 or an amino acid sequence having 90% or higher identity to the amino acid sequence as shown in SEQ ID NO: 5;

a third module comprising successively from the N terminus a second condensation domain comprising the amino acid sequence as shown in SEQ ID NO: 6 or an amino acid sequence having 90% or higher identity to the amino acid sequence as shown in SEQ ID NO: 6, a third adenylation domain comprising the amino acid sequence as shown in SEQ ID NO: 7 or an amino acid sequence having 90% or higher identity to the amino acid sequence as shown in SEQ ID NO: 7, a first N-methyl transferase domain comprising the amino acid sequence as shown in SEQ ID NO: 8 or an amino acid sequence having 90% or higher identity to the amino acid sequence as shown in SEQ ID NO: 8, and a third peptidyl carrier protein domain comprising the amino acid sequence as shown in SEQ ID NO: 9 or an amino acid sequence having 90% or higher identity to the amino acid sequence as shown in SEQ ID NO: 9;

a fourth module comprising successively from the N terminus a third condensation domain comprising the amino acid sequence as shown in SEQ ID NO: 10 or an amino acid sequence having 90% or higher identity to the amino acid sequence as shown in SEQ ID NO: 10, a fourth adenylation domain comprising the amino acid sequence as shown in SEQ ID NO: 11 or an amino acid sequence having 90% or higher identity to the amino acid sequence as shown in SEQ ID NO: 11, and a fourth peptidyl carrier protein domain comprising the amino acid sequence as shown in SEQ ID NO: 12 or an amino acid sequence having 90% or higher identity to the amino acid sequence as shown in SEQ ID NO: 12;

a fifth module comprising successively from the N terminus a fourth condensation domain comprising the amino acid sequence as shown in SEQ ID NO: 13 or an amino acid sequence having 90% or higher identity to the amino acid sequence as shown in SEQ ID NO: 13, a fifth adenylation domain comprising the amino acid sequence as shown in SEQ ID NO: 14 or an amino acid sequence having 90% or higher identity to the amino acid sequence as shown in SEQ ID NO: 14, a second N-methyl transferase domain comprising the amino acid sequence as shown in SEQ ID NO: 15 or an amino acid sequence having 90% or higher identity to the amino acid sequence as shown in SEQ ID NO: 15, and a fifth peptidyl carrier protein domain comprising the amino acid sequence as shown in SEQ ID NO: 16 or an amino acid sequence having 90% or higher identity to the amino acid sequence as shown in SEQ ID NO: 16;

a sixth module comprising successively from the N terminus a fifth condensation domain comprising the amino acid sequence as shown in SEQ ID NO: 17 or an amino acid sequence having 90% or higher identity to the amino acid sequence as shown in SEQ ID NO: 17, a sixth adenylation domain comprising the amino acid sequence as shown in SEQ ID NO: 18 or an amino acid sequence having 90% or higher identity to the amino acid sequence as shown in SEQ ID NO: 18, a third N-methyl transferase domain comprising the amino acid sequence as shown in SEQ ID NO: 19 or an amino acid sequence having 90% or higher identity to the amino acid sequence as shown in SEQ ID NO: 19, and a sixth peptidyl carrier protein domain comprising the amino acid sequence as shown in SEQ ID NO: 20 or an amino acid sequence having 90% or higher identity to the amino acid sequence as shown in SEQ ID NO: 20;

a seventh module comprising successively from the N terminus a sixth condensation domain comprising the amino acid sequence as shown in SEQ ID NO: 21 or an amino acid sequence having 90% or higher identity to the amino acid sequence as shown in SEQ ID NO: 21, a seventh adenylation domain comprising the amino acid sequence as shown in SEQ ID NO: 22 or an amino acid sequence having 90% or higher identity to the amino acid sequence as shown in SEQ ID NO: 22, a fourth N-methyl transferase domain comprising the amino acid sequence as shown in SEQ ID NO: 23 or an amino acid sequence having 90% or higher identity to the amino acid sequence as shown in SEQ ID NO: 23, and a seventh peptidyl carrier protein domain comprising the amino acid sequence as shown in SEQ ID NO: 24 or an amino acid sequence having 90% or higher identity to the amino acid sequence as shown in SEQ ID NO: 24;

an eighth module comprising successively from the N terminus a seventh condensation domain comprising the amino acid sequence as shown in SEQ ID NO: 25 or an amino acid sequence having 90% or higher identity to the amino acid sequence as shown in SEQ ID NO: 25, an eighth adenylation domain comprising the amino acid sequence as shown in SEQ ID NO: 26 or an amino acid sequence having 90% or higher identity to the amino acid sequence as shown in SEQ ID NO: 26, and an eighth peptidyl carrier protein domain comprising the amino acid sequence as shown in SEQ ID NO: 27 or an amino acid sequence having 90% or higher identity to the amino acid sequence as shown in SEQ ID NO: 27;

a ninth module comprising successively from the N terminus an eighth condensation domain comprising the amino acid sequence as shown in SEQ ID NO: 28 or an amino acid sequence having 90% or higher identity to the amino acid sequence as shown in SEQ ID NO: 28, a ninth adenylation domain comprising the amino acid sequence as shown in SEQ ID NO: 29 or an amino acid sequence having 90% or higher identity to the amino acid sequence as shown in SEQ ID NO: 29, a fifth N-methyl transferase domain comprising the amino acid sequence as shown in SEQ ID NO: 30 or an amino acid sequence having 90% or higher identity to the amino acid sequence as shown in SEQ ID NO: 30, and a ninth peptidyl carrier protein domain comprising the amino acid sequence as shown in SEQ ID NO: 31 or an amino acid sequence having 90% or higher identity to the amino acid sequence as shown in SEQ ID NO: 31; and a tenth module comprising successively from the N terminus a ninth condensation domain comprising the amino acid sequence as shown in SEQ ID NO: 32 or an amino acid sequence having 90% or higher identity to the amino acid sequence as shown in SEQ ID NO: 32, a tenth adenylation domain comprising the amino acid sequence as shown in SEQ ID NO: 33 or an amino acid sequence having 90% or higher identity to the amino acid sequence as shown in SEQ ID NO: 33, a tenth peptidyl carrier protein domain comprising the amino acid sequence as shown in SEQ ID NO: 34 or an amino acid sequence having 90% or higher identity to the amino acid sequence as shown in SEQ ID NO: 34, and a tenth condensation domain comprising the amino acid sequence as shown in SEQ ID NO: 35 or an amino acid sequence having 90% or higher identity to the amino acid sequence as shown in SEQ ID NO: 35;

wherein the transformant is not a *Curvularia* sp.

5. The transformant according to claim 4, wherein the transformant is further transformed with the following genes [1], [2], [3], [6] and [7] among genes [1] to [7] below:

[1] a gene encoding a protein comprising the amino acid sequence as shown in SEQ ID NO: 41 or an amino acid sequence having 90% or higher identity to the amino acid sequence as shown in SEQ ID NO: 41;

[2] a gene encoding a protein comprising the amino acid sequence as shown in SEQ ID NO: 43 or an amino acid sequence having 90% or higher identity to the amino acid sequence as shown in SEQ ID NO: 43;

[3] a gene encoding a protein comprising the amino acid sequence as shown in SEQ ID NO: 45 or an amino acid sequence having 90% or higher identity to the amino acid sequence as shown in SEQ ID NO: 45;

[4] a gene encoding a protein comprising the amino acid sequence as shown in SEQ ID NO: 47 or an amino acid sequence having 90% or higher identity to the amino acid sequence as shown in SEQ ID NO: 47;

[5] a gene encoding a protein comprising the amino acid sequence as shown in SEQ ID NO: 49 or an amino acid sequence having 90% or higher identity to the amino acid sequence as shown in SEQ ID NO: 49;

[6] a gene encoding a protein comprising the amino acid sequence as shown in SEQ ID NO: 51 or an amino acid sequence having 90% or higher identity to the amino acid sequence as shown in SEQ ID NO: 51; and

[7] a gene encoding a protein comprising the amino acid sequence as shown in SEQ ID NO: 53 or an amino acid sequence having 90% or higher identity to the amino acid sequence as shown in SEQ ID NO: 53.

* * * * *

SEQUENCE LISTING

<160> NUMBER OF SEQ ID NOS: 151

<210> SEQ ID NO 1
<211> LENGTH: 393
<212> TYPE: PRT
<213> ORGANISM: Curvularia clavata

<400> SEQUENCE: 1

```
Leu Thr Phe Ala Glu Leu Asp Ser Phe Ser Ser Cys Leu Ala Gln His
1               5                   10                  15

Ile Gln Ser Leu Glu Leu Gly Asp Ala Lys Ala Ile Pro Leu Cys Phe
            20                  25                  30

Glu Lys Ser Lys Trp Ala Ile Val Gly Met Leu Gly Val Leu Lys Ala
        35                  40                  45

Gly Arg Ala Phe Thr Leu Ile Asp Pro Ser Asn Pro Pro Ala Arg Ala
    50                  55                  60

Arg Gln Ile Cys Arg Gln Thr Ala Ala Thr Ile Ser Ile Ala Ser Pro
65                  70                  75                  80
```

```
Tyr Gln Cys Asp Met Met Arg Ala Leu Val Pro Asp Cys Ile Val Val
                85                  90                  95

Asp Asp Asp Phe Phe Lys Ser Leu Ala Phe Thr Asp Gln Phe Gln
            100                 105                 110

Pro Thr Ala Thr Pro Gln Thr Leu Ala Tyr Ile Leu Phe Thr Ser Gly
            115                 120                 125

Ser Thr Gly Glu Pro Lys Gly Ser Met Met Glu His His Gly Phe Val
130             135                 140

Ser Cys Cys Leu Glu Phe Gly Ala Ala Leu Gly Ile Asn Ser Asn Thr
145             150                 155                 160

Arg Ala Leu Gln Phe Ala Ser Tyr Ala Phe Gly Ala Cys Leu Leu Glu
                165                 170                 175

Ile Leu Thr Thr Leu Met His Gly Gly Thr Val Cys Ile Pro Ser Asp
            180                 185                 190

Asp Glu Arg Ile Asn Asp Ala Pro Gly Phe Ile Arg Arg Ala Asn Val
            195                 200                 205

Asn Trp Ala Ile Leu Thr Pro Ser Phe Ile Gly Ala Ile Gln Pro Thr
    210                 215                 220

Thr Val Pro Asn Leu Lys Thr Leu Val Leu Val Gly Glu Ala Met Pro
225                 230                 235                 240

Ser Asp Ile Arg Asp Val Trp Ala Ser His Val Gln Leu Lys Asn Ala
                245                 250                 255

Tyr Gly Gln Ser Glu Ser Ala Thr Ile Cys Ser Val Thr Glu Val Thr
                260                 265                 270

Pro Ala Thr Val Glu Ala His Asn Ile Gly His Ala Val Gly Ala Arg
            275                 280                 285

Phe Trp Ile Thr Asp Pro Asn Asn Pro Asn Lys Leu Ala Pro Ile Gly
    290                 295                 300

Cys Val Gly Glu Leu Leu Val Glu Ser Pro Gly Ile Ala Arg Gly Tyr
305                 310                 315                 320

Leu Ile Pro Leu Pro Ala Asp Ala Thr Pro Phe Ile Asp Thr Leu Pro
                325                 330                 335

Asp Trp Tyr Pro Arg Thr Gln Pro Leu Asp Asn Phe Lys Phe Tyr Arg
            340                 345                 350

Thr Gly Asp Leu Val Cys Tyr Arg Ser Asp Gly Thr Val Val Tyr Leu
            355                 360                 365

Gly Arg Arg Asp Ser Gln Ile Lys Ile Arg Gly Gln Arg Val Glu Ile
            370                 375                 380

Gly Glu Val Glu Thr Cys Leu Arg Gln
385                 390

<210> SEQ ID NO 2
<211> LENGTH: 69
<212> TYPE: PRT
<213> ORGANISM: Curvularia clavata

<400> SEQUENCE: 2

Ile Thr Leu Glu Arg Ile Trp Phe Gln Ser Leu Gly Leu Lys Pro Asn
1               5                   10                  15

Ser Thr Arg His Lys Ser Asn Phe Phe Asn Leu Gly Gly Asp Ser Ile
            20                  25                  30

Ala Ala Ile Arg Met Val Asn Met Ala Arg Ala Ala Gly Leu Leu Leu
            35                  40                  45
```

```
Ser Ile Ser Asp Ile Phe Gln Asn Pro Ser Leu Ala Gly Leu Ile Asn
 50                  55                  60

Val Met Gln Gln Ser
 65
```

<210> SEQ ID NO 3
<211> LENGTH: 298
<212> TYPE: PRT
<213> ORGANISM: Curvularia clavata

<400> SEQUENCE: 3

```
Gly Pro Val Glu Gln Ser Phe Ala Gln Gly Arg Leu Trp Phe Leu Asp
 1               5                  10                  15

Gln Leu Thr Thr Gly Ala Ser Trp Tyr Leu Met Pro Leu Ala Val Arg
            20                  25                  30

Ile His Gly Pro Leu Arg Val Gln Ala Leu Ser Ser Ala Leu His Ala
        35                  40                  45

Leu Glu Gln Arg His Glu Thr Leu Arg Thr Thr Phe Glu Gln Gln Asp
 50                  55                  60

Gly Met Gly Val Gln Ile Val His Pro Ser Ser Lys Arg Glu Leu Arg
 65                  70                  75                  80

Val Ile Asp Val Ser Gly Lys Gln Asn Gly Gly Tyr Asp Gln Val Leu
                85                  90                  95

Lys Arg Glu Gln Thr Thr Pro Ile Asp Leu Ala Lys Glu Pro Gly Trp
            100                 105                 110

Arg Ala Ala Leu Leu Arg Val Gly Asp Asp Glu His Ile Leu Ser Ile
        115                 120                 125

Val Ile His His Ile Ile Tyr Asp Gly Trp Ser Leu Gly Val Leu Arg
130                 135                 140

Glu Glu Leu Gly Asp Leu Tyr Ala Ala Ala Leu Arg Gly Pro Asp Pro
145                 150                 155                 160

Leu Ala His Met Ala Pro Leu Pro Ile Gln Tyr Arg Asp Phe Ser Val
                165                 170                 175

Trp Gln Lys Gln Pro Gln Gln Val Ala Gln His Gln Gln Leu Val
            180                 185                 190

Tyr Trp Thr Lys Gln Leu Glu Asp Ser Ala Pro Ala Glu Leu Leu Thr
        195                 200                 205

Asp Phe Pro Arg Pro Ala Glu Leu Ser Gly Arg Ala Gly Glu Val Arg
210                 215                 220

Phe Thr Ile Glu Gly Ser Val Phe Asp Ser Leu Leu Ala Phe Arg Arg
225                 230                 235                 240

Val His Gln Thr Thr Ser Phe Ala Val Leu Leu Ala Val Phe Arg Ala
                245                 250                 255

Ala His Tyr Arg Leu Thr Gly Thr Glu Asp Ala Thr Ile Gly Thr Pro
            260                 265                 270

Ile Ala Asn Arg Thr Arg Ala Glu Val Glu Lys Leu Ile Gly Phe Phe
        275                 280                 285

Val Asn Thr Gln Cys Met Arg Ile Ala Val
            290                 295
```

<210> SEQ ID NO 4
<211> LENGTH: 398
<212> TYPE: PRT
<213> ORGANISM: Curvularia clavata

<400> SEQUENCE: 4

```
Leu Thr Tyr Ala Gln Leu Asp Gln Glu Ser Asp Lys Ile Ala Val Trp
1               5                   10                  15

Leu Arg Lys Arg Asn Ile Pro Ala Glu Thr Leu Ile Ala Leu Leu Ala
            20                  25                  30

Pro Arg Ser Cys Asp Ser Val Ala Ala Phe Leu Gly Ile Leu Lys Ala
        35                  40                  45

Asn Leu Ala Tyr Leu Pro Leu Asp Val Asn Val Pro Ala Ala Arg Ile
    50                  55                  60

Glu Ala Ile Leu Ser Thr Val Ala Gly His Lys Leu Val Leu Leu Gly
65                  70                  75                  80

Arg Asp Val Pro Leu Leu Gly Thr Gln Leu Ala Asp Leu Glu Leu Val
                85                  90                  95

Arg Ile Gly Glu Ala Leu Arg Gly Ser Ser Gly Ser Val Ala Ala
            100                 105                 110

Asp Lys Ala Ile Arg Pro Thr Ala Thr Ser Leu Ala Tyr Val Ile Phe
        115                 120                 125

Thr Ser Gly Ser Thr Gly Gln Pro Lys Gly Ile Met Val Pro His Arg
    130                 135                 140

Ser Leu Val Asn Val Ile Lys Gln Arg Pro Ala Tyr Gly Asn Val Ala
145                 150                 155                 160

His Met Thr Asn Leu Ala Phe Asp Pro Ser Leu Phe Glu Met Cys Thr
                165                 170                 175

Ala Leu Phe Asn Gly Asn Thr Leu Ile Cys Ile Asp Thr Leu Val Ala
            180                 185                 190

Leu Asp Ala Thr Gln Leu Pro Thr Ile Phe Lys Gln Glu Ala Ile Arg
        195                 200                 205

Val Ala Met Met Thr Pro Ala Leu Leu Thr Arg Leu Leu Ala Gln Ala
    210                 215                 220

Thr Asp Ala Leu His Glu Leu Glu Ala Leu Tyr Val Leu Gly Asp Arg
225                 230                 235                 240

Phe Pro Pro Lys Asp Ala Ala Arg Ala Ser Glu Leu Val Lys Thr Ala
                245                 250                 255

Val Tyr Asn Ala Tyr Gly Pro Ser Glu Asn Ser Ile Cys Thr Thr Leu
            260                 265                 270

Phe His Ala Ala Thr Gly Ala Met Cys Thr Asn Gly Val Pro Val Gly
        275                 280                 285

Arg Val Ile Asn Asn Ser Gly Val Tyr Val Met Asp Pro Lys Gln Ser
    290                 295                 300

Leu Val Ser Tyr Gly Val Met Gly Glu Leu Val Val Ala Gly Glu Gly
305                 310                 315                 320

Leu Ala Ile Gly Tyr Thr Lys Pro Glu Leu Asn Glu Gly Arg Phe Leu
                325                 330                 335

Thr Leu Thr Met Asp Gly Lys Pro Val Arg Ala Phe Arg Thr Gly Asp
            340                 345                 350

Arg Val Arg Tyr Arg Pro Thr Asp Gly Gln Leu Glu Phe Phe Gly Arg
        355                 360                 365

Met Asp Phe Gln Ile Lys Ile Arg Gly His Arg Val Glu Leu Ala Glu
    370                 375                 380

Val Glu Arg Val Leu Asn Arg His Pro Ala Ile Lys Asp Ala
385                 390                 395
```

```
<210> SEQ ID NO 5
<211> LENGTH: 69
<212> TYPE: PRT
<213> ORGANISM: Curvularia clavata

<400> SEQUENCE: 5

Ile Glu Ala Val Leu Cys Glu Glu Phe Ala His Ile Leu Gly Val Glu
1               5                   10                  15

Ile Gly Val Thr Asp Asn Phe Phe Asp Leu Gly Gly His Ser Leu Met
            20                  25                  30

Ala Thr Thr Leu Ala Ala Arg Leu Ala Arg Arg Leu Asn Ala Ser Ile
        35                  40                  45

Ser Val Lys Asp Val Phe Asp Gln Pro Ile Val Ala Asn Leu Ala Ala
    50                  55                  60

Thr Ile Lys Arg Gly
65

<210> SEQ ID NO 6
<211> LENGTH: 297
<212> TYPE: PRT
<213> ORGANISM: Curvularia clavata

<400> SEQUENCE: 6

Gly Pro Val Glu Gln Ser Phe Ala Gln Gly Arg Leu Trp Phe Leu Asp
1               5                   10                  15

Gln Leu Asn Leu Gly Ala Ala Trp Tyr His Met Pro Leu Ala Val Arg
            20                  25                  30

Leu Arg Gly Pro Leu His Leu Glu Ala Leu Thr Ala Ala Leu His Ala
        35                  40                  45

Leu Glu Glu Arg His Glu Thr Leu Arg Thr Val Phe Glu Glu Gln Asp
    50                  55                  60

Gly Val Gly Met Gln Ile Val Arg Pro Ser Ser Lys Thr Pro Leu Arg
65                  70                  75                  80

Ile Ile Asp Val Ser Thr Lys Glu Arg Gly Tyr Ala Glu Leu Leu Lys
                85                  90                  95

Gln Glu Gln Thr Thr Pro Phe Asp Leu Ala Thr Glu Leu Gly Trp Arg
            100                 105                 110

Val Ala Leu Leu Arg Gln Gly Lys Asp Asp His Ile Leu Ser Ile Val
        115                 120                 125

Ile His His Ile Ile Ser Asp Gly Trp Ser Leu Asp Ile Leu Cys Glu
    130                 135                 140

Glu Leu Gly Gln Phe Tyr Ala Ala Val Leu Arg Gly Gln Asp Pro Leu
145                 150                 155                 160

Ala Gln Ile Ser Pro Leu Pro Ile Gln Tyr Arg Asp Phe Ser Leu Trp
                165                 170                 175

Gln Lys Gln Pro Glu Gln Val Ala Glu His His Arg Gln Leu Glu Tyr
            180                 185                 190

Trp Thr Thr Gln Leu Glu Gly Ser Val Pro Ala Glu Leu Leu Thr Asp
        195                 200                 205

Leu Pro Arg Pro Thr Ile Gln Ser Gly Lys Ala Gly Val Ile Pro Ile
    210                 215                 220

Thr Val Asn Gly Pro Val Tyr Glu Arg Leu Arg Ala Phe Ser Arg Ala
225                 230                 235                 240

His Gln Thr Thr Ala Phe Ala Val Leu Leu Ala Ala Phe Arg Ala Thr
                245                 250                 255
```

```
His Tyr Arg Leu Ser Gly Val Ala Asp Ala Thr Ile Gly Thr Pro Ile
            260                 265                 270

Ala Asn Arg Asn Arg Pro Glu Leu Glu Asn Met Ile Gly Phe Phe Val
        275                 280                 285

Asn Ala Gln Cys Met Arg Ile Thr Val
    290                 295

<210> SEQ ID NO 7
<211> LENGTH: 402
<212> TYPE: PRT
<213> ORGANISM: Curvularia clavata

<400> SEQUENCE: 7

Leu Thr Tyr Ala Gln Leu Asn Glu Gln Ser Asp Lys Val Ala Ala Trp
1               5                   10                  15

Leu His Gln Cys Asn Leu Pro Thr Glu Thr Leu Val Ala Val Leu Ala
            20                  25                  30

Pro Arg Ser Cys Gln Thr Val Val Ala Phe Leu Gly Ile Leu Lys Ala
        35                  40                  45

Asn Leu Ala Tyr Leu Pro Leu Asp Val Asn Val Pro Ala Ala Arg Ile
    50                  55                  60

Glu Ala Ile Leu Ser Glu Val Ser Gly His Ile Leu Val Leu Leu Gly
65                  70                  75                  80

Ser His Val Ser Ala Pro Lys Ile Glu Leu Ala Asp Val Glu Phe Val
                85                  90                  95

Lys Ile Asp Asn Thr Val Glu His Asn Leu Pro Gly Arg Ile Gly Ser
            100                 105                 110

Ala Pro Ser Ala Thr Ser Leu Ala Tyr Val Ile Phe Thr Ser Gly Ser
        115                 120                 125

Thr Gly Lys Pro Lys Gly Val Lys Val Glu His Arg Gly Ile Val Arg
    130                 135                 140

Leu Val Lys Glu Ser Asn Val Val Ala Lys Met Pro Gln Ala Ala Arg
145                 150                 155                 160

Ile Ala His Leu Ser Asn Ile Ala Phe Asp Ala Ala Thr Trp Glu Leu
                165                 170                 175

Tyr Ala Ala Leu Leu Asn Gly Gly Thr Leu Val Cys Ile Asn Tyr Leu
            180                 185                 190

Thr Thr Leu Asp Ser Lys Ala Leu Glu Ala Val Phe Glu Gln Glu Lys
        195                 200                 205

Ile Gln Ala Ala Met Leu Pro Pro Ala Leu Leu Lys Gln Tyr Leu Val
    210                 215                 220

Asn Ile Pro Ala Ala Ile Gly Ala Leu Glu Val Val Leu Val Ala Gly
225                 230                 235                 240

Asp Arg Phe Asp Arg Arg Asp Ala Ala Thr Gln Ala Leu Val Gly
                245                 250                 255

Ala Gly Val Tyr Asn Ala Tyr Gly Pro Thr Glu Asn Thr Thr Leu Ser
            260                 265                 270

Thr Ile Tyr Asn Val Val Gln Gly Asp Ala Asn Val Asn Gly Val Pro
        275                 280                 285

Ile Gly Arg Pro Val Ser Asn Ser Gly Ala Tyr Ile Met Asn Met Asn
    290                 295                 300

Gln Glu Leu Val Pro Ile Gly Val Ile Gly Glu Leu Val Val Val Gly
305                 310                 315                 320

Asp Gly Val Ala Arg Gly Tyr Thr Asp Pro Ala Leu Asp Val Asn Arg
                325                 330                 335
```

```
Phe Val Asn Val Thr Ile Glu Gly Gln Thr Met Arg Ala Tyr Arg Thr
                340                 345                 350

Gly Asp Arg Ala Arg Tyr Arg Pro Lys Asp Ala Gln Ile Glu Phe Phe
            355                 360                 365

Gly Arg Met Asp Gln Gln Ile Lys Ile Arg Gly His Arg Ile Glu Pro
        370                 375                 380

Ala Glu Val Glu His Ala Leu Leu Asn Asn Asp Leu Leu Gln Asp Ala
385                 390                 395                 400

Ala Val

<210> SEQ ID NO 8
<211> LENGTH: 224
<212> TYPE: PRT
<213> ORGANISM: Curvularia clavata

<400> SEQUENCE: 8

Asp Gly Ser Ala Ile Asp Lys Ala Glu Met Gln Glu Trp Leu Asp Asp
1               5                   10                  15

Thr Met Gln Thr Ile Leu Asp Gly Arg Pro Ala Gly Arg Val Leu Glu
            20                  25                  30

Ile Gly Thr Gly Thr Gly Met Ile Leu Phe Asn Leu Gly Glu Gly Leu
        35                  40                  45

Gln Ser Tyr Val Gly Leu Glu Pro Ser Thr Ser Ala Ala Ala Phe Val
    50                  55                  60

Asn Arg Arg Ile Gln Thr Leu Pro Ala Phe Ala Gly Lys Ala Glu Val
65                  70                  75                  80

His Val Gly Thr Ala Thr Asp Ile Ser Gln Leu Gln Asp Leu Arg Pro
                85                  90                  95

Glu Val Val Ile Asn Ser Val Ala Gln Tyr Phe Pro Ser Pro Glu
            100                 105                 110

Tyr Leu Ser Lys Val Leu Tyr Ala Leu Ala Gln Ile Pro Gly Val Lys
        115                 120                 125

Arg Leu Phe Phe Gly Asp Met Arg Ser Tyr Ala Ile Asn Asp Gln Phe
    130                 135                 140

Leu Ala Ala Arg Ala Leu His Asn Ile Gly Ser Lys Ala Thr Lys Ser
145                 150                 155                 160

Ala Ile Arg Ser Lys Met Val Asp Leu Glu Asn Ser Glu Glu Glu Leu
                165                 170                 175

Leu Val Asp Pro Thr Phe Phe Thr Asn Leu Ala Thr Glu Leu Pro Glu
            180                 185                 190

Val Glu His Val Glu Ile Leu Pro Lys Arg Met Gln Ala Thr Asn Glu
        195                 200                 205

Leu Ser Ala Tyr Arg Tyr Ala Ala Val Val His Ile Arg Asp Ser Ser
    210                 215                 220

<210> SEQ ID NO 9
<211> LENGTH: 69
<212> TYPE: PRT
<213> ORGANISM: Curvularia clavata

<400> SEQUENCE: 9

Thr Glu Ala Val Leu Cys Glu Glu Phe Thr Asp Val Leu Gly Leu Glu
1               5                   10                  15

Val Gly Ile Thr Asp Asn Phe Phe Asp Leu Gly Gly His Ser Leu Met
            20                  25                  30
```

```
Ala Thr Lys Leu Ala Ala Arg Ile Ser Arg Arg Leu Asp Ala Arg Val
         35                  40                  45

Ser Val Lys Asp Val Phe Asp Gln Pro Val Ile Val Asp Leu Ala Ala
 50                  55                  60

Ser Ile Arg Arg Gly
 65

<210> SEQ ID NO 10
<211> LENGTH: 295
<212> TYPE: PRT
<213> ORGANISM: Curvularia clavata

<400> SEQUENCE: 10

Gly Pro Val Glu Gln Ser Phe Ala Gln Gly Arg Leu Trp Phe Leu Asp
 1               5                  10                  15

Gln Leu Asn Leu Gly Ala Ser Leu Tyr Leu Met Pro Leu Ala Leu Arg
             20                  25                  30

Leu Arg Gly Pro Leu Arg Ile Asp Ala Leu Thr Ala Ala Leu Phe Ala
         35                  40                  45

Leu Glu Gln Arg His Glu Thr Leu Arg Thr Val Phe Lys Glu Gln Asp
 50                  55                  60

Gly Val Gly Ile Gln Ile Ile Gln Pro Ser Gln Lys Lys Lys Leu Arg
 65                  70                  75                  80

Thr Ile Asp Val Ser Ala Gly Asp Phe Ser Glu Ala Leu His His Glu
                 85                  90                  95

Arg Thr Ala Pro Phe Asp Leu Ala Ser Glu Pro Gly Phe Arg Val Ala
            100                 105                 110

Leu Leu Gln Leu Glu Pro Ser Asp His Val Leu Ser Ile Val Met His
        115                 120                 125

His Ile Ile Tyr Asp Gly Trp Ser Ile Asp Ile Leu Cys Gln Glu Leu
130                 135                 140

Gly Gln Phe Tyr Ala Ala Ile Gln Gly Gln Asp Pro Leu Gly Gln
145                 150                 155                 160

Val Ser Pro Leu Pro Ile Gln Tyr Arg Asp Phe Ser Val Trp Gln Lys
                165                 170                 175

Gln Pro Glu Gln Val Ala Glu His Glu Arg Gln Leu Ala Tyr Trp Ile
            180                 185                 190

Asp Gln Leu Ala Asp Ser Ala Pro Ala Glu Phe Leu Val Asp Leu Pro
        195                 200                 205

Arg Pro Pro Val Leu Ser Gly Asp Ala Gly Leu Val His Leu Thr Ile
    210                 215                 220

Asp Gly Pro Ile Tyr Asp Arg Leu Arg Ala Phe Cys Arg Val His Gln
225                 230                 235                 240

Thr Thr Thr Phe Ala Val Leu Leu Ala Ala Phe Arg Ala Thr His Tyr
                245                 250                 255

Arg Leu Thr Gly Ala Glu Asp Ala Thr Val Gly Thr Pro Ile Ala Asn
            260                 265                 270

Arg Asn Arg Pro Glu Leu Glu Asn Leu Val Gly Phe Phe Val Asn Thr
        275                 280                 285

Gln Cys Met Arg Ile Ser Val
    290                 295

<210> SEQ ID NO 11
<211> LENGTH: 404
<212> TYPE: PRT
<213> ORGANISM: Curvularia clavata
```

```
<400> SEQUENCE: 11

Leu Thr Tyr Ala Gln Leu Asp Glu Gln Ser Asp Glu Val Ala Val Trp
1               5                   10                  15

Leu His Gln Arg Lys Leu Pro Ala Glu Ser Leu Val Ala Val Leu Ala
            20                  25                  30

Pro Arg Ser Cys Glu Thr Ile Ile Thr Phe Phe Gly Ile Leu Lys Ala
        35                  40                  45

Asn Leu Ala Tyr Leu Pro Leu Asp Ile Asn Val Pro Ala Ala Arg Ile
    50                  55                  60

Gln Ala Ile Leu Ser Ser Val Ala Gly Lys Lys Ile Leu Leu Leu Gly
65                  70                  75                  80

Ser Asp Gln Ala Gln Pro Glu Ile Arg Leu Asp Asp Val Glu Phe Val
                85                  90                  95

Gln Ile Asn Glu Thr Ile Asp His Asn Met Ala Lys Asp Asn Thr Thr
            100                 105                 110

Arg Ser Gly Pro Leu Ala Thr Ser Leu Ala Tyr Val Ile Phe Thr Ser
        115                 120                 125

Gly Ser Thr Gly Gln Pro Lys Gly Val Lys Val Glu His Arg Gly Ile
130                 135                 140

Val Arg Leu Val Lys Asn Ser Asn Val Val Ala Lys Met Pro Glu Ala
145                 150                 155                 160

Ala Cys Val Ala His Leu Ser Asn Leu Ala Phe Asp Ala Ala Thr Trp
                165                 170                 175

Glu Ile Tyr Ala Ala Leu Leu Asn Gly Gly Ser Leu Ile Cys Ile Asp
            180                 185                 190

Tyr Phe Thr Thr Leu Asp Ser Lys Val Leu Glu Ala Val Phe Glu Arg
        195                 200                 205

Glu Gln Ile Arg Ala Ala Met Phe Pro Pro Ala Leu Leu Lys Gln Cys
    210                 215                 220

Leu Leu Asn Ile Pro Thr Thr Ile Ser Ala Leu Asp Val Ile Leu Ala
225                 230                 235                 240

Ala Gly Asp Arg Phe Asp Arg Arg Asp Ala Ile Ala Ala Gln Ala Leu
                245                 250                 255

Val Gly Gly Gly Val Tyr Asn Ala Tyr Gly Pro Thr Glu Asn Thr Thr
            260                 265                 270

Leu Ser Thr Ile Tyr Asn Val Val Asp Gly Asp Thr Asn Val Asn Gly
        275                 280                 285

Ile Pro Ile Gly Leu Pro Val Ser Asn Ser Gly Val Tyr Val Met Asp
    290                 295                 300

Pro Asn Gln Gln Leu Val Pro Leu Gly Val Met Gly Glu Leu Val Val
305                 310                 315                 320

Val Gly Asp Gly Val Ala Arg Gly Tyr Thr Asp Pro Ala Leu Asp Val
                325                 330                 335

Asp Arg Phe Ile Lys Val Glu Ile Asp Gly Gln Ile Val Arg Ala Tyr
            340                 345                 350

Arg Thr Gly Asp Arg Val Arg His Arg Pro Lys Asp Gly Gln Ile Glu
        355                 360                 365

Phe Phe Gly Arg Met Asp Gln Gln Val Lys Ile Arg Gly His Arg Ile
    370                 375                 380

Glu Leu Ala Glu Val Glu His Val Ile Leu Asp Asn Ser Leu Val Gln
385                 390                 395                 400

Asp Ala Ala Val
```

```
<210> SEQ ID NO 12
<211> LENGTH: 69
<212> TYPE: PRT
<213> ORGANISM: Curvularia clavata

<400> SEQUENCE: 12

Ile Glu Thr Ile Leu Cys Glu Glu Tyr Ala Glu Val Leu Gly Val Glu
1               5                   10                  15

Val Gly Val Met Asp Asn Phe Phe Asp Leu Gly Gly His Ser Leu Met
            20                  25                  30

Ala Thr Lys Leu Ala Ala Arg Ala Thr Arg Arg Leu Asp Ala Lys Leu
        35                  40                  45

Ser Val Lys Asp Ile Phe Asp Tyr Pro Ile Leu Ala Asn Leu Ala Ala
    50                  55                  60

Ala Val Gln Arg Gly
65

<210> SEQ ID NO 13
<211> LENGTH: 298
<212> TYPE: PRT
<213> ORGANISM: Curvularia clavata

<400> SEQUENCE: 13

Gly Pro Val Glu Gln Ser Phe Ala Gln Gly Arg Leu Trp Phe Leu Asp
1               5                   10                  15

Gln Leu Asn Val Gly Ser Asn Trp Tyr Leu Gln Pro Ile Ala Ile Arg
            20                  25                  30

Ile Arg Gly Ser Leu Asn Ile Asn Ala Leu Thr Thr Ala Leu His Ala
        35                  40                  45

Leu Glu Gln Arg His Glu Thr Leu Arg Thr Thr Phe Glu Glu Glu Asp
    50                  55                  60

Gly Val Gly Met Gln Val Val Gln Glu Tyr Asp Pro Ile Glu Leu Arg
65                  70                  75                  80

Ile Met Asp Ile Ala Ala Asp Tyr Asp Gly Asp Tyr Thr Glu Ala Leu
                85                  90                  95

Lys Gly Glu Gln Thr Thr Pro Phe Asp Leu Glu Ser Glu Pro Gly Trp
            100                 105                 110

Arg Val Ser Leu Leu Arg Met Asn Asp Asn Asp His Ile Leu Ser Leu
        115                 120                 125

Val Leu His His Ile Ile Ser Asp Gly Trp Ser Val Asp Val Leu Arg
    130                 135                 140

Gln Glu Leu Lys Gln Phe Tyr Ala Ala Ala Leu Gln Gly Leu Asp Pro
145                 150                 155                 160

Leu Ser Gly Ala Asp Pro Leu Pro Ile Gln Tyr Arg Asp Phe Ser Leu
                165                 170                 175

Trp Gln Lys Gln Pro Glu Gln Val Ala Glu His Glu Arg Gln Leu Lys
            180                 185                 190

Tyr Trp Val Glu Gln Leu Ala Asp Asn Ser Pro Ala Thr Leu Leu Ala
        195                 200                 205

Asp Arg Pro Arg Pro Ser Val Leu Ser Gly Ala Gly Ser Val Pro
    210                 215                 220

Leu Ser Ile Glu Gly Gln Val Tyr Glu Lys Leu Gln Ala Phe Cys Arg
225                 230                 235                 240

Ala His Gln Thr Thr Ser Phe Ser Val Leu Leu Ala Ala Phe Arg Ala
                245                 250                 255
```

```
Ala His Phe Arg Leu Thr Gly Val Asp Asp Ala Thr Ile Gly Ile Pro
            260                 265                 270

Ile Ala Asn Arg Asn Arg Pro Glu Leu Glu His Leu Ile Gly Phe Phe
            275                 280                 285

Val Asn Arg Gln Cys Met Arg Ile Thr Val
            290                 295

<210> SEQ ID NO 14
<211> LENGTH: 403
<212> TYPE: PRT
<213> ORGANISM: Curvularia clavata

<400> SEQUENCE: 14

Leu Thr Tyr Ala Gln Leu Asp Gln Gln Ser Asp Glu Ile Ala Thr Trp
1               5                   10                  15

Leu Arg Asn Lys Lys Met Ala Pro Glu Thr Leu Val Gly Val Leu Ala
            20                  25                  30

Pro Arg Ser Cys Gln Thr Ile Val Ala Phe Leu Gly Val Leu Lys Ala
            35                  40                  45

Asn Leu Ala Tyr Leu Pro Leu Asp Val Asn Ala Pro Met Ala Arg Val
        50                  55                  60

Glu Thr Ile Met Ser Ser Val Pro Gly Ser Lys Leu Leu Leu Leu Gly
65                  70                  75                  80

Ser Asp Val Pro Ala Gln Glu Ile Gln Leu Gln Asn Val Glu Leu Val
                85                  90                  95

Arg Ile Glu Asp Thr Leu Gly His Ala Ala Ser Ala Gly Thr Ala Thr
            100                 105                 110

Thr Glu Pro Ser Pro Thr Ser Leu Ala Tyr Val Ile Phe Thr Ser Gly
        115                 120                 125

Ser Thr Gly Lys Pro Lys Gly Val Met Val Glu His Arg Ser Val Ile
130                 135                 140

Arg Leu Val Arg Lys Glu Ser Asn Ser Met Ser Lys Met Ser Ser Arg
145                 150                 155                 160

Ala Arg Val Ala His Leu Thr Asn Ile Ala Phe Asp Val Ser Ala Trp
                165                 170                 175

Glu Val Tyr Ala Thr Leu Leu Asn Gly Gly Thr Leu Val Cys Val Asp
            180                 185                 190

Tyr Phe Thr Ser Phe Asp Ala Lys Ala Leu Gly Leu Leu Phe Glu Arg
        195                 200                 205

Glu Gln Ile Thr Ala Ala Met Ile Thr Pro Thr Leu Leu Lys Gln Cys
210                 215                 220

Ile Thr Ile Val Pro Glu Ala Leu Arg Lys Leu Ser Val Leu Tyr Thr
225                 230                 235                 240

Gly Gly Asp Arg Phe Asp Arg Arg Asp Ala Ile Ala Thr Lys Ala Leu
                245                 250                 255

Val Lys Gly Pro Val Tyr Asn Ala Trp Gly Pro Thr Glu Thr Thr Ile
            260                 265                 270

Val Ser Thr Ile Tyr Glu Leu Ala Asp Asp Gln Phe Thr Asn Gly
        275                 280                 285

Val Pro Ile Gly Lys Ala Val Ser Asn Ser Trp Ala Tyr Val Met Asp
        290                 295                 300

Leu Asn Gln Gln Leu Val Pro Val Gly Val Met Gly Glu Ala Val Val
305                 310                 315                 320

Ile Gly Asp Gly Leu Ala Arg Gly Tyr Thr Asp Pro Ala Leu Asp Cys
                325                 330                 335
```

-continued

```
Asn Arg Phe Val His Ile Thr Ile Asp Gly Lys Arg Val Arg Ala Tyr
            340                 345                 350

Arg Thr Gly Asp Arg Ala Arg Tyr Arg Pro Lys Asp Gly Glu Ile Glu
        355                 360                 365

Phe Phe Gly Arg Met Asp Arg Gln Leu Lys Ile Arg Gly His Arg Ile
    370                 375                 380

Glu Pro Ala Glu Ile Glu His Ala Met Leu Gly His Asn Asp Ile Val
385                 390                 395                 400

Asp Val Ala

<210> SEQ ID NO 15
<211> LENGTH: 224
<212> TYPE: PRT
<213> ORGANISM: Curvularia clavata

<400> SEQUENCE: 15

Asp Gly Gly Ala Ile Asp Gln Ala Glu Met Gln Glu Trp Leu Asp Asp
1               5                   10                  15

Thr Ile Gln Thr Ile Val Asp Gly Gln Pro Ala Gly His Val Phe Glu
            20                  25                  30

Ile Gly Thr Gly Thr Gly Met Ile Met Phe Gly Leu Gly Lys Gln Gly
        35                  40                  45

Leu Gln Ser Tyr Val Gly Leu Glu Pro Ser Thr Ser Ala Thr Thr Tyr
    50                  55                  60

Val Asn Arg Lys Ile Lys Thr Ala Pro Thr Val Ala Gly Lys Ala Lys
65                  70                  75                  80

Val Tyr Val Gly Thr Ala Met Glu Ala Ala Gln Leu Asn Gly Leu His
                85                  90                  95

Pro Glu Val Val Val Ile Asn Ser Val Ala Gln Tyr Phe Pro Thr Pro
            100                 105                 110

Glu Tyr Leu Leu Glu Val Val Gly Ile Leu Thr Gln Met Pro Gly Val
        115                 120                 125

Lys Arg Leu Phe Phe Gly Asp Ile Arg Ser Tyr Ala Thr Asn Arg Lys
    130                 135                 140

Phe Leu Ala Ala Arg Ala Leu His Met Leu Gly Ser Asn Ala Lys Lys
145                 150                 155                 160

His Asp Ile Arg Arg Lys Met Ala Glu Leu Asp Glu Phe Glu Glu Glu
                165                 170                 175

Leu Ile Val Asp Pro Ser Phe Phe Thr Gly Leu Val Ser Arg Leu Pro
            180                 185                 190

Gly Gln Val Lys His Val Glu Ile Leu Pro Lys Gln Met Ile Ala Thr
        195                 200                 205

Asn Glu Leu Ser Ala Tyr Arg Tyr Ala Ala Val Val His Leu Ala Leu
    210                 215                 220

<210> SEQ ID NO 16
<211> LENGTH: 69
<212> TYPE: PRT
<213> ORGANISM: Curvularia clavata

<400> SEQUENCE: 16

Val Glu Ala Val Leu Cys Glu Glu Phe Ser Glu Val Leu Gly Val Glu
1               5                   10                  15

Val Gly Val Thr Asp Asn Phe Phe Asp Leu Gly Gly His Ser Leu Met
            20                  25                  30
```

Ala Thr Lys Leu Ala Ala Arg Thr Gly Arg Arg Leu Asp Ala Lys Val
            35                  40                  45

Ser Val Lys Asp Val Phe Asp His Pro Val Leu Ala Asp Leu Ala Ala
50                  55                  60

Ala Ile Gln Arg Gly
65

<210> SEQ ID NO 17
<211> LENGTH: 298
<212> TYPE: PRT
<213> ORGANISM: Curvularia clavata

<400> SEQUENCE: 17

Gly Pro Val Glu Gln Ser Tyr Ala Gln Gly Arg Leu Trp Phe Leu Glu
1               5                   10                  15

Gln Leu Asn Phe Lys Ala Thr Trp Tyr Leu Leu Pro Leu Ala Val Arg
            20                  25                  30

Ile Arg Gly Pro Leu Asn Ile Lys Ala Leu Thr Thr Ala Leu His Ala
        35                  40                  45

Leu Glu Gln Arg His Glu Thr Leu Arg Thr Thr Phe Ile Glu Arg Asp
    50                  55                  60

Gly Val Gly Lys Gln Ala Val Gln Pro Phe Gln Pro Lys Glu Leu Glu
65                  70                  75                  80

Ile Val Asp Ile Ala Ala Asp His Gln Gly Asp Tyr Leu Lys Val Leu
                85                  90                  95

Arg Asp Glu Gln Thr Thr Met Phe Asn Leu Ala Thr Gln Pro Gly Trp
            100                 105                 110

Arg Val Thr Leu His Arg Val Asp Gln Asn Thr His Asn Leu Ser Ile
        115                 120                 125

Val Met His His Ile Ile Ser Asp Gly Trp Ser Val Asp Val Leu Arg
    130                 135                 140

His Glu Leu Arg Gln Phe Tyr Ala Ala Ala Leu Arg Gly Gln Asp Pro
145                 150                 155                 160

Leu Ala His Ile Ser Pro Leu Pro Ile Gln Tyr Arg Asp Phe Ser Leu
                165                 170                 175

Trp Gln Lys Gln Pro Asp Gln Ile Ile Glu His Ala Lys Gln Leu Glu
            180                 185                 190

Tyr Trp Thr Lys Gln Leu Ala Asp Ser Ser Pro Ala Glu Leu Pro Thr
        195                 200                 205

Asp Leu Pro Arg Pro Ala Val Leu Ser Gly Lys Ala Gly Glu Val Ala
    210                 215                 220

Leu Ser Val Lys Gly Pro Leu Tyr Glu Arg Leu Gln Ala Phe Cys Lys
225                 230                 235                 240

Thr His Gln Thr Thr Ala Phe Ala Thr Leu Leu Ala Ala Phe Arg Ala
                245                 250                 255

Thr His His Arg Leu Thr Gly Ala Glu Asp Ala Thr Ile Gly Thr Pro
            260                 265                 270

Ile Ala Asn Arg Asn Arg Pro Glu Leu Glu Asn Leu Ile Gly Phe Phe
        275                 280                 285

Val Asn Ala Gln Cys Met Arg Ile Thr Ile
    290                 295

<210> SEQ ID NO 18
<211> LENGTH: 402
<212> TYPE: PRT
<213> ORGANISM: Curvularia clavata

<400> SEQUENCE: 18

```
Leu Thr Tyr Ala Gln Leu Asn Glu Gln Ser Asp Lys Val Ala Ala Trp
1               5                   10                  15

Leu His Gln Cys Asn Leu Pro Thr Glu Thr Leu Val Ala Val Leu Ala
            20                  25                  30

Pro Arg Ser Cys Gln Thr Val Val Ala Phe Leu Gly Ile Leu Lys Ala
        35                  40                  45

Asn Leu Ala Tyr Leu Pro Leu Asp Val Asn Val Pro Ala Ala Arg Ile
    50                  55                  60

Glu Ala Ile Leu Ser Glu Val Ser Gly His Ile Leu Val Leu Leu Gly
65                  70                  75                  80

Ser His Val Ser Ala Pro Lys Ile Glu Leu Ala Asp Val Glu Phe Val
            85                  90                  95

Lys Ile Asp Asn Thr Val Glu His Asn Leu Pro Gly Arg Ile Gly Ser
        100                 105                 110

Ala Pro Ser Ala Thr Ser Leu Ala Tyr Val Ile Phe Thr Ser Gly Ser
    115                 120                 125

Thr Gly Lys Pro Lys Gly Val Lys Val Glu His Arg Gly Ile Val Arg
130                 135                 140

Leu Val Lys Glu Ser Asn Val Val Ala Lys Met Pro Gln Ala Ala Arg
145                 150                 155                 160

Ile Ala His Leu Ser Asn Ile Ala Phe Asp Ala Ala Thr Trp Glu Leu
            165                 170                 175

Tyr Ala Ala Leu Leu Asn Gly Gly Thr Leu Val Cys Ile Asn Tyr Leu
        180                 185                 190

Thr Thr Leu Asp Ser Lys Ala Leu Glu Ala Val Phe Glu Gln Glu Lys
    195                 200                 205

Ile Gln Ala Ala Met Leu Pro Pro Ala Leu Leu Lys Gln Tyr Leu Val
210                 215                 220

Asn Ile Pro Ala Ala Ile Gly Ala Leu Glu Val Val Leu Val Ala Gly
225                 230                 235                 240

Asp Arg Phe Asp Arg Arg Asp Ala Ala Ala Thr Gln Ala Leu Val Gly
            245                 250                 255

Ala Gly Val Tyr Asn Ala Tyr Gly Pro Thr Glu Asn Thr Thr Leu Ser
        260                 265                 270

Thr Ile Tyr Asn Val Val Gln Gly Asp Ala Asn Val Asn Gly Val Pro
    275                 280                 285

Ile Gly Arg Pro Val Ser Asn Ser Gly Ala Tyr Ile Met Asn Met Asn
290                 295                 300

Gln Glu Leu Val Pro Ile Gly Val Ile Gly Glu Leu Val Val Val Gly
305                 310                 315                 320

Asp Gly Val Ala Arg Gly Tyr Thr Asp Pro Ala Leu Asp Val Asn Arg
            325                 330                 335

Phe Val Asn Val Thr Ile Glu Gly Gln Thr Met Arg Ala Tyr Arg Thr
        340                 345                 350

Gly Asp Arg Ala Arg Tyr Arg Pro Lys Asp Ala Gln Ile Glu Phe Phe
    355                 360                 365

Gly Arg Met Asp Gln Gln Ile Lys Ile Arg Gly His Arg Ile Glu Pro
370                 375                 380

Ala Glu Val Glu His Ala Leu Leu Asn Asn Asp Leu Leu Gln Asp Ala
385                 390                 395                 400

Ala Val
```

```
<210> SEQ ID NO 19
<211> LENGTH: 222
<212> TYPE: PRT
<213> ORGANISM: Curvularia clavata

<400> SEQUENCE: 19

Asp Gly Ser Ala Ile Asp Lys Ala Glu Met Gln Glu Trp Leu Asp Asp
1               5                   10                  15

Thr Met Gln Thr Ile Leu Asp Gly Arg Pro Ala Gly Arg Val Leu Glu
            20                  25                  30

Ile Gly Thr Gly Thr Gly Met Ile Leu Phe Asn Leu Gly Glu Gly Leu
        35                  40                  45

Gln Ser Tyr Val Gly Leu Glu Pro Ser Thr Ser Ala Ala Ala Phe Val
    50                  55                  60

Asn Arg Arg Ile Gln Thr Leu Pro Ala Phe Ala Gly Lys Ala Glu Val
65                  70                  75                  80

His Val Gly Thr Ala Thr Asp Ile Ser Gln Leu Gln Asp Leu Arg Pro
                85                  90                  95

Glu Val Val Val Ile Asn Ser Val Ala Gln Tyr Phe Pro Ser Pro Glu
            100                 105                 110

Tyr Leu Ser Lys Val Leu Tyr Ala Leu Ala Gln Ile Pro Gly Val Lys
        115                 120                 125

Arg Leu Phe Phe Gly Asp Met Arg Ser Tyr Ala Ile Asn Asp Gln Phe
    130                 135                 140

Leu Ala Ala Arg Ala Leu His Asn Ile Gly Ser Lys Ala Thr Lys Ser
145                 150                 155                 160

Ala Ile Arg Ser Lys Met Val Asp Leu Glu Asn Ser Glu Glu Glu Leu
                165                 170                 175

Leu Val Asp Pro Thr Phe Phe Thr Asn Leu Ala Thr Glu Leu Pro Glu
            180                 185                 190

Val Glu His Val Glu Ile Leu Pro Lys Arg Met Gln Ala Thr Asn Glu
        195                 200                 205

Leu Ser Ala Tyr Arg Tyr Ala Ala Val Val His Ile Arg Asp
    210                 215                 220

<210> SEQ ID NO 20
<211> LENGTH: 69
<212> TYPE: PRT
<213> ORGANISM: Curvularia clavata

<400> SEQUENCE: 20

Ile Glu Ala Ala Leu Cys Glu Val Phe Val Asp Leu Leu Gly Thr Glu
1               5                   10                  15

Val Ser Ile Thr Asp Asn Phe Phe Asn Leu Gly Gly His Ser Leu Met
            20                  25                  30

Ala Thr Lys Leu Ala Ala Arg Ile Ser Arg Arg Leu Asp Ala Arg Ile
        35                  40                  45

Ser Val Lys Asp Val Phe Asp Tyr Pro Val Leu Ala Asp Leu Ala Gly
    50                  55                  60

Ala Val Gln Arg Gly
65

<210> SEQ ID NO 21
<211> LENGTH: 295
<212> TYPE: PRT
<213> ORGANISM: Curvularia clavata
```

<400> SEQUENCE: 21

```
Gly Pro Val Glu Gln Ser Phe Ala Gln Gly Arg Leu Trp Phe Leu Asp
1               5                   10                  15
Gln Leu Asn Ala Gly Ser Leu Trp Tyr Ile Gln Pro Ile Ala Val Arg
            20                  25                  30
Val Arg Gly Ser Leu Asn Ile Gly Ala Leu Thr Thr Ala Leu Asn Ala
        35                  40                  45
Leu Glu Lys Arg His Glu Pro Leu Arg Thr Thr Phe Glu His Asp
    50                  55                  60
Gly Ile Gly Val Gln Val Val Gln Pro His Gln Pro Lys Lys Leu Arg
65                  70                  75                  80
Ile Val Asp Thr Val Ala Asn Tyr Gln Gly Asp Phe Ile Arg Ala Leu
                85                  90                  95
Arg Lys Glu Gln Gln Thr Leu Phe Asn Leu Ala Thr Glu Pro Gly Trp
            100                 105                 110
Arg Val Ser Leu Leu Arg Ile Gly Glu Asp Asp Asn Ile Leu Ser Ile
        115                 120                 125
Val Met His His Ile Ile Ser Asp Gly Trp Ser Val Asp Ile Leu Arg
130                 135                 140
Gln Asp Leu Lys Leu Phe Tyr Ala Ala Ala Leu Lys Ser Gln Glu Pro
145                 150                 155                 160
Gln Val Asp Ala Leu Pro Ile Gln Tyr Arg Asp Phe Ala Phe Trp Gln
                165                 170                 175
Lys Gln Pro Glu Gln Val Ala Glu His Gln Arg Gln Leu Asp Tyr Trp
            180                 185                 190
Ile Glu Gln Leu Lys Asp Ser Lys Pro Ala Glu Leu Ile Thr Asp Phe
        195                 200                 205
Pro Arg Pro Glu Val Leu Ser Gly Thr Ala Gly Ile Val Gln Leu Ala
210                 215                 220
Val Asp Gly Gln Val Tyr Glu Gly Leu Arg Ala Phe Cys Arg Ile His
225                 230                 235                 240
Gln Thr Thr Ser Phe Val Val Leu Leu Ala Ala Phe Arg Ala Ala His
                245                 250                 255
Tyr Arg Leu Thr Gly Thr Glu Asp Ala Thr Ile Gly Ser Pro Ile Ala
            260                 265                 270
Asn Arg Asn Arg Pro Glu Leu Glu Ser Leu Ile Gly Phe Phe Val Asn
        275                 280                 285
Thr Gln Cys Met Arg Ile Met
    290                 295
```

<210> SEQ ID NO 22
<211> LENGTH: 406
<212> TYPE: PRT
<213> ORGANISM: Curvularia clavata

<400> SEQUENCE: 22

```
Leu Thr Tyr Ala Gln Leu Asp Glu Glu Ser Asn Lys Val Ala Thr Trp
1               5                   10                  15
Leu Ser Gln Arg Gln Leu Ala Pro Glu Thr Leu Val Gly Val Leu Ala
            20                  25                  30
Pro Arg Ser Cys Pro Thr Ile Val Thr Phe Phe Gly Ile Leu Lys Ala
        35                  40                  45
Ser Leu Ala Tyr Leu Pro Leu Asp Val Asn Val Pro Ser Ala Arg Ile
    50                  55                  60
```

```
Glu Ala Ile Leu Ser Ala Val Pro Asp His Lys Leu Val Phe Leu Gly
 65                  70                  75                  80

Ala Asp Val Pro Asp Pro Glu Ala Pro Leu Val Asn Val Glu Leu Val
             85                  90                  95

Arg Ile Asp Asp Ile Leu Arg Gln Ser Ile His Ala Ser Asn Ala Gly
            100                 105                 110

Leu Leu Ala Asn His Pro Leu Ala Thr Ser Leu Ala Tyr Val Met Phe
        115                 120                 125

Thr Ser Gly Ser Thr Gly Lys Pro Lys Gly Val Met Val Glu His Arg
    130                 135                 140

Ser Ile Val Arg Leu Val Lys Glu Thr Asn Leu Val Pro Ala Val Glu
145                 150                 155                 160

Ala Val Ser Ser Val Ala His Ile Ser Asn Val Ala Phe Asp Ala Ala
                165                 170                 175

Thr Trp Glu Ile Tyr Ala Ala Leu Leu Asn Gly Gly Thr Thr Val Cys
            180                 185                 190

Ile Asp His Ile Thr Val Leu Asp Pro Ala Lys Leu Ala Leu Val Phe
        195                 200                 205

Ser Ser Glu Lys Ile Lys Ala Ala Phe Phe Ser Thr Ala Leu Leu Lys
    210                 215                 220

Gln Arg Leu Tyr Glu Glu Pro Ser Thr Ile Thr Gly Leu Asp Leu Leu
225                 230                 235                 240

Tyr Ala Gly Gly Glu Arg Met Arg Pro Gln Asp Ala Leu Lys Thr Arg
                245                 250                 255

Glu Leu Val Arg Gly Ser Phe Cys His Val Tyr Gly Pro Thr Glu Asn
            260                 265                 270

Thr Thr Phe Ser Thr Val Tyr Pro Met Gly Val Glu Glu Arg Cys Val
        275                 280                 285

Asn Gly Leu Pro Ile Gly Arg Ala Val Ser His Ser Gly Ala Val Ile
    290                 295                 300

Met Asp Ala Asn Gln Arg Leu Val Pro Leu Gly Val Met Gly Glu Leu
305                 310                 315                 320

Val Val Thr Gly Asp Gly Leu Ala Arg Gly Tyr Thr Asp Pro Ala Leu
                325                 330                 335

Asn Arg Asp Arg Phe Val Glu Val Asn Ile His Gly Gln Val Leu Arg
            340                 345                 350

Ala Tyr Arg Thr Gly Asp Gln Ala Arg Tyr Arg Pro Lys Asp Gly Gln
        355                 360                 365

Ile Glu Phe Ser Gly Arg Met Asp Arg Gln Leu Lys Ile Arg Gly His
    370                 375                 380

Arg Ile Glu Pro Ala Glu Val Glu His Ala Ile Leu Ser His Asp Asp
385                 390                 395                 400

Ile Arg Asn Ala Val Val
                405

<210> SEQ ID NO 23
<211> LENGTH: 221
<212> TYPE: PRT
<213> ORGANISM: Curvularia clavata

<400> SEQUENCE: 23

Asp Gly Thr Ala Ile Asp Lys Ala Glu Met Gln Glu Trp Leu Asp Asp
1               5                   10                  15

Thr Met Arg Thr Leu His Asp Gly Arg Asp Pro Gly His Val Leu Glu
            20                  25                  30
```

```
Val Gly Thr Gly Thr Gly Met Ile Leu Phe Asn Leu Gly Lys Gly Leu
         35                  40                  45

Gln Ser Tyr Val Gly Leu Glu Pro Ser Thr Ser Ala Ala Ala Phe Val
 50                      55                  60

Asn Arg Lys Ile Glu Thr Ile Ser Ser Leu Ala Gly Lys Ala Lys Val
 65                  70                  75                  80

Glu Ile Gly Thr Ala Thr Asp Val Gly Gln Leu Lys Asn Leu Arg Ser
                 85                  90                  95

Asp Leu Val Val Ile Asn Ser Val Ala Gln Tyr Phe Pro Ser Pro Glu
            100                 105                 110

Tyr Leu Val Glu Ala Val Thr Ala Leu Val His Ile Pro Gly Val Lys
            115                 120                 125

Arg Leu Phe Phe Gly Asp Met Arg Ser Tyr Ala Met Asn Lys Gln Phe
        130                 135                 140

Leu Val Ala Arg Ala Leu Arg Thr Leu Gly Ala Lys Ala Asn Lys Asp
145                 150                 155                 160

Asp Val Arg Arg Lys Met Val Glu Leu Glu Phe Glu Glu Leu
                165                 170                 175

Leu Val Asp Pro Ala Phe Phe Thr Gly Leu Ala Asn Trp Leu Ser Glu
            180                 185                 190

Val Glu His Val Glu Ile Leu Pro Lys Gln Met Thr Ser Thr Asn Glu
        195                 200                 205

Leu Ser Ser Tyr Arg Tyr Ala Ala Ile Val His Leu Arg
        210                 215                 220

<210> SEQ ID NO 24
<211> LENGTH: 69
<212> TYPE: PRT
<213> ORGANISM: Curvularia clavata

<400> SEQUENCE: 24

Ile Glu Ala Leu Leu Cys Glu Glu Phe Ala Glu Val Leu Gly Val Glu
 1               5                  10                  15

Val Gly Ile Asn Asp Asp Phe Phe Asp Leu Gly Gly His Ser Leu Met
                 20                  25                  30

Ala Thr Lys Leu Ala Ala Arg Ser Ser Arg Arg Phe Asp Ala Lys Val
             35                  40                  45

Ser Val Lys Asp Val Phe Asp His Pro Ile Leu Ala Asp Leu Ala Ala
 50                      55                  60

Ser Ile Gln Arg Gly
 65

<210> SEQ ID NO 25
<211> LENGTH: 298
<212> TYPE: PRT
<213> ORGANISM: Curvularia clavata

<400> SEQUENCE: 25

Gly Pro Val Glu Gln Ser Phe Ala Gln Gly Arg Leu Trp Phe Leu Glu
 1               5                  10                  15

Gln Leu Asn Val Ser Ser Thr Trp Tyr Leu Gln Pro Ile Ala Val Arg
                 20                  25                  30

Met Arg Gly Pro Leu Lys Ile Glu Ala Leu Ala Ala Ala Phe His Ala
             35                  40                  45

Leu Glu Glu Arg His Glu Thr Leu Arg Thr Thr Phe Glu Glu His Asp
 50                      55                  60
```

```
Gly Ile Gly Met Gln Val Val Gln Pro His Arg Pro Lys Glu Leu Arg
 65                  70                  75                  80

Val Ile Asp Val Gln Ala Glu His Asp Gly Asp Tyr Thr Gln Ala Leu
                 85                  90                  95

His Thr Glu Gln Thr Thr Thr Phe Asn Leu Glu Thr Glu Pro Gly Trp
            100                 105                 110

Arg Val Ser Val Phe Arg Leu Asn Glu Asp Asp Asn Ile Leu Ser Ile
        115                 120                 125

Val Met His His Ile Ile Ser Asp Gly Trp Ser Phe Asp Ile Leu Arg
130                 135                 140

Lys Glu Ile Arg Glu Phe Tyr Asn Ala Ala Leu Lys Gly Lys Asp Pro
145                 150                 155                 160

Leu Ala Gln Met Ser Pro Leu His Ile Gln Tyr Arg Asp Phe Ser Val
                165                 170                 175

Trp Gln Lys Gln Leu Asn Gln Ile Thr Glu His Lys Arg Gln Leu Asp
            180                 185                 190

Tyr Trp Thr Lys Asn Leu Ala Asp Asn Thr Pro Ala Glu Leu Pro Thr
        195                 200                 205

Asp Leu Pro Arg Pro Ala Val Leu Ser Gly Lys Ala Gly Val Ile Gln
210                 215                 220

Leu Ser Ile Thr Gly Pro Val Tyr Asp Arg Leu Arg Ala Phe Cys Arg
225                 230                 235                 240

Val His Gln Thr Thr Leu Phe Thr Val Leu Leu Thr Val Phe Arg Ala
                245                 250                 255

Thr His Tyr Arg Leu Thr Gly Ala Glu Asp Ala Thr Ile Gly Thr Pro
            260                 265                 270

Ile Ala Asn Arg Asn Arg Pro Glu Leu Glu Asn Leu Ile Gly Phe Phe
        275                 280                 285

Val Asn Thr Gln Cys Met Arg Ile Thr Val
290                 295

<210> SEQ ID NO 26
<211> LENGTH: 405
<212> TYPE: PRT
<213> ORGANISM: Curvularia clavata

<400> SEQUENCE: 26

Leu Thr Tyr Ala Gln Leu Asp Leu His Ser Asp Glu Leu Ala Ser Trp
  1               5                  10                  15

Leu Arg Gln Lys Lys Met Ala Pro Glu Thr Leu Val Gly Val Leu Ala
             20                  25                  30

Pro Arg Ser Cys Gln Thr Ile Val Thr Phe Leu Gly Ile Leu Lys Ala
         35                  40                  45

Ser Leu Ala Tyr Leu Pro Leu Asp Val Lys Val Pro Val Ala Arg Ile
     50                  55                  60

Glu Ala Ile Leu Ser Ser Ile Ser Gly Gln Lys Leu Ile Leu Leu Gly
 65                  70                  75                  80

Gln Asp Val Pro Val Pro Glu Ile Gln Leu Pro Asp Val Asp Val Val
                 85                  90                  95

Pro Ile Ser Glu Ile Leu Gly Arg Ser Val Pro Ser Arg Ala Thr Asp
            100                 105                 110

Lys Ser Leu Gly Pro Leu Ala Arg Asn Leu Ala Tyr Val Leu Phe Thr
        115                 120                 125

Ser Gly Ser Thr Gly Lys Pro Lys Gly Val Met Ile Glu His Arg Ser
130                 135                 140
```

Ile Val Arg Leu Val Lys Glu Thr Asn Leu Ile Ser Lys Leu Pro Asn
145                 150                 155                 160

Ala Pro Arg Thr Ala His Leu Thr Asn Leu Val Phe Asp Asn Ser Ala
            165                 170                 175

Trp Glu Ile Tyr Ser Thr Leu Leu Asn Gly Gly Thr Leu Val Cys Ile
            180                 185                 190

Asp Tyr Ala Thr Val Leu Asp Ser Lys Ala Leu Glu Thr Val Phe Lys
            195                 200                 205

Glu Gln Arg Ile Gln Thr Ser Leu Met Pro Pro Ala Leu Leu Lys Glu
            210                 215                 220

Cys Leu Ala Asn Met Pro Thr Met Phe Asp Asp Val Glu Val Leu Tyr
225                 230                 235                 240

Ala Leu Gly Asp Arg Phe Asp Lys Gln Asp Ala Met Lys Ala Arg Ser
            245                 250                 255

Ile Val Lys Thr Ala Val Tyr Asn Ala Tyr Gly Pro Thr Glu Asn Thr
            260                 265                 270

Val Ile Ser Thr Ile Tyr Glu Ile Ala Lys Asp Ser Phe Val Asn
            275                 280                 285

Gly Val Pro Ile Gly Arg Ser Ile Ser Asn Ser Gly Ala Phe Ile Met
290                 295                 300

Asp Ser Arg Gln Gln Leu Val Pro Val Gly Val Leu Gly Glu Leu Val
305                 310                 315                 320

Val Ser Gly Asp Gly Leu Ala Arg Gly Tyr Thr Asp Pro Thr Leu Asp
            325                 330                 335

Val Asn Arg Phe Val Glu Val Thr Val Asp Gly Gln His Val Arg Val
            340                 345                 350

Tyr Arg Thr Gly Asp Arg Val Arg Phe Arg Pro Lys Asp Gly Gln Ile
            355                 360                 365

Glu Phe Phe Ser Arg Met Asp Gln Gln Val Lys Ile Arg Gly His Arg
            370                 375                 380

Ile Glu Pro Ala Glu Val Glu His Val Ile Leu Thr Asn Lys Ile Ile
385                 390                 395                 400

Arg Asp Ala Ala Val
            405

<210> SEQ ID NO 27
<211> LENGTH: 69
<212> TYPE: PRT
<213> ORGANISM: Curvularia clavata

<400> SEQUENCE: 27

Met Glu Arg Ile Leu Cys Glu Glu Phe Ala Asp Val Leu Gly Val Glu
1               5                   10                  15

Val Gly Ile Thr Asp Asn Phe Phe Asp Phe Gly Gly His Ser Leu Met
            20                  25                  30

Ala Thr Lys Leu Ala Ala Arg Ile Ser Arg Arg Val Asn Ala Arg Val
            35                  40                  45

Ser Val Lys Ser Val Phe Asp His Pro Val Leu Val Asp Leu Ala Ser
        50                  55                  60

Thr Ile Lys Gln Asp
65

<210> SEQ ID NO 28
<211> LENGTH: 299
<212> TYPE: PRT
<213> ORGANISM: Curvularia clavata

<400> SEQUENCE: 28

```
Gly Pro Val Glu Gln Ser Phe Ala Gln Gly Arg Leu Trp Phe Leu Asp
1               5                   10                  15

Gln Leu Asn Phe Gly Ala Ser Trp Tyr Leu Met Pro Leu Ala Leu Arg
            20                  25                  30

Leu Gln Gly Ser Leu His Val Lys Ser Leu Thr Thr Ala Leu Phe Ala
        35                  40                  45

Leu Glu Gln Arg His Glu Thr Leu Arg Thr Thr Phe Glu Gln Asp
    50                  55                  60

Gly Val Gly Ile Gln Ile Val His Pro Ala Asn Lys Lys Asp Leu Arg
65                  70                  75                  80

Ile Leu Asp Val Ser Lys Glu Gln Asn Ser Asp Tyr Ala Lys Val Leu
                85                  90                  95

His Lys Glu Arg Thr Ile Pro Ile Asp Leu Thr Ser Glu Pro Gly Trp
            100                 105                 110

Arg Val Ser Leu Ile Arg Leu Gly Glu Asp Asp His Ile Leu Ser Ile
        115                 120                 125

Val Met His His Ile Ile Ser Asp Gly Trp Ser Val Asp Val Leu Arg
130                 135                 140

Gln Glu Leu Lys Gln Phe Tyr Thr Ala Ala Leu Lys Gly Gln Asp Pro
145                 150                 155                 160

Leu Ala Gln Ile Asp Ala Leu Pro Ile Gln Tyr Arg Asp Phe Ser Leu
                165                 170                 175

Trp Gln Lys Leu Pro Asp Gln Val Ala Glu His Gln Arg Gln Leu Glu
            180                 185                 190

Tyr Trp Ala Glu Gln Leu Ala Asp Asn Thr Pro Ala Glu Leu Leu Thr
        195                 200                 205

Asp Leu Pro Arg Pro Asp Val Leu Ser Gly Lys Ala Gly Ala Val Gln
    210                 215                 220

Leu Thr Ile Asp Gly Pro Val Phe Asp Gln Leu Gln Ala Phe Cys Arg
225                 230                 235                 240

Ala His Gln Thr Thr Met Phe Thr Val Leu Leu Ala Val Phe Arg Thr
                245                 250                 255

Thr His Tyr Arg Leu Thr Gly Ala Thr Asp Ala Thr Ile Gly Thr Pro
            260                 265                 270

Ile Ala Asn Arg Asn Arg Pro Glu Leu Glu Arg Leu Val Gly Phe Phe
        275                 280                 285

Val Asn Thr Gln Cys Ile Arg Ile Thr Val Asp
    290                 295
```

<210> SEQ ID NO 29
<211> LENGTH: 403
<212> TYPE: PRT
<213> ORGANISM: Curvularia clavata

<400> SEQUENCE: 29

```
Leu Thr Tyr Ser Gln Leu Asp Asp Gln Ser Asp Lys Ile Thr Ala Trp
1               5                   10                  15

Leu Leu Gln Arg Lys Ile Pro Ala Glu Ser Leu Val Ala Val Tyr Ala
            20                  25                  30

Pro Arg Thr Cys Gln Thr Ile Ile Thr Phe Phe Gly Ile Leu Lys Ala
        35                  40                  45

Asn Leu Ala Tyr Leu Pro Leu Asp Ile Asn Val Pro Ala Ala Arg Ile
    50                  55                  60
```

```
Glu Ala Ile Leu Ser Thr Ile Ser Gly His Lys Leu Val Leu Leu Gly
 65                  70                  75                  80

Ser Gln Val Ser Ala Pro Ala Val Gln Leu Lys Asp Val Glu Tyr Val
                 85                  90                  95

Trp Ile Asp Glu Ala Met Ala Glu Thr Val Arg Thr Cys Thr Ser Pro
            100                 105                 110

Glu Pro Ser Ala Thr Ser Leu Ala Tyr Val Ile Phe Thr Ser Gly Ser
        115                 120                 125

Thr Gly Leu Pro Lys Gly Val Lys Val Glu His Arg Gly Val Val Arg
    130                 135                 140

Leu Val Lys Gln Ser Asn Val Val Ala Lys Met Pro Gln Ala Ala Arg
145                 150                 155                 160

Val Ala His Leu Ser Asn Ile Ala Phe Asp Ala Ala Thr Trp Glu Ile
                165                 170                 175

Tyr Ala Ala Leu Leu Asn Gly Gly Ser Leu Ile Cys Ile Asp Tyr Phe
            180                 185                 190

Thr Thr Leu Asp Ser Lys Glu Leu Glu Ala Val Phe Ala Arg Glu Lys
        195                 200                 205

Ile Gln Ala Ala Met Leu Pro Pro Ala Leu Leu Lys Gln Cys Leu Val
    210                 215                 220

Asn Ile Pro Ala Thr Ile Ser Ala Leu Asp Val Val Leu Ala Ala Gly
225                 230                 235                 240

Asp Arg Phe Asp Arg Asp Ala Ala Thr Gln Ala Leu Val Gly
                245                 250                 255

Gly Cys Val Tyr Asn Ala Tyr Gly Pro Thr Glu Asn Thr Thr Leu Ser
            260                 265                 270

Thr Ile Tyr Asn Val Val Lys Gly Asp Ala Asn Val Asn Gly Val Pro
        275                 280                 285

Ile Gly Arg Pro Val Ser Asn Ser Gly Ala Tyr Ile Met Asp Pro Asn
    290                 295                 300

Gln Gln Leu Val Pro Lys Gly Val Met Gly Glu Leu Ile Val Val Gly
305                 310                 315                 320

Asp Gly Val Ala Arg Gly Tyr Thr Asp Pro Ala Leu Asp Val Asn Arg
                325                 330                 335

Phe Ile Glu Ile Ala Ile Asp Gly Asp Gln Ala Val Arg Ala Tyr Arg
            340                 345                 350

Thr Gly Asp Arg Ala Arg Tyr Arg Pro Lys Gly Gln Ile Glu Phe
        355                 360                 365

Phe Gly Arg Met Asp Gln Gln Ile Lys Ile Arg Gly His Arg Ile Glu
370                 375                 380

Pro Ala Glu Val Glu His Ala Val Leu Asp Asn Ser Met Val Gln Asp
385                 390                 395                 400

Ala Ala Val

<210> SEQ ID NO 30
<211> LENGTH: 225
<212> TYPE: PRT
<213> ORGANISM: Curvularia clavata

<400> SEQUENCE: 30

Asp Gly Ser Ala Ile Asp Lys Asp Glu Met Gln Glu Trp Leu Asp Asp
1               5                   10                  15

Thr Met Ser Thr Leu Leu Asp Gly Arg Gln Pro Gly His Val Leu Glu
            20                  25                  30
```

Ile Gly Thr Gly Thr Gly Met Ile Leu Phe Asn Leu Ala Glu Arg Met
35 40 45

Gly Leu Lys Ser Tyr Val Gly Leu Asp Pro Ser Glu Lys Ala Thr Ser
50 55 60

Phe Val Lys Gln Ala Ile Lys Ser Arg Pro Ser Leu Ala Gly Lys Ala
65 70 75 80

Glu Val His Val Gly Thr Ala Thr Asp Val Ala Arg Met Arg Asp Leu
85 90 95

His Pro Glu Val Val Val Ile Asn Ser Val Ala Gln Tyr Phe Pro Ser
100 105 110

Pro Glu Tyr Leu Ala Asp Val Val Gly Ala Leu Val Arg Ile Pro Gly
115 120 125

Val Lys Arg Leu Phe Phe Gly Asp Ile Arg Ser Tyr Ala Thr Asn Asn
130 135 140

His Phe Leu Ala Ala Arg Ala Leu His Lys Leu Gly Glu Lys Ala Thr
145 150 155 160

Arg Asp Thr Val Arg Ser Lys Met Ala Glu Leu Glu Gly Tyr Glu Glu
165 170 175

Glu Leu Leu Val Asp Pro Thr Phe Phe Thr Ser Leu Thr Ala Lys Leu
180 185 190

His Gly Gln Val Glu His Val Glu Ile Leu Pro Lys Arg Met Gln Ala
195 200 205

Thr Asn Glu Leu Ser Ala Tyr Arg Tyr Ala Ala Ile Val Tyr Ile Arg
210 215 220

Asp
225

<210> SEQ ID NO 31
<211> LENGTH: 69
<212> TYPE: PRT
<213> ORGANISM: Curvularia clavata

<400> SEQUENCE: 31

Val Glu Ala Val Leu Cys Glu Glu Phe Thr Asp Val Leu Gly Val Glu
1 5 10 15

Val Gly Ile Thr Asp Asn Phe Phe Asp Leu Gly Gly His Ser Leu Met
20 25 30

Ala Thr Lys Leu Ala Ala Arg Ile Ser Lys His Leu Asp Ala Arg Val
35 40 45

Ser Val Lys Asp Val Phe Asp Tyr Pro Val Val Ala Asp Leu Ala Ala
50 55 60

Ser Ile Glu Arg Asn
65

<210> SEQ ID NO 32
<211> LENGTH: 296
<212> TYPE: PRT
<213> ORGANISM: Curvularia clavata

<400> SEQUENCE: 32

Gly Pro Val Glu Gln Ser Phe Ala Gln Gly Arg Leu Trp Phe Leu Asp
1 5 10 15

Gln Leu Asn Met Gly Val Ser Glu Leu Tyr Leu Met Pro Leu Ala Leu
20 25 30

Arg Leu Arg Gly Pro Leu Arg Val Asp Ala Phe Ala Ala Ala Val Ser
35 40 45

```
Ala Leu Glu Ala Arg His Glu Thr Leu Arg Thr Thr Phe Met Asp His
 50                  55                  60

Asp Gly Val Gly Met Gln Val Ile Leu Pro Ser Asn Ser Lys Lys Leu
 65                  70                  75                  80

Arg Val Ile Asp Ala Ser Glu Asn Asp Tyr Ile Asp Ile Leu Arg Gln
                 85                  90                  95

Glu Arg Thr Ala Pro Phe Asn Leu Thr Thr Glu Pro Gly Phe Arg Ile
            100                 105                 110

Ala Leu Leu Gln Leu Gly Gln Thr Asp Phe Ile Leu Ser Ile Val Met
        115                 120                 125

His His Ile Ile Tyr Asp Gly Trp Ser Ile Asp Val Leu Cys Arg Glu
    130                 135                 140

Leu Gly Arg Phe Tyr Ser Ala Ala Leu Gln Gly Gln Asp Pro Leu Ala
145                 150                 155                 160

Gln Val Ser Pro Leu Pro Ile Gln Tyr Arg Asp Phe Ser Ile Trp Gln
                165                 170                 175

Lys Arg Pro Glu Gln Val Ala Glu His Glu Arg Gln Leu Gln Tyr Trp
            180                 185                 190

Thr Glu Gln Leu Ala Asp Ser Ser Pro Ala Glu Leu Leu Thr Asp Leu
        195                 200                 205

Pro Arg Pro Leu Val Pro Thr Gly Lys Ala Gly Ile Val Gln Leu Thr
210                 215                 220

Ile Glu Gly Ala Val Tyr Glu Arg Leu Arg Ala Phe Cys Arg Val His
225                 230                 235                 240

Gln Thr Thr Ser Phe Ala Val Leu Leu Ala Ala Phe Arg Ala Thr His
                245                 250                 255

Tyr Arg Leu Thr Gly Ala Glu Asp Ala Thr Ile Gly Ser Pro Ile Ala
            260                 265                 270

Asn Arg Asn Arg Pro Glu Leu Glu Ser Leu Ile Gly Phe Phe Val Asn
        275                 280                 285

Thr Gln Cys Ile Arg Val Thr Ile
    290                 295

<210> SEQ ID NO 33
<211> LENGTH: 405
<212> TYPE: PRT
<213> ORGANISM: Curvularia clavata

<400> SEQUENCE: 33

Leu Thr Tyr Ala Gln Leu Asp Glu Lys Ser Asp Gln Leu Ala Ala Trp
1               5                   10                  15

Leu Cys Gln His Asn Ile Pro Ala Glu Thr Ile Val Gly Val Leu Ala
            20                  25                  30

Pro Arg Ser Cys Glu Thr Ile Ile Ala Phe Leu Gly Ile Leu Lys Ala
        35                  40                  45

Asn Leu Ala Tyr Leu Pro Leu Asp Asp Asn Val Pro Ala Ala Arg Ile
    50                  55                  60

Glu Thr Ile Leu Ser Ala Val Pro Gly His Thr Leu Val Leu Leu Gly
65                  70                  75                  80

Ser His Val Ala Ala Pro Ser Ile Gly Leu Ala Asp Ala Glu Phe Val
                85                  90                  95

Asn Ile Asn His Thr Leu Gly His Ser Leu Gln Leu Asn Ser Thr Cys
            100                 105                 110
```

Ala Lys Leu Gln Pro Ser Ala Thr Ser Leu Ala Tyr Val Ile Phe Thr
            115                 120                 125

Ser Gly Ser Thr Gly Lys Pro Lys Gly Val Met Ile Glu His Arg Ser
130                 135                 140

Ile Val Arg Leu Val Lys Asn Ser Asn Thr Leu Ala Lys Leu Pro Arg
145                 150                 155                 160

Ala Ala Arg Val Ala His Gln Phe Asn Leu Ala Phe Asp Ala Ala Asn
                165                 170                 175

Tyr Glu Ile Tyr Gly Thr Leu Leu Asn Gly Ala Leu Ile Cys Val
            180                 185                 190

Asp Tyr Ser Thr Leu Leu Asp Ile Asp Ala Leu Val Ala Met Phe Lys
        195                 200                 205

Arg Glu Lys Ile Thr Ala Ser Ser Leu Ser Pro Gly Leu Leu Lys Gln
    210                 215                 220

Cys Val Asn Ser Ala Pro Glu Met Leu Lys Ala Leu Gln Val Ile Tyr
225                 230                 235                 240

Thr Gly Gly Asp Arg Leu Asp Gly Arg Asp Ala Ile Glu Leu Gln Ala
                245                 250                 255

Leu Val Pro Gly Gly Val Tyr Asn Met Tyr Gly Pro Thr Glu Asn Thr
            260                 265                 270

Val Ile Ser Thr Leu Tyr Asn Leu Gly Asp Lys His Ser Tyr Val Asn
        275                 280                 285

Gly Val Pro Ile Gly Thr Thr Val Ser Asn Ser Gly Ala Tyr Val Met
    290                 295                 300

Asp Ala Leu Gln Gln Leu Val Pro Val Gly Val Met Gly Glu Leu Val
305                 310                 315                 320

Val Thr Gly Asp Gly Leu Ala Arg Gly Tyr Thr Asp Pro Glu Leu Asp
                325                 330                 335

Arg Asn Arg Phe Ile Lys Val Asn Ile Asp Gly Gln Val Val Arg Ala
            340                 345                 350

Tyr Arg Thr Gly Asp Arg Val Arg Tyr Arg Arg Ile Asp Gly Gln Leu
        355                 360                 365

Glu Phe Phe Gly Arg Met Asp Gln Gln Ile Lys Ile Arg Gly Phe Arg
    370                 375                 380

Ile Glu Thr Ala Glu Val Glu Asn Ala Met Leu Ser His Ser Ala Val
385                 390                 395                 400

Arg Asn Ala Ala Val
                405

<210> SEQ ID NO 34
<211> LENGTH: 67
<212> TYPE: PRT
<213> ORGANISM: Curvularia clavata

<400> SEQUENCE: 34

Leu Glu Ala Ser Leu Cys Lys Glu Phe Ala Glu Val Leu Gly Val Glu
1               5                   10                  15

Val Gly Ile Thr Asp Asn Phe Phe Asp Leu Gly Gly His Ser Leu Leu
            20                  25                  30

Ala Thr Lys Leu Ala Ala Arg Ile Ser Arg Arg Leu Asp Thr Arg Val
        35                  40                  45

Ser Val Lys Asp Val Phe Asp Gln Pro Val Pro Ala Asp Leu Ala Leu
    50                  55                  60

Lys Val Ser
65

```
<210> SEQ ID NO 35
<211> LENGTH: 277
<212> TYPE: PRT
<213> ORGANISM: Curvularia clavata

<400> SEQUENCE: 35

Val Asp Val Tyr Pro Val Thr Trp Ile Gln Lys His Phe Leu Val Asp
1               5                   10                  15

Pro Ala Thr Gly Leu Pro Arg Thr Pro Ser Leu Phe Phe Val Asp Phe
            20                  25                  30

Pro Ala Asn Ala Asp Cys Asp Lys Ile Cys Asn Ala Ser Arg Ser Leu
        35                  40                  45

Ile Gln Leu Phe Asp Ile Phe Arg Thr Val Phe Val Gln Ala Ala Gly
    50                  55                  60

Asn Phe Tyr Gln Val Val Leu Glu Glu Leu Asp Ile Pro Ile Ser Val
65                  70                  75                  80

Ile Glu Thr Glu Asp Ile Ser Thr Ala Thr Arg Val Leu Lys Glu Gln
                85                  90                  95

Asp Gln Gln Asn Pro Leu Gln Phe Gly Gln Gly Phe Leu Arg Phe Ala
            100                 105                 110

Val Val Lys Thr Arg Ser Ala Val Arg Leu Val Leu Arg Ile Ser His
        115                 120                 125

Cys Leu Tyr Asp Gly Leu Ser Phe Glu His Val Val Gln Ser Leu His
    130                 135                 140

Ala Leu Tyr Asn Gly Asp Arg Ile Pro Thr Gln Pro Lys Phe Val Gln
145                 150                 155                 160

Tyr Val Gln His Leu Thr Asp Ser Arg Lys Glu Gly Tyr Asp Phe Trp
                165                 170                 175

Leu Ser Val Leu Glu Glu Ser Ser Met Thr Val Val Glu Thr Gly Arg
            180                 185                 190

Arg Ala Gln Gln Leu Ser Ser Pro Glu Gly Ala Trp Phe Val Glu Lys
        195                 200                 205

Ile Ile Lys Ala Val Ile Pro Ala Asn Ser Asp Gly Ile Thr Gln Ala
    210                 215                 220

Thr Val Phe Thr Thr Ala Ser Thr Ile Leu Leu Ala Arg Met Thr Gly
225                 230                 235                 240

Ser Ser Asp Ile Thr Phe Ser Arg Leu Val Ser Gly Arg Gln Ser Leu
                245                 250                 255

Pro Ile Asn Asp Gln His Ile Val Gly Pro Cys Thr Asn Ile Val Pro
            260                 265                 270

Val Arg Ile Arg Met
        275

<210> SEQ ID NO 36
<211> LENGTH: 39126
<212> TYPE: DNA
<213> ORGANISM: Curvularia clavata
<220> FEATURE:
<221> NAME/KEY: CDS
<222> LOCATION: (1)..(39126)

<400> SEQUENCE: 36 atg gcc agc gac atc aat act cat cca gag gga gcg acc aag ttt tgg    48
Met Ala Ser Asp Ile Asn Thr His Pro Glu Gly Ala Thr Lys Phe Trp
1               5                   10                  15
```

-continued

| | |
|---|---|
| cag caa cac ttt gac ggc ttg aac gcc tct gtg ttt cct gct ctg tcc<br>Gln Gln His Phe Asp Gly Leu Asn Ala Ser Val Phe Pro Ala Leu Ser<br>20                       25                 30 | 96 |
| tcc cat ttg act gtc ccg cgt ccc aac gcg cag aca gca cat cgc att<br>Ser His Leu Thr Val Pro Arg Pro Asn Ala Gln Thr Ala His Arg Ile<br>35                       40                 45 | 144 |
| tcc tat tca acc ttg gcg aag caa aaa tgg gac aac acc agc ctt tgc<br>Ser Tyr Ser Thr Leu Ala Lys Gln Lys Trp Asp Asn Thr Ser Leu Cys<br>50                       55                 60 | 192 |
| cga gct gcg ctc gca ata ctg ctt gcc cgc tat tcg aat gca tct gaa<br>Arg Ala Ala Leu Ala Ile Leu Leu Ala Arg Tyr Ser Asn Ala Ser Glu<br>65                   70                 75                 80 | 240 |
| gca ctc ttc ggc gtc ttg gta gaa cag ttt ctc ccg tcc aac ggt gaa<br>Ala Leu Phe Gly Val Leu Val Glu Gln Phe Leu Pro Ser Asn Gly Glu<br>                     85                 90                 95 | 288 |
| cag gca tcg aca gag gaa tca cca caa agc atc ctt ccc atc cgc atc<br>Gln Ala Ser Thr Glu Glu Ser Pro Gln Ser Ile Leu Pro Ile Arg Ile<br>               100                     105               110 | 336 |
| cga ctt gac ctt gag gaa gct ggg ttg ggc ctt ttg caa gct atc aat<br>Arg Leu Asp Leu Glu Glu Ala Gly Leu Gly Leu Leu Gln Ala Ile Asn<br>             115                     120               125 | 384 |
| acc cta gat gca tct ctg cgc gag tgg aag cat atc ggt ctt gac gcc<br>Thr Leu Asp Ala Ser Leu Arg Glu Trp Lys His Ile Gly Leu Asp Ala<br>130                       135                 140 | 432 |
| att cgt ggc acg gga gag tac ggg tct gcc gga tgc gag ttc cag aca<br>Ile Arg Gly Thr Gly Glu Tyr Gly Ser Ala Gly Cys Glu Phe Gln Thr<br>145                       150                 155               160 | 480 |
| gta ctt gct gtc act act gga aag acg cca cga acg cat aga ctc gcg<br>Val Leu Ala Val Thr Thr Gly Lys Thr Pro Arg Thr His Arg Leu Ala<br>                     165                     170               175 | 528 |
| tct tgc act gat cgc gcc ctt ttg ctc gat tgc cga atg gac gac gat<br>Ser Cys Thr Asp Arg Ala Leu Leu Leu Asp Cys Arg Met Asp Asp Asp<br>             180                     185               190 | 576 |
| tcg gcc aca ctt ctc gca cgc tat gat ccc agt gtg att gat gac ctc<br>Ser Ala Thr Leu Leu Ala Arg Tyr Asp Pro Ser Val Ile Asp Asp Leu<br>             195                     200               205 | 624 |
| cag gtc gcc cgt ttc cta aaa cag ctc ggg cac gtg att gag caa ttg<br>Gln Val Ala Arg Phe Leu Lys Gln Leu Gly His Val Ile Glu Gln Leu<br>210                       215                 220 | 672 |
| cgt gtc cag gca gtc gat cta cct ctc tgg gaa ctt ggt att gtc acg<br>Arg Val Gln Ala Val Asp Leu Pro Leu Trp Glu Leu Gly Ile Val Thr<br>225                       230                 235               240 | 720 |
| caa gaa gat agc gca gag att caa aaa tgg aac tcg cag caa ctc caa<br>Gln Glu Asp Ser Ala Glu Ile Gln Lys Trp Asn Ser Gln Gln Leu Gln<br>                     245                     250               255 | 768 |
| ttc agc cag gaa tgc ata cac gac gtg ttc gcc aac agg gtg gtt gat<br>Phe Ser Gln Glu Cys Ile His Asp Val Phe Ala Asn Arg Val Val Asp<br>             260                     265               270 | 816 |
| acg ccg cag aaa atc gcc gta tcc gct tgg aac ggc gag cta acg ttt<br>Thr Pro Gln Lys Ile Ala Val Ser Ala Trp Asn Gly Glu Leu Thr Phe<br>275                       280                 285 | 864 |
| gct gaa ctt gac agc ttc tcc tca tgc ctc gcc cag cac atc caa tcg<br>Ala Glu Leu Asp Ser Phe Ser Ser Cys Leu Ala Gln His Ile Gln Ser<br>290                       295                 300 | 912 |
| ctt gaa ttg ggc gat gca aaa gcg ata ccg ctt tgc ttt gag aag tca<br>Leu Glu Leu Gly Asp Ala Lys Ala Ile Pro Leu Cys Phe Glu Lys Ser<br>305                       310                 315               320 | 960 |
| aaa tgg gct atc gtc ggg atg ctc ggt gtg ctc aag gct ggc cga gca<br>Lys Trp Ala Ile Val Gly Met Leu Gly Val Leu Lys Ala Gly Arg Ala<br>                     325                     330               335 | 1008 |

| | | |
|---|---|---|
| ttc aca ctg att gac cca tct aac cca ccc gct agg gct cgt caa atc<br>Phe Thr Leu Ile Asp Pro Ser Asn Pro Pro Ala Arg Ala Arg Gln Ile<br>340 345 350 | | 1056 |
| tgt cga caa aca gcc gcc acc att tcc atc gcg tct cca tac cag tgc<br>Cys Arg Gln Thr Ala Ala Thr Ile Ser Ile Ala Ser Pro Tyr Gln Cys<br>355 360 365 | | 1104 |
| gat atg atg cgc gct ctg gtg ccc gac tgc atc gtg gtc gac gac gac<br>Asp Met Met Arg Ala Leu Val Pro Asp Cys Ile Val Val Asp Asp Asp<br>370 375 380 | | 1152 |
| ttt ttc aag tca ttg gcg ttt gat aca gat caa ttc cag cct acg gca<br>Phe Phe Lys Ser Leu Ala Phe Asp Thr Asp Gln Phe Gln Pro Thr Ala<br>385 390 395 400 | | 1200 |
| acg ccg cag aca ttg gcc tac atc ctc ttc act tct ggt agt acc gga<br>Thr Pro Gln Thr Leu Ala Tyr Ile Leu Phe Thr Ser Gly Ser Thr Gly<br>405 410 415 | | 1248 |
| gag cca aaa ggc agt atg atg gag cat cac gga ttt gtg tct tgc tgt<br>Glu Pro Lys Gly Ser Met Met Glu His His Gly Phe Val Ser Cys Cys<br>420 425 430 | | 1296 |
| ctc gaa ttt ggt gcg gcg ctg ggc atc aac agc aac aca cgc gct ctt<br>Leu Glu Phe Gly Ala Ala Leu Gly Ile Asn Ser Asn Thr Arg Ala Leu<br>435 440 445 | | 1344 |
| caa ttt gcc tct tat gct ttc ggt gct tgc ctg cta gag att ttg acc<br>Gln Phe Ala Ser Tyr Ala Phe Gly Ala Cys Leu Leu Glu Ile Leu Thr<br>450 455 460 | | 1392 |
| acc cta atg cac ggc ggc acg gtc tgc atc cca tct gat gat gaa cgc<br>Thr Leu Met His Gly Gly Thr Val Cys Ile Pro Ser Asp Asp Glu Arg<br>465 470 475 480 | | 1440 |
| ata aat gat gca ccc ggg ttt atc aga cgc gca aac gtt aac tgg gca<br>Ile Asn Asp Ala Pro Gly Phe Ile Arg Arg Ala Asn Val Asn Trp Ala<br>485 490 495 | | 1488 |
| att ctc act cct tct ttc att ggc gcc atc cag ccc acc acc gta cct<br>Ile Leu Thr Pro Ser Phe Ile Gly Ala Ile Gln Pro Thr Thr Val Pro<br>500 505 510 | | 1536 |
| aac ctc aag acg ctg gta ttg gtg gga gaa gcc atg ccg tca gac ata<br>Asn Leu Lys Thr Leu Val Leu Val Gly Glu Ala Met Pro Ser Asp Ile<br>515 520 525 | | 1584 |
| cgc gat gtc tgg gcc tcg cac gtt cag ctt aaa aat gcc tat ggc cag<br>Arg Asp Val Trp Ala Ser His Val Gln Leu Lys Asn Ala Tyr Gly Gln<br>530 535 540 | | 1632 |
| agc gag agc gca acg atc tgt agc gta acg gaa gtc act ccc gcg acg<br>Ser Glu Ser Ala Thr Ile Cys Ser Val Thr Glu Val Thr Pro Ala Thr<br>545 550 555 560 | | 1680 |
| gtg gag gcg cac aat atc ggt cac gct gtg ggc gcc cga ttc tgg att<br>Val Glu Ala His Asn Ile Gly His Ala Val Gly Ala Arg Phe Trp Ile<br>565 570 575 | | 1728 |
| acc gac ccc aat aat ccc aac aaa ctt gcg cca atc ggc tgc gta ggc<br>Thr Asp Pro Asn Asn Pro Asn Lys Leu Ala Pro Ile Gly Cys Val Gly<br>580 585 590 | | 1776 |
| gag ctg ctt gtt gaa agt cct ggc atc gcg cgt gga tat ctg att cct<br>Glu Leu Leu Val Glu Ser Pro Gly Ile Ala Arg Gly Tyr Leu Ile Pro<br>595 600 605 | | 1824 |
| ctg cca gcg gac gca aca cct ttc att gac acg ctt cct gat tgg tac<br>Leu Pro Ala Asp Ala Thr Pro Phe Ile Asp Thr Leu Pro Asp Trp Tyr<br>610 615 620 | | 1872 |
| cca agg acg cag ccg ctc gac aac ttc aag ttc tac aga act ggc gat<br>Pro Arg Thr Gln Pro Leu Asp Asn Phe Lys Phe Tyr Arg Thr Gly Asp<br>625 630 635 640 | | 1920 |
| ctt gtc tgc tac cga tcc gac ggc acc gtg gtg tat ctg ggg cga cga<br>Leu Val Cys Tyr Arg Ser Asp Gly Thr Val Val Tyr Leu Gly Arg Arg<br>645 650 655 | | 1968 |

```
                                                      -continued gac tcg caa att aag atc cga gga cag cgc gtc gaa atc ggc gaa gta        2016
Asp Ser Gln Ile Lys Ile Arg Gly Gln Arg Val Glu Ile Gly Glu Val
            660                 665                 670 gaa aca tgc ttg cga caa cag ctt ccc agt caa ctg gta cca gtt gtc        2064
Glu Thr Cys Leu Arg Gln Gln Leu Pro Ser Gln Leu Val Pro Val Val
        675                 680                 685 gaa gct gtc agt ctg tcg ggc atg tcc aag agc atg acg ctg att gcc        2112
Glu Ala Val Ser Leu Ser Gly Met Ser Lys Ser Met Thr Leu Ile Ala
    690                 695                 700 ttt ctg gtt ggc gaa aac acc att ctg gaa gag gac gtt tac gtt ttg        2160
Phe Leu Val Gly Glu Asn Thr Ile Leu Glu Glu Asp Val Tyr Val Leu
705                 710                 715                 720 gag ggc agt gcc gcg cag cgc atc agt tcg aaa ctg cga cag att gta        2208
Glu Gly Ser Ala Ala Gln Arg Ile Ser Ser Lys Leu Arg Gln Ile Val
                725                 730                 735 ccc ggg tac tgc att ccg tct cac tat att cgc atc aac cat ctt ccc        2256
Pro Gly Tyr Cys Ile Pro Ser His Tyr Ile Arg Ile Asn His Leu Pro
            740                 745                 750 act acc gcc act gga aag tgt gat cgg aaa gca ctt cga gcc atc ggt        2304
Thr Thr Ala Thr Gly Lys Cys Asp Arg Lys Ala Leu Arg Ala Ile Gly
        755                 760                 765 acc aaa ttg ctt agg gaa gcc gtg gag ggc atg gcg tca cag gag gaa        2352
Thr Lys Leu Leu Arg Glu Ala Val Glu Gly Met Ala Ser Gln Glu Glu
    770                 775                 780 cag gag agt gct tcg tta atg acc gaa ggg att aca ctg gaa cgc atc        2400
Gln Glu Ser Ala Ser Leu Met Thr Glu Gly Ile Thr Leu Glu Arg Ile
785                 790                 795                 800 tgg ttc cag agc ctg ggt ctc aag ccc aac tcc acg aga cac aaa tct        2448
Trp Phe Gln Ser Leu Gly Leu Lys Pro Asn Ser Thr Arg His Lys Ser
                805                 810                 815 aac ttc ttc aat ctg ggc ggc gac tcc att gcg gca atc cgg atg gtg        2496
Asn Phe Phe Asn Leu Gly Gly Asp Ser Ile Ala Ala Ile Arg Met Val
            820                 825                 830 aac atg gca cgg gca gca ggc ttg ttg ctg agc atc tcc gat atc ttt        2544
Asn Met Ala Arg Ala Ala Gly Leu Leu Leu Ser Ile Ser Asp Ile Phe
        835                 840                 845 cag aac ccc tca ctg gcg ggg ctc atc aat gtg atg cag cag agc tcg        2592
Gln Asn Pro Ser Leu Ala Gly Leu Ile Asn Val Met Gln Gln Ser Ser
    850                 855                 860 act gca caa gac gct att ccc gcc acc gag tac agc ggg ccg gtc gag        2640
Thr Ala Gln Asp Ala Ile Pro Ala Thr Glu Tyr Ser Gly Pro Val Glu
865                 870                 875                 880 cag tcg ttt gca cag ggc cgt ttg tgg ttc ttg gat cag ctc acg acc        2688
Gln Ser Phe Ala Gln Gly Arg Leu Trp Phe Leu Asp Gln Leu Thr Thr
                885                 890                 895 ggc gca tcg tgg tac cta atg cca ctt gcg gtc cgc att cac ggg ccg        2736
Gly Ala Ser Trp Tyr Leu Met Pro Leu Ala Val Arg Ile His Gly Pro
            900                 905                 910 ctc cgc gtc caa gcc ctt tcc agc gcc ctg cat gct ttg gag cag cgc        2784
Leu Arg Val Gln Ala Leu Ser Ser Ala Leu His Ala Leu Glu Gln Arg
        915                 920                 925 cac gag acg cta cga acg acg ttc gag cag caa gac ggt atg ggc gtg        2832
His Glu Thr Leu Arg Thr Thr Phe Glu Gln Gln Asp Gly Met Gly Val
    930                 935                 940 cag att gtc cac cca agc agc aag agg gag ctg cgc gtc atc gac gtg        2880
Gln Ile Val His Pro Ser Ser Lys Arg Glu Leu Arg Val Ile Asp Val
945                 950                 955                 960 tcg ggt aag cag aac ggc ggc tac gat cag gtg ttg aag cga gag cag        2928
Ser Gly Lys Gln Asn Gly Gly Tyr Asp Gln Val Leu Lys Arg Glu Gln
                965                 970                 975
```

-continued

| | | | | | | | | | | | | | | | |
|---|---|---|---|---|---|---|---|---|---|---|---|---|---|---|---|
| aca | aca | ccc | atc | gac | ttg | gcc | aaa | gag | ccc | gga | tgg | aga | gcc | gcg | ctg | 2976 |
| Thr | Thr | Pro | Ile | Asp | Leu | Ala | Lys | Glu | Pro | Gly | Trp | Arg | Ala | Ala | Leu | |
| | | | 980 | | | | 985 | | | | | 990 | | | | |

```
aca aca ccc atc gac ttg gcc aaa gag ccc gga tgg aga gcc gcg ctg     2976
Thr Thr Pro Ile Asp Leu Ala Lys Glu Pro Gly Trp Arg Ala Ala Leu
            980             985                 990 cta cga gtg ggc gac gat gag cac atc ctc tcg att gtc atc cac cac     3024
Leu Arg Val Gly Asp Asp Glu His Ile Leu Ser Ile Val Ile His His
            995             1000                1005 atc ata tac gac ggt tgg tcg ctg ggc gta ctg cgt gag gaa ctc         3069
Ile Ile Tyr Asp Gly Trp Ser Leu Gly Val Leu Arg Glu Glu Leu
            1010            1015                1020 ggc gac ctt tat gcg gcg gcg ctg cga ggt ccc gat cca ctc gca         3114
Gly Asp Leu Tyr Ala Ala Ala Leu Arg Gly Pro Asp Pro Leu Ala
            1025            1030                1035 cac atg gcc ccg ctc ccg atc cag tac cgc gac ttc tct gtt tgg         3159
His Met Ala Pro Leu Pro Ile Gln Tyr Arg Asp Phe Ser Val Trp
            1040            1045                1050 cag aag cag cca cag caa gtg gcg cag cac caa caa cag ctc gtg         3204
Gln Lys Gln Pro Gln Gln Val Ala Gln His Gln Gln Gln Leu Val
            1055            1060                1065 tac tgg aca aag cag ctt gaa gac agc gcg cct gca gag ctg ctt         3249
Tyr Trp Thr Lys Gln Leu Glu Asp Ser Ala Pro Ala Glu Leu Leu
            1070            1075                1080 acc gac ttc ccc cgc cct gcc gag tta tct ggc cgt gcc ggt gag         3294
Thr Asp Phe Pro Arg Pro Ala Glu Leu Ser Gly Arg Ala Gly Glu
            1085            1090                1095 gtt cgt ttc act atc gaa ggc agt gtc ttc gac agc ctg ctc gct         3339
Val Arg Phe Thr Ile Glu Gly Ser Val Phe Asp Ser Leu Leu Ala
            1100            1105                1110 ttt cgt cgc gtc cac cag acg aca tca ttt gcg gtg cta cta gcc         3384
Phe Arg Arg Val His Gln Thr Thr Ser Phe Ala Val Leu Leu Ala
            1115            1120                1125 gtc ttc cgt gct gcc cac tat cgt ctc acc ggc aca gag gac gcc         3429
Val Phe Arg Ala Ala His Tyr Arg Leu Thr Gly Thr Glu Asp Ala
            1130            1135                1140 aca atc ggc acg ccc atc gct aat cgt act cgt gct gag gtc gag         3474
Thr Ile Gly Thr Pro Ile Ala Asn Arg Thr Arg Ala Glu Val Glu
            1145            1150                1155 aag ctc atc ggt ttc ttt gtc aac acg cag tgt atg cgc att gct         3519
Lys Leu Ile Gly Phe Phe Val Asn Thr Gln Cys Met Arg Ile Ala
            1160            1165                1170 gtc gcc gac gat gac acc ttc gca tcg ctc gtc agt caa gtc tgg         3564
Val Ala Asp Asp Asp Thr Phe Ala Ser Leu Val Ser Gln Val Trp
            1175            1180                1185 tcc gtc gcg act gcc gca ttc gag cat cag gat gtc ccc ttc gag         3609
Ser Val Ala Thr Ala Ala Phe Glu His Gln Asp Val Pro Phe Glu
            1190            1195                1200 cgt atc gtg tcg gcg ctc ctg ccc ggc gcc aga gac aca tct cgc         3654
Arg Ile Val Ser Ala Leu Leu Pro Gly Ala Arg Asp Thr Ser Arg
            1205            1210                1215 aac ccg ctg gcc cag ctc ctg ttt gcg ctc cat ctg gag cag gac         3699
Asn Pro Leu Ala Gln Leu Leu Phe Ala Leu His Leu Glu Gln Asp
            1220            1225                1230 ctc gac aag atc aat ctc gag ggc ttg gcc tgc gag act gta ccc         3744
Leu Asp Lys Ile Asn Leu Glu Gly Leu Ala Cys Glu Thr Val Pro
            1235            1240                1245 acg cca atg gcg act cgc ttc gac gtg gag ttc cat ctc ttc cag         3789
Thr Pro Met Ala Thr Arg Phe Asp Val Glu Phe His Leu Phe Gln
            1250            1255                1260 gaa gac gac aga ctg aac ggc gtc gtc aac ttc tcc acg gac ctc         3834
Glu Asp Asp Arg Leu Asn Gly Val Val Asn Phe Ser Thr Asp Leu
            1265            1270                1275
```

```
ttc gag ccc cag acc atc cac agc ctg gtc tct gtc ttt cag gag    3879
Phe Glu Pro Gln Thr Ile His Ser Leu Val Ser Val Phe Gln Glu
1280            1285            1290 atc ctg cgc cgc ggc ctc gac caa cca cag acg cct att gca cat    3924
Ile Leu Arg Arg Gly Leu Asp Gln Pro Gln Thr Pro Ile Ala His
1295            1300            1305 ctc cag ctg act gat ggg ctt gaa gag ctt cgc aat gcc ggc ctg    3969
Leu Gln Leu Thr Asp Gly Leu Glu Glu Leu Arg Asn Ala Gly Leu
1310            1315            1320 ctg gac atc aag agg atc gac tac ccg cgc gag gcg agc gtt gta    4014
Leu Asp Ile Lys Arg Ile Asp Tyr Pro Arg Glu Ala Ser Val Val
1325            1330            1335 gac atg ttc caa aag cag gta gcc gct tgc cct aac gtg act gcc    4059
Asp Met Phe Gln Lys Gln Val Ala Ala Cys Pro Asn Val Thr Ala
1340            1345            1350 gtc aaa gat tcg acc tcg cag ctc acg tat gct caa ctg gat cag    4104
Val Lys Asp Ser Thr Ser Gln Leu Thr Tyr Ala Gln Leu Asp Gln
1355            1360            1365 gag tct gac aag ata gcc gtt tgg ctg cgc aaa cgc aac att cca    4149
Glu Ser Asp Lys Ile Ala Val Trp Leu Arg Lys Arg Asn Ile Pro
1370            1375            1380 gcc gag aca ttg att gcg ctg cta gca cct cga tcc tgt gac tcc    4194
Ala Glu Thr Leu Ile Ala Leu Leu Ala Pro Arg Ser Cys Asp Ser
1385            1390            1395 gtg gct gcc ttc ctc ggt att ctc aaa gcc aat ctg gcc tat ctc    4239
Val Ala Ala Phe Leu Gly Ile Leu Lys Ala Asn Leu Ala Tyr Leu
1400            1405            1410 cct ctg gat gtt aat gtc ccc gct gct cgt atc gag gca atc ctg    4284
Pro Leu Asp Val Asn Val Pro Ala Ala Arg Ile Glu Ala Ile Leu
1415            1420            1425 tca acc gta gca ggt cac aaa ctg gtc ttg ctc gga cga gat gtg    4329
Ser Thr Val Ala Gly His Lys Leu Val Leu Leu Gly Arg Asp Val
1430            1435            1440 cct ctg cta ggt acg cag ctg gcc gac ctc gag ctt gtc cgt atc    4374
Pro Leu Leu Gly Thr Gln Leu Ala Asp Leu Glu Leu Val Arg Ile
1445            1450            1455 ggc gag gcg ctg cgt ggc tcg agt tca ggg agt gtc gcc gcc gac    4419
Gly Glu Ala Leu Arg Gly Ser Ser Ser Gly Ser Val Ala Ala Asp
1460            1465            1470 aag gct att cga cct aca gca aca agc ctg gcc tac gtt atc ttc    4464
Lys Ala Ile Arg Pro Thr Ala Thr Ser Leu Ala Tyr Val Ile Phe
1475            1480            1485 acg tct gga tct act ggc cag cca aag ggt atc atg gtt cct cat    4509
Thr Ser Gly Ser Thr Gly Gln Pro Lys Gly Ile Met Val Pro His
1490            1495            1500 cgc agc ttg gtc aac gtg atc aag cag cga cct gcc tat gga aat    4554
Arg Ser Leu Val Asn Val Ile Lys Gln Arg Pro Ala Tyr Gly Asn
1505            1510            1515 gtc gct cac atg aca aat ctc gcc ttt gat ccc tcc ctg ttc gag    4599
Val Ala His Met Thr Asn Leu Ala Phe Asp Pro Ser Leu Phe Glu
1520            1525            1530 atg tgc act gcc ttg ttc aat ggc aat acg ctg att tgc atc gac    4644
Met Cys Thr Ala Leu Phe Asn Gly Asn Thr Leu Ile Cys Ile Asp
1535            1540            1545 aca ttg gta gca ctc gat gca act cag ctt cct acc atc ttc aag    4689
Thr Leu Val Ala Leu Asp Ala Thr Gln Leu Pro Thr Ile Phe Lys
1550            1555            1560 cag gaa gca att cgt gtc gca atg atg acg ccg gcc ttg ctc acc    4734
Gln Glu Ala Ile Arg Val Ala Met Met Thr Pro Ala Leu Leu Thr
1565            1570            1575
```

```
aga ctc cta gcc cag gct act gac gca ctg cat gaa cta gag gca    4779
Arg Leu Leu Ala Gln Ala Thr Asp Ala Leu His Glu Leu Glu Ala
    1580            1585                1590 ctt tat gtt ctg gga gat cga ttc cct cca aaa gat gct gcc aga    4824
Leu Tyr Val Leu Gly Asp Arg Phe Pro Pro Lys Asp Ala Ala Arg
1595                1600                1605 gca agt gaa ctt gtc aaa acg gcc gta tac aat gcc tac gga ccg    4869
Ala Ser Glu Leu Val Lys Thr Ala Val Tyr Asn Ala Tyr Gly Pro
    1610                1615                1620 agt gag aac tcc atc tgc aca act ctc ttc cat gct gcc act ggc    4914
Ser Glu Asn Ser Ile Cys Thr Thr Leu Phe His Ala Ala Thr Gly
1625                1630                1635 gcc atg tgt acc aat ggt gtg cct gtt ggc cga gta atc aac aac    4959
Ala Met Cys Thr Asn Gly Val Pro Val Gly Arg Val Ile Asn Asn
    1640                1645                1650 tcg ggc gta tat gtt atg gat cca aag cag tcg ctt gtt tcc tac    5004
Ser Gly Val Tyr Val Met Asp Pro Lys Gln Ser Leu Val Ser Tyr
1655                1660                1665 ggc gtc atg ggt gag ctc gtc gtc gct ggc gaa ggc ctt gca att    5049
Gly Val Met Gly Glu Leu Val Val Ala Gly Glu Gly Leu Ala Ile
    1670                1675                1680 gga tat acc aag cca gaa ctc aac gaa ggc cgc ttt ctg acg ctt    5094
Gly Tyr Thr Lys Pro Glu Leu Asn Glu Gly Arg Phe Leu Thr Leu
1685                1690                1695 aca atg gac gga aaa cct gta aga gcg ttt cgt acc gga gat cgt    5139
Thr Met Asp Gly Lys Pro Val Arg Ala Phe Arg Thr Gly Asp Arg
    1700                1705                1710 gtt cga tac cgg ccg aca gat ggt caa ctg gaa ttt ttt ggc gcg    5184
Val Arg Tyr Arg Pro Thr Asp Gly Gln Leu Glu Phe Phe Gly Arg
1715                1720                1725 atg gac ttc caa att aag atc cga ggt cat cgt gtc gag ttg gct    5229
Met Asp Phe Gln Ile Lys Ile Arg Gly His Arg Val Glu Leu Ala
    1730                1735                1740 gaa gtg gaa cga gtt ttg aac agg cac cct gcc atc aaa gac gcc    5274
Glu Val Glu Arg Val Leu Asn Arg His Pro Ala Ile Lys Asp Ala
1745                1750                1755 atc aca ctg ctg agg cag cac ggc tcc tca gca caa gac aca gag    5319
Ile Thr Leu Leu Arg Gln His Gly Ser Ser Ala Gln Asp Thr Glu
    1760                1765                1770 ctt gtc agt ttt att gtg cta gga gag cag aag cct gta aag ccc    5364
Leu Val Ser Phe Ile Val Leu Gly Glu Gln Lys Pro Val Lys Pro
1775                1780                1785 cat cga aac gcc acc gac cat ggc gga atg gag att gag caa ttg    5409
His Arg Asn Ala Thr Asp His Gly Gly Met Glu Ile Glu Gln Leu
    1790                1795                1800 gac caa aag cta gaa gca aac ctg cgt gcc atg atg cag gct acg    5454
Asp Gln Lys Leu Glu Ala Asn Leu Arg Ala Met Met Gln Ala Thr
1805                1810                1815 ctg ccc tca tac atg gtt ccc tcg aga atc ata gtg cta gac cat    5499
Leu Pro Ser Tyr Met Val Pro Ser Arg Ile Ile Val Leu Asp His
    1820                1825                1830 atg ccg ctc gac aag aat gga aag gtt gac cga cga gga ttg aca    5544
Met Pro Leu Asp Lys Asn Gly Lys Val Asp Arg Arg Gly Leu Thr
1835                1840                1845 gga ctg acg ctg agc cca gcc atg gaa aca agc tcg cgt gtt gtt    5589
Gly Leu Thr Leu Ser Pro Ala Met Glu Thr Ser Ser Arg Val Val
    1850                1855                1860 gtg gca gca cgg aac gag atc gag gcc gta ctg tgc gag gag ttt    5634
Val Ala Ala Arg Asn Glu Ile Glu Ala Val Leu Cys Glu Glu Phe
1865                1870                1875
```

-continued

| | | | | | | | | | | | | | | |
|---|---|---|---|---|---|---|---|---|---|---|---|---|---|---|
| gct | cac | atc | ctt | ggt | gtt | gaa | att | ggc | gtc | act | gat | aac | ttc | ttc | 5679 |
| Ala | His | Ile | Leu | Gly | Val | Glu | Ile | Gly | Val | Thr | Asp | Asn | Phe | Phe | |
| | 1880 | | | | 1885 | | | | 1890 | | | | | | |
| gac | ctc | ggc | gga | cat | tca | ctc | atg | gct | act | act | ctc | gct | gct | cgc | 5724 |
| Asp | Leu | Gly | Gly | His | Ser | Leu | Met | Ala | Thr | Thr | Leu | Ala | Ala | Arg | |
| | 1895 | | | | 1900 | | | | 1905 | | | | | | |
| ctc | gct | cgc | cgt | ctt | aat | gct | agc | att | tcc | gtc | aag | gat | gtc | ttc | 5769 |
| Leu | Ala | Arg | Arg | Leu | Asn | Ala | Ser | Ile | Ser | Val | Lys | Asp | Val | Phe | |
| 1910 | | | | | 1915 | | | | 1920 | | | | | | |
| gat | cag | cct | att | gtc | gct | aat | ctc | gcc | gcc | aca | atc | aag | cga | ggc | 5814 |
| Asp | Gln | Pro | Ile | Val | Ala | Asn | Leu | Ala | Ala | Thr | Ile | Lys | Arg | Gly | |
| 1925 | | | | | 1930 | | | | 1935 | | | | | | |
| tcg | acc | cct | cac | aat | gca | atc | cct | cca | act | aaa | tac | tct | ggg | ccg | 5859 |
| Ser | Thr | Pro | His | Asn | Ala | Ile | Pro | Pro | Thr | Lys | Tyr | Ser | Gly | Pro | |
| 1940 | | | | | 1945 | | | | 1950 | | | | | | |
| gtt | gaa | cag | tcc | ttc | gca | caa | ggt | cgt | ctc | tgg | ttt | ctg | gac | caa | 5904 |
| Val | Glu | Gln | Ser | Phe | Ala | Gln | Gly | Arg | Leu | Trp | Phe | Leu | Asp | Gln | |
| 1955 | | | | | 1960 | | | | 1965 | | | | | | |
| ctg | aac | ctt | ggg | gct | gcc | tgg | tat | cat | atg | cct | ctt | gca | gtg | cgt | 5949 |
| Leu | Asn | Leu | Gly | Ala | Ala | Trp | Tyr | His | Met | Pro | Leu | Ala | Val | Arg | |
| 1970 | | | | | 1975 | | | | 1980 | | | | | | |
| ttg | cgc | ggg | cct | ctc | cat | ctt | gag | gca | ctc | act | gca | gcg | ctg | cat | 5994 |
| Leu | Arg | Gly | Pro | Leu | His | Leu | Glu | Ala | Leu | Thr | Ala | Ala | Leu | His | |
| 1985 | | | | | 1990 | | | | 1995 | | | | | | |
| gcc | ctt | gag | gag | cgc | cac | gag | acg | tta | cgg | aca | gta | ttt | gag | gaa | 6039 |
| Ala | Leu | Glu | Glu | Arg | His | Glu | Thr | Leu | Arg | Thr | Val | Phe | Glu | Glu | |
| 2000 | | | | | 2005 | | | | 2010 | | | | | | |
| caa | gat | ggt | gtg | ggc | atg | cag | atc | gtc | cgg | cca | agc | agc | aag | acg | 6084 |
| Gln | Asp | Gly | Val | Gly | Met | Gln | Ile | Val | Arg | Pro | Ser | Ser | Lys | Thr | |
| 2015 | | | | | 2020 | | | | 2025 | | | | | | |
| ccg | ctg | cga | ata | atc | gac | gtg | tcc | act | aaa | gag | cga | ggt | tat | gcc | 6129 |
| Pro | Leu | Arg | Ile | Ile | Asp | Val | Ser | Thr | Lys | Glu | Arg | Gly | Tyr | Ala | |
| 2030 | | | | | 2035 | | | | 2040 | | | | | | |
| gag | ttg | ctc | aag | cag | gag | caa | aca | aca | cca | ttc | gat | cta | gcc | aca | 6174 |
| Glu | Leu | Leu | Lys | Gln | Glu | Gln | Thr | Thr | Pro | Phe | Asp | Leu | Ala | Thr | |
| 2045 | | | | | 2050 | | | | 2055 | | | | | | |
| gag | tta | ggg | tgg | agg | gtg | gct | ctg | ctg | agg | caa | ggg | aag | gat | gac | 6219 |
| Glu | Leu | Gly | Trp | Arg | Val | Ala | Leu | Leu | Arg | Gln | Gly | Lys | Asp | Asp | |
| 2060 | | | | | 2065 | | | | 2070 | | | | | | |
| cat | att | ctg | tca | att | gtc | att | cac | cac | atc | att | tcc | gac | ggt | tgg | 6264 |
| His | Ile | Leu | Ser | Ile | Val | Ile | His | His | Ile | Ile | Ser | Asp | Gly | Trp | |
| 2075 | | | | | 2080 | | | | 2085 | | | | | | |
| tct | ctc | gat | atc | ttg | tgc | gag | gaa | ctt | ggt | cag | ttc | tac | gcc | gct | 6309 |
| Ser | Leu | Asp | Ile | Leu | Cys | Glu | Glu | Leu | Gly | Gln | Phe | Tyr | Ala | Ala | |
| 2090 | | | | | 2095 | | | | 2100 | | | | | | |
| gtg | ctc | cgt | ggc | cag | gac | cca | tta | gcc | caa | ata | agc | cct | ctg | cct | 6354 |
| Val | Leu | Arg | Gly | Gln | Asp | Pro | Leu | Ala | Gln | Ile | Ser | Pro | Leu | Pro | |
| 2105 | | | | | 2110 | | | | 2115 | | | | | | |
| atc | cag | tat | cgc | gat | ttc | tct | ctg | tgg | cag | aag | cag | cct | gag | caa | 6399 |
| Ile | Gln | Tyr | Arg | Asp | Phe | Ser | Leu | Trp | Gln | Lys | Gln | Pro | Glu | Gln | |
| 2120 | | | | | 2125 | | | | 2130 | | | | | | |
| gtt | gct | gag | cac | cac | cgg | caa | ctc | gag | tac | tgg | acc | acc | cag | ctc | 6444 |
| Val | Ala | Glu | His | His | Arg | Gln | Leu | Glu | Tyr | Trp | Thr | Thr | Gln | Leu | |
| 2135 | | | | | 2140 | | | | 2145 | | | | | | |
| gag | ggc | agc | gta | cct | gca | gag | ctt | cta | acc | gat | ctt | cct | cga | cca | 6489 |
| Glu | Gly | Ser | Val | Pro | Ala | Glu | Leu | Leu | Thr | Asp | Leu | Pro | Arg | Pro | |
| 2150 | | | | | 2155 | | | | 2160 | | | | | | |
| acc | ata | cag | tcc | ggc | aag | gca | ggc | gtc | atc | cca | ata | acc | gtc | aac | 6534 |
| Thr | Ile | Gln | Ser | Gly | Lys | Ala | Gly | Val | Ile | Pro | Ile | Thr | Val | Asn | |
| 2165 | | | | | 2170 | | | | 2175 | | | | | | |

-continued

| | | | | | | | | | | | | | | | |
|---|---|---|---|---|---|---|---|---|---|---|---|---|---|---|---|
| ggc | cct | gta | tac | gag | cgt | cta | cgg | gcc | ttc | tct | cga | gct | cat | caa | 6579 |
| Gly | Pro | Val | Tyr | Glu | Arg | Leu | Arg | Ala | Phe | Ser | Arg | Ala | His | Gln | |
| | 2180 | | | | 2185 | | | | | 2190 | | | | | |
| acg | acc | gct | ttt | gcg | gta | ctg | ttg | gcc | gcc | ttt | cga | gca | act | cat | 6624 |
| Thr | Thr | Ala | Phe | Ala | Val | Leu | Leu | Ala | Ala | Phe | Arg | Ala | Thr | His | |
| 2195 | | | | | 2200 | | | | | 2205 | | | | | |
| tac | cgt | ctc | tct | gga | gtc | gca | gac | gct | acc | atc | ggc | acg | cca | atc | 6669 |
| Tyr | Arg | Leu | Ser | Gly | Val | Ala | Asp | Ala | Thr | Ile | Gly | Thr | Pro | Ile | |
| | 2210 | | | | 2215 | | | | | 2220 | | | | | |
| gcc | aac | cgt | aat | cga | cct | gaa | ctg | gag | aat | atg | ata | ggc | ttt | ttc | 6714 |
| Ala | Asn | Arg | Asn | Arg | Pro | Glu | Leu | Glu | Asn | Met | Ile | Gly | Phe | Phe | |
| 2225 | | | | | 2230 | | | | | 2235 | | | | | |
| gta | aat | gcc | cag | tgt | atg | cgt | atc | act | gtc | gag | caa | gac | gat | act | 6759 |
| Val | Asn | Ala | Gln | Cys | Met | Arg | Ile | Thr | Val | Glu | Gln | Asp | Asp | Thr | |
| | 2240 | | | | 2245 | | | | | 2250 | | | | | |
| ttt | gag | aca | ctt | gtc | cgc | cag | atc | cga | ttt | acg | gca | act | gcc | gcc | 6804 |
| Phe | Glu | Thr | Leu | Val | Arg | Gln | Ile | Arg | Phe | Thr | Ala | Thr | Ala | Ala | |
| 2255 | | | | | 2260 | | | | | 2265 | | | | | |
| ttt | gcc | aac | caa | gat | gta | ccc | ttt | gag | cat | atc | gtc | tca | gcc | ctt | 6849 |
| Phe | Ala | Asn | Gln | Asp | Val | Pro | Phe | Glu | His | Ile | Val | Ser | Ala | Leu | |
| | 2270 | | | | 2275 | | | | | 2280 | | | | | |
| atg | cct | gac | tca | cgc | gat | aca | tcg | cgg | aat | ccg | cta | gtg | cag | ctc | 6894 |
| Met | Pro | Asp | Ser | Arg | Asp | Thr | Ser | Arg | Asn | Pro | Leu | Val | Gln | Leu | |
| 2285 | | | | | 2290 | | | | | 2295 | | | | | |
| atg | ttc | gca | ctc | cac | gcg | tac | aaa | gat | ctc | ggc | aag | att | gag | ctt | 6939 |
| Met | Phe | Ala | Leu | His | Ala | Tyr | Lys | Asp | Leu | Gly | Lys | Ile | Glu | Leu | |
| | 2300 | | | | 2305 | | | | | 2310 | | | | | |
| gaa | ggt | tat | gtt | gca | gag | cct | gtg | cat | aca | act | ctg | tca | acc | cgc | 6984 |
| Glu | Gly | Tyr | Val | Ala | Glu | Pro | Val | His | Thr | Thr | Leu | Ser | Thr | Arg | |
| 2315 | | | | | 2320 | | | | | 2325 | | | | | |
| ttc | gat | ctc | gaa | ttc | cac | atg | ttc | cag | gag | aca | aat | cac | ctc | agc | 7029 |
| Phe | Asp | Leu | Glu | Phe | His | Met | Phe | Gln | Glu | Thr | Asn | His | Leu | Ser | |
| | 2330 | | | | 2335 | | | | | 2340 | | | | | |
| ggc | tac | gta | ctg | tat | gca | aca | gac | ttg | ttc | gag | cct | gag | agc | att | 7074 |
| Gly | Tyr | Val | Leu | Tyr | Ala | Thr | Asp | Leu | Phe | Glu | Pro | Glu | Ser | Ile | |
| 2345 | | | | | 2350 | | | | | 2355 | | | | | |
| gag | ggg | atg | gtt | tcc | att | ttt | aaa | gaa | atc | ctc | gct | cga | gct | ctt | 7119 |
| Glu | Gly | Met | Val | Ser | Ile | Phe | Lys | Glu | Ile | Leu | Ala | Arg | Ala | Leu | |
| | 2360 | | | | 2365 | | | | | 2370 | | | | | |
| gac | caa | ccc | caa | acc | cca | ctg | gcg | ctt | cta | ccg | ctc | acc | gat | ggg | 7164 |
| Asp | Gln | Pro | Gln | Thr | Pro | Leu | Ala | Leu | Leu | Pro | Leu | Thr | Asp | Gly | |
| 2375 | | | | | 2380 | | | | | 2385 | | | | | |
| ctg | gct | gaa | ctt | cgc | agg | agg | ggg | ctg | ctt | gag | att | gaa | agg | ccc | 7209 |
| Leu | Ala | Glu | Leu | Arg | Arg | Arg | Gly | Leu | Leu | Glu | Ile | Glu | Arg | Pro | |
| | 2390 | | | | 2395 | | | | | 2400 | | | | | |
| agc | tat | cct | cgc | gag | tcg | agc | gtt | gtt | gac | gtc | ttc | tgt | agc | cag | 7254 |
| Ser | Tyr | Pro | Arg | Glu | Ser | Ser | Val | Val | Asp | Val | Phe | Cys | Ser | Gln | |
| 2405 | | | | | 2410 | | | | | 2415 | | | | | |
| gta | gcg | gct | tct | ccc | aac | gca | acc | gct | gtg | aag | gac | tcg | att | tca | 7299 |
| Val | Ala | Ala | Ser | Pro | Asn | Ala | Thr | Ala | Val | Lys | Asp | Ser | Ile | Ser | |
| | 2420 | | | | 2425 | | | | | 2430 | | | | | |
| cag | ctc | act | tac | gct | cag | cta | aat | gag | caa | tct | gac | aag | gtc | gct | 7344 |
| Gln | Leu | Thr | Tyr | Ala | Gln | Leu | Asn | Glu | Gln | Ser | Asp | Lys | Val | Ala | |
| 2435 | | | | | 2440 | | | | | 2445 | | | | | |
| gct | tgg | cta | cac | cag | tgc | aac | ctt | cca | act | gaa | act | ttg | gtc | gct | 7389 |
| Ala | Trp | Leu | His | Gln | Cys | Asn | Leu | Pro | Thr | Glu | Thr | Leu | Val | Ala | |
| | 2450 | | | | 2455 | | | | | 2460 | | | | | |
| gtg | cta | gcg | cct | cga | tct | tgc | caa | aca | gtt | gtg | gcc | ttc | ttg | ggt | 7434 |
| Val | Leu | Ala | Pro | Arg | Ser | Cys | Gln | Thr | Val | Val | Ala | Phe | Leu | Gly | |
| 2465 | | | | | 2470 | | | | | 2475 | | | | | |

| | | | | | | | | | | | | | | |
|---|---|---|---|---|---|---|---|---|---|---|---|---|---|---|
| att | ctg | aag | gcc | aac | cta | gca | tat | ctt | ccc | cta | gac | gtc | aat | gtt | 7479 |
| Ile | Leu | Lys | Ala | Asn | Leu | Ala | Tyr | Leu | Pro | Leu | Asp | Val | Asn | Val | |
| | 2480 | | | | 2485 | | | | 2490 | | | | | | |
| ccg | gca | gct | cgc | att | gag | gca | att | ctc | tca | gaa | gtc | tct | ggc | cac | 7524 |
| Pro | Ala | Ala | Arg | Ile | Glu | Ala | Ile | Leu | Ser | Glu | Val | Ser | Gly | His | |
| | 2495 | | | | 2500 | | | | 2505 | | | | | | |
| ata | ctt | gtc | tta | ctt | gga | tct | cat | gtt | tct | gct | ccc | aag | att | gag | 7569 |
| Ile | Leu | Val | Leu | Leu | Gly | Ser | His | Val | Ser | Ala | Pro | Lys | Ile | Glu | |
| 2510 | | | | | 2515 | | | | | 2520 | | | | | |
| ctc | gct | gat | gtc | gaa | ttc | gtc | aaa | att | gac | aac | aca | gtc | gag | cac | 7614 |
| Leu | Ala | Asp | Val | Glu | Phe | Val | Lys | Ile | Asp | Asn | Thr | Val | Glu | His | |
| 2525 | | | | | 2530 | | | | | 2535 | | | | | |
| aat | ttg | ccg | ggc | cgc | att | gga | tct | gct | cca | tct | gcc | acg | agc | ctc | 7659 |
| Asn | Leu | Pro | Gly | Arg | Ile | Gly | Ser | Ala | Pro | Ser | Ala | Thr | Ser | Leu | |
| 2540 | | | | | 2545 | | | | | 2550 | | | | | |
| gcc | tat | gtt | att | ttc | aca | tct | gga | tcg | act | ggc | aag | ccc | aaa | ggt | 7704 |
| Ala | Tyr | Val | Ile | Phe | Thr | Ser | Gly | Ser | Thr | Gly | Lys | Pro | Lys | Gly | |
| 2555 | | | | | 2560 | | | | | 2565 | | | | | |
| gtt | aag | gta | gag | cac | cgc | ggt | att | gtc | cgc | ctc | gtt | aaa | gag | agc | 7749 |
| Val | Lys | Val | Glu | His | Arg | Gly | Ile | Val | Arg | Leu | Val | Lys | Glu | Ser | |
| 2570 | | | | | 2575 | | | | | 2580 | | | | | |
| aat | gta | gta | gca | aaa | atg | cca | caa | gct | gcg | cgc | att | gct | cac | ttg | 7794 |
| Asn | Val | Val | Ala | Lys | Met | Pro | Gln | Ala | Ala | Arg | Ile | Ala | His | Leu | |
| 2585 | | | | | 2590 | | | | | 2595 | | | | | |
| tca | aac | att | gcc | ttt | gac | gcg | gct | acg | tgg | gaa | tta | tat | gct | gcg | 7839 |
| Ser | Asn | Ile | Ala | Phe | Asp | Ala | Ala | Thr | Trp | Glu | Leu | Tyr | Ala | Ala | |
| 2600 | | | | | 2605 | | | | | 2610 | | | | | |
| ttg | ctc | aac | ggc | ggc | acc | ctc | gtc | tgt | atc | aac | tat | tta | acc | acg | 7884 |
| Leu | Leu | Asn | Gly | Gly | Thr | Leu | Val | Cys | Ile | Asn | Tyr | Leu | Thr | Thr | |
| 2615 | | | | | 2620 | | | | | 2625 | | | | | |
| ctg | gat | agt | aaa | gca | ctc | gag | gcc | gtg | ttt | gag | cag | gaa | aag | atc | 7929 |
| Leu | Asp | Ser | Lys | Ala | Leu | Glu | Ala | Val | Phe | Glu | Gln | Glu | Lys | Ile | |
| 2630 | | | | | 2635 | | | | | 2640 | | | | | |
| caa | gcg | gct | atg | ctt | cca | cca | gca | ctg | ctc | aaa | cag | tat | ttg | gtt | 7974 |
| Gln | Ala | Ala | Met | Leu | Pro | Pro | Ala | Leu | Leu | Lys | Gln | Tyr | Leu | Val | |
| 2645 | | | | | 2650 | | | | | 2655 | | | | | |
| aac | att | ccc | gca | gct | atc | ggt | gca | cta | gaa | gtg | gtc | ctt | gtc | gct | 8019 |
| Asn | Ile | Pro | Ala | Ala | Ile | Gly | Ala | Leu | Glu | Val | Val | Leu | Val | Ala | |
| 2660 | | | | | 2665 | | | | | 2670 | | | | | |
| ggt | gac | cgt | ttc | gat | cga | cgc | gat | gct | gca | gcc | acg | cag | gct | ctt | 8064 |
| Gly | Asp | Arg | Phe | Asp | Arg | Arg | Asp | Ala | Ala | Ala | Thr | Gln | Ala | Leu | |
| 2675 | | | | | 2680 | | | | | 2685 | | | | | |
| gtt | gga | gca | ggc | gtg | tat | aac | gcc | tat | gga | ccg | acg | gag | aat | aca | 8109 |
| Val | Gly | Ala | Gly | Val | Tyr | Asn | Ala | Tyr | Gly | Pro | Thr | Glu | Asn | Thr | |
| 2690 | | | | | 2695 | | | | | 2700 | | | | | |
| aca | ctc | agc | act | atc | tac | aat | gtc | gtt | cag | ggc | gat | gcc | aat | gtg | 8154 |
| Thr | Leu | Ser | Thr | Ile | Tyr | Asn | Val | Val | Gln | Gly | Asp | Ala | Asn | Val | |
| 2705 | | | | | 2710 | | | | | 2715 | | | | | |
| aat | ggc | gtc | ccg | att | gga | cgc | cct | gtc | agc | aac | tct | ggc | gcc | tac | 8199 |
| Asn | Gly | Val | Pro | Ile | Gly | Arg | Pro | Val | Ser | Asn | Ser | Gly | Ala | Tyr | |
| 2720 | | | | | 2725 | | | | | 2730 | | | | | |
| atc | atg | aat | atg | aat | cag | gaa | ctc | gtt | cct | att | ggc | gtc | ata | ggc | 8244 |
| Ile | Met | Asn | Met | Asn | Gln | Glu | Leu | Val | Pro | Ile | Gly | Val | Ile | Gly | |
| 2735 | | | | | 2740 | | | | | 2745 | | | | | |
| gag | ctg | gtc | gta | gta | gga | gac | ggt | gtc | gcc | cga | gga | tac | acc | gac | 8289 |
| Glu | Leu | Val | Val | Val | Gly | Asp | Gly | Val | Ala | Arg | Gly | Tyr | Thr | Asp | |
| 2750 | | | | | 2755 | | | | | 2760 | | | | | |
| cca | gcc | ttg | gac | gtc | aac | cgc | ttc | gtc | aac | gtc | act | att | gaa | ggc | 8334 |
| Pro | Ala | Leu | Asp | Val | Asn | Arg | Phe | Val | Asn | Val | Thr | Ile | Glu | Gly | |
| 2765 | | | | | 2770 | | | | | 2775 | | | | | |

| | | |
|---|---|---|
| caa act atg agg gct tat agg act ggc gat cgt gcc cgc tat agg<br>Gln Thr Met Arg Ala Tyr Arg Thr Gly Asp Arg Ala Arg Tyr Arg<br>2780 2785 2790 | | 8379 |
| ccc aaa gac gca cag att gaa ttc ttt ggc cga atg gat caa cag<br>Pro Lys Asp Ala Gln Ile Glu Phe Phe Gly Arg Met Asp Gln Gln<br>2795 2800 2805 | | 8424 |
| atc aag att cga ggc cat cgt att gag cca gct gag gtc gag cat<br>Ile Lys Ile Arg Gly His Arg Ile Glu Pro Ala Glu Val Glu His<br>2810 2815 2820 | | 8469 |
| gcg ttg ctc aac aat gac ttg ctt cag gac gct gca gtc att atc<br>Ala Leu Leu Asn Asn Asp Leu Leu Gln Asp Ala Ala Val Ile Ile<br>2825 2830 2835 | | 8514 |
| cga aag caa caa aat gat gag ctg gag atg gtt gct ttt gta gaa<br>Arg Lys Gln Gln Asn Asp Glu Leu Glu Met Val Ala Phe Val Glu<br>2840 2845 2850 | | 8559 |
| gca aac agc aat aag tcg atc gaa caa gag gcg agc aac caa gta<br>Ala Asn Ser Asn Lys Ser Ile Glu Gln Glu Ala Ser Asn Gln Val<br>2855 2860 2865 | | 8604 |
| gaa gac tgg ggc gct caa ttc gag agc aac gtc tac gcc gag atc<br>Glu Asp Trp Gly Ala Gln Phe Glu Ser Asn Val Tyr Ala Glu Ile<br>2870 2875 2880 | | 8649 |
| gag gca atc gat gcc tct gct gtt ggt aac gac ttc atg ggt tgg<br>Glu Ala Ile Asp Ala Ser Ala Val Gly Asn Asp Phe Met Gly Trp<br>2885 2890 2895 | | 8694 |
| act tcc atg tac gac ggc agc gcg atc gac aag gct gag atg cag<br>Thr Ser Met Tyr Asp Gly Ser Ala Ile Asp Lys Ala Glu Met Gln<br>2900 2905 2910 | | 8739 |
| gaa tgg ctc gat gat act atg cag aca ata ctt gat ggt cga cca<br>Glu Trp Leu Asp Asp Thr Met Gln Thr Ile Leu Asp Gly Arg Pro<br>2915 2920 2925 | | 8784 |
| gcc ggc cgc gtt ctc gaa atc ggc act ggc acg ggt atg atc ctc<br>Ala Gly Arg Val Leu Glu Ile Gly Thr Gly Thr Gly Met Ile Leu<br>2930 2935 2940 | | 8829 |
| ttc aat ctt ggt gaa ggg tta cag agc tat gtc ggt ctc gaa cca<br>Phe Asn Leu Gly Glu Gly Leu Gln Ser Tyr Val Gly Leu Glu Pro<br>2945 2950 2955 | | 8874 |
| tct acc tcg gcg gct gcg ttc gtc aat cgc agg att cag aca ctt<br>Ser Thr Ser Ala Ala Ala Phe Val Asn Arg Arg Ile Gln Thr Leu<br>2960 2965 2970 | | 8919 |
| cca gct ttc gct ggt aaa gct gaa gtt cac gtg ggt aca gcg aca<br>Pro Ala Phe Ala Gly Lys Ala Glu Val His Val Gly Thr Ala Thr<br>2975 2980 2985 | | 8964 |
| gat ata agc caa ctt caa gat ctc cgc ccg gaa gta gtg gtt atc<br>Asp Ile Ser Gln Leu Gln Asp Leu Arg Pro Glu Val Val Val Ile<br>2990 2995 3000 | | 9009 |
| aac tcg gtg gct cag tac ttc cca tcg cct gag tac ttg tct aag<br>Asn Ser Val Ala Gln Tyr Phe Pro Ser Pro Glu Tyr Leu Ser Lys<br>3005 3010 3015 | | 9054 |
| gtt ttg tac gca cta gcc caa att cct ggc gtc aag cgt ttg ttc<br>Val Leu Tyr Ala Leu Ala Gln Ile Pro Gly Val Lys Arg Leu Phe<br>3020 3025 3030 | | 9099 |
| ttt gga gac atg cga tct tac gcc atc aac gac cag ttc ctt gca<br>Phe Gly Asp Met Arg Ser Tyr Ala Ile Asn Asp Gln Phe Leu Ala<br>3035 3040 3045 | | 9144 |
| gct cgc gcc tta cac aac ata ggt agc aag gct act aag agc gcc<br>Ala Arg Ala Leu His Asn Ile Gly Ser Lys Ala Thr Lys Ser Ala<br>3050 3055 3060 | | 9189 |
| att cga agc aag atg gtc gat ctg gaa aac tct gag gaa gaa ttg<br>Ile Arg Ser Lys Met Val Asp Leu Glu Asn Ser Glu Glu Glu Leu<br>3065 3070 3075 | | 9234 |

```
ctc gtc gac cca acc ttc ttc acc aac cta gcg acc gag ctt cca    9279
Leu Val Asp Pro Thr Phe Phe Thr Asn Leu Ala Thr Glu Leu Pro
3080             3085                 3090 gag gtt gag cat gtt gag att ctg cca aaa cgc atg cag gct acc    9324
Glu Val Glu His Val Glu Ile Leu Pro Lys Arg Met Gln Ala Thr
3095             3100                 3105 aac gaa ctt agc gcc tat cgt tat gca gct gtg gtg cac atc cgt    9369
Asn Glu Leu Ser Ala Tyr Arg Tyr Ala Ala Val Val His Ile Arg
3110             3115                 3120 gat tca tcg gaa cga gct cag acc gtg cat gcc atc aaa tcg agc    9414
Asp Ser Ser Glu Arg Ala Gln Thr Val His Ala Ile Lys Ser Ser
3125             3130                 3135 gca tgg gtc gac ttc agc aaa tct cag atg gac cgc aag gcc ctc    9459
Ala Trp Val Asp Phe Ser Lys Ser Gln Met Asp Arg Lys Ala Leu
3140             3145                 3150 atc agt ctt ctt caa agc tcg gta aac acc gag gct gtt gct atc    9504
Ile Ser Leu Leu Gln Ser Ser Val Asn Thr Glu Ala Val Ala Ile
3155             3160                 3165 ggc aat atc ccc tac agc aag act atc atg gcg cga cat gtc gtc    9549
Gly Asn Ile Pro Tyr Ser Lys Thr Ile Met Ala Arg His Val Val
3170             3175                 3180 caa tcg ctt gac gaa gac aat gca gac aag gac att gcg caa gat    9594
Gln Ser Leu Asp Glu Asp Asn Ala Asp Lys Asp Ile Ala Gln Asp
3185             3190                 3195 aaa ccc gat aag ccc acc tgg atc tcg gca gtt cgc tcc aat gcc    9639
Lys Pro Asp Lys Pro Thr Trp Ile Ser Ala Val Arg Ser Asn Ala
3200             3205                 3210 gaa cac tgc cca tca cta tcg gct ctc gac ctt gta cag ctt ggt    9684
Glu His Cys Pro Ser Leu Ser Ala Leu Asp Leu Val Gln Leu Gly
3215             3220                 3225 gag gag gca ggc ttc tgt gtg gag ctc agc tgg gct caa cag cga    9729
Glu Glu Ala Gly Phe Cys Val Glu Leu Ser Trp Ala Gln Gln Arg
3230             3235                 3240 tct cat cac gga gca atc gac gca gtc ttt cat cat tac cag ccc    9774
Ser His His Gly Ala Ile Asp Ala Val Phe His His Tyr Gln Pro
3245             3250                 3255 gct cga gaa gga agc cgt gtt ctg ttt cag ttc ccg acc gat acg    9819
Ala Arg Glu Gly Ser Arg Val Leu Phe Gln Phe Pro Thr Asp Thr
3260             3265                 3270 tat cga cgc caa tcc ggt ccg ctt aca aac cga ccc ttg cag cga    9864
Tyr Arg Arg Gln Ser Gly Pro Leu Thr Asn Arg Pro Leu Gln Arg
3275             3280                 3285 att cag agc cgg cga atg gaa aca cag gtt aga gaa aag cta cgg    9909
Ile Gln Ser Arg Arg Met Glu Thr Gln Val Arg Glu Lys Leu Arg
3290             3295                 3300 gcc gtt ttg cct tca tac atg att cca tcg ctc atc gtg ctg gtc    9954
Ala Val Leu Pro Ser Tyr Met Ile Pro Ser Leu Ile Val Leu Val
3305             3310                 3315 gac caa atg ccc ctg aac ccc aac ggc aaa gtg gat agg aag gcg    9999
Asp Gln Met Pro Leu Asn Pro Asn Gly Lys Val Asp Arg Lys Ala
3320             3325                 3330 ttg gaa cga cga gcc cag gca gtg cta cgg gtc gaa aaa cca act   10044
Leu Glu Arg Arg Ala Gln Ala Val Leu Arg Val Glu Lys Pro Thr
3335             3340                 3345 tcc gaa cgt gtt ggt gcc cgt aat gag act gag gct gtg ctt tgt   10089
Ser Glu Arg Val Gly Ala Arg Asn Glu Thr Glu Ala Val Leu Cys
3350             3355                 3360 gag gag ttt acc gac gtt ctc gga ctt gag gtt ggt att acg gat   10134
Glu Glu Phe Thr Asp Val Leu Gly Leu Glu Val Gly Ile Thr Asp
3365             3370                 3375
```

| | | | | | | | | | | | |
|---|---|---|---|---|---|---|---|---|---|---|---|
| aac | ttc | ttc | gac | ctc | ggt | ggg | cac | tcg | ctt | atg | gcg | acc | aaa | ctc | 10179 |
| Asn | Phe | Phe | Asp | Leu | Gly | Gly | His | Ser | Leu | Met | Ala | Thr | Lys | Leu | |
| | 3380 | | | | 3385 | | | | 3390 | | | | | | | gcg gcc cgt atc agt cga cgc ctt gac gcc cgc gtc tct gtt aaa  10224
Ala Ala Arg Ile Ser Arg Arg Leu Asp Ala Arg Val Ser Val Lys
    3395            3400            3405 gat gtc ttt gat cag cct gtc ata gtc gac ctc gcc gcc tcc att  10269
Asp Val Phe Asp Gln Pro Val Ile Val Asp Leu Ala Ala Ser Ile
3410            3415            3420 cgc cgt ggt tcg acc cct cac aat cct atc acc cca acc gag tat  10314
Arg Arg Gly Ser Thr Pro His Asn Pro Ile Thr Pro Thr Glu Tyr
    3425            3430            3435 tct ggt ccg gta gag caa tcg ttt gct cag ggc cgt ctc tgg ttc  10359
Ser Gly Pro Val Glu Gln Ser Phe Ala Gln Gly Arg Leu Trp Phe
3440            3445            3450 tta gac cag ttg aat ctc ggt gca tct tta tat ctc atg cct ctt  10404
Leu Asp Gln Leu Asn Leu Gly Ala Ser Leu Tyr Leu Met Pro Leu
    3455            3460            3465 gcg ttg cgt ttg cgt gga cct ctc cgc atc gat gct ctc aca gct  10449
Ala Leu Arg Leu Arg Gly Pro Leu Arg Ile Asp Ala Leu Thr Ala
3470            3475            3480 gcg ctc ttc gca ttg gaa cag cga cac gag act ctc cga acc gtc  10494
Ala Leu Phe Ala Leu Glu Gln Arg His Glu Thr Leu Arg Thr Val
    3485            3490            3495 ttc aag gag caa gat ggc gta ggc atc caa atc att caa cct agc  10539
Phe Lys Glu Gln Asp Gly Val Gly Ile Gln Ile Ile Gln Pro Ser
3500            3505            3510 caa aag aag aaa ctc aga acc att gat gta tct gca ggc gac ttt  10584
Gln Lys Lys Lys Leu Arg Thr Ile Asp Val Ser Ala Gly Asp Phe
    3515            3520            3525 tcc gag gcg ctg cat cac gaa cgc act gcc cca ttt gat ctc gca  10629
Ser Glu Ala Leu His His Glu Arg Thr Ala Pro Phe Asp Leu Ala
3530            3535            3540 tca gag ccg ggc ttc aga gtc gcc ctt ctt cag ctt gag ccg tct  10674
Ser Glu Pro Gly Phe Arg Val Ala Leu Leu Gln Leu Glu Pro Ser
    3545            3550            3555 gat cat gtg ctg tct atc gtc atg cac cat atc atc tac gac ggc  10719
Asp His Val Leu Ser Ile Val Met His His Ile Ile Tyr Asp Gly
3560            3565            3570 tgg tct atc gac att ttg tgt caa gaa ctg ggc cag ttc tac gct  10764
Trp Ser Ile Asp Ile Leu Cys Gln Glu Leu Gly Gln Phe Tyr Ala
    3575            3580            3585 gct gca atc cag ggc cag gat cca ttg gga caa gtg agc ccg ctc  10809
Ala Ala Ile Gln Gly Gln Asp Pro Leu Gly Gln Val Ser Pro Leu
3590            3595            3600 cca att caa tac cgt gac ttc tct gtc tgg caa aag caa cct gag  10854
Pro Ile Gln Tyr Arg Asp Phe Ser Val Trp Gln Lys Gln Pro Glu
    3605            3610            3615 cag gtc gct gag cat gag cgg cag ctt gcg tac tgg atc gat cag  10899
Gln Val Ala Glu His Glu Arg Gln Leu Ala Tyr Trp Ile Asp Gln
3620            3625            3630 ttg gcc gat agt gct ccc gct gag ttc ctt gtc gat ctc cca cgc  10944
Leu Ala Asp Ser Ala Pro Ala Glu Phe Leu Val Asp Leu Pro Arg
    3635            3640            3645 cca ccc gtc ttg tct ggt gat gcc gga cta gtc cac ctc act atc  10989
Pro Pro Val Leu Ser Gly Asp Ala Gly Leu Val His Leu Thr Ile
3650            3655            3660 gat ggt ccc atc tat gac cgc ctg aga gcc ttc tgt cga gtg cac  11034
Asp Gly Pro Ile Tyr Asp Arg Leu Arg Ala Phe Cys Arg Val His
    3665            3670            3675

```
cag acg aca act ttt gca gtg cta cta gca gct ttc cgc gca acg         11079
Gln Thr Thr Thr Phe Ala Val Leu Leu Ala Ala Phe Arg Ala Thr
    3680            3685                3690 cac tat cgt ctt aca ggt gcc gaa gat gct act gtt ggc aca cca         11124
His Tyr Arg Leu Thr Gly Ala Glu Asp Ala Thr Val Gly Thr Pro
    3695            3700                3705 atc gcc aac cgt aac cgg ccg gag ctt gaa aac ttg gtc gga ttc         11169
Ile Ala Asn Arg Asn Arg Pro Glu Leu Glu Asn Leu Val Gly Phe
    3710            3715                3720 ttc gtc aat act cag tgt atg aga att agt gtc gga gat gat gac         11214
Phe Val Asn Thr Gln Cys Met Arg Ile Ser Val Gly Asp Asp Asp
    3725            3730                3735 acg ttt gag cag cta gtg cgc cag gtt cga tct aca gca acg gct         11259
Thr Phe Glu Gln Leu Val Arg Gln Val Arg Ser Thr Ala Thr Ala
    3740            3745                3750 gca ttt gca aac caa gac gtt cct ttt gaa cgc atc gtg tca aca         11304
Ala Phe Ala Asn Gln Asp Val Pro Phe Glu Arg Ile Val Ser Thr
    3755            3760                3765 ctc ctg ccg ggc tct cgc gat acc gcc cgc aat cca ctg gta cag         11349
Leu Leu Pro Gly Ser Arg Asp Thr Ala Arg Asn Pro Leu Val Gln
    3770            3775                3780 ctc atg ttt gct gtc cat tct ctc aag gac ctt ggc aaa att cag         11394
Leu Met Phe Ala Val His Ser Leu Lys Asp Leu Gly Lys Ile Gln
    3785            3790                3795 ttc gag ggt ctc gtg ggc gag aca att ccc acg gct tct ttc act         11439
Phe Glu Gly Leu Val Gly Glu Thr Ile Pro Thr Ala Ser Phe Thr
    3800            3805                3810 cga ttc gac gtc gag ttt cat ttg ttc cag gaa gtc ggt cgt ctt         11484
Arg Phe Asp Val Glu Phe His Leu Phe Gln Glu Val Gly Arg Leu
    3815            3820                3825 agc gga aat gtg ctc ttc tcg act gat cta ttt gag ccg gag act         11529
Ser Gly Asn Val Leu Phe Ser Thr Asp Leu Phe Glu Pro Glu Thr
    3830            3835                3840 atc cag ggc atg gtc tct gtg ttc atg gag atc ttg cgc gga gct         11574
Ile Gln Gly Met Val Ser Val Phe Met Glu Ile Leu Arg Gly Ala
    3845            3850                3855 ctt gac cag cct cag atc ccc att gcc gtc cta ccg ctc aca gac         11619
Leu Asp Gln Pro Gln Ile Pro Ile Ala Val Leu Pro Leu Thr Asp
    3860            3865                3870 ggc ctc acg gag ctt cgc aac aga ggc ctg ctt gaa gtt gag cag         11664
Gly Leu Thr Glu Leu Arg Asn Arg Gly Leu Leu Glu Val Glu Gln
    3875            3880                3885 cct caa tat ccc cgc gac tcg agc gtc att gac gtg ttc cgc gct         11709
Pro Gln Tyr Pro Arg Asp Ser Ser Val Ile Asp Val Phe Arg Ala
    3890            3895                3900 cag gtc gtt gct tgc cca gat gca atc gct gtg aaa gat tcg acg         11754
Gln Val Val Ala Cys Pro Asp Ala Ile Ala Val Lys Asp Ser Thr
    3905            3910                3915 tcg cag ctc acc tat gcc caa ctt gat gag cag tcc gat gag gtg         11799
Ser Gln Leu Thr Tyr Ala Gln Leu Asp Glu Gln Ser Asp Glu Val
    3920            3925                3930 gct gta tgg cta cat caa cga aag ttg cca gcg gaa tcc ctg gtt         11844
Ala Val Trp Leu His Gln Arg Lys Leu Pro Ala Glu Ser Leu Val
    3935            3940                3945 gcc gtg cta gca cct aga tca tgc gag act atc att acc ttc ttc         11889
Ala Val Leu Ala Pro Arg Ser Cys Glu Thr Ile Ile Thr Phe Phe
    3950            3955                3960 ggt att ttg aag gct aat cta gcc tat ctt cca ctc gat att aac         11934
Gly Ile Leu Lys Ala Asn Leu Ala Tyr Leu Pro Leu Asp Ile Asn
    3965            3970                3975
```

```
gtc  ccg  gca  gcc  cgt  att  cag  gca  atc  tta  tcg  tcc  gtt  gca  ggg    11979
Val  Pro  Ala  Ala  Arg  Ile  Gln  Ala  Ile  Leu  Ser  Ser  Val  Ala  Gly
     3980                3985                3990 aag  aaa  atc  ctc  cta  ctt  ggt  tct  gat  cag  gct  cag  ccg  gaa  att    12024
Lys  Lys  Ile  Leu  Leu  Leu  Gly  Ser  Asp  Gln  Ala  Gln  Pro  Glu  Ile
     3995                4000                4005 cgg  ctt  gat  gat  gtt  gaa  ttt  gta  caa  atc  aat  gaa  acg  att  gac    12069
Arg  Leu  Asp  Asp  Val  Glu  Phe  Val  Gln  Ile  Asn  Glu  Thr  Ile  Asp
     4010                4015                4020 cac  aat  atg  gcg  aag  gat  aat  act  acc  cgc  tct  gga  ccc  tta  gct    12114
His  Asn  Met  Ala  Lys  Asp  Asn  Thr  Thr  Arg  Ser  Gly  Pro  Leu  Ala
     4025                4030                4035 aca  agt  ctt  gct  tat  gtt  atc  ttc  act  tct  gga  tcc  act  ggc  cag    12159
Thr  Ser  Leu  Ala  Tyr  Val  Ile  Phe  Thr  Ser  Gly  Ser  Thr  Gly  Gln
     4040                4045                4050 ccg  aag  ggc  gtc  aag  gtg  gaa  cac  cgc  ggt  att  gtt  cgc  ctc  gtc    12204
Pro  Lys  Gly  Val  Lys  Val  Glu  His  Arg  Gly  Ile  Val  Arg  Leu  Val
     4055                4060                4065 aag  aat  agc  aac  gtg  gta  gca  aag  atg  cca  gag  gcg  gca  tgt  gtt    12249
Lys  Asn  Ser  Asn  Val  Val  Ala  Lys  Met  Pro  Glu  Ala  Ala  Cys  Val
     4070                4075                4080 gca  cac  ctt  tca  aat  ctc  gcg  ttt  gac  gcc  gcg  aca  tgg  gaa  atc    12294
Ala  His  Leu  Ser  Asn  Leu  Ala  Phe  Asp  Ala  Ala  Thr  Trp  Glu  Ile
     4085                4090                4095 tac  gct  gca  ctc  ttg  aat  ggt  ggc  tcg  ctc  atc  tgt  atc  gac  tac    12339
Tyr  Ala  Ala  Leu  Leu  Asn  Gly  Gly  Ser  Leu  Ile  Cys  Ile  Asp  Tyr
     4100                4105                4110 ttc  acc  acg  cta  gac  agc  aag  gtc  ctc  gag  gca  gtt  ttc  gag  cga    12384
Phe  Thr  Thr  Leu  Asp  Ser  Lys  Val  Leu  Glu  Ala  Val  Phe  Glu  Arg
     4115                4120                4125 gaa  caa  atc  cgt  gca  gcc  atg  ttc  cca  ccg  gcg  ctt  ctg  aaa  caa    12429
Glu  Gln  Ile  Arg  Ala  Ala  Met  Phe  Pro  Pro  Ala  Leu  Leu  Lys  Gln
     4130                4135                4140 tgc  cta  ctc  aat  atc  ccc  acg  acc  atc  agc  gcg  cta  gat  gtt  atc    12474
Cys  Leu  Leu  Asn  Ile  Pro  Thr  Thr  Ile  Ser  Ala  Leu  Asp  Val  Ile
     4145                4150                4155 ctc  gct  gct  ggt  gac  cga  ttt  gat  agg  cgc  gac  gct  att  gcg  gcg    12519
Leu  Ala  Ala  Gly  Asp  Arg  Phe  Asp  Arg  Arg  Asp  Ala  Ile  Ala  Ala
     4160                4165                4170 cag  gcg  ctt  gtt  gga  ggt  ggt  gta  tac  aat  gcc  tac  ggt  cct  acg    12564
Gln  Ala  Leu  Val  Gly  Gly  Gly  Val  Tyr  Asn  Ala  Tyr  Gly  Pro  Thr
     4175                4180                4185 gaa  aat  act  acg  ctt  agc  aca  ata  tac  aac  gtt  gtg  gat  ggc  gat    12609
Glu  Asn  Thr  Thr  Leu  Ser  Thr  Ile  Tyr  Asn  Val  Val  Asp  Gly  Asp
     4190                4195                4200 acc  aac  gtc  aac  ggt  att  cca  atc  ggg  ctt  cct  gtc  agc  aac  tct    12654
Thr  Asn  Val  Asn  Gly  Ile  Pro  Ile  Gly  Leu  Pro  Val  Ser  Asn  Ser
     4205                4210                4215 ggc  gtg  tat  gtc  atg  gat  ccc  aac  cag  cag  ctt  gtc  ccg  ttg  ggc    12699
Gly  Val  Tyr  Val  Met  Asp  Pro  Asn  Gln  Gln  Leu  Val  Pro  Leu  Gly
     4220                4225                4230 gtc  atg  gga  gag  ctt  gtt  gtg  gtt  ggc  gat  ggt  gta  gcc  cga  ggt    12744
Val  Met  Gly  Glu  Leu  Val  Val  Val  Gly  Asp  Gly  Val  Ala  Arg  Gly
     4235                4240                4245 tac  act  gat  cca  gct  ctt  gat  gtt  gat  cgt  ttc  atc  aag  gtt  gaa    12789
Tyr  Thr  Asp  Pro  Ala  Leu  Asp  Val  Asp  Arg  Phe  Ile  Lys  Val  Glu
     4250                4255                4260 atc  gac  ggc  cag  atc  gta  cga  gcc  tac  cgc  act  ggt  gac  cgt  gtt    12834
Ile  Asp  Gly  Gln  Ile  Val  Arg  Ala  Tyr  Arg  Thr  Gly  Asp  Arg  Val
     4265                4270                4275
```

| | | | | | | | | | | | | | | |
|---|---|---|---|---|---|---|---|---|---|---|---|---|---|---|
| cga | cac | cga | ccc | aag | gac | ggt | cag | att | gag | ttc | ttt | ggc | cga | atg | 12879 |
| Arg | His | Arg | Pro | Lys | Asp | Gly | Gln | Ile | Glu | Phe | Phe | Gly | Arg | Met | |
| | 4280 | | | | 4285 | | | | 4290 | | | | | | |

| gat | cag | caa | gtc | aag | att | cga | gga | cat | cgc | att | gaa | ttg | gct | gag | 12924 |
|---|---|---|---|---|---|---|---|---|---|---|---|---|---|---|---|
| Asp | Gln | Gln | Val | Lys | Ile | Arg | Gly | His | Arg | Ile | Glu | Leu | Ala | Glu | |
| | 4295 | | | | 4300 | | | | 4305 | | | | | | |

| gta | gag | cac | gtc | atc | ctc | gat | aac | agc | tta | gtc | cag | gac | gct | gca | 12969 |
|---|---|---|---|---|---|---|---|---|---|---|---|---|---|---|---|
| Val | Glu | His | Val | Ile | Leu | Asp | Asn | Ser | Leu | Val | Gln | Asp | Ala | Ala | |
| 4310 | | | | | 4315 | | | | | 4320 | | | | | |

| gtc | att | gtc | cac | aag | caa | gct | gac | cag | gag | atc | gaa | atg | atc | gca | 13014 |
|---|---|---|---|---|---|---|---|---|---|---|---|---|---|---|---|
| Val | Ile | Val | His | Lys | Gln | Ala | Asp | Gln | Glu | Ile | Glu | Met | Ile | Ala | |
| 4325 | | | | | 4330 | | | | | 4335 | | | | | |

| ttt | gct | ata | gtc | cga | ggc | gat | aac | gac | agc | aag | cac | cca | gag | aag | 13059 |
|---|---|---|---|---|---|---|---|---|---|---|---|---|---|---|---|
| Phe | Ala | Ile | Val | Arg | Gly | Asp | Asn | Asp | Ser | Lys | His | Pro | Glu | Lys | |
| 4340 | | | | | 4345 | | | | | 4350 | | | | | |

| gat | att | cta | gat | cga | gtg | aag | gct | ttg | ctt | cca | tca | tac | atg | gtg | 13104 |
|---|---|---|---|---|---|---|---|---|---|---|---|---|---|---|---|
| Asp | Ile | Leu | Asp | Arg | Val | Lys | Ala | Leu | Leu | Pro | Ser | Tyr | Met | Val | |
| 4355 | | | | | 4360 | | | | | 4365 | | | | | |

| cca | gct | caa | atg | gtg | ctg | ctt | aac | agc | atg | cct | ctc | aat | gcc | aac | 13149 |
|---|---|---|---|---|---|---|---|---|---|---|---|---|---|---|---|
| Pro | Ala | Gln | Met | Val | Leu | Leu | Asn | Ser | Met | Pro | Leu | Asn | Ala | Asn | |
| 4370 | | | | | 4375 | | | | | 4380 | | | | | |

| ggc | aag | gtc | gat | cgc | aaa | gag | ctt | gct | aag | agg | gcg | ggg | act | gtg | 13194 |
|---|---|---|---|---|---|---|---|---|---|---|---|---|---|---|---|
| Gly | Lys | Val | Asp | Arg | Lys | Glu | Leu | Ala | Lys | Arg | Ala | Gly | Thr | Val | |
| 4385 | | | | | 4390 | | | | | 4395 | | | | | |

| ccg | cga | agc | gag | atg | gca | tac | gtc | gct | cca | gag | agg | gtt | ccg | cct | 13239 |
|---|---|---|---|---|---|---|---|---|---|---|---|---|---|---|---|
| Pro | Arg | Ser | Glu | Met | Ala | Tyr | Val | Ala | Pro | Glu | Arg | Val | Pro | Pro | |
| 4400 | | | | | 4405 | | | | | 4410 | | | | | |

| cgc | aat | gaa | atc | gaa | aca | att | ctt | tgc | gaa | gaa | tac | gcc | gag | gtc | 13284 |
|---|---|---|---|---|---|---|---|---|---|---|---|---|---|---|---|
| Arg | Asn | Glu | Ile | Glu | Thr | Ile | Leu | Cys | Glu | Glu | Tyr | Ala | Glu | Val | |
| 4415 | | | | | 4420 | | | | | 4425 | | | | | |

| ctt | ggc | gtc | gag | gtt | ggt | gtc | atg | gac | aac | ttt | ttc | gat | ctt | gga | 13329 |
|---|---|---|---|---|---|---|---|---|---|---|---|---|---|---|---|
| Leu | Gly | Val | Glu | Val | Gly | Val | Met | Asp | Asn | Phe | Phe | Asp | Leu | Gly | |
| 4430 | | | | | 4435 | | | | | 4440 | | | | | |

| ggg | cac | tct | ctc | atg | gcg | acc | aag | ctt | gca | gcc | cgc | gcc | act | cgt | 13374 |
|---|---|---|---|---|---|---|---|---|---|---|---|---|---|---|---|
| Gly | His | Ser | Leu | Met | Ala | Thr | Lys | Leu | Ala | Ala | Arg | Ala | Thr | Arg | |
| 4445 | | | | | 4450 | | | | | 4455 | | | | | |

| cga | ctt | gat | gca | aag | ttg | tcc | gtt | aag | gac | att | ttt | gat | tac | cca | 13419 |
|---|---|---|---|---|---|---|---|---|---|---|---|---|---|---|---|
| Arg | Leu | Asp | Ala | Lys | Leu | Ser | Val | Lys | Asp | Ile | Phe | Asp | Tyr | Pro | |
| 4460 | | | | | 4465 | | | | | 4470 | | | | | |

| att | tta | gcc | aac | ctt | gca | gca | gcg | gtt | caa | cga | ggc | tcg | act | cca | 13464 |
|---|---|---|---|---|---|---|---|---|---|---|---|---|---|---|---|
| Ile | Leu | Ala | Asn | Leu | Ala | Ala | Ala | Val | Gln | Arg | Gly | Ser | Thr | Pro | |
| 4475 | | | | | 4480 | | | | | 4485 | | | | | |

| cat | aat | gcg | att | ctc | gca | acc | aca | tac | tcc | gga | cca | gtt | gaa | caa | 13509 |
|---|---|---|---|---|---|---|---|---|---|---|---|---|---|---|---|
| His | Asn | Ala | Ile | Leu | Ala | Thr | Thr | Tyr | Ser | Gly | Pro | Val | Glu | Gln | |
| 4490 | | | | | 4495 | | | | | 4500 | | | | | |

| tca | ttc | gcc | cag | ggg | cgc | ctg | tgg | ttc | ttg | gac | cag | ctg | aat | gtt | 13554 |
|---|---|---|---|---|---|---|---|---|---|---|---|---|---|---|---|
| Ser | Phe | Ala | Gln | Gly | Arg | Leu | Trp | Phe | Leu | Asp | Gln | Leu | Asn | Val | |
| 4505 | | | | | 4510 | | | | | 4515 | | | | | |

| ggc | tcg | aat | tgg | tac | ctt | cag | cca | att | gcc | ata | cgc | ata | cgc | gga | 13599 |
|---|---|---|---|---|---|---|---|---|---|---|---|---|---|---|---|
| Gly | Ser | Asn | Trp | Tyr | Leu | Gln | Pro | Ile | Ala | Ile | Arg | Ile | Arg | Gly | |
| 4520 | | | | | 4525 | | | | | 4530 | | | | | |

| tca | ctc | aat | att | aac | gcg | ctc | act | acc | gcg | ctt | cat | gcc | cta | gaa | 13644 |
|---|---|---|---|---|---|---|---|---|---|---|---|---|---|---|---|
| Ser | Leu | Asn | Ile | Asn | Ala | Leu | Thr | Thr | Ala | Leu | His | Ala | Leu | Glu | |
| 4535 | | | | | 4540 | | | | | 4545 | | | | | |

| caa | cgt | cac | gag | acg | ttg | cgc | acc | act | ttt | gag | gaa | gag | gac | ggc | 13689 |
|---|---|---|---|---|---|---|---|---|---|---|---|---|---|---|---|
| Gln | Arg | His | Glu | Thr | Leu | Arg | Thr | Thr | Phe | Glu | Glu | Glu | Asp | Gly | |
| 4550 | | | | | 4555 | | | | | 4560 | | | | | |

| gtt | ggt | atg | cag | gtc | gtc | caa | gaa | tat | gac | ccg | ata | gag | ctc | agg | 13734 |
|---|---|---|---|---|---|---|---|---|---|---|---|---|---|---|---|
| Val | Gly | Met | Gln | Val | Val | Gln | Glu | Tyr | Asp | Pro | Ile | Glu | Leu | Arg | |
| 4565 | | | | | 4570 | | | | | 4575 | | | | | |

| | | | | | | | | | | | | |
|---|---|---|---|---|---|---|---|---|---|---|---|---|
| ata | atg | gat | att | gct | gcc | gat | tat | gac | ggc | gat | tat | aca | gaa | gcg | 13779 |
| Ile | Met | Asp | Ile | Ala | Ala | Asp | Tyr | Asp | Gly | Asp | Tyr | Thr | Glu | Ala | |
| | 4580 | | | | 4585 | | | | 4590 | | | | | | |
| ttg | aag | gga | gag | cag | acg | acc | ccc | ttc | gat | cta | gag | tcg | gag | cca | 13824 |
| Leu | Lys | Gly | Glu | Gln | Thr | Thr | Pro | Phe | Asp | Leu | Glu | Ser | Glu | Pro | |
| | 4595 | | | | 4600 | | | | 4605 | | | | | | |
| gga | tgg | agg | gta | tcg | ctg | ctc | cgt | atg | aac | gac | aac | gat | cat | atc | 13869 |
| Gly | Trp | Arg | Val | Ser | Leu | Leu | Arg | Met | Asn | Asp | Asn | Asp | His | Ile | |
| | 4610 | | | | 4615 | | | | 4620 | | | | | | |
| ttg | tct | ctg | gtt | cta | cat | cac | atc | atc | tcc | gat | gga | tgg | tct | gtc | 13914 |
| Leu | Ser | Leu | Val | Leu | His | His | Ile | Ile | Ser | Asp | Gly | Trp | Ser | Val | |
| | 4625 | | | | 4630 | | | | 4635 | | | | | | |
| gac | gtt | cta | cgc | cag | gag | ttg | aag | caa | ttc | tat | gcc | gct | gca | ctc | 13959 |
| Asp | Val | Leu | Arg | Gln | Glu | Leu | Lys | Gln | Phe | Tyr | Ala | Ala | Ala | Leu | |
| | 4640 | | | | 4645 | | | | 4650 | | | | | | |
| caa | ggc | ctg | gat | cct | ctg | tca | ggg | gct | gat | cca | ctc | ccc | atc | cag | 14004 |
| Gln | Gly | Leu | Asp | Pro | Leu | Ser | Gly | Ala | Asp | Pro | Leu | Pro | Ile | Gln | |
| | 4655 | | | | 4660 | | | | 4665 | | | | | | |
| tac | cgc | gac | ttc | tct | ctc | tgg | caa | aag | cag | cca | gag | caa | gtt | gct | 14049 |
| Tyr | Arg | Asp | Phe | Ser | Leu | Trp | Gln | Lys | Gln | Pro | Glu | Gln | Val | Ala | |
| | 4670 | | | | 4675 | | | | 4680 | | | | | | |
| gag | cac | gaa | cga | cag | ctc | aag | tac | tgg | gtt | gag | cag | ttg | gct | gac | 14094 |
| Glu | His | Glu | Arg | Gln | Leu | Lys | Tyr | Trp | Val | Glu | Gln | Leu | Ala | Asp | |
| | 4685 | | | | 4690 | | | | 4695 | | | | | | |
| aat | tcc | cct | gct | acg | ctt | ctt | gcg | gac | cgg | cca | cgt | cca | tct | gtg | 14139 |
| Asn | Ser | Pro | Ala | Thr | Leu | Leu | Ala | Asp | Arg | Pro | Arg | Pro | Ser | Val | |
| | 4700 | | | | 4705 | | | | 4710 | | | | | | |
| ctg | tcg | ggc | caa | gcc | ggc | tcg | gtc | ccg | ctc | tct | atc | gaa | ggt | cag | 14184 |
| Leu | Ser | Gly | Gln | Ala | Gly | Ser | Val | Pro | Leu | Ser | Ile | Glu | Gly | Gln | |
| | 4715 | | | | 4720 | | | | 4725 | | | | | | |
| gtc | tat | gag | aaa | ctt | cag | gcc | ttc | tgc | cga | gct | cat | caa | acg | acc | 14229 |
| Val | Tyr | Glu | Lys | Leu | Gln | Ala | Phe | Cys | Arg | Ala | His | Gln | Thr | Thr | |
| | 4730 | | | | 4735 | | | | 4740 | | | | | | |
| tcc | ttt | tcc | gtt | ttg | ctc | gct | gcc | ttc | cga | gct | gct | cac | ttc | cgc | 14274 |
| Ser | Phe | Ser | Val | Leu | Leu | Ala | Ala | Phe | Arg | Ala | Ala | His | Phe | Arg | |
| | 4745 | | | | 4750 | | | | 4755 | | | | | | |
| ctg | acg | ggt | gtt | gac | gac | gcg | acg | att | ggc | ata | ccg | atc | gcc | aat | 14319 |
| Leu | Thr | Gly | Val | Asp | Asp | Ala | Thr | Ile | Gly | Ile | Pro | Ile | Ala | Asn | |
| | 4760 | | | | 4765 | | | | 4770 | | | | | | |
| cgt | aat | cga | cct | gag | cta | gag | cac | ctg | atc | ggc | ttt | ttc | gtt | aac | 14364 |
| Arg | Asn | Arg | Pro | Glu | Leu | Glu | His | Leu | Ile | Gly | Phe | Phe | Val | Asn | |
| | 4775 | | | | 4780 | | | | 4785 | | | | | | |
| agg | cag | tgt | atg | cgg | atc | acg | gtt | ggg | gaa | gat | gat | acg | ttc | gaa | 14409 |
| Arg | Gln | Cys | Met | Arg | Ile | Thr | Val | Gly | Glu | Asp | Asp | Thr | Phe | Glu | |
| | 4790 | | | | 4795 | | | | 4800 | | | | | | |
| tct | ctt | atc | cgc | cag | gtt | cac | tca | aca | gcc | act | gca | gcg | tat | gct | 14454 |
| Ser | Leu | Ile | Arg | Gln | Val | His | Ser | Thr | Ala | Thr | Ala | Ala | Tyr | Ala | |
| | 4805 | | | | 4810 | | | | 4815 | | | | | | |
| aat | caa | gac | gtg | ccg | ttc | gag | cga | atc | gta | tcg | tcc | ctt | ctt | tct | 14499 |
| Asn | Gln | Asp | Val | Pro | Phe | Glu | Arg | Ile | Val | Ser | Ser | Leu | Leu | Ser | |
| | 4820 | | | | 4825 | | | | 4830 | | | | | | |
| ggc | tca | aga | gac | aca | tct | cgt | aat | cca | ctc | gtc | cag | cta | gta | ttc | 14544 |
| Gly | Ser | Arg | Asp | Thr | Ser | Arg | Asn | Pro | Leu | Val | Gln | Leu | Val | Phe | |
| | 4835 | | | | 4840 | | | | 4845 | | | | | | |
| gcc | gtt | cac | tcc | cag | aag | aac | ctt | ggc | aag | ttt | gag | ttg | caa | gac | 14589 |
| Ala | Val | His | Ser | Gln | Lys | Asn | Leu | Gly | Lys | Phe | Glu | Leu | Gln | Asp | |
| | 4850 | | | | 4855 | | | | 4860 | | | | | | |
| ttg | aca | tct | gag | cca | gtt | gct | gga | gct | atc | tct | act | cga | ttt | gat | 14634 |
| Leu | Thr | Ser | Glu | Pro | Val | Ala | Gly | Ala | Ile | Ser | Thr | Arg | Phe | Asp | |
| | 4865 | | | | 4870 | | | | 4875 | | | | | | |

-continued

| | | | | | | | | | | | |
|---|---|---|---|---|---|---|---|---|---|---|---|
| gcg | gaa | ttt | cat | cta | ttc | cag | gaa | gaa | gag | agg | ttg | aac | ggt | gtt | 14679 |
| Ala | Glu | Phe | His | Leu | Phe | Gln | Glu | Glu | Glu | Arg | Leu | Asn | Gly | Val | |
| | 4880 | | | | 4885 | | | | | 4890 | | | | | |

| gtg | tat | tac | gca | acc | gat | ctg | ttc | gat | gcg | gag | act | atc | caa | ggg | 14724 |
| Val | Tyr | Tyr | Ala | Thr | Asp | Leu | Phe | Asp | Ala | Glu | Thr | Ile | Gln | Gly | |
| | 4895 | | | | 4900 | | | | | 4905 | | | | | |

| gtg | gtg | tct | gtt | ttc | caa | gaa | atc | tta | cgt | cgc | ggc | ctc | aac | cat | 14769 |
| Val | Val | Ser | Val | Phe | Gln | Glu | Ile | Leu | Arg | Arg | Gly | Leu | Asn | His | |
| | 4910 | | | | 4915 | | | | | 4920 | | | | | |

| cca | cga | acg | ccg | atc | gca | gct | ctg | tcg | ctt | acg | gac | ggg | ctg | gat | 14814 |
| Pro | Arg | Thr | Pro | Ile | Ala | Ala | Leu | Ser | Leu | Thr | Asp | Gly | Leu | Asp | |
| | 4925 | | | | 4930 | | | | | 4935 | | | | | |

| aat | ctt | cgc | aag | atg | aat | ctg | gtt | cac | ttc | aag | cgg | act | gat | tat | 14859 |
| Asn | Leu | Arg | Lys | Met | Asn | Leu | Val | His | Phe | Lys | Arg | Thr | Asp | Tyr | |
| | 4940 | | | | 4945 | | | | | 4950 | | | | | |

| ccc | cgc | gac | tct | agc | atg | gtc | gac | att | ttc | cgc | gag | caa | gtc | gct | 14904 |
| Pro | Arg | Asp | Ser | Ser | Met | Val | Asp | Ile | Phe | Arg | Glu | Gln | Val | Ala | |
| | 4955 | | | | 4960 | | | | | 4965 | | | | | |

| acc | tat | ccg | gac | gtg | att | gct | gtc | aag | gac | tcg | act | tta | cag | ctg | 14949 |
| Thr | Tyr | Pro | Asp | Val | Ile | Ala | Val | Lys | Asp | Ser | Thr | Leu | Gln | Leu | |
| | 4970 | | | | 4975 | | | | | 4980 | | | | | |

| acc | tac | gcg | caa | ctt | gat | caa | caa | tcc | gat | gag | ata | gcc | acc | tgg | 14994 |
| Thr | Tyr | Ala | Gln | Leu | Asp | Gln | Gln | Ser | Asp | Glu | Ile | Ala | Thr | Trp | |
| | 4985 | | | | 4990 | | | | | 4995 | | | | | |

| ttg | cga | aac | aaa | aaa | atg | gcg | cca | gaa | act | ctg | gtg | ggt | gtc | ctt | 15039 |
| Leu | Arg | Asn | Lys | Lys | Met | Ala | Pro | Glu | Thr | Leu | Val | Gly | Val | Leu | |
| | 5000 | | | | 5005 | | | | | 5010 | | | | | |

| gct | ccg | cga | tcg | tgc | cag | act | atc | gta | gcc | ttc | ctt | ggt | gtc | ctc | 15084 |
| Ala | Pro | Arg | Ser | Cys | Gln | Thr | Ile | Val | Ala | Phe | Leu | Gly | Val | Leu | |
| | 5015 | | | | 5020 | | | | | 5025 | | | | | |

| aag | gcg | aac | cta | gcc | tat | cta | cct | ctc | gat | gtc | aat | gcc | ccg | atg | 15129 |
| Lys | Ala | Asn | Leu | Ala | Tyr | Leu | Pro | Leu | Asp | Val | Asn | Ala | Pro | Met | |
| | 5030 | | | | 5035 | | | | | 5040 | | | | | |

| gcc | cgc | gtt | gag | aca | atc | atg | tct | tct | gtg | cca | ggg | agc | aag | ctg | 15174 |
| Ala | Arg | Val | Glu | Thr | Ile | Met | Ser | Ser | Val | Pro | Gly | Ser | Lys | Leu | |
| | 5045 | | | | 5050 | | | | | 5055 | | | | | |

| ctt | ctt | cta | ggt | tct | gat | gtg | cct | gcc | cag | gag | atc | cag | ctg | cag | 15219 |
| Leu | Leu | Leu | Gly | Ser | Asp | Val | Pro | Ala | Gln | Glu | Ile | Gln | Leu | Gln | |
| | 5060 | | | | 5065 | | | | | 5070 | | | | | |

| aat | gtt | gag | ttg | gtg | cgt | atc | gaa | gac | acc | ctc | ggc | cac | gct | gcc | 15264 |
| Asn | Val | Glu | Leu | Val | Arg | Ile | Glu | Asp | Thr | Leu | Gly | His | Ala | Ala | |
| | 5075 | | | | 5080 | | | | | 5085 | | | | | |

| tct | gcc | ggt | aca | gcg | aca | aca | gaa | ccc | tct | cca | acc | agc | cta | gcg | 15309 |
| Ser | Ala | Gly | Thr | Ala | Thr | Thr | Glu | Pro | Ser | Pro | Thr | Ser | Leu | Ala | |
| | 5090 | | | | 5095 | | | | | 5100 | | | | | |

| tac | gtc | ata | ttc | aca | tct | gga | tcg | acg | ggt | aag | cca | aag | ggt | gtg | 15354 |
| Tyr | Val | Ile | Phe | Thr | Ser | Gly | Ser | Thr | Gly | Lys | Pro | Lys | Gly | Val | |
| | 5105 | | | | 5110 | | | | | 5115 | | | | | |

| atg | gtc | gag | cat | cga | agc | gtc | att | cgc | ctc | gtg | aga | aaa | gaa | agc | 15399 |
| Met | Val | Glu | His | Arg | Ser | Val | Ile | Arg | Leu | Val | Arg | Lys | Glu | Ser | |
| | 5120 | | | | 5125 | | | | | 5130 | | | | | |

| aat | tcc | atg | tcc | aag | atg | tct | tcc | aga | gct | cgg | gtt | gcg | cac | ttg | 15444 |
| Asn | Ser | Met | Ser | Lys | Met | Ser | Ser | Arg | Ala | Arg | Val | Ala | His | Leu | |
| | 5135 | | | | 5140 | | | | | 5145 | | | | | |

| act | aac | atc | gcg | ttc | gac | gtc | tca | gca | tgg | gag | gta | tat | gct | acg | 15489 |
| Thr | Asn | Ile | Ala | Phe | Asp | Val | Ser | Ala | Trp | Glu | Val | Tyr | Ala | Thr | |
| | 5150 | | | | 5155 | | | | | 5160 | | | | | |

| ctt | ctc | aac | gga | ggg | act | ctg | gtc | tgt | gtc | gat | tat | ttc | act | tcg | 15534 |
| Leu | Leu | Asn | Gly | Gly | Thr | Leu | Val | Cys | Val | Asp | Tyr | Phe | Thr | Ser | |
| | 5165 | | | | 5170 | | | | | 5175 | | | | | |

```
ttc gat gct aaa gcc ctc ggt ctg ctg ttc gag cgg gag cag att    15579
Phe Asp Ala Lys Ala Leu Gly Leu Leu Phe Glu Arg Glu Gln Ile
    5180            5185                5190 act gcg gct atg atc acg cct acg ttg ctc aaa cag tgc atc act    15624
Thr Ala Ala Met Ile Thr Pro Thr Leu Leu Lys Gln Cys Ile Thr
    5195            5200                5205 att gta cca gaa gct ctc cgc aag ttg tcc gtt ctg tac acc ggt    15669
Ile Val Pro Glu Ala Leu Arg Lys Leu Ser Val Leu Tyr Thr Gly
    5210            5215                5220 ggc gat cgc ttt gat agg cgc gat gct atc gcg aca aaa gcg ctt    15714
Gly Asp Arg Phe Asp Arg Arg Asp Ala Ile Ala Thr Lys Ala Leu
    5225            5230                5235 gtc aag ggc cca gtt tac aat gca tgg ggc cct aca gaa acc aca    15759
Val Lys Gly Pro Val Tyr Asn Ala Trp Gly Pro Thr Glu Thr Thr
    5240            5245                5250 atc gtc agc aca atc tat gag ctt gcc gat gac gat cag ttc acc    15804
Ile Val Ser Thr Ile Tyr Glu Leu Ala Asp Asp Asp Gln Phe Thr
    5255            5260                5265 aat ggt gtg cct atc gga aag gct gtg agc aat tct tgg gcc tac    15849
Asn Gly Val Pro Ile Gly Lys Ala Val Ser Asn Ser Trp Ala Tyr
    5270            5275                5280 gtc atg gat ctc aat caa caa ctc gtt cca gtt ggt gtc atg gga    15894
Val Met Asp Leu Asn Gln Gln Leu Val Pro Val Gly Val Met Gly
    5285            5290                5295 gaa gct gtc gtt att gga gac ggc ctt gcc cga gga tat aca gat    15939
Glu Ala Val Val Ile Gly Asp Gly Leu Ala Arg Gly Tyr Thr Asp
    5300            5305                5310 ccc gcc ctg gat tgc aac cgc ttt gtg cat atc act atc gat ggc    15984
Pro Ala Leu Asp Cys Asn Arg Phe Val His Ile Thr Ile Asp Gly
    5315            5320                5325 aaa cgc gtg cgc gcc tat cga act ggt gac cgc gcg cgt tat cga    16029
Lys Arg Val Arg Ala Tyr Arg Thr Gly Asp Arg Ala Arg Tyr Arg
    5330            5335                5340 cct aaa gat ggc gaa atc gaa ttc ttt ggg cgt atg gac cga cag    16074
Pro Lys Asp Gly Glu Ile Glu Phe Phe Gly Arg Met Asp Arg Gln
    5345            5350                5355 ctc aag att cgt ggt cat cgt att gag ccc gcc gag att gag cat    16119
Leu Lys Ile Arg Gly His Arg Ile Glu Pro Ala Glu Ile Glu His
    5360            5365                5370 gcc atg ctt ggc cac aat gac atc gtt gat gta gcc att gtc act    16164
Ala Met Leu Gly His Asn Asp Ile Val Asp Val Ala Ile Val Thr
    5375            5380                5385 cgc cat caa gat ggt gca ggc tta gaa atg gtt gcc ttt gtt aca    16209
Arg His Gln Asp Gly Ala Gly Leu Glu Met Val Ala Phe Val Thr
    5390            5395                5400 gcc cac act aac aag tct atc gaa cgc aat gaa gcc acc aat caa    16254
Ala His Thr Asn Lys Ser Ile Glu Arg Asn Glu Ala Thr Asn Gln
    5405            5410                5415 gta gct gga tgg ggg gac cac ttc gaa tcg agt aca tat gca gag    16299
Val Ala Gly Trp Gly Asp His Phe Glu Ser Ser Thr Tyr Ala Glu
    5420            5425                5430 ctc gac acc ctt gtc aag tct gat gtt ggc aag gac ttt gtc ggc    16344
Leu Asp Thr Leu Val Lys Ser Asp Val Gly Lys Asp Phe Val Gly
    5435            5440                5445 tgg acg aac atg tat gat ggc ggc gcg atc gat cag gcc gag atg    16389
Trp Thr Asn Met Tyr Asp Gly Gly Ala Ile Asp Gln Ala Glu Met
    5450            5455                5460 cag gaa tgg ctt gac gat acc ata cag acg att gtt gat ggt cag    16434
Gln Glu Trp Leu Asp Asp Thr Ile Gln Thr Ile Val Asp Gly Gln
    5465            5470                5475
```

| | |
|---|---|
| cct gct ggt cat gtc ttt gag atc ggt act ggt acc ggt atg atc<br>Pro Ala Gly His Val Phe Glu Ile Gly Thr Gly Thr Gly Met Ile<br>5480               5485                   5490 | 16479 |
| atg ttt ggt ctc ggg aaa cag gga ctg caa agc tac gtc ggc ctt<br>Met Phe Gly Leu Gly Lys Gln Gly Leu Gln Ser Tyr Val Gly Leu<br>5495               5500                   5505 | 16524 |
| gag ccc tca acc tcg gcc act acg tac gtc aac agg aag atc aag<br>Glu Pro Ser Thr Ser Ala Thr Thr Tyr Val Asn Arg Lys Ile Lys<br>5510               5515                   5520 | 16569 |
| acc gct cca acg gta gct ggc aaa gcc aag gta tat gtc ggc act<br>Thr Ala Pro Thr Val Ala Gly Lys Ala Lys Val Tyr Val Gly Thr<br>5525               5530                   5535 | 16614 |
| gca atg gag gcg gct caa ctc aat gga ctc cat ccg gaa gtt gtc<br>Ala Met Glu Ala Ala Gln Leu Asn Gly Leu His Pro Glu Val Val<br>5540               5545                   5550 | 16659 |
| gtc atc aac tct gtg gct caa tac ttc cct acg cca gaa tat ctc<br>Val Ile Asn Ser Val Ala Gln Tyr Phe Pro Thr Pro Glu Tyr Leu<br>5555               5560                   5565 | 16704 |
| ctc gag gtc gtc ggt att ctc act cag atg cca ggt gtc aaa cgc<br>Leu Glu Val Val Gly Ile Leu Thr Gln Met Pro Gly Val Lys Arg<br>5570               5575                   5580 | 16749 |
| ttg ttc ttt gga gac ata cga tcg tat gct act aac agg aaa ttc<br>Leu Phe Phe Gly Asp Ile Arg Ser Tyr Ala Thr Asn Arg Lys Phe<br>5585               5590                   5595 | 16794 |
| ctt gca gcc aga gcc ctt cat atg cta ggg tcc aac gcg aag aaa<br>Leu Ala Ala Arg Ala Leu His Met Leu Gly Ser Asn Ala Lys Lys<br>5600               5605                   5610 | 16839 |
| cat gac att cgc cgg aaa atg gct gag ttg gat gaa ttc gaa gaa<br>His Asp Ile Arg Arg Lys Met Ala Glu Leu Asp Glu Phe Glu Glu<br>5615               5620                   5625 | 16884 |
| gag ttg att gtc gat cct tct ttc ttc act ggt ctg gtc agc cga<br>Glu Leu Ile Val Asp Pro Ser Phe Phe Thr Gly Leu Val Ser Arg<br>5630               5635                   5640 | 16929 |
| ctg cca ggc cag gtc aag cat gtg gag att ctt cca aaa caa atg<br>Leu Pro Gly Gln Val Lys His Val Glu Ile Leu Pro Lys Gln Met<br>5645               5650                   5655 | 16974 |
| atc gcc aca aat gag ctc agc gcg tat cgt tat gca gcc gtt gtt<br>Ile Ala Thr Asn Glu Leu Ser Ala Tyr Arg Tyr Ala Ala Val Val<br>5660               5665                   5670 | 17019 |
| cat cta gct ctt ccc gaa gag cag cac ata gcg aaa atc gaa aag<br>His Leu Ala Leu Pro Glu Glu Gln His Ile Ala Lys Ile Glu Lys<br>5675               5680                   5685 | 17064 |
| ggc gcc tgg gtc gac ttc aca gcc acc aag atg gat cga agc gct<br>Gly Ala Trp Val Asp Phe Thr Ala Thr Lys Met Asp Arg Ser Ala<br>5690               5695                   5700 | 17109 |
| ctt gtt cat cat ctg cag agc tcg tca aac gct gaa att gta gct<br>Leu Val His His Leu Gln Ser Ser Ser Asn Ala Glu Ile Val Ala<br>5705               5710                   5715 | 17154 |
| atc agt aac att cca ttc agc aaa act aat ttc gat tgt cat ctt<br>Ile Ser Asn Ile Pro Phe Ser Lys Thr Asn Phe Asp Cys His Leu<br>5720               5725                   5730 | 17199 |
| ctc gca tct ctg gat gag gac gaa gaa cac tcg ctt gac gga tcc<br>Leu Ala Ser Leu Asp Glu Asp Glu Glu His Ser Leu Asp Gly Ser<br>5735               5740                   5745 | 17244 |
| gcc tgg atc aaa act att cat tcc agc gcc gaa cag tgt cca tcg<br>Ala Trp Ile Lys Thr Ile His Ser Ser Ala Glu Gln Cys Pro Ser<br>5750               5755                   5760 | 17289 |
| cta tcc gca acc gat ctc gtc gaa gtt gct aaa gag gtg ggc ttc<br>Leu Ser Ala Thr Asp Leu Val Glu Val Ala Lys Glu Val Gly Phe<br>5765               5770                   5775 | 17334 |

| | | | | | | | | | | | |
|---|---|---|---|---|---|---|---|---|---|---|---|
| cgt | gtc | gag | ctc | agc | tgg | gct | cgg | caa | aag | tct | caa | aac | ggt | gca | 17379 |
| Arg | Val | Glu | Leu | Ser | Trp | Ala | Arg | Gln | Lys | Ser | Gln | Asn | Gly | Ala | |
| | 5780 | | | | 5785 | | | | | 5790 | | | | | |
| ctt | gac | gct | atc | ttc | cac | caa | tac | caa | tct | ccc | aaa | gaa | ggt | agc | 17424 |
| Leu | Asp | Ala | Ile | Phe | His | Gln | Tyr | Gln | Ser | Pro | Lys | Glu | Gly | Ser | |
| | 5795 | | | | 5800 | | | | | 5805 | | | | | |
| cgt | gtt | cta | ata | cag | ttc | ccg | act | gac | gac | cag | ggt | cga | tcg | atg | 17469 |
| Arg | Val | Leu | Ile | Gln | Phe | Pro | Thr | Asp | Asp | Gln | Gly | Arg | Ser | Met | |
| | 5810 | | | | 5815 | | | | | 5820 | | | | | |
| gag | tct | ctt | acg | aac | cga | ccg | tta | cag | cga | gtt | cag | agc | cgc | cgg | 17514 |
| Glu | Ser | Leu | Thr | Asn | Arg | Pro | Leu | Gln | Arg | Val | Gln | Ser | Arg | Arg | |
| | 5825 | | | | 5830 | | | | | 5835 | | | | | |
| atc | gaa | aca | cag | att | cgt | gag | cga | cta | cag | gct | gtg | cta | cca | tca | 17559 |
| Ile | Glu | Thr | Gln | Ile | Arg | Glu | Arg | Leu | Gln | Ala | Val | Leu | Pro | Ser | |
| | 5840 | | | | 5845 | | | | | 5850 | | | | | |
| tac | atg | att | cca | gct | cgg | atc | gtg | gtg | cta | aat | gag | atg | cca | gtc | 17604 |
| Tyr | Met | Ile | Pro | Ala | Arg | Ile | Val | Val | Leu | Asn | Glu | Met | Pro | Val | |
| | 5855 | | | | 5860 | | | | | 5865 | | | | | |
| aat | gcc | aac | ggc | aaa | gtc | gac | cgc | aag | gag | ctg | acg | cgc | aga | gcg | 17649 |
| Asn | Ala | Asn | Gly | Lys | Val | Asp | Arg | Lys | Glu | Leu | Thr | Arg | Arg | Ala | |
| | 5870 | | | | 5875 | | | | | 5880 | | | | | |
| aag | gtg | gtc | cca | aga | atc | gaa | aca | gct | gcg | gag | cgt | att | caa | ccc | 17694 |
| Lys | Val | Val | Pro | Arg | Ile | Glu | Thr | Ala | Ala | Glu | Arg | Ile | Gln | Pro | |
| | 5885 | | | | 5890 | | | | | 5895 | | | | | |
| cga | aat | gaa | gtc | gaa | gcg | gtt | ctg | tgc | gag | gaa | ttc | agt | gaa | gtc | 17739 |
| Arg | Asn | Glu | Val | Glu | Ala | Val | Leu | Cys | Glu | Glu | Phe | Ser | Glu | Val | |
| | 5900 | | | | 5905 | | | | | 5910 | | | | | |
| ctc | ggc | gtc | gaa | gtt | ggt | gtc | acg | gac | aac | ttc | ttc | gat | ctt | ggt | 17784 |
| Leu | Gly | Val | Glu | Val | Gly | Val | Thr | Asp | Asn | Phe | Phe | Asp | Leu | Gly | |
| | 5915 | | | | 5920 | | | | | 5925 | | | | | |
| gga | cac | tcg | ctc | atg | gct | acg | aag | ctg | gct | gca | cgt | act | ggg | cgc | 17829 |
| Gly | His | Ser | Leu | Met | Ala | Thr | Lys | Leu | Ala | Ala | Arg | Thr | Gly | Arg | |
| | 5930 | | | | 5935 | | | | | 5940 | | | | | |
| cga | ctt | gat | gca | aag | gtg | tct | gtc | aaa | gac | gtt | ttc | gac | cac | cca | 17874 |
| Arg | Leu | Asp | Ala | Lys | Val | Ser | Val | Lys | Asp | Val | Phe | Asp | His | Pro | |
| | 5945 | | | | 5950 | | | | | 5955 | | | | | |
| gta | cta | gcg | gat | ctt | gcc | gct | gct | att | cag | cga | ggc | tcg | act | ccc | 17919 |
| Val | Leu | Ala | Asp | Leu | Ala | Ala | Ala | Ile | Gln | Arg | Gly | Ser | Thr | Pro | |
| | 5960 | | | | 5965 | | | | | 5970 | | | | | |
| cac | tcg | gcg | atc | gtt | act | act | gag | tac | tct | gga | cct | gta | gag | cag | 17964 |
| His | Ser | Ala | Ile | Val | Thr | Thr | Glu | Tyr | Ser | Gly | Pro | Val | Glu | Gln | |
| | 5975 | | | | 5980 | | | | | 5985 | | | | | |
| tca | tac | gcc | cag | ggc | cgc | ctt | tgg | ttc | ctt | gaa | caa | ctc | aat | ttc | 18009 |
| Ser | Tyr | Ala | Gln | Gly | Arg | Leu | Trp | Phe | Leu | Glu | Gln | Leu | Asn | Phe | |
| | 5990 | | | | 5995 | | | | | 6000 | | | | | |
| aag | gca | acg | tgg | tat | ctc | cta | ccg | ctt | gcg | gtg | cgg | att | cgt | ggg | 18054 |
| Lys | Ala | Thr | Trp | Tyr | Leu | Leu | Pro | Leu | Ala | Val | Arg | Ile | Arg | Gly | |
| | 6005 | | | | 6010 | | | | | 6015 | | | | | |
| cca | ctc | aat | atc | aag | gcc | ctt | acc | acg | gcg | tta | cat | gcg | cta | gaa | 18099 |
| Pro | Leu | Asn | Ile | Lys | Ala | Leu | Thr | Thr | Ala | Leu | His | Ala | Leu | Glu | |
| | 6020 | | | | 6025 | | | | | 6030 | | | | | |
| cag | cga | cat | gag | act | tta | aga | aca | aca | ttc | att | gag | cgg | gat | ggt | 18144 |
| Gln | Arg | His | Glu | Thr | Leu | Arg | Thr | Thr | Phe | Ile | Glu | Arg | Asp | Gly | |
| | 6035 | | | | 6040 | | | | | 6045 | | | | | |
| gtg | ggc | aag | cag | gcc | gtt | cag | cca | ttt | cag | ccg | aag | gaa | ctc | gaa | 18189 |
| Val | Gly | Lys | Gln | Ala | Val | Gln | Pro | Phe | Gln | Pro | Lys | Glu | Leu | Glu | |
| | 6050 | | | | 6055 | | | | | 6060 | | | | | |
| atc | gtc | gac | ata | gcg | gcc | gac | cac | cag | ggc | gac | tac | ctt | aaa | gtg | 18234 |
| Ile | Val | Asp | Ile | Ala | Ala | Asp | His | Gln | Gly | Asp | Tyr | Leu | Lys | Val | |
| | 6065 | | | | 6070 | | | | | 6075 | | | | | |

| | | | | | | | | | | | |
|---|---|---|---|---|---|---|---|---|---|---|---|
| cta | cgt | gac | gag | cag | act | acc | atg | ttc | aat | cta | gca | act | cag | cct | 18279 |
| Leu | Arg | Asp | Glu | Gln | Thr | Thr | Met | Phe | Asn | Leu | Ala | Thr | Gln | Pro | |
| 6080 | | | | 6085 | | | | | 6090 | | | | | | |

| ggt | tgg | agg | gtg | act | tta | cac | aga | gtg | gat | caa | aac | acg | cat | aat | 18324 |
| Gly | Trp | Arg | Val | Thr | Leu | His | Arg | Val | Asp | Gln | Asn | Thr | His | Asn | |
| 6095 | | | | 6100 | | | | | 6105 | | | | | | |

| ctt | tcc | atc | gtc | atg | cac | cac | atc | att | tca | gac | ggc | tgg | tca | gtc | 18369 |
| Leu | Ser | Ile | Val | Met | His | His | Ile | Ile | Ser | Asp | Gly | Trp | Ser | Val | |
| 6110 | | | | 6115 | | | | | 6120 | | | | | | |

| gat | gtt | ctg | cgc | cac | gag | ctg | agg | cag | ttc | tat | gct | gct | gcc | ctc | 18414 |
| Asp | Val | Leu | Arg | His | Glu | Leu | Arg | Gln | Phe | Tyr | Ala | Ala | Ala | Leu | |
| 6125 | | | | 6130 | | | | | 6135 | | | | | | |

| cgg | ggt | cag | gat | ccc | ctc | gcg | cat | atc | agc | ccg | ctc | cca | att | caa | 18459 |
| Arg | Gly | Gln | Asp | Pro | Leu | Ala | His | Ile | Ser | Pro | Leu | Pro | Ile | Gln | |
| 6140 | | | | 6145 | | | | | 6150 | | | | | | |

| tac | cgc | gac | ttc | tcg | ctc | tgg | caa | aag | cag | cca | gac | cag | atc | atc | 18504 |
| Tyr | Arg | Asp | Phe | Ser | Leu | Trp | Gln | Lys | Gln | Pro | Asp | Gln | Ile | Ile | |
| 6155 | | | | 6160 | | | | | 6165 | | | | | | |

| gaa | cat | gca | aaa | caa | ctt | gag | tac | tgg | acc | aag | caa | ctg | gca | gac | 18549 |
| Glu | His | Ala | Lys | Gln | Leu | Glu | Tyr | Trp | Thr | Lys | Gln | Leu | Ala | Asp | |
| 6170 | | | | 6175 | | | | | 6180 | | | | | | |

| agc | tcc | cca | gct | gag | ctc | cca | act | gat | tta | ccc | cgc | ccg | gcc | gta | 18594 |
| Ser | Ser | Pro | Ala | Glu | Leu | Pro | Thr | Asp | Leu | Pro | Arg | Pro | Ala | Val | |
| 6185 | | | | 6190 | | | | | 6195 | | | | | | |

| ctg | tca | ggg | aaa | gct | ggc | gaa | gtg | gcc | ctt | tcc | gtc | aag | ggc | ccg | 18639 |
| Leu | Ser | Gly | Lys | Ala | Gly | Glu | Val | Ala | Leu | Ser | Val | Lys | Gly | Pro | |
| 6200 | | | | 6205 | | | | | 6210 | | | | | | |

| cta | tat | gag | cgt | ctg | caa | gct | ttc | tgc | aag | act | cat | cag | aca | act | 18684 |
| Leu | Tyr | Glu | Arg | Leu | Gln | Ala | Phe | Cys | Lys | Thr | His | Gln | Thr | Thr | |
| 6215 | | | | 6220 | | | | | 6225 | | | | | | |

| gcc | ttc | gcc | aca | ctc | cta | gca | gcc | ttc | cgt | gca | aca | cat | cat | cgc | 18729 |
| Ala | Phe | Ala | Thr | Leu | Leu | Ala | Ala | Phe | Arg | Ala | Thr | His | His | Arg | |
| 6230 | | | | 6235 | | | | | 6240 | | | | | | |

| ctt | aca | gga | gcc | gaa | gac | gct | acc | atc | ggc | aca | cct | atc | gcc | aac | 18774 |
| Leu | Thr | Gly | Ala | Glu | Asp | Ala | Thr | Ile | Gly | Thr | Pro | Ile | Ala | Asn | |
| 6245 | | | | 6250 | | | | | 6255 | | | | | | |

| cgc | aac | agg | ccc | gaa | tta | gag | aac | ctg | att | ggc | ttc | ttc | gtg | aat | 18819 |
| Arg | Asn | Arg | Pro | Glu | Leu | Glu | Asn | Leu | Ile | Gly | Phe | Phe | Val | Asn | |
| 6260 | | | | 6265 | | | | | 6270 | | | | | | |

| gct | cag | tgt | atg | cgc | att | act | atc | gat | gga | gac | gag | act | ttc | gag | 18864 |
| Ala | Gln | Cys | Met | Arg | Ile | Thr | Ile | Asp | Gly | Asp | Glu | Thr | Phe | Glu | |
| 6275 | | | | 6280 | | | | | 6285 | | | | | | |

| agt | ctt | ata | cgt | cag | gtc | cga | gcc | act | gcg | acg | gct | gcc | atc | gca | 18909 |
| Ser | Leu | Ile | Arg | Gln | Val | Arg | Ala | Thr | Ala | Thr | Ala | Ala | Ile | Ala | |
| 6290 | | | | 6295 | | | | | 6300 | | | | | | |

| aat | caa | gat | gtc | ccc | ttt | gaa | cgt | atc | gtg | tct | acc | atg | caa | tct | 18954 |
| Asn | Gln | Asp | Val | Pro | Phe | Glu | Arg | Ile | Val | Ser | Thr | Met | Gln | Ser | |
| 6305 | | | | 6310 | | | | | 6315 | | | | | | |

| acc | tca | cga | gac | acg | tca | agg | aat | ccg | ctt | gta | cag | ctc | atg | ttc | 18999 |
| Thr | Ser | Arg | Asp | Thr | Ser | Arg | Asn | Pro | Leu | Val | Gln | Leu | Met | Phe | |
| 6320 | | | | 6325 | | | | | 6330 | | | | | | |

| gcc | ctc | cac | tct | caa | cag | gac | ctc | gga | aaa | atc | caa | cta | gaa | ggc | 19044 |
| Ala | Leu | His | Ser | Gln | Gln | Asp | Leu | Gly | Lys | Ile | Gln | Leu | Glu | Gly | |
| 6335 | | | | 6340 | | | | | 6345 | | | | | | |

| tgc | gaa | acg | gag | cct | att | ccc | cga | gct | gta | cgc | act | cgc | ttc | gat | 19089 |
| Cys | Glu | Thr | Glu | Pro | Ile | Pro | Arg | Ala | Val | Arg | Thr | Arg | Phe | Asp | |
| 6350 | | | | 6355 | | | | | 6360 | | | | | | |

| ctc | gag | ttc | cat | ctc | tat | caa | gag | caa | ggg | agc | cta | ggc | ggc | att | 19134 |
| Leu | Glu | Phe | His | Leu | Tyr | Gln | Glu | Gln | Gly | Ser | Leu | Gly | Gly | Ile | |
| 6365 | | | | 6370 | | | | | 6375 | | | | | | |

| | | | | | | | | | | |
|---|---|---|---|---|---|---|---|---|---|---|
| gtg | tac | ttt | gcc | acc | gat | ttg | ttc | gag | cct | gag agc att gag ggg | 19179 |
| Val | Tyr | Phe | Ala | Thr | Asp | Leu | Phe | Glu | Pro | Glu Ser Ile Glu Gly |
| | 6380 | | | | 6385 | | | | 6390 | | atg gtt tcc att ttt aaa gaa atc ctc gct cga gct ctt gac caa  19224
Met Val Ser Ile Phe Lys Glu Ile Leu Ala Arg Ala Leu Asp Gln
        6395                6400                6405 ccc caa acc cca ctg gcg ctt cta ccg ctc acc gat ggg ctg gct  19269
Pro Gln Thr Pro Leu Ala Leu Leu Pro Leu Thr Asp Gly Leu Ala
    6410                6415                6420 gaa ctt cgc agg agg ggg ctg ctt gag att gaa agg ccc agc tat  19314
Glu Leu Arg Arg Arg Gly Leu Leu Glu Ile Glu Arg Pro Ser Tyr
    6425                6430                6435 cct cgc gag tcg agc gtt gtt gac gtc ttc tgt agc cag gta gcg  19359
Pro Arg Glu Ser Ser Val Val Asp Val Phe Cys Ser Gln Val Ala
    6440                6445                6450 gct tct ccc aac gca acc gct gtg aag gac tcg att tca cag ctc  19404
Ala Ser Pro Asn Ala Thr Ala Val Lys Asp Ser Ile Ser Gln Leu
    6455                6460                6465 act tac gct cag cta aat gag caa tct gac aag gtc gct gct tgg  19449
Thr Tyr Ala Gln Leu Asn Glu Gln Ser Asp Lys Val Ala Ala Trp
    6470                6475                6480 cta cac cag tgc aac ctt cca act gaa act ttg gtc gct gtg cta  19494
Leu His Gln Cys Asn Leu Pro Thr Glu Thr Leu Val Ala Val Leu
    6485                6490                6495 gcg cct cga tct tgc caa aca gtt gtg gcc ttc ttg ggt att ctg  19539
Ala Pro Arg Ser Cys Gln Thr Val Val Ala Phe Leu Gly Ile Leu
    6500                6505                6510 aag gcc aac cta gca tat ctt ccc cta gac gtc aat gtt ccg gca  19584
Lys Ala Asn Leu Ala Tyr Leu Pro Leu Asp Val Asn Val Pro Ala
    6515                6520                6525 gct cgc att gag gca att ctc tca gaa gtc tct ggc cac ata ctt  19629
Ala Arg Ile Glu Ala Ile Leu Ser Glu Val Ser Gly His Ile Leu
    6530                6535                6540 gtc tta ctt gga tct cat gtt tct gct ccc aag att gag ctc gct  19674
Val Leu Leu Gly Ser His Val Ser Ala Pro Lys Ile Glu Leu Ala
    6545                6550                6555 gat gtc gaa ttc gtc aaa att gac aac aca gtc gag cac aat ttg  19719
Asp Val Glu Phe Val Lys Ile Asp Asn Thr Val Glu His Asn Leu
    6560                6565                6570 ccg ggc cgc att gga tct gct cca tct gcc acg agc ctc gcc tat  19764
Pro Gly Arg Ile Gly Ser Ala Pro Ser Ala Thr Ser Leu Ala Tyr
    6575                6580                6585 gtt att ttc aca tct gga tcg act ggc aag ccc aaa ggt gtt aag  19809
Val Ile Phe Thr Ser Gly Ser Thr Gly Lys Pro Lys Gly Val Lys
    6590                6595                6600 gta gag cac cgc ggt att gtc cgc ctc gtt aaa gag agc aat gta  19854
Val Glu His Arg Gly Ile Val Arg Leu Val Lys Glu Ser Asn Val
    6605                6610                6615 gta gca aaa atg cca caa gct gcg cgc att gct cac ttg tca aac  19899
Val Ala Lys Met Pro Gln Ala Ala Arg Ile Ala His Leu Ser Asn
    6620                6625                6630 att gcc ttt gac gcg gct acg tgg gaa tta tat gct gcg ttg ctc  19944
Ile Ala Phe Asp Ala Ala Thr Trp Glu Leu Tyr Ala Ala Leu Leu
    6635                6640                6645 aac ggc ggc acc ctc gtc tgt atc aac tat tta acc acg ctg gat  19989
Asn Gly Gly Thr Leu Val Cys Ile Asn Tyr Leu Thr Thr Leu Asp
    6650                6655                6660 agt aaa gca ctc gag gcc gtg ttt gag cag gaa aag atc caa gcg  20034
Ser Lys Ala Leu Glu Ala Val Phe Glu Gln Glu Lys Ile Gln Ala
    6665                6670                6675

| | | | | | | | | | | | | |
|---|---|---|---|---|---|---|---|---|---|---|---|---|
| gct | atg | ctt | cca | cca | gca | ctg | ctc | aaa | cag | tat | ttg | gtt aac att | 20079 |
| Ala | Met | Leu | Pro | Pro | Ala | Leu | Leu | Lys | Gln | Tyr | Leu | Val Asn Ile | |
| | 6680 | | | | 6685 | | | | 6690 | | | | |

| ccc | gca | gct | atc | ggt | gca | cta | gaa | gtg | gtc | ctt | gtc | gct ggt gac | 20124 |
| Pro | Ala | Ala | Ile | Gly | Ala | Leu | Glu | Val | Val | Leu | Val | Ala Gly Asp | |
| | 6695 | | | | 6700 | | | | 6705 | | | | |

| cgt | ttc | gat | cga | cgc | gat | gct | gca | gcc | acg | cag | gct | ctt gtt gga | 20169 |
| Arg | Phe | Asp | Arg | Arg | Asp | Ala | Ala | Ala | Thr | Gln | Ala | Leu Val Gly | |
| | 6710 | | | | 6715 | | | | 6720 | | | | |

| gca | ggc | gtg | tat | aac | gcc | tat | gga | ccg | acg | gag | aat | aca aca ctc | 20214 |
| Ala | Gly | Val | Tyr | Asn | Ala | Tyr | Gly | Pro | Thr | Glu | Asn | Thr Thr Leu | |
| | 6725 | | | | 6730 | | | | 6735 | | | | |

| agc | act | atc | tac | aat | gtc | gtt | cag | ggc | gat | gcc | aat | gtg aat ggc | 20259 |
| Ser | Thr | Ile | Tyr | Asn | Val | Val | Gln | Gly | Asp | Ala | Asn | Val Asn Gly | |
| | 6740 | | | | 6745 | | | | 6750 | | | | |

| gtc | ccg | att | gga | cgc | cct | gtc | agc | aac | tct | ggc | gcc | tac atc atg | 20304 |
| Val | Pro | Ile | Gly | Arg | Pro | Val | Ser | Asn | Ser | Gly | Ala | Tyr Ile Met | |
| | 6755 | | | | 6760 | | | | 6765 | | | | |

| aat | atg | aat | cag | gaa | ctc | gtt | cct | att | ggc | gtc | ata | ggc gag ctg | 20349 |
| Asn | Met | Asn | Gln | Glu | Leu | Val | Pro | Ile | Gly | Val | Ile | Gly Glu Leu | |
| | 6770 | | | | 6775 | | | | 6780 | | | | |

| gtc | gta | gta | gga | gac | ggt | gtc | gcc | cga | gga | tac | acc | gac cca gcc | 20394 |
| Val | Val | Val | Gly | Asp | Gly | Val | Ala | Arg | Gly | Tyr | Thr | Asp Pro Ala | |
| | 6785 | | | | 6790 | | | | 6795 | | | | |

| ttg | gac | gtc | aac | cgc | ttc | gtc | aac | gtc | act | att | gaa | ggc caa act | 20439 |
| Leu | Asp | Val | Asn | Arg | Phe | Val | Asn | Val | Thr | Ile | Glu | Gly Gln Thr | |
| | 6800 | | | | 6805 | | | | 6810 | | | | |

| atg | agg | gct | tat | agg | act | ggc | gat | cgt | gcc | cgc | tat | agg ccc aaa | 20484 |
| Met | Arg | Ala | Tyr | Arg | Thr | Gly | Asp | Arg | Ala | Arg | Tyr | Arg Pro Lys | |
| | 6815 | | | | 6820 | | | | 6825 | | | | |

| gac | gca | cag | att | gaa | ttc | ttt | ggc | cga | atg | gat | caa | cag atc aag | 20529 |
| Asp | Ala | Gln | Ile | Glu | Phe | Phe | Gly | Arg | Met | Asp | Gln | Gln Ile Lys | |
| | 6830 | | | | 6835 | | | | 6840 | | | | |

| att | cga | ggc | cat | cgt | att | gag | cca | gct | gag | gtc | gag | cat gcg ttg | 20574 |
| Ile | Arg | Gly | His | Arg | Ile | Glu | Pro | Ala | Glu | Val | Glu | His Ala Leu | |
| | 6845 | | | | 6850 | | | | 6855 | | | | |

| ctc | aac | aat | gac | ttg | ctt | cag | gac | gct | gca | gtc | att | atc cga aag | 20619 |
| Leu | Asn | Asn | Asp | Leu | Leu | Gln | Asp | Ala | Ala | Val | Ile | Ile Arg Lys | |
| | 6860 | | | | 6865 | | | | 6870 | | | | |

| caa | caa | aat | gat | gag | ctg | gag | atg | gtt | gct | ttt | gta | gaa gca aac | 20664 |
| Gln | Gln | Asn | Asp | Glu | Leu | Glu | Met | Val | Ala | Phe | Val | Glu Ala Asn | |
| | 6875 | | | | 6880 | | | | 6885 | | | | |

| agc | aat | aag | tcg | atc | gaa | caa | gag | gcg | agc | aac | caa | gta gaa gac | 20709 |
| Ser | Asn | Lys | Ser | Ile | Glu | Gln | Glu | Ala | Ser | Asn | Gln | Val Glu Asp | |
| | 6890 | | | | 6895 | | | | 6900 | | | | |

| tgg | ggc | gct | caa | ttc | gag | agc | aac | gtc | tac | gcc | gag | atc gag gca | 20754 |
| Trp | Gly | Ala | Gln | Phe | Glu | Ser | Asn | Val | Tyr | Ala | Glu | Ile Glu Ala | |
| | 6905 | | | | 6910 | | | | 6915 | | | | |

| atc | gat | gcc | tct | gct | gtt | ggt | aac | gac | ttc | atg | ggt | tgg act tcc | 20799 |
| Ile | Asp | Ala | Ser | Ala | Val | Gly | Asn | Asp | Phe | Met | Gly | Trp Thr Ser | |
| | 6920 | | | | 6925 | | | | 6930 | | | | |

| atg | tac | gac | ggc | agc | gcg | atc | gac | aag | gct | gag | atg | cag gaa tgg | 20844 |
| Met | Tyr | Asp | Gly | Ser | Ala | Ile | Asp | Lys | Ala | Glu | Met | Gln Glu Trp | |
| | 6935 | | | | 6940 | | | | 6945 | | | | |

| ctc | gat | gat | act | atg | cag | aca | ata | ctt | gat | ggt | cga | cca gcc ggc | 20889 |
| Leu | Asp | Asp | Thr | Met | Gln | Thr | Ile | Leu | Asp | Gly | Arg | Pro Ala Gly | |
| | 6950 | | | | 6955 | | | | 6960 | | | | |

| cgc | gtt | ctc | gaa | atc | ggc | act | ggc | acg | ggt | atg | atc | ctc ttc aat | 20934 |
| Arg | Val | Leu | Glu | Ile | Gly | Thr | Gly | Thr | Gly | Met | Ile | Leu Phe Asn | |
| | 6965 | | | | 6970 | | | | 6975 | | | | |

| | | | | | | | | | | | |
|---|---|---|---|---|---|---|---|---|---|---|---|
| ctt | ggt | gaa | ggg | tta | cag | agc | tat | gtc | ggt | ctc | gaa | cca | tct | acc | 20979 |
| Leu | Gly | Glu | Gly | Leu | Gln | Ser | Tyr | Val | Gly | Leu | Glu | Pro | Ser | Thr | |
| | 6980 | | | | 6985 | | | | | 6990 | | | | | |

| tcg | gcg | gct | gcg | ttc | gtc | aat | cgc | agg | att | cag | aca | ctt | cca | gct | 21024 |
| Ser | Ala | Ala | Ala | Phe | Val | Asn | Arg | Arg | Ile | Gln | Thr | Leu | Pro | Ala | |
| 6995 | | | | | 7000 | | | | | 7005 | | | | | |

| ttc | gct | ggt | aaa | gct | gaa | gtt | cac | gtg | ggt | aca | gcg | aca | gat | ata | 21069 |
| Phe | Ala | Gly | Lys | Ala | Glu | Val | His | Val | Gly | Thr | Ala | Thr | Asp | Ile | |
| 7010 | | | | | 7015 | | | | | 7020 | | | | | |

| agc | caa | ctt | caa | gat | ctc | cgc | ccg | gaa | gta | gtg | gtt | atc | aac | tcg | 21114 |
| Ser | Gln | Leu | Gln | Asp | Leu | Arg | Pro | Glu | Val | Val | Val | Ile | Asn | Ser | |
| 7025 | | | | | 7030 | | | | | 7035 | | | | | |

| gtg | gct | cag | tac | ttc | cca | tcg | cct | gag | tac | ttg | tct | aag | gtt | ttg | 21159 |
| Val | Ala | Gln | Tyr | Phe | Pro | Ser | Pro | Glu | Tyr | Leu | Ser | Lys | Val | Leu | |
| 7040 | | | | | 7045 | | | | | 7050 | | | | | |

| tac | gca | cta | gcc | caa | att | cct | ggc | gtc | aag | cgt | ttg | ttc | ttt | gga | 21204 |
| Tyr | Ala | Leu | Ala | Gln | Ile | Pro | Gly | Val | Lys | Arg | Leu | Phe | Phe | Gly | |
| 7055 | | | | | 7060 | | | | | 7065 | | | | | |

| gac | atg | cga | tct | tac | gcc | atc | aac | gac | cag | ttc | ctt | gca | gct | cgc | 21249 |
| Asp | Met | Arg | Ser | Tyr | Ala | Ile | Asn | Asp | Gln | Phe | Leu | Ala | Ala | Arg | |
| 7070 | | | | | 7075 | | | | | 7080 | | | | | |

| gcc | tta | cac | aac | ata | ggt | agc | aag | gct | act | aag | agc | gcc | att | cga | 21294 |
| Ala | Leu | His | Asn | Ile | Gly | Ser | Lys | Ala | Thr | Lys | Ser | Ala | Ile | Arg | |
| 7085 | | | | | 7090 | | | | | 7095 | | | | | |

| agc | aag | atg | gtc | gat | ctg | gaa | aac | tct | gag | gaa | gaa | ttg | ctc | gtc | 21339 |
| Ser | Lys | Met | Val | Asp | Leu | Glu | Asn | Ser | Glu | Glu | Glu | Leu | Leu | Val | |
| 7100 | | | | | 7105 | | | | | 7110 | | | | | |

| gac | cca | acc | ttc | ttc | acc | aac | cta | gcg | acc | gag | ctt | cca | gag | gtt | 21384 |
| Asp | Pro | Thr | Phe | Phe | Thr | Asn | Leu | Ala | Thr | Glu | Leu | Pro | Glu | Val | |
| 7115 | | | | | 7120 | | | | | 7125 | | | | | |

| gag | cat | gtt | gag | att | ctg | cca | aaa | cgc | atg | cag | gct | acc | aac | gaa | 21429 |
| Glu | His | Val | Glu | Ile | Leu | Pro | Lys | Arg | Met | Gln | Ala | Thr | Asn | Glu | |
| 7130 | | | | | 7135 | | | | | 7140 | | | | | |

| ctt | agc | gca | tac | cga | tac | gct | gcg | gtt | gtt | cat | att | cga | gac | cca | 21474 |
| Leu | Ser | Ala | Tyr | Arg | Tyr | Ala | Ala | Val | Val | His | Ile | Arg | Asp | Pro | |
| 7145 | | | | | 7150 | | | | | 7155 | | | | | |

| gca | agg | cag | gcg | cag | aca | gtg | cac | acc | att | gat | cct | acc | gct | tgg | 21519 |
| Ala | Arg | Gln | Ala | Gln | Thr | Val | His | Thr | Ile | Asp | Pro | Thr | Ala | Trp | |
| 7160 | | | | | 7165 | | | | | 7170 | | | | | |

| atc | gat | ttt | agc | gca | tct | caa | atg | aat | cgt | act | gct | ctt | gcc | aac | 21564 |
| Ile | Asp | Phe | Ser | Ala | Ser | Gln | Met | Asn | Arg | Thr | Ala | Leu | Ala | Asn | |
| 7175 | | | | | 7180 | | | | | 7185 | | | | | |

| ctc | ttg | caa | aac | tca | gca | gat | gct | gca | gct | atc | gct | gtc | agc | aac | 21609 |
| Leu | Leu | Gln | Asn | Ser | Ala | Asp | Ala | Ala | Ala | Ile | Ala | Val | Ser | Asn | |
| 7190 | | | | | 7195 | | | | | 7200 | | | | | |

| atc | ccg | tac | agc | aag | acg | atc | ttg | gcg | cgc | cac | att | gtt | cag | tcg | 21654 |
| Ile | Pro | Tyr | Ser | Lys | Thr | Ile | Leu | Ala | Arg | His | Ile | Val | Gln | Ser | |
| 7205 | | | | | 7210 | | | | | 7215 | | | | | |

| ctt | gat | gac | gat | ctc | aca | gac | agc | gat | gat | cca | caa | gat | gag | ctt | 21699 |
| Leu | Asp | Asp | Asp | Leu | Thr | Asp | Ser | Asp | Asp | Pro | Gln | Asp | Glu | Leu | |
| 7220 | | | | | 7225 | | | | | 7230 | | | | | |

| gaa | gga | gct | gct | tgg | atg | tct | gct | atc | cgg | tcc | aat | atc | aaa | acc | 21744 |
| Glu | Gly | Ala | Ala | Trp | Met | Ser | Ala | Ile | Arg | Ser | Asn | Ile | Lys | Thr | |
| 7235 | | | | | 7240 | | | | | 7245 | | | | | |

| tgt | gca | tcg | ctg | tcc | gcc | ttc | gac | ctt | gcg | caa | ctt | gcc | cag | gag | 21789 |
| Cys | Ala | Ser | Leu | Ser | Ala | Phe | Asp | Leu | Ala | Gln | Leu | Ala | Gln | Glu | |
| 7250 | | | | | 7255 | | | | | 7260 | | | | | |

| aaa | ggc | ttc | cgt | gtg | gag | ctt | agt | tgg | gca | aga | caa | cga | acc | cat | 21834 |
| Lys | Gly | Phe | Arg | Val | Glu | Leu | Ser | Trp | Ala | Arg | Gln | Arg | Thr | His | |
| 7265 | | | | | 7270 | | | | | 7275 | | | | | |

| | | | | | | | | | | |
|---|---|---|---|---|---|---|---|---|---|---|
| cat | gga | gct | tta | gac | gct | gtt | ttc | cat | cat | tac | aag | tct | aac | cag | 21879 |
| His | Gly | Ala | Leu | Asp | Ala | Val | Phe | His | His | Tyr | Lys | Ser | Asn | Gln | |
| | 7280 | | | | 7285 | | | | 7290 | | | | | | |

| gat | ggt | ggt | cgt | gtc | ctg | gtg | cag | ttc | ccg | act | gat | agt | cga | cct | 21924 |
| Asp | Gly | Gly | Arg | Val | Leu | Val | Gln | Phe | Pro | Thr | Asp | Ser | Arg | Pro | |
| | 7295 | | | | 7300 | | | | 7305 | | | | | | |

| cgt | cta | tca | gga | caa | ctc | aca | aac | caa | ccg | ctg | cag | cgg | cta | cag | 21969 |
| Arg | Leu | Ser | Gly | Gln | Leu | Thr | Asn | Gln | Pro | Leu | Gln | Arg | Leu | Gln | |
| | 7310 | | | | 7315 | | | | 7320 | | | | | | |

| agt | cga | cga | ttg | gag | gca | cag | att | cga | gat | cag | ctc | agc | gct | tta | 22014 |
| Ser | Arg | Arg | Leu | Glu | Ala | Gln | Ile | Arg | Asp | Gln | Leu | Ser | Ala | Leu | |
| | 7325 | | | | 7330 | | | | 7335 | | | | | | |

| ctt | cca | tct | tac | atg | atc | ccg | tcg | ctt | atc | gtg | atg | gtc | gat | gag | 22059 |
| Leu | Pro | Ser | Tyr | Met | Ile | Pro | Ser | Leu | Ile | Val | Met | Val | Asp | Glu | |
| | 7340 | | | | 7345 | | | | 7350 | | | | | | |

| atg | ccc | ttg | aat | gcc | aat | ggc | aag | gta | gac | agg | aaa | gcc | cta | gag | 22104 |
| Met | Pro | Leu | Asn | Ala | Asn | Gly | Lys | Val | Asp | Arg | Lys | Ala | Leu | Glu | |
| | 7355 | | | | 7360 | | | | 7365 | | | | | | |

| cga | agg | gct | cgc | atg | gtt | cag | aaa | gtt | gaa | aag | cca | gct | tct | gag | 22149 |
| Arg | Arg | Ala | Arg | Met | Val | Gln | Lys | Val | Glu | Lys | Pro | Ala | Ser | Glu | |
| | 7370 | | | | 7375 | | | | 7380 | | | | | | |

| cga | gtc | ggt | gca | cgt | aac | gag | atc | gaa | gcc | gcg | ctg | tgc | gaa | gta | 22194 |
| Arg | Val | Gly | Ala | Arg | Asn | Glu | Ile | Glu | Ala | Ala | Leu | Cys | Glu | Val | |
| | 7385 | | | | 7390 | | | | 7395 | | | | | | |

| ttc | gta | gat | cta | ctc | ggc | act | gag | gtc | agc | att | act | gac | aac | ttc | 22239 |
| Phe | Val | Asp | Leu | Leu | Gly | Thr | Glu | Val | Ser | Ile | Thr | Asp | Asn | Phe | |
| | 7400 | | | | 7405 | | | | 7410 | | | | | | |

| ttt | aat | ctt | ggc | ggt | cat | tcg | ctc | atg | gcc | aca | aaa | ttg | gct | gct | 22284 |
| Phe | Asn | Leu | Gly | Gly | His | Ser | Leu | Met | Ala | Thr | Lys | Leu | Ala | Ala | |
| | 7415 | | | | 7420 | | | | 7425 | | | | | | |

| cga | att | agc | aga | cgc | ctt | gac | gca | cgc | atc | tct | gtc | aag | gat | gtg | 22329 |
| Arg | Ile | Ser | Arg | Arg | Leu | Asp | Ala | Arg | Ile | Ser | Val | Lys | Asp | Val | |
| | 7430 | | | | 7435 | | | | 7440 | | | | | | |

| ttt | gac | tac | cct | gtt | ctc | gcc | gac | ctt | gcg | ggc | gcc | gtt | cag | cga | 22374 |
| Phe | Asp | Tyr | Pro | Val | Leu | Ala | Asp | Leu | Ala | Gly | Ala | Val | Gln | Arg | |
| | 7445 | | | | 7450 | | | | 7455 | | | | | | |

| ggc | tca | act | cca | cac | aac | cca | atc | gtc | gcg | acg | ccc | tac | tca | ggg | 22419 |
| Gly | Ser | Thr | Pro | His | Asn | Pro | Ile | Val | Ala | Thr | Pro | Tyr | Ser | Gly | |
| | 7460 | | | | 7465 | | | | 7470 | | | | | | |

| ccc | gtc | gag | cag | tcc | ttt | gct | cag | ggc | cgc | ctg | tgg | ttc | ttg | gac | 22464 |
| Pro | Val | Glu | Gln | Ser | Phe | Ala | Gln | Gly | Arg | Leu | Trp | Phe | Leu | Asp | |
| | 7475 | | | | 7480 | | | | 7485 | | | | | | |

| cag | ctt | aac | gcc | ggt | tcg | ctg | tgg | tac | atc | cag | cca | atc | gcc | gta | 22509 |
| Gln | Leu | Asn | Ala | Gly | Ser | Leu | Trp | Tyr | Ile | Gln | Pro | Ile | Ala | Val | |
| | 7490 | | | | 7495 | | | | 7500 | | | | | | |

| cgc | gta | cgc | ggt | tcg | ctc | aat | att | ggt | gcg | ctg | act | aca | gca | ctc | 22554 |
| Arg | Val | Arg | Gly | Ser | Leu | Asn | Ile | Gly | Ala | Leu | Thr | Thr | Ala | Leu | |
| | 7505 | | | | 7510 | | | | 7515 | | | | | | |

| aat | gcg | ctt | gag | aag | cgc | cac | gaa | ccg | ttg | cgc | acg | act | ttc | gaa | 22599 |
| Asn | Ala | Leu | Glu | Lys | Arg | His | Glu | Pro | Leu | Arg | Thr | Thr | Phe | Glu | |
| | 7520 | | | | 7525 | | | | 7530 | | | | | | |

| gag | cat | gac | ggc | att | ggt | gtg | caa | gtc | gtt | caa | ccg | cat | cag | ccg | 22644 |
| Glu | His | Asp | Gly | Ile | Gly | Val | Gln | Val | Val | Gln | Pro | His | Gln | Pro | |
| | 7535 | | | | 7540 | | | | 7545 | | | | | | |

| aag | aag | ctt | aga | att | gtc | gat | acg | gtg | gct | aac | tat | cag | ggt | gac | 22689 |
| Lys | Lys | Leu | Arg | Ile | Val | Asp | Thr | Val | Ala | Asn | Tyr | Gln | Gly | Asp | |
| | 7550 | | | | 7555 | | | | 7560 | | | | | | |

| ttc | atc | agg | gct | cta | cgg | aag | gag | cag | cag | act | cta | ttc | aat | ctc | 22734 |
| Phe | Ile | Arg | Ala | Leu | Arg | Lys | Glu | Gln | Gln | Thr | Leu | Phe | Asn | Leu | |
| | 7565 | | | | 7570 | | | | 7575 | | | | | | |

-continued

| | | | | | | | | | | | | | | |
|---|---|---|---|---|---|---|---|---|---|---|---|---|---|---|
| gcg | acc | gag | cca | ggc | tgg | aga | gtg | tct | ctg | cta | cgc | att | ggg | gag | 22779 |
| Ala | Thr | Glu | Pro | Gly | Trp | Arg | Val | Ser | Leu | Leu | Arg | Ile | Gly | Glu | |
| 7580 | | | | 7585 | | | | | 7590 | | | | | | |

| gac | gac | aac | att | ctc | tcc | atc | gtc | atg | cac | cac | atc | att | tca | gac | 22824 |
| Asp | Asp | Asn | Ile | Leu | Ser | Ile | Val | Met | His | His | Ile | Ile | Ser | Asp | |
| 7595 | | | | 7600 | | | | | 7605 | | | | | | |

| ggt | tgg | tct | gtt | gac | atc | ttg | cgt | caa | gat | cta | aaa | cta | ttc | tat | 22869 |
| Gly | Trp | Ser | Val | Asp | Ile | Leu | Arg | Gln | Asp | Leu | Lys | Leu | Phe | Tyr | |
| 7610 | | | | 7615 | | | | | 7620 | | | | | | |

| gcc | gcc | gct | ctc | aaa | agc | cag | gag | ccg | caa | gta | gac | gcg | ctc | cca | 22914 |
| Ala | Ala | Ala | Leu | Lys | Ser | Gln | Glu | Pro | Gln | Val | Asp | Ala | Leu | Pro | |
| 7625 | | | | 7630 | | | | | 7635 | | | | | | |

| atc | caa | tat | cgt | gac | ttt | gcc | ttc | tgg | cag | aaa | cag | ccg | gag | cag | 22959 |
| Ile | Gln | Tyr | Arg | Asp | Phe | Ala | Phe | Trp | Gln | Lys | Gln | Pro | Glu | Gln | |
| 7640 | | | | 7645 | | | | | 7650 | | | | | | |

| gta | gct | gag | cac | cag | cga | caa | ctc | gac | tac | tgg | att | gaa | caa | ttg | 23004 |
| Val | Ala | Glu | His | Gln | Arg | Gln | Leu | Asp | Tyr | Trp | Ile | Glu | Gln | Leu | |
| 7655 | | | | 7660 | | | | | 7665 | | | | | | |

| aaa | gac | agc | aag | cct | gct | gag | ctt | atc | acc | gat | ttt | ccg | cgg | cca | 23049 |
| Lys | Asp | Ser | Lys | Pro | Ala | Glu | Leu | Ile | Thr | Asp | Phe | Pro | Arg | Pro | |
| 7670 | | | | 7675 | | | | | 7680 | | | | | | |

| gag | gtg | ctg | tct | ggc | act | gct | ggc | atc | gta | cag | ctt | gcc | gtg | gac | 23094 |
| Glu | Val | Leu | Ser | Gly | Thr | Ala | Gly | Ile | Val | Gln | Leu | Ala | Val | Asp | |
| 7685 | | | | 7690 | | | | | 7695 | | | | | | |

| ggc | caa | gtc | tac | gag | ggt | ctc | cgg | gct | ttc | tgc | aga | att | cat | caa | 23139 |
| Gly | Gln | Val | Tyr | Glu | Gly | Leu | Arg | Ala | Phe | Cys | Arg | Ile | His | Gln | |
| 7700 | | | | 7705 | | | | | 7710 | | | | | | |

| aca | acg | tcc | ttc | gtg | gta | ctt | ctt | gca | gcc | ttt | aga | gct | gcc | cat | 23184 |
| Thr | Thr | Ser | Phe | Val | Val | Leu | Leu | Ala | Ala | Phe | Arg | Ala | Ala | His | |
| 7715 | | | | 7720 | | | | | 7725 | | | | | | |

| tac | cgt | cta | aca | ggc | acc | gag | gac | gcg | aca | atc | ggt | tct | ccc | atc | 23229 |
| Tyr | Arg | Leu | Thr | Gly | Thr | Glu | Asp | Ala | Thr | Ile | Gly | Ser | Pro | Ile | |
| 7730 | | | | 7735 | | | | | 7740 | | | | | | |

| gcc | aac | cgg | aat | cgg | ccc | gaa | ctg | gag | agc | ctc | att | ggc | ttc | ttc | 23274 |
| Ala | Asn | Arg | Asn | Arg | Pro | Glu | Leu | Glu | Ser | Leu | Ile | Gly | Phe | Phe | |
| 7745 | | | | 7750 | | | | | 7755 | | | | | | |

| gtc | aat | acc | caa | tgt | atg | cgc | att | atg | gtc | gga | gag | gac | gac | aca | 23319 |
| Val | Asn | Thr | Gln | Cys | Met | Arg | Ile | Met | Val | Gly | Glu | Asp | Asp | Thr | |
| 7760 | | | | 7765 | | | | | 7770 | | | | | | |

| ttc | gaa | cga | ttg | gta | cag | cag | gtc | cga | tca | acg | aca | aca | gct | gca | 23364 |
| Phe | Glu | Arg | Leu | Val | Gln | Gln | Val | Arg | Ser | Thr | Thr | Thr | Ala | Ala | |
| 7775 | | | | 7780 | | | | | 7785 | | | | | | |

| ttt | gct | aac | cag | gac | gtt | ccc | ttc | gaa | cga | atc | gtt | tca | tcc | gtc | 23409 |
| Phe | Ala | Asn | Gln | Asp | Val | Pro | Phe | Glu | Arg | Ile | Val | Ser | Ser | Val | |
| 7790 | | | | 7795 | | | | | 7800 | | | | | | |

| cag | tca | acc | tca | aga | gat | gcc | tcc | cga | aac | cct | ttg | gta | cag | ctc | 23454 |
| Gln | Ser | Thr | Ser | Arg | Asp | Ala | Ser | Arg | Asn | Pro | Leu | Val | Gln | Leu | |
| 7805 | | | | 7810 | | | | | 7815 | | | | | | |

| atg | ttt | gca | ctt | cat | tca | cag | cag | ggt | atc | ggc | ctg | atg | gaa | ctc | 23499 |
| Met | Phe | Ala | Leu | His | Ser | Gln | Gln | Gly | Ile | Gly | Leu | Met | Glu | Leu | |
| 7820 | | | | 7825 | | | | | 7830 | | | | | | |

| gaa | ggt | gtt | gag | aca | gag | cca | att | gca | aga | gat | gta | tcg | acg | cgc | 23544 |
| Glu | Gly | Val | Glu | Thr | Glu | Pro | Ile | Ala | Arg | Asp | Val | Ser | Thr | Arg | |
| 7835 | | | | 7840 | | | | | 7845 | | | | | | |

| ttc | gac | atc | gag | ttc | cat | ctt | tac | cag | aag | gaa | gag | agc | tta | cac | 23589 |
| Phe | Asp | Ile | Glu | Phe | His | Leu | Tyr | Gln | Lys | Glu | Glu | Ser | Leu | His | |
| 7850 | | | | 7855 | | | | | 7860 | | | | | | |

| ggt | gtt | gtc | cac | ttt | gct | gcc | gac | ttg | ttc | gag | cct | gag | act | att | 23634 |
| Gly | Val | Val | His | Phe | Ala | Ala | Asp | Leu | Phe | Glu | Pro | Glu | Thr | Ile | |
| 7865 | | | | 7870 | | | | | 7875 | | | | | | |

| | | | | | | | | | | | |
|---|---|---|---|---|---|---|---|---|---|---|---|
| caa | ggc | ttg | gtc | tcc | gtc | ttc | cag | gaa | att | ctt | cgc | cga | gga | ctc | 23679 |
| Gln | Gly | Leu | Val | Ser | Val | Phe | Gln | Glu | Ile | Leu | Arg | Arg | Gly | Leu | |
| | 7880 | | | | 7885 | | | | | 7890 | | | | | |

| gag | aca | cct | cga | ttg | cca | atc | agc | att | ctg | cct | ctt | gat | aac | aac | 23724 |
| Glu | Thr | Pro | Arg | Leu | Pro | Ile | Ser | Ile | Leu | Pro | Leu | Asp | Asn | Asn | |
| | 7895 | | | | 7900 | | | | | 7905 | | | | | |

| att | ccg | gag | ctt | ctc | gtc | ggt | atg | ctc | gat | gtc | gac | act | cca | gag | 23769 |
| Ile | Pro | Glu | Leu | Leu | Val | Gly | Met | Leu | Asp | Val | Asp | Thr | Pro | Glu | |
| | 7910 | | | | 7915 | | | | | 7920 | | | | | |

| tat | cct | cgc | gat | tca | agc | gtg | gtt | gat | gtg | ttc | cgc | acc | caa | gtt | 23814 |
| Tyr | Pro | Arg | Asp | Ser | Ser | Val | Val | Asp | Val | Phe | Arg | Thr | Gln | Val | |
| | 7925 | | | | 7930 | | | | | 7935 | | | | | |

| gct | gcc | agc | ccg | gat | gcg | atc | gcc | gtt | aaa | gat | tca | act | tcg | cag | 23859 |
| Ala | Ala | Ser | Pro | Asp | Ala | Ile | Ala | Val | Lys | Asp | Ser | Thr | Ser | Gln | |
| | 7940 | | | | 7945 | | | | | 7950 | | | | | |

| ctc | acc | tac | gct | cag | ctt | gat | gaa | gaa | tcc | aac | aaa | gtg | gct | aca | 23904 |
| Leu | Thr | Tyr | Ala | Gln | Leu | Asp | Glu | Glu | Ser | Asn | Lys | Val | Ala | Thr | |
| | 7955 | | | | 7960 | | | | | 7965 | | | | | |

| tgg | ttg | agt | caa | agg | cag | ctg | gct | ccc | gaa | acg | ctg | gta | ggc | gtc | 23949 |
| Trp | Leu | Ser | Gln | Arg | Gln | Leu | Ala | Pro | Glu | Thr | Leu | Val | Gly | Val | |
| | 7970 | | | | 7975 | | | | | 7980 | | | | | |

| ctt | gcg | cct | aga | tcg | tgc | cca | aca | atc | gtt | aca | ttc | ttt | ggt | atc | 23994 |
| Leu | Ala | Pro | Arg | Ser | Cys | Pro | Thr | Ile | Val | Thr | Phe | Phe | Gly | Ile | |
| | 7985 | | | | 7990 | | | | | 7995 | | | | | |

| ctc | aag | gcc | agt | ctg | gcg | tat | ctc | ccg | cta | gac | gtc | aac | gta | cca | 24039 |
| Leu | Lys | Ala | Ser | Leu | Ala | Tyr | Leu | Pro | Leu | Asp | Val | Asn | Val | Pro | |
| | 8000 | | | | 8005 | | | | | 8010 | | | | | |

| tct | gct | cgt | atc | gag | gcg | atc | ctc | tcg | gca | gtc | cct | gac | cat | aag | 24084 |
| Ser | Ala | Arg | Ile | Glu | Ala | Ile | Leu | Ser | Ala | Val | Pro | Asp | His | Lys | |
| | 8015 | | | | 8020 | | | | | 8025 | | | | | |

| ttg | gtc | ttc | ctt | ggt | gct | gac | gtc | ccc | gat | cca | gag | gct | cca | ctt | 24129 |
| Leu | Val | Phe | Leu | Gly | Ala | Asp | Val | Pro | Asp | Pro | Glu | Ala | Pro | Leu | |
| | 8030 | | | | 8035 | | | | | 8040 | | | | | |

| gtc | aac | gtg | gag | ctg | gtg | cgg | atc | gac | gac | atc | tta | cgc | caa | agc | 24174 |
| Val | Asn | Val | Glu | Leu | Val | Arg | Ile | Asp | Asp | Ile | Leu | Arg | Gln | Ser | |
| | 8045 | | | | 8050 | | | | | 8055 | | | | | |

| att | cac | gct | tcg | aat | gca | ggg | ctt | cta | gca | aat | cac | ccc | tta | gca | 24219 |
| Ile | His | Ala | Ser | Asn | Ala | Gly | Leu | Leu | Ala | Asn | His | Pro | Leu | Ala | |
| | 8060 | | | | 8065 | | | | | 8070 | | | | | |

| act | agt | ctt | gcc | tac | gtc | atg | ttt | aca | tct | gga | tct | aca | ggc | aag | 24264 |
| Thr | Ser | Leu | Ala | Tyr | Val | Met | Phe | Thr | Ser | Gly | Ser | Thr | Gly | Lys | |
| | 8075 | | | | 8080 | | | | | 8085 | | | | | |

| cct | aag | ggt | gtc | atg | gtt | gag | cat | cga | agt | att | gta | cgc | ttg | gta | 24309 |
| Pro | Lys | Gly | Val | Met | Val | Glu | His | Arg | Ser | Ile | Val | Arg | Leu | Val | |
| | 8090 | | | | 8095 | | | | | 8100 | | | | | |

| aag | gaa | acg | aac | cta | gtc | cca | gca | gta | gag | gca | gtt | tcc | tca | gta | 24354 |
| Lys | Glu | Thr | Asn | Leu | Val | Pro | Ala | Val | Glu | Ala | Val | Ser | Ser | Val | |
| | 8105 | | | | 8110 | | | | | 8115 | | | | | |

| gct | cac | atc | tct | aat | gtt | gct | ttc | gat | gct | gca | act | tgg | gag | ata | 24399 |
| Ala | His | Ile | Ser | Asn | Val | Ala | Phe | Asp | Ala | Ala | Thr | Trp | Glu | Ile | |
| | 8120 | | | | 8125 | | | | | 8130 | | | | | |

| tac | gct | gcg | ctc | cta | aat | ggc | gga | act | act | gtt | tgc | att | gat | cac | 24444 |
| Tyr | Ala | Ala | Leu | Leu | Asn | Gly | Gly | Thr | Thr | Val | Cys | Ile | Asp | His | |
| | 8135 | | | | 8140 | | | | | 8145 | | | | | |

| att | act | gtg | ttg | gat | cct | gct | aaa | cta | gct | ctc | gtc | ttc | tca | agc | 24489 |
| Ile | Thr | Val | Leu | Asp | Pro | Ala | Lys | Leu | Ala | Leu | Val | Phe | Ser | Ser | |
| | 8150 | | | | 8155 | | | | | 8160 | | | | | |

| gag | aag | atc | aaa | gct | gcg | ttc | ttc | tca | act | gct | ttg | ctc | aag | cag | 24534 |
| Glu | Lys | Ile | Lys | Ala | Ala | Phe | Phe | Ser | Thr | Ala | Leu | Leu | Lys | Gln | |
| | 8165 | | | | 8170 | | | | | 8175 | | | | | |

```
cgg ctc tac gaa gag cca tct act atc act gga ctc gat ctt tta   24579
Arg Leu Tyr Glu Glu Pro Ser Thr Ile Thr Gly Leu Asp Leu Leu
    8180            8185            8190 tat gct ggc ggt gag aga atg agg cct caa gac gct ctt aag acg   24624
Tyr Ala Gly Gly Glu Arg Met Arg Pro Gln Asp Ala Leu Lys Thr
    8195            8200            8205 cga gaa cta gtt cgt ggt agc ttc tgc cac gtc tat ggg ccg aca   24669
Arg Glu Leu Val Arg Gly Ser Phe Cys His Val Tyr Gly Pro Thr
    8210            8215            8220 gaa aat aca aca ttc agc act gtc tat cct atg ggg gta gaa gaa   24714
Glu Asn Thr Thr Phe Ser Thr Val Tyr Pro Met Gly Val Glu Glu
    8225            8230            8235 cgc tgc gtc aac gga cta cct atc ggc cgc gca gtc agc cat tca   24759
Arg Cys Val Asn Gly Leu Pro Ile Gly Arg Ala Val Ser His Ser
    8240            8245            8250 ggc gca gtg atc atg gat gcc aat cag cgc ctc gtg ccg tta ggg   24804
Gly Ala Val Ile Met Asp Ala Asn Gln Arg Leu Val Pro Leu Gly
    8255            8260            8265 gtg atg ggc gaa ctt gtt gtc aca ggt gat ggt ctc gcc cga gga   24849
Val Met Gly Glu Leu Val Val Thr Gly Asp Gly Leu Ala Arg Gly
    8270            8275            8280 tac acc gat ccc gct ctg aat cgt gat cgc ttc gtg gaa gtc aat   24894
Tyr Thr Asp Pro Ala Leu Asn Arg Asp Arg Phe Val Glu Val Asn
    8285            8290            8295 atc cac ggt cag gtc ctg agg gca tat cgc aca ggc gac caa gcc   24939
Ile His Gly Gln Val Leu Arg Ala Tyr Arg Thr Gly Asp Gln Ala
    8300            8305            8310 cgc tat cga ccc aaa gat ggc cag att gag ttc tcc ggg cgt atg   24984
Arg Tyr Arg Pro Lys Asp Gly Gln Ile Glu Phe Ser Gly Arg Met
    8315            8320            8325 gac aga cag ctg aaa att cga ggc cat cgt atc gag cca gct gag   25029
Asp Arg Gln Leu Lys Ile Arg Gly His Arg Ile Glu Pro Ala Glu
    8330            8335            8340 gtc gag cac gcc ata ctt agc cac gac gat atc cga aac gca gtt   25074
Val Glu His Ala Ile Leu Ser His Asp Asp Ile Arg Asn Ala Val
    8345            8350            8355 gtg gtt act cga caa cag gaa ggc caa gat ctg gaa atg gtc gct   25119
Val Val Thr Arg Gln Gln Glu Gly Gln Asp Leu Glu Met Val Ala
    8360            8365            8370 ttc gtc tct act ccc aac gat caa acc gta gaa cgc gac gaa gct   25164
Phe Val Ser Thr Pro Asn Asp Gln Thr Val Glu Arg Asp Glu Ala
    8375            8380            8385 agg aat caa gtt gag gac tgg ggg gct caa ttc gag agc aac gtt   25209
Arg Asn Gln Val Glu Asp Trp Gly Ala Gln Phe Glu Ser Asn Val
    8390            8395            8400 tac gcc gag atc gag gag atc gac tcc tct gcc gtt ggg aat gac   25254
Tyr Ala Glu Ile Glu Glu Ile Asp Ser Ser Ala Val Gly Asn Asp
    8405            8410            8415 ttc atg ggc tgg acg tct atg tac gac ggt act gcg atc gat aaa   25299
Phe Met Gly Trp Thr Ser Met Tyr Asp Gly Thr Ala Ile Asp Lys
    8420            8425            8430 gca gag atg cag gag tgg ctc gac gat act atg aga acc ctc cat   25344
Ala Glu Met Gln Glu Trp Leu Asp Asp Thr Met Arg Thr Leu His
    8435            8440            8445 gac ggc cga gat cct ggc cac gtc ctc gaa gtt ggt aca ggc acg   25389
Asp Gly Arg Asp Pro Gly His Val Leu Glu Val Gly Thr Gly Thr
    8450            8455            8460 ggc atg atc cta ttc aat ctc ggc aag ggc ctg cag agc tac gtc   25434
Gly Met Ile Leu Phe Asn Leu Gly Lys Gly Leu Gln Ser Tyr Val
    8465            8470            8475
```

| | | | | | | | | | | | |
|---|---|---|---|---|---|---|---|---|---|---|---|
| ggc | ctc | gag | ccg | tcg | act | tcg | gca | gct | gca | ttc | gtc | aat | cgc | aag | 25479 |
| Gly | Leu | Glu | Pro | Ser | Thr | Ser | Ala | Ala | Ala | Phe | Val | Asn | Arg | Lys | |
| | 8480 | | | | 8485 | | | | | 8490 | | | | | |

| att | gag | act | atc | tca | tca | ttg | gcg | ggt | aag | gct | aaa | gtt | gag | att | 25524 |
| Ile | Glu | Thr | Ile | Ser | Ser | Leu | Ala | Gly | Lys | Ala | Lys | Val | Glu | Ile | |
| | 8495 | | | | 8500 | | | | | 8505 | | | | | |

| ggc | aca | gca | acc | gac | gta | ggc | cag | ctc | aag | aac | ctc | cgc | tcc | gat | 25569 |
| Gly | Thr | Ala | Thr | Asp | Val | Gly | Gln | Leu | Lys | Asn | Leu | Arg | Ser | Asp | |
| | 8510 | | | | 8515 | | | | | 8520 | | | | | |

| ttg | gtc | gtt | att | aat | tcg | gta | gct | caa | tac | ttc | cct | tcc | ccc | gag | 25614 |
| Leu | Val | Val | Ile | Asn | Ser | Val | Ala | Gln | Tyr | Phe | Pro | Ser | Pro | Glu | |
| | 8525 | | | | 8530 | | | | | 8535 | | | | | |

| tat | cta | gtc | gaa | gca | gta | act | gct | cta | gtc | cac | atc | cca | ggt | gta | 25659 |
| Tyr | Leu | Val | Glu | Ala | Val | Thr | Ala | Leu | Val | His | Ile | Pro | Gly | Val | |
| | 8540 | | | | 8545 | | | | | 8550 | | | | | |

| aaa | cgc | ttg | ttc | ttc | ggc | gac | atg | cga | tcc | tac | gcc | atg | aat | aag | 25704 |
| Lys | Arg | Leu | Phe | Phe | Gly | Asp | Met | Arg | Ser | Tyr | Ala | Met | Asn | Lys | |
| | 8555 | | | | 8560 | | | | | 8565 | | | | | |

| cag | ttc | ctg | gtt | gct | agg | gct | ctc | cgt | acg | cta | gga | gcc | aag | gca | 25749 |
| Gln | Phe | Leu | Val | Ala | Arg | Ala | Leu | Arg | Thr | Leu | Gly | Ala | Lys | Ala | |
| | 8570 | | | | 8575 | | | | | 8580 | | | | | |

| aac | aag | gac | gat | gtt | cgc | agg | aag | atg | gtg | gag | cta | gag | gaa | ttc | 25794 |
| Asn | Lys | Asp | Asp | Val | Arg | Arg | Lys | Met | Val | Glu | Leu | Glu | Glu | Phe | |
| | 8585 | | | | 8590 | | | | | 8595 | | | | | |

| gaa | gag | gaa | cta | ctc | gtg | gat | cca | gcc | ttc | ttc | aca | ggc | ctc | gca | 25839 |
| Glu | Glu | Glu | Leu | Leu | Val | Asp | Pro | Ala | Phe | Phe | Thr | Gly | Leu | Ala | |
| | 8600 | | | | 8605 | | | | | 8610 | | | | | |

| aac | tgg | ctg | tca | gaa | gtc | gaa | cat | gtc | gag | att | cta | ccc | aaa | cag | 25884 |
| Asn | Trp | Leu | Ser | Glu | Val | Glu | His | Val | Glu | Ile | Leu | Pro | Lys | Gln | |
| | 8615 | | | | 8620 | | | | | 8625 | | | | | |

| atg | aca | tct | acc | aac | gag | ctg | agc | tca | tac | cgt | tat | gca | gcc | atc | 25929 |
| Met | Thr | Ser | Thr | Asn | Glu | Leu | Ser | Ser | Tyr | Arg | Tyr | Ala | Ala | Ile | |
| | 8630 | | | | 8635 | | | | | 8640 | | | | | |

| gta | cac | cta | cgg | ctt | cca | ggc | cag | gag | gca | caa | cca | gtc | gtg | aca | 25974 |
| Val | His | Leu | Arg | Leu | Pro | Gly | Gln | Glu | Ala | Gln | Pro | Val | Val | Thr | |
| | 8645 | | | | 8650 | | | | | 8655 | | | | | |

| gtc | aat | caa | gac | gcc | tgg | gtt | gac | ttc | gga | gga | tcc | aag | atg | gat | 26019 |
| Val | Asn | Gln | Asp | Ala | Trp | Val | Asp | Phe | Gly | Gly | Ser | Lys | Met | Asp | |
| | 8660 | | | | 8665 | | | | | 8670 | | | | | |

| cga | cac | gct | ctt | ctt | cac | cac | cta | caa | agc | tca | cca | aag | gcc | gaa | 26064 |
| Arg | His | Ala | Leu | Leu | His | His | Leu | Gln | Ser | Ser | Pro | Lys | Ala | Glu | |
| | 8675 | | | | 8680 | | | | | 8685 | | | | | |

| act | gta | gcc | atc | agc | aac | atc | ccc | tat | agc | aag | acg | att | tat | gag | 26109 |
| Thr | Val | Ala | Ile | Ser | Asn | Ile | Pro | Tyr | Ser | Lys | Thr | Ile | Tyr | Glu | |
| | 8690 | | | | 8695 | | | | | 8700 | | | | | |

| cgc | cat | gtc | ctc | gca | tct | ttg | gat | gac | gat | gaa | gtc | gag | gac | tcg | 26154 |
| Arg | His | Val | Leu | Ala | Ser | Leu | Asp | Asp | Asp | Glu | Val | Glu | Asp | Ser | |
| | 8705 | | | | 8710 | | | | | 8715 | | | | | |

| tta | gat | ggg | tca | gca | tgg | cta | tcg | gct | gtt | cgc | tct | acc | gcc | gaa | 26199 |
| Leu | Asp | Gly | Ser | Ala | Trp | Leu | Ser | Ala | Val | Arg | Ser | Thr | Ala | Glu | |
| | 8720 | | | | 8725 | | | | | 8730 | | | | | |

| cag | tgc | gcg | tca | ctc | tcc | gga | gtc | gac | tta | gtt | caa | atc | gcc | aag | 26244 |
| Gln | Cys | Ala | Ser | Leu | Ser | Gly | Val | Asp | Leu | Val | Gln | Ile | Ala | Lys | |
| | 8735 | | | | 8740 | | | | | 8745 | | | | | |

| gag | gcc | ggc | ttc | cgc | gtg | gag | ctc | agc | tgg | gcg | cga | cag | agg | tct | 26289 |
| Glu | Ala | Gly | Phe | Arg | Val | Glu | Leu | Ser | Trp | Ala | Arg | Gln | Arg | Ser | |
| | 8750 | | | | 8755 | | | | | 8760 | | | | | |

| cag | aag | ggt | gga | atc | gac | gcg | gtc | ttc | cac | cac | tac | gag | tca | gtg | 26334 |
| Gln | Lys | Gly | Gly | Ile | Asp | Ala | Val | Phe | His | His | Tyr | Glu | Ser | Val | |
| | 8765 | | | | 8770 | | | | | 8775 | | | | | |

```
cac gat gga gct cgc gtc atg gtc aag ttc ccg aca gat gat caa    26379
His Asp Gly Ala Arg Val Met Val Lys Phe Pro Thr Asp Asp Gln
    8780            8785            8790 ggc cga gcg ctc gat tcg ctt gcg aac agg ccg ctg caa cga ctc    26424
Gly Arg Ala Leu Asp Ser Leu Ala Asn Arg Pro Leu Gln Arg Leu
    8795            8800            8805 cag agt cga cga atc gag gtg caa att cgg gag cgg cta caa gct    26469
Gln Ser Arg Arg Ile Glu Val Gln Ile Arg Glu Arg Leu Gln Ala
    8810            8815            8820 gta ctg ccg tcc tat atg atg cca gtc cgc att gta gtc ttg gac    26514
Val Leu Pro Ser Tyr Met Met Pro Val Arg Ile Val Val Leu Asp
    8825            8830            8835 gag atg cct atg aat gcg aac ggc aag gtt gac aga aaa gtg ctt    26559
Glu Met Pro Met Asn Ala Asn Gly Lys Val Asp Arg Lys Val Leu
    8840            8845            8850 acc cgc aga gct aag atg att tcg agg gtc gag aca acc gct gaa    26604
Thr Arg Arg Ala Lys Met Ile Ser Arg Val Glu Thr Thr Ala Glu
    8855            8860            8865 cgc gtt ggg cct cgc aac gag ata gag gct ctc ctc tgt gag gag    26649
Arg Val Gly Pro Arg Asn Glu Ile Glu Ala Leu Leu Cys Glu Glu
    8870            8875            8880 ttt gct gaa gtg ctt ggt gtc gag gtt ggc att aat gac gac ttc    26694
Phe Ala Glu Val Leu Gly Val Glu Val Gly Ile Asn Asp Asp Phe
    8885            8890            8895 ttc gat ctt ggc gga cac tct ctc atg gcc acg aag ctt gca gct    26739
Phe Asp Leu Gly Gly His Ser Leu Met Ala Thr Lys Leu Ala Ala
    8900            8905            8910 cgc agt agc cgt cgc ttc gat gcg aag gtc tct gtc aaa gac gtg    26784
Arg Ser Ser Arg Arg Phe Asp Ala Lys Val Ser Val Lys Asp Val
    8915            8920            8925 ttt gat cat cct atc cta gcg gac cta gca gct tcg att cag cga    26829
Phe Asp His Pro Ile Leu Ala Asp Leu Ala Ala Ser Ile Gln Arg
    8930            8935            8940 ggc tca act cca cac aac ccc atc ctc gca aca caa tat agc ggg    26874
Gly Ser Thr Pro His Asn Pro Ile Leu Ala Thr Gln Tyr Ser Gly
    8945            8950            8955 cct gtg gag cag tct ttc gct cag ggt cgg ctg tgg ttc ctt gaa    26919
Pro Val Glu Gln Ser Phe Ala Gln Gly Arg Leu Trp Phe Leu Glu
    8960            8965            8970 cag ctg aac gtc agt tca aca tgg tat ctg caa cca atc gca gtg    26964
Gln Leu Asn Val Ser Ser Thr Trp Tyr Leu Gln Pro Ile Ala Val
    8975            8980            8985 cgt atg cgc gga ccg ctt aag att gag gcg ctc gcg gcg gcg ttt    27009
Arg Met Arg Gly Pro Leu Lys Ile Glu Ala Leu Ala Ala Ala Phe
    8990            8995            9000 cac gct ctg gag gag cgt cac gaa acc ctg cga acg acg ttt gaa    27054
His Ala Leu Glu Glu Arg His Glu Thr Leu Arg Thr Thr Phe Glu
    9005            9010            9015 gag cac gac ggc att ggt atg cag gtt gtt cag cca cat cgc ccc    27099
Glu His Asp Gly Ile Gly Met Gln Val Val Gln Pro His Arg Pro
    9020            9025            9030 aaa gaa ctc aga gtg att gat gta cag gct gag cat gat ggc gat    27144
Lys Glu Leu Arg Val Ile Asp Val Gln Ala Glu His Asp Gly Asp
    9035            9040            9045 tat act cag gct ctg cac aca gag caa aca act acg ttc aat tta    27189
Tyr Thr Gln Ala Leu His Thr Glu Gln Thr Thr Thr Phe Asn Leu
    9050            9055            9060 gaa acg gaa cca gga tgg agg gta tcg gtg ttt cgc ctg aac gaa    27234
Glu Thr Glu Pro Gly Trp Arg Val Ser Val Phe Arg Leu Asn Glu
    9065            9070            9075
```

```
gat gac aac atc ctc tct ata gtg atg cac cat atc atc tct gat    27279
Asp Asp Asn Ile Leu Ser Ile Val Met His His Ile Ile Ser Asp
9080            9085            9090 ggt tgg tcg ttc gat atc ctg cgt aag gag atc aga gag ttt tac    27324
Gly Trp Ser Phe Asp Ile Leu Arg Lys Glu Ile Arg Glu Phe Tyr
    9095            9100            9105 aac gcc gcg ctc aag ggc aag gac ccc ttg gcg caa atg agc ccc    27369
Asn Ala Ala Leu Lys Gly Lys Asp Pro Leu Ala Gln Met Ser Pro
9110            9115            9120 ttg cat atc caa tat cgc gac ttt tcc gtt tgg caa aag cag ctg    27414
Leu His Ile Gln Tyr Arg Asp Phe Ser Val Trp Gln Lys Gln Leu
    9125            9130            9135 aat cag atc acc gag cat aaa cgg cag ctt gat tac tgg acg aag    27459
Asn Gln Ile Thr Glu His Lys Arg Gln Leu Asp Tyr Trp Thr Lys
9140            9145            9150 aac cta gcc gac aat act cca gcc gag ctc cca acc gat ctg cct    27504
Asn Leu Ala Asp Asn Thr Pro Ala Glu Leu Pro Thr Asp Leu Pro
    9155            9160            9165 cgg cca gcc gtt cta tcc ggt aag gct gga gtc atc cag ctc tct    27549
Arg Pro Ala Val Leu Ser Gly Lys Ala Gly Val Ile Gln Leu Ser
9170            9175            9180 att aca ggt cca gtc tat gat cgt ctc cgc gcg ttc tgc cga gtc    27594
Ile Thr Gly Pro Val Tyr Asp Arg Leu Arg Ala Phe Cys Arg Val
    9185            9190            9195 cac cag acc acc tta ttc acg gtg ctc ctc act gta ttt cga gcc    27639
His Gln Thr Thr Leu Phe Thr Val Leu Leu Thr Val Phe Arg Ala
9200            9205            9210 acc cac tat cgc ctc act gga gca gag gat gct acg att ggt acg    27684
Thr His Tyr Arg Leu Thr Gly Ala Glu Asp Ala Thr Ile Gly Thr
    9215            9220            9225 cct atc gct aat cgt aac aga cca gag ctt gag aac ttg atc ggg    27729
Pro Ile Ala Asn Arg Asn Arg Pro Glu Leu Glu Asn Leu Ile Gly
9230            9235            9240 ttt ttt gtt aac act cag tgc atg cgg att acc gta gaa gag gag    27774
Phe Phe Val Asn Thr Gln Cys Met Arg Ile Thr Val Glu Glu Glu
    9245            9250            9255 gac acg ttc gag aca ctc atc cac cag gtt cgg act aca act aca    27819
Asp Thr Phe Glu Thr Leu Ile His Gln Val Arg Thr Thr Thr Thr
9260            9265            9270 gcc gct ttc gcc aac caa gac gta cct ttt gag cga att gtg tca    27864
Ala Ala Phe Ala Asn Gln Asp Val Pro Phe Glu Arg Ile Val Ser
    9275            9280            9285 gcc cta ctc cca ggc tcc cga gac acg tcc cgc aac ccg ctc tct    27909
Ala Leu Leu Pro Gly Ser Arg Asp Thr Ser Arg Asn Pro Leu Ser
9290            9295            9300 cag atc atg ttt gcc gta cat tct cag aaa aac atc agc aag atc    27954
Gln Ile Met Phe Ala Val His Ser Gln Lys Asn Ile Ser Lys Ile
    9305            9310            9315 gaa ctg gac ggc cta gag agc gag gcc att tca cga gcc aca tca    27999
Glu Leu Asp Gly Leu Glu Ser Glu Ala Ile Ser Arg Ala Thr Ser
9320            9325            9330 act cgt ttc gat cta gag ttc cat ctt ttc cag gaa gag aag ggc    28044
Thr Arg Phe Asp Leu Glu Phe His Leu Phe Gln Glu Glu Lys Gly
    9335            9340            9345 cta ggc ggc att gta ttg ttt gcg gca gat ctg ttc gag ccg gag    28089
Leu Gly Gly Ile Val Leu Phe Ala Ala Asp Leu Phe Glu Pro Glu
9350            9355            9360 acg atc gac agc ctc gtc ttc gtc ttc caa gag atc ctc cgc cag    28134
Thr Ile Asp Ser Leu Val Phe Val Phe Gln Glu Ile Leu Arg Gln
    9365            9370            9375
```

| | | | | | | | | | | |
|---|---|---|---|---|---|---|---|---|---|---|
| agt | ctc | gag | aca | ccc | aag | act | cca | att | gcg | gtc | ttg | cct | ctt | acc | 28179 |
| Ser | Leu | Glu | Thr | Pro | Lys | Thr | Pro | Ile | Ala | Val | Leu | Pro | Leu | Thr | |
| | 9380 | | | | 9385 | | | | 9390 | | | | | | |

| aat | ggt | att | gcg | cag | ctt | cgc | agc | atg | tgt | gtg | cta | gat | att | gag | 28224 |
| Asn | Gly | Ile | Ala | Gln | Leu | Arg | Ser | Met | Cys | Val | Leu | Asp | Ile | Glu | |
| | 9395 | | | | 9400 | | | | 9405 | | | | | | |

| aag | acc | gcc | tac | cct | caa | gac | tcc | agc | gtc | atc | gat | atc | ttc | cgc | 28269 |
| Lys | Thr | Ala | Tyr | Pro | Gln | Asp | Ser | Ser | Val | Ile | Asp | Ile | Phe | Arg | |
| | 9410 | | | | 9415 | | | | 9420 | | | | | | |

| cag | cag | gtt | gct | gcc | cgc | ccg | gat | gcc | acg | gcc | gtc | aca | gat | tct | 28314 |
| Gln | Gln | Val | Ala | Ala | Arg | Pro | Asp | Ala | Thr | Ala | Val | Thr | Asp | Ser | |
| | 9425 | | | | 9430 | | | | 9435 | | | | | | |

| acc | tct | cag | ctc | acc | tac | gca | caa | ctg | gat | ctc | cac | tct | gac | gag | 28359 |
| Thr | Ser | Gln | Leu | Thr | Tyr | Ala | Gln | Leu | Asp | Leu | His | Ser | Asp | Glu | |
| | 9440 | | | | 9445 | | | | 9450 | | | | | | |

| cta | gcc | agc | tgg | ctg | cgt | cag | aaa | aag | atg | gca | ccc | gag | act | ttg | 28404 |
| Leu | Ala | Ser | Trp | Leu | Arg | Gln | Lys | Lys | Met | Ala | Pro | Glu | Thr | Leu | |
| | 9455 | | | | 9460 | | | | 9465 | | | | | | |

| gtg | ggt | gtg | cta | gca | cca | cgg | tct | tgc | caa | acg | atc | gtt | acc | ttt | 28449 |
| Val | Gly | Val | Leu | Ala | Pro | Arg | Ser | Cys | Gln | Thr | Ile | Val | Thr | Phe | |
| | 9470 | | | | 9475 | | | | 9480 | | | | | | |

| ctt | ggt | att | tta | aag | gcg | agc | tta | gcc | tat | tta | ccg | cta | gac | gtc | 28494 |
| Leu | Gly | Ile | Leu | Lys | Ala | Ser | Leu | Ala | Tyr | Leu | Pro | Leu | Asp | Val | |
| | 9485 | | | | 9490 | | | | 9495 | | | | | | |

| aaa | gtg | ccg | gtt | gcc | cgc | ata | gag | gcc | att | ttg | tcg | tcc | att | tca | 28539 |
| Lys | Val | Pro | Val | Ala | Arg | Ile | Glu | Ala | Ile | Leu | Ser | Ser | Ile | Ser | |
| | 9500 | | | | 9505 | | | | 9510 | | | | | | |

| ggg | cag | aaa | ctg | att | ctg | ctt | ggg | cag | gac | gta | cct | gtc | cca | gaa | 28584 |
| Gly | Gln | Lys | Leu | Ile | Leu | Leu | Gly | Gln | Asp | Val | Pro | Val | Pro | Glu | |
| | 9515 | | | | 9520 | | | | 9525 | | | | | | |

| atc | cag | ctc | cca | gac | gtc | gat | gtc | gta | cca | atc | agt | gaa | atc | tta | 28629 |
| Ile | Gln | Leu | Pro | Asp | Val | Asp | Val | Val | Pro | Ile | Ser | Glu | Ile | Leu | |
| | 9530 | | | | 9535 | | | | 9540 | | | | | | |

| ggc | cgc | tct | gtc | cct | tct | cgt | gct | aca | gat | aag | agt | tta | gga | cca | 28674 |
| Gly | Arg | Ser | Val | Pro | Ser | Arg | Ala | Thr | Asp | Lys | Ser | Leu | Gly | Pro | |
| | 9545 | | | | 9550 | | | | 9555 | | | | | | |

| ttg | gca | aga | aat | ctt | gcg | tat | gtt | ctg | ttc | aca | tct | gga | tcc | aca | 28719 |
| Leu | Ala | Arg | Asn | Leu | Ala | Tyr | Val | Leu | Phe | Thr | Ser | Gly | Ser | Thr | |
| | 9560 | | | | 9565 | | | | 9570 | | | | | | |

| ggc | aag | ccc | aag | ggt | gtc | atg | atc | gag | cac | cgt | agt | att | gtg | cgc | 28764 |
| Gly | Lys | Pro | Lys | Gly | Val | Met | Ile | Glu | His | Arg | Ser | Ile | Val | Arg | |
| | 9575 | | | | 9580 | | | | 9585 | | | | | | |

| ctt | gtc | aaa | gag | aca | aat | ctt | atc | tct | aag | cta | cca | aac | gcg | cct | 28809 |
| Leu | Val | Lys | Glu | Thr | Asn | Leu | Ile | Ser | Lys | Leu | Pro | Asn | Ala | Pro | |
| | 9590 | | | | 9595 | | | | 9600 | | | | | | |

| cgc | acg | gca | cat | ctc | acc | aat | ctc | gtc | ttt | gac | aac | tct | gca | tgg | 28854 |
| Arg | Thr | Ala | His | Leu | Thr | Asn | Leu | Val | Phe | Asp | Asn | Ser | Ala | Trp | |
| | 9605 | | | | 9610 | | | | 9615 | | | | | | |

| gaa | att | tac | tcc | acc | ctt | ctc | aac | ggg | gga | acg | cta | gtc | tgc | atc | 28899 |
| Glu | Ile | Tyr | Ser | Thr | Leu | Leu | Asn | Gly | Gly | Thr | Leu | Val | Cys | Ile | |
| | 9620 | | | | 9625 | | | | 9630 | | | | | | |

| gac | tat | gcc | acc | gtt | ctg | gat | agc | aaa | gcc | ctc | gag | acc | gtg | ttc | 28944 |
| Asp | Tyr | Ala | Thr | Val | Leu | Asp | Ser | Lys | Ala | Leu | Glu | Thr | Val | Phe | |
| | 9635 | | | | 9640 | | | | 9645 | | | | | | |

| aag | gag | caa | cgc | att | cag | aca | tct | ctg | atg | cct | cct | gcg | cta | ctt | 28989 |
| Lys | Glu | Gln | Arg | Ile | Gln | Thr | Ser | Leu | Met | Pro | Pro | Ala | Leu | Leu | |
| | 9650 | | | | 9655 | | | | 9660 | | | | | | |

| aaa | gag | tgc | tta | gcc | aac | atg | cct | act | atg | ttc | gat | gac | gta | gag | 29034 |
| Lys | Glu | Cys | Leu | Ala | Asn | Met | Pro | Thr | Met | Phe | Asp | Asp | Val | Glu | |
| | 9665 | | | | 9670 | | | | 9675 | | | | | | |

| | | | | | | | | | | | | | | |
|---|---|---|---|---|---|---|---|---|---|---|---|---|---|---|
| gtg | ctc | tac | gcg | ctt | gga | gat | cga | ttc | gac | aaa | cag | gat | gcc | atg | 29079 |
| Val | Leu | Tyr | Ala | Leu | Gly | Asp | Arg | Phe | Asp | Lys | Gln | Asp | Ala | Met | |
| | 9680 | | | | 9685 | | | | 9690 | | | | | | |

| aaa | gcg | cgc | tcg | ata | gtc | aag | acc | gcc | gtc | tac | aac | gcc | tat | ggt | 29124 |
|---|---|---|---|---|---|---|---|---|---|---|---|---|---|---|---|
| Lys | Ala | Arg | Ser | Ile | Val | Lys | Thr | Ala | Val | Tyr | Asn | Ala | Tyr | Gly | |
| 9695 | | | | | 9700 | | | | | 9705 | | | | | |

| ccc | acg | gaa | aac | acg | gtc | atc | agt | act | atc | tac | gag | att | gcc | aag | 29169 |
|---|---|---|---|---|---|---|---|---|---|---|---|---|---|---|---|
| Pro | Thr | Glu | Asn | Thr | Val | Ile | Ser | Thr | Ile | Tyr | Glu | Ile | Ala | Lys | |
| 9710 | | | | | 9715 | | | | | 9720 | | | | | |

| gac | gat | tcg | ttc | gtg | aac | ggt | gtt | ccc | atc | ggt | cgg | agc | atc | agc | 29214 |
|---|---|---|---|---|---|---|---|---|---|---|---|---|---|---|---|
| Asp | Asp | Ser | Phe | Val | Asn | Gly | Val | Pro | Ile | Gly | Arg | Ser | Ile | Ser | |
| 9725 | | | | | 9730 | | | | | 9735 | | | | | |

| aac | tcc | gga | gcc | ttc | atc | atg | gac | tcc | cgg | caa | cag | ctc | gtc | ccc | 29259 |
|---|---|---|---|---|---|---|---|---|---|---|---|---|---|---|---|
| Asn | Ser | Gly | Ala | Phe | Ile | Met | Asp | Ser | Arg | Gln | Gln | Leu | Val | Pro | |
| 9740 | | | | | 9745 | | | | | 9750 | | | | | |

| gtt | ggc | gtg | cta | ggc | gag | ctc | gtc | gtt | tct | ggc | gat | ggc | ctt | gcg | 29304 |
|---|---|---|---|---|---|---|---|---|---|---|---|---|---|---|---|
| Val | Gly | Val | Leu | Gly | Glu | Leu | Val | Val | Ser | Gly | Asp | Gly | Leu | Ala | |
| 9755 | | | | | 9760 | | | | | 9765 | | | | | |

| aga | gga | tat | act | gat | ccc | aca | ctg | gat | gta | aat | cgc | ttc | gtt | gag | 29349 |
|---|---|---|---|---|---|---|---|---|---|---|---|---|---|---|---|
| Arg | Gly | Tyr | Thr | Asp | Pro | Thr | Leu | Asp | Val | Asn | Arg | Phe | Val | Glu | |
| 9770 | | | | | 9775 | | | | | 9780 | | | | | |

| gtg | act | gtt | gat | ggc | caa | cat | gtt | aga | gta | tac | cgg | acc | ggt | gat | 29394 |
|---|---|---|---|---|---|---|---|---|---|---|---|---|---|---|---|
| Val | Thr | Val | Asp | Gly | Gln | His | Val | Arg | Val | Tyr | Arg | Thr | Gly | Asp | |
| 9785 | | | | | 9790 | | | | | 9795 | | | | | |

| cgc | gta | cgc | ttc | cgt | cca | aag | gat | ggt | cag | att | gaa | ttt | ttt | agt | 29439 |
|---|---|---|---|---|---|---|---|---|---|---|---|---|---|---|---|
| Arg | Val | Arg | Phe | Arg | Pro | Lys | Asp | Gly | Gln | Ile | Glu | Phe | Phe | Ser | |
| 9800 | | | | | 9805 | | | | | 9810 | | | | | |

| cgc | atg | gat | cag | caa | gtc | aag | att | cga | ggc | cat | cgt | atc | gag | ccg | 29484 |
|---|---|---|---|---|---|---|---|---|---|---|---|---|---|---|---|
| Arg | Met | Asp | Gln | Gln | Val | Lys | Ile | Arg | Gly | His | Arg | Ile | Glu | Pro | |
| 9815 | | | | | 9820 | | | | | 9825 | | | | | |

| gct | gag | gta | gag | cac | gtt | att | ctc | acc | aac | aag | att | atc | cgt | gat | 29529 |
|---|---|---|---|---|---|---|---|---|---|---|---|---|---|---|---|
| Ala | Glu | Val | Glu | His | Val | Ile | Leu | Thr | Asn | Lys | Ile | Ile | Arg | Asp | |
| 9830 | | | | | 9835 | | | | | 9840 | | | | | |

| gcg | gct | gtt | gca | atc | cgg | cga | cct | gag | ggt | caa | gaa | cca | gaa | atg | 29574 |
|---|---|---|---|---|---|---|---|---|---|---|---|---|---|---|---|
| Ala | Ala | Val | Ala | Ile | Arg | Arg | Pro | Glu | Gly | Gln | Glu | Pro | Glu | Met | |
| 9845 | | | | | 9850 | | | | | 9855 | | | | | |

| gtt | gct | ttc | gtt | act | acc | cat | gaa | aat | act | tct | att | gag | aag | cag | 29619 |
|---|---|---|---|---|---|---|---|---|---|---|---|---|---|---|---|
| Val | Ala | Phe | Val | Thr | Thr | His | Glu | Asn | Thr | Ser | Ile | Glu | Lys | Gln | |
| 9860 | | | | | 9865 | | | | | 9870 | | | | | |

| tca | gtc | gag | gaa | ttc | gca | gca | cgg | atc | gag | aat | gaa | gtc | cgt | cgc | 29664 |
|---|---|---|---|---|---|---|---|---|---|---|---|---|---|---|---|
| Ser | Val | Glu | Glu | Phe | Ala | Ala | Arg | Ile | Glu | Asn | Glu | Val | Arg | Arg | |
| 9875 | | | | | 9880 | | | | | 9885 | | | | | |

| tgg | atc | aag | acc | tta | ctt | ccg | ctc | tac | atg | gtt | cct | aca | cag | att | 29709 |
|---|---|---|---|---|---|---|---|---|---|---|---|---|---|---|---|
| Trp | Ile | Lys | Thr | Leu | Leu | Pro | Leu | Tyr | Met | Val | Pro | Thr | Gln | Ile | |
| 9890 | | | | | 9895 | | | | | 9900 | | | | | |

| gtt | gta | ttg | gat | cga | atg | cct | gtc | aat | gct | aac | ggt | aag | gtt | gac | 29754 |
|---|---|---|---|---|---|---|---|---|---|---|---|---|---|---|---|
| Val | Val | Leu | Asp | Arg | Met | Pro | Val | Asn | Ala | Asn | Gly | Lys | Val | Asp | |
| 9905 | | | | | 9910 | | | | | 9915 | | | | | |

| agg | aaa | gag | ctc | gcg | caa | aga | gca | caa | acc | cta | cag | aag | agc | gag | 29799 |
|---|---|---|---|---|---|---|---|---|---|---|---|---|---|---|---|
| Arg | Lys | Glu | Leu | Ala | Gln | Arg | Ala | Gln | Thr | Leu | Gln | Lys | Ser | Glu | |
| 9920 | | | | | 9925 | | | | | 9930 | | | | | |

| gcc | ggt | tcc | ctt | cct | tcc | gtg | aga | gtt | cct | ccc | acc | aac | gac | atg | 29844 |
|---|---|---|---|---|---|---|---|---|---|---|---|---|---|---|---|
| Ala | Gly | Ser | Leu | Pro | Ser | Val | Arg | Val | Pro | Pro | Thr | Asn | Asp | Met | |
| 9935 | | | | | 9940 | | | | | 9945 | | | | | |

| gag | agg | ata | ttg | tgc | gaa | gag | ttt | gcc | gac | gtt | ctc | ggc | gtg | gag | 29889 |
|---|---|---|---|---|---|---|---|---|---|---|---|---|---|---|---|
| Glu | Arg | Ile | Leu | Cys | Glu | Glu | Phe | Ala | Asp | Val | Leu | Gly | Val | Glu | |
| 9950 | | | | | 9955 | | | | | 9960 | | | | | |

| gtc | ggc | att | acc | gac | aac | ttc | ttc | gac | ttt | gga | gga | cac | tca | ctc | 29934 |
|---|---|---|---|---|---|---|---|---|---|---|---|---|---|---|---|
| Val | Gly | Ile | Thr | Asp | Asn | Phe | Phe | Asp | Phe | Gly | Gly | His | Ser | Leu | |
| 9965 | | | | | 9970 | | | | | 9975 | | | | | |

| | | | | | | | | | | | | | | |
|---|---|---|---|---|---|---|---|---|---|---|---|---|---|---|
| atg | gca | acc | aag | ctc | gca | gcg | cgt | att | agt | cgc | cgc | gtg | aac | gcc | 29979 |
| Met | Ala | Thr | Lys | Leu | Ala | Ala | Arg | Ile | Ser | Arg | Arg | Val | Asn | Ala | |
| | 9980 | | | | 9985 | | | | | 9990 | | | | | | cga gta tcc gtc aag agc gtt ttc gac cac ccc gtc ctt gtt gac 30024
Arg Val Ser Val Lys Ser Val Phe Asp His Pro Val Leu Val Asp
    9995                10000              10005 ctt gca tcc act att aaa caa gac tca atc atg cac aaa cct atc 30069
Leu Ala Ser Thr Ile Lys Gln Asp Ser Ile Met His Lys Pro Ile
    10010               10015              10020 cca cag acc gcc tac acc ggg ccc gtg gaa cag tcc ttt gcc caa 30114
Pro Gln Thr Ala Tyr Thr Gly Pro Val Glu Gln Ser Phe Ala Gln
    10025               10030              10035 ggc cgt ctc tgg ttc tta gac cag ctt aac ttc ggt gcc tcg tgg 30159
Gly Arg Leu Trp Phe Leu Asp Gln Leu Asn Phe Gly Ala Ser Trp
    10040               10045              10050 tac ctc atg cct ctc gcg cta cgc ttg caa gga tct ctt cac gtc 30204
Tyr Leu Met Pro Leu Ala Leu Arg Leu Gln Gly Ser Leu His Val
    10055               10060              10065 aag tcc ctc act act gcg ttg ttt gca cta gaa cag cgt cat gag 30249
Lys Ser Leu Thr Thr Ala Leu Phe Ala Leu Glu Gln Arg His Glu
    10070               10075              10080 acc ctg aga aca aca ttt gag gaa caa gat ggc gtg ggc atc caa 30294
Thr Leu Arg Thr Thr Phe Glu Glu Gln Asp Gly Val Gly Ile Gln
    10085               10090              10095 att gta cac cct gcc aac aag aaa gac ctt aga atc ctg gac gta 30339
Ile Val His Pro Ala Asn Lys Lys Asp Leu Arg Ile Leu Asp Val
    10100               10105              10110 tct aaa gag caa aac agc gac tat gct aaa gtc ctg cac aag gag 30384
Ser Lys Glu Gln Asn Ser Asp Tyr Ala Lys Val Leu His Lys Glu
    10115               10120              10125 cgc acg atc ccc att gat ctg act tcg gag cca ggt tgg agg gta 30429
Arg Thr Ile Pro Ile Asp Leu Thr Ser Glu Pro Gly Trp Arg Val
    10130               10135              10140 tcg ctc att cgc ttg ggc gaa gac gat cat atc ctc tcc atc gtc 30474
Ser Leu Ile Arg Leu Gly Glu Asp Asp His Ile Leu Ser Ile Val
    10145               10150              10155 atg cat cac att atc tca gat gga tgg tcc gtg gat gtt ctg cgc 30519
Met His His Ile Ile Ser Asp Gly Trp Ser Val Asp Val Leu Arg
    10160               10165              10170 caa gaa ctg aag caa ttc tat act gct gcg ctc aag ggt caa gat 30564
Gln Glu Leu Lys Gln Phe Tyr Thr Ala Ala Leu Lys Gly Gln Asp
    10175               10180              10185 cct ctg gcg cag att gac gct ctg cca atc caa tac cgc gac ttc 30609
Pro Leu Ala Gln Ile Asp Ala Leu Pro Ile Gln Tyr Arg Asp Phe
    10190               10195              10200 tca ttg tgg cag aag ttg cca gat caa gtt gct gag cac caa cga 30654
Ser Leu Trp Gln Lys Leu Pro Asp Gln Val Ala Glu His Gln Arg
    10205               10210              10215 cag ctc gag tac tgg gcc gag cag ttg gca gat aac act cca gcc 30699
Gln Leu Glu Tyr Trp Ala Glu Gln Leu Ala Asp Asn Thr Pro Ala
    10220               10225              10230 gag ctc ctg acc gat cta ccc cgg ccg gac gtc cta tct ggc aag 30744
Glu Leu Leu Thr Asp Leu Pro Arg Pro Asp Val Leu Ser Gly Lys
    10235               10240              10245 gct gga gcc gta caa ctc act atc gat ggt ccg gtg ttc gat cag 30789
Ala Gly Ala Val Gln Leu Thr Ile Asp Gly Pro Val Phe Asp Gln
    10250               10255              10260 ctc cag gcg ttc tgc cga gca cat cag aca aca atg ttc acg gtt 30834
Leu Gln Ala Phe Cys Arg Ala His Gln Thr Thr Met Phe Thr Val
    10265               10270              10275

```
ctg ctg gca gtc ttc cga aca act cat tac cgc ttg aca ggc gct    30879
Leu Leu Ala Val Phe Arg Thr Thr His Tyr Arg Leu Thr Gly Ala
    10280           10285               10290 act gac gcc act atc ggt acc ccg att gcc aac cgt aac agg ccg    30924
Thr Asp Ala Thr Ile Gly Thr Pro Ile Ala Asn Arg Asn Arg Pro
    10295           10300               10305 gaa ctt gaa aga ttg gtg ggc ttc ttc gtc aat act caa tgt atc    30969
Glu Leu Glu Arg Leu Val Gly Phe Phe Val Asn Thr Gln Cys Ile
    10310           10315               10320 agg atc acg gta gac gtg gag gat aca ttt gaa gca ttg gta cga    31014
Arg Ile Thr Val Asp Val Glu Asp Thr Phe Glu Ala Leu Val Arg
    10325           10330               10335 caa gtc cat tct acg tcg acg acg gcc ttt gcc aat cag gat gtt    31059
Gln Val His Ser Thr Ser Thr Thr Ala Phe Ala Asn Gln Asp Val
    10340           10345               10350 ccg ttc gag cga att gtg tcc aca att cta cca ggc tcg cga gac    31104
Pro Phe Glu Arg Ile Val Ser Thr Ile Leu Pro Gly Ser Arg Asp
    10355           10360               10365 gcc tcc cgg aat cct ctt gct caa ctc atg ttt gcc gtc cat tct    31149
Ala Ser Arg Asn Pro Leu Ala Gln Leu Met Phe Ala Val His Ser
    10370           10375               10380 cag agg gat atc agt aaa ttc cag ctt gaa ggc cta gac acg aag    31194
Gln Arg Asp Ile Ser Lys Phe Gln Leu Glu Gly Leu Asp Thr Lys
    10385           10390               10395 cct atc ccc acg gct gca tcc act cgc ttt gac att gag ttc cat    31239
Pro Ile Pro Thr Ala Ala Ser Thr Arg Phe Asp Ile Glu Phe His
    10400           10405               10410 atg ttt cag cag gca gaa cgc ctt tct gga agg gtt ctt ttc gca    31284
Met Phe Gln Gln Ala Glu Arg Leu Ser Gly Arg Val Leu Phe Ala
    10415           10420               10425 gag gat ctg ttc gaa cta gag act atc caa gga atg gtt gta atc    31329
Glu Asp Leu Phe Glu Leu Glu Thr Ile Gln Gly Met Val Val Ile
    10430           10435               10440 ttc aaa gag att ctc cga aga ggc ctt gaa acg cca cag acc cca    31374
Phe Lys Glu Ile Leu Arg Arg Gly Leu Glu Thr Pro Gln Thr Pro
    10445           10450               10455 ctt gcg gtt ctc cca ctc act gat ggg ctg gca cat ctt cgc agt    31419
Leu Ala Val Leu Pro Leu Thr Asp Gly Leu Ala His Leu Arg Ser
    10460           10465               10470 caa ggc cta ctt gag att gag agg cca gag tat ccg cgc gac tca    31464
Gln Gly Leu Leu Glu Ile Glu Arg Pro Glu Tyr Pro Arg Asp Ser
    10475           10480               10485 agc atg atc gac gtt ttc cgt gct cag gtt gcc gca tgc cct gac    31509
Ser Met Ile Asp Val Phe Arg Ala Gln Val Ala Ala Cys Pro Asp
    10490           10495               10500 gcg att gcg gtc aaa gac tcc acc tca cag ctt acc tac agt caa    31554
Ala Ile Ala Val Lys Asp Ser Thr Ser Gln Leu Thr Tyr Ser Gln
    10505           10510               10515 ctc gac gac caa tct gat aag atc act gcc tgg ctt ctc caa cgc    31599
Leu Asp Asp Gln Ser Asp Lys Ile Thr Ala Trp Leu Leu Gln Arg
    10520           10525               10530 aaa atc cca gct gag agt ttg gtt gct gta tac gct cca aga acg    31644
Lys Ile Pro Ala Glu Ser Leu Val Ala Val Tyr Ala Pro Arg Thr
    10535           10540               10545 tgt caa acc atc att aca ttc ttt ggt att ctc aag gct aat cta    31689
Cys Gln Thr Ile Ile Thr Phe Phe Gly Ile Leu Lys Ala Asn Leu
    10550           10555               10560 gcc tac ctt cca ttg gat atc aat gtc cca gcc gcc cgt att gag    31734
Ala Tyr Leu Pro Leu Asp Ile Asn Val Pro Ala Ala Arg Ile Glu
    10565           10570               10575
```

| | | | | | | | | | | | |
|---|---|---|---|---|---|---|---|---|---|---|---|
| gca | atc | tta | tca | acc | ata | tct | ggt | cac | aag | cta | gta | ctg | ctt | ggg | 31779 |
| Ala | Ile | Leu | Ser | Thr | Ile | Ser | Gly | His | Lys | Leu | Val | Leu | Leu | Gly | |
| | 10580 | | | | 10585 | | | | 10590 | | | | | | |
| tct | caa | gtc | tcc | gct | cct | gcg | gta | caa | ttg | aag | gac | gtc | gaa | tat | 31824 |
| Ser | Gln | Val | Ser | Ala | Pro | Ala | Val | Gln | Leu | Lys | Asp | Val | Glu | Tyr | |
| | | 10595 | | | | 10600 | | | | 10605 | | | | | |
| gtt | tgg | att | gat | gaa | gcc | atg | gct | gag | act | gtt | cgt | aca | tgc | acc | 31869 |
| Val | Trp | Ile | Asp | Glu | Ala | Met | Ala | Glu | Thr | Val | Arg | Thr | Cys | Thr | |
| | 10610 | | | | 10615 | | | | 10620 | | | | | | |
| agc | ccc | gaa | cct | tct | gcc | aca | agt | ctt | gca | tac | gtc | atc | ttc | aca | 31914 |
| Ser | Pro | Glu | Pro | Ser | Ala | Thr | Ser | Leu | Ala | Tyr | Val | Ile | Phe | Thr | |
| | | 10625 | | | | 10630 | | | | 10635 | | | | | |
| tcc | gga | tct | aca | ggt | cta | ccc | aag | ggc | gtc | aag | gtc | gag | cac | cgt | 31959 |
| Ser | Gly | Ser | Thr | Gly | Leu | Pro | Lys | Gly | Val | Lys | Val | Glu | His | Arg | |
| | 10640 | | | | 10645 | | | | 10650 | | | | | | |
| ggt | gtc | gta | cgt | ctc | gtc | aag | cag | agt | aat | gtg | gta | gca | aag | atg | 32004 |
| Gly | Val | Val | Arg | Leu | Val | Lys | Gln | Ser | Asn | Val | Val | Ala | Lys | Met | |
| | 10655 | | | | 10660 | | | | 10665 | | | | | | |
| cct | caa | gca | gca | cgc | gtt | gcc | cat | cta | tca | aat | atc | gct | ttc | gac | 32049 |
| Pro | Gln | Ala | Ala | Arg | Val | Ala | His | Leu | Ser | Asn | Ile | Ala | Phe | Asp | |
| | 10670 | | | | 10675 | | | | 10680 | | | | | | |
| gct | gcc | acg | tgg | gag | atc | tat | gct | gcg | ctc | ctt | aac | ggc | ggc | tct | 32094 |
| Ala | Ala | Thr | Trp | Glu | Ile | Tyr | Ala | Ala | Leu | Leu | Asn | Gly | Gly | Ser | |
| | 10685 | | | | 10690 | | | | 10695 | | | | | | |
| ctc | ata | tgt | att | gac | tat | ttc | act | aca | ttg | gat | agc | aag | gag | ctt | 32139 |
| Leu | Ile | Cys | Ile | Asp | Tyr | Phe | Thr | Thr | Leu | Asp | Ser | Lys | Glu | Leu | |
| | 10700 | | | | 10705 | | | | 10710 | | | | | | |
| gaa | gcc | gtg | ttt | gca | cga | gaa | aaa | atc | caa | gcg | gcc | atg | ctt | ccg | 32184 |
| Glu | Ala | Val | Phe | Ala | Arg | Glu | Lys | Ile | Gln | Ala | Ala | Met | Leu | Pro | |
| | 10715 | | | | 10720 | | | | 10725 | | | | | | |
| ccg | gcg | ctg | ctc | aag | cag | tgt | ttg | gtc | aac | atc | cct | gcg | act | atc | 32229 |
| Pro | Ala | Leu | Leu | Lys | Gln | Cys | Leu | Val | Asn | Ile | Pro | Ala | Thr | Ile | |
| | 10730 | | | | 10735 | | | | 10740 | | | | | | |
| agc | gcc | tta | gac | gtg | gta | ctt | gca | gcg | ggc | gac | cgt | ttc | gac | agg | 32274 |
| Ser | Ala | Leu | Asp | Val | Val | Leu | Ala | Ala | Gly | Asp | Arg | Phe | Asp | Arg | |
| | 10745 | | | | 10750 | | | | 10755 | | | | | | |
| cgc | gac | gcg | gcg | gcg | aca | caa | gcg | ctc | gtc | gga | ggc | tgt | gtc | tac | 32319 |
| Arg | Asp | Ala | Ala | Ala | Thr | Gln | Ala | Leu | Val | Gly | Gly | Cys | Val | Tyr | |
| | 10760 | | | | 10765 | | | | 10770 | | | | | | |
| aac | gcg | tac | ggc | ccc | acc | gag | aac | acg | act | ctc | agt | acc | atc | tac | 32364 |
| Asn | Ala | Tyr | Gly | Pro | Thr | Glu | Asn | Thr | Thr | Leu | Ser | Thr | Ile | Tyr | |
| | 10775 | | | | 10780 | | | | 10785 | | | | | | |
| aat | gtg | gtc | aaa | ggc | gat | gcc | aac | gtc | aac | gga | gtt | cca | atc | ggt | 32409 |
| Asn | Val | Val | Lys | Gly | Asp | Ala | Asn | Val | Asn | Gly | Val | Pro | Ile | Gly | |
| | 10790 | | | | 10795 | | | | 10800 | | | | | | |
| cgc | cct | gtt | agc | aac | tca | ggt | gcc | tac | atc | atg | gat | ccc | aat | caa | 32454 |
| Arg | Pro | Val | Ser | Asn | Ser | Gly | Ala | Tyr | Ile | Met | Asp | Pro | Asn | Gln | |
| | 10805 | | | | 10810 | | | | 10815 | | | | | | |
| cag | ctg | gtc | ccc | aag | ggt | gtt | atg | gga | gag | ctt | atc | gtg | gta | gga | 32499 |
| Gln | Leu | Val | Pro | Lys | Gly | Val | Met | Gly | Glu | Leu | Ile | Val | Val | Gly | |
| | 10820 | | | | 10825 | | | | 10830 | | | | | | |
| gac | gga | gtc | gct | cga | gga | tat | acc | gat | cca | gca | cta | gat | gtc | aat | 32544 |
| Asp | Gly | Val | Ala | Arg | Gly | Tyr | Thr | Asp | Pro | Ala | Leu | Asp | Val | Asn | |
| | 10835 | | | | 10840 | | | | 10845 | | | | | | |
| cgt | ttc | att | gag | atc | gcg | att | gat | ggt | gat | cag | gcg | gtg | cgc | gcc | 32589 |
| Arg | Phe | Ile | Glu | Ile | Ala | Ile | Asp | Gly | Asp | Gln | Ala | Val | Arg | Ala | |
| | 10850 | | | | 10855 | | | | 10860 | | | | | | |
| tat | cga | aca | ggt | gat | cgc | gct | cgt | tac | cga | cct | aaa | gac | ggt | caa | 32634 |
| Tyr | Arg | Thr | Gly | Asp | Arg | Ala | Arg | Tyr | Arg | Pro | Lys | Asp | Gly | Gln | |
| | 10865 | | | | 10870 | | | | 10875 | | | | | | |

| | | | | | | | | | | | |
|---|---|---|---|---|---|---|---|---|---|---|---|
| atc | gag | ttc | ttc | ggc | cgc | atg | gac | caa | caa | atc | aag | att | cgt | ggc | 32679 |
| Ile | Glu | Phe | Phe | Gly | Arg | Met | Asp | Gln | Gln | Ile | Lys | Ile | Arg | Gly | |
| | 10880 | | | | 10885 | | | | 10890 | | | | | | |

| cat | cgt | att | gaa | cca | gcc | gaa | gtg | gag | cac | gcc | gta | ctt | gat | aac | 32724 |
| His | Arg | Ile | Glu | Pro | Ala | Glu | Val | Glu | His | Ala | Val | Leu | Asp | Asn | |
| | 10895 | | | | 10900 | | | | 10905 | | | | | | |

| agt | atg | gtg | caa | gat | gct | gcc | gta | att | act | cgc | aag | caa | gat | cag | 32769 |
| Ser | Met | Val | Gln | Asp | Ala | Ala | Val | Ile | Thr | Arg | Lys | Gln | Asp | Gln | |
| | 10910 | | | | 10915 | | | | 10920 | | | | | | |

| gag | cta | gag | atg | atc | gct | ttt | gtt | act | aca | cgt | agc | gat | aag | gaa | 32814 |
| Glu | Leu | Glu | Met | Ile | Ala | Phe | Val | Thr | Thr | Arg | Ser | Asp | Lys | Glu | |
| | 10925 | | | | 10930 | | | | 10935 | | | | | | |

| att | gac | aac | gac | gaa | gcc | agc | aac | caa | gtc | gaa | gat | tgg | ggt | aac | 32859 |
| Ile | Asp | Asn | Asp | Glu | Ala | Ser | Asn | Gln | Val | Glu | Asp | Trp | Gly | Asn | |
| | 10940 | | | | 10945 | | | | 10950 | | | | | | |

| cag | ttt | gag | agt | aac | ata | tat | gct | gag | atc | gaa | gag | atc | gat | tcc | 32904 |
| Gln | Phe | Glu | Ser | Asn | Ile | Tyr | Ala | Glu | Ile | Glu | Glu | Ile | Asp | Ser | |
| | 10955 | | | | 10960 | | | | 10965 | | | | | | |

| tct | gcc | att | ggc | aaa | gac | ttc | atg | ggc | tgg | acg | tcc | atg | tac | gac | 32949 |
| Ser | Ala | Ile | Gly | Lys | Asp | Phe | Met | Gly | Trp | Thr | Ser | Met | Tyr | Asp | |
| | 10970 | | | | 10975 | | | | 10980 | | | | | | |

| ggt | agt | gct | atc | gac | aaa | gac | gaa | atg | cag | gag | tgg | cta | gac | gac | 32994 |
| Gly | Ser | Ala | Ile | Asp | Lys | Asp | Glu | Met | Gln | Glu | Trp | Leu | Asp | Asp | |
| | 10985 | | | | 10990 | | | | 10995 | | | | | | |

| act | atg | agc | aca | ctg | ctc | gac | ggt | cga | caa | cca | ggc | cac | gta | ctc | 33039 |
| Thr | Met | Ser | Thr | Leu | Leu | Asp | Gly | Arg | Gln | Pro | Gly | His | Val | Leu | |
| | 11000 | | | | 11005 | | | | 11010 | | | | | | |

| gaa | atc | ggt | act | ggt | act | ggc | atg | atc | ttg | ttc | aac | cta | gcc | gag | 33084 |
| Glu | Ile | Gly | Thr | Gly | Thr | Gly | Met | Ile | Leu | Phe | Asn | Leu | Ala | Glu | |
| | 11015 | | | | 11020 | | | | 11025 | | | | | | |

| aga | atg | gga | ttg | aag | agc | tac | gta | ggc | ctc | gat | ccc | tcg | gag | aag | 33129 |
| Arg | Met | Gly | Leu | Lys | Ser | Tyr | Val | Gly | Leu | Asp | Pro | Ser | Glu | Lys | |
| | 11030 | | | | 11035 | | | | 11040 | | | | | | |

| gca | acc | tca | ttc | gtt | aaa | cag | gcc | atc | aag | tct | cgc | cca | tct | ctg | 33174 |
| Ala | Thr | Ser | Phe | Val | Lys | Gln | Ala | Ile | Lys | Ser | Arg | Pro | Ser | Leu | |
| | 11045 | | | | 11050 | | | | 11055 | | | | | | |

| gca | ggc | aag | gct | gag | gtt | cac | gtc | ggc | aca | gca | aca | gat | gtg | gct | 33219 |
| Ala | Gly | Lys | Ala | Glu | Val | His | Val | Gly | Thr | Ala | Thr | Asp | Val | Ala | |
| | 11060 | | | | 11065 | | | | 11070 | | | | | | |

| cga | atg | cga | gat | ctg | cac | ccc | gaa | gtg | gtg | gtt | atc | aat | tcg | gta | 33264 |
| Arg | Met | Arg | Asp | Leu | His | Pro | Glu | Val | Val | Val | Ile | Asn | Ser | Val | |
| | 11075 | | | | 11080 | | | | 11085 | | | | | | |

| gct | caa | tac | ttt | cca | tcg | cct | gag | tat | ctg | gcc | gat | gtc | gtt | ggc | 33309 |
| Ala | Gln | Tyr | Phe | Pro | Ser | Pro | Glu | Tyr | Leu | Ala | Asp | Val | Val | Gly | |
| | 11090 | | | | 11095 | | | | 11100 | | | | | | |

| gct | ttg | gtt | cgc | att | cca | ggc | gtg | aaa | cga | ctc | ttc | ttc | ggc | gac | 33354 |
| Ala | Leu | Val | Arg | Ile | Pro | Gly | Val | Lys | Arg | Leu | Phe | Phe | Gly | Asp | |
| | 11105 | | | | 11110 | | | | 11115 | | | | | | |

| ata | cga | tcc | tac | gct | act | aat | aat | cat | ttc | ctt | gca | gcc | aga | gcc | 33399 |
| Ile | Arg | Ser | Tyr | Ala | Thr | Asn | Asn | His | Phe | Leu | Ala | Ala | Arg | Ala | |
| | 11120 | | | | 11125 | | | | 11130 | | | | | | |

| cta | cac | aag | cta | gga | gaa | aag | gca | act | agg | gat | act | gta | cga | agc | 33444 |
| Leu | His | Lys | Leu | Gly | Glu | Lys | Ala | Thr | Arg | Asp | Thr | Val | Arg | Ser | |
| | 11135 | | | | 11140 | | | | 11145 | | | | | | |

| aaa | atg | gct | gag | ctc | gaa | ggc | tac | gag | gag | gaa | ctg | ctt | gtc | gac | 33489 |
| Lys | Met | Ala | Glu | Leu | Glu | Gly | Tyr | Glu | Glu | Glu | Leu | Leu | Val | Asp | |
| | 11150 | | | | 11155 | | | | 11160 | | | | | | |

| cca | aca | ttc | ttc | acc | agt | cta | acg | gcc | aag | ctt | cac | ggc | cag | gtc | 33534 |
| Pro | Thr | Phe | Phe | Thr | Ser | Leu | Thr | Ala | Lys | Leu | His | Gly | Gln | Val | |
| | 11165 | | | | 11170 | | | | 11175 | | | | | | |

| | | | | | | | | | | | | | |
|---|---|---|---|---|---|---|---|---|---|---|---|---|---|
| gag | cac | gtt | gag | atc | cta | cct | aag | cgt | atg | cag | gcc | acc | aac | gaa | 33579 |
| Glu | His | Val | Glu | Ile | Leu | Pro | Lys | Arg | Met | Gln | Ala | Thr | Asn | Glu | |
| | 11180 | | | | 11185 | | | | 11190 | | | | | | |
| ctc | agc | gca | tac | cga | tac | gcg | gct | ata | gtc | tac | atc | cgt | gat | cca | 33624 |
| Leu | Ser | Ala | Tyr | Arg | Tyr | Ala | Ala | Ile | Val | Tyr | Ile | Arg | Asp | Pro | |
| | 11195 | | | | 11200 | | | | 11205 | | | | | | |
| aaa | cga | gcg | cag | act | gtg | cag | acg | gtc | aaa | tcg | gac | gcc | tgg | gtc | 33669 |
| Lys | Arg | Ala | Gln | Thr | Val | Gln | Thr | Val | Lys | Ser | Asp | Ala | Trp | Val | |
| | 11210 | | | | 11215 | | | | 11220 | | | | | | |
| gat | ttc | agc | acc | tct | caa | atg | gac | cgc | agt | gtg | ctc | gtc | agt | ctc | 33714 |
| Asp | Phe | Ser | Thr | Ser | Gln | Met | Asp | Arg | Ser | Val | Leu | Val | Ser | Leu | |
| | 11225 | | | | 11230 | | | | 11235 | | | | | | |
| tta | cag | agc | tca | gat | gct | gaa | gct | atc | gct | gtc | agc | aat | att | ccc | 33759 |
| Leu | Gln | Ser | Ser | Asp | Ala | Glu | Ala | Ile | Ala | Val | Ser | Asn | Ile | Pro | |
| | 11240 | | | | 11245 | | | | 11250 | | | | | | |
| tac | agc | aag | acg | atc | gtg | gcg | cgg | cat | atc | gtt | gag | tca | ctc | agc | 33804 |
| Tyr | Ser | Lys | Thr | Ile | Val | Ala | Arg | His | Ile | Val | Glu | Ser | Leu | Ser | |
| | 11255 | | | | 11260 | | | | 11265 | | | | | | |
| gca | gag | gat | tca | caa | gag | atg | ctg | gac | ggc | cct | gct | tgg | atc | tca | 33849 |
| Ala | Glu | Asp | Ser | Gln | Glu | Met | Leu | Asp | Gly | Pro | Ala | Trp | Ile | Ser | |
| | 11270 | | | | 11275 | | | | 11280 | | | | | | |
| gca | gtc | cgc | tcc | agc | gct | gaa | cag | tgc | gca | tcc | ttg | tct | gcg | atc | 33894 |
| Ala | Val | Arg | Ser | Ser | Ala | Glu | Gln | Cys | Ala | Ser | Leu | Ser | Ala | Ile | |
| | 11285 | | | | 11290 | | | | 11295 | | | | | | |
| gac | ctt | gta | cag | gtt | gct | aaa | gag | aac | ggc | ttc | cga | gtg | gag | ctc | 33939 |
| Asp | Leu | Val | Gln | Val | Ala | Lys | Glu | Asn | Gly | Phe | Arg | Val | Glu | Leu | |
| | 11300 | | | | 11305 | | | | 11310 | | | | | | |
| agc | tgc | gca | cga | cag | cgg | tct | cat | aat | gga | gcg | att | gat | gcg | gta | 33984 |
| Ser | Cys | Ala | Arg | Gln | Arg | Ser | His | Asn | Gly | Ala | Ile | Asp | Ala | Val | |
| | 11315 | | | | 11320 | | | | 11325 | | | | | | |
| ttc | cat | cac | tac | aag | cct | gcg | caa | gaa | ggt | agc | cgt | gtc | ttg | cta | 34029 |
| Phe | His | His | Tyr | Lys | Pro | Ala | Gln | Glu | Gly | Ser | Arg | Val | Leu | Leu | |
| | 11330 | | | | 11335 | | | | 11340 | | | | | | |
| caa | ttt | cca | acc | gac | aat | cac | atc | cgg | gca | ggc | tcg | ctt | acg | aac | 34074 |
| Gln | Phe | Pro | Thr | Asp | Asn | His | Ile | Arg | Ala | Gly | Ser | Leu | Thr | Asn | |
| | 11345 | | | | 11350 | | | | 11355 | | | | | | |
| cga | cca | cta | caa | cgt | ctc | gag | agt | cga | agg | gtg | gag | aca | aaa | ctc | 34119 |
| Arg | Pro | Leu | Gln | Arg | Leu | Glu | Ser | Arg | Arg | Val | Glu | Thr | Lys | Leu | |
| | 11360 | | | | 11365 | | | | 11370 | | | | | | |
| aag | gaa | cac | ctt | ttt | agt | gtg | ctt | cca | tcg | tac | atg | att | cca | tca | 34164 |
| Lys | Glu | His | Leu | Phe | Ser | Val | Leu | Pro | Ser | Tyr | Met | Ile | Pro | Ser | |
| | 11375 | | | | 11380 | | | | 11385 | | | | | | |
| cat | att | gtg | atg | gtt | gac | cag | atg | cct | ctg | aat | gcg | aac | ggc | aag | 34209 |
| His | Ile | Val | Met | Val | Asp | Gln | Met | Pro | Leu | Asn | Ala | Asn | Gly | Lys | |
| | 11390 | | | | 11395 | | | | 11400 | | | | | | |
| gtt | gac | cgg | aaa | gcc | ctg | gca | caa | aga | gct | gaa | gca | gtt | ctc | aag | 34254 |
| Val | Asp | Arg | Lys | Ala | Leu | Ala | Gln | Arg | Ala | Glu | Ala | Val | Leu | Lys | |
| | 11405 | | | | 11410 | | | | 11415 | | | | | | |
| atc | gag | aaa | cca | gct | tct | gag | aga | gtc | agt | gca | cgg | aac | gaa | gtg | 34299 |
| Ile | Glu | Lys | Pro | Ala | Ser | Glu | Arg | Val | Ser | Ala | Arg | Asn | Glu | Val | |
| | 11420 | | | | 11425 | | | | 11430 | | | | | | |
| gaa | gct | gta | ctg | tgt | gaa | gag | ttc | acc | gat | gtc | ctt | ggt | gtg | gag | 34344 |
| Glu | Ala | Val | Leu | Cys | Glu | Glu | Phe | Thr | Asp | Val | Leu | Gly | Val | Glu | |
| | 11435 | | | | 11440 | | | | 11445 | | | | | | |
| gtc | ggc | att | acc | gac | aac | ttc | ttc | gac | ctg | ggc | gga | cac | tcg | ctc | 34389 |
| Val | Gly | Ile | Thr | Asp | Asn | Phe | Phe | Asp | Leu | Gly | Gly | His | Ser | Leu | |
| | 11450 | | | | 11455 | | | | 11460 | | | | | | |
| atg | gcc | acc | aaa | ctc | gca | gcc | cgt | atc | agc | aag | cac | ctc | gac | gct | 34434 |
| Met | Ala | Thr | Lys | Leu | Ala | Ala | Arg | Ile | Ser | Lys | His | Leu | Asp | Ala | |
| | 11465 | | | | 11470 | | | | 11475 | | | | | | |

| | | | | | | | | | | | | | | |
|---|---|---|---|---|---|---|---|---|---|---|---|---|---|---|
| cgc | gtc | tct | gtc | aag | gac | gtt | ttt | gat | tac | cct | gtc | gtt | gct | gat | 34479 |
| Arg | Val | Ser | Val | Lys | Asp | Val | Phe | Asp | Tyr | Pro | Val | Val | Ala | Asp | |
| | 11480 | | | | | 11485 | | | | | 11490 | | | | |

| | | | | | | | | | | | | | | |
|---|---|---|---|---|---|---|---|---|---|---|---|---|---|---|
| cta | gca | gcg | tca | att | gaa | cga | aac | tcg | atc | cct | cat | aac | ccc | att | 34524 |
| Leu | Ala | Ala | Ser | Ile | Glu | Arg | Asn | Ser | Ile | Pro | His | Asn | Pro | Ile | |
| | 11495 | | | | | 11500 | | | | | 11505 | | | | |

| | | | | | | | | | | | | | | |
|---|---|---|---|---|---|---|---|---|---|---|---|---|---|---|
| ccc | tcg | acc | aac | tac | tct | gga | ccc | gtg | gag | caa | tct | ttc | gcg | caa | 34569 |
| Pro | Ser | Thr | Asn | Tyr | Ser | Gly | Pro | Val | Glu | Gln | Ser | Phe | Ala | Gln | |
| | 11510 | | | | | 11515 | | | | | 11520 | | | | |

| | | | | | | | | | | | | | | |
|---|---|---|---|---|---|---|---|---|---|---|---|---|---|---|
| ggc | cga | ctt | tgg | ttc | ctg | gat | caa | ctg | aat | atg | ggc | gta | tcg | gaa | 34614 |
| Gly | Arg | Leu | Trp | Phe | Leu | Asp | Gln | Leu | Asn | Met | Gly | Val | Ser | Glu | |
| | 11525 | | | | | 11530 | | | | | 11535 | | | | |

| | | | | | | | | | | | | | | |
|---|---|---|---|---|---|---|---|---|---|---|---|---|---|---|
| tta | tat | cta | atg | cct | ctt | gct | cta | cgc | ctg | cgc | gga | cct | ctg | cgc | 34659 |
| Leu | Tyr | Leu | Met | Pro | Leu | Ala | Leu | Arg | Leu | Arg | Gly | Pro | Leu | Arg | |
| | 11540 | | | | | 11545 | | | | | 11550 | | | | |

| | | | | | | | | | | | | | | |
|---|---|---|---|---|---|---|---|---|---|---|---|---|---|---|
| gtt | gac | gcc | ttc | gca | gct | gca | gta | tct | gct | ctc | gag | gca | cgc | cat | 34704 |
| Val | Asp | Ala | Phe | Ala | Ala | Ala | Val | Ser | Ala | Leu | Glu | Ala | Arg | His | |
| | 11555 | | | | | 11560 | | | | | 11565 | | | | |

| | | | | | | | | | | | | | | |
|---|---|---|---|---|---|---|---|---|---|---|---|---|---|---|
| gaa | act | ctc | cga | aca | acc | ttc | atg | gat | cac | gac | ggt | gta | ggc | atg | 34749 |
| Glu | Thr | Leu | Arg | Thr | Thr | Phe | Met | Asp | His | Asp | Gly | Val | Gly | Met | |
| | 11570 | | | | | 11575 | | | | | 11580 | | | | |

| | | | | | | | | | | | | | | |
|---|---|---|---|---|---|---|---|---|---|---|---|---|---|---|
| caa | gtc | att | ctg | ccc | agt | aac | agc | aag | aaa | ctg | aga | gtc | att | gac | 34794 |
| Gln | Val | Ile | Leu | Pro | Ser | Asn | Ser | Lys | Lys | Leu | Arg | Val | Ile | Asp | |
| | 11585 | | | | | 11590 | | | | | 11595 | | | | |

| | | | | | | | | | | | | | | |
|---|---|---|---|---|---|---|---|---|---|---|---|---|---|---|
| gcg | tcc | gag | aac | gac | tat | ata | gac | atc | ctg | cga | cag | gaa | cgg | aca | 34839 |
| Ala | Ser | Glu | Asn | Asp | Tyr | Ile | Asp | Ile | Leu | Arg | Gln | Glu | Arg | Thr | |
| | 11600 | | | | | 11605 | | | | | 11610 | | | | |

| | | | | | | | | | | | | | | |
|---|---|---|---|---|---|---|---|---|---|---|---|---|---|---|
| gct | cca | ttc | aat | ctc | acg | acc | gag | cca | ggg | ttt | agg | atc | gcc | ctc | 34884 |
| Ala | Pro | Phe | Asn | Leu | Thr | Thr | Glu | Pro | Gly | Phe | Arg | Ile | Ala | Leu | |
| | 11615 | | | | | 11620 | | | | | 11625 | | | | |

| | | | | | | | | | | | | | | |
|---|---|---|---|---|---|---|---|---|---|---|---|---|---|---|
| ttg | cag | ctg | ggt | caa | acc | gac | ttc | att | ctg | tca | att | gtc | atg | cac | 34929 |
| Leu | Gln | Leu | Gly | Gln | Thr | Asp | Phe | Ile | Leu | Ser | Ile | Val | Met | His | |
| | 11630 | | | | | 11635 | | | | | 11640 | | | | |

| | | | | | | | | | | | | | | |
|---|---|---|---|---|---|---|---|---|---|---|---|---|---|---|
| cat | atc | ata | tat | gac | ggt | tgg | tct | att | gat | gtt | cta | tgc | aga | gag | 34974 |
| His | Ile | Ile | Tyr | Asp | Gly | Trp | Ser | Ile | Asp | Val | Leu | Cys | Arg | Glu | |
| | 11645 | | | | | 11650 | | | | | 11655 | | | | |

| | | | | | | | | | | | | | | |
|---|---|---|---|---|---|---|---|---|---|---|---|---|---|---|
| ctt | ggc | cga | ttc | tat | agc | gct | gca | cta | cag | ggc | cag | gat | cca | ttg | 35019 |
| Leu | Gly | Arg | Phe | Tyr | Ser | Ala | Ala | Leu | Gln | Gly | Gln | Asp | Pro | Leu | |
| | 11660 | | | | | 11665 | | | | | 11670 | | | | |

| | | | | | | | | | | | | | | |
|---|---|---|---|---|---|---|---|---|---|---|---|---|---|---|
| gcg | caa | gtg | agc | cct | ctg | cct | atc | cag | tac | cga | gat | ttc | tct | atc | 35064 |
| Ala | Gln | Val | Ser | Pro | Leu | Pro | Ile | Gln | Tyr | Arg | Asp | Phe | Ser | Ile | |
| | 11675 | | | | | 11680 | | | | | 11685 | | | | |

| | | | | | | | | | | | | | | |
|---|---|---|---|---|---|---|---|---|---|---|---|---|---|---|
| tgg | caa | aag | cgg | cca | gag | caa | gtg | gcc | gag | cat | gag | cgc | cag | cta | 35109 |
| Trp | Gln | Lys | Arg | Pro | Glu | Gln | Val | Ala | Glu | His | Glu | Arg | Gln | Leu | |
| | 11690 | | | | | 11695 | | | | | 11700 | | | | |

| | | | | | | | | | | | | | | |
|---|---|---|---|---|---|---|---|---|---|---|---|---|---|---|
| caa | tac | tgg | act | gaa | caa | ctg | gca | gat | agc | tct | cca | gct | gag | ctt | 35154 |
| Gln | Tyr | Trp | Thr | Glu | Gln | Leu | Ala | Asp | Ser | Ser | Pro | Ala | Glu | Leu | |
| | 11705 | | | | | 11710 | | | | | 11715 | | | | |

| | | | | | | | | | | | | | | |
|---|---|---|---|---|---|---|---|---|---|---|---|---|---|---|
| ctt | acg | gat | cta | ccc | cgg | cca | ttg | gtg | cca | acc | ggt | aag | gcc | ggt | 35199 |
| Leu | Thr | Asp | Leu | Pro | Arg | Pro | Leu | Val | Pro | Thr | Gly | Lys | Ala | Gly | |
| | 11720 | | | | | 11725 | | | | | 11730 | | | | |

| | | | | | | | | | | | | | | |
|---|---|---|---|---|---|---|---|---|---|---|---|---|---|---|
| atc | gtt | caa | ctc | acg | att | gag | ggc | gca | gtc | tac | gag | cgc | ctt | cga | 35244 |
| Ile | Val | Gln | Leu | Thr | Ile | Glu | Gly | Ala | Val | Tyr | Glu | Arg | Leu | Arg | |
| | 11735 | | | | | 11740 | | | | | 11745 | | | | |

| | | | | | | | | | | | | | | |
|---|---|---|---|---|---|---|---|---|---|---|---|---|---|---|
| gcc | ttt | tgc | cgt | gtt | cat | caa | acg | acc | tcg | ttc | gct | gta | ctc | ctc | 35289 |
| Ala | Phe | Cys | Arg | Val | His | Gln | Thr | Thr | Ser | Phe | Ala | Val | Leu | Leu | |
| | 11750 | | | | | 11755 | | | | | 11760 | | | | |

| | | | | | | | | | | | | | | |
|---|---|---|---|---|---|---|---|---|---|---|---|---|---|---|
| gca | gcc | ttc | cgt | gcg | acc | cac | tac | cgt | ctc | acg | ggc | gct | gag | gat | 35334 |
| Ala | Ala | Phe | Arg | Ala | Thr | His | Tyr | Arg | Leu | Thr | Gly | Ala | Glu | Asp | |
| | 11765 | | | | | 11770 | | | | | 11775 | | | | |

```
gct acc atc ggc tct cca att gct aat cgt aac cgc cca gaa cta    35379
Ala Thr Ile Gly Ser Pro Ile Ala Asn Arg Asn Arg Pro Glu Leu
    11780               11785               11790 gaa agt ctg att ggc ttc ttt gtc aat acc cag tgt ata cgc gtg    35424
Glu Ser Leu Ile Gly Phe Phe Val Asn Thr Gln Cys Ile Arg Val
    11795               11800               11805 aca atc aga gag gac gat acc ttc gac aaa ttg gtg cag caa gtc    35469
Thr Ile Arg Glu Asp Asp Thr Phe Asp Lys Leu Val Gln Gln Val
    11810               11815               11820 cgg gca acg aca aca gcc gcg cag gtc aac cag gat gtc cca ttc    35514
Arg Ala Thr Thr Thr Ala Ala Gln Val Asn Gln Asp Val Pro Phe
    11825               11830               11835 gaa cgc atc gtc tca gct ctg atg cct ggc tca aga gac acg tcc    35559
Glu Arg Ile Val Ser Ala Leu Met Pro Gly Ser Arg Asp Thr Ser
    11840               11845               11850 cga aat cca cta gtg cag ctc agc ttt gct ctt cac tca cag cat    35604
Arg Asn Pro Leu Val Gln Leu Ser Phe Ala Leu His Ser Gln His
    11855               11860               11865 gac ctt gga aga atc gat ctc cag gat ctg aca gga gaa gct ctt    35649
Asp Leu Gly Arg Ile Asp Leu Gln Asp Leu Thr Gly Glu Ala Leu
    11870               11875               11880 ccc aca cca gtg ttc acc aga ctg gat gta gag ttc cat ctt ttc    35694
Pro Thr Pro Val Phe Thr Arg Leu Asp Val Glu Phe His Leu Phe
    11885               11890               11895 cag caa gct gag aag ttc ggt ggt agc gta ttg ttt gca aca gac    35739
Gln Gln Ala Glu Lys Phe Gly Gly Ser Val Leu Phe Ala Thr Asp
    11900               11905               11910 ttg ttt gag ccg gag act att caa gga ctg gtc tcc gtc ttc cag    35784
Leu Phe Glu Pro Glu Thr Ile Gln Gly Leu Val Ser Val Phe Gln
    11915               11920               11925 gag gtc tta cgc cga gga ctt gag caa ccc caa acg cct att gca    35829
Glu Val Leu Arg Arg Gly Leu Glu Gln Pro Gln Thr Pro Ile Ala
    11930               11935               11940 gtt ctg ccc ctt gac aac gcg tcc gag gat ctt cgg agc atg ggt    35874
Val Leu Pro Leu Asp Asn Ala Ser Glu Asp Leu Arg Ser Met Gly
    11945               11950               11955 ctg ctt caa atg gag aga acc aac tat cca cgg gac tct agt gtg    35919
Leu Leu Gln Met Glu Arg Thr Asn Tyr Pro Arg Asp Ser Ser Val
    11960               11965               11970 gtt gat gtc ttc cgt gat cag gtg gca gcc aat cct aga gca ata    35964
Val Asp Val Phe Arg Asp Gln Val Ala Ala Asn Pro Arg Ala Ile
    11975               11980               11985 gcc gtc aag gat tca gtc tta gag ctg acc tac gct cag ctg gac    36009
Ala Val Lys Asp Ser Val Leu Glu Leu Thr Tyr Ala Gln Leu Asp
    11990               11995               12000 gag aaa tct gac cag ttg gct gcc tgg ctc tgc caa cat aac att    36054
Glu Lys Ser Asp Gln Leu Ala Ala Trp Leu Cys Gln His Asn Ile
    12005               12010               12015 ccg gca gag aca atc gtt ggc gtt ctg gct ccg aga tct tgc gag    36099
Pro Ala Glu Thr Ile Val Gly Val Leu Ala Pro Arg Ser Cys Glu
    12020               12025               12030 aca att att gcc ttc ctc gga atc ctc aag gcc aac ctc gca tac    36144
Thr Ile Ile Ala Phe Leu Gly Ile Leu Lys Ala Asn Leu Ala Tyr
    12035               12040               12045 ttg cca tta gac gat aat gtt cca gct gct cgc att gag act ata    36189
Leu Pro Leu Asp Asp Asn Val Pro Ala Ala Arg Ile Glu Thr Ile
    12050               12055               12060 ttg tca gca gtc cct ggc cac aca tta gtc cta ctc ggc tca cat    36234
Leu Ser Ala Val Pro Gly His Thr Leu Val Leu Leu Gly Ser His
    12065               12070               12075
```

-continued

| | | | | | | | | | | | | |
|---|---|---|---|---|---|---|---|---|---|---|---|---|
| gtg<br>Val | gct<br>Ala<br>12080 | gct<br>Ala | cca<br>Pro | agc<br>Ser | att<br>Ile<br>12085 | gga<br>Gly | tta<br>Leu | gca<br>Ala | gat<br>Asp<br>12090 | gct<br>Ala | gaa<br>Glu | ttc<br>Phe | gtt<br>Val | aat<br>Asn | 36279 |

| atc<br>Ile | aat<br>Asn<br>12095 | cat<br>His | act<br>Thr | tta<br>Leu | ggc<br>Gly<br>12100 | cac<br>His | agt<br>Ser | ttg<br>Leu | caa<br>Gln | ctc<br>Leu<br>12105 | aac<br>Asn | agc<br>Ser | aca<br>Thr | tgc<br>Cys | 36324 |

| gcc<br>Ala | aag<br>Lys<br>12110 | ttg<br>Leu | cag<br>Gln | ccc<br>Pro | tcc<br>Ser | gct<br>Ala<br>12115 | aca<br>Thr | agc<br>Ser | ctt<br>Leu | gca<br>Ala | tat<br>Tyr<br>12120 | gtt<br>Val | atc<br>Ile | ttt<br>Phe | 36369 |

| aca<br>Thr | tct<br>Ser<br>12125 | ggg<br>Gly | tcg<br>Ser | aca<br>Thr | ggc<br>Gly | aag<br>Lys<br>12130 | cca<br>Pro | aaa<br>Lys | ggc<br>Gly | gtt<br>Val | atg<br>Met<br>12135 | att<br>Ile | gag<br>Glu | cac<br>His | 36414 |

| aga<br>Arg | agc<br>Ser<br>12140 | att<br>Ile | gtg<br>Val | cga<br>Arg | ctt<br>Leu | gtc<br>Val<br>12145 | aaa<br>Lys | aac<br>Asn | agc<br>Ser | aat<br>Asn | acc<br>Thr<br>12150 | ctc<br>Leu | gcc<br>Ala | aag<br>Lys | 36459 |

| ctc<br>Leu | cca<br>Pro<br>12155 | cga<br>Arg | gcc<br>Ala | gct<br>Ala | cgt<br>Arg | gtc<br>Val<br>12160 | gct<br>Ala | cat<br>His | caa<br>Gln | ttc<br>Phe | aac<br>Asn<br>12165 | ctt<br>Leu | gcc<br>Ala | ttc<br>Phe | 36504 |

| gat<br>Asp | gca<br>Ala<br>12170 | gca<br>Ala | aac<br>Asn | tac<br>Tyr | gag<br>Glu | atc<br>Ile<br>12175 | tat<br>Tyr | ggt<br>Gly | aca<br>Thr | ctg<br>Leu | ctg<br>Leu<br>12180 | aat<br>Asn | ggg<br>Gly | ggt<br>Gly | 36549 |

| gcc<br>Ala | ctg<br>Leu<br>12185 | atc<br>Ile | tgt<br>Cys | gtc<br>Val | gat<br>Asp | tac<br>Tyr<br>12190 | tcc<br>Ser | acc<br>Thr | ctc<br>Leu | ttg<br>Leu | gac<br>Asp<br>12195 | att<br>Ile | gat<br>Asp | gct<br>Ala | 36594 |

| ctc<br>Leu | gtg<br>Val<br>12200 | gcc<br>Ala | atg<br>Met | ttc<br>Phe | aag<br>Lys | cga<br>Arg<br>12205 | gag<br>Glu | aaa<br>Lys | atc<br>Ile | acc<br>Thr | gca<br>Ala<br>12210 | tcc<br>Ser | tca<br>Ser | ctg<br>Leu | 36639 |

| tct<br>Ser | cct<br>Pro<br>12215 | ggt<br>Gly | ttg<br>Leu | ctc<br>Leu | aag<br>Lys | cag<br>Gln<br>12220 | tgt<br>Cys | gtg<br>Val | aac<br>Asn | agt<br>Ser | gca<br>Ala<br>12225 | ccc<br>Pro | gaa<br>Glu | atg<br>Met | 36684 |

| ctc<br>Leu | aag<br>Lys<br>12230 | gct<br>Ala | tta<br>Leu | cag<br>Gln | gtg<br>Val | atc<br>Ile<br>12235 | tac<br>Tyr | aca<br>Thr | ggt<br>Gly | gga<br>Gly | gac<br>Asp<br>12240 | cga<br>Arg | ctc<br>Leu | gat<br>Asp | 36729 |

| ggt<br>Gly | cgc<br>Arg<br>12245 | gat<br>Asp | gcc<br>Ala | att<br>Ile | gag<br>Glu | ttg<br>Leu<br>12250 | caa<br>Gln | gca<br>Ala | ctt<br>Leu | gtt<br>Val | ccc<br>Pro<br>12255 | gga<br>Gly | ggc<br>Gly | gtt<br>Val | 36774 |

| tac<br>Tyr | aac<br>Asn<br>12260 | atg<br>Met | tac<br>Tyr | gga<br>Gly | cct<br>Pro | acc<br>Thr<br>12265 | gaa<br>Glu | aac<br>Asn | aca<br>Thr | gtc<br>Val | atc<br>Ile<br>12270 | agc<br>Ser | acg<br>Thr | ctt<br>Leu | 36819 |

| tac<br>Tyr | aat<br>Asn<br>12275 | ctc<br>Leu | ggc<br>Gly | gac<br>Asp | aag<br>Lys | cat<br>His<br>12280 | tcg<br>Ser | tat<br>Tyr | gtg<br>Val | aat<br>Asn | ggc<br>Gly<br>12285 | gtt<br>Val | ccc<br>Pro | att<br>Ile | 36864 |

| gga<br>Gly | aca<br>Thr<br>12290 | acc<br>Thr | gtc<br>Val | agc<br>Ser | aat<br>Asn | tcg<br>Ser<br>12295 | gga<br>Gly | gcc<br>Ala | tac<br>Tyr | gtc<br>Val | atg<br>Met<br>12300 | gat<br>Asp | gcc<br>Ala | ctg<br>Leu | 36909 |

| caa<br>Gln | cag<br>Gln<br>12305 | ctc<br>Leu | gtc<br>Val | cct<br>Pro | gtc<br>Val | gga<br>Gly<br>12310 | gta<br>Val | atg<br>Met | gga<br>Gly | gag<br>Glu | ctc<br>Leu<br>12315 | gtc<br>Val | gtc<br>Val | act<br>Thr | 36954 |

| ggg<br>Gly | gat<br>Asp<br>12320 | gga<br>Gly | ctt<br>Leu | gct<br>Ala | cga<br>Arg | ggg<br>Gly<br>12325 | tac<br>Tyr | act<br>Thr | gat<br>Asp | ccg<br>Pro | gaa<br>Glu<br>12330 | cta<br>Leu | gac<br>Asp | cgc<br>Arg | 36999 |

| aac<br>Asn | cga<br>Arg<br>12335 | ttc<br>Phe | atc<br>Ile | aag<br>Lys | gtc<br>Val | aac<br>Asn<br>12340 | att<br>Ile | gat<br>Asp | ggt<br>Gly | cag<br>Gln | gtc<br>Val<br>12345 | gtc<br>Val | agg<br>Arg | gcg<br>Ala | 37044 |

| tac<br>Tyr | cga<br>Arg<br>12350 | aca<br>Thr | ggc<br>Gly | gat<br>Asp | cgc<br>Arg | gtc<br>Val<br>12355 | cgc<br>Arg | tac<br>Tyr | cga<br>Arg | aga<br>Arg | ata<br>Ile<br>12360 | gac<br>Asp | ggt<br>Gly | caa<br>Gln | 37089 |

| tta<br>Leu | gaa<br>Glu<br>12365 | ttc<br>Phe | ttc<br>Phe | ggg<br>Gly | cgc<br>Arg | atg<br>Met<br>12370 | gat<br>Asp | cag<br>Gln | caa<br>Gln | att<br>Ile | aag<br>Lys<br>12375 | att<br>Ile | cga<br>Arg | ggc<br>Gly | 37134 |

|  |  |  |  |  |  |  |  |  |  |  |
|---|---|---|---|---|---|---|---|---|---|---|
| ttc | cgt | atc | gag | acg | gcg | gaa | gtt | gag | aac | gcc | atg | ctc | agt | cac | 37179 |
| Phe | Arg | Ile | Glu | Thr | Ala | Glu | Val | Glu | Asn | Ala | Met | Leu | Ser | His |  |
|  | 12380 |  |  | 12385 |  |  |  | 12390 |  |  |  |  |  |  |  |
| agc | gca | gtt | cgc | aat | gct | gct | gtt | gtc | gtc | cct | acc | caa | gac | att | 37224 |
| Ser | Ala | Val | Arg | Asn | Ala | Ala | Val | Val | Val | Pro | Thr | Gln | Asp | Ile |  |
|  | 12395 |  |  | 12400 |  |  |  | 12405 |  |  |  |  |  |  |  |
| caa | gag | aag | gga | atg | att | ggt | ttc | gtg | gtg | att | gaa | aac | aat | aca | 37269 |
| Gln | Glu | Lys | Gly | Met | Ile | Gly | Phe | Val | Val | Ile | Glu | Asn | Asn | Thr |  |
|  | 12410 |  |  | 12415 |  |  |  | 12420 |  |  |  |  |  |  |  |
| ccc | aag | aac | gag | gag | agc | aag | gaa | gaa | cac | ttg | cta | caa | act | gaa | 37314 |
| Pro | Lys | Asn | Glu | Glu | Ser | Lys | Glu | Glu | His | Leu | Leu | Gln | Thr | Glu |  |
|  | 12425 |  |  | 12430 |  |  |  | 12435 |  |  |  |  |  |  |  |
| ttg | gcg | atc | ctc | aac | cgg | atg | aag | agc | atc | ctt | cct | cct | tac | atg | 37359 |
| Leu | Ala | Ile | Leu | Asn | Arg | Met | Lys | Ser | Ile | Leu | Pro | Pro | Tyr | Met |  |
|  | 12440 |  |  | 12445 |  |  |  | 12450 |  |  |  |  |  |  |  |
| ctc | cca | tct | cgc | atc | atc | atc | ctt | gat | cag | atg | cct | tcg | aat | ttc | 37404 |
| Leu | Pro | Ser | Arg | Ile | Ile | Ile | Leu | Asp | Gln | Met | Pro | Ser | Asn | Phe |  |
|  | 12455 |  |  | 12460 |  |  |  | 12465 |  |  |  |  |  |  |  |
| aat | gga | aag | gtc | gat | cgt | aaa | gag | ctt | gat | cgc | atg | gct | cag | agc | 37449 |
| Asn | Gly | Lys | Val | Asp | Arg | Lys | Glu | Leu | Asp | Arg | Met | Ala | Gln | Ser |  |
|  | 12470 |  |  | 12475 |  |  |  | 12480 |  |  |  |  |  |  |  |
| gta | cct | aga | cag | aag | act | acg | gca | ggg | cgc | ata | gtt | ccc | cgc | aat | 37494 |
| Val | Pro | Arg | Gln | Lys | Thr | Thr | Ala | Gly | Arg | Ile | Val | Pro | Arg | Asn |  |
|  | 12485 |  |  | 12490 |  |  |  | 12495 |  |  |  |  |  |  |  |
| gaa | ttg | gaa | gct | tcg | ctc | tgt | aag | gag | ttc | gct | gaa | gtg | ctc | ggc | 37539 |
| Glu | Leu | Glu | Ala | Ser | Leu | Cys | Lys | Glu | Phe | Ala | Glu | Val | Leu | Gly |  |
|  | 12500 |  |  | 12505 |  |  |  | 12510 |  |  |  |  |  |  |  |
| gtt | gag | gtc | ggc | atc | act | gac | aat | ttc | ttc | gac | ctc | ggt | ggg | cac | 37584 |
| Val | Glu | Val | Gly | Ile | Thr | Asp | Asn | Phe | Phe | Asp | Leu | Gly | Gly | His |  |
|  | 12515 |  |  | 12520 |  |  |  | 12525 |  |  |  |  |  |  |  |
| tcg | cta | ctg | gca | acc | aag | ctc | gca | gct | cgc | att | agc | cgc | agg | ctg | 37629 |
| Ser | Leu | Leu | Ala | Thr | Lys | Leu | Ala | Ala | Arg | Ile | Ser | Arg | Arg | Leu |  |
|  | 12530 |  |  | 12535 |  |  |  | 12540 |  |  |  |  |  |  |  |
| gat | act | cgc | gtg | tct | gtt | aaa | gac | gta | ttc | gat | cag | cct | gtg | ccc | 37674 |
| Asp | Thr | Arg | Val | Ser | Val | Lys | Asp | Val | Phe | Asp | Gln | Pro | Val | Pro |  |
|  | 12545 |  |  | 12550 |  |  |  | 12555 |  |  |  |  |  |  |  |
| gca | gat | cta | gca | ctc | aag | gtt | tcg | tct | tac | atc | tcc | caa | ggt | cat | 37719 |
| Ala | Asp | Leu | Ala | Leu | Lys | Val | Ser | Ser | Tyr | Ile | Ser | Gln | Gly | His |  |
|  | 12560 |  |  | 12565 |  |  |  | 12570 |  |  |  |  |  |  |  |
| gca | atg | gac | aac | gga | acc | ttg | tcg | aca | acg | aac | agc | atc | ccc | ttc | 37764 |
| Ala | Met | Asp | Asn | Gly | Thr | Leu | Ser | Thr | Thr | Asn | Ser | Ile | Pro | Phe |  |
|  | 12575 |  |  | 12580 |  |  |  | 12585 |  |  |  |  |  |  |  |
| cag | cta | cta | cat | ttt | gaa | gat | tcg | cag | aaa | ttt | atc | gac | cgc | gac | 37809 |
| Gln | Leu | Leu | His | Phe | Glu | Asp | Ser | Gln | Lys | Phe | Ile | Asp | Arg | Asp |  |
|  | 12590 |  |  | 12595 |  |  |  | 12600 |  |  |  |  |  |  |  |
| att | gtc | ccg | caa | ctt | gct | cat | cag | tca | gct | aaa | att | gtg | gat | gtc | 37854 |
| Ile | Val | Pro | Gln | Leu | Ala | His | Gln | Ser | Ala | Lys | Ile | Val | Asp | Val |  |
|  | 12605 |  |  | 12610 |  |  |  | 12615 |  |  |  |  |  |  |  |
| tat | cct | gtt | acg | tgg | ata | cag | aag | cac | ttc | ctt | gtt | gat | cca | gca | 37899 |
| Tyr | Pro | Val | Thr | Trp | Ile | Gln | Lys | His | Phe | Leu | Val | Asp | Pro | Ala |  |
|  | 12620 |  |  | 12625 |  |  |  | 12630 |  |  |  |  |  |  |  |
| aca | gga | ctt | cca | cgt | aca | cca | tca | ctc | ttc | ttt | gtc | gat | ttc | cca | 37944 |
| Thr | Gly | Leu | Pro | Arg | Thr | Pro | Ser | Leu | Phe | Phe | Val | Asp | Phe | Pro |  |
|  | 12635 |  |  | 12640 |  |  |  | 12645 |  |  |  |  |  |  |  |
| gcc | aac | gct | gac | tgc | gac | aaa | att | tgc | aat | gcg | agc | cgg | tct | ctc | 37989 |
| Ala | Asn | Ala | Asp | Cys | Asp | Lys | Ile | Cys | Asn | Ala | Ser | Arg | Ser | Leu |  |
|  | 12650 |  |  | 12655 |  |  |  | 12660 |  |  |  |  |  |  |  |
| att | cag | ctt | ttc | gat | atc | ttc | agg | act | gtc | ttt | gtc | cag | gct | gcc | 38034 |
| Ile | Gln | Leu | Phe | Asp | Ile | Phe | Arg | Thr | Val | Phe | Val | Gln | Ala | Ala |  |
|  | 12665 |  |  | 12670 |  |  |  | 12675 |  |  |  |  |  |  |  |

```
ggc aat ttt tac caa gtc gtt  ctg gaa gag ctt gac  ata ccc atc   38079
Gly Asn Phe Tyr Gln Val Val  Leu Glu Glu Leu Asp  Ile Pro Ile
    12680           12685                  12690 tcg gtc atc gaa acc gaa gac  atc agt act gca act  cgc gtc ctg   38124
Ser Val Ile Glu Thr Glu Asp  Ile Ser Thr Ala Thr  Arg Val Leu
    12695           12700                  12705 aag gaa cag gat caa caa aat  ccg ctc caa ttc gga  caa gga ttc   38169
Lys Glu Gln Asp Gln Gln Asn  Pro Leu Gln Phe Gly  Gln Gly Phe
    12710           12715                  12720 tta cgc ttt gca gtc gtg aag  acg agg tca gct gtg  cgc ttg gta   38214
Leu Arg Phe Ala Val Val Lys  Thr Arg Ser Ala Val  Arg Leu Val
    12725           12730                  12735 ctt cgc atc tct cat tgc ttg  tac gat ggc ttg agt  ttc gag cat   38259
Leu Arg Ile Ser His Cys Leu  Tyr Asp Gly Leu Ser  Phe Glu His
    12740           12745                  12750 gtt gtg caa tca ctt cat gct  ttg tat aat ggc gac  cgc atc cca   38304
Val Val Gln Ser Leu His Ala  Leu Tyr Asn Gly Asp  Arg Ile Pro
    12755           12760                  12765 aca cag ccc aag ttc gtt cag  tat gtt cag cat ctg  act gac agc   38349
Thr Gln Pro Lys Phe Val Gln  Tyr Val Gln His Leu  Thr Asp Ser
    12770           12775                  12780 cgc aaa gaa ggt tac gat ttc  tgg cta tct gtc ctg  gag gag tcc   38394
Arg Lys Glu Gly Tyr Asp Phe  Trp Leu Ser Val Leu  Glu Glu Ser
    12785           12790                  12795 tcg atg aca gtc gta gag act  ggc cgt cgc gct caa  caa cta tca   38439
Ser Met Thr Val Val Glu Thr  Gly Arg Arg Ala Gln  Gln Leu Ser
    12800           12805                  12810 tca cct gag ggt gct tgg ttc  gtc gag aag att atc  aag gct gtt   38484
Ser Pro Glu Gly Ala Trp Phe  Val Glu Lys Ile Ile  Lys Ala Val
    12815           12820                  12825 atc cca gcc aac tca gat ggt  att acg cag gca aca  gta ttt acc   38529
Ile Pro Ala Asn Ser Asp Gly  Ile Thr Gln Ala Thr  Val Phe Thr
    12830           12835                  12840 act gct tcc acc atc ctg ctt  gcc aga atg acc gga  tca agc gac   38574
Thr Ala Ser Thr Ile Leu Leu  Ala Arg Met Thr Gly  Ser Ser Asp
    12845           12850                  12855 atc acc ttc agc cga ctc gta  tct ggg cgt caa tct  ttg ccg atc   38619
Ile Thr Phe Ser Arg Leu Val  Ser Gly Arg Gln Ser  Leu Pro Ile
    12860           12865                  12870 aat gac caa cat atc gtc ggc  cct tgc aca aac atc  gtc ccc gtt   38664
Asn Asp Gln His Ile Val Gly  Pro Cys Thr Asn Ile  Val Pro Val
    12875           12880                  12885 cgt att cgc atg act gat ggc  act aat gca aga gag  ctt ctc ggc   38709
Arg Ile Arg Met Thr Asp Gly  Thr Asn Ala Arg Glu  Leu Leu Gly
    12890           12895                  12900 atg gtg caa gac caa tac atc  gac agc ttg cca ttt  gaa acg cta   38754
Met Val Gln Asp Gln Tyr Ile  Asp Ser Leu Pro Phe  Glu Thr Leu
    12905           12910                  12915 ggg ttc gat gac atc aag gag  aac tgc act aaa tgg  cca gcg tcg   38799
Gly Phe Asp Asp Ile Lys Glu  Asn Cys Thr Lys Trp  Pro Ala Ser
    12920           12925                  12930 act acg aac tac ggc tgc tgc  agc aca ttc cag aac  ttc gag atg   38844
Thr Thr Asn Tyr Gly Cys Cys  Ser Thr Phe Gln Asn  Phe Glu Met
    12935           12940                  12945 cag cct caa agt caa gtc cag  gac gaa cgt gtt cga  ttg gct ggt   38889
Gln Pro Gln Ser Gln Val Gln  Asp Glu Arg Val Arg  Leu Ala Gly
    12950           12955                  12960 ttg aca aat ttc aaa gat gca  gaa cta cta aat ggc  gct acc gct   38934
Leu Thr Asn Phe Lys Asp Ala  Glu Leu Leu Asn Gly  Ala Thr Ala
    12965           12970                  12975
```

```
aca  aac  aag  aga  gtt  cta  gat       gac  gta  cca  atg  cat       gag  att  gat    38979
Thr  Asn  Lys  Arg  Val  Leu  Asp       Asp  Val  Pro  Met  His       Glu  Ile  Asp
     12980                12985                         12990 atg  att       gga  atc  cct  gag  ccg       gat  gga  ctt  cat  gta       cga  gtt  gtc    39024
Met  Ile       Gly  Ile  Pro  Glu  Pro       Asp  Gly  Leu  His  Val       Arg  Val  Val
     12995                     13000                        13005 ctt  acc  gct  agc  agg  cag  att       ttc  gag  gag  gag  gtt       gtg  gac  cgc    39069
Leu  Thr  Ala  Ser  Arg  Gln  Ile       Phe  Glu  Glu  Glu  Val       Val  Asp  Arg
     13010               13015                         13020 atg  cac  gaa  gag  ttc  tgc  gat       atc  atc  ttg  ggt  ttg       aac  aag  atc    39114
Met  His  Glu  Glu  Phe  Cys  Asp       Ile  Ile  Leu  Gly  Leu       Asn  Lys  Ile
     13025               13030                         13035 ttg  caa  aaa  tag                                                                      39126
Leu  Gln  Lys
     13040
```

<210> SEQ ID NO 37
<211> LENGTH: 13041
<212> TYPE: PRT
<213> ORGANISM: Curvularia clavata

<400> SEQUENCE: 37

Met Ala Ser Asp Ile Asn Thr His Pro Glu Gly Ala Thr Lys Phe Trp
1               5                   10                  15

Gln Gln His Phe Asp Gly Leu Asn Ala Ser Val Phe Pro Ala Leu Ser
            20                  25                  30

Ser His Leu Thr Val Pro Arg Pro Asn Ala Gln Thr Ala His Arg Ile
        35                  40                  45

Ser Tyr Ser Thr Leu Ala Lys Gln Lys Trp Asp Asn Thr Ser Leu Cys
    50                  55                  60

Arg Ala Ala Leu Ala Ile Leu Leu Ala Arg Tyr Ser Asn Ala Ser Glu
65                  70                  75                  80

Ala Leu Phe Gly Val Leu Val Glu Gln Phe Leu Pro Ser Asn Gly Glu
                85                  90                  95

Gln Ala Ser Thr Glu Glu Ser Pro Gln Ser Ile Leu Pro Ile Arg Ile
            100                 105                 110

Arg Leu Asp Leu Glu Glu Ala Gly Leu Gly Leu Leu Gln Ala Ile Asn
        115                 120                 125

Thr Leu Asp Ala Ser Leu Arg Glu Trp Lys His Ile Gly Leu Asp Ala
    130                 135                 140

Ile Arg Gly Thr Gly Glu Tyr Gly Ser Ala Gly Cys Glu Phe Gln Thr
145                 150                 155                 160

Val Leu Ala Val Thr Thr Gly Lys Thr Pro Arg Thr His Arg Leu Ala
                165                 170                 175

Ser Cys Thr Asp Arg Ala Leu Leu Leu Asp Cys Arg Met Asp Asp Asp
            180                 185                 190

Ser Ala Thr Leu Leu Ala Arg Tyr Asp Pro Ser Val Ile Asp Asp Leu
        195                 200                 205

Gln Val Ala Arg Phe Leu Lys Gln Leu Gly His Val Ile Glu Gln Leu
    210                 215                 220

Arg Val Gln Ala Val Asp Leu Pro Leu Trp Glu Leu Gly Ile Val Thr
225                 230                 235                 240

Gln Glu Asp Ser Ala Glu Ile Gln Lys Trp Asn Ser Gln Gln Leu Gln
                245                 250                 255

Phe Ser Gln Glu Cys Ile His Asp Val Phe Ala Asn Arg Val Val Asp
            260                 265                 270

-continued

Thr Pro Gln Lys Ile Ala Val Ser Ala Trp Asn Gly Glu Leu Thr Phe
            275                 280                 285

Ala Glu Leu Asp Ser Phe Ser Ser Cys Leu Ala Gln His Ile Gln Ser
    290                 295                 300

Leu Glu Leu Gly Asp Ala Lys Ala Ile Pro Leu Cys Phe Glu Lys Ser
305                 310                 315                 320

Lys Trp Ala Ile Val Gly Met Leu Gly Val Leu Lys Ala Gly Arg Ala
                325                 330                 335

Phe Thr Leu Ile Asp Pro Ser Asn Pro Ala Arg Ala Arg Gln Ile
            340                 345                 350

Cys Arg Gln Thr Ala Ala Thr Ile Ser Ile Ala Ser Pro Tyr Gln Cys
        355                 360                 365

Asp Met Met Arg Ala Leu Val Pro Asp Cys Ile Val Val Asp Asp Asp
    370                 375                 380

Phe Phe Lys Ser Leu Ala Phe Asp Thr Asp Gln Phe Gln Pro Thr Ala
385                 390                 395                 400

Thr Pro Gln Thr Leu Ala Tyr Ile Leu Phe Thr Ser Gly Ser Thr Gly
                405                 410                 415

Glu Pro Lys Gly Ser Met Met Glu His His Gly Phe Val Ser Cys Cys
            420                 425                 430

Leu Glu Phe Gly Ala Ala Leu Gly Ile Asn Ser Asn Thr Arg Ala Leu
        435                 440                 445

Gln Phe Ala Ser Tyr Ala Phe Gly Ala Cys Leu Leu Glu Ile Leu Thr
    450                 455                 460

Thr Leu Met His Gly Gly Thr Val Cys Ile Pro Ser Asp Asp Glu Arg
465                 470                 475                 480

Ile Asn Asp Ala Pro Gly Phe Ile Arg Arg Ala Asn Val Asn Trp Ala
                485                 490                 495

Ile Leu Thr Pro Ser Phe Ile Gly Ala Ile Gln Pro Thr Thr Val Pro
            500                 505                 510

Asn Leu Lys Thr Leu Val Leu Val Gly Glu Ala Met Pro Ser Asp Ile
        515                 520                 525

Arg Asp Val Trp Ala Ser His Val Gln Leu Lys Asn Ala Tyr Gly Gln
    530                 535                 540

Ser Glu Ser Ala Thr Ile Cys Ser Val Thr Glu Val Thr Pro Ala Thr
545                 550                 555                 560

Val Glu Ala His Asn Ile Gly His Ala Val Gly Ala Arg Phe Trp Ile
                565                 570                 575

Thr Asp Pro Asn Asn Pro Asn Lys Leu Ala Pro Ile Gly Cys Val Gly
            580                 585                 590

Glu Leu Leu Val Glu Ser Pro Gly Ile Ala Arg Gly Tyr Leu Ile Pro
        595                 600                 605

Leu Pro Ala Asp Ala Thr Pro Phe Ile Asp Thr Leu Pro Asp Trp Tyr
    610                 615                 620

Pro Arg Thr Gln Pro Leu Asp Asn Phe Lys Phe Tyr Arg Thr Gly Asp
625                 630                 635                 640

Leu Val Cys Tyr Arg Ser Asp Gly Thr Val Val Tyr Leu Gly Arg Arg
                645                 650                 655

Asp Ser Gln Ile Lys Ile Arg Gly Gln Arg Val Glu Ile Gly Glu Val
            660                 665                 670

Glu Thr Cys Leu Arg Gln Gln Leu Pro Ser Gln Leu Val Pro Val Val
        675                 680                 685

-continued

```
Glu Ala Val Ser Leu Ser Gly Met Ser Lys Ser Met Thr Leu Ile Ala
690                 695                 700
Phe Leu Val Gly Glu Asn Thr Ile Leu Glu Asp Val Tyr Val Leu
705                 710                 715                 720
Glu Gly Ser Ala Ala Gln Arg Ile Ser Ser Lys Leu Arg Gln Ile Val
            725                 730                 735
Pro Gly Tyr Cys Ile Pro Ser His Tyr Ile Arg Ile Asn His Leu Pro
            740                 745                 750
Thr Thr Ala Thr Gly Lys Cys Asp Arg Lys Ala Leu Arg Ala Ile Gly
            755                 760                 765
Thr Lys Leu Leu Arg Glu Ala Val Glu Gly Met Ala Ser Gln Glu Glu
770                 775                 780
Gln Glu Ser Ala Ser Leu Met Thr Glu Gly Ile Thr Leu Glu Arg Ile
785                 790                 795                 800
Trp Phe Gln Ser Leu Gly Leu Lys Pro Asn Ser Thr Arg His Lys Ser
                805                 810                 815
Asn Phe Phe Asn Leu Gly Gly Asp Ser Ile Ala Ala Ile Arg Met Val
                820                 825                 830
Asn Met Ala Arg Ala Ala Gly Leu Leu Leu Ser Ile Ser Asp Ile Phe
835                 840                 845
Gln Asn Pro Ser Leu Ala Gly Leu Ile Asn Val Met Gln Gln Ser Ser
850                 855                 860
Thr Ala Gln Asp Ala Ile Pro Ala Thr Glu Tyr Ser Gly Pro Val Glu
865                 870                 875                 880
Gln Ser Phe Ala Gln Gly Arg Leu Trp Phe Leu Asp Gln Leu Thr Thr
                885                 890                 895
Gly Ala Ser Trp Tyr Leu Met Pro Leu Ala Val Arg Ile His Gly Pro
                900                 905                 910
Leu Arg Val Gln Ala Leu Ser Ser Ala Leu His Ala Leu Glu Gln Arg
                915                 920                 925
His Glu Thr Leu Arg Thr Thr Phe Glu Gln Gln Asp Gly Met Gly Val
930                 935                 940
Gln Ile Val His Pro Ser Ser Lys Arg Glu Leu Arg Val Ile Asp Val
945                 950                 955                 960
Ser Gly Lys Gln Asn Gly Gly Tyr Asp Gln Val Leu Lys Arg Glu Gln
                965                 970                 975
Thr Thr Pro Ile Asp Leu Ala Lys Glu Pro Gly Trp Arg Ala Ala Leu
                980                 985                 990
Leu Arg Val Gly Asp Asp Glu His Ile Leu Ser Ile Val Ile His His
                995                 1000                1005
Ile Ile Tyr Asp Gly Trp Ser Leu Gly Val Leu Arg Glu Glu Leu
        1010                1015                1020
Gly Asp Leu Tyr Ala Ala Ala Leu Arg Gly Pro Asp Pro Leu Ala
        1025                1030                1035
His Met Ala Pro Leu Pro Ile Gln Tyr Arg Asp Phe Ser Val Trp
        1040                1045                1050
Gln Lys Gln Pro Gln Gln Val Ala Gln His Gln Gln Leu Val
        1055                1060                1065
Tyr Trp Thr Lys Gln Leu Glu Asp Ser Ala Pro Ala Glu Leu Leu
        1070                1075                1080
Thr Asp Phe Pro Arg Pro Ala Glu Leu Ser Gly Arg Ala Gly Glu
        1085                1090                1095
```

-continued

| | | | | | | | | | | | |
|---|---|---|---|---|---|---|---|---|---|---|---|
| Val | Arg | Phe | Thr | Ile | Glu | Gly | Ser | Val | Phe | Asp | Ser | Leu | Leu | Ala |
| 1100 | | | | | 1105 | | | | | 1110 | |

Val Arg Phe Thr Ile Glu Gly Ser Val Phe Asp Ser Leu Leu Ala
    1100                1105               1110

Phe Arg Arg Val His Gln Thr Thr Ser Phe Ala Val Leu Leu Ala
    1115                1120               1125

Val Phe Arg Ala Ala His Tyr Arg Leu Thr Gly Thr Glu Asp Ala
    1130                1135               1140

Thr Ile Gly Thr Pro Ile Ala Asn Arg Thr Arg Ala Glu Val Glu
    1145                1150               1155

Lys Leu Ile Gly Phe Phe Val Asn Thr Gln Cys Met Arg Ile Ala
    1160                1165               1170

Val Ala Asp Asp Asp Thr Phe Ala Ser Leu Val Ser Gln Val Trp
    1175                1180               1185

Ser Val Ala Thr Ala Ala Phe Glu His Gln Asp Val Pro Phe Glu
    1190                1195               1200

Arg Ile Val Ser Ala Leu Leu Pro Gly Ala Arg Asp Thr Ser Arg
    1205                1210               1215

Asn Pro Leu Ala Gln Leu Leu Phe Ala Leu His Leu Glu Gln Asp
    1220                1225               1230

Leu Asp Lys Ile Asn Leu Glu Gly Leu Ala Cys Glu Thr Val Pro
    1235                1240               1245

Thr Pro Met Ala Thr Arg Phe Asp Val Glu Phe His Leu Phe Gln
    1250                1255               1260

Glu Asp Asp Arg Leu Asn Gly Val Val Asn Phe Ser Thr Asp Leu
    1265                1270               1275

Phe Glu Pro Gln Thr Ile His Ser Leu Val Ser Val Phe Gln Glu
    1280                1285               1290

Ile Leu Arg Arg Gly Leu Asp Gln Pro Gln Thr Pro Ile Ala His
    1295                1300               1305

Leu Gln Leu Thr Asp Gly Leu Glu Glu Leu Arg Asn Ala Gly Leu
    1310                1315               1320

Leu Asp Ile Lys Arg Ile Asp Tyr Pro Arg Glu Ala Ser Val Val
    1325                1330               1335

Asp Met Phe Gln Lys Gln Val Ala Ala Cys Pro Asn Val Thr Ala
    1340                1345               1350

Val Lys Asp Ser Thr Ser Gln Leu Thr Tyr Ala Gln Leu Asp Gln
    1355                1360               1365

Glu Ser Asp Lys Ile Ala Val Trp Leu Arg Lys Arg Asn Ile Pro
    1370                1375               1380

Ala Glu Thr Leu Ile Ala Leu Leu Ala Pro Arg Ser Cys Asp Ser
    1385                1390               1395

Val Ala Ala Phe Leu Gly Ile Leu Lys Ala Asn Leu Ala Tyr Leu
    1400                1405               1410

Pro Leu Asp Val Asn Val Pro Ala Ala Arg Ile Glu Ala Ile Leu
    1415                1420               1425

Ser Thr Val Ala Gly His Lys Leu Val Leu Leu Gly Arg Asp Val
    1430                1435               1440

Pro Leu Leu Gly Thr Gln Leu Ala Asp Leu Glu Leu Val Arg Ile
    1445                1450               1455

Gly Glu Ala Leu Arg Gly Ser Ser Ser Gly Ser Val Ala Ala Asp
    1460                1465               1470

Lys Ala Ile Arg Pro Thr Ala Thr Ser Leu Ala Tyr Val Ile Phe
    1475                1480               1485

```
Thr Ser Gly Ser Thr Gly Gln Pro Lys Gly Ile Met Val Pro His
1490                1495                1500

Arg Ser Leu Val Asn Val Ile Lys Gln Arg Pro Ala Tyr Gly Asn
1505                1510                1515

Val Ala His Met Thr Asn Leu Ala Phe Asp Pro Ser Leu Phe Glu
1520                1525                1530

Met Cys Thr Ala Leu Phe Asn Gly Asn Thr Leu Ile Cys Ile Asp
1535                1540                1545

Thr Leu Val Ala Leu Asp Ala Thr Gln Leu Pro Thr Ile Phe Lys
1550                1555                1560

Gln Glu Ala Ile Arg Val Ala Met Met Thr Pro Ala Leu Leu Thr
1565                1570                1575

Arg Leu Leu Ala Gln Ala Thr Asp Ala Leu His Glu Leu Glu Ala
1580                1585                1590

Leu Tyr Val Leu Gly Asp Arg Phe Pro Pro Lys Asp Ala Ala Arg
1595                1600                1605

Ala Ser Glu Leu Val Lys Thr Ala Val Tyr Asn Ala Tyr Gly Pro
1610                1615                1620

Ser Glu Asn Ser Ile Cys Thr Thr Leu Phe His Ala Ala Thr Gly
1625                1630                1635

Ala Met Cys Thr Asn Gly Val Pro Val Gly Arg Val Ile Asn Asn
1640                1645                1650

Ser Gly Val Tyr Val Met Asp Pro Lys Gln Ser Leu Val Ser Tyr
1655                1660                1665

Gly Val Met Gly Glu Leu Val Ala Gly Glu Gly Leu Ala Ile
1670                1675                1680

Gly Tyr Thr Lys Pro Glu Leu Asn Glu Gly Arg Phe Leu Thr Leu
1685                1690                1695

Thr Met Asp Gly Lys Pro Val Arg Ala Phe Arg Thr Gly Asp Arg
1700                1705                1710

Val Arg Tyr Arg Pro Thr Asp Gly Gln Leu Glu Phe Phe Gly Arg
1715                1720                1725

Met Asp Phe Gln Ile Lys Ile Arg Gly His Arg Val Glu Leu Ala
1730                1735                1740

Glu Val Glu Arg Val Leu Asn Arg His Pro Ala Ile Lys Asp Ala
1745                1750                1755

Ile Thr Leu Leu Arg Gln His Gly Ser Ser Ala Gln Asp Thr Glu
1760                1765                1770

Leu Val Ser Phe Ile Val Leu Gly Glu Gln Lys Pro Val Lys Pro
1775                1780                1785

His Arg Asn Ala Thr Asp His Gly Gly Met Glu Ile Glu Gln Leu
1790                1795                1800

Asp Gln Lys Leu Glu Ala Asn Leu Arg Ala Met Met Gln Ala Thr
1805                1810                1815

Leu Pro Ser Tyr Met Val Pro Ser Arg Ile Ile Val Leu Asp His
1820                1825                1830

Met Pro Leu Asp Lys Asn Gly Lys Val Asp Arg Arg Gly Leu Thr
1835                1840                1845

Gly Leu Thr Leu Ser Pro Ala Met Glu Thr Ser Ser Arg Val Val
1850                1855                1860

Val Ala Ala Arg Asn Glu Ile Glu Ala Val Leu Cys Glu Glu Phe
1865                1870                1875
```

```
Ala His Ile Leu Gly Val Glu Ile Gly Val Thr Asp Asn Phe Phe
    1880            1885            1890

Asp Leu Gly Gly His Ser Leu Met Ala Thr Thr Leu Ala Ala Arg
    1895            1900            1905

Leu Ala Arg Arg Leu Asn Ala Ser Ile Ser Val Lys Asp Val Phe
    1910            1915            1920

Asp Gln Pro Ile Val Ala Asn Leu Ala Ala Thr Ile Lys Arg Gly
    1925            1930            1935

Ser Thr Pro His Asn Ala Ile Pro Pro Thr Lys Tyr Ser Gly Pro
    1940            1945            1950

Val Glu Gln Ser Phe Ala Gln Gly Arg Leu Trp Phe Leu Asp Gln
    1955            1960            1965

Leu Asn Leu Gly Ala Ala Trp Tyr His Met Pro Leu Ala Val Arg
    1970            1975            1980

Leu Arg Gly Pro Leu His Leu Glu Ala Leu Thr Ala Ala Leu His
    1985            1990            1995

Ala Leu Glu Glu Arg His Glu Thr Leu Arg Thr Val Phe Glu Glu
    2000            2005            2010

Gln Asp Gly Val Gly Met Gln Ile Val Arg Pro Ser Ser Lys Thr
    2015            2020            2025

Pro Leu Arg Ile Ile Asp Val Ser Thr Lys Glu Arg Gly Tyr Ala
    2030            2035            2040

Glu Leu Leu Lys Gln Glu Gln Thr Thr Pro Phe Asp Leu Ala Thr
    2045            2050            2055

Glu Leu Gly Trp Arg Val Ala Leu Leu Arg Gln Gly Lys Asp Asp
    2060            2065            2070

His Ile Leu Ser Ile Val Ile His His Ile Ile Ser Asp Gly Trp
    2075            2080            2085

Ser Leu Asp Ile Leu Cys Glu Glu Leu Gly Gln Phe Tyr Ala Ala
    2090            2095            2100

Val Leu Arg Gly Gln Asp Pro Leu Ala Gln Ile Ser Pro Leu Pro
    2105            2110            2115

Ile Gln Tyr Arg Asp Phe Ser Leu Trp Gln Lys Gln Pro Glu Gln
    2120            2125            2130

Val Ala Glu His His Arg Gln Leu Glu Tyr Trp Thr Thr Gln Leu
    2135            2140            2145

Glu Gly Ser Val Pro Ala Glu Leu Leu Thr Asp Leu Pro Arg Pro
    2150            2155            2160

Thr Ile Gln Ser Gly Lys Ala Gly Val Ile Pro Ile Thr Val Asn
    2165            2170            2175

Gly Pro Val Tyr Glu Arg Leu Arg Ala Phe Ser Arg Ala His Gln
    2180            2185            2190

Thr Thr Ala Phe Ala Val Leu Leu Ala Ala Phe Arg Ala Thr His
    2195            2200            2205

Tyr Arg Leu Ser Gly Val Ala Asp Ala Thr Ile Gly Thr Pro Ile
    2210            2215            2220

Ala Asn Arg Asn Arg Pro Glu Leu Glu Asn Met Ile Gly Phe Phe
    2225            2230            2235

Val Asn Ala Gln Cys Met Arg Ile Thr Val Glu Gln Asp Asp Thr
    2240            2245            2250

Phe Glu Thr Leu Val Arg Gln Ile Arg Phe Thr Ala Thr Ala Ala
    2255            2260            2265
```

```
Phe Ala Asn Gln Asp Val Pro Phe Glu His Ile Val Ser Ala Leu
2270                2275                2280

Met Pro Asp Ser Arg Asp Thr Ser Arg Asn Pro Leu Val Gln Leu
2285                2290                2295

Met Phe Ala Leu His Ala Tyr Lys Asp Leu Gly Lys Ile Glu Leu
2300                2305                2310

Glu Gly Tyr Val Ala Glu Pro Val His Thr Thr Leu Ser Thr Arg
2315                2320                2325

Phe Asp Leu Glu Phe His Met Phe Gln Glu Thr Asn His Leu Ser
2330                2335                2340

Gly Tyr Val Leu Tyr Ala Thr Asp Leu Phe Glu Pro Glu Ser Ile
2345                2350                2355

Glu Gly Met Val Ser Ile Phe Lys Glu Ile Leu Ala Arg Ala Leu
2360                2365                2370

Asp Gln Pro Gln Thr Pro Leu Ala Leu Leu Pro Leu Thr Asp Gly
2375                2380                2385

Leu Ala Glu Leu Arg Arg Arg Gly Leu Leu Glu Ile Glu Arg Pro
2390                2395                2400

Ser Tyr Pro Arg Glu Ser Ser Val Val Asp Val Phe Cys Ser Gln
2405                2410                2415

Val Ala Ala Ser Pro Asn Ala Thr Ala Val Lys Asp Ser Ile Ser
2420                2425                2430

Gln Leu Thr Tyr Ala Gln Leu Asn Glu Gln Ser Asp Lys Val Ala
2435                2440                2445

Ala Trp Leu His Gln Cys Asn Leu Pro Thr Glu Thr Leu Val Ala
2450                2455                2460

Val Leu Ala Pro Arg Ser Cys Gln Thr Val Val Ala Phe Leu Gly
2465                2470                2475

Ile Leu Lys Ala Asn Leu Ala Tyr Leu Pro Leu Asp Val Asn Val
2480                2485                2490

Pro Ala Ala Arg Ile Glu Ala Ile Leu Ser Glu Val Ser Gly His
2495                2500                2505

Ile Leu Val Leu Leu Gly Ser His Val Ser Ala Pro Lys Ile Glu
2510                2515                2520

Leu Ala Asp Val Glu Phe Val Lys Ile Asp Asn Thr Val Glu His
2525                2530                2535

Asn Leu Pro Gly Arg Ile Gly Ser Ala Pro Ser Ala Thr Ser Leu
2540                2545                2550

Ala Tyr Val Ile Phe Thr Ser Gly Ser Thr Gly Lys Pro Lys Gly
2555                2560                2565

Val Lys Val Glu His Arg Gly Ile Val Arg Leu Val Lys Glu Ser
2570                2575                2580

Asn Val Val Ala Lys Met Pro Gln Ala Ala Arg Ile Ala His Leu
2585                2590                2595

Ser Asn Ile Ala Phe Asp Ala Ala Thr Trp Glu Leu Tyr Ala Ala
2600                2605                2610

Leu Leu Asn Gly Gly Thr Leu Val Cys Ile Asn Tyr Leu Thr Thr
2615                2620                2625

Leu Asp Ser Lys Ala Leu Glu Ala Val Phe Glu Gln Glu Lys Ile
2630                2635                2640

Gln Ala Ala Met Leu Pro Pro Ala Leu Leu Lys Gln Tyr Leu Val
2645                2650                2655
```

```
Asn Ile Pro Ala Ala Ile Gly Ala Leu Glu Val Val Leu Val Ala
    2660            2665            2670

Gly Asp Arg Phe Asp Arg Arg Asp Ala Ala Thr Gln Ala Leu
    2675            2680            2685

Val Gly Ala Gly Val Tyr Asn Ala Tyr Gly Pro Thr Glu Asn Thr
    2690            2695            2700

Thr Leu Ser Thr Ile Tyr Asn Val Val Gln Gly Asp Ala Asn Val
    2705            2710            2715

Asn Gly Val Pro Ile Gly Arg Pro Val Ser Asn Ser Gly Ala Tyr
    2720            2725            2730

Ile Met Asn Met Asn Gln Glu Leu Val Pro Ile Gly Val Ile Gly
    2735            2740            2745

Glu Leu Val Val Val Gly Asp Gly Val Ala Arg Gly Tyr Thr Asp
    2750            2755            2760

Pro Ala Leu Asp Val Asn Arg Phe Val Asn Val Thr Ile Glu Gly
    2765            2770            2775

Gln Thr Met Arg Ala Tyr Arg Thr Gly Asp Arg Ala Arg Tyr Arg
    2780            2785            2790

Pro Lys Asp Ala Gln Ile Glu Phe Phe Gly Arg Met Asp Gln Gln
    2795            2800            2805

Ile Lys Ile Arg Gly His Arg Ile Glu Pro Ala Glu Val Glu His
    2810            2815            2820

Ala Leu Leu Asn Asn Asp Leu Leu Gln Asp Ala Ala Val Ile Ile
    2825            2830            2835

Arg Lys Gln Gln Asn Asp Glu Leu Glu Met Val Ala Phe Val Glu
    2840            2845            2850

Ala Asn Ser Asn Lys Ser Ile Glu Gln Glu Ala Ser Asn Gln Val
    2855            2860            2865

Glu Asp Trp Gly Ala Gln Phe Glu Ser Asn Val Tyr Ala Glu Ile
    2870            2875            2880

Glu Ala Ile Asp Ala Ser Ala Val Gly Asn Asp Phe Met Gly Trp
    2885            2890            2895

Thr Ser Met Tyr Asp Gly Ser Ala Ile Asp Lys Ala Glu Met Gln
    2900            2905            2910

Glu Trp Leu Asp Asp Thr Met Gln Thr Ile Leu Asp Gly Arg Pro
    2915            2920            2925

Ala Gly Arg Val Leu Glu Ile Gly Thr Gly Thr Gly Met Ile Leu
    2930            2935            2940

Phe Asn Leu Gly Glu Gly Leu Gln Ser Tyr Val Gly Leu Glu Pro
    2945            2950            2955

Ser Thr Ser Ala Ala Ala Phe Val Asn Arg Arg Ile Gln Thr Leu
    2960            2965            2970

Pro Ala Phe Ala Gly Lys Ala Glu Val His Val Gly Thr Ala Thr
    2975            2980            2985

Asp Ile Ser Gln Leu Gln Asp Leu Arg Pro Glu Val Val Val Ile
    2990            2995            3000

Asn Ser Val Ala Gln Tyr Phe Pro Ser Pro Glu Tyr Leu Ser Lys
    3005            3010            3015

Val Leu Tyr Ala Leu Ala Gln Ile Pro Gly Val Lys Arg Leu Phe
    3020            3025            3030

Phe Gly Asp Met Arg Ser Tyr Ala Ile Asn Asp Gln Phe Leu Ala
    3035            3040            3045
```

-continued

Ala Arg Ala Leu His Asn Ile Gly Ser Lys Ala Thr Lys Ser Ala
3050                3055                3060

Ile Arg Ser Lys Met Val Asp Leu Glu Asn Ser Glu Glu Glu Leu
3065                3070                3075

Leu Val Asp Pro Thr Phe Phe Thr Asn Leu Ala Thr Glu Leu Pro
3080                3085                3090

Glu Val Glu His Val Glu Ile Leu Pro Lys Arg Met Gln Ala Thr
3095                3100                3105

Asn Glu Leu Ser Ala Tyr Arg Tyr Ala Ala Val Val His Ile Arg
3110                3115                3120

Asp Ser Ser Glu Arg Ala Gln Thr Val His Ala Ile Lys Ser Ser
3125                3130                3135

Ala Trp Val Asp Phe Ser Lys Ser Gln Met Asp Arg Lys Ala Leu
3140                3145                3150

Ile Ser Leu Leu Gln Ser Ser Val Asn Thr Glu Ala Val Ala Ile
3155                3160                3165

Gly Asn Ile Pro Tyr Ser Lys Thr Ile Met Ala Arg His Val Val
3170                3175                3180

Gln Ser Leu Asp Glu Asp Asn Ala Asp Lys Asp Ile Ala Gln Asp
3185                3190                3195

Lys Pro Asp Lys Pro Thr Trp Ile Ser Ala Val Arg Ser Asn Ala
3200                3205                3210

Glu His Cys Pro Ser Leu Ser Ala Leu Asp Leu Val Gln Leu Gly
3215                3220                3225

Glu Glu Ala Gly Phe Cys Val Glu Leu Ser Trp Ala Gln Gln Arg
3230                3235                3240

Ser His His Gly Ala Ile Asp Ala Val Phe His His Tyr Gln Pro
3245                3250                3255

Ala Arg Glu Gly Ser Arg Val Leu Phe Gln Phe Pro Thr Asp Thr
3260                3265                3270

Tyr Arg Arg Gln Ser Gly Pro Leu Thr Asn Arg Pro Leu Gln Arg
3275                3280                3285

Ile Gln Ser Arg Arg Met Glu Thr Gln Val Arg Glu Lys Leu Arg
3290                3295                3300

Ala Val Leu Pro Ser Tyr Met Ile Pro Ser Leu Ile Val Leu Val
3305                3310                3315

Asp Gln Met Pro Leu Asn Pro Asn Gly Lys Val Asp Arg Lys Ala
3320                3325                3330

Leu Glu Arg Arg Ala Gln Ala Val Leu Arg Val Glu Lys Pro Thr
3335                3340                3345

Ser Glu Arg Val Gly Ala Arg Asn Glu Thr Glu Ala Val Leu Cys
3350                3355                3360

Glu Glu Phe Thr Asp Val Leu Gly Leu Glu Val Gly Ile Thr Asp
3365                3370                3375

Asn Phe Phe Asp Leu Gly Gly His Ser Leu Met Ala Thr Lys Leu
3380                3385                3390

Ala Ala Arg Ile Ser Arg Arg Leu Asp Ala Arg Val Ser Val Lys
3395                3400                3405

Asp Val Phe Asp Gln Pro Val Ile Val Asp Leu Ala Ala Ser Ile
3410                3415                3420

Arg Arg Gly Ser Thr Pro His Asn Pro Ile Thr Pro Thr Glu Tyr
3425                3430                3435

```
Ser Gly Pro Val Glu Gln Ser Phe Ala Gln Gly Arg Leu Trp Phe
3440                3445                3450

Leu Asp Gln Leu Asn Leu Gly Ala Ser Leu Tyr Leu Met Pro Leu
3455                3460                3465

Ala Leu Arg Leu Arg Gly Pro Leu Arg Ile Asp Ala Leu Thr Ala
3470                3475                3480

Ala Leu Phe Ala Leu Glu Gln Arg His Glu Thr Leu Arg Thr Val
3485                3490                3495

Phe Lys Glu Gln Asp Gly Val Gly Ile Gln Ile Ile Gln Pro Ser
3500                3505                3510

Gln Lys Lys Lys Leu Arg Thr Ile Asp Val Ser Ala Gly Asp Phe
3515                3520                3525

Ser Glu Ala Leu His His Glu Arg Thr Ala Pro Phe Asp Leu Ala
3530                3535                3540

Ser Glu Pro Gly Phe Arg Val Ala Leu Leu Gln Leu Glu Pro Ser
3545                3550                3555

Asp His Val Leu Ser Ile Val Met His His Ile Ile Tyr Asp Gly
3560                3565                3570

Trp Ser Ile Asp Ile Leu Cys Gln Glu Leu Gly Gln Phe Tyr Ala
3575                3580                3585

Ala Ala Ile Gln Gly Gln Asp Pro Leu Gly Gln Val Ser Pro Leu
3590                3595                3600

Pro Ile Gln Tyr Arg Asp Phe Ser Val Trp Gln Lys Gln Pro Glu
3605                3610                3615

Gln Val Ala Glu His Glu Arg Gln Leu Ala Tyr Trp Ile Asp Gln
3620                3625                3630

Leu Ala Asp Ser Ala Pro Ala Glu Phe Leu Val Asp Leu Pro Arg
3635                3640                3645

Pro Pro Val Leu Ser Gly Asp Ala Gly Leu Val His Leu Thr Ile
3650                3655                3660

Asp Gly Pro Ile Tyr Asp Arg Leu Arg Ala Phe Cys Arg Val His
3665                3670                3675

Gln Thr Thr Thr Phe Ala Val Leu Leu Ala Ala Phe Arg Ala Thr
3680                3685                3690

His Tyr Arg Leu Thr Gly Ala Glu Asp Ala Thr Val Gly Thr Pro
3695                3700                3705

Ile Ala Asn Arg Asn Arg Pro Glu Leu Glu Asn Leu Val Gly Phe
3710                3715                3720

Phe Val Asn Thr Gln Cys Met Arg Ile Ser Val Gly Asp Asp Asp
3725                3730                3735

Thr Phe Glu Gln Leu Val Arg Gln Val Arg Ser Thr Ala Thr Ala
3740                3745                3750

Ala Phe Ala Asn Gln Asp Val Pro Phe Glu Arg Ile Val Ser Thr
3755                3760                3765

Leu Leu Pro Gly Ser Arg Asp Thr Ala Arg Asn Pro Leu Val Gln
3770                3775                3780

Leu Met Phe Ala Val His Ser Leu Lys Asp Leu Gly Lys Ile Gln
3785                3790                3795

Phe Glu Gly Leu Val Gly Glu Thr Ile Pro Thr Ala Ser Phe Thr
3800                3805                3810

Arg Phe Asp Val Glu Phe His Leu Phe Gln Glu Val Gly Arg Leu
3815                3820                3825
```

```
Ser Gly Asn Val Leu Phe Ser Thr Asp Leu Phe Glu Pro Glu Thr
3830                3835                3840

Ile Gln Gly Met Val Ser Val Phe Met Glu Ile Leu Arg Gly Ala
3845                3850                3855

Leu Asp Gln Pro Gln Ile Pro Ile Ala Val Leu Pro Leu Thr Asp
3860                3865                3870

Gly Leu Thr Glu Leu Arg Asn Arg Gly Leu Leu Glu Val Glu Gln
3875                3880                3885

Pro Gln Tyr Pro Arg Asp Ser Ser Val Ile Asp Val Phe Arg Ala
3890                3895                3900

Gln Val Val Ala Cys Pro Asp Ala Ile Ala Val Lys Asp Ser Thr
3905                3910                3915

Ser Gln Leu Thr Tyr Ala Gln Leu Asp Glu Gln Ser Asp Glu Val
3920                3925                3930

Ala Val Trp Leu His Gln Arg Lys Leu Pro Ala Glu Ser Leu Val
3935                3940                3945

Ala Val Leu Ala Pro Arg Ser Cys Glu Thr Ile Ile Thr Phe Phe
3950                3955                3960

Gly Ile Leu Lys Ala Asn Leu Ala Tyr Leu Pro Leu Asp Ile Asn
3965                3970                3975

Val Pro Ala Ala Arg Ile Gln Ala Ile Leu Ser Ser Val Ala Gly
3980                3985                3990

Lys Lys Ile Leu Leu Leu Gly Ser Asp Gln Ala Gln Pro Glu Ile
3995                4000                4005

Arg Leu Asp Asp Val Glu Phe Val Gln Ile Asn Glu Thr Ile Asp
4010                4015                4020

His Asn Met Ala Lys Asp Asn Thr Thr Arg Ser Gly Pro Leu Ala
4025                4030                4035

Thr Ser Leu Ala Tyr Val Ile Phe Thr Ser Gly Ser Thr Gly Gln
4040                4045                4050

Pro Lys Gly Val Lys Val Glu His Arg Gly Ile Val Arg Leu Val
4055                4060                4065

Lys Asn Ser Asn Val Val Ala Lys Met Pro Glu Ala Ala Cys Val
4070                4075                4080

Ala His Leu Ser Asn Leu Ala Phe Asp Ala Ala Thr Trp Glu Ile
4085                4090                4095

Tyr Ala Ala Leu Leu Asn Gly Gly Ser Leu Ile Cys Ile Asp Tyr
4100                4105                4110

Phe Thr Thr Leu Asp Ser Lys Val Leu Glu Ala Val Phe Glu Arg
4115                4120                4125

Glu Gln Ile Arg Ala Ala Met Phe Pro Pro Ala Leu Leu Lys Gln
4130                4135                4140

Cys Leu Leu Asn Ile Pro Thr Thr Ile Ser Ala Leu Asp Val Ile
4145                4150                4155

Leu Ala Ala Gly Asp Arg Phe Asp Arg Arg Asp Ala Ile Ala Ala
4160                4165                4170

Gln Ala Leu Val Gly Gly Val Tyr Asn Ala Tyr Gly Pro Thr
4175                4180                4185

Glu Asn Thr Thr Leu Ser Thr Ile Tyr Asn Val Val Asp Gly Asp
4190                4195                4200

Thr Asn Val Asn Gly Ile Pro Ile Gly Leu Pro Val Ser Asn Ser
4205                4210                4215
```

```
Gly Val Tyr Val Met Asp Pro Asn Gln Gln Leu Val Pro Leu Gly
4220                4225                4230

Val Met Gly Glu Leu Val Val Val Gly Asp Gly Val Ala Arg Gly
4235                4240                4245

Tyr Thr Asp Pro Ala Leu Asp Val Asp Arg Phe Ile Lys Val Glu
4250                4255                4260

Ile Asp Gly Gln Ile Val Arg Ala Tyr Arg Thr Gly Asp Arg Val
4265                4270                4275

Arg His Arg Pro Lys Asp Gly Gln Ile Glu Phe Phe Gly Arg Met
4280                4285                4290

Asp Gln Gln Val Lys Ile Arg Gly His Arg Ile Glu Leu Ala Glu
4295                4300                4305

Val Glu His Val Ile Leu Asp Asn Ser Leu Val Gln Asp Ala Ala
4310                4315                4320

Val Ile Val His Lys Gln Ala Asp Gln Glu Ile Glu Met Ile Ala
4325                4330                4335

Phe Ala Ile Val Arg Gly Asp Asn Asp Ser Lys His Pro Glu Lys
4340                4345                4350

Asp Ile Leu Asp Arg Val Lys Ala Leu Leu Pro Ser Tyr Met Val
4355                4360                4365

Pro Ala Gln Met Val Leu Leu Asn Ser Met Pro Leu Asn Ala Asn
4370                4375                4380

Gly Lys Val Asp Arg Lys Glu Leu Ala Lys Arg Ala Gly Thr Val
4385                4390                4395

Pro Arg Ser Glu Met Ala Tyr Val Ala Pro Glu Arg Val Pro Pro
4400                4405                4410

Arg Asn Glu Ile Glu Thr Ile Leu Cys Glu Glu Tyr Ala Glu Val
4415                4420                4425

Leu Gly Val Glu Val Gly Val Met Asp Asn Phe Phe Asp Leu Gly
4430                4435                4440

Gly His Ser Leu Met Ala Thr Lys Leu Ala Ala Arg Ala Thr Arg
4445                4450                4455

Arg Leu Asp Ala Lys Leu Ser Val Lys Asp Ile Phe Asp Tyr Pro
4460                4465                4470

Ile Leu Ala Asn Leu Ala Ala Ala Val Gln Arg Gly Ser Thr Pro
4475                4480                4485

His Asn Ala Ile Leu Ala Thr Thr Tyr Ser Gly Pro Val Glu Gln
4490                4495                4500

Ser Phe Ala Gln Gly Arg Leu Trp Phe Leu Asp Gln Leu Asn Val
4505                4510                4515

Gly Ser Asn Trp Tyr Leu Gln Pro Ile Ala Ile Arg Ile Arg Gly
4520                4525                4530

Ser Leu Asn Ile Asn Ala Leu Thr Thr Ala Leu His Ala Leu Glu
4535                4540                4545

Gln Arg His Glu Thr Leu Arg Thr Thr Phe Glu Glu Glu Asp Gly
4550                4555                4560

Val Gly Met Gln Val Val Gln Glu Tyr Asp Pro Ile Glu Leu Arg
4565                4570                4575

Ile Met Asp Ile Ala Ala Asp Tyr Asp Gly Asp Tyr Thr Glu Ala
4580                4585                4590

Leu Lys Gly Glu Gln Thr Thr Pro Phe Asp Leu Glu Ser Glu Pro
4595                4600                4605
```

```
Gly Trp Arg Val Ser Leu Leu Arg Met Asn Asp Asn Asp His Ile
4610                4615                4620

Leu Ser Leu Val Leu His His Ile Ile Ser Asp Gly Trp Ser Val
4625                4630                4635

Asp Val Leu Arg Gln Glu Leu Lys Gln Phe Tyr Ala Ala Ala Leu
4640                4645                4650

Gln Gly Leu Asp Pro Leu Ser Gly Ala Asp Pro Leu Pro Ile Gln
4655                4660                4665

Tyr Arg Asp Phe Ser Leu Trp Gln Lys Gln Pro Glu Gln Val Ala
4670                4675                4680

Glu His Glu Arg Gln Leu Lys Tyr Trp Val Glu Gln Leu Ala Asp
4685                4690                4695

Asn Ser Pro Ala Thr Leu Leu Ala Asp Arg Pro Arg Pro Ser Val
4700                4705                4710

Leu Ser Gly Gln Ala Gly Ser Val Pro Leu Ser Ile Glu Gly Gln
4715                4720                4725

Val Tyr Glu Lys Leu Gln Ala Phe Cys Arg Ala His Gln Thr Thr
4730                4735                4740

Ser Phe Ser Val Leu Leu Ala Ala Phe Arg Ala Ala His Phe Arg
4745                4750                4755

Leu Thr Gly Val Asp Asp Ala Thr Ile Gly Ile Pro Ile Ala Asn
4760                4765                4770

Arg Asn Arg Pro Glu Leu Glu His Leu Ile Gly Phe Phe Val Asn
4775                4780                4785

Arg Gln Cys Met Arg Ile Thr Val Gly Glu Asp Asp Thr Phe Glu
4790                4795                4800

Ser Leu Ile Arg Gln Val His Ser Thr Ala Thr Ala Ala Tyr Ala
4805                4810                4815

Asn Gln Asp Val Pro Phe Glu Arg Ile Val Ser Ser Leu Leu Ser
4820                4825                4830

Gly Ser Arg Asp Thr Ser Arg Asn Pro Leu Val Gln Leu Val Phe
4835                4840                4845

Ala Val His Ser Gln Lys Asn Leu Gly Lys Phe Glu Leu Gln Asp
4850                4855                4860

Leu Thr Ser Glu Pro Val Ala Gly Ala Ile Ser Thr Arg Phe Asp
4865                4870                4875

Ala Glu Phe His Leu Phe Gln Glu Glu Glu Arg Leu Asn Gly Val
4880                4885                4890

Val Tyr Tyr Ala Thr Asp Leu Phe Asp Ala Glu Thr Ile Gln Gly
4895                4900                4905

Val Val Ser Val Phe Gln Glu Ile Leu Arg Arg Gly Leu Asn His
4910                4915                4920

Pro Arg Thr Pro Ile Ala Ala Leu Ser Leu Thr Asp Gly Leu Asp
4925                4930                4935

Asn Leu Arg Lys Met Asn Leu Val His Phe Lys Arg Thr Asp Tyr
4940                4945                4950

Pro Arg Asp Ser Ser Met Val Asp Ile Phe Arg Glu Gln Val Ala
4955                4960                4965

Thr Tyr Pro Asp Val Ile Ala Val Lys Asp Ser Thr Leu Gln Leu
4970                4975                4980

Thr Tyr Ala Gln Leu Asp Gln Gln Ser Asp Glu Ile Ala Thr Trp
4985                4990                4995
```

-continued

```
Leu Arg Asn Lys Lys Met Ala Pro Glu Thr Leu Val Gly Val Leu
5000                5005                5010

Ala Pro Arg Ser Cys Gln Thr Ile Val Ala Phe Leu Gly Val Leu
5015                5020                5025

Lys Ala Asn Leu Ala Tyr Leu Pro Leu Asp Val Asn Ala Pro Met
5030                5035                5040

Ala Arg Val Glu Thr Ile Met Ser Ser Val Pro Gly Ser Lys Leu
5045                5050                5055

Leu Leu Leu Gly Ser Asp Val Pro Ala Gln Glu Ile Gln Leu Gln
5060                5065                5070

Asn Val Glu Leu Val Arg Ile Glu Asp Thr Leu Gly His Ala Ala
5075                5080                5085

Ser Ala Gly Thr Ala Thr Thr Glu Pro Ser Pro Thr Ser Leu Ala
5090                5095                5100

Tyr Val Ile Phe Thr Ser Gly Ser Thr Gly Lys Pro Lys Gly Val
5105                5110                5115

Met Val Glu His Arg Ser Val Ile Arg Leu Val Arg Lys Glu Ser
5120                5125                5130

Asn Ser Met Ser Lys Met Ser Ser Arg Ala Arg Val Ala His Leu
5135                5140                5145

Thr Asn Ile Ala Phe Asp Val Ser Ala Trp Glu Val Tyr Ala Thr
5150                5155                5160

Leu Leu Asn Gly Gly Thr Leu Val Cys Val Asp Tyr Phe Thr Ser
5165                5170                5175

Phe Asp Ala Lys Ala Leu Gly Leu Leu Phe Glu Arg Glu Gln Ile
5180                5185                5190

Thr Ala Ala Met Ile Thr Pro Thr Leu Leu Lys Gln Cys Ile Thr
5195                5200                5205

Ile Val Pro Glu Ala Leu Arg Lys Leu Ser Val Leu Tyr Thr Gly
5210                5215                5220

Gly Asp Arg Phe Asp Arg Arg Asp Ala Ile Ala Thr Lys Ala Leu
5225                5230                5235

Val Lys Gly Pro Val Tyr Asn Ala Trp Gly Pro Thr Glu Thr Thr
5240                5245                5250

Ile Val Ser Thr Ile Tyr Glu Leu Ala Asp Asp Gln Phe Thr
5255                5260                5265

Asn Gly Val Pro Ile Gly Lys Ala Val Ser Asn Ser Trp Ala Tyr
5270                5275                5280

Val Met Asp Leu Asn Gln Gln Leu Val Pro Val Gly Val Met Gly
5285                5290                5295

Glu Ala Val Val Ile Gly Asp Gly Leu Ala Arg Gly Tyr Thr Asp
5300                5305                5310

Pro Ala Leu Asp Cys Asn Arg Phe Val His Ile Thr Ile Asp Gly
5315                5320                5325

Lys Arg Val Arg Ala Tyr Arg Thr Gly Asp Arg Ala Arg Tyr Arg
5330                5335                5340

Pro Lys Asp Gly Glu Ile Glu Phe Phe Gly Arg Met Asp Arg Gln
5345                5350                5355

Leu Lys Ile Arg Gly His Arg Ile Glu Pro Ala Glu Ile Glu His
5360                5365                5370

Ala Met Leu Gly His Asn Asp Ile Val Asp Val Ala Ile Val Thr
5375                5380                5385
```

```
Arg His Gln Asp Gly Ala Gly Leu Glu Met Val Ala Phe Val Thr
5390            5395             5400

Ala His Thr Asn Lys Ser Ile Glu Arg Asn Glu Ala Thr Asn Gln
5405            5410             5415

Val Ala Gly Trp Gly Asp His Phe Glu Ser Ser Thr Tyr Ala Glu
5420            5425             5430

Leu Asp Thr Leu Val Lys Ser Asp Val Gly Lys Asp Phe Val Gly
5435            5440             5445

Trp Thr Asn Met Tyr Asp Gly Gly Ala Ile Asp Gln Ala Glu Met
5450            5455             5460

Gln Glu Trp Leu Asp Asp Thr Ile Gln Thr Ile Val Asp Gly Gln
5465            5470             5475

Pro Ala Gly His Val Phe Glu Ile Gly Thr Gly Thr Gly Met Ile
5480            5485             5490

Met Phe Gly Leu Gly Lys Gln Gly Leu Gln Ser Tyr Val Gly Leu
5495            5500             5505

Glu Pro Ser Thr Ser Ala Thr Thr Tyr Val Asn Arg Lys Ile Lys
5510            5515             5520

Thr Ala Pro Thr Val Ala Gly Lys Ala Lys Val Tyr Val Gly Thr
5525            5530             5535

Ala Met Glu Ala Ala Gln Leu Asn Gly Leu His Pro Glu Val Val
5540            5545             5550

Val Ile Asn Ser Val Ala Gln Tyr Phe Pro Thr Pro Glu Tyr Leu
5555            5560             5565

Leu Glu Val Val Gly Ile Leu Thr Gln Met Pro Gly Val Lys Arg
5570            5575             5580

Leu Phe Phe Gly Asp Ile Arg Ser Tyr Ala Thr Asn Arg Lys Phe
5585            5590             5595

Leu Ala Ala Arg Ala Leu His Met Leu Gly Ser Asn Ala Lys Lys
5600            5605             5610

His Asp Ile Arg Arg Lys Met Ala Glu Leu Asp Glu Phe Glu Glu
5615            5620             5625

Glu Leu Ile Val Asp Pro Ser Phe Phe Thr Gly Leu Val Ser Arg
5630            5635             5640

Leu Pro Gly Gln Val Lys His Val Glu Ile Leu Pro Lys Gln Met
5645            5650             5655

Ile Ala Thr Asn Glu Leu Ser Ala Tyr Arg Tyr Ala Ala Val Val
5660            5665             5670

His Leu Ala Leu Pro Glu Glu Gln His Ile Ala Lys Ile Glu Lys
5675            5680             5685

Gly Ala Trp Val Asp Phe Thr Ala Thr Lys Met Asp Arg Ser Ala
5690            5695             5700

Leu Val His His Leu Gln Ser Ser Ser Asn Ala Glu Ile Val Ala
5705            5710             5715

Ile Ser Asn Ile Pro Phe Ser Lys Thr Asn Phe Asp Cys His Leu
5720            5725             5730

Leu Ala Ser Leu Asp Glu Asp Glu Glu His Ser Leu Asp Gly Ser
5735            5740             5745

Ala Trp Ile Lys Thr Ile His Ser Ser Ala Glu Gln Cys Pro Ser
5750            5755             5760

Leu Ser Ala Thr Asp Leu Val Glu Val Ala Lys Glu Val Gly Phe
5765            5770             5775
```

```
Arg Val Glu Leu Ser Trp Ala Arg Gln Lys Ser Gln Asn Gly Ala
5780            5785                5790

Leu Asp Ala Ile Phe His Gln Tyr Gln Ser Pro Lys Glu Gly Ser
5795            5800                5805

Arg Val Leu Ile Gln Phe Pro Thr Asp Asp Gln Gly Arg Ser Met
5810            5815                5820

Glu Ser Leu Thr Asn Arg Pro Leu Gln Arg Val Gln Ser Arg Arg
5825            5830                5835

Ile Glu Thr Gln Ile Arg Glu Arg Leu Gln Ala Val Leu Pro Ser
5840            5845                5850

Tyr Met Ile Pro Ala Arg Ile Val Val Leu Asn Glu Met Pro Val
5855            5860                5865

Asn Ala Asn Gly Lys Val Asp Arg Lys Glu Leu Thr Arg Arg Ala
5870            5875                5880

Lys Val Val Pro Arg Ile Glu Thr Ala Ala Glu Arg Ile Gln Pro
5885            5890                5895

Arg Asn Glu Val Glu Ala Val Leu Cys Glu Glu Phe Ser Glu Val
5900            5905                5910

Leu Gly Val Glu Val Gly Val Thr Asp Asn Phe Phe Asp Leu Gly
5915            5920                5925

Gly His Ser Leu Met Ala Thr Lys Leu Ala Ala Arg Thr Gly Arg
5930            5935                5940

Arg Leu Asp Ala Lys Val Ser Val Lys Asp Val Phe Asp His Pro
5945            5950                5955

Val Leu Ala Asp Leu Ala Ala Ile Gln Arg Gly Ser Thr Pro
5960            5965                5970

His Ser Ala Ile Val Thr Thr Glu Tyr Ser Gly Pro Val Glu Gln
5975            5980                5985

Ser Tyr Ala Gln Gly Arg Leu Trp Phe Leu Glu Gln Leu Asn Phe
5990            5995                6000

Lys Ala Thr Trp Tyr Leu Leu Pro Leu Ala Val Arg Ile Arg Gly
6005            6010                6015

Pro Leu Asn Ile Lys Ala Leu Thr Thr Ala Leu His Ala Leu Glu
6020            6025                6030

Gln Arg His Glu Thr Leu Arg Thr Thr Phe Ile Glu Arg Asp Gly
6035            6040                6045

Val Gly Lys Gln Ala Val Gln Pro Phe Gln Pro Lys Glu Leu Glu
6050            6055                6060

Ile Val Asp Ile Ala Ala Asp His Gln Gly Asp Tyr Leu Lys Val
6065            6070                6075

Leu Arg Asp Glu Gln Thr Thr Met Phe Asn Leu Ala Thr Gln Pro
6080            6085                6090

Gly Trp Arg Val Thr Leu His Arg Val Asp Gln Asn Thr His Asn
6095            6100                6105

Leu Ser Ile Val Met His His Ile Ile Ser Asp Gly Trp Ser Val
6110            6115                6120

Asp Val Leu Arg His Glu Leu Arg Gln Phe Tyr Ala Ala Ala Leu
6125            6130                6135

Arg Gly Gln Asp Pro Leu Ala His Ile Ser Pro Leu Pro Ile Gln
6140            6145                6150

Tyr Arg Asp Phe Ser Leu Trp Gln Lys Gln Pro Asp Gln Ile Ile
6155            6160                6165
```

| | | | | | | | | | | |
|---|---|---|---|---|---|---|---|---|---|---|
|Glu|His|Ala|Lys|Gln|Leu|Glu|Tyr|Trp|Thr|Lys|Gln|Leu|Ala|Asp|
|6170| | | | |6175| | | | |6180| | | | |
|Ser|Ser|Pro|Ala|Glu|Leu|Pro|Thr|Asp|Leu|Pro|Arg|Pro|Ala|Val|
|6185| | | | |6190| | | | |6195| | | | |
|Leu|Ser|Gly|Lys|Ala|Gly|Glu|Val|Ala|Leu|Ser|Val|Lys|Gly|Pro|
|6200| | | | |6205| | | | |6210| | | | |
|Leu|Tyr|Glu|Arg|Leu|Gln|Ala|Phe|Cys|Lys|Thr|His|Gln|Thr|Thr|
|6215| | | | |6220| | | | |6225| | | | |
|Ala|Phe|Ala|Thr|Leu|Leu|Ala|Ala|Phe|Arg|Ala|Thr|His|His|Arg|
|6230| | | | |6235| | | | |6240| | | | |
|Leu|Thr|Gly|Ala|Glu|Asp|Ala|Thr|Ile|Gly|Thr|Pro|Ile|Ala|Asn|
|6245| | | | |6250| | | | |6255| | | | |
|Arg|Asn|Arg|Pro|Glu|Leu|Glu|Asn|Leu|Ile|Gly|Phe|Phe|Val|Asn|
|6260| | | | |6265| | | | |6270| | | | |
|Ala|Gln|Cys|Met|Arg|Ile|Thr|Ile|Asp|Gly|Asp|Glu|Thr|Phe|Glu|
|6275| | | | |6280| | | | |6285| | | | |
|Ser|Leu|Ile|Arg|Gln|Val|Arg|Ala|Thr|Ala|Thr|Ala|Ala|Ile|Ala|
|6290| | | | |6295| | | | |6300| | | | |
|Asn|Gln|Asp|Val|Pro|Phe|Glu|Arg|Ile|Val|Ser|Thr|Met|Gln|Ser|
|6305| | | | |6310| | | | |6315| | | | |
|Thr|Ser|Arg|Asp|Thr|Ser|Arg|Asn|Pro|Leu|Val|Gln|Leu|Met|Phe|
|6320| | | | |6325| | | | |6330| | | | |
|Ala|Leu|His|Ser|Gln|Gln|Asp|Leu|Gly|Lys|Ile|Gln|Leu|Glu|Gly|
|6335| | | | |6340| | | | |6345| | | | |
|Cys|Glu|Thr|Glu|Pro|Ile|Pro|Arg|Ala|Val|Arg|Thr|Arg|Phe|Asp|
|6350| | | | |6355| | | | |6360| | | | |
|Leu|Glu|Phe|His|Leu|Tyr|Gln|Glu|Gln|Gly|Ser|Leu|Gly|Gly|Ile|
|6365| | | | |6370| | | | |6375| | | | |
|Val|Tyr|Phe|Ala|Thr|Asp|Leu|Phe|Glu|Pro|Glu|Ser|Ile|Glu|Gly|
|6380| | | | |6385| | | | |6390| | | | |
|Met|Val|Ser|Ile|Phe|Lys|Glu|Ile|Leu|Ala|Arg|Ala|Leu|Asp|Gln|
|6395| | | | |6400| | | | |6405| | | | |
|Pro|Gln|Thr|Pro|Leu|Ala|Leu|Leu|Pro|Leu|Thr|Asp|Gly|Leu|Ala|
|6410| | | | |6415| | | | |6420| | | | |
|Glu|Leu|Arg|Arg|Arg|Gly|Leu|Leu|Glu|Ile|Glu|Arg|Pro|Ser|Tyr|
|6425| | | | |6430| | | | |6435| | | | |
|Pro|Arg|Glu|Ser|Ser|Val|Val|Asp|Val|Phe|Cys|Ser|Gln|Val|Ala|
|6440| | | | |6445| | | | |6450| | | | |
|Ala|Ser|Pro|Asn|Ala|Thr|Ala|Val|Lys|Asp|Ser|Ile|Ser|Gln|Leu|
|6455| | | | |6460| | | | |6465| | | | |
|Thr|Tyr|Ala|Gln|Leu|Asn|Glu|Gln|Ser|Asp|Lys|Val|Ala|Ala|Trp|
|6470| | | | |6475| | | | |6480| | | | |
|Leu|His|Gln|Cys|Asn|Leu|Pro|Thr|Glu|Thr|Leu|Val|Ala|Val|Leu|
|6485| | | | |6490| | | | |6495| | | | |
|Ala|Pro|Arg|Ser|Cys|Gln|Thr|Val|Val|Ala|Phe|Leu|Gly|Ile|Leu|
|6500| | | | |6505| | | | |6510| | | | |
|Lys|Ala|Asn|Leu|Ala|Tyr|Leu|Pro|Leu|Asp|Val|Asn|Val|Pro|Ala|
|6515| | | | |6520| | | | |6525| | | | |
|Ala|Arg|Ile|Glu|Ala|Ile|Leu|Ser|Glu|Val|Ser|Gly|His|Ile|Leu|
|6530| | | | |6535| | | | |6540| | | | |
|Val|Leu|Leu|Gly|Ser|His|Val|Ser|Ala|Pro|Lys|Ile|Glu|Leu|Ala|
|6545| | | | |6550| | | | |6555| | | | |

```
Asp Val Glu Phe Val Lys Ile Asp Asn Thr Val Glu His Asn Leu
6560                6565                6570

Pro Gly Arg Ile Gly Ser Ala Pro Ser Ala Thr Ser Leu Ala Tyr
6575                6580                6585

Val Ile Phe Thr Ser Gly Ser Thr Gly Lys Pro Lys Gly Val Lys
6590                6595                6600

Val Glu His Arg Gly Ile Val Arg Leu Val Lys Glu Ser Asn Val
6605                6610                6615

Val Ala Lys Met Pro Gln Ala Ala Arg Ile Ala His Leu Ser Asn
6620                6625                6630

Ile Ala Phe Asp Ala Ala Thr Trp Glu Leu Tyr Ala Ala Leu Leu
6635                6640                6645

Asn Gly Gly Thr Leu Val Cys Ile Asn Tyr Leu Thr Thr Leu Asp
6650                6655                6660

Ser Lys Ala Leu Glu Ala Val Phe Glu Gln Glu Lys Ile Gln Ala
6665                6670                6675

Ala Met Leu Pro Pro Ala Leu Leu Lys Gln Tyr Leu Val Asn Ile
6680                6685                6690

Pro Ala Ala Ile Gly Ala Leu Glu Val Val Leu Val Ala Gly Asp
6695                6700                6705

Arg Phe Asp Arg Arg Asp Ala Ala Thr Gln Ala Leu Val Gly
6710                6715                6720

Ala Gly Val Tyr Asn Ala Tyr Gly Pro Thr Glu Asn Thr Thr Leu
6725                6730                6735

Ser Thr Ile Tyr Asn Val Val Gln Gly Asp Ala Asn Val Asn Gly
6740                6745                6750

Val Pro Ile Gly Arg Pro Val Ser Asn Ser Gly Ala Tyr Ile Met
6755                6760                6765

Asn Met Asn Gln Glu Leu Val Pro Ile Gly Val Ile Gly Glu Leu
6770                6775                6780

Val Val Val Gly Asp Gly Val Ala Arg Gly Tyr Thr Asp Pro Ala
6785                6790                6795

Leu Asp Val Asn Arg Phe Val Asn Val Thr Ile Glu Gly Gln Thr
6800                6805                6810

Met Arg Ala Tyr Arg Thr Gly Asp Arg Ala Arg Tyr Arg Pro Lys
6815                6820                6825

Asp Ala Gln Ile Glu Phe Phe Gly Arg Met Asp Gln Gln Ile Lys
6830                6835                6840

Ile Arg Gly His Arg Ile Glu Pro Ala Glu Val Glu His Ala Leu
6845                6850                6855

Leu Asn Asn Asp Leu Leu Gln Asp Ala Ala Val Ile Ile Arg Lys
6860                6865                6870

Gln Gln Asn Asp Glu Leu Glu Met Val Ala Phe Val Glu Ala Asn
6875                6880                6885

Ser Asn Lys Ser Ile Glu Gln Glu Ala Ser Asn Gln Val Glu Asp
6890                6895                6900

Trp Gly Ala Gln Phe Glu Ser Asn Val Tyr Ala Glu Ile Glu Ala
6905                6910                6915

Ile Asp Ala Ser Ala Val Gly Asn Asp Phe Met Gly Trp Thr Ser
6920                6925                6930

Met Tyr Asp Gly Ser Ala Ile Asp Lys Ala Glu Met Gln Glu Trp
6935                6940                6945
```

```
Leu Asp Asp Thr Met Gln Thr Ile Leu Asp Gly Arg Pro Ala Gly
6950                 6955                 6960

Arg Val Leu Glu Ile Gly Thr Gly Thr Gly Met Ile Leu Phe Asn
6965                 6970                 6975

Leu Gly Glu Gly Leu Gln Ser Tyr Val Gly Leu Glu Pro Ser Thr
6980                 6985                 6990

Ser Ala Ala Ala Phe Val Asn Arg Arg Ile Gln Thr Leu Pro Ala
6995                 7000                 7005

Phe Ala Gly Lys Ala Glu Val His Val Gly Thr Ala Thr Asp Ile
7010                 7015                 7020

Ser Gln Leu Gln Asp Leu Arg Pro Glu Val Val Ile Asn Ser
7025                 7030                 7035

Val Ala Gln Tyr Phe Pro Ser Pro Glu Tyr Leu Ser Lys Val Leu
7040                 7045                 7050

Tyr Ala Leu Ala Gln Ile Pro Gly Val Lys Arg Leu Phe Phe Gly
7055                 7060                 7065

Asp Met Arg Ser Tyr Ala Ile Asn Asp Gln Phe Leu Ala Ala Arg
7070                 7075                 7080

Ala Leu His Asn Ile Gly Ser Lys Ala Thr Lys Ser Ala Ile Arg
7085                 7090                 7095

Ser Lys Met Val Asp Leu Glu Asn Ser Glu Glu Glu Leu Leu Val
7100                 7105                 7110

Asp Pro Thr Phe Phe Thr Asn Leu Ala Thr Glu Leu Pro Glu Val
7115                 7120                 7125

Glu His Val Glu Ile Leu Pro Lys Arg Met Gln Ala Thr Asn Glu
7130                 7135                 7140

Leu Ser Ala Tyr Arg Tyr Ala Ala Val Val His Ile Arg Asp Pro
7145                 7150                 7155

Ala Arg Gln Ala Gln Thr Val His Thr Ile Asp Pro Thr Ala Trp
7160                 7165                 7170

Ile Asp Phe Ser Ala Ser Gln Met Asn Arg Thr Ala Leu Ala Asn
7175                 7180                 7185

Leu Leu Gln Asn Ser Ala Asp Ala Ala Ala Ile Ala Val Ser Asn
7190                 7195                 7200

Ile Pro Tyr Ser Lys Thr Ile Leu Ala Arg His Ile Val Gln Ser
7205                 7210                 7215

Leu Asp Asp Asp Leu Thr Asp Ser Asp Asp Pro Gln Asp Glu Leu
7220                 7225                 7230

Glu Gly Ala Ala Trp Met Ser Ala Ile Arg Ser Asn Ile Lys Thr
7235                 7240                 7245

Cys Ala Ser Leu Ser Ala Phe Asp Leu Ala Gln Leu Ala Gln Glu
7250                 7255                 7260

Lys Gly Phe Arg Val Glu Leu Ser Trp Ala Arg Gln Arg Thr His
7265                 7270                 7275

His Gly Ala Leu Asp Ala Val Phe His His Tyr Lys Ser Asn Gln
7280                 7285                 7290

Asp Gly Gly Arg Val Leu Val Gln Phe Pro Thr Asp Ser Arg Pro
7295                 7300                 7305

Arg Leu Ser Gly Gln Leu Thr Asn Gln Pro Leu Gln Arg Leu Gln
7310                 7315                 7320

Ser Arg Arg Leu Glu Ala Gln Ile Arg Asp Gln Leu Ser Ala Leu
7325                 7330                 7335
```

```
Leu Pro Ser Tyr Met Ile Pro Ser Leu Ile Val Met Val Asp Glu
    7340            7345                7350

Met Pro Leu Asn Ala Asn Gly Lys Val Asp Arg Lys Ala Leu Glu
    7355            7360                7365

Arg Arg Ala Arg Met Val Gln Lys Val Glu Lys Pro Ala Ser Glu
    7370            7375                7380

Arg Val Gly Ala Arg Asn Glu Ile Glu Ala Ala Leu Cys Glu Val
    7385            7390                7395

Phe Val Asp Leu Leu Gly Thr Glu Val Ser Ile Thr Asp Asn Phe
    7400            7405                7410

Phe Asn Leu Gly Gly His Ser Leu Met Ala Thr Lys Leu Ala Ala
    7415            7420                7425

Arg Ile Ser Arg Arg Leu Asp Ala Arg Ile Ser Val Lys Asp Val
    7430            7435                7440

Phe Asp Tyr Pro Val Leu Ala Asp Leu Ala Gly Ala Val Gln Arg
    7445            7450                7455

Gly Ser Thr Pro His Asn Pro Ile Val Ala Thr Pro Tyr Ser Gly
    7460            7465                7470

Pro Val Glu Gln Ser Phe Ala Gln Gly Arg Leu Trp Phe Leu Asp
    7475            7480                7485

Gln Leu Asn Ala Gly Ser Leu Trp Tyr Ile Gln Pro Ile Ala Val
    7490            7495                7500

Arg Val Arg Gly Ser Leu Asn Ile Gly Ala Leu Thr Thr Ala Leu
    7505            7510                7515

Asn Ala Leu Glu Lys Arg His Glu Pro Leu Arg Thr Thr Phe Glu
    7520            7525                7530

Glu His Asp Gly Ile Gly Val Gln Val Val Gln Pro His Gln Pro
    7535            7540                7545

Lys Lys Leu Arg Ile Val Asp Thr Val Ala Asn Tyr Gln Gly Asp
    7550            7555                7560

Phe Ile Arg Ala Leu Arg Lys Glu Gln Gln Thr Leu Phe Asn Leu
    7565            7570                7575

Ala Thr Glu Pro Gly Trp Arg Val Ser Leu Leu Arg Ile Gly Glu
    7580            7585                7590

Asp Asp Asn Ile Leu Ser Ile Val Met His His Ile Ile Ser Asp
    7595            7600                7605

Gly Trp Ser Val Asp Ile Leu Arg Gln Asp Leu Lys Leu Phe Tyr
    7610            7615                7620

Ala Ala Ala Leu Lys Ser Gln Glu Pro Gln Val Asp Ala Leu Pro
    7625            7630                7635

Ile Gln Tyr Arg Asp Phe Ala Phe Trp Gln Lys Gln Pro Glu Gln
    7640            7645                7650

Val Ala Glu His Gln Arg Gln Leu Asp Tyr Trp Ile Glu Gln Leu
    7655            7660                7665

Lys Asp Ser Lys Pro Ala Glu Leu Ile Thr Asp Phe Pro Arg Pro
    7670            7675                7680

Glu Val Leu Ser Gly Thr Ala Gly Ile Val Gln Leu Ala Val Asp
    7685            7690                7695

Gly Gln Val Tyr Glu Gly Leu Arg Ala Phe Cys Arg Ile His Gln
    7700            7705                7710

Thr Thr Ser Phe Val Val Leu Leu Ala Ala Phe Arg Ala Ala His
    7715            7720                7725
```

```
Tyr Arg Leu Thr Gly Thr Glu Asp Ala Thr Ile Gly Ser Pro Ile
            7730                7735                7740

Ala Asn Arg Asn Arg Pro Glu Leu Glu Ser Leu Ile Gly Phe Phe
    7745                7750                7755

Val Asn Thr Gln Cys Met Arg Ile Met Val Gly Glu Asp Asp Thr
    7760                7765                7770

Phe Glu Arg Leu Val Gln Gln Val Arg Ser Thr Thr Thr Ala Ala
    7775                7780                7785

Phe Ala Asn Gln Asp Val Pro Phe Glu Arg Ile Val Ser Ser Val
    7790                7795                7800

Gln Ser Thr Ser Arg Asp Ala Ser Arg Asn Pro Leu Val Gln Leu
    7805                7810                7815

Met Phe Ala Leu His Ser Gln Gln Gly Ile Gly Leu Met Glu Leu
    7820                7825                7830

Glu Gly Val Glu Thr Glu Pro Ile Ala Arg Asp Val Ser Thr Arg
    7835                7840                7845

Phe Asp Ile Glu Phe His Leu Tyr Gln Lys Glu Glu Ser Leu His
    7850                7855                7860

Gly Val Val His Phe Ala Ala Asp Leu Phe Glu Pro Glu Thr Ile
    7865                7870                7875

Gln Gly Leu Val Ser Val Phe Gln Glu Ile Leu Arg Arg Gly Leu
    7880                7885                7890

Glu Thr Pro Arg Leu Pro Ile Ser Ile Leu Pro Leu Asp Asn Asn
    7895                7900                7905

Ile Pro Glu Leu Leu Val Gly Met Leu Asp Val Asp Thr Pro Glu
    7910                7915                7920

Tyr Pro Arg Asp Ser Ser Val Val Asp Val Phe Arg Thr Gln Val
    7925                7930                7935

Ala Ala Ser Pro Asp Ala Ile Ala Val Lys Asp Ser Thr Ser Gln
    7940                7945                7950

Leu Thr Tyr Ala Gln Leu Asp Glu Glu Ser Asn Lys Val Ala Thr
    7955                7960                7965

Trp Leu Ser Gln Arg Gln Leu Ala Pro Glu Thr Leu Val Gly Val
    7970                7975                7980

Leu Ala Pro Arg Ser Cys Pro Thr Ile Val Thr Phe Phe Gly Ile
    7985                7990                7995

Leu Lys Ala Ser Leu Ala Tyr Leu Pro Leu Asp Val Asn Val Pro
    8000                8005                8010

Ser Ala Arg Ile Glu Ala Ile Leu Ser Ala Val Pro Asp His Lys
    8015                8020                8025

Leu Val Phe Leu Gly Ala Asp Val Pro Asp Pro Glu Ala Pro Leu
    8030                8035                8040

Val Asn Val Glu Leu Val Arg Ile Asp Asp Ile Leu Arg Gln Ser
    8045                8050                8055

Ile His Ala Ser Asn Ala Gly Leu Leu Ala Asn His Pro Leu Ala
    8060                8065                8070

Thr Ser Leu Ala Tyr Val Met Phe Thr Ser Gly Ser Thr Gly Lys
    8075                8080                8085

Pro Lys Gly Val Met Val Glu His Arg Ser Ile Val Arg Leu Val
    8090                8095                8100

Lys Glu Thr Asn Leu Val Pro Ala Val Glu Ala Val Ser Ser Val
    8105                8110                8115
```

-continued

Ala His Ile Ser Asn Val Ala Phe Asp Ala Thr Trp Glu Ile
8120            8125            8130

Tyr Ala Ala Leu Leu Asn Gly Gly Thr Thr Val Cys Ile Asp His
8135            8140            8145

Ile Thr Val Leu Asp Pro Ala Lys Leu Ala Leu Val Phe Ser Ser
8150            8155            8160

Glu Lys Ile Lys Ala Ala Phe Phe Ser Thr Ala Leu Leu Lys Gln
8165            8170            8175

Arg Leu Tyr Glu Glu Pro Ser Thr Ile Thr Gly Leu Asp Leu Leu
8180            8185            8190

Tyr Ala Gly Gly Glu Arg Met Arg Pro Gln Asp Ala Leu Lys Thr
8195            8200            8205

Arg Glu Leu Val Arg Gly Ser Phe Cys His Val Tyr Gly Pro Thr
8210            8215            8220

Glu Asn Thr Thr Phe Ser Thr Val Tyr Pro Met Gly Val Glu Glu
8225            8230            8235

Arg Cys Val Asn Gly Leu Pro Ile Gly Arg Ala Val Ser His Ser
8240            8245            8250

Gly Ala Val Ile Met Asp Ala Asn Gln Arg Leu Val Pro Leu Gly
8255            8260            8265

Val Met Gly Glu Leu Val Val Thr Gly Asp Gly Leu Ala Arg Gly
8270            8275            8280

Tyr Thr Asp Pro Ala Leu Asn Arg Asp Arg Phe Val Glu Val Asn
8285            8290            8295

Ile His Gly Gln Val Leu Arg Ala Tyr Arg Thr Gly Asp Gln Ala
8300            8305            8310

Arg Tyr Arg Pro Lys Asp Gly Gln Ile Glu Phe Ser Gly Arg Met
8315            8320            8325

Asp Arg Gln Leu Lys Ile Arg Gly His Arg Ile Glu Pro Ala Glu
8330            8335            8340

Val Glu His Ala Ile Leu Ser His Asp Asp Ile Arg Asn Ala Val
8345            8350            8355

Val Val Thr Arg Gln Gln Glu Gly Gln Asp Leu Glu Met Val Ala
8360            8365            8370

Phe Val Ser Thr Pro Asn Asp Gln Thr Val Glu Arg Asp Glu Ala
8375            8380            8385

Arg Asn Gln Val Glu Asp Trp Gly Ala Gln Phe Glu Ser Asn Val
8390            8395            8400

Tyr Ala Glu Ile Glu Glu Ile Asp Ser Ser Ala Val Gly Asn Asp
8405            8410            8415

Phe Met Gly Trp Thr Ser Met Tyr Asp Gly Thr Ala Ile Asp Lys
8420            8425            8430

Ala Glu Met Gln Glu Trp Leu Asp Asp Thr Met Arg Thr Leu His
8435            8440            8445

Asp Gly Arg Asp Pro Gly His Val Leu Glu Val Gly Thr Gly Thr
8450            8455            8460

Gly Met Ile Leu Phe Asn Leu Gly Lys Gly Leu Gln Ser Tyr Val
8465            8470            8475

Gly Leu Glu Pro Ser Thr Ser Ala Ala Ala Phe Val Asn Arg Lys
8480            8485            8490

Ile Glu Thr Ile Ser Ser Leu Ala Gly Lys Ala Lys Val Glu Ile
8495            8500            8505

```
Gly Thr Ala Thr Asp Val Gly Gln Leu Lys Asn Leu Arg Ser Asp
8510                8515                8520

Leu Val Val Ile Asn Ser Val Ala Gln Tyr Phe Pro Ser Pro Glu
8525                8530                8535

Tyr Leu Val Glu Ala Val Thr Ala Leu Val His Ile Pro Gly Val
8540                8545                8550

Lys Arg Leu Phe Phe Gly Asp Met Arg Ser Tyr Ala Met Asn Lys
8555                8560                8565

Gln Phe Leu Val Ala Arg Ala Leu Arg Thr Leu Gly Ala Lys Ala
8570                8575                8580

Asn Lys Asp Asp Val Arg Arg Lys Met Val Glu Leu Glu Glu Phe
8585                8590                8595

Glu Glu Glu Leu Leu Val Asp Pro Ala Phe Phe Thr Gly Leu Ala
8600                8605                8610

Asn Trp Leu Ser Glu Val Glu His Val Glu Ile Leu Pro Lys Gln
8615                8620                8625

Met Thr Ser Thr Asn Glu Leu Ser Ser Tyr Arg Tyr Ala Ala Ile
8630                8635                8640

Val His Leu Arg Leu Pro Gly Gln Glu Ala Gln Pro Val Val Thr
8645                8650                8655

Val Asn Gln Asp Ala Trp Val Asp Phe Gly Gly Ser Lys Met Asp
8660                8665                8670

Arg His Ala Leu Leu His His Leu Gln Ser Ser Pro Lys Ala Glu
8675                8680                8685

Thr Val Ala Ile Ser Asn Ile Pro Tyr Ser Lys Thr Ile Tyr Glu
8690                8695                8700

Arg His Val Leu Ala Ser Leu Asp Asp Asp Glu Val Glu Asp Ser
8705                8710                8715

Leu Asp Gly Ser Ala Trp Leu Ser Ala Val Arg Ser Thr Ala Glu
8720                8725                8730

Gln Cys Ala Ser Leu Ser Gly Val Asp Leu Val Gln Ile Ala Lys
8735                8740                8745

Glu Ala Gly Phe Arg Val Glu Leu Ser Trp Ala Arg Gln Arg Ser
8750                8755                8760

Gln Lys Gly Gly Ile Asp Ala Val Phe His His Tyr Glu Ser Val
8765                8770                8775

His Asp Gly Ala Arg Val Met Val Lys Phe Pro Thr Asp Asp Gln
8780                8785                8790

Gly Arg Ala Leu Asp Ser Leu Ala Asn Arg Pro Leu Gln Arg Leu
8795                8800                8805

Gln Ser Arg Arg Ile Glu Val Gln Ile Arg Glu Arg Leu Gln Ala
8810                8815                8820

Val Leu Pro Ser Tyr Met Met Pro Val Arg Ile Val Val Leu Asp
8825                8830                8835

Glu Met Pro Met Asn Ala Asn Gly Lys Val Asp Arg Lys Val Leu
8840                8845                8850

Thr Arg Arg Ala Lys Met Ile Ser Arg Val Glu Thr Thr Ala Glu
8855                8860                8865

Arg Val Gly Pro Arg Asn Glu Ile Glu Ala Leu Leu Cys Glu Glu
8870                8875                8880

Phe Ala Glu Val Leu Gly Val Glu Val Gly Ile Asn Asp Asp Phe
8885                8890                8895
```

-continued

```
Phe Asp Leu Gly Gly His Ser Leu Met Ala Thr Lys Leu Ala Ala
    8900                8905                8910

Arg Ser Ser Arg Arg Phe Asp Ala Lys Val Ser Val Lys Asp Val
    8915                8920                8925

Phe Asp His Pro Ile Leu Ala Asp Leu Ala Ala Ser Ile Gln Arg
    8930                8935                8940

Gly Ser Thr Pro His Asn Pro Ile Leu Ala Thr Gln Tyr Ser Gly
    8945                8950                8955

Pro Val Glu Gln Ser Phe Ala Gln Gly Arg Leu Trp Phe Leu Glu
    8960                8965                8970

Gln Leu Asn Val Ser Ser Thr Trp Tyr Leu Gln Pro Ile Ala Val
    8975                8980                8985

Arg Met Arg Gly Pro Leu Lys Ile Glu Ala Leu Ala Ala Ala Phe
    8990                8995                9000

His Ala Leu Glu Glu Arg His Glu Thr Leu Arg Thr Thr Phe Glu
    9005                9010                9015

Glu His Asp Gly Ile Gly Met Gln Val Val Gln Pro His Arg Pro
    9020                9025                9030

Lys Glu Leu Arg Val Ile Asp Val Gln Ala Glu His Asp Gly Asp
    9035                9040                9045

Tyr Thr Gln Ala Leu His Thr Glu Gln Thr Thr Thr Phe Asn Leu
    9050                9055                9060

Glu Thr Glu Pro Gly Trp Arg Val Ser Val Phe Arg Leu Asn Glu
    9065                9070                9075

Asp Asp Asn Ile Leu Ser Ile Val Met His His Ile Ile Ser Asp
    9080                9085                9090

Gly Trp Ser Phe Asp Ile Leu Arg Lys Glu Ile Arg Glu Phe Tyr
    9095                9100                9105

Asn Ala Ala Leu Lys Gly Lys Asp Pro Leu Ala Gln Met Ser Pro
    9110                9115                9120

Leu His Ile Gln Tyr Arg Asp Phe Ser Val Trp Gln Lys Gln Leu
    9125                9130                9135

Asn Gln Ile Thr Glu His Lys Arg Gln Leu Asp Tyr Trp Thr Lys
    9140                9145                9150

Asn Leu Ala Asp Asn Thr Pro Ala Glu Leu Pro Thr Asp Leu Pro
    9155                9160                9165

Arg Pro Ala Val Leu Ser Gly Lys Ala Gly Val Ile Gln Leu Ser
    9170                9175                9180

Ile Thr Gly Pro Val Tyr Asp Arg Leu Arg Ala Phe Cys Arg Val
    9185                9190                9195

His Gln Thr Thr Leu Phe Thr Val Leu Leu Thr Val Phe Arg Ala
    9200                9205                9210

Thr His Tyr Arg Leu Thr Gly Ala Glu Asp Ala Thr Ile Gly Thr
    9215                9220                9225

Pro Ile Ala Asn Arg Asn Arg Pro Glu Leu Glu Asn Leu Ile Gly
    9230                9235                9240

Phe Phe Val Asn Thr Gln Cys Met Arg Ile Thr Val Glu Glu Glu
    9245                9250                9255

Asp Thr Phe Glu Thr Leu Ile His Gln Val Arg Thr Thr Thr Thr
    9260                9265                9270

Ala Ala Phe Ala Asn Gln Asp Val Pro Phe Glu Arg Ile Val Ser
    9275                9280                9285
```

```
Ala Leu Leu Pro Gly Ser Arg Asp Thr Ser Arg Asn Pro Leu Ser
9290                 9295                 9300

Gln Ile Met Phe Ala Val His Ser Gln Lys Asn Ile Ser Lys Ile
9305                 9310                 9315

Glu Leu Asp Gly Leu Glu Ser Glu Ala Ile Ser Arg Ala Thr Ser
9320                 9325                 9330

Thr Arg Phe Asp Leu Glu Phe His Leu Phe Gln Glu Glu Lys Gly
9335                 9340                 9345

Leu Gly Gly Ile Val Leu Phe Ala Ala Asp Leu Phe Glu Pro Glu
9350                 9355                 9360

Thr Ile Asp Ser Leu Val Phe Val Phe Gln Glu Ile Leu Arg Gln
9365                 9370                 9375

Ser Leu Glu Thr Pro Lys Thr Pro Ile Ala Val Leu Pro Leu Thr
9380                 9385                 9390

Asn Gly Ile Ala Gln Leu Arg Ser Met Cys Val Leu Asp Ile Glu
9395                 9400                 9405

Lys Thr Ala Tyr Pro Gln Asp Ser Ser Val Ile Asp Ile Phe Arg
9410                 9415                 9420

Gln Gln Val Ala Ala Arg Pro Asp Ala Thr Ala Val Thr Asp Ser
9425                 9430                 9435

Thr Ser Gln Leu Thr Tyr Ala Gln Leu Asp Leu His Ser Asp Glu
9440                 9445                 9450

Leu Ala Ser Trp Leu Arg Gln Lys Lys Met Ala Pro Glu Thr Leu
9455                 9460                 9465

Val Gly Val Leu Ala Pro Arg Ser Cys Gln Thr Ile Val Thr Phe
9470                 9475                 9480

Leu Gly Ile Leu Lys Ala Ser Leu Ala Tyr Leu Pro Leu Asp Val
9485                 9490                 9495

Lys Val Pro Val Ala Arg Ile Glu Ala Ile Leu Ser Ser Ile Ser
9500                 9505                 9510

Gly Gln Lys Leu Ile Leu Leu Gly Gln Asp Val Pro Val Pro Glu
9515                 9520                 9525

Ile Gln Leu Pro Asp Val Asp Val Val Pro Ile Ser Glu Ile Leu
9530                 9535                 9540

Gly Arg Ser Val Pro Ser Arg Ala Thr Asp Lys Ser Leu Gly Pro
9545                 9550                 9555

Leu Ala Arg Asn Leu Ala Tyr Val Leu Phe Thr Ser Gly Ser Thr
9560                 9565                 9570

Gly Lys Pro Lys Gly Val Met Ile Glu His Arg Ser Ile Val Arg
9575                 9580                 9585

Leu Val Lys Glu Thr Asn Leu Ile Ser Lys Leu Pro Asn Ala Pro
9590                 9595                 9600

Arg Thr Ala His Leu Thr Asn Leu Val Phe Asp Asn Ser Ala Trp
9605                 9610                 9615

Glu Ile Tyr Ser Thr Leu Leu Asn Gly Gly Thr Leu Val Cys Ile
9620                 9625                 9630

Asp Tyr Ala Thr Val Leu Asp Ser Lys Ala Leu Glu Thr Val Phe
9635                 9640                 9645

Lys Glu Gln Arg Ile Gln Thr Ser Leu Met Pro Pro Ala Leu Leu
9650                 9655                 9660

Lys Glu Cys Leu Ala Asn Met Pro Thr Met Phe Asp Asp Val Glu
9665                 9670                 9675
```

```
Val Leu Tyr Ala Leu Gly Asp Arg Phe Asp Lys Gln Asp Ala Met
9680                9685                9690

Lys Ala Arg Ser Ile Val Lys Thr Ala Val Tyr Asn Ala Tyr Gly
9695                9700                9705

Pro Thr Glu Asn Thr Val Ile Ser Thr Ile Tyr Glu Ile Ala Lys
9710                9715                9720

Asp Asp Ser Phe Val Asn Gly Val Pro Ile Gly Arg Ser Ile Ser
9725                9730                9735

Asn Ser Gly Ala Phe Ile Met Asp Ser Arg Gln Gln Leu Val Pro
9740                9745                9750

Val Gly Val Leu Gly Glu Leu Val Val Ser Gly Asp Gly Leu Ala
9755                9760                9765

Arg Gly Tyr Thr Asp Pro Thr Leu Asp Val Asn Arg Phe Val Glu
9770                9775                9780

Val Thr Val Asp Gly Gln His Val Arg Val Tyr Arg Thr Gly Asp
9785                9790                9795

Arg Val Arg Phe Arg Pro Lys Asp Gly Gln Ile Glu Phe Phe Ser
9800                9805                9810

Arg Met Asp Gln Gln Val Lys Ile Arg Gly His Arg Ile Glu Pro
9815                9820                9825

Ala Glu Val Glu His Val Ile Leu Thr Asn Lys Ile Ile Arg Asp
9830                9835                9840

Ala Ala Val Ala Ile Arg Arg Pro Glu Gly Gln Glu Pro Glu Met
9845                9850                9855

Val Ala Phe Val Thr Thr His Glu Asn Thr Ser Ile Glu Lys Gln
9860                9865                9870

Ser Val Glu Glu Phe Ala Ala Arg Ile Glu Asn Glu Val Arg Arg
9875                9880                9885

Trp Ile Lys Thr Leu Leu Pro Leu Tyr Met Val Pro Thr Gln Ile
9890                9895                9900

Val Val Leu Asp Arg Met Pro Val Asn Ala Asn Gly Lys Val Asp
9905                9910                9915

Arg Lys Glu Leu Ala Gln Arg Ala Gln Thr Leu Gln Lys Ser Glu
9920                9925                9930

Ala Gly Ser Leu Pro Ser Val Arg Val Pro Pro Thr Asn Asp Met
9935                9940                9945

Glu Arg Ile Leu Cys Glu Glu Phe Ala Asp Val Leu Gly Val Glu
9950                9955                9960

Val Gly Ile Thr Asp Asn Phe Phe Asp Phe Gly Gly His Ser Leu
9965                9970                9975

Met Ala Thr Lys Leu Ala Ala Arg Ile Ser Arg Arg Val Asn Ala
9980                9985                9990

Arg Val Ser Val Lys Ser Val Phe Asp His Pro Val Leu Val Asp
9995                10000               10005

Leu Ala Ser Thr Ile Lys Gln Asp Ser Ile Met His Lys Pro Ile
10010               10015               10020

Pro Gln Thr Ala Tyr Thr Gly Pro Val Glu Gln Ser Phe Ala Gln
10025               10030               10035

Gly Arg Leu Trp Phe Leu Asp Gln Leu Asn Phe Gly Ala Ser Trp
10040               10045               10050

Tyr Leu Met Pro Leu Ala Leu Arg Leu Gln Gly Ser Leu His Val
10055               10060               10065
```

| | | | | | | | | | | | |
|---|---|---|---|---|---|---|---|---|---|---|---|
|Lys|Ser|Leu|Thr|Thr|Ala|Leu|Phe|Ala|Leu|Glu|Gln|Arg|His|Glu|
| |10070| | | |10075| | | |10080| | | | | |

Lys Ser Leu Thr Thr Ala Leu Phe Ala Leu Glu Gln Arg His Glu
      10070               10075            10080

Thr Leu Arg Thr Thr Phe Glu Glu Gln Asp Gly Val Gly Ile Gln
      10085               10090            10095

Ile Val His Pro Ala Asn Lys Lys Asp Leu Arg Ile Leu Asp Val
      10100               10105            10110

Ser Lys Glu Gln Asn Ser Asp Tyr Ala Lys Val Leu His Lys Glu
      10115               10120            10125

Arg Thr Ile Pro Ile Asp Leu Thr Ser Glu Pro Gly Trp Arg Val
      10130               10135            10140

Ser Leu Ile Arg Leu Gly Glu Asp Asp His Ile Leu Ser Ile Val
      10145               10150            10155

Met His His Ile Ile Ser Asp Gly Trp Ser Val Asp Val Leu Arg
      10160               10165            10170

Gln Glu Leu Lys Gln Phe Tyr Thr Ala Ala Leu Lys Gly Gln Asp
      10175               10180            10185

Pro Leu Ala Gln Ile Asp Ala Leu Pro Ile Gln Tyr Arg Asp Phe
      10190               10195            10200

Ser Leu Trp Gln Lys Leu Pro Asp Gln Val Ala Glu His Gln Arg
      10205               10210            10215

Gln Leu Glu Tyr Trp Ala Glu Gln Leu Ala Asp Asn Thr Pro Ala
      10220               10225            10230

Glu Leu Leu Thr Asp Leu Pro Arg Pro Asp Val Leu Ser Gly Lys
      10235               10240            10245

Ala Gly Ala Val Gln Leu Thr Ile Asp Gly Pro Val Phe Asp Gln
      10250               10255            10260

Leu Gln Ala Phe Cys Arg Ala His Gln Thr Thr Met Phe Thr Val
      10265               10270            10275

Leu Leu Ala Val Phe Arg Thr Thr His Tyr Arg Leu Thr Gly Ala
      10280               10285            10290

Thr Asp Ala Thr Ile Gly Thr Pro Ile Ala Asn Arg Asn Arg Pro
      10295               10300            10305

Glu Leu Glu Arg Leu Val Gly Phe Phe Val Asn Thr Gln Cys Ile
      10310               10315            10320

Arg Ile Thr Val Asp Val Glu Asp Thr Phe Glu Ala Leu Val Arg
      10325               10330            10335

Gln Val His Ser Thr Ser Thr Thr Ala Phe Ala Asn Gln Asp Val
      10340               10345            10350

Pro Phe Glu Arg Ile Val Ser Thr Ile Leu Pro Gly Ser Arg Asp
      10355               10360            10365

Ala Ser Arg Asn Pro Leu Ala Gln Leu Met Phe Ala Val His Ser
      10370               10375            10380

Gln Arg Asp Ile Ser Lys Phe Gln Leu Glu Gly Leu Asp Thr Lys
      10385               10390            10395

Pro Ile Pro Thr Ala Ala Ser Thr Arg Phe Asp Ile Glu Phe His
      10400               10405            10410

Met Phe Gln Gln Ala Glu Arg Leu Ser Gly Arg Val Leu Phe Ala
      10415               10420            10425

Glu Asp Leu Phe Glu Leu Glu Thr Ile Gln Gly Met Val Val Ile
      10430               10435            10440

Phe Lys Glu Ile Leu Arg Arg Gly Leu Glu Thr Pro Gln Thr Pro
      10445               10450            10455

-continued

| | | | | | | | | | | | |
|---|---|---|---|---|---|---|---|---|---|---|---|
| Leu | Ala | Val | Leu | Pro | Leu | Thr | Asp | Gly | Leu | Ala | His | Leu | Arg | Ser |
| 10460 | | | | | 10465 | | | | | 10470 | | | | |
| Gln | Gly | Leu | Leu | Glu | Ile | Glu | Arg | Pro | Glu | Tyr | Pro | Arg | Asp | Ser |
| 10475 | | | | | 10480 | | | | | 10485 | | | | |
| Ser | Met | Ile | Asp | Val | Phe | Arg | Ala | Gln | Val | Ala | Ala | Cys | Pro | Asp |
| 10490 | | | | | 10495 | | | | | 10500 | | | | |
| Ala | Ile | Ala | Val | Lys | Asp | Ser | Thr | Ser | Gln | Leu | Thr | Tyr | Ser | Gln |
| 10505 | | | | | 10510 | | | | | 10515 | | | | |
| Leu | Asp | Asp | Gln | Ser | Asp | Lys | Ile | Thr | Ala | Trp | Leu | Leu | Gln | Arg |
| 10520 | | | | | 10525 | | | | | 10530 | | | | |
| Lys | Ile | Pro | Ala | Glu | Ser | Leu | Val | Ala | Val | Tyr | Ala | Pro | Arg | Thr |
| 10535 | | | | | 10540 | | | | | 10545 | | | | |
| Cys | Gln | Thr | Ile | Ile | Thr | Phe | Phe | Gly | Ile | Leu | Lys | Ala | Asn | Leu |
| 10550 | | | | | 10555 | | | | | 10560 | | | | |
| Ala | Tyr | Leu | Pro | Leu | Asp | Ile | Asn | Val | Pro | Ala | Ala | Arg | Ile | Glu |
| 10565 | | | | | 10570 | | | | | 10575 | | | | |
| Ala | Ile | Leu | Ser | Thr | Ile | Ser | Gly | His | Lys | Leu | Val | Leu | Leu | Gly |
| 10580 | | | | | 10585 | | | | | 10590 | | | | |
| Ser | Gln | Val | Ser | Ala | Pro | Ala | Val | Gln | Leu | Lys | Asp | Val | Glu | Tyr |
| 10595 | | | | | 10600 | | | | | 10605 | | | | |
| Val | Trp | Ile | Asp | Glu | Ala | Met | Ala | Glu | Thr | Val | Arg | Thr | Cys | Thr |
| 10610 | | | | | 10615 | | | | | 10620 | | | | |
| Ser | Pro | Glu | Pro | Ser | Ala | Thr | Ser | Leu | Ala | Tyr | Val | Ile | Phe | Thr |
| 10625 | | | | | 10630 | | | | | 10635 | | | | |
| Ser | Gly | Ser | Thr | Gly | Leu | Pro | Lys | Gly | Val | Lys | Val | Glu | His | Arg |
| 10640 | | | | | 10645 | | | | | 10650 | | | | |
| Gly | Val | Val | Arg | Leu | Val | Lys | Gln | Ser | Asn | Val | Val | Ala | Lys | Met |
| 10655 | | | | | 10660 | | | | | 10665 | | | | |
| Pro | Gln | Ala | Ala | Arg | Val | Ala | His | Leu | Ser | Asn | Ile | Ala | Phe | Asp |
| 10670 | | | | | 10675 | | | | | 10680 | | | | |
| Ala | Ala | Thr | Trp | Glu | Ile | Tyr | Ala | Ala | Leu | Leu | Asn | Gly | Gly | Ser |
| 10685 | | | | | 10690 | | | | | 10695 | | | | |
| Leu | Ile | Cys | Ile | Asp | Tyr | Phe | Thr | Thr | Leu | Asp | Ser | Lys | Glu | Leu |
| 10700 | | | | | 10705 | | | | | 10710 | | | | |
| Glu | Ala | Val | Phe | Ala | Arg | Glu | Lys | Ile | Gln | Ala | Ala | Met | Leu | Pro |
| 10715 | | | | | 10720 | | | | | 10725 | | | | |
| Pro | Ala | Leu | Leu | Lys | Gln | Cys | Leu | Val | Asn | Ile | Pro | Ala | Thr | Ile |
| 10730 | | | | | 10735 | | | | | 10740 | | | | |
| Ser | Ala | Leu | Asp | Val | Val | Leu | Ala | Ala | Gly | Asp | Arg | Phe | Asp | Arg |
| 10745 | | | | | 10750 | | | | | 10755 | | | | |
| Arg | Asp | Ala | Ala | Ala | Thr | Gln | Ala | Leu | Val | Gly | Gly | Cys | Val | Tyr |
| 10760 | | | | | 10765 | | | | | 10770 | | | | |
| Asn | Ala | Tyr | Gly | Pro | Thr | Glu | Asn | Thr | Thr | Leu | Ser | Thr | Ile | Tyr |
| 10775 | | | | | 10780 | | | | | 10785 | | | | |
| Asn | Val | Val | Lys | Gly | Asp | Ala | Asn | Val | Asn | Gly | Val | Pro | Ile | Gly |
| 10790 | | | | | 10795 | | | | | 10800 | | | | |
| Arg | Pro | Val | Ser | Asn | Ser | Gly | Ala | Tyr | Ile | Met | Asp | Pro | Asn | Gln |
| 10805 | | | | | 10810 | | | | | 10815 | | | | |
| Gln | Leu | Val | Pro | Lys | Gly | Val | Met | Gly | Glu | Leu | Ile | Val | Val | Gly |
| 10820 | | | | | 10825 | | | | | 10830 | | | | |
| Asp | Gly | Val | Ala | Arg | Gly | Tyr | Thr | Asp | Pro | Ala | Leu | Asp | Val | Asn |
| 10835 | | | | | 10840 | | | | | 10845 | | | | |

```
Arg Phe Ile Glu Ile Ala Ile Asp Gly Asp Gln Ala Val Arg Ala
10850              10855               10860

Tyr Arg Thr Gly Asp Arg Ala Arg Tyr Arg Pro Lys Asp Gly Gln
10865              10870               10875

Ile Glu Phe Phe Gly Arg Met Asp Gln Gln Ile Lys Ile Arg Gly
10880              10885               10890

His Arg Ile Glu Pro Ala Glu Val Glu His Ala Val Leu Asp Asn
10895              10900               10905

Ser Met Val Gln Asp Ala Ala Val Ile Thr Arg Lys Gln Asp Gln
10910              10915               10920

Glu Leu Glu Met Ile Ala Phe Val Thr Thr Arg Ser Asp Lys Glu
10925              10930               10935

Ile Asp Asn Asp Glu Ala Ser Asn Gln Val Glu Asp Trp Gly Asn
10940              10945               10950

Gln Phe Glu Ser Asn Ile Tyr Ala Glu Ile Glu Glu Ile Asp Ser
10955              10960               10965

Ser Ala Ile Gly Lys Asp Phe Met Gly Trp Thr Ser Met Tyr Asp
10970              10975               10980

Gly Ser Ala Ile Asp Lys Asp Glu Met Gln Glu Trp Leu Asp Asp
10985              10990               10995

Thr Met Ser Thr Leu Leu Asp Gly Arg Gln Pro Gly His Val Leu
11000              11005               11010

Glu Ile Gly Thr Gly Thr Gly Met Ile Leu Phe Asn Leu Ala Glu
11015              11020               11025

Arg Met Gly Leu Lys Ser Tyr Val Gly Leu Asp Pro Ser Glu Lys
11030              11035               11040

Ala Thr Ser Phe Val Lys Gln Ala Ile Lys Ser Arg Pro Ser Leu
11045              11050               11055

Ala Gly Lys Ala Glu Val His Val Gly Thr Ala Thr Asp Val Ala
11060              11065               11070

Arg Met Arg Asp Leu His Pro Glu Val Val Val Ile Asn Ser Val
11075              11080               11085

Ala Gln Tyr Phe Pro Ser Pro Glu Tyr Leu Ala Asp Val Val Gly
11090              11095               11100

Ala Leu Val Arg Ile Pro Gly Val Lys Arg Leu Phe Phe Gly Asp
11105              11110               11115

Ile Arg Ser Tyr Ala Thr Asn Asn His Phe Leu Ala Ala Arg Ala
11120              11125               11130

Leu His Lys Leu Gly Glu Lys Ala Thr Arg Asp Thr Val Arg Ser
11135              11140               11145

Lys Met Ala Glu Leu Glu Gly Tyr Glu Glu Glu Leu Leu Val Asp
11150              11155               11160

Pro Thr Phe Phe Thr Ser Leu Thr Ala Lys Leu His Gly Gln Val
11165              11170               11175

Glu His Val Glu Ile Leu Pro Lys Arg Met Gln Ala Thr Asn Glu
11180              11185               11190

Leu Ser Ala Tyr Arg Tyr Ala Ala Ile Val Tyr Ile Arg Asp Pro
11195              11200               11205

Lys Arg Ala Gln Thr Val Gln Thr Val Lys Ser Asp Ala Trp Val
11210              11215               11220

Asp Phe Ser Thr Ser Gln Met Asp Arg Ser Val Leu Val Ser Leu
11225              11230               11235
```

```
Leu Gln Ser Ser Asp Ala Glu     Ala Ile Ala Val Ser     Asn Ile Pro
    11240               11245                   11250

Tyr Ser Lys Thr Ile Val Ala     Arg His Ile Val Glu     Ser Leu Ser
    11255               11260                   11265

Ala Glu Asp Ser Gln Glu Met     Leu Asp Gly Pro Ala     Trp Ile Ser
    11270               11275                   11280

Ala Val Arg Ser Ser Ala Glu     Gln Cys Ala Ser Leu     Ser Ala Ile
    11285               11290                   11295

Asp Leu Val Gln Val Ala Lys     Glu Asn Gly Phe Arg     Val Glu Leu
    11300               11305                   11310

Ser Cys Ala Arg Gln Arg Ser     His Asn Gly Ala Ile     Asp Ala Val
    11315               11320                   11325

Phe His His Tyr Lys Pro Ala     Gln Glu Gly Ser Arg     Val Leu Leu
    11330               11335                   11340

Gln Phe Pro Thr Asp Asn His     Ile Arg Ala Gly Ser     Leu Thr Asn
    11345               11350                   11355

Arg Pro Leu Gln Arg Leu Glu     Ser Arg Arg Val Glu     Thr Lys Leu
    11360               11365                   11370

Lys Glu His Leu Phe Ser Val     Leu Pro Ser Tyr Met     Ile Pro Ser
    11375               11380                   11385

His Ile Val Met Val Asp Gln     Met Pro Leu Asn Ala     Asn Gly Lys
    11390               11395                   11400

Val Asp Arg Lys Ala Leu Ala     Gln Arg Ala Glu Ala     Val Leu Lys
    11405               11410                   11415

Ile Glu Lys Pro Ala Ser Glu     Arg Val Ser Ala Arg     Asn Glu Val
    11420               11425                   11430

Glu Ala Val Leu Cys Glu Glu     Phe Thr Asp Val Leu     Gly Val Glu
    11435               11440                   11445

Val Gly Ile Thr Asp Asn Phe     Phe Asp Leu Gly Gly     His Ser Leu
    11450               11455                   11460

Met Ala Thr Lys Leu Ala Ala     Arg Ile Ser Lys His     Leu Asp Ala
    11465               11470                   11475

Arg Val Ser Val Lys Asp Val     Phe Asp Tyr Pro Val     Val Ala Asp
    11480               11485                   11490

Leu Ala Ala Ser Ile Glu Arg     Asn Ser Ile Pro His     Asn Pro Ile
    11495               11500                   11505

Pro Ser Thr Asn Tyr Ser Gly     Pro Val Glu Gln Ser     Phe Ala Gln
    11510               11515                   11520

Gly Arg Leu Trp Phe Leu Asp     Gln Leu Asn Met Gly     Val Ser Glu
    11525               11530                   11535

Leu Tyr Leu Met Pro Leu Ala     Leu Arg Leu Arg Gly     Pro Leu Arg
    11540               11545                   11550

Val Asp Ala Phe Ala Ala Ala     Val Ser Ala Leu Glu     Ala Arg His
    11555               11560                   11565

Glu Thr Leu Arg Thr Thr Phe     Met Asp His Asp Gly     Val Gly Met
    11570               11575                   11580

Gln Val Ile Leu Pro Ser Asn     Ser Lys Lys Leu Arg     Val Ile Asp
    11585               11590                   11595

Ala Ser Glu Asn Asp Tyr Ile     Asp Ile Leu Arg Gln     Glu Arg Thr
    11600               11605                   11610

Ala Pro Phe Asn Leu Thr Thr     Glu Pro Gly Phe Arg     Ile Ala Leu
    11615               11620                   11625
```

```
Leu Gln Leu Gly Gln Thr Asp Phe Ile Leu Ser Ile Val Met His
    11630               11635               11640

His Ile Ile Tyr Asp Gly Trp Ser Ile Asp Val Leu Cys Arg Glu
    11645               11650               11655

Leu Gly Arg Phe Tyr Ser Ala Ala Leu Gln Gly Gln Asp Pro Leu
    11660               11665               11670

Ala Gln Val Ser Pro Leu Pro Ile Gln Tyr Arg Asp Phe Ser Ile
    11675               11680               11685

Trp Gln Lys Arg Pro Glu Gln Val Ala Glu His Glu Arg Gln Leu
    11690               11695               11700

Gln Tyr Trp Thr Glu Gln Leu Ala Asp Ser Ser Pro Ala Glu Leu
    11705               11710               11715

Leu Thr Asp Leu Pro Arg Pro Leu Val Pro Thr Gly Lys Ala Gly
    11720               11725               11730

Ile Val Gln Leu Thr Ile Glu Gly Ala Val Tyr Glu Arg Leu Arg
    11735               11740               11745

Ala Phe Cys Arg Val His Gln Thr Thr Ser Phe Ala Val Leu Leu
    11750               11755               11760

Ala Ala Phe Arg Ala Thr His Tyr Arg Leu Thr Gly Ala Glu Asp
    11765               11770               11775

Ala Thr Ile Gly Ser Pro Ile Ala Asn Arg Asn Arg Pro Glu Leu
    11780               11785               11790

Glu Ser Leu Ile Gly Phe Phe Val Asn Thr Gln Cys Ile Arg Val
    11795               11800               11805

Thr Ile Arg Glu Asp Asp Thr Phe Asp Lys Leu Val Gln Gln Val
    11810               11815               11820

Arg Ala Thr Thr Thr Ala Ala Gln Val Asn Gln Asp Val Pro Phe
    11825               11830               11835

Glu Arg Ile Val Ser Ala Leu Met Pro Gly Ser Arg Asp Thr Ser
    11840               11845               11850

Arg Asn Pro Leu Val Gln Leu Ser Phe Ala Leu His Ser Gln His
    11855               11860               11865

Asp Leu Gly Arg Ile Asp Leu Gln Asp Leu Thr Gly Glu Ala Leu
    11870               11875               11880

Pro Thr Pro Val Phe Thr Arg Leu Asp Val Glu Phe His Leu Phe
    11885               11890               11895

Gln Gln Ala Glu Lys Phe Gly Gly Ser Val Leu Phe Ala Thr Asp
    11900               11905               11910

Leu Phe Glu Pro Glu Thr Ile Gln Gly Leu Val Ser Val Phe Gln
    11915               11920               11925

Glu Val Leu Arg Arg Gly Leu Glu Gln Pro Gln Thr Pro Ile Ala
    11930               11935               11940

Val Leu Pro Leu Asp Asn Ala Ser Glu Asp Leu Arg Ser Met Gly
    11945               11950               11955

Leu Leu Gln Met Glu Arg Thr Asn Tyr Pro Arg Asp Ser Ser Val
    11960               11965               11970

Val Asp Val Phe Arg Asp Gln Val Ala Ala Asn Pro Arg Ala Ile
    11975               11980               11985

Ala Val Lys Asp Ser Val Leu Glu Leu Thr Tyr Ala Gln Leu Asp
    11990               11995               12000

Glu Lys Ser Asp Gln Leu Ala Ala Trp Leu Cys Gln His Asn Ile
    12005               12010               12015
```

```
Pro Ala  Glu Thr Ile Val Gly  Val Leu Ala Pro Arg  Ser Cys Glu
    12020            12025                 12030

Thr Ile  Ile Ala Phe Leu Gly  Ile Leu Lys Ala Asn  Leu Ala Tyr
    12035            12040                 12045

Leu Pro  Leu Asp Asp Asn Val  Pro Ala Ala Arg Ile  Glu Thr Ile
    12050            12055                 12060

Leu Ser  Ala Val Pro Gly His  Thr Leu Val Leu Leu  Gly Ser His
    12065            12070                 12075

Val Ala  Ala Pro Ser Ile Gly  Leu Ala Asp Ala Glu  Phe Val Asn
    12080            12085                 12090

Ile Asn  His Thr Leu Gly His  Ser Leu Gln Leu Asn  Ser Thr Cys
    12095            12100                 12105

Ala Lys  Leu Gln Pro Ser Ala  Thr Ser Leu Ala Tyr  Val Ile Phe
    12110            12115                 12120

Thr Ser  Gly Ser Thr Gly Lys  Pro Lys Gly Val Met  Ile Glu His
    12125            12130                 12135

Arg Ser  Ile Val Arg Leu Val  Lys Asn Ser Asn Thr  Leu Ala Lys
    12140            12145                 12150

Leu Pro  Arg Ala Ala Arg Val  Ala His Gln Phe Asn  Leu Ala Phe
    12155            12160                 12165

Asp Ala  Ala Asn Tyr Glu Ile  Tyr Gly Thr Leu Leu  Asn Gly Gly
    12170            12175                 12180

Ala Leu  Ile Cys Val Asp Tyr  Ser Thr Leu Leu Asp  Ile Asp Ala
    12185            12190                 12195

Leu Val  Ala Met Phe Lys Arg  Glu Lys Ile Thr Ala  Ser Ser Leu
    12200            12205                 12210

Ser Pro  Gly Leu Leu Lys Gln  Cys Val Asn Ser Ala  Pro Glu Met
    12215            12220                 12225

Leu Lys  Ala Leu Gln Val Ile  Tyr Thr Gly Gly Asp  Arg Leu Asp
    12230            12235                 12240

Gly Arg  Asp Ala Ile Glu Leu  Gln Ala Leu Val Pro  Gly Gly Val
    12245            12250                 12255

Tyr Asn  Met Tyr Gly Pro Thr  Glu Asn Thr Val Ile  Ser Thr Leu
    12260            12265                 12270

Tyr Asn  Leu Gly Asp Lys His  Ser Tyr Val Asn Gly  Val Pro Ile
    12275            12280                 12285

Gly Thr  Thr Val Ser Asn Ser  Gly Ala Tyr Val Met  Asp Ala Leu
    12290            12295                 12300

Gln Gln  Leu Val Pro Val Gly  Val Met Gly Glu Leu  Val Val Thr
    12305            12310                 12315

Gly Asp  Gly Leu Ala Arg Gly  Tyr Thr Asp Pro Glu  Leu Asp Arg
    12320            12325                 12330

Asn Arg  Phe Ile Lys Val Asn  Ile Asp Gly Gln Val  Val Arg Ala
    12335            12340                 12345

Tyr Arg  Thr Gly Asp Arg Val  Arg Tyr Arg Arg Ile  Asp Gly Gln
    12350            12355                 12360

Leu Glu  Phe Phe Gly Arg Met  Asp Gln Gln Ile Lys  Ile Arg Gly
    12365            12370                 12375

Phe Arg  Ile Glu Thr Ala Glu  Val Glu Asn Ala Met  Leu Ser His
    12380            12385                 12390

Ser Ala  Val Arg Asn Ala Ala  Val Val Val Pro Thr  Gln Asp Ile
    12395            12400                 12405
```

-continued

```
Gln Glu Lys Gly Met Ile Gly Phe Val Val Ile Glu Asn Asn Thr
    12410            12415            12420

Pro Lys Asn Glu Glu Ser Lys Glu Glu His Leu Leu Gln Thr Glu
    12425            12430            12435

Leu Ala Ile Leu Asn Arg Met Lys Ser Ile Leu Pro Pro Tyr Met
    12440            12445            12450

Leu Pro Ser Arg Ile Ile Ile Leu Asp Gln Met Pro Ser Asn Phe
    12455            12460            12465

Asn Gly Lys Val Asp Arg Lys Glu Leu Asp Arg Met Ala Gln Ser
    12470            12475            12480

Val Pro Arg Gln Lys Thr Thr Ala Gly Arg Ile Val Pro Arg Asn
    12485            12490            12495

Glu Leu Glu Ala Ser Leu Cys Lys Glu Phe Ala Glu Val Leu Gly
    12500            12505            12510

Val Glu Val Gly Ile Thr Asp Asn Phe Phe Asp Leu Gly Gly His
    12515            12520            12525

Ser Leu Leu Ala Thr Lys Leu Ala Ala Arg Ile Ser Arg Arg Leu
    12530            12535            12540

Asp Thr Arg Val Ser Val Lys Asp Val Phe Asp Gln Pro Val Pro
    12545            12550            12555

Ala Asp Leu Ala Leu Lys Val Ser Ser Tyr Ile Ser Gln Gly His
    12560            12565            12570

Ala Met Asp Asn Gly Thr Leu Ser Thr Thr Asn Ser Ile Pro Phe
    12575            12580            12585

Gln Leu Leu His Phe Glu Asp Ser Gln Lys Phe Ile Asp Arg Asp
    12590            12595            12600

Ile Val Pro Gln Leu Ala His Gln Ser Ala Lys Ile Val Asp Val
    12605            12610            12615

Tyr Pro Val Thr Trp Ile Gln Lys His Phe Leu Val Asp Pro Ala
    12620            12625            12630

Thr Gly Leu Pro Arg Thr Pro Ser Leu Phe Phe Val Asp Phe Pro
    12635            12640            12645

Ala Asn Ala Asp Cys Asp Lys Ile Cys Asn Ala Ser Arg Ser Leu
    12650            12655            12660

Ile Gln Leu Phe Asp Ile Phe Arg Thr Val Phe Val Gln Ala Ala
    12665            12670            12675

Gly Asn Phe Tyr Gln Val Val Leu Glu Glu Leu Asp Ile Pro Ile
    12680            12685            12690

Ser Val Ile Glu Thr Glu Asp Ile Ser Thr Ala Thr Arg Val Leu
    12695            12700            12705

Lys Glu Gln Asp Gln Gln Asn Pro Leu Gln Phe Gly Gln Gly Phe
    12710            12715            12720

Leu Arg Phe Ala Val Val Lys Thr Arg Ser Ala Val Arg Leu Val
    12725            12730            12735

Leu Arg Ile Ser His Cys Leu Tyr Asp Gly Leu Ser Phe Glu His
    12740            12745            12750

Val Val Gln Ser Leu His Ala Leu Tyr Asn Gly Asp Arg Ile Pro
    12755            12760            12765

Thr Gln Pro Lys Phe Val Gln Tyr Val Gln His Leu Thr Asp Ser
    12770            12775            12780

Arg Lys Glu Gly Tyr Asp Phe Trp Leu Ser Val Leu Glu Glu Ser
    12785            12790            12795
```

```
Ser Met Thr Val Val Glu Thr Gly Arg Arg Ala Gln Gln Leu Ser
    12800               12805           12810

Ser Pro Glu Gly Ala Trp Phe Val Glu Lys Ile Ile Lys Ala Val
12815               12820           12825

Ile Pro Ala Asn Ser Asp Gly Ile Thr Gln Ala Thr Val Phe Thr
12830               12835           12840

Thr Ala Ser Thr Ile Leu Leu Ala Arg Met Thr Gly Ser Ser Asp
12845               12850           12855

Ile Thr Phe Ser Arg Leu Val Ser Gly Arg Gln Ser Leu Pro Ile
    12860               12865           12870

Asn Asp Gln His Ile Val Gly Pro Cys Thr Asn Ile Val Pro Val
    12875               12880           12885

Arg Ile Arg Met Thr Asp Gly Thr Asn Ala Arg Glu Leu Leu Gly
    12890               12895           12900

Met Val Gln Asp Gln Tyr Ile Asp Ser Leu Pro Phe Glu Thr Leu
    12905               12910           12915

Gly Phe Asp Asp Ile Lys Glu Asn Cys Thr Lys Trp Pro Ala Ser
    12920               12925           12930

Thr Thr Asn Tyr Gly Cys Cys Ser Thr Phe Gln Asn Phe Glu Met
    12935               12940           12945

Gln Pro Gln Ser Gln Val Gln Asp Glu Arg Val Arg Leu Ala Gly
    12950               12955           12960

Leu Thr Asn Phe Lys Asp Ala Glu Leu Leu Asn Gly Ala Thr Ala
    12965               12970           12975

Thr Asn Lys Arg Val Leu Asp Asp Val Pro Met His Glu Ile Asp
    12980               12985           12990

Met Ile Gly Ile Pro Glu Pro Asp Gly Leu His Val Arg Val Val
    12995               13000           13005

Leu Thr Ala Ser Arg Gln Ile Phe Glu Glu Val Val Asp Arg
    13010               13015           13020

Met His Glu Glu Phe Cys Asp Ile Ile Leu Gly Leu Asn Lys Ile
    13025               13030           13035

Leu Gln Lys
    13040

<210> SEQ ID NO 38
<211> LENGTH: 1197
<212> TYPE: DNA
<213> ORGANISM: Curvularia clavata
<220> FEATURE:
<221> NAME/KEY: CDS
<222> LOCATION: (1)..(1197)

<400> SEQUENCE: 38 atg acc ttt gtc gag act gta gcc gtc ccg gac aat gag gag cgt cct    48
Met Thr Phe Val Glu Thr Val Ala Val Pro Asp Asn Glu Glu Arg Pro
1               5                   10                  15 tcg gct gga cac aat cgt cct gta gcc gac agc acc aag tgt ccc aac    96
Ser Ala Gly His Asn Arg Pro Val Ala Asp Ser Thr Lys Cys Pro Asn
            20                  25                  30 gcg agg gag atg aag gtt cag aat cgt gtc gcc caa agg aca cat cat   144
Ala Arg Glu Met Lys Val Gln Asn Arg Val Ala Gln Arg Thr His His
        35                  40                  45 cgc cgt tta aaa aca aag ctg gaa gtg cta cgg gaa aga ttg aaa gag   192
Arg Arg Leu Lys Thr Lys Leu Glu Val Leu Arg Glu Arg Leu Lys Glu
    50                  55                  60
```

-continued

| | | | | | | | | | | | | | | | | |
|---|---|---|---|---|---|---|---|---|---|---|---|---|---|---|---|---|
| cct | gag | aag | caa | gtt | ggg | gaa | cct | gcc | agg | gtc | cag | aca | tcc | acc | tcc | 240 |
| Pro | Glu | Lys | Gln | Val | Gly | Glu | Pro | Ala | Arg | Val | Gln | Thr | Ser | Thr | Ser | |
| 65 | | | | 70 | | | | | 75 | | | | | 80 | | |
| acg | ctg | gtg | tcg | gat | gcg | gca | acc | agc | ttg | gca | gat | tcg | atg | tgc | ttg | 288 |
| Thr | Leu | Val | Ser | Asp | Ala | Ala | Thr | Ser | Leu | Ala | Asp | Ser | Met | Cys | Leu | |
| | | | | 85 | | | | | 90 | | | | | 95 | | |
| gtg | cca | gca | gtg | caa | aat | gac | cag | gcc | atg | gcg | ttt | gat | ttc | ctg | atg | 336 |
| Val | Pro | Ala | Val | Gln | Asn | Asp | Gln | Ala | Met | Ala | Phe | Asp | Phe | Leu | Met | |
| | | | 100 | | | | | 105 | | | | | 110 | | | |
| acg | cca | tca | cct | tct | gtt | ggt | aat | gat | tgt | cct | tca | aat | gac | ctg | gaa | 384 |
| Thr | Pro | Ser | Pro | Ser | Val | Gly | Asn | Asp | Cys | Pro | Ser | Asn | Asp | Leu | Glu | |
| | | 115 | | | | | 120 | | | | | 125 | | | | |
| acc | atg | cgc | caa | gct | gcg | tct | gtt | cat | tcc | aac | acc | tta | ggc | ggg | gcc | 432 |
| Thr | Met | Arg | Gln | Ala | Ala | Ser | Val | His | Ser | Asn | Thr | Leu | Gly | Gly | Ala | |
| | 130 | | | | | 135 | | | | | 140 | | | | | |
| ttc | ccg | cta | aac | agg | tcg | ccc | tgt | act | gag | aac | atg | acg | ccc | gaa | tcg | 480 |
| Phe | Pro | Leu | Asn | Arg | Ser | Pro | Cys | Thr | Glu | Asn | Met | Thr | Pro | Glu | Ser | |
| 145 | | | | | 150 | | | | | 155 | | | | | 160 | |
| caa | gtt | agt | tta | tct | acc | gca | cca | tta | tgt | ttt | act | tct | gtc | gtc | ccg | 528 |
| Gln | Val | Ser | Leu | Ser | Thr | Ala | Pro | Leu | Cys | Phe | Thr | Ser | Val | Val | Pro | |
| | | | | 165 | | | | | 170 | | | | | 175 | | |
| gcg | gag | ttg | gac | atg | gac | gct | ttc | tgc | acg | ctt | gac | agc | agt | gat | tgg | 576 |
| Ala | Glu | Leu | Asp | Met | Asp | Ala | Phe | Cys | Thr | Leu | Asp | Ser | Ser | Asp | Trp | |
| | | | 180 | | | | | 185 | | | | | 190 | | | |
| tcg | cgg | ccg | aat | gaa | gaa | tct | ctc | cta | cgt | ttg | gcc | aat | tat | tct | acc | 624 |
| Ser | Arg | Pro | Asn | Glu | Glu | Ser | Leu | Leu | Arg | Leu | Ala | Asn | Tyr | Ser | Thr | |
| | | 195 | | | | | 200 | | | | | 205 | | | | |
| tct | gtg | tca | cct | aca | aac | gtt | caa | tgg | ggc | gta | gat | gag | aat | gct | ccg | 672 |
| Ser | Val | Ser | Pro | Thr | Asn | Val | Gln | Trp | Gly | Val | Asp | Glu | Asn | Ala | Pro | |
| | 210 | | | | | 215 | | | | | 220 | | | | | |
| ctc | caa | gat | cgt | gtg | cgc | tac | atg | agg | gac | caa | gcc | gtc | gcc | atg | ggc | 720 |
| Leu | Gln | Asp | Arg | Val | Arg | Tyr | Met | Arg | Asp | Gln | Ala | Val | Ala | Met | Gly | |
| 225 | | | | | 230 | | | | | 235 | | | | | 240 | |
| ttc | ggc | tct | ctc | gat | gac | gtc | gtc | gag | gcg | cac | tac | aca | cag | aag | ctt | 768 |
| Phe | Gly | Ser | Leu | Asp | Asp | Val | Val | Glu | Ala | His | Tyr | Thr | Gln | Lys | Leu | |
| | | | | 245 | | | | | 250 | | | | | 255 | | |
| gag | tgc | acc | agc | cca | tcg | ttc | caa | gag | cag | cga | ctg | agt | cgc | aat | cgg | 816 |
| Glu | Cys | Thr | Ser | Pro | Ser | Phe | Gln | Glu | Gln | Arg | Leu | Ser | Arg | Asn | Arg | |
| | | | 260 | | | | | 265 | | | | | 270 | | | |
| cga | ctg | tcg | cga | ctg | ttg | agc | acg | ctg | cac | aat | gca | gcc | aaa | gac | tgg | 864 |
| Arg | Leu | Ser | Arg | Leu | Leu | Ser | Thr | Leu | His | Asn | Ala | Ala | Lys | Asp | Trp | |
| | | 275 | | | | | 280 | | | | | 285 | | | | |
| tcg | gag | tgg | gag | cga | cgc | ggg | ttg | caa | gag | caa | gtt | acc | caa | ggt | gcc | 912 |
| Ser | Glu | Trp | Glu | Arg | Arg | Gly | Leu | Gln | Glu | Gln | Val | Thr | Gln | Gly | Ala | |
| | 290 | | | | | 295 | | | | | 300 | | | | | |
| gaa | gac | atc | ttg | gtc | tcc | gag | cta | aat | tcg | tac | att | aca | cag | cgc | tcg | 960 |
| Glu | Asp | Ile | Leu | Val | Ser | Glu | Leu | Asn | Ser | Tyr | Ile | Thr | Gln | Arg | Ser | |
| 305 | | | | | 310 | | | | | 315 | | | | | 320 | |
| atg | aac | tca | acg | gac | gac | aaa | atc | atc | acg | ggc | ggc | ctc | ctg | gac | gag | 1008 |
| Met | Asn | Ser | Thr | Asp | Asp | Lys | Ile | Ile | Thr | Gly | Gly | Leu | Leu | Asp | Glu | |
| | | | | 325 | | | | | 330 | | | | | 335 | | |
| cag | tct | aga | ctg | agg | cag | gac | gtg | gaa | gaa | agg | cgg | aga | ctc | cag | gac | 1056 |
| Gln | Ser | Arg | Leu | Arg | Gln | Asp | Val | Glu | Glu | Arg | Arg | Arg | Leu | Gln | Asp | |
| | | | 340 | | | | | 345 | | | | | 350 | | | |
| agt | ctc | ccc | aac | cta | ggt | gcc | ctc | ctc | acc | act | ctg | ctg | tca | agg | tcc | 1104 |
| Ser | Leu | Pro | Asn | Leu | Gly | Ala | Leu | Leu | Thr | Thr | Leu | Leu | Ser | Arg | Ser | |
| | | 355 | | | | | 360 | | | | | 365 | | | | |
| aac | gca | ccc | aac | caa | gac | gcc | cgt | cga | gac | act | gta | ctc | gcc | atg | atc | 1152 |
| Asn | Ala | Pro | Asn | Gln | Asp | Ala | Arg | Arg | Asp | Thr | Val | Leu | Ala | Met | Ile | |
| | 370 | | | | | 375 | | | | | 380 | | | | | |

```
aag aca atg tgc ttt gat caa gac gag aac atg agt ata tca tag      1197
Lys Thr Met Cys Phe Asp Gln Asp Glu Asn Met Ser Ile Ser
385                 390                 395
```

<210> SEQ ID NO 39
<211> LENGTH: 398
<212> TYPE: PRT
<213> ORGANISM: Curvularia clavata

<400> SEQUENCE: 39

```
Met Thr Phe Val Glu Thr Val Ala Val Pro Asp Asn Glu Glu Arg Pro
1               5                   10                  15

Ser Ala Gly His Asn Arg Pro Val Ala Asp Ser Thr Lys Cys Pro Asn
                20                  25                  30

Ala Arg Glu Met Lys Val Gln Asn Arg Val Ala Gln Arg Thr His His
            35                  40                  45

Arg Arg Leu Lys Thr Lys Leu Glu Val Leu Arg Glu Arg Leu Lys Glu
        50                  55                  60

Pro Glu Lys Gln Val Gly Glu Pro Ala Arg Val Gln Thr Ser Thr Ser
65                  70                  75                  80

Thr Leu Val Ser Asp Ala Ala Thr Ser Leu Ala Asp Ser Met Cys Leu
                85                  90                  95

Val Pro Ala Val Gln Asn Asp Gln Ala Met Ala Phe Asp Phe Leu Met
            100                 105                 110

Thr Pro Ser Pro Ser Val Gly Asn Asp Cys Pro Ser Asn Asp Leu Glu
        115                 120                 125

Thr Met Arg Gln Ala Ala Ser Val His Ser Asn Thr Leu Gly Gly Ala
130                 135                 140

Phe Pro Leu Asn Arg Ser Pro Cys Thr Glu Asn Met Thr Pro Glu Ser
145                 150                 155                 160

Gln Val Ser Leu Ser Thr Ala Pro Leu Cys Phe Thr Ser Val Val Pro
                165                 170                 175

Ala Glu Leu Asp Met Asp Ala Phe Cys Thr Leu Asp Ser Ser Asp Trp
            180                 185                 190

Ser Arg Pro Asn Glu Glu Ser Leu Leu Arg Leu Ala Asn Tyr Ser Thr
        195                 200                 205

Ser Val Ser Pro Thr Asn Val Gln Trp Gly Val Asp Glu Asn Ala Pro
    210                 215                 220

Leu Gln Asp Arg Val Arg Tyr Met Arg Asp Gln Ala Val Ala Met Gly
225                 230                 235                 240

Phe Gly Ser Leu Asp Asp Val Val Glu Ala His Tyr Thr Gln Lys Leu
                245                 250                 255

Glu Cys Thr Ser Pro Ser Phe Gln Glu Gln Arg Leu Ser Arg Asn Arg
            260                 265                 270

Arg Leu Ser Arg Leu Leu Ser Thr Leu His Asn Ala Ala Lys Asp Trp
        275                 280                 285

Ser Glu Trp Glu Arg Arg Gly Leu Gln Glu Gln Val Thr Gln Gly Ala
    290                 295                 300

Glu Asp Ile Leu Val Ser Glu Leu Asn Ser Tyr Ile Thr Gln Arg Ser
305                 310                 315                 320

Met Asn Ser Thr Asp Asp Lys Ile Ile Thr Gly Gly Leu Leu Asp Glu
                325                 330                 335

Gln Ser Arg Leu Arg Gln Asp Val Glu Glu Arg Arg Leu Gln Asp
            340                 345                 350
```

```
Ser Leu Pro Asn Leu Gly Ala Leu Leu Thr Thr Leu Leu Ser Arg Ser
            355                 360                 365

Asn Ala Pro Asn Gln Asp Ala Arg Arg Asp Thr Val Leu Ala Met Ile
    370                 375                 380

Lys Thr Met Cys Phe Asp Gln Asp Glu Asn Met Ser Ile Ser
385                 390                 395

<210> SEQ ID NO 40
<211> LENGTH: 1269
<212> TYPE: DNA
<213> ORGANISM: Curvularia clavata
<220> FEATURE:
<221> NAME/KEY: CDS
<222> LOCATION: (1)..(1269)

<400> SEQUENCE: 40 atg gac ccg aga cag tca cgg atc acg gag ctg gca ata gcc atc aaa      48
Met Asp Pro Arg Gln Ser Arg Ile Thr Glu Leu Ala Ile Ala Ile Lys
1               5                   10                  15 aag cag acg gaa aca ctg cag tca cta ttg gac agt ctc aaa gtt gcg      96
Lys Gln Thr Glu Thr Leu Gln Ser Leu Leu Asp Ser Leu Lys Val Ala
                20                  25                  30 acg cct tct ttt tct gta aac gcc aat cag gag ttg cct cgc aat gca     144
Thr Pro Ser Phe Ser Val Asn Ala Asn Gln Glu Leu Pro Arg Asn Ala
            35                  40                  45 gct gtt cag ctc gcg cag tcc tct atc ctc gac tcc tgt acg gaa ctg     192
Ala Val Gln Leu Ala Gln Ser Ser Ile Leu Asp Ser Cys Thr Glu Leu
        50                  55                  60 cag gat ttg gtc gaa ggc cct ctg gca cat gtt ggg cga ata atg agc     240
Gln Asp Leu Val Glu Gly Pro Leu Ala His Val Gly Arg Ile Met Ser
65                  70                  75                  80 cct cga gtt cat ata tcg tca gct ctg caa gct att gta cat ttc aat     288
Pro Arg Val His Ile Ser Ser Ala Leu Gln Ala Ile Val His Phe Asn
                85                  90                  95 ata gca gag aaa atc gca aaa cac gag act atc tca ttt ggc gag atc     336
Ile Ala Glu Lys Ile Ala Lys His Glu Thr Ile Ser Phe Gly Glu Ile
            100                 105                 110 gca aaa aga tgc aaa atg gac gta gat gat gtc aag cga att atg cga     384
Ala Lys Arg Cys Lys Met Asp Val Asp Asp Val Lys Arg Ile Met Arg
        115                 120                 125 tta gcc atc tcg tac cga atc ttc aaa gag tct cat atc gga ttt gta     432
Leu Ala Ile Ser Tyr Arg Ile Phe Lys Glu Ser His Ile Gly Phe Val
    130                 135                 140 aat cac acg gct agc tca ttc ttg att gcg gaa aac ctt ctt gtg agg     480
Asn His Thr Ala Ser Ser Phe Leu Ile Ala Glu Asn Leu Leu Val Arg
145                 150                 155                 160 caa tgg att agt ctt tgc tgt gat gag ttc ata cca gcg ggt tcg ttc     528
Gln Trp Ile Ser Leu Cys Cys Asp Glu Phe Ile Pro Ala Gly Ser Phe
                165                 170                 175 ctt gtt cct gcc atg aaa aaa tgg cct agc tct gaa gag cct aac gag     576
Leu Val Pro Ala Met Lys Lys Trp Pro Ser Ser Glu Glu Pro Asn Glu
            180                 185                 190 acc gcg ttt gcg ctg ctt cat aag gga gat agt cta tgg gaa gtc ctt     624
Thr Ala Phe Ala Leu Leu His Lys Gly Asp Ser Leu Trp Glu Val Leu
        195                 200                 205 aaa aag cag cct gaa aaa gct cag cgc ttt gct cac gga atg gag tac     672
Lys Lys Gln Pro Glu Lys Ala Gln Arg Phe Ala His Gly Met Glu Tyr
    210                 215                 220 atg cgg aca ctc ccg cca ttc gac atc aac cat ctg ttt acc tcg ttg     720
Met Arg Thr Leu Pro Pro Phe Asp Ile Asn His Leu Phe Thr Ser Leu
225                 230                 235                 240
```

```
aac tgg gag atc gac tgt gag atg gtt ttg gtg gac gtg ggc ggt tct      768
Asn Trp Glu Ile Asp Cys Glu Met Val Leu Val Asp Val Gly Gly Ser
                245                 250                 255 caa ggc tcc att gct gaa gct tta ctt cga aga cac ccg cga cta cga      816
Gln Gly Ser Ile Ala Glu Ala Leu Leu Arg Arg His Pro Arg Leu Arg
            260                 265                 270 tgt tac gtt caa gac ctt cca gag acc ttg agc aaa gcc gtc gtg ccc      864
Cys Tyr Val Gln Asp Leu Pro Glu Thr Leu Ser Lys Ala Val Val Pro
        275                 280                 285 aag gat ctc aag ggt cgt ctt gag ttc gta agc cac agc atg ttc aaa      912
Lys Asp Leu Lys Gly Arg Leu Glu Phe Val Ser His Ser Met Phe Lys
    290                 295                 300 gag cag cct ata aaa gcc gac gta tac ttg ctc agg tca att ttg cac      960
Glu Gln Pro Ile Lys Ala Asp Val Tyr Leu Leu Arg Ser Ile Leu His
305                 310                 315                 320 gac tgg tta gat gga tac gcc ctg caa atc atc cgg aac ctg att ccc     1008
Asp Trp Leu Asp Gly Tyr Ala Leu Gln Ile Ile Arg Asn Leu Ile Pro
                325                 330                 335 gct ctc gag gtt gga tcc aag gtg att ata aat gag atc tgt cta ccg     1056
Ala Leu Glu Val Gly Ser Lys Val Ile Ile Asn Glu Ile Cys Leu Pro
            340                 345                 350 gag cca aac gcc atc tca gca tat gag gca cag ctt att cgc ggg tac     1104
Glu Pro Asn Ala Ile Ser Ala Tyr Glu Ala Gln Leu Ile Arg Gly Tyr
        355                 360                 365 gat ctt tca atg aag caa caa ttt aat tcg aaa gag cga gat gtg cac     1152
Asp Leu Ser Met Lys Gln Gln Phe Asn Ser Lys Glu Arg Asp Val His
    370                 375                 380 gag tgg gaa act ctg ttc cga ctt gca gac aga cgg ttc aaa cta aat     1200
Glu Trp Glu Thr Leu Phe Arg Leu Ala Asp Arg Arg Phe Lys Leu Asn
385                 390                 395                 400 cgc atc gtc aat cca cca ggc tca ttc ctt gcc gtt cta gaa ttc gaa     1248
Arg Ile Val Asn Pro Pro Gly Ser Phe Leu Ala Val Leu Glu Phe Glu
                405                 410                 415 tgg caa ccc acc aca cca taa                                         1269
Trp Gln Pro Thr Thr Pro
            420

<210> SEQ ID NO 41
<211> LENGTH: 422
<212> TYPE: PRT
<213> ORGANISM: Curvularia clavata

<400> SEQUENCE: 41

Met Asp Pro Arg Gln Ser Arg Ile Thr Glu Leu Ala Ile Ala Ile Lys
1               5                   10                  15

Lys Gln Thr Glu Thr Leu Gln Ser Leu Leu Asp Ser Leu Lys Val Ala
            20                  25                  30

Thr Pro Ser Phe Ser Val Asn Ala Asn Gln Glu Leu Pro Arg Asn Ala
        35                  40                  45

Ala Val Gln Leu Ala Gln Ser Ser Ile Leu Asp Ser Cys Thr Glu Leu
    50                  55                  60

Gln Asp Leu Val Glu Gly Pro Leu Ala His Val Gly Arg Ile Met Ser
65                  70                  75                  80

Pro Arg Val His Ile Ser Ser Ala Leu Gln Ala Ile Val His Phe Asn
                85                  90                  95

Ile Ala Glu Lys Ile Ala Lys His Glu Thr Ile Ser Phe Gly Glu Ile
            100                 105                 110

Ala Lys Arg Cys Lys Met Asp Val Asp Asp Val Lys Arg Ile Met Arg
        115                 120                 125
```

```
Leu Ala Ile Ser Tyr Arg Ile Phe Lys Glu Ser His Ile Gly Phe Val
        130                 135                 140

Asn His Thr Ala Ser Ser Phe Leu Ile Ala Glu Asn Leu Leu Val Arg
145                 150                 155                 160

Gln Trp Ile Ser Leu Cys Cys Asp Glu Phe Ile Pro Ala Gly Ser Phe
                165                 170                 175

Leu Val Pro Ala Met Lys Lys Trp Pro Ser Ser Glu Glu Pro Asn Glu
            180                 185                 190

Thr Ala Phe Ala Leu Leu His Lys Gly Asp Ser Leu Trp Glu Val Leu
        195                 200                 205

Lys Lys Gln Pro Glu Lys Ala Gln Arg Phe Ala His Gly Met Glu Tyr
210                 215                 220

Met Arg Thr Leu Pro Pro Phe Asp Ile Asn His Leu Phe Thr Ser Leu
225                 230                 235                 240

Asn Trp Glu Ile Asp Cys Glu Met Val Leu Val Asp Val Gly Gly Ser
                245                 250                 255

Gln Gly Ser Ile Ala Glu Ala Leu Leu Arg Arg His Pro Arg Leu Arg
            260                 265                 270

Cys Tyr Val Gln Asp Leu Pro Glu Thr Leu Ser Lys Ala Val Val Pro
        275                 280                 285

Lys Asp Leu Lys Gly Arg Leu Glu Phe Val Ser His Ser Met Phe Lys
290                 295                 300

Glu Gln Pro Ile Lys Ala Asp Val Tyr Leu Leu Arg Ser Ile Leu His
305                 310                 315                 320

Asp Trp Leu Asp Gly Tyr Ala Leu Gln Ile Ile Arg Asn Leu Ile Pro
                325                 330                 335

Ala Leu Glu Val Gly Ser Lys Val Ile Ile Asn Glu Ile Cys Leu Pro
            340                 345                 350

Glu Pro Asn Ala Ile Ser Ala Tyr Glu Ala Gln Leu Ile Arg Gly Tyr
        355                 360                 365

Asp Leu Ser Met Lys Gln Gln Phe Asn Ser Lys Glu Arg Asp Val His
370                 375                 380

Glu Trp Glu Thr Leu Phe Arg Leu Ala Asp Arg Arg Phe Lys Leu Asn
385                 390                 395                 400

Arg Ile Val Asn Pro Pro Gly Ser Phe Leu Ala Val Leu Glu Phe Glu
                405                 410                 415

Trp Gln Pro Thr Thr Pro
        420

<210> SEQ ID NO 42
<211> LENGTH: 1617
<212> TYPE: DNA
<213> ORGANISM: Curvularia clavata
<220> FEATURE:
<221> NAME/KEY: CDS
<222> LOCATION: (1)..(1617)

<400> SEQUENCE: 42 atg act gaa ccc aca tgg aag aca gtt gca tcg gag aaa cag cag cag      48
Met Thr Glu Pro Thr Trp Lys Thr Val Ala Ser Glu Lys Gln Gln Gln
1               5                   10                  15 cgt gaa tcc aaa atc cct tca gaa tgg caa att ccg aag tcg tcg cat      96
Arg Glu Ser Lys Ile Pro Ser Glu Trp Gln Ile Pro Lys Ser Ser His
            20                  25                  30
```

-continued

| | |
|---|---|
| cca gct ccc gaa gta acc ttt gtt caa gac ttc cca gcc aaa tcg gga<br>Pro Ala Pro Glu Val Thr Phe Val Gln Asp Phe Pro Ala Lys Ser Gly<br>        35                      40                      45 | 144 |
| atg ttc acc aat cga gag ctg caa cta aca gcg gcg act gca tcg gat<br>Met Phe Thr Asn Arg Glu Leu Gln Leu Thr Ala Ala Thr Ala Ser Asp<br> 50                      55                      60 | 192 |
| gta acg gcc aag atc tcc act ggc gaa tgg acg gcc gtg gag gtc acg<br>Val Thr Ala Lys Ile Ser Thr Gly Glu Trp Thr Ala Val Glu Val Thr<br>65                    70                      75                      80 | 240 |
| act gct gtg tgc aag cga gct gcc gtg gct caa caa ttg ttg aat tgt<br>Thr Ala Val Cys Lys Arg Ala Ala Val Ala Gln Gln Leu Leu Asn Cys<br>                      85                      90                      95 | 288 |
| gta acg gag atc tgc ttt gat caa gct ata gca aga gcg aag gag ctt<br>Val Thr Glu Ile Cys Phe Asp Gln Ala Ile Ala Arg Ala Lys Glu Leu<br>                   100                    105                    110 | 336 |
| gac gcg tat ttt gaa aaa gaa gga aag acc gtg ggc cca ctc cac gga<br>Asp Ala Tyr Phe Glu Lys Glu Gly Lys Thr Val Gly Pro Leu His Gly<br>               115                    120                    125 | 384 |
| tta cca att agc ttc aaa gac cag ttc aat gtc aaa ggc ttc gac tcc<br>Leu Pro Ile Ser Phe Lys Asp Gln Phe Asn Val Lys Gly Phe Asp Ser<br>130                    135                    140 | 432 |
| acc atc ggc tac tgc agt tat gct agc aag cca gca acg gca gac tca<br>Thr Ile Gly Tyr Cys Ser Tyr Ala Ser Lys Pro Ala Thr Ala Asp Ser<br>145                    150                    155                    160 | 480 |
| act ctc gtc aag ctc ctg gtc aag gct ggg gca atc atc tat gtc aag<br>Thr Leu Val Lys Leu Leu Val Lys Ala Gly Ala Ile Ile Tyr Val Lys<br>                   165                    170                    175 | 528 |
| tcc aat gtt cct atc acg cta atg atg ggc gag tca ttc aac aac atc<br>Ser Asn Val Pro Ile Thr Leu Met Met Gly Glu Ser Phe Asn Asn Ile<br>                   180                    185                    190 | 576 |
| ttt gga cgc aca ctc aac ccc cgc aat cgg gag ttg acc aca gga ggc<br>Phe Gly Arg Thr Leu Asn Pro Arg Asn Arg Glu Leu Thr Thr Gly Gly<br>               195                    200                    205 | 624 |
| tca tca ggc gga gaa gca gca ctg gtc acg ttc tgt gcc agc ttc ctc<br>Ser Ser Gly Gly Glu Ala Ala Leu Val Thr Phe Cys Ala Ser Phe Leu<br>210                    215                    220 | 672 |
| ggt gtg ggc acc gac atc ggt ggc agc ctt cgc ata cca tgc tca ttc<br>Gly Val Gly Thr Asp Ile Gly Gly Ser Leu Arg Ile Pro Cys Ser Phe<br>225                    230                    235                    240 | 720 |
| acc ggg ctg tat ggg cta aga cca tcc cac ggc aga gtg tca tat caa<br>Thr Gly Leu Tyr Gly Leu Arg Pro Ser His Gly Arg Val Ser Tyr Gln<br>                   245                    250                    255 | 768 |
| cat gtg cag aac acc ttg ctc gga cag gaa gca gtc aga tca tgt gct<br>His Val Gln Asn Thr Leu Leu Gly Gln Glu Ala Val Arg Ser Cys Ala<br>                   260                    265                    270 | 816 |
| gga ccc atg tgc cgt gca ccg gaa gat atc cgc ttg ttc atg tcg agt<br>Gly Pro Met Cys Arg Ala Pro Glu Asp Ile Arg Leu Phe Met Ser Ser<br>               275                    280                    285 | 864 |
| cta gct gcc cag cag ccc tgg ctt tgg gat ccc cag agt ctg cca ctc<br>Leu Ala Ala Gln Gln Pro Trp Leu Trp Asp Pro Gln Ser Leu Pro Leu<br>290                    295                    300 | 912 |
| cca tgg cgg gcg gag gaa gag gtc tta ccg aag aag ttg tgt ttc ggt<br>Pro Trp Arg Ala Glu Glu Glu Val Leu Pro Lys Lys Leu Cys Phe Gly<br>305                    310                    315                    320 | 960 |
| ttt gct cta ggt gat ggc cat gta ggc ccg aaa aag tta aag caa gca<br>Phe Ala Leu Gly Asp Gly His Val Gly Pro Lys Lys Leu Lys Gln Ala<br>                   325                    330                    335 | 1008 |
| ggg cat gct gtc att aac ttc aat ctc aca gaa gga aaa gaa gta aat<br>Gly His Ala Val Ile Asn Phe Asn Leu Thr Glu Gly Lys Glu Val Asn<br>                   340                    345                    350 | 1056 |

```
gag atc atg aac aag atg ttc act gcg gat ggg ggt gcc gag ttt cag    1104
Glu Ile Met Asn Lys Met Phe Thr Ala Asp Gly Gly Ala Glu Phe Gln
        355                 360                 365 cgc gac acc gat gcc acg ggc gag ccc ctg cca cct aca gta gaa tac    1152
Arg Asp Thr Asp Ala Thr Gly Glu Pro Leu Pro Thr Val Glu Tyr
370                 375                 380 tgg ctc ggc cac agc tcg caa atc aaa gcc tca acc gta agc gag aca    1200
Trp Leu Gly His Ser Ser Gln Ile Lys Ala Ser Thr Val Ser Glu Thr
385                 390                 395                 400 tgg aaa aat cag cac aag aag gcg ttg ctt gcg caa aag ttc cta gag    1248
Trp Lys Asn Gln His Lys Lys Ala Leu Leu Ala Gln Lys Phe Leu Glu
                405                 410                 415 aag tgg caa gca acc aaa ggg cga acg ggc acg agt cgc cct atc gat    1296
Lys Trp Gln Ala Thr Lys Gly Arg Thr Gly Thr Ser Arg Pro Ile Asp
            420                 425                 430 ggg ctg atc atg cca tcg acg cca ttt ccg gcc agt cgt cac ggc agc    1344
Gly Leu Ile Met Pro Ser Thr Pro Phe Pro Ala Ser Arg His Gly Ser
        435                 440                 445 ggc tgg cca tgg cac ttt ggt gat ctc tct gcc cta cta gat ctg acc    1392
Gly Trp Pro Trp His Phe Gly Asp Leu Ser Ala Leu Leu Asp Leu Thr
450                 455                 460 acg ggc gtt ttc cca gtc acc cgg gtc aat ctg gag aaa gac gcc gtg    1440
Thr Gly Val Phe Pro Val Thr Arg Val Asn Leu Glu Lys Asp Ala Val
465                 470                 475                 480 ccg ccg agc tgg acg ccc atg tct gtg aaa gac aag gag gcg atg gat    1488
Pro Pro Ser Trp Thr Pro Met Ser Val Lys Asp Lys Glu Ala Met Asp
                485                 490                 495 tac tat gag aag cca gag aat cac gag aat gcc cta gtc ggc ctc caa    1536
Tyr Tyr Glu Lys Pro Glu Asn His Glu Asn Ala Leu Val Gly Leu Gln
            500                 505                 510 ttg att ggt aga agg ttg gag gag gaa aag gta aca gct atg ctt acg    1584
Leu Ile Gly Arg Arg Leu Glu Glu Glu Lys Val Thr Ala Met Leu Thr
        515                 520                 525 ctt att agg aat gtg ctt gaa gta gat tat taa                        1617
Leu Ile Arg Asn Val Leu Glu Val Asp Tyr
530                 535

<210> SEQ ID NO 43
<211> LENGTH: 538
<212> TYPE: PRT
<213> ORGANISM: Curvularia clavata

<400> SEQUENCE: 43

Met Thr Glu Pro Thr Trp Lys Thr Val Ala Ser Glu Lys Gln Gln
1               5                   10                  15

Arg Glu Ser Lys Ile Pro Ser Glu Trp Gln Ile Pro Lys Ser Ser His
            20                  25                  30

Pro Ala Pro Glu Val Thr Phe Val Gln Asp Phe Pro Lys Ser Gly
        35                  40                  45

Met Phe Thr Asn Arg Glu Leu Gln Leu Thr Ala Ala Thr Ala Ser Asp
50                  55                  60

Val Thr Ala Lys Ile Ser Thr Gly Glu Trp Thr Ala Val Glu Val Thr
65                  70                  75                  80

Thr Ala Val Cys Lys Arg Ala Ala Val Ala Gln Gln Leu Leu Asn Cys
                85                  90                  95

Val Thr Glu Ile Cys Phe Asp Gln Ala Ile Ala Arg Ala Lys Glu Leu
            100                 105                 110

Asp Ala Tyr Phe Glu Lys Glu Gly Lys Thr Val Gly Pro Leu His Gly
        115                 120                 125
```

```
Leu Pro Ile Ser Phe Lys Asp Gln Phe Asn Val Lys Gly Phe Asp Ser
        130                 135                 140
Thr Ile Gly Tyr Cys Ser Tyr Ala Ser Lys Pro Ala Thr Ala Asp Ser
145                 150                 155                 160
Thr Leu Val Lys Leu Leu Val Lys Ala Gly Ile Ile Tyr Val Lys
                165                 170                 175
Ser Asn Val Pro Ile Thr Leu Met Met Gly Glu Ser Phe Asn Asn Ile
                180                 185                 190
Phe Gly Arg Thr Leu Asn Pro Arg Asn Arg Glu Leu Thr Thr Gly Gly
            195                 200                 205
Ser Ser Gly Gly Glu Ala Ala Leu Val Thr Phe Cys Ala Ser Phe Leu
        210                 215                 220
Gly Val Gly Thr Asp Ile Gly Gly Ser Leu Arg Ile Pro Cys Ser Phe
225                 230                 235                 240
Thr Gly Leu Tyr Gly Leu Arg Pro Ser His Gly Arg Val Ser Tyr Gln
                245                 250                 255
His Val Gln Asn Thr Leu Leu Gly Gln Glu Ala Val Arg Ser Cys Ala
                260                 265                 270
Gly Pro Met Cys Arg Ala Pro Glu Asp Ile Arg Leu Phe Met Ser Ser
            275                 280                 285
Leu Ala Ala Gln Gln Pro Trp Leu Trp Asp Pro Gln Ser Leu Pro Leu
        290                 295                 300
Pro Trp Arg Ala Glu Glu Val Leu Pro Lys Lys Leu Cys Phe Gly
305                 310                 315                 320
Phe Ala Leu Gly Asp Gly His Val Gly Pro Lys Lys Leu Lys Gln Ala
                325                 330                 335
Gly His Ala Val Ile Asn Phe Asn Leu Thr Glu Gly Lys Glu Val Asn
                340                 345                 350
Glu Ile Met Asn Lys Met Phe Thr Ala Asp Gly Gly Ala Glu Phe Gln
            355                 360                 365
Arg Asp Thr Asp Ala Thr Gly Glu Pro Leu Pro Pro Thr Val Glu Tyr
        370                 375                 380
Trp Leu Gly His Ser Ser Gln Ile Lys Ala Ser Thr Val Ser Glu Thr
385                 390                 395                 400
Trp Lys Asn Gln His Lys Lys Ala Leu Leu Ala Gln Lys Phe Leu Glu
                405                 410                 415
Lys Trp Gln Ala Thr Lys Gly Arg Thr Gly Thr Ser Arg Pro Ile Asp
            420                 425                 430
Gly Leu Ile Met Pro Ser Thr Pro Phe Pro Ala Ser Arg His Gly Ser
        435                 440                 445
Gly Trp Pro Trp His Phe Gly Asp Leu Ser Ala Leu Leu Asp Leu Thr
450                 455                 460
Thr Gly Val Phe Pro Val Thr Arg Val Asn Leu Glu Lys Asp Ala Val
465                 470                 475                 480
Pro Pro Ser Trp Thr Pro Met Ser Val Lys Asp Lys Glu Ala Met Asp
                485                 490                 495
Tyr Tyr Glu Lys Pro Glu Asn His Glu Asn Ala Leu Val Gly Leu Gln
            500                 505                 510
Leu Ile Gly Arg Arg Leu Glu Glu Lys Val Thr Ala Met Leu Thr
        515                 520                 525
Leu Ile Arg Asn Val Leu Glu Val Asp Tyr
        530                 535
```

```
<210> SEQ ID NO 44
<211> LENGTH: 2991
<212> TYPE: DNA
<213> ORGANISM: Curvularia clavata
<220> FEATURE:
<221> NAME/KEY: CDS
<222> LOCATION: (1)..(2991)

<400> SEQUENCE: 44
```

| | | | | | | | | | | | | | | | | |
|---|---|---|---|---|---|---|---|---|---|---|---|---|---|---|---|---|
| atg | gcg | ttg | caa | gag | cgc | cgt | gcc | gcg | gtc | aca | agt | tcc | gat | atc | ctc | 48 |
| Met | Ala | Leu | Gln | Glu | Arg | Arg | Ala | Ala | Val | Thr | Ser | Ser | Asp | Ile | Leu | |
| 1 | | | | 5 | | | | | 10 | | | | | 15 | | |
| tca | gcg | cat | gct | atc | tcg | tct | ccc | gcc | ttg | gcc | gca | gcg | gcc | atc | aat | 96 |
| Ser | Ala | His | Ala | Ile | Ser | Ser | Pro | Ala | Leu | Ala | Ala | Ala | Ala | Ile | Asn | |
| | | | 20 | | | | | 25 | | | | | 30 | | | |
| ttc | gcc | gcc | agc | ttc | cat | cga | gat | gcc | cgc | acc | tgt | tgc | agc | gct | cat | 144 |
| Phe | Ala | Ala | Ser | Phe | His | Arg | Asp | Ala | Arg | Thr | Cys | Cys | Ser | Ala | His | |
| | | 35 | | | | | 40 | | | | | 45 | | | | |
| gag | cgt | agc | cag | ctc | cag | aaa | gtc | tac | cgc | gac | aag | atc | ctc | gcc | aac | 192 |
| Glu | Arg | Ser | Gln | Leu | Gln | Lys | Val | Tyr | Arg | Asp | Lys | Ile | Leu | Ala | Asn | |
| 50 | | | | | 55 | | | | | 60 | | | | | | |
| gac | aag | ttt | acg | gcc | aac | att | gct | gct | gcc | ttc | ctc | tct | gtc | ctg | ggc | 240 |
| Asp | Lys | Phe | Thr | Ala | Asn | Ile | Ala | Ala | Ala | Phe | Leu | Ser | Val | Leu | Gly | |
| 65 | | | | | 70 | | | | | 75 | | | | | 80 | |
| ccc | aac | gcc | ggc | cgt | aac | gat | gca | ggt | gcc | gag | cgc | gag | cgc | tgg | ggc | 288 |
| Pro | Asn | Ala | Gly | Arg | Asn | Asp | Ala | Gly | Ala | Glu | Arg | Glu | Arg | Trp | Gly | |
| | | | | 85 | | | | | 90 | | | | | 95 | | |
| gac | ttt | gac | cgc | ctg | gcg | cag | cga | ggc | aag | aac | atg | cgc | gac | cgc | gag | 336 |
| Asp | Phe | Asp | Arg | Leu | Ala | Gln | Arg | Gly | Lys | Asn | Met | Arg | Asp | Arg | Glu | |
| | | | 100 | | | | | 105 | | | | | 110 | | | |
| agc | cag | cat | ttg | caa | cat | cag | tca | ggc | atc | att | gcc | gcc | tgg | ggg | cct | 384 |
| Ser | Gln | His | Leu | Gln | His | Gln | Ser | Gly | Ile | Ile | Ala | Ala | Trp | Gly | Pro | |
| | | 115 | | | | | 120 | | | | | 125 | | | | |
| cga | tgc | ttc | gag | tac | tac | ggc | tgg | cat | gtc | ctg | ccg | ctg | ccg | ctg | ctg | 432 |
| Arg | Cys | Phe | Glu | Tyr | Tyr | Gly | Trp | His | Val | Leu | Pro | Leu | Pro | Leu | Leu | |
| 130 | | | | | 135 | | | | | 140 | | | | | | |
| cgt | cag | gtg | cac | gac | ctt | gcc | gtg | ctg | ata | cct | agc | tgg | gac | gac | gcc | 480 |
| Arg | Gln | Val | His | Asp | Leu | Ala | Val | Leu | Ile | Pro | Ser | Trp | Asp | Asp | Ala | |
| 145 | | | | | 150 | | | | | 155 | | | | | 160 | |
| gtt | gag | ctg | ctg | aat | tcc | agg | atg | ctg | ttg | cgc | cac | gaa | ctg | cgt | gtg | 528 |
| Val | Glu | Leu | Leu | Asn | Ser | Arg | Met | Leu | Leu | Arg | His | Glu | Leu | Arg | Val | |
| | | | | 165 | | | | | 170 | | | | | 175 | | |
| ctg | cac | ggc | aac | aac | aag | gcc | ctc | cga | atc | ggt | gaa | cac | tct | gcc | gct | 576 |
| Leu | His | Gly | Asn | Asn | Lys | Ala | Leu | Arg | Ile | Gly | Glu | His | Ser | Ala | Ala | |
| | | | 180 | | | | | 185 | | | | | 190 | | | |
| tcc | aaa | gtt | cag | gac | tca | cgc | tca | cct | gtt | gag | cgt | acc | gac | atc | gtg | 624 |
| Ser | Lys | Val | Gln | Asp | Ser | Arg | Ser | Pro | Val | Glu | Arg | Thr | Asp | Ile | Val | |
| | | 195 | | | | | 200 | | | | | 205 | | | | |
| gct | gct | ctc | gac | tgg | gct | cgt | gcc | aac | gca | act | tcg | gct | gcg | gca | cgt | 672 |
| Ala | Ala | Leu | Asp | Trp | Ala | Arg | Ala | Asn | Ala | Thr | Ser | Ala | Ala | Ala | Arg | |
| 210 | | | | | 215 | | | | | 220 | | | | | | |
| caa | gcg | gtc | aag | gaa | gcg | gcg | cag | ggc | atg | aat | ggg | act | ccg | atc | aac | 720 |
| Gln | Ala | Val | Lys | Glu | Ala | Ala | Gln | Gly | Met | Asn | Gly | Thr | Pro | Ile | Asn | |
| 225 | | | | | 230 | | | | | 235 | | | | | 240 | |
| aca | ttc | ggt | ttg | aag | cga | gat | tgc | tat | ggt | atg | gtc | gta | ccg | tcg | gtc | 768 |
| Thr | Phe | Gly | Leu | Lys | Arg | Asp | Cys | Tyr | Gly | Met | Val | Val | Pro | Ser | Val | |
| | | | | 245 | | | | | 250 | | | | | 255 | | |
| ggc | ccc | tac | gat | cct | gat | gga | gat | gat | gac | aat | gat | gaa | gac | gtt | gtc | 816 |
| Gly | Pro | Tyr | Asp | Pro | Asp | Gly | Asp | Asp | Asp | Asn | Asp | Glu | Asp | Val | Val | |
| | | | 260 | | | | | 265 | | | | | 270 | | | |

```
gat gtg tcc cct cgg cca gcg aag cac atc aaa ttg tca gcc gca gag      864
Asp Val Ser Pro Arg Pro Ala Lys His Ile Lys Leu Ser Ala Ala Glu
        275                 280                 285 ccg ctt cgt ctg atg ttt cca ggt tca ttg agt cat gtc cag gct tgt      912
Pro Leu Arg Leu Met Phe Pro Gly Ser Leu Ser His Val Gln Ala Cys
        290                 295                 300 caa aga cat gac act gac ggc gag aag gcc agt act gca ccc att cgt      960
Gln Arg His Asp Thr Asp Gly Glu Lys Ala Ser Thr Ala Pro Ile Arg
305                 310                 315                 320 agt aac aaa ctg tcc cag tcc aaa cag cca gag cta gac aca gca gcc     1008
Ser Asn Lys Leu Ser Gln Ser Lys Gln Pro Glu Leu Asp Thr Ala Ala
                325                 330                 335 gag agt ctt cgt acg agg cat att cac aat gaa cgc atc aac gag ccc     1056
Glu Ser Leu Arg Thr Arg His Ile His Asn Glu Arg Ile Asn Glu Pro
                340                 345                 350 ctc gac gaa gtc tcg gac tgc agt cta tct ctc caa aca ata gcc gtg     1104
Leu Asp Glu Val Ser Asp Cys Ser Leu Ser Leu Gln Thr Ile Ala Val
                355                 360                 365 gga ggg ggg agc gct cag gag gaa acg cca gac caa gat gtg gaa cat     1152
Gly Gly Gly Ser Ala Gln Glu Glu Thr Pro Asp Gln Asp Val Glu His
        370                 375                 380 gca cat cct gaa gtt gag ata aca tcc gcc ata agc agt gag ctt agg     1200
Ala His Pro Glu Val Glu Ile Thr Ser Ala Ile Ser Ser Glu Leu Arg
385                 390                 395                 400 aag gta gac gag cgt acc gat ggt ata agg ata ggg cgt gtg att atg     1248
Lys Val Asp Glu Arg Thr Asp Gly Ile Arg Ile Gly Arg Val Ile Met
                405                 410                 415 agg cgc agt cac tgt atg gta aga gaa cag gac aac cag act aac gag     1296
Arg Arg Ser His Cys Met Val Arg Glu Gln Asp Asn Gln Thr Asn Glu
                420                 425                 430 gag ggg aca gga gaa gta cag tca cag cgg gac agg aga gcg agg gac     1344
Glu Gly Thr Gly Glu Val Gln Ser Gln Arg Asp Arg Arg Ala Arg Asp
        435                 440                 445 ttg gga aag gat atg gag acg gat atg gat att gac agc cag ctg gag     1392
Leu Gly Lys Asp Met Glu Thr Asp Met Asp Ile Asp Ser Gln Leu Glu
        450                 455                 460 gag atg ctg gac ata cat gct ctg gag gcg caa aga aat cac gaa gaa     1440
Glu Met Leu Asp Ile His Ala Leu Glu Ala Gln Arg Asn His Glu Glu
465                 470                 475                 480 atg tcg gat ggt gaa gat gtt gtt gca gga gtg gcg ggc ccg gga acg     1488
Met Ser Asp Gly Glu Asp Val Val Ala Gly Val Ala Gly Pro Gly Thr
                485                 490                 495 cca acg cac agg gcg gcg gaa gaa gga gga tgc aga gaa aaa gaa gca     1536
Pro Thr His Arg Ala Ala Glu Glu Gly Gly Cys Arg Glu Lys Glu Ala
        500                 505                 510 gag aat gcc aaa acg gat gag gag caa gtg cag gac aaa gca gct ctg     1584
Glu Asn Ala Lys Thr Asp Glu Glu Gln Val Gln Asp Lys Ala Ala Leu
        515                 520                 525 gat cag gcg gga aat act aat acg aat cga gag gta gaa aac gca gca     1632
Asp Gln Ala Gly Asn Thr Asn Thr Asn Arg Glu Val Glu Asn Ala Ala
        530                 535                 540 cca aaa gcg cac agc caa gaa ggt gcc ctg cgt gca tcg cga acg ggc     1680
Pro Lys Ala His Ser Gln Glu Gly Ala Leu Arg Ala Ser Arg Thr Gly
545                 550                 555                 560 acg atc gtg gaa agg aca gtg gag tta cac tca acg cac tca att cat     1728
Thr Ile Val Glu Arg Thr Val Glu Leu His Ser Thr His Ser Ile His
                565                 570                 575 caa aga gcg agt gtg aat acg acg gct cca acc gtg gcg cga tca agc     1776
Gln Arg Ala Ser Val Asn Thr Thr Ala Pro Thr Val Ala Arg Ser Ser
        580                 585                 590
```

-continued

```
gat agc gac gac agc gat tca ctc cat tca ccc acg gcg ctt caa aat      1824
Asp Ser Asp Asp Ser Asp Ser Leu His Ser Pro Thr Ala Leu Gln Asn
        595                 600                 605 ctg caa gcc tat atc gat acc aga act cac caa ctc act caa gtg ctg      1872
Leu Gln Ala Tyr Ile Asp Thr Arg Thr His Gln Leu Thr Gln Val Leu
610                 615                 620 agc cag ctc aac tca aca cct gac gtc aga cac cac gct caa ctg cag      1920
Ser Gln Leu Asn Ser Thr Pro Asp Val Arg His His Ala Gln Leu Gln
625                 630                 635                 640 ctt gac tgg tta agt ccg caa cga tgg gcc agt gtc tac gtg gag cca      1968
Leu Asp Trp Leu Ser Pro Gln Arg Trp Ala Ser Val Tyr Val Glu Pro
                645                 650                 655 gaa cat cac atg ggc gcc act tcc tca gca tca tca gac agc gct gac      2016
Glu His His Met Gly Ala Thr Ser Ser Ala Ser Ser Asp Ser Ala Asp
                    660                 665                 670 att tgg tgt ctg gac tgg gat acg ttc cac cag tat gct gac agc aac      2064
Ile Trp Cys Leu Asp Trp Asp Thr Phe His Gln Tyr Ala Asp Ser Asn
                675                 680                 685 cat gtc ttc cgg cgg cct gtt gtt atc aag caa aag ttc cag gac agc      2112
His Val Phe Arg Arg Pro Val Val Ile Lys Gln Lys Phe Gln Asp Ser
690                 695                 700 ggt atg tat gag gtt gac aga tac gtg gat atg ctg tgg cag cgc ttt      2160
Gly Met Tyr Glu Val Asp Arg Tyr Val Asp Met Leu Trp Gln Arg Phe
705                 710                 715                 720 ccg gag cag cat att gag gtc caa aac agc att aca ggc act agt cga      2208
Pro Glu Gln His Ile Glu Val Gln Asn Ser Ile Thr Gly Thr Ser Arg
                725                 730                 735 ttg atg agc atg gcc gag tat tgc tct acg gct ttg act gtt acg gag      2256
Leu Met Ser Met Ala Glu Tyr Cys Ser Thr Ala Leu Thr Val Thr Glu
                740                 745                 750 gct ggc acg agt ctg tct gac aat act acc tcc gtg agc aac gct gtt      2304
Ala Gly Thr Ser Leu Ser Asp Asn Thr Thr Ser Val Ser Asn Ala Val
                755                 760                 765 aac ctt cgc tgt ctg gct cgc gca gac gag ccg ctc ttg aca cgg ctc      2352
Asn Leu Arg Cys Leu Ala Arg Ala Asp Glu Pro Leu Leu Thr Arg Leu
770                 775                 780 gag cgc ttt caa ctg ctc tcg acg ctc gca tct cgc gtt gca ggc aca      2400
Glu Arg Phe Gln Leu Leu Ser Thr Leu Ala Ser Arg Val Ala Gly Thr
785                 790                 795                 800 att ggc agg acc gaa cat tct cca cct agc aat ctc gag agt ctc ctc      2448
Ile Gly Arg Thr Glu His Ser Pro Pro Ser Asn Leu Glu Ser Leu Leu
                805                 810                 815 gga ttc gac gcg ctc agc ttt gcc gac gcg ttt tca agc tca cat gcc      2496
Gly Phe Asp Ala Leu Ser Phe Ala Asp Ala Phe Ser Ser Ser His Ala
                820                 825                 830 aat ctc ttt ggc gga agt tgg gtg cgg tgc ctc gat ggc ctc aag att      2544
Asn Leu Phe Gly Gly Ser Trp Val Arg Cys Leu Asp Gly Leu Lys Ile
                835                 840                 845 tat gcc atc gct gca gac tta gat gca gaa gac tgg cgg cgc ttc gca      2592
Tyr Ala Ile Ala Ala Asp Leu Asp Ala Glu Asp Trp Arg Arg Phe Ala
850                 855                 860 gat gaa gga tac aaa tgg tcg cct cga ggc aaa ggg cgc ttg atc gcc      2640
Asp Glu Gly Tyr Lys Trp Ser Pro Arg Gly Lys Gly Arg Leu Ile Ala
865                 870                 875                 880 cta gag gaa gac gat gtt ctg ttc att ccg cct ggc ctg cgg gcc ata      2688
Leu Glu Glu Asp Asp Val Leu Phe Ile Pro Pro Gly Leu Arg Ala Ile
                885                 890                 895 cat gcc agc ttc acg cca gag ccc tgt ttg atg gaa ggc ggt atg ctg      2736
His Ala Ser Phe Thr Pro Glu Pro Cys Leu Met Glu Gly Gly Met Leu
                900                 905                 910
```

```
tgg gac gaa tgc gcc atc cct gag atc tta gac gag ctg ctc tgg att        2784
Trp Asp Glu Cys Ala Ile Pro Glu Ile Leu Asp Glu Leu Leu Trp Ile
        915                 920                 925 gca cga cac cag gca ggc act gtc cag cct ctc gaa ttt cag ctt tca        2832
Ala Arg His Gln Ala Gly Thr Val Gln Pro Leu Glu Phe Gln Leu Ser
930                 935                 940 agt ctg att gat gcg ctg gag cag tgg ttg aat gag aat aac cac att        2880
Ser Leu Ile Asp Ala Leu Glu Gln Trp Leu Asn Glu Asn Asn His Ile
945                 950                 955                 960 aac cag tcg tcg cca tca cac act gca gct gaa gag cgt cag acg ctc        2928
Asn Gln Ser Ser Pro Ser His Thr Ala Ala Glu Glu Arg Gln Thr Leu
                965                 970                 975 aag gct agc att cag tcg ctt cgc gac tgt tta agc ggc aga tca gcg        2976
Lys Ala Ser Ile Gln Ser Leu Arg Asp Cys Leu Ser Gly Arg Ser Ala
            980                 985                 990 gct ttc cca tct tga                                                    2991
Ala Phe Pro Ser
        995

<210> SEQ ID NO 45
<211> LENGTH: 996
<212> TYPE: PRT
<213> ORGANISM: Curvularia clavata

<400> SEQUENCE: 45

Met Ala Leu Gln Glu Arg Arg Ala Ala Val Thr Ser Ser Asp Ile Leu
1               5                   10                  15

Ser Ala His Ala Ile Ser Ser Pro Ala Leu Ala Ala Ala Ile Asn
            20                  25                  30

Phe Ala Ala Ser Phe His Arg Asp Ala Arg Thr Cys Cys Ser Ala His
        35                  40                  45

Glu Arg Ser Gln Leu Gln Lys Val Tyr Arg Asp Lys Ile Leu Ala Asn
    50                  55                  60

Asp Lys Phe Thr Ala Asn Ile Ala Ala Ala Phe Leu Ser Val Leu Gly
65                  70                  75                  80

Pro Asn Ala Gly Arg Asn Asp Ala Gly Ala Glu Arg Glu Arg Trp Gly
                85                  90                  95

Asp Phe Asp Arg Leu Ala Gln Arg Gly Lys Asn Met Arg Asp Arg Glu
            100                 105                 110

Ser Gln His Leu Gln His Gln Ser Gly Ile Ile Ala Ala Trp Gly Pro
        115                 120                 125

Arg Cys Phe Glu Tyr Tyr Gly Trp His Val Leu Pro Leu Pro Leu Leu
    130                 135                 140

Arg Gln Val His Asp Leu Ala Val Leu Ile Pro Ser Trp Asp Asp Ala
145                 150                 155                 160

Val Glu Leu Leu Asn Ser Arg Met Leu Leu Arg His Glu Leu Arg Val
                165                 170                 175

Leu His Gly Asn Asn Lys Ala Leu Arg Ile Gly Glu His Ser Ala Ala
            180                 185                 190

Ser Lys Val Gln Asp Ser Arg Ser Pro Val Glu Arg Thr Asp Ile Val
        195                 200                 205

Ala Ala Leu Asp Trp Ala Arg Ala Asn Ala Thr Ser Ala Ala Ala Arg
    210                 215                 220

Gln Ala Val Lys Glu Ala Ala Gln Gly Met Asn Gly Thr Pro Ile Asn
225                 230                 235                 240

Thr Phe Gly Leu Lys Arg Asp Cys Tyr Gly Met Val Val Pro Ser Val
                245                 250                 255
```

```
Gly Pro Tyr Asp Pro Asp Gly Asp Asp Asn Asp Glu Asp Val Val
            260                 265                 270

Asp Val Ser Pro Arg Pro Ala Lys His Ile Lys Leu Ser Ala Ala Glu
        275                 280                 285

Pro Leu Arg Leu Met Phe Pro Gly Ser Leu Ser His Val Gln Ala Cys
        290                 295                 300

Gln Arg His Asp Thr Asp Gly Glu Lys Ala Ser Thr Ala Pro Ile Arg
305                 310                 315                 320

Ser Asn Lys Leu Ser Gln Ser Lys Gln Pro Glu Leu Asp Thr Ala Ala
            325                 330                 335

Glu Ser Leu Arg Thr Arg His Ile His Asn Glu Arg Ile Asn Glu Pro
            340                 345                 350

Leu Asp Glu Val Ser Asp Cys Ser Leu Ser Leu Gln Thr Ile Ala Val
            355                 360                 365

Gly Gly Gly Ser Ala Gln Glu Thr Pro Asp Gln Asp Val Glu His
        370                 375                 380

Ala His Pro Glu Val Glu Ile Thr Ser Ala Ile Ser Ser Glu Leu Arg
385                 390                 395                 400

Lys Val Asp Glu Arg Thr Asp Gly Ile Arg Ile Gly Arg Val Ile Met
                405                 410                 415

Arg Arg Ser His Cys Met Val Arg Glu Gln Asp Asn Gln Thr Asn Glu
            420                 425                 430

Glu Gly Thr Gly Glu Val Gln Ser Gln Arg Asp Arg Ala Arg Asp
        435                 440                 445

Leu Gly Lys Asp Met Glu Thr Asp Met Asp Ile Asp Ser Gln Leu Glu
            450                 455                 460

Glu Met Leu Asp Ile His Ala Leu Glu Ala Gln Arg Asn His Glu Glu
465                 470                 475                 480

Met Ser Asp Gly Glu Asp Val Val Ala Gly Val Ala Gly Pro Gly Thr
                485                 490                 495

Pro Thr His Arg Ala Ala Glu Glu Gly Gly Cys Arg Glu Lys Glu Ala
            500                 505                 510

Glu Asn Ala Lys Thr Asp Glu Glu Gln Val Gln Asp Lys Ala Ala Leu
            515                 520                 525

Asp Gln Ala Gly Asn Thr Asn Thr Asn Arg Glu Val Glu Asn Ala Ala
530                 535                 540

Pro Lys Ala His Ser Gln Glu Gly Ala Leu Arg Ala Ser Arg Thr Gly
545                 550                 555                 560

Thr Ile Val Glu Arg Thr Val Glu Leu His Ser Thr His Ser Ile His
                565                 570                 575

Gln Arg Ala Ser Val Asn Thr Thr Ala Pro Thr Val Ala Arg Ser Ser
            580                 585                 590

Asp Ser Asp Ser Asp Ser Leu His Ser Pro Thr Ala Leu Gln Asn
            595                 600                 605

Leu Gln Ala Tyr Ile Asp Thr Arg Thr His Gln Leu Thr Gln Val Leu
            610                 615                 620

Ser Gln Leu Asn Ser Thr Pro Asp Val Arg His His Ala Gln Leu Gln
625                 630                 635                 640

Leu Asp Trp Leu Ser Pro Gln Arg Trp Ala Ser Val Tyr Val Glu Pro
                645                 650                 655

Glu His His Met Gly Ala Thr Ser Ser Ala Ser Ser Asp Ser Ala Asp
            660                 665                 670
```

```
Ile Trp Cys Leu Asp Trp Asp Thr Phe His Gln Tyr Ala Asp Ser Asn
            675                 680                 685

His Val Phe Arg Arg Pro Val Ile Lys Gln Lys Phe Gln Asp Ser
    690                 695                 700

Gly Met Tyr Glu Val Asp Arg Tyr Val Asp Met Leu Trp Gln Arg Phe
705                 710                 715                 720

Pro Glu Gln His Ile Glu Val Gln Asn Ser Ile Thr Gly Thr Ser Arg
                725                 730                 735

Leu Met Ser Met Ala Glu Tyr Cys Ser Thr Ala Leu Thr Val Thr Glu
            740                 745                 750

Ala Gly Thr Ser Leu Ser Asp Asn Thr Thr Ser Val Ser Asn Ala Val
        755                 760                 765

Asn Leu Arg Cys Leu Ala Arg Ala Asp Glu Pro Leu Leu Thr Arg Leu
    770                 775                 780

Glu Arg Phe Gln Leu Leu Ser Thr Leu Ala Ser Arg Val Ala Gly Thr
785                 790                 795                 800

Ile Gly Arg Thr Glu His Ser Pro Pro Ser Asn Leu Glu Ser Leu Leu
                805                 810                 815

Gly Phe Asp Ala Leu Ser Phe Ala Asp Ala Phe Ser Ser Ser His Ala
            820                 825                 830

Asn Leu Phe Gly Gly Ser Trp Val Arg Cys Leu Asp Gly Leu Lys Ile
        835                 840                 845

Tyr Ala Ile Ala Ala Asp Leu Asp Ala Glu Asp Trp Arg Arg Phe Ala
    850                 855                 860

Asp Glu Gly Tyr Lys Trp Ser Pro Arg Gly Lys Gly Arg Leu Ile Ala
865                 870                 875                 880

Leu Glu Glu Asp Asp Val Leu Phe Ile Pro Pro Gly Leu Arg Ala Ile
                885                 890                 895

His Ala Ser Phe Thr Pro Glu Pro Cys Leu Met Glu Gly Gly Met Leu
            900                 905                 910

Trp Asp Glu Cys Ala Ile Pro Glu Ile Leu Asp Glu Leu Leu Trp Ile
        915                 920                 925

Ala Arg His Gln Ala Gly Thr Val Gln Pro Leu Glu Phe Gln Leu Ser
    930                 935                 940

Ser Leu Ile Asp Ala Leu Glu Gln Trp Leu Asn Glu Asn Asn His Ile
945                 950                 955                 960

Asn Gln Ser Ser Pro Ser His Thr Ala Ala Glu Arg Gln Thr Leu
                965                 970                 975

Lys Ala Ser Ile Gln Ser Leu Arg Asp Cys Leu Ser Gly Arg Ser Ala
            980                 985                 990

Ala Phe Pro Ser
        995

<210> SEQ ID NO 46
<211> LENGTH: 234
<212> TYPE: DNA
<213> ORGANISM: Curvularia clavata
<220> FEATURE:
<221> NAME/KEY: CDS
<222> LOCATION: (1)..(234)

<400> SEQUENCE: 46 atg tca aac aag aag aac gag ggc ctt gag aag gga ggc aat ggg tcg      48
Met Ser Asn Lys Lys Asn Glu Gly Leu Glu Lys Gly Gly Asn Gly Ser
1               5                   10                  15
```

| | |
|---|---|
| gct gag cac gag agc ttt ctg ccc aag tcg gcg ctt cac tac cgc gct<br>Ala Glu His Glu Ser Phe Leu Pro Lys Ser Ala Leu His Tyr Arg Ala<br>    20                  25                  30 | 96 |
| cgc gtc gat ggc gga aca agc ggc ctt ctt gcg cgg ctc gac aat agt<br>Arg Val Asp Gly Gly Thr Ser Gly Leu Leu Ala Arg Leu Asp Asn Ser<br>        35                  40                  45 | 144 |
| ccc ggc gct gct gtc ttg gct tat tgc ttc tcc tcg gtc agc acc ctt<br>Pro Gly Ala Ala Val Leu Ala Tyr Cys Phe Ser Ser Val Ser Thr Leu<br> 50                  55                  60 | 192 |
| gga tat gtt ccg gac tgc gag gat aac ctt tgc ggc tcc taa<br>Gly Tyr Val Pro Asp Cys Glu Asp Asn Leu Cys Gly Ser<br>65                  70                  75 | 234 |

<210> SEQ ID NO 47
<211> LENGTH: 77
<212> TYPE: PRT
<213> ORGANISM: Curvularia clavata

<400> SEQUENCE: 47

Met Ser Asn Lys Lys Asn Glu Gly Leu Glu Lys Gly Gly Asn Gly Ser
1               5                   10                  15

Ala Glu His Glu Ser Phe Leu Pro Lys Ser Ala Leu His Tyr Arg Ala
            20                  25                  30

Arg Val Asp Gly Gly Thr Ser Gly Leu Leu Ala Arg Leu Asp Asn Ser
        35                  40                  45

Pro Gly Ala Ala Val Leu Ala Tyr Cys Phe Ser Ser Val Ser Thr Leu
    50                  55                  60

Gly Tyr Val Pro Asp Cys Glu Asp Asn Leu Cys Gly Ser
65                  70                  75

<210> SEQ ID NO 48
<211> LENGTH: 4017
<212> TYPE: DNA
<213> ORGANISM: Curvularia clavata
<220> FEATURE:
<221> NAME/KEY: CDS
<222> LOCATION: (1)..(4017)

<400> SEQUENCE: 48

| | |
|---|---|
| atg agt gct atc gag ctg ccg ccg ctg cgc tcg cgg tct gaa gaa gca<br>Met Ser Ala Ile Glu Leu Pro Pro Leu Arg Ser Arg Ser Glu Glu Ala<br>1               5                   10                  15 | 48 |
| gcg agg gca gaa cac aat gcg cag aca ctc gca cac gaa aat gca aat<br>Ala Arg Ala Glu His Asn Ala Gln Thr Leu Ala His Glu Asn Ala Asn<br>            20                  25                  30 | 96 |
| atc gcg ggc tat gat gag agc ccg gca gtc caa caa gtc gag acc gat<br>Ile Ala Gly Tyr Asp Glu Ser Pro Ala Val Gln Gln Val Glu Thr Asp<br>        35                  40                  45 | 144 |
| gct cca gag act aaa gga gcc ccg cag gct tct ttc aag aat tac ttt<br>Ala Pro Glu Thr Lys Gly Ala Pro Gln Ala Ser Phe Lys Asn Tyr Phe<br>    50                  55                  60 | 192 |
| cgt gtc ttt tca tat ggg aca aag ctt gac tac ttt tta att tcg cta<br>Arg Val Phe Ser Tyr Gly Thr Lys Leu Asp Tyr Phe Leu Ile Ser Leu<br>65                  70                  75                  80 | 240 |
| tgt tgc ttt acg tct att gga gca ggt act gcg atg ccg ctg atg aac<br>Cys Cys Phe Thr Ser Ile Gly Ala Gly Thr Ala Met Pro Leu Met Asn<br>                85                  90                  95 | 288 |
| att gtc ttt ggc aag ctc gta gga aat ttt aca gac tac ttc atc cca<br>Ile Val Phe Gly Lys Leu Val Gly Asn Phe Thr Asp Tyr Phe Ile Pro<br>            100                 105                 110 | 336 |

```
gga tca aat gtc acc cga caa gaa ttc gag gca gag att aac aaa cta      384
Gly Ser Asn Val Thr Arg Gln Glu Phe Glu Ala Glu Ile Asn Lys Leu
        115                 120                 125 gcc ctc tat atc ttc tac ctc ttc ata ggc aag ttt gcc atg tcg tac      432
Ala Leu Tyr Ile Phe Tyr Leu Phe Ile Gly Lys Phe Ala Met Ser Tyr
        130                 135                 140 att tcc atg ctc gca att cga atc agc ggt atg aga ata tcg gct gcg      480
Ile Ser Met Leu Ala Ile Arg Ile Ser Gly Met Arg Ile Ser Ala Ala
145                 150                 155                 160 ctt cgc ctg gca tac ctg cgt gca ctc ttc gcc cag cca gtg agc gtt      528
Leu Arg Leu Ala Tyr Leu Arg Ala Leu Phe Ala Gln Pro Val Ser Val
                165                 170                 175 atc gac acc gtc agt ccc ggc aag gtt gcc aat cgc atc acg acg tca      576
Ile Asp Thr Val Ser Pro Gly Lys Val Ala Asn Arg Ile Thr Thr Ser
                180                 185                 190 tcg aat atc gtc cag ctt gct atc tcg cag cat ttt gca acc ctg ttt      624
Ser Asn Ile Val Gln Leu Ala Ile Ser Gln His Phe Ala Thr Leu Phe
            195                 200                 205 cag tct ctt gcc ttc acc gtc gga tta tac gtg gtg gcg tta gta aaa      672
Gln Ser Leu Ala Phe Thr Val Gly Leu Tyr Val Val Ala Leu Val Lys
        210                 215                 220 ggg tgg aag ttg acg ctg atc gcc tcg acg ggt ctc cct ttc atc cta      720
Gly Trp Lys Leu Thr Leu Ile Ala Ser Thr Gly Leu Pro Phe Ile Leu
225                 230                 235                 240 atc gta tac ggc gcc atg ttc ccg ccc ttt ctc cgg atc cac cag atc      768
Ile Val Tyr Gly Ala Met Phe Pro Pro Phe Leu Arg Ile His Gln Ile
                245                 250                 255 acc gac aag ttc caa gag gaa gca tcg gct atg gcg tat gaa atg ttc      816
Thr Asp Lys Phe Gln Glu Glu Ala Ser Ala Met Ala Tyr Glu Met Phe
                260                 265                 270 tcc tcc att agg atg att gtc gcc ttt ggc acc gag tcg aga ctt gct      864
Ser Ser Ile Arg Met Ile Val Ala Phe Gly Thr Glu Ser Arg Leu Ala
            275                 280                 285 aag cag cac gga gtc atg ctc tcc aaa gct gca agc aat gag aaa aga      912
Lys Gln His Gly Val Met Leu Ser Lys Ala Ala Ser Asn Glu Lys Arg
        290                 295                 300 gct gcg ccg tta atg ggc ttg acc atg tct ccg gct atg gtg gcc atg      960
Ala Ala Pro Leu Met Gly Leu Thr Met Ser Pro Ala Met Val Ala Met
305                 310                 315                 320 tac ggt atc ttc ggt atc acc ttc tgg ttc gga atc aag gaa tat aca     1008
Tyr Gly Ile Phe Gly Ile Thr Phe Trp Phe Gly Ile Lys Glu Tyr Thr
                325                 330                 335 aaa ggg aga atc tca agc gtc ggc gac atc acc gtt gtg ctc ttc tca     1056
Lys Gly Arg Ile Ser Ser Val Gly Asp Ile Thr Val Val Leu Phe Ser
                340                 345                 350 gtc atg atg gcc gta atg aat att ggg cga gtc gcg tct ccg att ata     1104
Val Met Met Ala Val Met Asn Ile Gly Arg Val Ala Ser Pro Ile Ile
            355                 360                 365 tcc atc gca aaa gcc gcg act gct gcg acc gag ctc ttt gtc aca atc     1152
Ser Ile Ala Lys Ala Ala Thr Ala Ala Thr Glu Leu Phe Val Thr Ile
        370                 375                 380
```

| | |
|---|---|
| gac gct tcg ttc cac gat aca tct ggt gtc atg gag ccc gag gtt aca<br>Asp Ala Ser Phe His Asp Thr Ser Gly Val Met Glu Pro Glu Val Thr<br>385                              390                         395                      400 | 1200 |
| ggt aat gct gct atc act ttc atc aat gtt gct ttt tcg tac ccc agc<br>Gly Asn Ala Ala Ile Thr Phe Ile Asn Val Ala Phe Ser Tyr Pro Ser<br>               405                        410                       415 | 1248 |
| cgg ccg ggt gtc cca att ctc aag gga ctt gat ttg aca att act gct<br>Arg Pro Gly Val Pro Ile Leu Lys Gly Leu Asp Leu Thr Ile Thr Ala<br>             420                       425                       430 | 1296 |
| ggc aaa gtc act gcc att gta ggt cca tcg ggg tcc ggg aaa agc acg<br>Gly Lys Val Thr Ala Ile Val Gly Pro Ser Gly Ser Gly Lys Ser Thr<br>       435                       440                       445 | 1344 |
| att gtt ggc ctt atc caa cga tgg tac gac ctc ctc ggc aca aca gct<br>Ile Val Gly Leu Ile Gln Arg Trp Tyr Asp Leu Leu Gly Thr Thr Ala<br>450                              455                         460 | 1392 |
| act gct aag aaa atc gac gag aca gag att cct tca tca tcc act atg<br>Thr Ala Lys Lys Ile Asp Glu Thr Glu Ile Pro Ser Ser Ser Thr Met<br>465                              470                         475                   480 | 1440 |
| gcg tcc agc cca ata gaa gca gtc tat gac aat aca gac aag aaa tcc<br>Ala Ser Ser Pro Ile Glu Ala Val Tyr Asp Asn Thr Asp Lys Lys Ser<br>               485                        490                       495 | 1488 |
| aaa aag ggg aag gcc ggg gaa gaa gaa gaa cca gaa caa gat ctc ggg<br>Lys Lys Gly Lys Ala Gly Glu Glu Glu Glu Pro Glu Gln Asp Leu Gly<br>       500                       505                       510 | 1536 |
| cca aat acg tgc act ggc tcg ttg agt gtt ggt aga aca aat ctt cgt<br>Pro Asn Thr Cys Thr Gly Ser Leu Ser Val Gly Arg Thr Asn Leu Arg<br>             515                       520                      525 | 1584 |
| aat gtg gat gta agg tgg tgg cgt tcg caa atc ggc atg gtc cag cag<br>Asn Val Asp Val Arg Trp Trp Arg Ser Gln Ile Gly Met Val Gln Gln<br>530                              535                         540 | 1632 |
| gag cct ttc ctg ttc aat gat aca ata tac aac aat att gtg ttt gga<br>Glu Pro Phe Leu Phe Asn Asp Thr Ile Tyr Asn Asn Ile Val Phe Gly<br>545                              550                         555                   560 | 1680 |
| ctc tgc ggg acc cgt tat gaa gga ctg tcc aaa gat gaa aag aaa ata<br>Leu Cys Gly Thr Arg Tyr Glu Gly Leu Ser Lys Asp Glu Lys Lys Ile<br>               565                        570                       575 | 1728 |
| atg gtc gat gag gcg tgt cgc gag gct tgc gcg gag gag ttt atc tcg<br>Met Val Asp Glu Ala Cys Arg Glu Ala Cys Ala Glu Glu Phe Ile Ser<br>       580                       585                       590 | 1776 |
| cgg ctc cca caa ggg ttg gac acg ctt gtg ggc gag agc ggc atc aaa<br>Arg Leu Pro Gln Gly Leu Asp Thr Leu Val Gly Glu Ser Gly Ile Lys<br>             595                       600                      605 | 1824 |
| ctt tct ggt ggc cag cgt cag cgt atc gcc att gcc agg agt att atc<br>Leu Ser Gly Gly Gln Arg Gln Arg Ile Ala Ile Ala Arg Ser Ile Ile<br>610                              615                         620 | 1872 |
| aaa cga ccg cct att ctc att cta gac gag gca acg agt gcc atc gat<br>Lys Arg Pro Pro Ile Leu Ile Leu Asp Glu Ala Thr Ser Ala Ile Asp<br>625                              630                         635                   640 | 1920 |
| gtc aga acg gag cga att gtt caa gaa gcg ctt gat cgt gtt tct aag<br>Val Arg Thr Glu Arg Ile Val Gln Glu Ala Leu Asp Arg Val Ser Lys<br>                       645                         650                   655 | 1968 |
| aac cgt acc acg att gtc atc gca cat cgc cta tcc aca atc aaa cgg<br>Asn Arg Thr Thr Ile Val Ile Ala His Arg Leu Ser Thr Ile Lys Arg<br>             660                        665                       670 | 2016 |
| gcg gac agc ata gtc gtc tta cgg cag ggc cag ctg gtt gag caa ggc<br>Ala Asp Ser Ile Val Val Leu Arg Gln Gly Gln Leu Val Glu Gln Gly<br>       675                       680                       685 | 2064 |
| acg cat gaa gag ctg ctg aaa aac gga gat ggg gtc tat tac ggc tta<br>Thr His Glu Glu Leu Leu Lys Asn Gly Asp Gly Val Tyr Tyr Gly Leu<br>690                              695                         700 | 2112 |

```
gtt cat gcc caa gag ctg gaa atg gac gct gaa gac gat gat gac cac    2160
Val His Ala Gln Glu Leu Glu Met Asp Ala Glu Asp Asp Asp His
705             710                 715                 720 agc tca agc tta gag aac atc aaa atg aac gac act aag gag gac act    2208
Ser Ser Ser Leu Glu Asn Ile Lys Met Asn Asp Thr Lys Glu Asp Thr
            725                 730                 735 gct agt agc gga ttc gag gga cac gct tct aga gaa gat tca aca tat    2256
Ala Ser Ser Gly Phe Glu Gly His Ala Ser Arg Glu Asp Ser Thr Tyr
        740                 745                 750 cag aat gta ggt cta ctt cac agt ctc ggt cga ctt gtt gta gag caa    2304
Gln Asn Val Gly Leu Leu His Ser Leu Gly Arg Leu Val Val Glu Gln
    755                 760                 765 cgt cac cat tgg atc ctc tac agc gtt tgc tgc ata ggc ata ctc gga    2352
Arg His His Trp Ile Leu Tyr Ser Val Cys Cys Ile Gly Ile Leu Gly
770                 775                 780 gcc ggc gca gtc tac cca ctc caa gcg tac att ttc gca agg att atc    2400
Ala Gly Ala Val Tyr Pro Leu Gln Ala Tyr Ile Phe Ala Arg Ile Ile
785             790                 795                 800 aac gtc ttc aca ctt aca ggt ccc gag ctc gtc aaa caa ggc aac ttc    2448
Asn Val Phe Thr Leu Thr Gly Pro Glu Leu Val Lys Gln Gly Asn Phe
            805                 810                 815 tgg gca ggc atg ttc ggc gta ctt gcg ggt ggg gtt gga ctg tcg tac    2496
Trp Ala Gly Met Phe Gly Val Leu Ala Gly Gly Val Gly Leu Ser Tyr
        820                 825                 830 tat ctg ctt ggt gct gcc tca cat cta att tct gtc gaa tta aca cgc    2544
Tyr Leu Leu Gly Ala Ala Ser His Leu Ile Ser Val Glu Leu Thr Arg
    835                 840                 845 aag tat cga tca gaa tac ctc agc aac atg atc cga aaa cca atc ctc    2592
Lys Tyr Arg Ser Glu Tyr Leu Ser Asn Met Ile Arg Lys Pro Ile Leu
850                 855                 860 ttt ttt gac gat aaa gtt cac agc cca ggc tct ctt acg tca aga ctg    2640
Phe Phe Asp Asp Lys Val His Ser Pro Gly Ser Leu Thr Ser Arg Leu
865             870                 875                 880 agc tcg gac agt caa cag gtc cag cag ttg ttg tcg atg gag atg agc    2688
Ser Ser Asp Ser Gln Gln Val Gln Gln Leu Leu Ser Met Glu Met Ser
            885                 890                 895 atg gcg ctc att gcc tgc acc aac ctt ctc gga tgt aca att atc gcc    2736
Met Ala Leu Ile Ala Cys Thr Asn Leu Leu Gly Cys Thr Ile Ile Ala
        900                 905                 910 ttc gtt tac ggc tgg aag ctt tcc ctt gtt ggt tta ttt gct gcc ttg    2784
Phe Val Tyr Gly Trp Lys Leu Ser Leu Val Gly Leu Phe Ala Ala Leu
    915                 920                 925 cct ctc att ctt ggt gcc gga ctc gtg cgc acg cgt ctc gag ata caa    2832
Pro Leu Ile Leu Gly Ala Gly Leu Val Arg Thr Arg Leu Glu Ile Gln
930                 935                 940 ctc gag gct gag aac gca aaa gtt ttc gag aac agc agc cag ttt gcc    2880
Leu Glu Ala Glu Asn Ala Lys Val Phe Glu Asn Ser Ser Gln Phe Ala
945             950                 955                 960 aca gaa gcg gtg gca ggt ttc cgc act gtg cta agt ctg ctc atg gag    2928
Thr Glu Ala Val Ala Gly Phe Arg Thr Val Leu Ser Leu Leu Met Glu
            965                 970                 975 ccg atg att aga agc cgc tac gac aag ttg ctc aag ggc cac gtt gtg    2976
Pro Met Ile Arg Ser Arg Tyr Asp Lys Leu Leu Lys Gly His Val Val
        980                 985                 990 gaa gct ttg gcc aag gca aaa tat ggt acc atc att ttc gct gca agt    3024
Glu Ala Leu Ala Lys Ala Lys Tyr Gly Thr Ile Ile Phe Ala Ala Ser
    995                 1000                1005 gac agt ctt gag ctt gca tgt atg tct ctg acc ttc tgg tac ggc       3069
Asp Ser Leu Glu Leu Ala Cys Met Ser Leu Thr Phe Trp Tyr Gly
    1010                1015                1020
```

```
gga aaa ctc ctt gcg tct cgt gaa tat gat ctc att cag ttc ttc    3114
Gly Lys Leu Leu Ala Ser Arg Glu Tyr Asp Leu Ile Gln Phe Phe
    1025            1030                1035 att gtc tac acg gcc atc att caa ggc gct acg gca gca gga atc    3159
Ile Val Tyr Thr Ala Ile Ile Gln Gly Ala Thr Ala Ala Gly Ile
    1040            1045                1050 tgg ttc tct ttt act cca agc atg gct caa gcg aca ggt gct gca    3204
Trp Phe Ser Phe Thr Pro Ser Met Ala Gln Ala Thr Gly Ala Ala
    1055            1060                1065 aac cga atc ctt agc atg cgg ccg aca tcg acg gat cca tca tct    3249
Asn Arg Ile Leu Ser Met Arg Pro Thr Ser Thr Asp Pro Ser Ser
    1070            1075                1080 tac tcg cct ctt cca tgc tca gat gag gga gtg ggc att gaa ttt    3294
Tyr Ser Pro Leu Pro Cys Ser Asp Glu Gly Val Gly Ile Glu Phe
    1085            1090                1095 caa cac gtc tcc ttc aaa tac cag tct cga gac gtg ccc gtt ctt    3339
Gln His Val Ser Phe Lys Tyr Gln Ser Arg Asp Val Pro Val Leu
    1100            1105                1110 tcc aac ctc aat ctg caa atc cta ccg ggt cag gtt gct gcg tta    3384
Ser Asn Leu Asn Leu Gln Ile Leu Pro Gly Gln Val Ala Ala Leu
    1115            1120                1125 gta ggc agt agt ggc tgt ggt aaa tca aca aca ctg tct ctt ctc    3429
Val Gly Ser Ser Gly Cys Gly Lys Ser Thr Thr Leu Ser Leu Leu
    1130            1135                1140 gaa cgc ttc tac gat gcg agt tcg ggc cat att cta tac aac ggg    3474
Glu Arg Phe Tyr Asp Ala Ser Ser Gly His Ile Leu Tyr Asn Gly
    1145            1150                1155 caa gac atc acc acg ttc agc ccg gca gag tac cgg aaa caa atg    3519
Gln Asp Ile Thr Thr Phe Ser Pro Ala Glu Tyr Arg Lys Gln Met
    1160            1165                1170 agc ctg gtg agc caa gag ccc acg ctc tac caa ggc agc att cga    3564
Ser Leu Val Ser Gln Glu Pro Thr Leu Tyr Gln Gly Ser Ile Arg
    1175            1180                1185 gaa aac ata tct ctg agt gta gag tct gca tcc gac gac gac atc    3609
Glu Asn Ile Ser Leu Ser Val Glu Ser Ala Ser Asp Asp Asp Ile
    1190            1195                1200 aaa cag gcc tgc cgt gat gcg caa att cat gac ttc atc acc tcg    3654
Lys Gln Ala Cys Arg Asp Ala Gln Ile His Asp Phe Ile Thr Ser
    1205            1210                1215 ctt cca gaa ggc tac gag acg cgc ttg gga ccg aaa gga atg tct    3699
Leu Pro Glu Gly Tyr Glu Thr Arg Leu Gly Pro Lys Gly Met Ser
    1220            1225                1230 ctc tca ggt ggt caa aga cag cga atc tct ctt gcc agg gcg ctg    3744
Leu Ser Gly Gly Gln Arg Gln Arg Ile Ser Leu Ala Arg Ala Leu
    1235            1240                1245 ttg cgc aaa cca aaa atc cta ctc ctc gat gaa gca acc agc tcg    3789
Leu Arg Lys Pro Lys Ile Leu Leu Leu Asp Glu Ala Thr Ser Ser
    1250            1255                1260 cta gat tca gag agc gag aaa tac gtc cag gaa gct atc gag cga    3834
Leu Asp Ser Glu Ser Glu Lys Tyr Val Gln Glu Ala Ile Glu Arg
    1265            1270                1275 gct gca agc gag ggt gac aga acc gtc ata att gtt gcg cat agg    3879
Ala Ala Ser Glu Gly Asp Arg Thr Val Ile Ile Val Ala His Arg
    1280            1285                1290 ctg gct aca att cag aag gcg gat gtt atc ttt gta ctg ggc agt    3924
Leu Ala Thr Ile Gln Lys Ala Asp Val Ile Phe Val Leu Gly Ser
    1295            1300                1305 gga aag gtg cta gag aag ggg gat cat cag gca ctg ctc cgg aaa    3969
Gly Lys Val Leu Glu Lys Gly Asp His Gln Ala Leu Leu Arg Lys
    1310            1315                1320
```

```
aag ggc gtg tac tgg cag atg tgt caa gcc cag gcc ctc aat cgc    4014
Lys Gly Val Tyr Trp Gln Met Cys Gln Ala Gln Ala Leu Asn Arg
1325            1330                1335 tga                                                             4017
```

<210> SEQ ID NO 49
<211> LENGTH: 1338
<212> TYPE: PRT
<213> ORGANISM: Curvularia clavata

<400> SEQUENCE: 49

```
Met Ser Ala Ile Glu Leu Pro Pro Leu Arg Ser Arg Ser Glu Glu Ala
1               5                   10                  15

Ala Arg Ala Glu His Asn Ala Gln Thr Leu Ala His Glu Asn Ala Asn
                20                  25                  30

Ile Ala Gly Tyr Asp Glu Ser Pro Ala Val Gln Gln Val Glu Thr Asp
            35                  40                  45

Ala Pro Glu Thr Lys Gly Ala Pro Gln Ala Ser Phe Lys Asn Tyr Phe
        50                  55                  60

Arg Val Phe Ser Tyr Gly Thr Lys Leu Asp Tyr Phe Leu Ile Ser Leu
65                  70                  75                  80

Cys Cys Phe Thr Ser Ile Gly Ala Gly Thr Ala Met Pro Leu Met Asn
                85                  90                  95

Ile Val Phe Gly Lys Leu Val Gly Asn Phe Thr Asp Tyr Phe Ile Pro
            100                 105                 110

Gly Ser Asn Val Thr Arg Gln Glu Phe Glu Ala Glu Ile Asn Lys Leu
        115                 120                 125

Ala Leu Tyr Ile Phe Tyr Leu Phe Ile Gly Lys Phe Ala Met Ser Tyr
    130                 135                 140

Ile Ser Met Leu Ala Ile Arg Ile Ser Gly Met Arg Ile Ser Ala Ala
145                 150                 155                 160

Leu Arg Leu Ala Tyr Leu Arg Ala Leu Phe Ala Gln Pro Val Ser Val
                165                 170                 175

Ile Asp Thr Val Ser Pro Gly Lys Val Ala Asn Arg Ile Thr Thr Ser
            180                 185                 190

Ser Asn Ile Val Gln Leu Ala Ile Ser Gln His Phe Ala Thr Leu Phe
        195                 200                 205

Gln Ser Leu Ala Phe Thr Val Gly Leu Tyr Val Val Ala Leu Val Lys
    210                 215                 220

Gly Trp Lys Leu Thr Leu Ile Ala Ser Thr Gly Leu Pro Phe Ile Leu
225                 230                 235                 240

Ile Val Tyr Gly Ala Met Phe Pro Pro Phe Leu Arg Ile His Gln Ile
                245                 250                 255

Thr Asp Lys Phe Gln Glu Glu Ala Ser Ala Met Ala Tyr Glu Met Phe
            260                 265                 270

Ser Ser Ile Arg Met Ile Val Ala Phe Gly Thr Glu Ser Arg Leu Ala
        275                 280                 285

Lys Gln His Gly Val Met Leu Ser Lys Ala Ala Ser Asn Glu Lys Arg
    290                 295                 300

Ala Ala Pro Leu Met Gly Leu Thr Met Ser Pro Ala Met Val Ala Met
305                 310                 315                 320

Tyr Gly Ile Phe Gly Ile Thr Phe Trp Phe Gly Ile Lys Glu Tyr Thr
                325                 330                 335

Lys Gly Arg Ile Ser Ser Val Gly Asp Ile Thr Val Val Leu Phe Ser
            340                 345                 350
```

```
Val Met Met Ala Val Met Asn Ile Gly Arg Val Ala Ser Pro Ile Ile
            355                 360                 365

Ser Ile Ala Lys Ala Ala Thr Ala Ala Thr Glu Leu Phe Val Thr Ile
    370                 375                 380

Asp Ala Ser Phe His Asp Thr Ser Gly Val Met Glu Pro Glu Val Thr
385                 390                 395                 400

Gly Asn Ala Ala Ile Thr Phe Ile Asn Val Ala Phe Ser Tyr Pro Ser
                405                 410                 415

Arg Pro Gly Val Pro Ile Leu Lys Gly Leu Asp Leu Thr Ile Thr Ala
            420                 425                 430

Gly Lys Val Thr Ala Ile Val Gly Pro Ser Gly Ser Gly Lys Ser Thr
        435                 440                 445

Ile Val Gly Leu Ile Gln Arg Trp Tyr Asp Leu Leu Gly Thr Thr Ala
    450                 455                 460

Thr Ala Lys Lys Ile Asp Glu Thr Glu Ile Pro Ser Ser Ser Thr Met
465                 470                 475                 480

Ala Ser Ser Pro Ile Glu Ala Val Tyr Asp Asn Thr Asp Lys Lys Ser
                485                 490                 495

Lys Lys Gly Lys Ala Gly Glu Glu Glu Pro Glu Gln Asp Leu Gly
            500                 505                 510

Pro Asn Thr Cys Thr Gly Ser Leu Ser Val Gly Arg Thr Asn Leu Arg
        515                 520                 525

Asn Val Asp Val Arg Trp Trp Arg Ser Gln Ile Gly Met Val Gln Gln
    530                 535                 540

Glu Pro Phe Leu Phe Asn Asp Thr Ile Tyr Asn Asn Ile Val Phe Gly
545                 550                 555                 560

Leu Cys Gly Thr Arg Tyr Glu Gly Leu Ser Lys Asp Glu Lys Lys Ile
                565                 570                 575

Met Val Asp Glu Ala Cys Arg Glu Ala Cys Ala Glu Glu Phe Ile Ser
            580                 585                 590

Arg Leu Pro Gln Gly Leu Asp Thr Leu Val Gly Glu Ser Gly Ile Lys
        595                 600                 605

Leu Ser Gly Gly Gln Arg Gln Arg Ile Ala Ile Ala Arg Ser Ile Ile
    610                 615                 620

Lys Arg Pro Pro Ile Leu Ile Leu Asp Glu Ala Thr Ser Ala Ile Asp
625                 630                 635                 640

Val Arg Thr Glu Arg Ile Val Gln Glu Ala Leu Asp Arg Val Ser Lys
                645                 650                 655

Asn Arg Thr Thr Ile Val Ile Ala His Arg Leu Ser Thr Ile Lys Arg
            660                 665                 670

Ala Asp Ser Ile Val Val Leu Arg Gln Gly Gln Leu Val Glu Gln Gly
        675                 680                 685

Thr His Glu Glu Leu Leu Lys Asn Gly Asp Gly Val Tyr Tyr Gly Leu
    690                 695                 700

Val His Ala Gln Glu Leu Glu Met Asp Ala Glu Asp Asp His
705                 710                 715                 720

Ser Ser Ser Leu Glu Asn Ile Lys Met Asn Asp Thr Lys Glu Asp Thr
                725                 730                 735

Ala Ser Ser Gly Phe Glu Gly His Ala Ser Arg Glu Asp Ser Thr Tyr
            740                 745                 750

Gln Asn Val Gly Leu Leu His Ser Leu Gly Arg Leu Val Val Glu Gln
        755                 760                 765
```

-continued

```
Arg His His Trp Ile Leu Tyr Ser Val Cys Cys Ile Gly Ile Leu Gly
770                 775                 780

Ala Gly Ala Val Tyr Pro Leu Gln Ala Tyr Ile Phe Ala Arg Ile Ile
785                 790                 795                 800

Asn Val Phe Thr Leu Thr Gly Pro Glu Leu Val Lys Gln Gly Asn Phe
                805                 810                 815

Trp Ala Gly Met Phe Gly Val Leu Ala Gly Gly Val Gly Leu Ser Tyr
                820                 825                 830

Tyr Leu Leu Gly Ala Ala Ser His Leu Ile Ser Val Glu Leu Thr Arg
                835                 840                 845

Lys Tyr Arg Ser Glu Tyr Leu Ser Asn Met Ile Arg Lys Pro Ile Leu
850                 855                 860

Phe Phe Asp Asp Lys Val His Ser Pro Gly Ser Leu Thr Ser Arg Leu
865                 870                 875                 880

Ser Ser Asp Ser Gln Gln Val Gln Gln Leu Leu Ser Met Glu Met Ser
                885                 890                 895

Met Ala Leu Ile Ala Cys Thr Asn Leu Leu Gly Cys Thr Ile Ile Ala
                900                 905                 910

Phe Val Tyr Gly Trp Lys Leu Ser Leu Val Gly Leu Phe Ala Ala Leu
                915                 920                 925

Pro Leu Ile Leu Gly Ala Gly Leu Val Arg Thr Arg Leu Glu Ile Gln
930                 935                 940

Leu Glu Ala Glu Asn Ala Lys Val Phe Glu Asn Ser Ser Gln Phe Ala
945                 950                 955                 960

Thr Glu Ala Val Ala Gly Phe Arg Thr Val Leu Ser Leu Leu Met Glu
                965                 970                 975

Pro Met Ile Arg Ser Arg Tyr Asp Lys Leu Leu Lys Gly His Val Val
                980                 985                 990

Glu Ala Leu Ala Lys Ala Lys Tyr Gly Thr Ile Ile Phe Ala Ala Ser
    995                 1000                1005

Asp Ser Leu Glu Leu Ala Cys Met Ser Leu Thr Phe Trp Tyr Gly
    1010                1015                1020

Gly Lys Leu Leu Ala Ser Arg Glu Tyr Asp Leu Ile Gln Phe Phe
    1025                1030                1035

Ile Val Tyr Thr Ala Ile Ile Gln Gly Ala Thr Ala Ala Gly Ile
    1040                1045                1050

Trp Phe Ser Phe Thr Pro Ser Met Ala Gln Ala Thr Gly Ala Ala
    1055                1060                1065

Asn Arg Ile Leu Ser Met Arg Pro Thr Ser Thr Asp Pro Ser Ser
    1070                1075                1080

Tyr Ser Pro Leu Pro Cys Ser Asp Glu Gly Val Gly Ile Glu Phe
    1085                1090                1095

Gln His Val Ser Phe Lys Tyr Gln Ser Arg Asp Val Pro Val Leu
    1100                1105                1110

Ser Asn Leu Asn Leu Gln Ile Leu Pro Gly Gln Val Ala Ala Leu
    1115                1120                1125

Val Gly Ser Ser Gly Cys Gly Lys Ser Thr Thr Leu Ser Leu Leu
    1130                1135                1140

Glu Arg Phe Tyr Asp Ala Ser Ser Gly His Ile Leu Tyr Asn Gly
    1145                1150                1155

Gln Asp Ile Thr Thr Phe Ser Pro Ala Glu Tyr Arg Lys Gln Met
    1160                1165                1170
```

```
Ser Leu Val Ser Gln Glu Pro Thr Leu Tyr Gln Gly Ser Ile Arg
    1175                1180                1185

Glu Asn Ile Ser Leu Ser Val Glu Ser Ala Ser Asp Asp Ile
    1190                1195                1200

Lys Gln Ala Cys Arg Asp Ala Gln Ile His Asp Phe Ile Thr Ser
    1205                1210                1215

Leu Pro Glu Gly Tyr Glu Thr Arg Leu Gly Pro Lys Gly Met Ser
    1220                1225                1230

Leu Ser Gly Gly Gln Arg Gln Arg Ile Ser Leu Ala Arg Ala Leu
    1235                1240                1245

Leu Arg Lys Pro Lys Ile Leu Leu Leu Asp Glu Ala Thr Ser Ser
    1250                1255                1260

Leu Asp Ser Glu Ser Glu Lys Tyr Val Gln Glu Ala Ile Glu Arg
    1265                1270                1275

Ala Ala Ser Glu Gly Asp Arg Thr Val Ile Ile Val Ala His Arg
    1280                1285                1290

Leu Ala Thr Ile Gln Lys Ala Asp Val Ile Phe Val Leu Gly Ser
    1295                1300                1305

Gly Lys Val Leu Glu Lys Gly Asp His Gln Ala Leu Leu Arg Lys
    1310                1315                1320

Lys Gly Val Tyr Trp Gln Met Cys Gln Ala Gln Ala Leu Asn Arg
    1325                1330                1335

<210> SEQ ID NO 50
<211> LENGTH: 1047
<212> TYPE: DNA
<213> ORGANISM: Curvularia clavata
<220> FEATURE:
<221> NAME/KEY: CDS
<222> LOCATION: (1)..(1047)

<400> SEQUENCE: 50 atg aag ctc acc gtt ttc agt gca aaa ccc tac gat atc gaa tac ctg      48
Met Lys Leu Thr Val Phe Ser Ala Lys Pro Tyr Asp Ile Glu Tyr Leu
1               5                   10                  15 ggt ggc atc gct act aat caa aac tcc tcg cct gca att gag atc aac      96
Gly Gly Ile Ala Thr Asn Gln Asn Ser Ser Pro Ala Ile Glu Ile Asn
            20                  25                  30 ttc ctg cat gtc ccg ctc tcc agc gag acg gcc gcg ttc gcg aac ggc     144
Phe Leu His Val Pro Leu Ser Ser Glu Thr Ala Ala Phe Ala Asn Gly
        35                  40                  45 gct gat gcc gtc tgc gtc ttc gtt cac gat gtg ctt gac gcc aac gtc     192
Ala Asp Ala Val Cys Val Phe Val His Asp Val Leu Asp Ala Asn Val
    50                  55                  60 ctc cgc gaa cta tac gcc gcc ggc gtg cgc gcc att ctc ttc cgc tgc     240
Leu Arg Glu Leu Tyr Ala Ala Gly Val Arg Ala Ile Leu Phe Arg Cys
65                  70                  75                  80 tca ggg tat aac aat att gac cta agg gag gct gag cgc tta ggc ttc     288
Ser Gly Tyr Asn Asn Ile Asp Leu Arg Glu Ala Glu Arg Leu Gly Phe
                85                  90                  95 ttc gtc gcc aac gtc cct tcg tac tcg ccg gag gca gtc gcc gag ttc     336
Phe Val Ala Asn Val Pro Ser Tyr Ser Pro Glu Ala Val Ala Glu Phe
            100                 105                 110 gca gtc gcg ctc atc caa aca ctt aac cgg aag acg cac cgg gca tac     384
Ala Val Ala Leu Ile Gln Thr Leu Asn Arg Lys Thr His Arg Ala Tyr
        115                 120                 125 aac cgc gtg cgg gac ggc aat ttc aac ctc gac ggc cta ctc gga cga     432
Asn Arg Val Arg Asp Gly Asn Phe Asn Leu Asp Gly Leu Leu Gly Arg
    130                 135                 140
```

| | | |
|---|---|---|
| aca cta cac ggc aaa aca gtc ggc att gta ggg tca ggc cgg atc gga<br>Thr Leu His Gly Lys Thr Val Gly Ile Val Gly Ser Gly Arg Ile Gly<br>145                          150                            155                        160 | 480 |
| ctc gcc atg gcg cag atc gtt cag ggc ttc gga tgc aag ctg ttg gca<br>Leu Ala Met Ala Gln Ile Val Gln Gly Phe Gly Cys Lys Leu Leu Ala<br>                        165                            170                        175 | 528 |
| tac gat cct cgg cct aca gaa gcc ttc aag aag tac ggc gaa tac gtg<br>Tyr Asp Pro Arg Pro Thr Glu Ala Phe Lys Lys Tyr Gly Glu Tyr Val<br>                    180                            185                        190 | 576 |
| gat ctc gat acg ctg ctg tca caa tgc gac att gta agc tta cac tgc<br>Asp Leu Asp Thr Leu Leu Ser Gln Cys Asp Ile Val Ser Leu His Cys<br>         195                           200                            205 | 624 |
| ccg ctg atg gac tcg acg cag cac atc atc aac gac aca act gtc agc<br>Pro Leu Met Asp Ser Thr Gln His Ile Ile Asn Asp Thr Thr Val Ser<br>        210                            215                          220 | 672 |
| aaa atg aag cgc ggc gcg atg ctc gtc aac acg tcg cgt ggc ggg ctg<br>Lys Met Lys Arg Gly Ala Met Leu Val Asn Thr Ser Arg Gly Gly Leu<br>225                          230                            235                        240 | 720 |
| atc gac acg cag agc gtg atg aag gcg ctg aag agc aag cgt ctg ggc<br>Ile Asp Thr Gln Ser Val Met Lys Ala Leu Lys Ser Lys Arg Leu Gly<br>                        245                            250                        255 | 768 |
| ggg cta gcc ctc gac gtt tac gag ggc gag cgc gcg ctc ttc tac aaa<br>Gly Leu Ala Leu Asp Val Tyr Glu Gly Glu Arg Ala Leu Phe Tyr Lys<br>        260                            265                          270 | 816 |
| gac cat tcg ggt gac atc atc cat gac gat ttg ctc atg cgc ctc acc<br>Asp His Ser Gly Asp Ile Ile His Asp Asp Leu Leu Met Arg Leu Thr<br>         275                           280                          285 | 864 |
| acg ttt cac aac gtc gtt gtg tct ggc cac cag gcg tat ttc act gaa<br>Thr Phe His Asn Val Val Val Ser Gly His Gln Ala Tyr Phe Thr Glu<br>        290                            295                          300 | 912 |
| gag gca ctc acg gaa att gcg gag tgt acg ctg agg aat ctg gat gat<br>Glu Ala Leu Thr Glu Ile Ala Glu Cys Thr Leu Arg Asn Leu Asp Asp<br>305                          310                            315                        320 | 960 |
| tgg gcg aag gga gtg cca acg gcg aat gcg ctg gtg cag ggc agg aat<br>Trp Ala Lys Gly Val Pro Thr Ala Asn Ala Leu Val Gln Gly Arg Asn<br>                        325                            330                        335 | 1008 |
| tcg aat ggg agg agg gag cgg ggg ttg gcg cgg ctc tga<br>Ser Asn Gly Arg Arg Glu Arg Gly Leu Ala Arg Leu<br>        340                            345 | 1047 |

<210> SEQ ID NO 51
<211> LENGTH: 348
<212> TYPE: PRT
<213> ORGANISM: Curvularia clavata

<400> SEQUENCE: 51

Met Lys Leu Thr Val Phe Ser Ala Lys Pro Tyr Asp Ile Glu Tyr Leu
1                   5                     10                    15

Gly Gly Ile Ala Thr Asn Gln Asn Ser Ser Pro Ala Ile Glu Ile Asn
                   20                     25                     30

Phe Leu His Val Pro Leu Ser Ser Glu Thr Ala Ala Phe Ala Asn Gly
                35                     40                     45

Ala Asp Ala Val Cys Val Phe Val His Asp Val Leu Asp Ala Asn Val
        50                          55                          60

Leu Arg Glu Leu Tyr Ala Ala Gly Val Arg Ala Ile Leu Phe Arg Cys
65                  70                     75                     80

Ser Gly Tyr Asn Asn Ile Asp Leu Arg Glu Ala Glu Arg Leu Gly Phe
                85                     90                     95

```
Phe Val Ala Asn Val Pro Ser Tyr Ser Pro Glu Ala Val Ala Glu Phe
                100                 105                 110

Ala Val Ala Leu Ile Gln Thr Leu Asn Arg Lys Thr His Arg Ala Tyr
            115                 120                 125

Asn Arg Val Arg Asp Gly Asn Phe Asn Leu Asp Gly Leu Leu Gly Arg
        130                 135                 140

Thr Leu His Gly Lys Thr Val Gly Ile Val Gly Ser Gly Arg Ile Gly
145                 150                 155                 160

Leu Ala Met Ala Gln Ile Val Gln Gly Phe Gly Cys Lys Leu Leu Ala
                165                 170                 175

Tyr Asp Pro Arg Pro Thr Glu Ala Phe Lys Lys Tyr Gly Glu Tyr Val
                180                 185                 190

Asp Leu Asp Thr Leu Leu Ser Gln Cys Asp Ile Val Ser Leu His Cys
            195                 200                 205

Pro Leu Met Asp Ser Thr Gln His Ile Ile Asn Asp Thr Thr Val Ser
        210                 215                 220

Lys Met Lys Arg Gly Ala Met Leu Val Asn Thr Ser Arg Gly Gly Leu
225                 230                 235                 240

Ile Asp Thr Gln Ser Val Met Lys Ala Leu Lys Ser Lys Arg Leu Gly
                245                 250                 255

Gly Leu Ala Leu Asp Val Tyr Glu Gly Glu Arg Ala Leu Phe Tyr Lys
                260                 265                 270

Asp His Ser Gly Asp Ile Ile His Asp Asp Leu Leu Met Arg Leu Thr
            275                 280                 285

Thr Phe His Asn Val Val Ser Gly His Gln Ala Tyr Phe Thr Glu
        290                 295                 300

Glu Ala Leu Thr Glu Ile Ala Glu Cys Thr Leu Arg Asn Leu Asp Asp
305                 310                 315                 320

Trp Ala Lys Gly Val Pro Thr Ala Asn Ala Leu Val Gln Gly Arg Asn
                325                 330                 335

Ser Asn Gly Arg Arg Glu Arg Gly Leu Ala Arg Leu
            340                 345
```

<210> SEQ ID NO 52
<211> LENGTH: 936
<212> TYPE: DNA
<213> ORGANISM: Curvularia clavata
<220> FEATURE:
<221> NAME/KEY: CDS
<222> LOCATION: (1)..(936)

<400> SEQUENCE: 52

```
atg acg aaa agg gaa agc aac act cta gcg gtt ctc gga tgc ggt atg      48
Met Thr Lys Arg Glu Ser Asn Thr Leu Ala Val Leu Gly Cys Gly Met
1               5                   10                  15 gtt ttt ctt gta tca tta tta gat ctg gct aac aga ctg tta ggt gcg     96
Val Phe Leu Val Ser Leu Leu Asp Leu Ala Asn Arg Leu Leu Gly Ala
                20                  25                  30 ctt ggc acc gcc att ctc tca ggc ata ctt gct tct atg gca gat cag    144
Leu Gly Thr Ala Ile Leu Ser Gly Ile Leu Ala Ser Met Ala Asp Gln
            35                  40                  45 aca gcc gat gat tcg ggt cgc ctg ttt acg aat ttc act gcc tgt gtg    192
Thr Ala Asp Asp Ser Gly Arg Leu Phe Thr Asn Phe Thr Ala Cys Val
        50                  55                  60 cgt cgc aaa gag acc ggt gct gct gtt agt gat aag atc agt tcg cac    240
Arg Arg Lys Glu Thr Gly Ala Ala Val Ser Asp Lys Ile Ser Ser His
65                  70                  75                  80
```

```
gcc aat gca aac aaa gtc gag ata ttg aac aag gaa aat cta cgg ggc    288
Ala Asn Ala Asn Lys Val Glu Ile Leu Asn Lys Glu Asn Leu Arg Gly
                85                  90                  95 gtc aag caa gca gat gct gtt ctc tta gcc tgc caa acg cac cta tac    336
Val Lys Gln Ala Asp Ala Val Leu Leu Ala Cys Gln Thr His Leu Tyr
            100                 105                 110 aaa gct ctg ttc gac gag cca ggg atg cga gag gca ctg aag aag aaa    384
Lys Ala Leu Phe Asp Glu Pro Gly Met Arg Glu Ala Leu Lys Lys Lys
        115                 120                 125 ctg atc atc agc gtg ctg gct ggt gtt acc aca gca caa ctc gaa gca    432
Leu Ile Ile Ser Val Leu Ala Gly Val Thr Thr Ala Gln Leu Glu Ala
    130                 135                 140 gcg ctg ggg aat ggt gag gat tac ttt gta atc cga gct atg cca aat    480
Ala Leu Gly Asn Gly Glu Asp Tyr Phe Val Ile Arg Ala Met Pro Asn
145                 150                 155                 160 atc gca tgt ttt gta cga gat tct gca acc gtc atc gag aag cct cag    528
Ile Ala Cys Phe Val Arg Asp Ser Ala Thr Val Ile Glu Lys Pro Gln
                165                 170                 175 cga act ttc cca gag gca ttg ctt cac gtc acc gac acc gtc ttc aaa    576
Arg Thr Phe Pro Glu Ala Leu Leu His Val Thr Asp Thr Val Phe Lys
            180                 185                 190 gcc gtg ggc aac gtc ttt tac atc caa cca tct gcc tat gac ata tgt    624
Ala Val Gly Asn Val Phe Tyr Ile Gln Pro Ser Ala Tyr Asp Ile Cys
        195                 200                 205 act gct ctc tgt ggt tca tca ccc gca ttt ctt gca gta ttt att gac    672
Thr Ala Leu Cys Gly Ser Ser Pro Ala Phe Leu Ala Val Phe Ile Asp
    210                 215                 220 tct atg gtg gat ggt gcg gta gcc atg ggg cta agt cac aag gac gcg    720
Ser Met Val Asp Gly Ala Val Ala Met Gly Leu Ser His Lys Asp Ala
225                 230                 235                 240 gtc gac atg gcg gcc tgc aca atg agg gga gct gcc agt ttg gtg cta    768
Val Asp Met Ala Ala Cys Thr Met Arg Gly Ala Ala Ser Leu Val Leu
                245                 250                 255 gag agc ggc aat cct tgg acg ata cga cac cag gtg gcg tca cct gga    816
Glu Ser Gly Asn Pro Trp Thr Ile Arg His Gln Val Ala Ser Pro Gly
            260                 265                 270 ggc tcg acc atg cag ggt cta ctg gca ctt gaa caa gga aat gtg aga    864
Gly Ser Thr Met Gln Gly Leu Leu Ala Leu Glu Gln Gly Asn Val Arg
        275                 280                 285 tca acc atc tcc aac gcg ttg atg gtc gcc gcg aaa gaa gca aaa aag    912
Ser Thr Ile Ser Asn Ala Leu Met Val Ala Ala Lys Glu Ala Lys Lys
    290                 295                 300 ctg ggg tcg aaa gaa aac gcg tag                                    936
Leu Gly Ser Lys Glu Asn Ala
305                 310
```

<210> SEQ ID NO 53
<211> LENGTH: 311
<212> TYPE: PRT
<213> ORGANISM: Curvularia clavata

<400> SEQUENCE: 53

```
Met Thr Lys Arg Glu Ser Asn Thr Leu Ala Val Leu Gly Cys Gly Met
1               5                   10                  15

Val Phe Leu Val Ser Leu Leu Asp Leu Ala Asn Arg Leu Leu Gly Ala
            20                  25                  30

Leu Gly Thr Ala Ile Leu Ser Gly Ile Leu Ala Ser Met Ala Asp Gln
        35                  40                  45

Thr Ala Asp Asp Ser Gly Arg Leu Phe Thr Asn Phe Thr Ala Cys Val
    50                  55                  60
```

```
Arg Arg Lys Glu Thr Gly Ala Ala Val Ser Asp Lys Ile Ser Ser His
 65                  70                  75                  80

Ala Asn Ala Asn Lys Val Glu Ile Leu Asn Lys Glu Asn Leu Arg Gly
                 85                  90                  95

Val Lys Gln Ala Asp Ala Val Leu Leu Ala Cys Gln Thr His Leu Tyr
            100                 105                 110

Lys Ala Leu Phe Asp Glu Pro Gly Met Arg Glu Ala Leu Lys Lys Lys
            115                 120                 125

Leu Ile Ile Ser Val Leu Ala Gly Val Thr Thr Ala Gln Leu Glu Ala
            130                 135                 140

Ala Leu Gly Asn Gly Glu Asp Tyr Phe Val Ile Arg Ala Met Pro Asn
145                 150                 155                 160

Ile Ala Cys Phe Val Arg Asp Ser Ala Thr Val Ile Glu Lys Pro Gln
                165                 170                 175

Arg Thr Phe Pro Glu Ala Leu Leu His Val Thr Asp Thr Val Phe Lys
                180                 185                 190

Ala Val Gly Asn Val Phe Tyr Ile Gln Pro Ser Ala Tyr Asp Ile Cys
                195                 200                 205

Thr Ala Leu Cys Gly Ser Ser Pro Ala Phe Leu Ala Val Phe Ile Asp
210                 215                 220

Ser Met Val Asp Gly Ala Val Ala Met Gly Leu Ser His Lys Asp Ala
225                 230                 235                 240

Val Asp Met Ala Ala Cys Thr Met Arg Gly Ala Ala Ser Leu Val Leu
                245                 250                 255

Glu Ser Gly Asn Pro Trp Thr Ile Arg His Gln Val Ala Ser Pro Gly
                260                 265                 270

Gly Ser Thr Met Gln Gly Leu Leu Ala Leu Glu Gln Gly Asn Val Arg
                275                 280                 285

Ser Thr Ile Ser Asn Ala Leu Met Val Ala Ala Lys Glu Ala Lys Lys
                290                 295                 300

Leu Gly Ser Lys Glu Asn Ala
305                 310

<210> SEQ ID NO 54
<211> LENGTH: 924
<212> TYPE: DNA
<213> ORGANISM: Curvularia clavata
<220> FEATURE:
<221> NAME/KEY: CDS
<222> LOCATION: (1)..(924)

<400> SEQUENCE: 54 atg gag agc gaa gac aat cca ttg agg ata caa acc ggc tcg ctc tgc      48
Met Glu Ser Glu Asp Asn Pro Leu Arg Ile Gln Thr Gly Ser Leu Cys
 1               5                  10                  15 tca ttc caa cga ccg act ccg ctg gta ctc att cac gac tct agt ggc      96
Ser Phe Gln Arg Pro Thr Pro Leu Val Leu Ile His Asp Ser Ser Gly
                20                  25                  30 acg acc ttt agt tat ttc cgc ctg ggc agc ttg aac cgt gat gtc tgg     144
Thr Thr Phe Ser Tyr Phe Arg Leu Gly Ser Leu Asn Arg Asp Val Trp
            35                  40                  45 gct att cat gac cca cac ttt gat aaa agc acg ccg tgg aag ggc ggg     192
Ala Ile His Asp Pro His Phe Asp Lys Ser Thr Pro Trp Lys Gly Gly
        50                  55                  60 ttt ggc gag att gcc gag cac tac ata aaa ttg att gaa acg gca gga     240
Phe Gly Glu Ile Ala Glu His Tyr Ile Lys Leu Ile Glu Thr Ala Gly
 65                  70                  75                  80
```

| | | |
|---|---|---|
| att cga ggt tcg atc ttg ctc gga gga tgg tcg ctc ggg ggt tat ctc<br>Ile Arg Gly Ser Ile Leu Leu Gly Gly Trp Ser Leu Gly Gly Tyr Leu<br>                85                90              95 | 288 |
| gcg ctc acg att gct cac aaa tta acg gct atc aca aat cct acc ttc<br>Ala Leu Thr Ile Ala His Lys Leu Thr Ala Ile Thr Asn Pro Thr Phe<br>          100              105                110 | 336 |
| tct gtc acc ggc atc ttg ctt gtt gac tct ccg tat cac acc cca atg<br>Ser Val Thr Gly Ile Leu Leu Val Asp Ser Pro Tyr His Thr Pro Met<br>        115                120              125 | 384 |
| agt aag ctg cca cct cac gcc cca gat ccc aac ttt caa cac ctt ccg<br>Ser Lys Leu Pro Pro His Ala Pro Asp Pro Asn Phe Gln His Leu Pro<br>130                135              140 | 432 |
| gaa ctc gtc cgt aag tca ttc gag aat tac gat gtc ctt tta gac aga<br>Glu Leu Val Arg Lys Ser Phe Glu Asn Tyr Asp Val Leu Leu Asp Arg<br>145                150              155              160 | 480 |
| tgg gaa cta cct cca tgg acc gcg cct gct ttg gaa ggc aaa act ata<br>Trp Glu Leu Pro Pro Trp Thr Ala Pro Ala Leu Glu Gly Lys Thr Ile<br>                165              170              175 | 528 |
| cgt tgt agc gcg ggt ggc aag acc ttc acg gta gca aac ggc agg atc<br>Arg Cys Ser Ala Gly Gly Lys Thr Phe Thr Val Ala Asn Gly Arg Ile<br>        180                185              190 | 576 |
| cta tac aag ccc cta ggt aag ggc tgg gaa gat gtc aaa atg caa agc<br>Leu Tyr Lys Pro Leu Gly Lys Gly Trp Glu Asp Val Lys Met Gln Ser<br>          195              200              205 | 624 |
| ttc gag cat ggc acc tct act ttg gaa cgc tac atc gaa tta ccc cca<br>Phe Glu His Gly Thr Ser Thr Leu Glu Arg Tyr Ile Glu Leu Pro Pro<br>210                215              220 | 672 |
| gca gct ctg atc aga tgc gct cag gcc ata cca act gat aca gat tcg<br>Ala Ala Leu Ile Arg Cys Ala Gln Ala Ile Pro Thr Asp Thr Asp Ser<br>225                230              235              240 | 720 |
| aaa atg ccg tgt ttc gta gat cga ttc cgt cac gag aca ctg cta ggt<br>Lys Met Pro Cys Phe Val Asp Arg Phe Arg His Glu Thr Leu Leu Gly<br>                245              250              255 | 768 |
| tgg gat agt aat ttc ccc agt ttc atc aag gcc gcc gtg gac acg aac<br>Trp Asp Ser Asn Phe Pro Ser Phe Ile Lys Ala Ala Val Asp Thr Asn<br>        260                265              270 | 816 |
| act cac cac ttc aac ata ttc gag tct cag aat ctc aaa cga tta acg<br>Thr His His Phe Asn Ile Phe Glu Ser Gln Asn Leu Lys Arg Leu Thr<br>          275              280              285 | 864 |
| ata caa ttg aat gaa tgt cta gaa gtt cta gat agc tgt tgc ccg atg<br>Ile Gln Leu Asn Glu Cys Leu Glu Val Leu Asp Ser Cys Cys Pro Met<br>290                295              300 | 912 |
| gga tac tgc tga<br>Gly Tyr Cys<br>305 | 924 |

```
<210> SEQ ID NO 55
<211> LENGTH: 307
<212> TYPE: PRT
<213> ORGANISM: Curvularia clavata

<400> SEQUENCE: 55
```

Met Glu Ser Glu Asp Asn Pro Leu Arg Ile Gln Thr Gly Ser Leu Cys
1                 5                   10                 15

Ser Phe Gln Arg Pro Thr Pro Leu Val Leu Ile His Asp Ser Ser Gly
                20                   25                   30

Thr Thr Phe Ser Tyr Phe Arg Leu Gly Ser Leu Asn Arg Asp Val Trp
                  35                   40                   45

Ala Ile His Asp Pro His Phe Asp Lys Ser Thr Pro Trp Lys Gly Gly
    50                   55                   60

Phe Gly Glu Ile Ala Glu His Tyr Ile Lys Leu Ile Glu Thr Ala Gly
65                  70                  75                  80

Ile Arg Gly Ser Ile Leu Leu Gly Gly Trp Ser Leu Gly Gly Tyr Leu
                85                  90                  95

Ala Leu Thr Ile Ala His Lys Leu Thr Ala Ile Thr Asn Pro Thr Phe
            100                 105                 110

Ser Val Thr Gly Ile Leu Leu Val Asp Ser Pro Tyr His Thr Pro Met
        115                 120                 125

Ser Lys Leu Pro Pro His Ala Pro Asp Pro Asn Phe Gln His Leu Pro
130                 135                 140

Glu Leu Val Arg Lys Ser Phe Glu Asn Tyr Asp Val Leu Leu Asp Arg
145                 150                 155                 160

Trp Glu Leu Pro Pro Trp Thr Ala Pro Ala Leu Glu Gly Lys Thr Ile
                165                 170                 175

Arg Cys Ser Ala Gly Gly Lys Thr Phe Thr Val Ala Asn Gly Arg Ile
            180                 185                 190

Leu Tyr Lys Pro Leu Gly Lys Gly Trp Glu Asp Val Lys Met Gln Ser
        195                 200                 205

Phe Glu His Gly Thr Ser Thr Leu Glu Arg Tyr Ile Glu Leu Pro Pro
210                 215                 220

Ala Ala Leu Ile Arg Cys Ala Gln Ala Ile Pro Thr Asp Thr Asp Ser
225                 230                 235                 240

Lys Met Pro Cys Phe Val Asp Arg Phe Arg His Glu Thr Leu Leu Gly
                245                 250                 255

Trp Asp Ser Asn Phe Pro Ser Phe Ile Lys Ala Ala Val Asp Thr Asn
            260                 265                 270

Thr His His Phe Asn Ile Phe Glu Ser Gln Asn Leu Lys Arg Leu Thr
        275                 280                 285

Ile Gln Leu Asn Glu Cys Leu Glu Val Leu Asp Ser Cys Cys Pro Met
290                 295                 300

Gly Tyr Cys
305

<210> SEQ ID NO 56
<211> LENGTH: 33
<212> TYPE: DNA
<213> ORGANISM: Artificial
<220> FEATURE:
<223> OTHER INFORMATION: Synthetic DNA

<400> SEQUENCE: 56
cggtacccgg ggatctagtc tgttgattac tcg                                    33

<210> SEQ ID NO 57
<211> LENGTH: 35
<212> TYPE: DNA
<213> ORGANISM: Artificial
<220> FEATURE:
<223> OTHER INFORMATION: Synthetic DNA

<400> SEQUENCE: 57
ctcgacaaag gtcatttga ctttgaatac cggtg                                   35

<210> SEQ ID NO 58
<211> LENGTH: 22
<212> TYPE: DNA
<213> ORGANISM: Artificial
<220> FEATURE:
<223> OTHER INFORMATION: Synthetic DNA

```
<400> SEQUENCE: 58
gcagttgccg ttggaccaga gg                                              22

<210> SEQ ID NO 59
<211> LENGTH: 37
<212> TYPE: DNA
<213> ORGANISM: Artificial
<220> FEATURE:
<223> OTHER INFORMATION: Synthetic DNA

<400> SEQUENCE: 59
atagtcataa caagccgcga cactgtaata ttaaagc                              37

<210> SEQ ID NO 60
<211> LENGTH: 24
<212> TYPE: DNA
<213> ORGANISM: Artificial
<220> FEATURE:
<223> OTHER INFORMATION: Synthetic DNA

<400> SEQUENCE: 60
atgacctttg tcgagactgt agcc                                            24

<210> SEQ ID NO 61
<211> LENGTH: 39
<212> TYPE: DNA
<213> ORGANISM: Artificial
<220> FEATURE:
<223> OTHER INFORMATION: Synthetic DNA

<400> SEQUENCE: 61
tccaacggca actgcctatg atatactcat gttctcgtc                            39

<210> SEQ ID NO 62
<211> LENGTH: 35
<212> TYPE: DNA
<213> ORGANISM: Artificial
<220> FEATURE:
<223> OTHER INFORMATION: Synthetic DNA

<400> SEQUENCE: 62
cgactctaga ggatcctgat ggtcagatgg atctg                                35

<210> SEQ ID NO 63
<211> LENGTH: 28
<212> TYPE: DNA
<213> ORGANISM: Artificial
<220> FEATURE:
<223> OTHER INFORMATION: Synthetic DNA

<400> SEQUENCE: 63
gcttgttatg actatgtata catatgcg                                        28

<210> SEQ ID NO 64
<211> LENGTH: 21
<212> TYPE: DNA
<213> ORGANISM: Artificial
<220> FEATURE:
<223> OTHER INFORMATION: Synthetic DNA

<400> SEQUENCE: 64
gacagactct tcgtcgacgt c                                               21

<210> SEQ ID NO 65
<211> LENGTH: 22
```

<212> TYPE: DNA
<213> ORGANISM: Artificial
<220> FEATURE:
<223> OTHER INFORMATION: Synthetic DNA

<400> SEQUENCE: 65
gttgtggttg gtgttcctga gg                                    22

<210> SEQ ID NO 66
<211> LENGTH: 22
<212> TYPE: DNA
<213> ORGANISM: Artificial
<220> FEATURE:
<223> OTHER INFORMATION: Synthetic DNA

<400> SEQUENCE: 66
cactcgatct accaaatcga cg                                    22

<210> SEQ ID NO 67
<211> LENGTH: 21
<212> TYPE: DNA
<213> ORGANISM: Artificial
<220> FEATURE:
<223> OTHER INFORMATION: Synthetic DNA

<400> SEQUENCE: 67
cctatccgga tatgcagtca c                                     21

<210> SEQ ID NO 68
<211> LENGTH: 38
<212> TYPE: DNA
<213> ORGANISM: Artificial
<220> FEATURE:
<223> OTHER INFORMATION: Synthetic DNA

<400> SEQUENCE: 68
cggtacccgg ggatcctctg aagcggtcaa ggataacg                   38

<210> SEQ ID NO 69
<211> LENGTH: 37
<212> TYPE: DNA
<213> ORGANISM: Artificial
<220> FEATURE:
<223> OTHER INFORMATION: Synthetic DNA

<400> SEQUENCE: 69
atgaagcaga gcggcgagcc taagatatgc caggagg                    37

<210> SEQ ID NO 70
<211> LENGTH: 37
<212> TYPE: DNA
<213> ORGANISM: Artificial
<220> FEATURE:
<223> OTHER INFORMATION: Synthetic DNA

<400> SEQUENCE: 70
ctagcaaccg tcatgccata gacgtggcac tcgaacg                    37

<210> SEQ ID NO 71
<211> LENGTH: 38
<212> TYPE: DNA
<213> ORGANISM: Artificial
<220> FEATURE:
<223> OTHER INFORMATION: Synthetic DNA

<400> SEQUENCE: 71
cgactctaga ggatccgtct taaggatggt tcagctgc                        38

<210> SEQ ID NO 72
<211> LENGTH: 20
<212> TYPE: DNA
<213> ORGANISM: Artificial
<220> FEATURE:
<223> OTHER INFORMATION: Synthetic DNA

<400> SEQUENCE: 72
catgacggtt gctagggtcg                                            20

<210> SEQ ID NO 73
<211> LENGTH: 20
<212> TYPE: DNA
<213> ORGANISM: Artificial
<220> FEATURE:
<223> OTHER INFORMATION: Synthetic DNA

<400> SEQUENCE: 73
gccgctctgc ttcattgctg                                            20

<210> SEQ ID NO 74
<211> LENGTH: 33
<212> TYPE: DNA
<213> ORGANISM: Artificial
<220> FEATURE:
<223> OTHER INFORMATION: Synthetic DNA

<400> SEQUENCE: 74
cggtacccgg ggatcgaccc attgcagctt gtg                             33

<210> SEQ ID NO 75
<211> LENGTH: 37
<212> TYPE: DNA
<213> ORGANISM: Artificial
<220> FEATURE:
<223> OTHER INFORMATION: Synthetic DNA

<400> SEQUENCE: 75
atgaagcaga gcggcgtgca gtatggtgtc taaaacg                         37

<210> SEQ ID NO 76
<211> LENGTH: 36
<212> TYPE: DNA
<213> ORGANISM: Artificial
<220> FEATURE:
<223> OTHER INFORMATION: Synthetic DNA

<400> SEQUENCE: 76
ctagcaaccg tcatggatga atgagcaccc tgttag                          36

<210> SEQ ID NO 77
<211> LENGTH: 39
<212> TYPE: DNA
<213> ORGANISM: Artificial
<220> FEATURE:
<223> OTHER INFORMATION: Synthetic DNA

<400> SEQUENCE: 77
cgactctaga ggatcgtaca ttacaaaaac ctgttgcag                       39

<210> SEQ ID NO 78
<211> LENGTH: 35

<212> TYPE: DNA
<213> ORGANISM: Artificial
<220> FEATURE:
<223> OTHER INFORMATION: Synthetic DNA

<400> SEQUENCE: 78
cggtacccgg ggatcgtccc acgtgcagct tcaac                                35

<210> SEQ ID NO 79
<211> LENGTH: 35
<212> TYPE: DNA
<213> ORGANISM: Artificial
<220> FEATURE:
<223> OTHER INFORMATION: Synthetic DNA

<400> SEQUENCE: 79
atgaagcaga gcggccgtgg agtatcccag gatgg                                35

<210> SEQ ID NO 80
<211> LENGTH: 35
<212> TYPE: DNA
<213> ORGANISM: Artificial
<220> FEATURE:
<223> OTHER INFORMATION: Synthetic DNA

<400> SEQUENCE: 80
ctagcaaccg tcatgccagc caaagggtat catgg                                35

<210> SEQ ID NO 81
<211> LENGTH: 33
<212> TYPE: DNA
<213> ORGANISM: Artificial
<220> FEATURE:
<223> OTHER INFORMATION: Synthetic DNA

<400> SEQUENCE: 81
cgactctaga ggatctgagg gcagcgtagc ctg                                  33

<210> SEQ ID NO 82
<211> LENGTH: 37
<212> TYPE: DNA
<213> ORGANISM: Artificial
<220> FEATURE:
<223> OTHER INFORMATION: Synthetic DNA

<400> SEQUENCE: 82
cggtacccgg ggatcgtgga taaattcgta ccctttg                              37

<210> SEQ ID NO 83
<211> LENGTH: 36
<212> TYPE: DNA
<213> ORGANISM: Artificial
<220> FEATURE:
<223> OTHER INFORMATION: Synthetic DNA

<400> SEQUENCE: 83
atgaagcaga gcggcctgat ctttgttgtg gtcgtg                               36

<210> SEQ ID NO 84
<211> LENGTH: 35
<212> TYPE: DNA
<213> ORGANISM: Artificial
<220> FEATURE:
<223> OTHER INFORMATION: Synthetic DNA

<400> SEQUENCE: 84
ctagcaaccg tcatgcagtt tggcacttga gcatc                                    35

<210> SEQ ID NO 85
<211> LENGTH: 36
<212> TYPE: DNA
<213> ORGANISM: Artificial
<220> FEATURE:
<223> OTHER INFORMATION: Synthetic DNA

<400> SEQUENCE: 85
cgactctaga ggatccacgg aaaggaactc ctacag                                   36

<210> SEQ ID NO 86
<211> LENGTH: 34
<212> TYPE: DNA
<213> ORGANISM: Artificial
<220> FEATURE:
<223> OTHER INFORMATION: Synthetic DNA

<400> SEQUENCE: 86
cggtacccgg ggatcctctg ggaaaagcgg ttag                                     34

<210> SEQ ID NO 87
<211> LENGTH: 34
<212> TYPE: DNA
<213> ORGANISM: Artificial
<220> FEATURE:
<223> OTHER INFORMATION: Synthetic DNA

<400> SEQUENCE: 87
atgaagcaga gcggcgaaga accgagagcg agag                                     34

<210> SEQ ID NO 88
<211> LENGTH: 40
<212> TYPE: DNA
<213> ORGANISM: Artificial
<220> FEATURE:
<223> OTHER INFORMATION: Synthetic DNA

<400> SEQUENCE: 88
ctagcaaccg tcatgcttgc atctacctag atatttcacg                               40

<210> SEQ ID NO 89
<211> LENGTH: 36
<212> TYPE: DNA
<213> ORGANISM: Artificial
<220> FEATURE:
<223> OTHER INFORMATION: Synthetic DNA

<400> SEQUENCE: 89
cgactctaga ggatccagag aatcagcaga gacacc                                   36

<210> SEQ ID NO 90
<211> LENGTH: 39
<212> TYPE: DNA
<213> ORGANISM: Artificial
<220> FEATURE:
<223> OTHER INFORMATION: Synthetic DNA

<400> SEQUENCE: 90
cggtacccgg ggatcccctg gtagttcagt ggaagtaag                                39

<210> SEQ ID NO 91
<211> LENGTH: 34

```
<212> TYPE: DNA
<213> ORGANISM: Artificial
<220> FEATURE:
<223> OTHER INFORMATION: Synthetic DNA

<400> SEQUENCE: 91
atgaagcaga gcggctgata gaggtacggg ggtg                               34

<210> SEQ ID NO 92
<211> LENGTH: 34
<212> TYPE: DNA
<213> ORGANISM: Artificial
<220> FEATURE:
<223> OTHER INFORMATION: Synthetic DNA

<400> SEQUENCE: 92
ctagcaaccg tcatgtgctt ggctgcttca aatc                               34

<210> SEQ ID NO 93
<211> LENGTH: 39
<212> TYPE: DNA
<213> ORGANISM: Artificial
<220> FEATURE:
<223> OTHER INFORMATION: Synthetic DNA

<400> SEQUENCE: 93
cgactctaga ggatcctaat acttgtcgtc ccactgatg                          39

<210> SEQ ID NO 94
<211> LENGTH: 34
<212> TYPE: DNA
<213> ORGANISM: Artificial
<220> FEATURE:
<223> OTHER INFORMATION: Synthetic DNA

<400> SEQUENCE: 94
cggtacccgg ggatcgcagt acatcgtcag ggtc                               34

<210> SEQ ID NO 95
<211> LENGTH: 36
<212> TYPE: DNA
<213> ORGANISM: Artificial
<220> FEATURE:
<223> OTHER INFORMATION: Synthetic DNA

<400> SEQUENCE: 95
atgaagcaga gcggcgatga ataaggcgaa ggaaag                             36

<210> SEQ ID NO 96
<211> LENGTH: 37
<212> TYPE: DNA
<213> ORGANISM: Artificial
<220> FEATURE:
<223> OTHER INFORMATION: Synthetic DNA

<400> SEQUENCE: 96
ctagcaaccg tcatgccctc tttttttcttg ctgtctc                           37

<210> SEQ ID NO 97
<211> LENGTH: 35
<212> TYPE: DNA
<213> ORGANISM: Artificial
<220> FEATURE:
<223> OTHER INFORMATION: Synthetic DNA
```

```
<400> SEQUENCE: 97
cgactctaga ggatcgaagg aaggacggat actgg                          35

<210> SEQ ID NO 98
<211> LENGTH: 39
<212> TYPE: DNA
<213> ORGANISM: Artificial
<220> FEATURE:
<223> OTHER INFORMATION: Synthetic DNA

<400> SEQUENCE: 98
cggtacccgg ggatcgatga gcgtagaatt cgtaaaaag                      39

<210> SEQ ID NO 99
<211> LENGTH: 32
<212> TYPE: DNA
<213> ORGANISM: Artificial
<220> FEATURE:
<223> OTHER INFORMATION: Synthetic DNA

<400> SEQUENCE: 99
atgaagcaga gcggcgcgaa cgggcgtttt tc                             32

<210> SEQ ID NO 100
<211> LENGTH: 35
<212> TYPE: DNA
<213> ORGANISM: Artificial
<220> FEATURE:
<223> OTHER INFORMATION: Synthetic DNA

<400> SEQUENCE: 100
ctagcaaccg tcatggaagg aaggacggat actgg                          35

<210> SEQ ID NO 101
<211> LENGTH: 37
<212> TYPE: DNA
<213> ORGANISM: Artificial
<220> FEATURE:
<223> OTHER INFORMATION: Synthetic DNA

<400> SEQUENCE: 101
cgactctaga ggatccccctc ttttttcttg ctgtctc                       37

<210> SEQ ID NO 102
<211> LENGTH: 40
<212> TYPE: DNA
<213> ORGANISM: Artificial
<220> FEATURE:
<223> OTHER INFORMATION: Synthetic DNA

<400> SEQUENCE: 102
cggtacccgg ggatcctcct tattttgcaa cttctgatac                     40

<210> SEQ ID NO 103
<211> LENGTH: 37
<212> TYPE: DNA
<213> ORGANISM: Artificial
<220> FEATURE:
<223> OTHER INFORMATION: Synthetic DNA

<400> SEQUENCE: 103
atgaagcaga gcggccgtgt tgattttggt aattttg                        37

<210> SEQ ID NO 104
<211> LENGTH: 39
```

<210> SEQ ID NO 105
<211> LENGTH: 32
<212> TYPE: DNA
<213> ORGANISM: Artificial
<220> FEATURE:
<223> OTHER INFORMATION: Synthetic DNA

<400> SEQUENCE: 104
ctagcaaccg tcatggatga gcgtagaatt cgtaaaaag                    39

<210> SEQ ID NO 105
<211> LENGTH: 32
<212> TYPE: DNA
<213> ORGANISM: Artificial
<220> FEATURE:
<223> OTHER INFORMATION: Synthetic DNA

<400> SEQUENCE: 105
cgactctaga ggatcgcgaa cgggcgtttt tc                           32

<210> SEQ ID NO 106
<211> LENGTH: 37
<212> TYPE: DNA
<213> ORGANISM: Artificial
<220> FEATURE:
<223> OTHER INFORMATION: Synthetic DNA

<400> SEQUENCE: 106
cggtacccgg ggatccgtgt tgattttggt aattttg                      37

<210> SEQ ID NO 107
<211> LENGTH: 40
<212> TYPE: DNA
<213> ORGANISM: Artificial
<220> FEATURE:
<223> OTHER INFORMATION: Synthetic DNA

<400> SEQUENCE: 107
atgaagcaga gcggcctcct tattttgcaa cttctgatac                   40

<210> SEQ ID NO 108
<211> LENGTH: 39
<212> TYPE: DNA
<213> ORGANISM: Artificial
<220> FEATURE:
<223> OTHER INFORMATION: Synthetic DNA

<400> SEQUENCE: 108
ctagcaaccg tcatgctagc agccataaga gacgtaacc                    39

<210> SEQ ID NO 109
<211> LENGTH: 34
<212> TYPE: DNA
<213> ORGANISM: Artificial
<220> FEATURE:
<223> OTHER INFORMATION: Synthetic DNA

<400> SEQUENCE: 109
cgactctaga ggatcgtttt cattgcatgc tccg                         34

<210> SEQ ID NO 110
<211> LENGTH: 59
<212> TYPE: DNA
<213> ORGANISM: Artificial
<220> FEATURE:
<223> OTHER INFORMATION: Synthetic DNA

<400> SEQUENCE: 110
tcgacaagct tgcggccgcc acgtgactag tatggccagc gacatcaata ctcatccag     59

<210> SEQ ID NO 111
<211> LENGTH: 47
<212> TYPE: DNA
<213> ORGANISM: Artificial
<220> FEATURE:
<223> OTHER INFORMATION: Synthetic DNA

<400> SEQUENCE: 111
actagtcacg tggcggccgc ggcgcgccaa gatcgtcttg ctgtacg     47

<210> SEQ ID NO 112
<211> LENGTH: 41
<212> TYPE: DNA
<213> ORGANISM: Artificial
<220> FEATURE:
<223> OTHER INFORMATION: Synthetic DNA

<400> SEQUENCE: 112
gatgcgctag cggccgcgaa gtggtccttg tcgctggtga c     41

<210> SEQ ID NO 113
<211> LENGTH: 28
<212> TYPE: DNA
<213> ORGANISM: Artificial
<220> FEATURE:
<223> OTHER INFORMATION: Synthetic DNA

<400> SEQUENCE: 113
tgccgttcgc attcataggc atctcgtc     28

<210> SEQ ID NO 114
<211> LENGTH: 25
<212> TYPE: DNA
<213> ORGANISM: Artificial
<220> FEATURE:
<223> OTHER INFORMATION: Synthetic DNA

<400> SEQUENCE: 114
tgaatgcgaa cggcaaggtt gacag     25

<210> SEQ ID NO 115
<211> LENGTH: 25
<212> TYPE: DNA
<213> ORGANISM: Artificial
<220> FEATURE:
<223> OTHER INFORMATION: Synthetic DNA

<400> SEQUENCE: 115
cttggttgct ggcttcgtcg ttgtc     25

<210> SEQ ID NO 116
<211> LENGTH: 25
<212> TYPE: DNA
<213> ORGANISM: Artificial
<220> FEATURE:
<223> OTHER INFORMATION: Synthetic DNA

<400> SEQUENCE: 116
aagccagcaa ccaagtcgaa gattg     25

<210> SEQ ID NO 117
<211> LENGTH: 43

<212> TYPE: DNA
<213> ORGANISM: Artificial
<220> FEATURE:
<223> OTHER INFORMATION: Synthetic DNA

<400> SEQUENCE: 117
gtcactagtg cggccgccta tttttgcaag atcttgttca aac             43

<210> SEQ ID NO 118
<211> LENGTH: 29
<212> TYPE: DNA
<213> ORGANISM: Artificial
<220> FEATURE:
<223> OTHER INFORMATION: Synthetic DNA

<400> SEQUENCE: 118
ggactagtat gactgaaccc acatggaag                             29

<210> SEQ ID NO 119
<211> LENGTH: 29
<212> TYPE: DNA
<213> ORGANISM: Artificial
<220> FEATURE:
<223> OTHER INFORMATION: Synthetic DNA

<400> SEQUENCE: 119
ggactagttt aataatctac ttcaagcac                             29

<210> SEQ ID NO 120
<211> LENGTH: 33
<212> TYPE: DNA
<213> ORGANISM: Artificial
<220> FEATURE:
<223> OTHER INFORMATION: Synthetic DNA

<400> SEQUENCE: 120
ataagaatgc ggccgcatgg cgttgcaaga gcg                        33

<210> SEQ ID NO 121
<211> LENGTH: 36
<212> TYPE: DNA
<213> ORGANISM: Artificial
<220> FEATURE:
<223> OTHER INFORMATION: Synthetic DNA

<400> SEQUENCE: 121
ataagaatgc ggccgctcaa gatgggaaag ccgctg                     36

<210> SEQ ID NO 122
<211> LENGTH: 28
<212> TYPE: DNA
<213> ORGANISM: Artificial
<220> FEATURE:
<223> OTHER INFORMATION: Synthetic DNA

<400> SEQUENCE: 122
ctagctagca tgagtgctat cgagctgc                              28

<210> SEQ ID NO 123
<211> LENGTH: 28
<212> TYPE: DNA
<213> ORGANISM: Artificial
<220> FEATURE:
<223> OTHER INFORMATION: Synthetic DNA

```
<400> SEQUENCE: 123
ctagctagct cagcgattga gggcctgg                                          28

<210> SEQ ID NO 124
<211> LENGTH: 36
<212> TYPE: DNA
<213> ORGANISM: Artificial
<220> FEATURE:
<223> OTHER INFORMATION: Synthetic DNA

<400> SEQUENCE: 124
ataagaatgc ggccgcatga agctcaccgt tttcag                                 36

<210> SEQ ID NO 125
<211> LENGTH: 32
<212> TYPE: DNA
<213> ORGANISM: Artificial
<220> FEATURE:
<223> OTHER INFORMATION: Synthetic DNA

<400> SEQUENCE: 125
ataagaatgc ggccgctcag agccgcgcca ac                                     32

<210> SEQ ID NO 126
<211> LENGTH: 29
<212> TYPE: DNA
<213> ORGANISM: Artificial
<220> FEATURE:
<223> OTHER INFORMATION: Synthetic DNA

<400> SEQUENCE: 126
ggactagtat gacgaaaagg gaaagcaac                                         29

<210> SEQ ID NO 127
<211> LENGTH: 27
<212> TYPE: DNA
<213> ORGANISM: Artificial
<220> FEATURE:
<223> OTHER INFORMATION: Synthetic DNA

<400> SEQUENCE: 127
ggactagtct acgcgttttc tttcgac                                           27

<210> SEQ ID NO 128
<211> LENGTH: 29
<212> TYPE: DNA
<213> ORGANISM: Artificial
<220> FEATURE:
<223> OTHER INFORMATION: Synthetic DNA

<400> SEQUENCE: 128
ctagctagca tggagagcga agacaatcc                                         29

<210> SEQ ID NO 129
<211> LENGTH: 27
<212> TYPE: DNA
<213> ORGANISM: Artificial
<220> FEATURE:
<223> OTHER INFORMATION: Synthetic DNA

<400> SEQUENCE: 129
ctagctagct cagcagtatc ccatcgg                                           27

<210> SEQ ID NO 130
<211> LENGTH: 36
```

<212> TYPE: DNA
<213> ORGANISM: Artificial
<220> FEATURE:
<223> OTHER INFORMATION: Synthetic DNA

<400> SEQUENCE: 130
atttgcggcc gcatggaccc gagacagtca cggatc                          36

<210> SEQ ID NO 131
<211> LENGTH: 36
<212> TYPE: DNA
<213> ORGANISM: Artificial
<220> FEATURE:
<223> OTHER INFORMATION: Synthetic DNA

<400> SEQUENCE: 131
atttgcggcc gcttatggtg tggtgggttg ccattc                          36

<210> SEQ ID NO 132
<211> LENGTH: 20
<212> TYPE: DNA
<213> ORGANISM: Artificial
<220> FEATURE:
<223> OTHER INFORMATION: Synthetic DNA

<400> SEQUENCE: 132
gacgccacga acgcatagac                                            20

<210> SEQ ID NO 133
<211> LENGTH: 21
<212> TYPE: DNA
<213> ORGANISM: Artificial
<220> FEATURE:
<223> OTHER INFORMATION: Synthetic DNA

<400> SEQUENCE: 133
ttcccagaga ggtagatcga c                                          21

<210> SEQ ID NO 134
<211> LENGTH: 20
<212> TYPE: DNA
<213> ORGANISM: Artificial
<220> FEATURE:
<223> OTHER INFORMATION: Synthetic DNA

<400> SEQUENCE: 134
gaccgttaca gcgagttcag                                            20

<210> SEQ ID NO 135
<211> LENGTH: 20
<212> TYPE: DNA
<213> ORGANISM: Artificial
<220> FEATURE:
<223> OTHER INFORMATION: Synthetic DNA

<400> SEQUENCE: 135
ctgaattcct cgcacagaac                                            20

<210> SEQ ID NO 136
<211> LENGTH: 20
<212> TYPE: DNA
<213> ORGANISM: Artificial
<220> FEATURE:
<223> OTHER INFORMATION: Synthetic DNA

<400> SEQUENCE: 136
gaagttgaga acgccatgct                                               20

<210> SEQ ID NO 137
<211> LENGTH: 20
<212> TYPE: DNA
<213> ORGANISM: Artificial
<220> FEATURE:
<223> OTHER INFORMATION: Synthetic DNA

<400> SEQUENCE: 137
gatgcgagat gggagcatgt                                               20

<210> SEQ ID NO 138
<211> LENGTH: 20
<212> TYPE: DNA
<213> ORGANISM: Artificial
<220> FEATURE:
<223> OTHER INFORMATION: Synthetic DNA

<400> SEQUENCE: 138
gccctactag atctgaccac                                               20

<210> SEQ ID NO 139
<211> LENGTH: 20
<212> TYPE: DNA
<213> ORGANISM: Artificial
<220> FEATURE:
<223> OTHER INFORMATION: Synthetic DNA

<400> SEQUENCE: 139
gctgttacct tttcctcctc                                               20

<210> SEQ ID NO 140
<211> LENGTH: 20
<212> TYPE: DNA
<213> ORGANISM: Artificial
<220> FEATURE:
<223> OTHER INFORMATION: Synthetic DNA

<400> SEQUENCE: 140
agatcttaga cgagctgctc                                               20

<210> SEQ ID NO 141
<211> LENGTH: 20
<212> TYPE: DNA
<213> ORGANISM: Artificial
<220> FEATURE:
<223> OTHER INFORMATION: Synthetic DNA

<400> SEQUENCE: 141
aaacagtcgc gaagcgactg                                               20

<210> SEQ ID NO 142
<211> LENGTH: 20
<212> TYPE: DNA
<213> ORGANISM: Artificial
<220> FEATURE:
<223> OTHER INFORMATION: Synthetic DNA

<400> SEQUENCE: 142
acgtccagga agctatcgag                                               20

<210> SEQ ID NO 143
<211> LENGTH: 20

```
<212> TYPE: DNA
<213> ORGANISM: Artificial
<220> FEATURE:
<223> OTHER INFORMATION: Synthetic DNA

<400> SEQUENCE: 143
attgagggcc tgggcttgac                                            20

<210> SEQ ID NO 144
<211> LENGTH: 20
<212> TYPE: DNA
<213> ORGANISM: Artificial
<220> FEATURE:
<223> OTHER INFORMATION: Synthetic DNA

<400> SEQUENCE: 144
gtgatgaagg cgctgaagag                                            20

<210> SEQ ID NO 145
<211> LENGTH: 20
<212> TYPE: DNA
<213> ORGANISM: Artificial
<220> FEATURE:
<223> OTHER INFORMATION: Synthetic DNA

<400> SEQUENCE: 145
ctccgcaatt tccgtgagtg                                            20

<210> SEQ ID NO 146
<211> LENGTH: 20
<212> TYPE: DNA
<213> ORGANISM: Artificial
<220> FEATURE:
<223> OTHER INFORMATION: Synthetic DNA

<400> SEQUENCE: 146
tgactctatg gtggatggtg                                            20

<210> SEQ ID NO 147
<211> LENGTH: 20
<212> TYPE: DNA
<213> ORGANISM: Artificial
<220> FEATURE:
<223> OTHER INFORMATION: Synthetic DNA

<400> SEQUENCE: 147
ccttgttcaa gtgccagtag                                            20

<210> SEQ ID NO 148
<211> LENGTH: 20
<212> TYPE: DNA
<213> ORGANISM: Artificial
<220> FEATURE:
<223> OTHER INFORMATION: Synthetic DNA

<400> SEQUENCE: 148
gattccgtca cgagacactg                                            20

<210> SEQ ID NO 149
<211> LENGTH: 20
<212> TYPE: DNA
<213> ORGANISM: Artificial
<220> FEATURE:
<223> OTHER INFORMATION: Synthetic DNA
```

```
<400> SEQUENCE: 149
agtatcccat cgggcaacag                                          20

<210> SEQ ID NO 150
<211> LENGTH: 18
<212> TYPE: DNA
<213> ORGANISM: Artificial
<220> FEATURE:
<223> OTHER INFORMATION: Synthetic DNA

<400> SEQUENCE: 150
acgttcaaga ccttccag                                            18

<210> SEQ ID NO 151
<211> LENGTH: 18
<212> TYPE: DNA
<213> ORGANISM: Artificial
<220> FEATURE:
<223> OTHER INFORMATION: Synthetic DNA

<400> SEQUENCE: 151
gttccggatg atttgcag                                            18
```